US009320739B2

(12) United States Patent
Abraham et al.

(10) Patent No.: US 9,320,739 B2
(45) Date of Patent: *Apr. 26, 2016

(54) RAF KINASE MODULATOR COMPOUNDS AND METHODS OF USE THEREOF

(71) Applicant: AMBIT BIOSCIENCES CORPORATION, San Diego, CA (US)

(72) Inventors: Sunny Abraham, San Diego, CA (US); Shripad S. Bhagwat, San Diego, CA (US); Brian T. Campbell, Burlington, NY (US); Qi Chao, San Diego, CA (US); Raffaella Faraoni, San Diego, CA (US); Mark W. Holladay, San Diego, CA (US); Andiliy G. Lai, San Diego, CA (US); Martin W. Rowbottom, San Diego, CA (US); Eduardo Setti, San Mateo, CA (US); Kelly G. Sprankle, Vista, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,834

(22) Filed: Jan. 26, 2015

(65) Prior Publication Data
US 2015/0246042 A1 Sep. 3, 2015

Related U.S. Application Data

(63) Continuation of application No. 14/048,655, filed on Oct. 8, 2013, now Pat. No. 8,969,587, which is a continuation of application No. 12/933,402, filed as application No. PCT/US2009/001659 on Mar. 17, 2009, now Pat. No. 8,618,289.

(60) Provisional application No. 61/069,763, filed on Mar. 17, 2008, provisional application No. 61/110,508, filed on Oct. 31, 2008.

(51) Int. Cl.
| A61K 31/517 | (2006.01) |
| C07D 239/88 | (2006.01) |
| C07D 239/93 | (2006.01) |
| C07D 413/12 | (2006.01) |
| A61K 9/20 | (2006.01) |
| A61K 9/48 | (2006.01) |
| A61K 45/06 | (2006.01) |

(52) U.S. Cl.
CPC .......... *A61K 31/517* (2013.01); *A61K 9/20* (2013.01); *A61K 9/48* (2013.01); *A61K 45/06* (2013.01); *C07D 239/88* (2013.01); *C07D 239/93* (2013.01); *C07D 413/12* (2013.01)

(58) Field of Classification Search
None
See application file for complete search history.

(56) References Cited

U.S. PATENT DOCUMENTS

| 3,536,809 A | 10/1970 | Applezweig |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 4,728,743 A | 3/1988 | Drauz et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |

(Continued)

FOREIGN PATENT DOCUMENTS

| WO | WO 97/17329 | 5/1997 |
| WO | WO 00/43366 | 7/2000 |

(Continued)

OTHER PUBLICATIONS

Monia et al., Jun. 1996, Antitumor activitiy of a phosphorothioate antisense oligodeoxynucleotide targeted against C-raf kinase, Nature Medicine, 2(6):668-675.
Holladay et al., 2011, 4-quinazolinyloxy-diaryl ureas as novel BRAF$^{V600E}$ inhibitors, Biooganic & Medicinal Chemistry Letters, 21:5342-5346.
Rowbottom et al., 2012, Identification of 1-(3-(6,7-dimethoxyquinazolin-4-yloxy)phenyl)-3-(5-(1,1,1-trifluoro-2-2-methylpropan-2-yl)isoxazol-3-yl)urea hydochloride (CEP-32496), a highly potent and orally efficacious inhibitor of V-Raf murine sacrome viral ongocene homologue B1 (braf) V600E, Journal of Medicinal Chemistry, 55:1082-1105.
International Search Report and Written Opinion dated Aug. 6, 2009 in PCT/US09/001659.

(Continued)

Primary Examiner — Jeffrey H Murray
(74) Attorney, Agent, or Firm — Knobbe, Martens, Olson & Bear, LLP

(57) ABSTRACT

Compositions of 1-(3-((6,7-dimethoxyquinazolin-4-yl)oxy) phenyl)-3-(5-(1,1,1,-trifluoro-2-methylpropan-2-yl)isoxazol-3-yl)urea are provided for modulating the activity of RAF kinases, including BRAF kinase and for the treatment, prevention, or amelioration of one or more symptoms of disease or disorder mediated by RAF kinases.

11 Claims, No Drawings

(56) References Cited

U.S. PATENT DOCUMENTS

| | | | |
|---|---|---|---|
| 5,985,307 A | 11/1999 | Hanson et al. | |
| 5,993,855 A | 11/1999 | Yoshimoto et al. | |
| 6,004,534 A | 12/1999 | Langer et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,143,764 A | 11/2000 | Kubo et al. | |
| 6,197,350 B1 | 3/2001 | Yamagata et al. | |
| 6,248,363 B1 | 6/2001 | Patel et al. | |
| 6,253,872 B1 | 7/2001 | Neumann | |
| 6,264,970 B1 | 7/2001 | Hata et al. | |
| 6,267,981 B1 | 7/2001 | Okamoto et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,350,458 B1 | 2/2002 | Modi | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 6,797,823 B1 | 9/2004 | Kubo et al. | |
| 6,821,987 B2 | 11/2004 | Kubo et al. | |
| 7,135,466 B2 | 11/2006 | Sakai et al. | |
| 7,169,789 B2 | 1/2007 | Kubo et al. | |
| 7,211,587 B2 | 5/2007 | Kubo et al | |
| 7,253,286 B2 | 8/2007 | Funahashi et al. | |
| 7,579,473 B2 | 8/2009 | Bannen et al. | |
| 7,750,160 B2 | 7/2010 | Milanov et al. | |
| 8,618,289 B2 * | 12/2013 | Abraham | C07D 239/88 544/253 |
| 8,969,587 B2 * | 3/2015 | Abraham | C07D 239/88 548/246 |
| 2003/0087907 A1 | 5/2003 | Kubo et al. | |
| 2004/0242603 A1 | 12/2004 | Fujiwara et al. | |
| 2005/0165024 A1 | 7/2005 | Milanov et al. | |
| 2005/0165031 A1 | 7/2005 | Grotzfeld et al. | |
| 2005/0192314 A1 | 9/2005 | Mehta et al. | |
| 2005/0197371 A1 | 9/2005 | Milanov et al. | |
| 2005/0267182 A1 | 12/2005 | Milanov et al. | |
| 2006/0069077 A1 | 3/2006 | Rice et al. | |
| 2006/0142570 A1 | 6/2006 | Herz et al. | |
| 2007/0021446 A1 | 1/2007 | Ehlert et al. | |
| 2007/0244120 A1 | 10/2007 | Dumas et al. | |

FOREIGN PATENT DOCUMENTS

| | | |
|---|---|---|
| WO | WO0217918 | 3/2002 |
| WO | WO 02/088110 | 7/2002 |
| WO | WO2004006846 | 1/2004 |
| WO | 2005030140 | 4/2005 |
| WO | WO 2005/037285 | 4/2005 |
| WO | WO2007103370 | 9/2007 |
| WO | WO2008005310 | 1/2008 |
| WO | 2008051493 | 5/2008 |
| WO | WO2008051494 | 5/2008 |

OTHER PUBLICATIONS

Ballard et al., "Inhibitors of epidermal growth factor receptor tyrosine kinase: Novel C-5 substituted anilinoquinazolines designed to target the ribose pocket," Bioorg. Med. Chem. Lett. 16(6):1633-1637 (2006) (Epub Dec. 27, 2005).

Brose et al., "BRAF and RAS mutations in human lung cancer and melanoma," Cancer Res., 62(23):6997-7000 (2002).

Davies et al., "Mutations of the BRAF gene in human cancer," Nature 417(6892):949-954 (2002) (Epub Jun. 9, 2002).

Dong et al., "MAP kinases in the immune response," Annu. Rev. Immunol. 20:55-72 (2002) (Epub Oct. 4, 2001).

Eddington et al., "Synthesis and anticonvulsant activity of enaminones. 4. Investigations on isoxazole derivatives," Eur. J. Med. Chem. 37(8):635-648 (2002).

Fabian et al., "A small molecule-kinase interaction map for clinical kinase inhibitors," Nat. Biotechnol. 23(3):329-336 (2005) (Epub Feb. 13, 2005).

Fecher et al., "Toward a molecular classification of melanoma," J. Clin. Oncol. 25(12):1606-1620 (2007).

Foster, "Deuterium Isotope Effects in the Metabolism of Drugs and Xenobiotics: Implications for Drug Design," Adv. Drug Res. 14:1-36 (1985).

Garnett and Marais, "Guilty as charged: B-RAF is a human oncogene," Cancer Cell 6(4):313-319 (2004).

Gately et al., "Deuterioglucose: alteration of biodistribution by an isotope effect," J. Nucl. Med. 27(3):388-394 (1986).

Gordon et al., "The metabolism of the abortifacient terpene, (R)-(+)-pulegone, to a proximate toxin, menthofuran," Drug Metab. Dispos. 15(5): 589-594 (1987).

Greenman et al., "Patterns of somatic mutation in human cancer genomes," Nature 446(7132):153-158 (2007).

Haluska et al., "Genetic alterations in signaling pathways in melanoma," Clin. Cancer Res. 12(7 Pt 2):2301s-2307s (2006).

Herrera and Sebolt-Leopold, "Unraveling the complexities of the Raf/MAP kinase pathway for pharmacological intervention," Trends Mol. Med. 8(4 Suppl):S27-31 (2002).

Hofman, "Molecular Regulation of Neutrophil Apoptosis and Potential Targets for Therapeutic Strategy Against the Inflammatory Process," Curr. Drug Targets, Inflamm. Allergy 3:1-9 (2004).

Hoshino et al., "Constitutive activation of the 41-/43-kDa mitogen-activated protein kinase signaling pathway in human tumors," Oncogene 18(3):813-822 (1999).

Ikediobi et al., "Mutation analysis of 24 known cancer genes in the NCI-60 cell line set," Mol. Cancer Ther. 5 (11):2606-2612 (2006) (Epub Nov. 6, 2006).

Ji et al., "Mutations in BRAF and KRAS converge on activation of the mitogen-activated protein kinase pathway in lung cancer mouse models," Cancer Res. 67(10):4933-4939 (2007).

Johnson et al., "MAPK kinase kinases (MKKKs) as a target class for small-molecule inhibition to modulate signaling networks and gene expression," Curr. Opin. Chem. Biol. 9(3):325-331 (2005).

Kushner et al., "Pharmacological uses and perspectives of heavy water and deuterated compounds," Can. J. Physiol. Pharmacol. 77(2):79-88 (1999).

Kyriakis and Avruch, "Mammalian mitogen-activated protein kinase signal transduction pathways activated by stress and inflammation." Physiol. Rev. 81(2):807-869 (2001).

Lijinsky, et al., "Dose-response studies in carcinogenesis by nitroso-N-methyl-N-(2-phenyl)ethylamine in rats and the effects of deuterium substitution," Food Chem. Toxicol. 20(4):393-399 (1982).

Lijinsky et al., "Dose-response studies with nitrosoheptamethyleneimine and its alpha-deuterium-labeled derivative in F344 rats," J. Natl. Cancer Inst 69(5):1127-1133 (1982).

Lowinger et al., "Design and discovery of small molecules targeting raf-1 kinase," Curr. Pharm. Des. 8 (25):2269-2278 (2002).

Mangold et al., "Effects of deuterium labeling on azido amino acid mutagenicity in *Salmonella typhimurium*," Mutat. Res. 308(1):33-42 (1994).

Melillo et al., "The RET/PTC-RAS-BRAF linear signaling cascade mediates the motile and mitogenic phenotype of thyroid cancer cells," J. Clin. Invest. 115(4):1068-1081 (2005) (Epub Mar. 10, 2005).

Nakamura et al., "KRN951, a highly potent inhibitor of vascular endothelial growth factor receptor tyrosine kinases, has antitumor activities and affects functional vascular properties," Cancer Res. 66(18):9134-9142 (2006).

Ouyang et al., "Inhibitors of Raf kinase activity block growth of thyroid cancer cells with RET/PTC or BRAF mutations in vitro and in vivo," Clin. Cancer Res. 12(6):1785-1793 (2006).

(56) References Cited

OTHER PUBLICATIONS

Santus and Baker, "Osmotic drug delivery: a review of the patent literature," J. Control. Release, 35:1-21 (1995).

Sawatzky et al., "The involvement of the apoptosis-modulating proteins ERK 1/2, Bcl-xL and Bax in the resolution of acute inflammation in vivo," Am. J. Pathol. 168(1):33-41 (2006).

Sharma et al., "Mutant V599EB-Raf regulates growth and vascular development of malignant melanoma tumors," Cancer Res. 65(6):2412-2421 (2005).

Sharma et al., "Targeting mitogen-activated protein kinase/extracellular signal-regulated kinase kinase in the mutant (V600E) B-Raf signaling cascade effectively inhibits melanoma lung metastases," Cancer Res. (66)16:8200-8209 (2006).

Stanton et al., "MAP kinases in chondrocyte differentiation," Dev. Biol. 263(2):165-175 (2003).

Still et al., "Rapid Chromatographic Technique for Preparative Separations with Moderate Resolution," J. Org. Chem. 43(14):2923-2925 (1978).

Takase et al., "Cyclic GMP phosphodiesterase inhibitors. 2. Requirement of 6-substitution of quinazoline derivatives for potent and selective inhibitory activity," J. Med. Chem. 37(13):2106-2111 (1994).

Takase et al., "Practical Synthesis of 3-Amino-5-tert-Butylisoxazole from 4,4-Dimethyl-3-Oxopentanenitrile with Hydroxylamine," Heterocycles 32(6):1153-1158 (1991).

Thaimattam et al., "3D-QSAR CoMFA, CoMSIA studies on substituted ureas as Raf-1 kinase inhibitors and its confirmation with structure-based studies," Bioorg. Med. Chem. 12(24):6415-6425 (2004).

Verma, et al., Drug Development and Industrial Pharmacy, 26, pp. 695-708, 2000.

Verma et al., "Formulation aspects in the development of osmotically controlled oral drug delivery systems," J. Control. Release 79(1-3):7-27 (2002).

Wade, "Deuterium isotope effects on noncovalent interactions between molecules," Chem. Biol. Interact. 117(3):191-217 (1999).

Wan et al., "Mechanism of activation of the RAF-ERK signaling pathway by oncogenic mutations of B-RAF," Cell 116(6):855-867 (2004).

Wilhelm et al., "Discovery and development of sorafenib: a multikinase inhibitor for treating cancer," Nat. Rev. Drug Discov. 5(10):835-844 (2006).

Zello et al., "Plasma and urine enrichments following infusion of L-[1-13C]phenylalanine and L-[ring-2H5]phenylalanine in humans: evidence for an isotope effect in renal tubular reabsorption," Metabolism 43(4):487-491 (1994).

\* cited by examiner

RAF KINASE MODULATOR COMPOUNDS AND METHODS OF USE THEREOF

RELATED APPLICATIONS

This application is a continuation of U.S. patent application No. 14/048,655, filed Oct. 8, 2013, now U.S. Pat. No. 8,969,587, which is a continuation of U.S. patent application No. 12/933,402, filed Dec. 20,2010, now U.S. Pat. No. 8,618, 289, which is a National Stage Entry under 35 U.S.C. §371(c) of International Application No. PCT/US2009/001659, filed Mar. 17, 2009, which designated the United States of America and published in the English language, which claims the benefit of priority to U.S. Provisional Patent Application Nos. 61/069,763, filed Mar. 17, 2008 and 61/110,508, filed Oct. 31, 2008; all of the aforementioned applications are hereby expressly incorporated by reference in their entireties. Any and all applications for which a foreign or domestic priority claim is identified in the Application Data Sheet as filed with the present application are hereby incorporated by reference under 37 CFR 1.57.

FIELD

Provided herein are compounds that are modulators of RAF kinases, including BRAF kinase, compositions comprising the compounds and methods of use thereof. The compounds provided are useful in the treatment, prevention, or amelioration of a disease or disorder related to RAF, including BRAF kinase, activity or one or more symptoms thereof.

BACKGROUND

Protein kinases (PKs) are enzymes that catalyze the phosphorylation of hydroxyl groups on tyrosine, serine or threonine residues of proteins. Protein kinases act primarily as growth factor receptors and play a central role in signal transduction pathways regulating a number of cellular functions, such as cell cycle, cell growth, cell differentiation and cell death.

One important signal transduction pathway is the mitogen-activated protein kinase (MAPK) pathway. The MAPK signaling pathway is responsible for the regulation of cell growth, differentiation, proliferation and survival and its dysregulation is implicated in a broad spectrum of cancer. (Hoshino, et al., *Oncogene,* 1999, 18, 813-822)

The MAPK signaling pathway is one of multiple signaling pathways activated by GTP-bound RAS. Initially, extracellular stimuli such as mitogens, hormones or neurotransmitters induce receptor tyrosine kinase dimerization leading to increased levels of GTP-bound RAS. Activated RAS recruits dimerized RAF kinase to the plasma membrane whereby RAF is activated by autophosphorylation or phosphorylation by other kinases. The activation of RAF initiates the phosphorylation cascade down the MEK/ERK pathway, in which activated RAF phosphorylates and activates MEK1/2 which in turn phosphorylates and activates ERK (or extracellular signal-regulated kinase, also called p44/42 MAPK) which in turn phosphorylates a number of targets including nuclear transcription factors that lead to changes in gene expression.

RAF is a family of serine/threonine kinases comprising three isoforms called ARAF, BRAF and CRAF (also called raf-1). BRAF is currently a cancer therapeutic target, as mutations in the BRAF gene are among the most common in cancer (Haluska, et al., Clin Cancer Res 2006, 12(7 Pt 2), 2301s-2307s; Ikediobi, et al., *Mol. Cancer Ther.* 2006 5(11), 2606-2612; Greenman, et al., *Nature* 2007 226(7132), 153-158). The majority of mutant BRAF have been found to exhibit elevated kinase activity as measured by levels of phosphorylated MEK or ERK found endogenously in COS cells (Wan et al. *Cell* 2004 116, 855-867). BRAF mutations have been identified in about 7% of all known cancers, including 27-70% of melanoma (Davies et al. *Nature,* 2002 417, 949-954), 42-50% of papillary thyroid carcinoma, 36-53% colorectal cancers, and 5-22% serous ovarian cancers and to a lesser extent in breast cancer, endometrial cancer, liver cancer, sarcoma, stomach cancer, Barret's adenocarcinoma, gliomas including ependymomas and lung cancer including 1-2% of non small cell lung cancer (See Davies et al. *Nature,* 2002, 417, 949-954; Garnett and Marais, *Cancer Cell,* 2004 6, 313-319; Ouyang et al. *Clin Cancer Res* 2006 12(6), 1785-1793; Melillo, et al., *J. Clin. Invest.* 2005, 115, 1068-1081; Wilhelm, et al., *Nat. Rev. Drug Discov.,* 2006 5, 835-844; and Ji et al. *Cancer Res* 2007 67(10), 4933-4939). Over forty different missense mutations of BRAF have been identified, but among them, the V600E mutation, has been found to be the most predominant (Fecher, et al., *J. Clin. Oncology* 2007, 25(12), 1606-1620), accounting for nearly 90% of the mutations in melanoma and thyroid cancer and for a high proportion in colorectal cancer, which makes this mutation a particularly attractive target for molecular therapy. A study of the crystal structures of both wild type and V600 mutants suggests that substitution at the 600 position destabilizes the inactive conformation of the enzyme (Wan et al. op cit.). However, V600E mutation is comparatively rare in non-small cell lung cancer, which is more likely than not to be associated with non-V600E BRAF missense mutations (Brose et al. *Cancer Res.,* 2002 62, 6997-7000). Other non-V600E BRAF missense mutations are also implicated in melanoma, breast cancer, lung cancer, colorectal cancer, liver cancer, ovarian cancer, leukemia including acute lymphoblastic leukemia (ALL), non-Hodgkin's lymphoma, Barret's adenocarcinoma, endometrial cancer, liver cancer, stomach cancer, thyroid cancer and endometrial cancer (Garnett and Marais, op. cit.).

In vivo efficacy has been demonstrated for BRAF inhibitors NVP-AAL881-NX (also AAL881) and NVP-L T613-AG-8 (LBT613) in mouse tumor xenograft models using human cell lines (See, Ouyang et al. op. cit.). Preclinical studies have also shown that BRAF inhibition by siRNA or by the small molecule RAF kinase inhibitor Sorafenib resulted in a decrease in tumor growth or metastases in animals (Sharma et al. *Cancer Res.,* 2005, 65(6), 2412-2421; Sharma et al. *Cancer Res.,* 2006, (66)16, 8200-8209). RAF inhibitors that have entered clinical trials include antisense oligonucleotides against CRAF such as ISIS 5132 and LErafAON and small molecule BRAF inhibitors such as BAY 43-9006 (Sorafenib), Raf-265 (formerly CHIR-265, Novartis), PLX-4032 (Plexxikon) and XL281 (Exelixis).

Although most BRAF mutations are activating mutations, mutants having impaired kinase activity have been identified, and shown to stimulate ERK activity, presumably through recruitment of CRAF (Wan op cit.). Therefore, CRAF represents another target for the treatment of diseases associated with this particular subset of BRAF mutants.

Outside of cancer, the MAPK (Raf-Mek-Erk) signaling pathway could provide targets for inflammation and inflammatory diseases. The MAPK pathway is known to control cell survival and apoptosis of inflammatory cells such as basophils, macrophages, neutrophils and monocytes (See Dong et al., *Annu. Rev. Immunol.,* 2002, 20, 55-72; Johnson, et al., *Curr. Opin. Chem. Biol.,* 2005, 9, 325-331; R. Herrera and J. S. Sebolt-Leopold, *Trends Mol. Med.,* 2002, 8, S27-S3; and Kyriakis et al., *Physiol. Rev.,* 2002, 81, 807-869). In the carrageenan-induced pleurisy rat model, it has been shown that the Erk1/2 inhibitor PD98059 inhibits eosinophilic proinflammtory cytokine release by increasing the rate of neutrophil apoptosis thereby decreasing the number of macrophage and neutrophils that perpetuate the inflammatory response (Sawatzky et al., *Am J Pathol* 2006, 168(1), 33-41). It is therefore possible that one downstream effect of inhibiting RAF might be the resolution of an inflammatory response and BRAF inhibitors could be useful for the treatment of inflammatory diseases or immune system disorders including inflammatory bowel disease, Crohn's disease, ulcerative colitis, systemic lupus erythematosis (SLE), rheumatoid arthritis, multiple sclerosis, thyroiditis, type 1 diabetes, sarcoidosis, psoriasis, allergic rhinitis, asthma, COPD (chronic obstructive pulmonary disease) (See Stanton et al. *Dev. Biol.* 2003 263, 165-175, Hofman et al. Curr. *Drug Targets. Inflamm. Allergy* 2004 2, 1-9).

Given the multitude of diseases attributed to the dysregulation of MAPK signaling, there is an ever-existing need to provide novel classes of compounds that are useful as inhibitors of enzymes in the MAPK signaling pathway, as discussed herein.

SUMMARY

Provided herein are compounds of formula I. In one embodiment, compounds provided herein have activity as modulators of RAF kinase, including BRAF kinase. The compounds are useful in medical treatment, pharmaceutical compositions and methods for modulating the activity of RAF kinase, including BRAF kinase such as wildtype and/or mutated forms of BRAF kinase. In one embodiment, the compounds have formula (I):

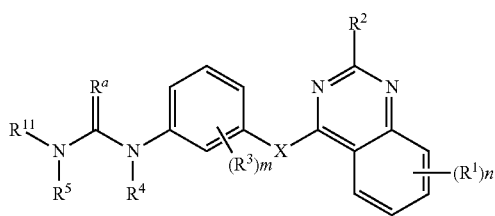

or pharmaceutically acceptable salts, solvates, hydrates or clathrates thereof, wherein X is O, S(O)$_t$;

R$^a$ is O or S;

R$^1$ is selected as follows:

i) each R$^1$ is independently selected from a group consisting of halo, nitro, alkyl, alkenyl, alkynyl, cycloalkyl, cycloalkylalkyl, heterocyclyl, heterocyclylalkyl, aryl, aralkyl, heteroaryl, heteroaralkyl, —R$^6$OR$^7$, —R$^6$SR$^7$, —R$^6$S(O)$_t$R$^8$, —R$^6$N(R$^7$)$_2$, —R$^6$OR$^9$OR$^7$, —R$^6$OR$^9$SR$^7$, —R$^6$OR$^9$S(O)$_t$R$^8$, —R$^6$OR$^9$S(O)$_t$N(R$^7$)$_2$, —R$^6$OR$^9$N(R$^7$)$_2$, —R$^6$SR$^9$OR$^7$, —R$^6$SR$^9$SR$^7$, —R$^6$SR$^9$N(R$^7$)$_2$, —R$^6$N(R$^7$)R$^9$N(R$^7$)$_2$, —R$^6$N(R$^7$)R$^9$OR, —R$^6$N(R$^7$)R$^9$SR$^7$, —R$^6$CN, —R$^6$C(O)R$^7$, —R$^6$C(O)OR$^7$, —R$^6$C(O)OR$^9$OR$^7$, —R$^6$C(O)N(R$^7$)$_2$, —R$^6$C(O)N(R$^7$)OR$^7$, —R$^6$C(NR$^7$)N(R$^7$)$_2$, —R$^6$C(O)N(R$^7$)R$^9$N(R$^7$)$_2$, —R$^6$C(O)N(R$^7$)R$^9$OR$^7$, —R$^6$C(O)N(R$^7$)R$^9$SR$^7$, —R$^6$C(O)SR$^8$, —R$^6$S(O)$_t$OR$^7$, —R$^6$S(O)$_t$N(R$^7$)$_2$, —R$^6$S(O)$_t$N(R$^7$)N(R$^7$)$_2$, —R$^6$S(O)$_t$N(R$^7$)N═C(R$^7$)$_2$, —R$^6$S(O)$_t$N(R$^7$)C(O)R$^8$, —R$^6$S(O)$_t$N(R$^7$)C(O)N(R$^7$)$_2$, —R$^6$S(O)$_t$N(R$^7$)C(NR$^7$)N(R$^7$)$_2$, —R$^6$OC(O)N(R$^7$)$_2$, —R$^6$N(R$^7$)C(O)R$^8$, —R$^6$N(R$^7$)C(O)OR$^8$, —R$^6$N(R$^7$)C(O)N(R$^7$)$_2$, —R$^6$N(R$^7$)C(NR$^7$)N(R$^7$)$_2$, —R$^6$N(R$^7$)C(S)N(R$^7$)$_2$, and —R$^6$N(R$^7$)S(O)$_t$R$^8$, or ii) any two adjacent R$^1$ groups together form an alkylenedioxy group;

each R$^6$ is independently a direct bond, alkylene chain or alkenylene chain;

each R$^7$ is independently selected from (i) or (ii) below:

(i) each R$^7$ is selected from a group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two R$^7$ groups together with the N atom to which they are attached form a heterocyclyl or heteroaryl;

each R$^8$ is independently selected from a group consisting of alkyl, alkenyl, alkynyl, cycloalkyl, cycloalkylalkyl, aryl, aralkyl, heterocyclyl, heterocyclylalkyl, heteroaryl and heteroaralkyl;

each R$^9$ is independently an alkylene chain or an alkenylene chain;

R$^2$ is hydrogen, halo, alkyl, amino or alkylamino;

R$^3$ is halo or alkyl;

R$^4$ and R$^5$ are each independently selected as follows:

a) R$^4$ and R$^5$ are each independently hydrogen or alkyl, or b) R$^4$ and R$^5$, together with the N atom to which they are attached, form an oxo-substituted heterocyclyl;

R$^{11}$ is aryl, heteroaryl or heterocyclyl;

m is an integer from 0 to 4;

n is an integer from 0 to 4;

t is an integer from 0 to 2; and

R$^1$, R$^2$, R$^3$, R$^4$, R$^5$, R$^6$, R$^7$, R$^8$, R$^9$ and R$^{11}$ are optionally substituted with one or more substituents independently selected from Q$^1$, wherein Q$^1$ is nitro, halo, azido, cyano, oxo, thioxo, imino, alkyl, alkenyl, alkynyl, cycloalkyl, cycloalkylalkyl, aryl, aralkyl, heteroaryl, heteroaralkyl, heterocyclyl, heterocyclylalkyl, —R$^u$OR$^x$, —R$^u$OR$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)SR$^x$, —R$^u$S(O)$_t$R$^w$, —R$^u$OC(J)R$^x$, —R$^u$OC(J)OR$^x$, —R$^u$OC(J)N(R$^y$)(R$^z$), —R$^u$OC(J)SR$^x$, —R$^u$N(R$^x$)C(J)R$^x$, —R$^u$N(R$^x$)C(J)OR$^x$, —R$^u$N(R$^x$)C(J)N(R$^y$)(R$^z$), —R$^u$N(R$^x$)C(J)SR$^x$, —R$^u$Si(R$^w$)$_3$, —R$^u$N(R$^x$)S(O)$_t$R$^w$, —R$^u$N(R$^x$)—R$^u$S(O)$_2$R$^w$, —R$^u$N(R$^x$)S(O)$_2$N(R$^y$)(R$^z$), —R$^u$S(O)$_2$N(R$^y$)(R$^z$) —R$^u$P(O)(R$^v$)$_2$, —R$^u$OP(O)(R$^v$)$_2$, —R$^u$C(J)N(R$^x$)S(O)$_2$R$^w$, —R$^u$C(J)N(R$^x$)N(R$^x$)S(O)$_2$R$^w$, R$^u$C(R$^x$)═N(OR$^x$) and —R$^u$C(R$^x$)═NN(R$^y$)(R$^z$), when Q$^1$ is alkyl, alkenyl or alkynyl, each Q$^1$ is optionally substituted with halo, cyano, hydroxy or alkoxy, when Q$^1$ is cycloalkyl, cycloalkylalkyl, aryl, aralkyl, heteroaryl, heteroaralkyl, heterocyclyl, or heterocyclylalkyl, each Q$^1$ is optionally substituted with halo, alkyl, haloalkyl, hydroxyalkyl, alkoxyalkyl, cyanoalkyl, alkoxy, hydroxyl, oxo or cyano, each R$^u$ is independently alkylene or a direct bond;

each R$^v$ is independently alkyl, alkenyl, alkynyl, cycloalkyl, cycloalkylalkyl, heterocyclyl, heterocyclylalkyl, aryl, aralkyl, heteroaralkyl, hydroxy, —OR$^x$ or —N(R$^y$)(R$^z$);

R$^w$ is alkyl, alkenyl, alkynyl, cycloalkyl, cycloalkylalkyl, heterocyclyl, heterocyclylalkyl, aryl, aralkyl, heteroaryl, or heteroaralkyl;

each R$^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

each $R^y$ and $R^z$ is independently selected from (i) or (ii) below:

(i) $R^y$ and Rz are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl, or (ii) $R^y$ and $R^z$, together with the nitrogen atom to which they are attached, form a heterocyclyl or heteroaryl; and J is O, $NR^x$ or S.

In one embodiment, the compound provided herein is a pharmaceutically acceptable salt of the compound of formula (I). In one embodiment, the compound provided herein is a solvate of the compound of formula (I). In one embodiment, the compound provided herein is a hydrate of compound of formula (I).

Also provided are pharmaceutical compositions formulated for administration by an appropriate route and means containing effective concentrations of one or more of the compounds provided herein, or pharmaceutically acceptable salts, solvates, and hydrates thereof, and optionally comprising at least one pharmaceutical carrier.

Such pharmaceutical compositions deliver amounts effective for the treatment, prevention, or amelioration of diseases or disorders that are modulated or otherwise affected by RAF kinases, including BRAF kinase, or one or more symptoms or causes thereof. Such diseases or disorders include without limitation: cancers, including melanoma, papillary thyroid carcinoma, colorectal, ovarian, breast cancer, endometrial cancer, liver cancer, sarcoma, stomach cancer, Barret's adenocarcinoma, glioma (including ependymoma), lung cancer (including non small cell lung cancer), head and neck cancer, acute lymphoblastic leukemia and non-Hodgkin's lymphoma; and inflammatory diseases or immune system disorders, including inflammatory bowel disease, Crohn's disease, ulcerative colitis, systemic lupus erythematosis (SLE), rheumatoid arthritis, multiple sclerosis (MS), thyroiditis, type 1 diabetes, sarcoidosis, psoriasis, allergic rhinitis, asthma, and chronic obstructive pulmonary disease (COPD).

Also provided herein are combination therapies using one or more compounds or compositions provided herein, or or pharmaceutically acceptable salts, solvates, hydrates or clathrates thereof, in combination with other pharmaceutically active agents for the treatment of the diseases and disorders described herein.

In one embodiment, such additional pharmaceutical agents include one or more chemotherapeutic agents, anti-proliferative agents, anti-inflammatory agents, immunomodulatory agents or immunosuppressive agents.

The compounds or compositions provided herein, or or pharmaceutically acceptable salts, solvates, hydrates or clathrates thereof, may be administered simultaneously with, prior to, or after administration of one or more of the above agents. Pharmaceutical compositions containing a compound provided herein and one or more of the above agents are also provided.

In certain embodiments, provided herein are methods of treating, preventing or ameliorating a disease or disorder that is modulated or otherwise affected by RAF kinases, including BRAF kinase such as wild type and/or mutant BRAF kinase, or one or more symptoms or causes thereof. In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

DETAILED DESCRIPTION

Provided herein are compounds of formula (I) that have activity as RAF kinase, including BRAF kinase, modulators. Further provided are methods of treating, preventing or ameliorating diseases that are modulated by RAF kinases, including BRAF kinase, and pharmaceutical compositions and dosage forms useful for such methods. The methods and compositions are described in detail in the sections below.

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain radical consisting solely of carbon and hydrogen atoms, containing no unsaturation, having from one to ten carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain radical consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain radical consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from two to eight carbon atoms, wherein the unsaturation is present only as double bonds and wherein the double bond can exist between any two carbon atoms in the chain, e.g., ethenylene, prop-1- enylene, but-2-enylene and the like. The alkenylene chain may be attached to the rest of the molecule through any two carbons within the chain.

"Alkoxy" refers to the radical having the formula —OR wherein R is alkyl or haloalkyl. An "optionally substituted alkoxy" refers to the radical having the formula —OR wherein R is an optionally substituted alkyl as defined herein.

"Alkynylene" or "alkynylene chain" refers to a straight or branched chain unsaturated divalent radical consisting solely of carbon and hydrogen atoms, having from two to eight carbon atoms, wherein the unsaturation is present only as triple bonds and wherein the triple bond can exist between any two carbon atoms in the chain, e.g., ethynylene, prop-1-ynylene, but-2-ynylene, pent-1-ynylene, pent-3-ynylene and the like. The alkynylene chain may be attached to the rest of the molecule through any two carbons within the chain.

"Amino" refers to a radical having the formula —NR'R" wherein R' and R" are each independently hydrogen, alkyl or haloalkyl. An "optionally substituted amino" refers to a radical having the formula NR'R" wherein one or both of R' and R" are optionally substituted alkyl as defined herein.

"Aryl" refers to a radical of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Aralkyl" refers to a radical of the formula —$R_aR_b$ where $R_a$ is an alkyl radical as defined above, substituted by $R_b$, an aryl radical, as defined above, e.g., benzyl. Both the alkyl and aryl radicals may be optionally substituted as defined herein.

"Aralkoxy" refers to a radical of the formula —$OR_aR_b$ where —$R_aR_b$ is an aralkyl radical as defined above. Both the alkyl and aryl radicals may be optionally substituted as defined herein.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined herein.

"Halo", "halogen" or "halide" refers to F, Cl, Br or I.

"Haloalkyl" refers to an alkyl group, in certain embodiments, $C_{1-4}$alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, (trifluoromethyl)cyclopropyl and 2,2,2-trifluoro-1,1-dimethyl-ethyl.

"Haloalkenyl" refers to an alkenyl group in which one or more of the hydrogen atoms are replaced by halogen. Such groups include, but are not limited to, 1-chloro-2-fluoroethenyl.

"Heterocyclyl" refers to a stable 3- to 15-membered non-aromatic ring radical which consists of carbon atoms and from one to five heteroatoms selected from a group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated. The heterocyclic ring system may be attached to the main structureat any heteroatom or carbon atom which results in the creation of a stable compound. Exemplary heterocylic radicals include, morpholinyl, tetrahydropyranyl, piperidinyl, piperazinyl and pyrrolidinyl.

"Heteroaryl" refers to a monocyclic or multicyclic aromatic ring system, a heterocyclyl radical as defined above which is aromatic, in certain embodiments, of about 5 to about 20 members where one or more, in one embodiment 1 to 5, of the atoms in the ring system is a heteroatom, that is, an element other than carbon, including but not limited to, nitrogen, oxygen or sulfur. The heteroaryl group may be optionally fused to a benzene ring. The heteroaryl radical may be attached to the main structureat any heteroatom or carbon atom which results in the creation of a stable compound. Examples of such heteroaryl radicals include, but are not limited to: acridinyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, isoxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thienyl, triazinyl and triazolyl.

In certain embodiments, the heterocyclic or heteroaryl radicals include, but are not limited to: acridinyl, azepinyl, benzimidazolyl, benzindolyl, benzoisoxazolyl, benzisoxazinyl, benzo[4,6]imidazo[1,2-a]pyridinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl and 1,3,5-trithianyl.

"Heteroaralkyl" refers to a radical of the formula —$R_aR_f$ where $R_a$ is an alkyl radical as defined above and $R_f$ is a heteroaryl radical as defined herein. The alkyl radical and the heteroaryl radical may be optionally substituted as defined herein.

"Heterocyclylalkyl" refers to a radical of the formula $R_aR_e$ wherein $R_a$ is an alkyl radical as defined above and $R_e$ is a heterocyclyl radical as defined herein, where the alkyl radical $R_a$ may attach at either the carbon atom or the heteroatom of the heterocyclyl radical $R_e$. The alkyl radical and the heterocyclyl radical may be optionally substituted as defined herein.

"$IC_{50}$" refers to an amount, concentration or dosage of a particular test compound that achieves a 50% inhibition of a maximal response, such as cell growth or proliferation measured via any the in vitro or cell based assay described herein.

Unless stated otherwise specifically described in the specification, it is understood that the substitution can occur on any atom of the alkyl, alkenyl, alkynyl, cycloalkyl, heterocyclyl, aryl or heteroaryl group.

"Oxo" refers to =O.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

"Sulfide" refers to the radical having the formula SR wherein R is an alkyl or haloalkyl group. An "optionally substituted sulfide" refers to the radical having the formula SR wherein R is an optionally substituted alkyl as defined herein.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

It is to be understood that the compounds provided herein may contain chiral centers. Such chiral centers may be of either the (R) or (S) configuration, or may be a mixture thereof Optically active (+) and (−), (R)- and (S)-, or (D)- and (L)-isomers may be prepared using chiral synthons or chiral reagents, or resolved using conventional techniques, such as reverse phase HPLC.

As used herein, the term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the desired enantiomer.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure preferably controls. As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition. As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. Compounds

In one embodiment, the compounds provided are of formula (I) as described above. In one embodiment, the compounds provided are of formula (I) as described above, where X is O. In one embodiment, the compounds provided are of formula (I) as described above, where X is $S(O)_t$ and t is an integer from 0 to 2.

In one embodiment, the compounds have formula (I) or pharmaceutically acceptable salts, solvates, hydrates or clathrates thereof, wherein X is O, $S(O)_t$;

$R^a$ is O or S;

$R^1$ is selected as follows:

i) each $R^1$ is independently selected from a group consisting of halo, nitro, alkyl, alkenyl, alkynyl, cycloalkyl, cycloalkylalkyl, heterocyclyl, heterocyclylalkyl, aryl, aralkyl, heteroaryl, heteroaralkyl, —$R^6OR^7$, —$R^6SR^7$, —$R^6S(O)_tR^8$, —$R^6N(R^7)_2$, —$R^6OR^9OR^7$, —$R^6OR^9SR^7$, —$R^6OR^9S(O)_tR^8$, —$R^6OR^9S(O)_tN(R^7)_2$, —$R^6OR^9N(R^7)_2$, —$R^6SR^9OR^7$, —$R^6SR^9SR^7$, —$R^6SR^9N(R^7)_2$, —$R^6N(R^7)$ $R^9N(R^7)_2$, —$R^6N(R^7)R^9OR$, —$R^6N(R^7)R^9SR^7$, —$R^6CN$, —$R^6C(O)R^7$, —$R^6C(O)OR^7$, —$R^6C(O)OR^9OR^7$, —$R^6C(O)N(R^7)_2$, —$R^6C(O)N(R^7)OR^7$, —$R^6C(NR^7)N(R^7)_2$, —$R^6C(O)N(R^7)R^9N(R^7)_2$, —$R^6C(O)N(R^7)R^9OR^7$, —$R^6C(O)N(R^7)R^9SR^7$, —$R^6C(O)SR^8$, —$R^6S(O)_tOR^7$, —$R^6S(O)_tN(R^7)_2$, —$R^6S(O)_tN(R^7)N(R^7)_2$, —$R^6S(O)_tN(R^7)N=C(R^7)_2$, —$R^6S(O)_tN(R^7)C(O)R^8$, —$R^6S(O)_tN(R^7)C(O)N(R^7)_2$, —$R^6S(O)_tN(R^7)C(NR^7)N(R^7)_2$, —$R^6OC(O)N(R^7)_2$, —$R^6N(R^7)C(O)R^8$, —$R^6N(R^7)C(O)OR^8$, —$R^6N(R^7)C(O)N(R^7)_2$, —$R^6N(R^7)C(NR^7)N(R^7)_2$, —$R^6N(R^7)C(S)N(R^7)_2$, and —$R^6N(R^7)S(O)_tR^8$, or ii) any two adjacent $R^1$ groups together form an alkylenedioxy group;

each $R^6$ is independently a direct bond, alkylene chain or alkenylene chain;

each $R^7$ is independently selected from (i) or (ii) below:

(i) each $R^7$ is selected from a group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two $R^7$ groups together with the N atom to which they are attached form a heterocyclyl or heteroaryl;

each $R^8$ is independently selected from a group consisting of alkyl, alkenyl, alkynyl, cycloalkyl, cycloalkylalkyl, aryl, aralkyl, heterocyclyl, heterocyclylalkyl, heteroaryl and heteroaralkyl;

each $R^9$ is independently an alkylene chain or an alkenylene chain;

$R^2$ is hydrogen, halo, alkyl, amino or alkylamino;

$R^3$ is halo or alkyl;

$R^4$ and $R^5$ are each independently selected as follows:

a) $R^4$ and $R^5$ are each independently hydrogen or alkyl, or b) $R^4$ and $R^5$, together with the N atom to which they are attached, form an oxo-substituted heterocyclyl;

$R^{11}$ is aryl, heteroaryl or heterocyclyl;

m is an integer from 0 to 4;

n is an integer from 0 to 4;

t is an integer from 0 to 2; and $R^1$, $R^2$, $R^3$, $R^4$, $R^5$, $R^6$, $R^7$, $R^8$, $R^9$ and $R^{11}$ are optionally substituted with one or more substituents independently selected from $Q^1$, wherein $Q^1$ is nitro, halo, azido, cyano, oxo, thioxo, imino, alkyl, alkenyl, alkynyl, cycloalkyl, cycloalkylalkyl, aryl, aralkyl, heteroaryl, heteroaralkyl, heterocyclyl, heterocyclylalkyl, —$R^uOR^x$, —$R^uOR^vOR^x$, —$R^uOR^vN(R^y)$ $(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)SR^x$, —$R^uS(O)_tR^w$, —$R^uOC(J)R^x$, —$R^uOC(J)OR^x$, —$R^uOC(J)N(R^y)(R^z)$, —$R^uOC(J)SR^x$, —$R^u N(R^x)C(J)R^x$, —$R^uN(R^x)C(J)OR^x$, —$R^uN(R^x)C(J)N(R^y)(R^z)$, —$R^uN(R^x)C(J)SR^x$, —$R^uSi(R^w)_3$, —$R^uN(R^x)S(O)_tR^w$, —$R^uN(R^x)$—$R^uS(O)_2R^w$, —$R^uN(R^x)S(O)_2N(R^y)$ $(R^z)$, —$R^uS(O)_2N(R^y)(R^z)$, —$R^uP(O)(R^v)_2$, —$R^uOP(O)$ $(R^v)_2$, —$R^uC(J)N(R^x)S(O)_2R^w$, —$R^uC(J)N(R^x)N(R^x)S(O)_2$ $R^w$, $R^uC(R^x)=N(OR^x)$ and —$R^uC(R^x)=NN(R^y)(R^z)$, when $Q^1$ is alkyl, alkenyl or alkynyl, each $Q^1$ is optionally substituted with halo, cyano, hydroxy or alkoxy, when $Q^1$ is cycloalkyl, cycloalkylalkyl, aryl, aralkyl, heteroaryl, heteroaralkyl, heterocyclyl, or heterocyclylalkyl, each $Q^1$ is optionally substituted with halo, alkyl, haloalkyl, hydroxyalkyl, alkoxyalkyl, cyanoalkyl, alkoxy or hydroxyl, each $R^u$ is independently alkylene or a direct bond;

each $R^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

each $R^y$ and $R^z$ is independently selected from (i) or (ii) below:

(i) $R^y$ and $R^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl, or (ii) $R^y$ and $R^z$, together with the nitrogen atom to which they are attached, form a heterocyclyl or heteroaryl; and J is O, $NR^x$ or S.

In one embodiment, the compounds provided are of formula (II):

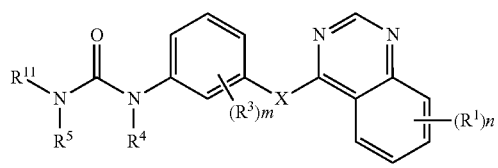

or a pharmaceutically acceptable salt, solvate, clathrate or hydrate thereof, wherein X is O, S, S(O) or $SO_2$;

$R^1$ is selected as follows:

i) each $R^1$ is independently selected from the group consisting of, halo, alkyl, alkenyl, alkynyl, cycloalkyl, cycloalkylalkyl, heterocyclyl, heterocyclylalkyl, aryl, aralkyl, heteroaryl, heteroaralkyl, $-R^6OR^7$, $-R^6SR^7$, $-R^6S(O)_tR^8$, $-R^6N(R^7)_2$, $-R^6OR^9OR^7$, $-R^6OR^9SR^7$, $-R^6OR^9S(O)_tR^8$, $-R^6OR^9S(O)_tN(R^7)_2$, $-R^6OR^9N(R^7)_2$, $-R^6SR^9OR^7$, $-R^6SR^9SR^7$, $-R^6SR^9N(R^7)_2$, $-R^6N(R^7)R^9N(R^7)_2$, $-R^6N(R^7)R^9OR^7$, $-R^6N(R^7)R^9SR^7$, $-R^6CN$, $-R^6C(O)R^7$, $-R^6C(O)OR^7$, $-R^6C(O)OR^9OR^7$, $-R^6C(O)N(R^7)_2$, $-R^6C(O)N(R^7)OR^7$, $-R^6C(O)N(R^7)R^9OR^7$, $-R^6C(O)N(R^7)R^9SR^7$, $-R^6C(O)SR^8$, $-R^6S(O)_tOR^7$, $-R^6OC(O)N(R^7)_2$, $-R^6N(R^7)C(O)R^8$, $-R^6S(O)_tN(R^7)_2$; or ii) any two adjacent $R^1$ groups form an alkylenedioxy group;

each $R^6$ is independently a direct bond, alkylene chain or alkenylene chain;

each $R^7$ is independently selected from (i) or (ii) below:

(i) each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two $R^7$ groups together with the N atom to which they are attached form a heterocyclyl or heteroaryl;

each $R^9$ is independently an alkylene chain or an alkenylene chain;

$R^2$ is hydrogen, halo, alkyl, amino or alkylamino;

$R^3$ is halo or alkyl;

$R^4$ and $R^5$ are each independently hydrogen or alkyl;

$R^{11}$ is aryl or heteroaryl;

m is an integer from 0 to 4;

n is an integer from 0 to 4;

$R^1$, $R^2$, $R^3$, $R^4$, $R^5$, $R^6$, $R^7$, $R^8$, $R^9$ and $R^{11}$ are optionally substituted with one or more substituents independently selected from $Q^1$, wherein $Q^1$ is nitro, halo, azido, cyano, oxo, thioxo, imino, alkyl, alkenyl, alkynyl, cycloalkyl, cycloalkylalkyl, heterocyclyl, heterocyclylalkyl, heteroaryl, heteroaralkyl, $-R''OR^x$, $-R''OR''OR^x$, $-R''OR''N(R^y)(R^z)$, $-R''N(R^y)(R^z)$, $-R''SR^x$, $-R''C(J)R^x$, $-R''C(J)OR^x$, $-R''C(J)N(R^y)(R^z)$, $-R''C(J)SR^x$, $-R''S(O)_tR^w$, $-R''OC(J)R^x$, $-R''OC(J)OR^x$, $-R''OC(J)N(R^y)(R^z)$, $-R''OC(J)SR^x$, $-R''N(R^x)C(J)R^x$, $-R''N(R^x)C(J)OR^x$, $-R''N(R^x)C(J)N(R^y)(R^z)$, $-R''N(R^x)C(J)SR^x$, $-R''Si(R^w)_3$, $-R''N(R^x)S(O)_2R^w$, $-R''N(R^x)S(O)_2N(R^y)(R^z)$, $-R''S(O)_2N(R^y)(R^z)$, $-R''P(O)(R^v)_2$, $-R''OP(O)(R^v)_2$, $-R''C(J)N(R^x)S(O)_2R^w$, $-R''C(J)N(R^x)N(R^x)S(O)_2R^w$, $-R''C(R^x)=N(OR^x)$ and $-R''C(R^x)=NN(R^y)(R^z)$, when $Q^1$ is alkyl, alkenyl or alkynyl, each $Q^1$ is optionally substituted with halo, cyano, hydroxy or alkoxy, when $Q^1$ is cycloalkyl, cycloalkylalkyl, aryl, aralkyl, heteroaryl, heteroaralkyl, heterocyclyl, or heterocyclylalkyl, each $Q^1$ is optionally substituted with halo, alkyl, haloalkyl, hydroxyalkyl, alkoxyalkyl, cyanoalkyl, alkoxy or hydroxyl, each $R^u$ is independently alkylene or a direct bond;

each $R^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, $-OR^x$ or $-N(R^y)(R^z)$;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$, together with the nitrogen atom to which they are attached, form a heterocycle or heteroaryl;

t is an integer from 0 to 2; and

J is O, $NR^x$ or S.

In one embodiment, the compounds provided are of formula (II) or a pharmaceutically acceptable salt, solvate, clathrate or hydrate thereof, wherein X is O, S, S(O) or $SO_2$;

$R^1$ is selected as follows:

i) each $R^1$ is independently selected from the group consisting of, halo, alkyl, alkenyl, alkynyl, cycloalkyl, cycloalkylalkyl, heterocyclyl, heterocyclylalkyl, aryl, aralkyl, heteroaryl, heteroaralkyl, $-R^6OR^7$, $-R^6SR^7$, $-R^6S(O)_tR^8$, $-R^6N(R^7)_2$, $-R^6OR^9OR^7$, $-R^6OR^9SR^7$, $-R^6OR^9S(O)_tR^8$, $-R^6OR^9S(O)_tN(R^7)_2$, $-R^6OR^9N(R^7)_2$, $-R^6SR^9OR^7$, $-R^6SR^9SR^7$, $-R^6SR^9N(R^7)_2$, $-R^6N(R^7)R^9N(R^7)_2$, $-R^6N(R^7)R^9OR^7$, $-R^6N(R^7)R^9SR^7$, $-R^6CN$, $-R^6C(O)R^7$, $-R^6C(O)OR^7$, $-R^6C(O)OR^9OR^7$, $-R^6C(O)N(R^7)_2$, $-R^6C(O)N(R^7)OR^7$, $-R^6C(O)N(R^7)R^9OR^7$, $-R^6C(O)N(R^7)R^9SR^7$, $-R^6C(O)SR^8$, $-R^6S(O)_tOR^7$, $-R^6OC(O)N(R^7)_2$, $-R^6N(R^7)C(O)R^8$, $-R^6S(O)_tN(R^7)_2$; or ii) any two adjacent $R^1$ groups form an alkylenedioxy group;

each $R^6$ is independently a direct bond, alkylene chain or alkenylene chain;

each $R^7$ is independently selected from (i) or (ii) below:

(i) each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two $R^7$ groups together with the N atom to which they are attached form a heterocyclyl or heteroaryl;

each $R^9$ is independently an alkylene chain or an alkenylene chain;

$R^2$ is hydrogen, halo, alkyl, amino or alkylamino;

$R^3$ is halo or alkyl;

$R^4$ and $R^5$ are each independently hydrogen or alkyl;

$R^{11}$ is aryl or heteroaryl;

m is an integer from 0 to 4;

n is an integer from 0 to 4;

$R^1$, $R^2$, $R^3$, $R^4$, $R^5$, $R^6$, $R^7$, $R^8$, $R^9$ and $R^{11}$ are optionally substituted with one or more substituents independently selected from $Q^1$, wherein $Q^1$ is nitro, halo, azido, cyano, oxo, thioxo, imino, alkyl, alkenyl, alkynyl, cycloalkyl, cycloalkylalkyl, heterocyclyl, heterocyclylalkyl, heteroaryl, heteroaralkyl, —R"OR$^x$, —R"OR"OR$^x$, —R"OR"N(R$^y$)(R$^z$), —R" N(R$^y$)(R$^z$), —R" SR$^x$, —R" C(J)R$^x$, —R"C(J)OR$^x$, —R"C(J)N(R$^y$)(R$^z$), —R"C(J)SR$^x$, —R"S(O)$_t$R$^w$, —R"OC(J)R$^x$, —R"OC(J)OR$^x$, —R"OC(J)N(R$^y$)(R$^z$), —R"OC(J)SR$^x$, —R" N(R$^x$)C(J)R$^x$, —R"N(R$^x$)C(J)OR$^x$, —R"N(R$^x$)C(J)N(R$^y$)(R$^z$), —R"N(R$^x$)C(J)SR$^x$, —R"Si(R$^w$)$_3$, —R"N(R$^x$)S(O)$_2$R$^w$, —R"N(R$^x$) R"S(O)$_2$R$^w$, —R"N(R$^x$)S(O)$_2$N(R$^y$)(R$^z$), —R"S(O)$_2$N(R$^y$)(R$^z$), —R"P(O)(R$^y$)$_2$, —R"OP(O)(R$^y$)$_2$, —R"C(J)N(R$^x$)S(O)$_2$R$^w$, —R"C(J)N(R$^x$)N(R$^x$)S(O)$_2$R$^w$, —R"C(R$^x$)=N(OR$^x$) and —R"C(R$^x$)=NN(R$^y$)(R$^z$), when $Q^1$ is alkyl, alkenyl or alkynyl, each $Q^1$ is optionally substituted with halo, cyano, hydroxy or alkoxy, when $Q^1$ is cycloalkyl, cycloalkylalkyl, aryl, aralkyl, heteroaryl, heteroaralkyl, heterocyclyl, or heterocyclylalkyl, each $Q^1$ is optionally substituted with halo, alkyl, haloalkyl, hydroxyalkyl, alkoxyalkyl, cyanoalkyl, oxo, cyano, thioxo, alkoxy or hydroxyl, each $R^u$ is independently alkylene or a direct bond;

each $R^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —OR$^x$ or —N(R$^y$)(R$^z$);

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$, together with the nitrogen atom to which they are attached, form a heterocycle or heteroaryl;

t is an integer from 0 to 2; and

J is O, NR$^x$ or S.

In one embodiment, the compound is a single isomer, including a stereoisomer, a mixture of isomers, a racemic mixture of isomers, a solvate, a hydrate or a pharmaceutically acceptable salt thereof In one embodiment, the compound provided herein is a pharmaceutically acceptable salt of the compound of formula (I). In one embodiment, the compounds provided herein is a solvate of the compound of formula (I). In one embodiment, the compounds provided herein is a hydrate of compound of formula (I).

In one embodiment, X is O or S. In one embodiment, X is O. In one embodiment, X is S(O)$_t$ and t is an integer from 0 to 2. In one embodiment X is S. In one embodiment, $R^a$ is O.

In one embodiment, n is an integer from 1 to 4. In one embodiment, n is 1. In one embodiment, n is 2. In one embodiment, n is 3.

In one embodiment, m is an integer from 0 to 2. In one embodiment, m is 0. In one embodiment, m is 1. In one embodiment, m is 2.

In one embodiment, $R^2$ is hydrogen.

In one embodiment, $R^3$ is lower alkyl or halo. In one embodiment, $R^3$ is methyl, chloro or fluoro. In another embodiment, $R^3$ is methyl, chloro or fluoro.

In one embodiment, $R^4$ is hydrogen or alkyl and $R^5$ is hydrogen. In one embodiment, $R^5$ is hydrogen or alkyl and $R^4$ is hydrogen. In one embodiment, $R^4$ and $R^5$ are each independently hydrogen or methyl. In one embodiment, $R^4$ and $R^5$ are each hydrogen.

In one embodiment, $Q^1$ is nitro, halo, azido, cyano, oxo, thioxo, imino, alkyl, alkenyl, alkynyl, cycloalkyl, cycloalkylalkyl, aryl, aralkyl, heterocyclyl, heterocyclylalkyl, heteroaryl, heteroaralkyl, —R"OR$^x$, —R"OR"OR$^x$, —R"OR"N(R$^y$)(R$^z$), —R"N(R$^y$)(R$^z$), —R" SR$^x$, —R" C(J)R$^x$, —R"C(J)OR$^x$, —R"C(J)N(R$^y$)(R$^z$), —R"C(J)SR$^x$, —R"S(O)$_t$R$^w$, —R"OC(J)R$^x$, —R"OC(J)OR$^x$, —R"OC(J)N(R$^y$)(R$^z$), —R"OC(J)SR$^x$, —R" N(R$^x$)C(J)R$^x$, —R"N(R$^x$)C(J)OR$^x$, —R"N(R$^x$)C(J)N(R$^y$)(R$^z$), —R"N(R$^x$)C(J)SR$^x$, —R"Si(R$^w$)$_3$, —R"N(R$^x$)S(O)$_2$R$^w$, —R"N(R$^x$) R"S(O)$_2$R$^w$, —R"N(R$^x$)S(O)$_2$N(R$^y$)(R$^z$), —R"S(O)$_2$N(R$^y$)(R$^z$), —R"P(O)(R$^y$)$_2$, —R"OP(O)(R$^y$)$_2$, —R"C(J)N(R$^x$)S(O)$_2$R$^w$, —R"C(J)N(R$^x$)N(R$^x$)S(O)$_2$R$^w$, —R"C(R$^x$)=N(OR$^x$) and —R"C(R$^x$)=NN(R$^y$)(R$^z$), when $Q^1$ is alkyl, alkenyl or alkynyl, each $Q^1$ is optionally substituted with halo, cyano, hydroxy or alkoxy, when $Q^1$ is cycloalkyl, cycloalkylalkyl, aryl, aralkyl, heteroaryl, heteroaralkyl, heterocyclyl, or heterocyclylalkyl, each $Q^1$ is optionally substituted with halo, alkyl, haloalkyl, hydroxyalkyl, alkoxyalkyl, cyanoalkyl, oxo, thioxo, alkoxy or hydroxyl, wherein the variables are as described elsewhere herein.

In one embodiment, $Q^1$ is halo, alkyl, —R"OR$^x$, —R"OR"OR$^x$, —R"OR"N(R$^3$)(R$^z$), —R" N(R$^y$)(R$^z$), —R"C(J)OR$^x$, —R"S(O)$_t$R$^w$, —R"N(R$^x$)S(O)$_2$R$^w$ or —R"N(R$^x$) R"S(O)$_2$R$^w$, when $Q^1$ is alkyl, each $Q^1$ is optionally substituted with halo, cyano, hydroxy or alkoxy, wherein the variables are as described elsewhere herein.

In one embodiment, $Q^1$ is halo, alkyl, cycloalkyl, haloalkyl, —R"OR$^x$, —R"OR"OR$^x$, —R"OR"N(R$^y$)(R$^z$), —R" N(R$^y$)(R$^z$), —R"C(J)OR$^x$, —R"S(O)$_t$R$^w$, —R"N(R$^x$)S(O)$_2$R$^w$ or —R"N(R$^x$) R"S(O)$_2$R$^w$, when $Q^1$ is alkyl, each $Q^1$ is optionally substituted with halo, cyano, hydroxy or alkoxy, each $R^u$ is independently alkylene or a direct bond;

$R^w$ is alkyl, cycloalkyl, cycloalkylalkyl, heterocyclyl, heterocyclylalkyl, aryl, aralkyl, heteroaryl, or heteroaralkyl;

$R^x$ is hydrogen, alkyl, haloalkyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, cycloalkyl, cycloalkylalkyl, heterocyclyl, heterocyclylalkyl, aryl, aralkyl, heteroaryl, or heteroaralkyl; or $R^y$ and $R^z$, together with the nitrogen atom to which they are attached, form a heterocyclyl or heteroaryl.

In one embodiment, $Q^1$ is halo, alkyl, cycloalkyl, haloalkyl, —$R^uOR^x$, —$R^uOR^uOR^x$, —$R^uOR^uN(R^y)(R^z)$, —$R^u N(R^y)(R^z)$, —$R^uC(J)OR^x$, —$R^uS(O)_zR^w$, —$R^uN(R^x)S(O)_2R^w$ or —$R^uN(R^x) R^uS(O)_2R^w$, where $Q^1$, when alkyl is optionally substituted with halo, cyano, and where $Q^1$, when cycloalkyl is optionally substituted with haloalkyl and the other variables are as described elsewhere herein.

In one embodiment, $Q^1$ is haloalkyl, alkyl, —$R^uOR^x$, —$R^uOR^uOR^x$, —$R^uOR^uN(R^y)(R^z)$—$R^uC(J)OR^x$, —$R^uS(O)_2 R^w$, —$R^uN(R^x)S(O)_2R^w$ or —$R^uN(R^x) R^uS(O)_2R^w$, wherein $R^u$ is direct bond or alkylene, $R^x$ is hydrogen or alkyl; WI is alkyl and J is O, S or $NR^x$.

In one embodiment, $Q^1$ is halo, hydroxy, alkyl, hydroxyalkyl, alkyloxycarbonyl, alkylsulfonyl or haloalkyl.

In one embodiment, the compounds provided herein have formula III:

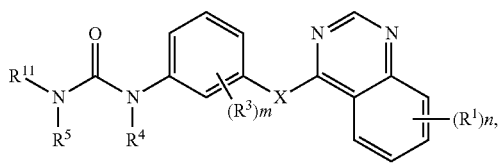

III or pharmaceutically acceptable salts, solvates or hydrates thereof, wherein m is an integer from 0 to 4 and wherein the other variables are as described elsewhere herein.

In one embodiment, the compounds provided herein have formula IV:

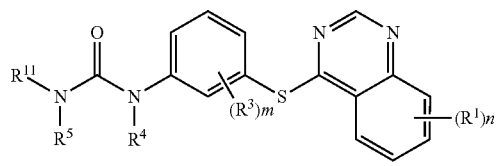

IV or pharmaceutically acceptable salts, solvates or hydrates thereof, wherein m is an integer from 0 to 4 and wherein the other variables are as described elsewhere herein.

In one embodiment, $R^{11}$ is optionally substituted aryl, optionally substituted heterocyclyl or optionally substituted heteroaryl, wherein the substituents, when present are selected from one or more $R^{10}$ groups, wherein each $R^{10}$ is independently selected from halo, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with 1, 2 or 3 groups selected from halo, cyano, haloalkyl, hydroxy, alkoxy, cycloalkyl, heterocyclyl, alkylcarbonyl and alkoxycarbonyl.

In one embodiment, $R^{11}$ is optionally substituted aryl, optionally substituted heterocyclyl or optionally substituted heteroaryl, wherein the substituents, when present, are selected from one or more $R^{10}$ groups, wherein each $R^{10}$ is independently selected from halo, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with 1, 2 or 3 groups selected from halo, cyano, haloalkyl, hydroxy, alkoxy, cycloalkyl, alkylcarbonyl and alkoxycarbonyl.

In another embodiment, $R^{11}$ is optionally substituted aryl, optionally substituted heterocyclyl or optionally substituted heteroaryl, wherein the substituents, when present, are selected from one or more $R^{10}$ groups, wherein each $R^{10}$ is independently selected from halo, alkyl, haloalkyl, alkoxy, haloalkoxy, cycloalkyl, alkoxyalkoxy, aryl, aralkyl, heterocyclyl, heterocyclylcarbonyl, alkoxycarbonyl, heteroaryl and heteroaralkyl where the alkyl group is optionally substituted with 1, 2 or 3 groups selected from halo, cyano, haloalkyl, hydroxy, alkoxy, cycloalkyl, heterocyclyl, alkylcarbonyl and alkoxycarbonyl and where the cycloalkyl, aryl and heteroaryl group is optionally substituted with 1, 2 or 3 groups selected from halo, cyano, alkyl, haloalkyl, hydroxy and alkoxy. In another embodiment, $R^{11}$ is optionally substituted aryl, optionally substituted heterocyclyl or optionally substituted heteroaryl, wherein the substituents, when present, are selected from one or more $R^{10}$ groups, wherein each $R^{10}$ is independently selected from halo, alkyl, haloalkyl, cycloalkyl, aryl, aralkyl, heterocyclyl, heteroaryl and heteroaralkyl where the alkyl group is optionally substituted with 1, 2 or 3 groups selected from halo, cyano, haloalkyl, and cycloalkyl, and where the cycloalkyl, aryl and heteroaryl group is optionally substituted with 1, 2 or 3 groups selected from $Q^1$. In another embodiment, $R^{11}$ is optionally substituted aryl, optionally substituted heterocyclyl or optionally substituted heteroaryl, wherein the substituents, when present, are selected from one or more $R^{10}$ groups, wherein each $R^{10}$ is independently selected from halo, alkyl, haloalkyl, cycloalkyl, aryl, aralkyl, heterocyclyl, heteroaryl and heteroaralkyl where the alkyl group is optionally substituted with 1, 2 or 3 groups selected from halo, cyano, haloalkyl, and cycloalkyl, and where the cycloalkyl, aryl and heteroaryl groups are optionally substituted with 1, 2 or 3 groups selected halo, cyano, alkyl and haloalkyl.

In one embodiment, $R^{11}$ is 5-12 membered optionally substituted heteroaryl having one or more heteroatoms, wherein the heteroatoms are each independently selected from nitrogen, sulfur and oxygen. In one embodiment, $R^{11}$ is 5-6 membered optionally substituted heteroaryl. In one embodiment, $R^{11}$ is 5-membered optionally substituted heteroaryl. In one embodiment, $R^{11}$ is pyrazole optionally substituted with one, two or three substitutents, each independently selected from $R^{10}$. In another embodiment, $R^{11}$ is isoxazole optionally substituted with one, two or three substituents, each independently selected from $R^{10}$.

In one embodiment, $R^{10}$ is independently selected from halo, haloalkyl, alkyl, cycloalkyl, aryl, heterocyclyl, and heteroaryl where the alkyl group is optionally substituted with 1 or 2 groups selected from halo, cyano, and cycloalkyl and where the cycloalkyl, aryl and heteroaryl is optionally substituted with 1 or 2 groups selected from $Q^1$. In another embodiment, $R^{10}$ is independently selected from halo, haloalkyl, alkyl, cycloalkyl, aryl, heterocyclyl, and heteroaryl where the alkyl group is optionally substituted with 1 or 2 groups selected from halo, cyano, and cycloalkyl and where the cycloalkyl, aryl and heteroaryl is optionally substituted with 1 or 2 groups selected from halo, cyano, alkyl and haloalkyl.

In one embodiment, $R^{10}$ is independently selected from halo, alkyl, haloalkyl, cycloalkyl, aryl, aralkyl, heterocyclyl, heterocyclylcarbonyl, alkoxycarbonyl, heteroaryl and heteroaralkyl where the alkyl group is optionally substituted with 1, 2 or 3 groups selected from halo, cyano, haloalkyl, hydroxy, alkoxy, cycloalkyl, heterocyclyl, alkylcarbonyl and alkoxycarbonyl.

In one embodiment, $R^{10}$ is independently selected from halo, haloalkyl, alkyl, cycloalkyl, aryl, aralkyl, heteroaryl and heteroaralkyl where the alkyl group is optionally substituted with 1 or 2 groups selected from halo, cyano, and cycloalkyl and where the cycloalkyl, aryl and heteroaryl is optionally substituted with 1 or 2 groups selected from $Q^1$. In another embodiment, $R^{10}$ is independently selected from halo, haloalkyl, alkyl, cycloalkyl, aryl, aralkyl, heteroaryl and heteroaralkyl where the alkyl group is optionally substituted with 1 or 2 groups selected from halo, cyano, and cycloalkyl and where the cycloalkyl, aryl and heteroaryl is optionally substituted with 1 or 2 groups selected from halo, cyano, alkyl and haloalkyl.

In one embodiment, each $R^{10}$ is independently selected from hydrogen, halo, alkyl, haloalkyl, cyanoalkyl, haloalkoxy, hydroxyalkyl, cycloalkyl, cycloalkylalkyl, alkoxy, alkoxyalkyl, alkoxyalkoxy, aryl, heterocyclyl, heterocyclylcarbonyl, alkoxycarbonyl, alkoxycarbonylalkyl, alkylcarbonylalkyl, heterocyclylalkyl and heteroaryl.

In one embodiment, one $R^{10}$ is alkyl or haloalkyl and the other $R^{10}$ is cycloalkyl, aryl or heteroaryl optionally substituted with 1, 2 or 3 groups selected from $Q^1$.

In one embodiment, $R^{10}$ is alkyl or haloalkyl.

In another embodiment, $R^{11}$ is optionally substituted aryl, optionally substituted heterocyclyl or optionally substituted heteroaryl, wherein the substituents, when present are selected from F, Cl, methyl, ethyl, n-propyl, —C(CH$_3$)$_3$, —CH(CH$_3$)$_2$, —C(CH$_3$)$_2$CN, —C(CH$_3$)$_2$CF$_3$, —CF(CH$_3$)$_2$, —CF$_2$(CH$_3$), —C(CH$_3$)(CH$_2$F)$_2$, —CF$_3$, phenyl, pyridinyl, cyclopropyl, cyclopentyl, cyclohexyl and

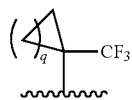

where q is an integer from 1-5 and where the phenyl, pyridinyl, cyclopropyl, cyclopentyl or cyclohexyl may be optionally substituted with 1 or 2 groups selected from halo, cyano, alkyl, haloalkyl and cyanoalkyl.

In another embodiment, $R^{11}$ is selected from a group consisting of:

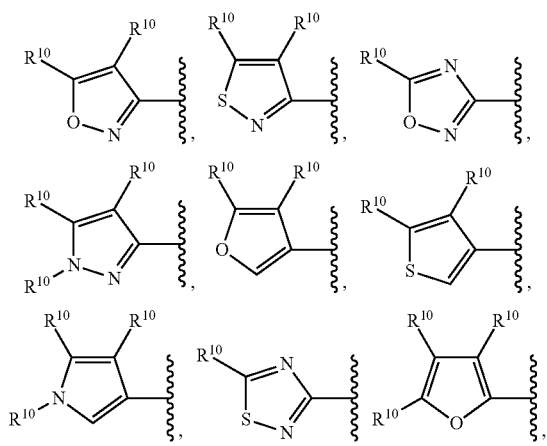

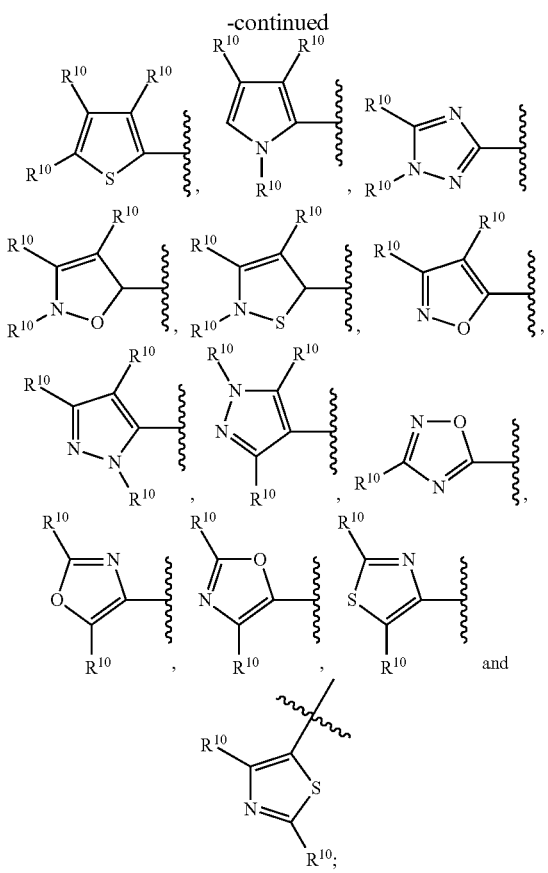

and each $R^{10}$ is independently selected from hydrogen, halo, haloalkyl, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with, in one embodiment, 1 to 5, in another embodiment, 1 or 2 groups selected from halo, cyano, hydroxy, alkoxy, cycloalkyl, heterocyclyl, alkylcarbonyl and alkoxycarbonyl. In one embodiment, alkyl, cycloalkyl, heterocyclyl and heteroaryl groups in $R^{10}$ are each independently optionally substituted with 1, 2 or 3 groups selected from halo, cyano, hydroxyl and alkoxy. In one embodiment, $R^{10}$ is C$_{3-5}$ alkyl optionally substituted with 1, 2 or 3 groups selected from halo, cyano, hydroxyl and alkoxy. In one embodiment, $R^{10}$ is C$_4$ alkyl optionally substituted with 1, 2 or 3 groups selected from halo, cyano, hydroxyl and alkoxy.

In one embodiment, $R^{11}$ is

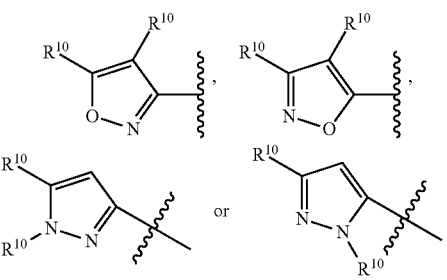

where $R^{10}$ is as described elsewhere herein. In one embodiment, $R^{10}$ is hydrogen, alkyl, hydroxyalkyl, cycloalkyl, haloalkyl, cyanoalkyl, alkoxyalkyl, aryl or heteroaryl. In one embodiment, $R^{10}$ is alkyl. In one embodiment, one $R^{10}$ is alkyl and the other $R^{10}$ is hydrogen. In one embodiment, one $R^{10}$ is haloalkyl and the other $R^{10}$ is hydrogen. In one embodiment, one $R^{10}$ is alkyl and the other $R^{10}$ is aryl. In one embodiment, $R^{10}$ is other than methyl. In one embodiment, $R^{10}$ is t-butyl.

In one embodiment, $R^{11}$ is

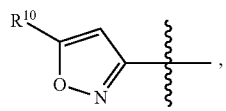

where $R^{10}$ is as described elsewhere herein. In one embodiment, $R^{10}$ is hydrogen, alkyl, hydroxyalkyl, cycloalkyl, haloalkyl, cyanoalkyl, alkoxyalkyl or aryl. In one embodiment, $R^{10}$ is $C(CH_3)_3$, $-CH(CH_3)_2$, $-C(CH_3)_2CN$, $-C(CH_3)_2CF_3$, $-CF(CH_3)_2$, $-CF_2(CH_3)$, $-C(CH_3)_2CH_2OH$, $-C(CH_3)(CH_2F)_2$, $-C(CH_3)_2CH_2OCH_3$, $CF_3$, phenyl, cyclopentyl or

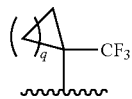

where q is an integer from 1-5.

In one embodiment, $R^{11}$ is

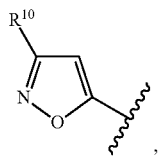

where $R^{10}$ is as described elsewhere herein. In one embodiment, $R^{10}$ is hydrogen, alkyl, hydroxyalkyl, cycloalkyl, haloalkyl, cyanoalkyl, alkoxyalkyl or aryl. In one embodiment, $R^{10}$ is $-C(CH_3)_3$, $-CH(CH_3)_2$, $-C(CH_3)_2CN$, $-C(CH_3)_2CF_3$, $-CF(CH_3)_2$, $-CF_2(CH_3)$, $-C(CH_3)_2CH_2OH$, $-C(CH_3)(CH_2F)_2$, $-C(CH_3)_2CH_2OCH_3$, $CF_3$, phenyl, cyclopentyl or

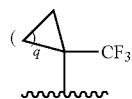

where q is an integer from 1-5.

In one embodiment, $R^{11}$ is

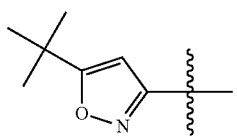

In one embodiment, $R^{11}$ is

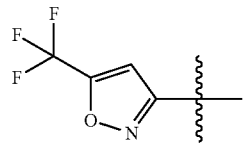

In one embodiment, $R^{11}$ is

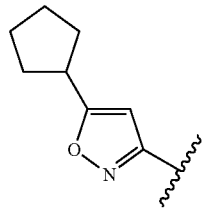

In one embodiment, $R^{11}$ is

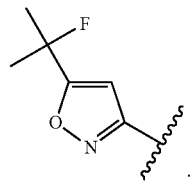

In one embodiment, $R^{11}$ is

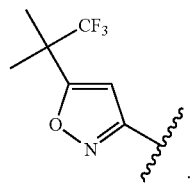 [SMILES: *c1cc(C(C)(C)C(F)(F)F)on1]

In one embodiment, $R^{11}$ is

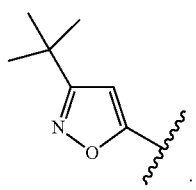 [SMILES: *c1cc(C(C)(C)C)no1]

In one embodiment, $R^{11}$ is

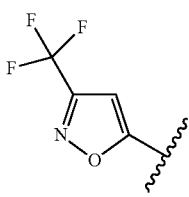

In one embodiment, $R^{11}$ is

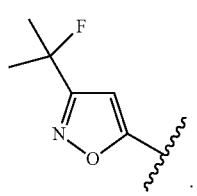 [SMILES: *c1cc(C(C)(C)F)no1]

In one embodiment, $R^{11}$ is

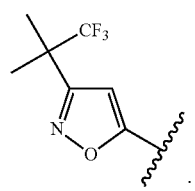 [SMILES: *c1cc(C(C)(C)C(F)(F)F)no1]

In one embodiment, the compounds provided herein have formula VA or VB:

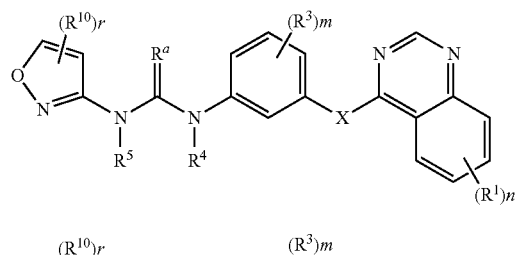

VA

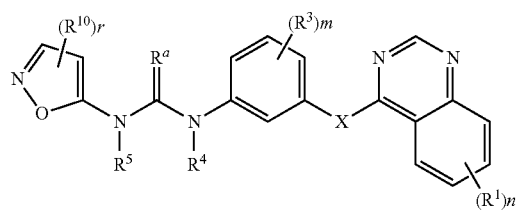

VB or pharmaceutically acceptable salts, solvates or hydrates thereof, wherein r is 0, 1 or 2 and the other variables are as described elsewhere herein. In one embodiment, $R^{10}$ is independently selected from halo, haloalkyl, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with 1 or 2 groups selected from halo, cyano, hydroxy, alkoxy, cycloalkyl, heterocyclyl, alkylcarbonyl and alkoxycarbonyl.

In one embodiment, the compounds provided herein have formula:

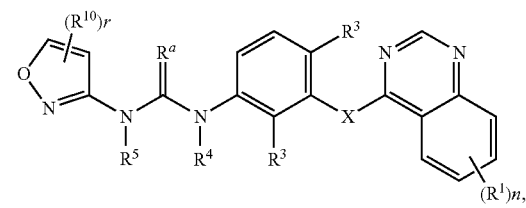

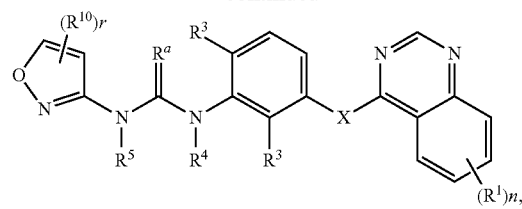

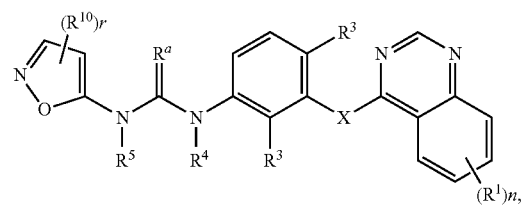

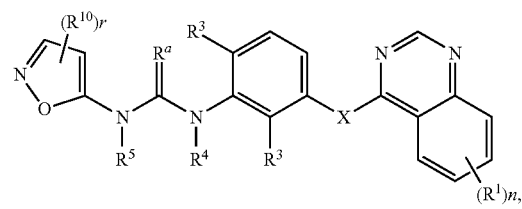

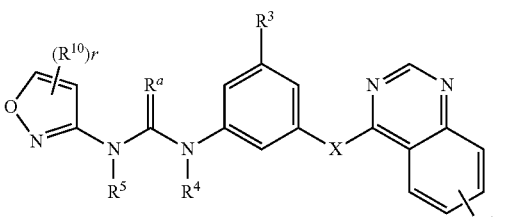

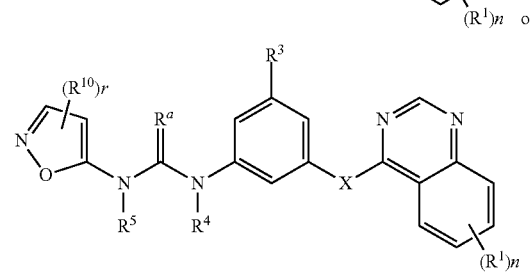

or pharmaceutically acceptable salts, solvates or hydrates thereof, wherein r is 0, 1 or 2 and the other variables are as described elsewhere herein. In one embodiment, $R^{10}$ is independently selected from halo, haloalkyl, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with 1 or 2 groups selected from halo, cyano, hydroxy, alkoxy, cycloalkyl, heterocyclyl, alkylcarbonyl and alkoxycarbonyl.

In one embodiment, the compounds provided herein have formula:

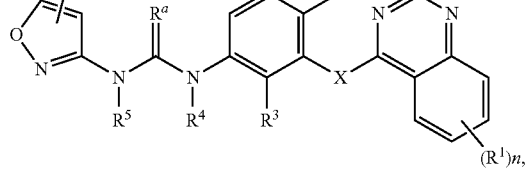

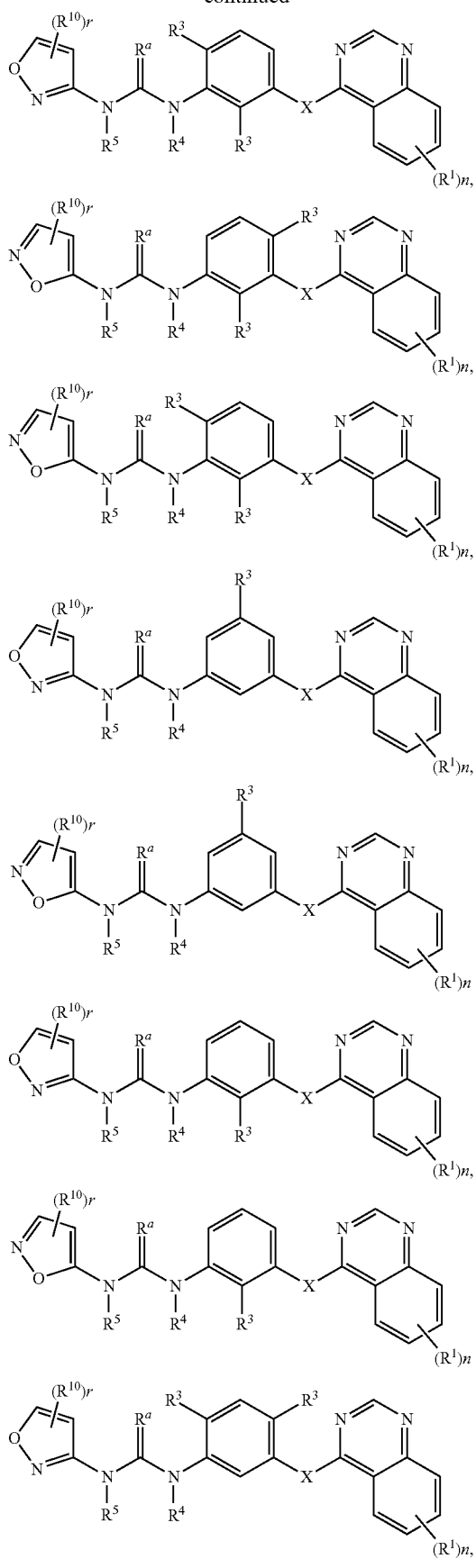

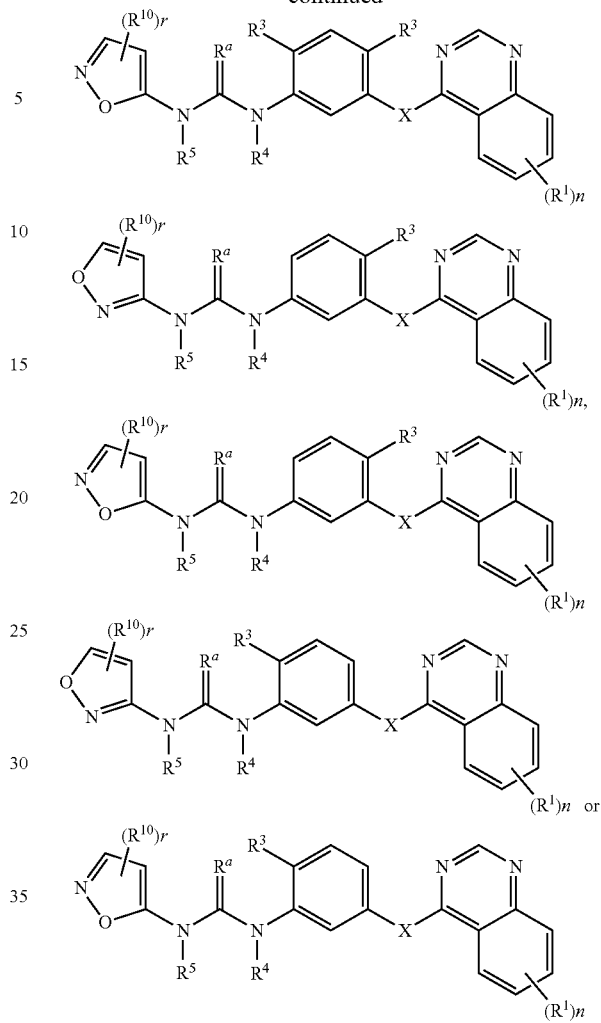

or pharmaceutically acceptable salts, solvates or hydrates thereof, wherein r is 0, 1 or 2 and the other variables are as described elsewhere herein. In one embodiment, $R^{10}$ is independently selected from halo, haloalkyl, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with 1 or 2 groups selected from halo, cyano, hydroxy, alkoxy, cycloalkyl, heterocyclyl, alkylcarbonyl and alkoxycarbonyl.

In one embodiment, the compounds provided herein have formula VI:

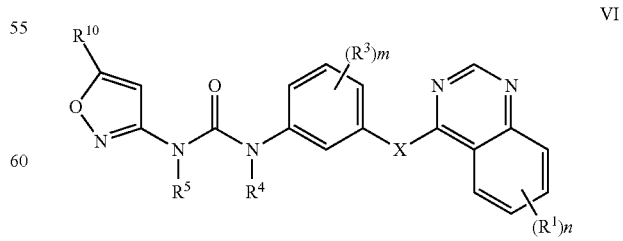

or pharmaceutically acceptable salts, solvates or hydrates thereof, wherein the variables are as described elsewhere herein.

In one embodiment, the compounds provided herein have formula VIa:

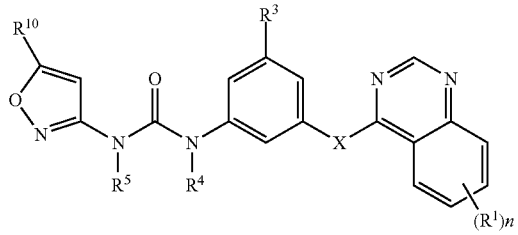

VIa or pharmaceutically acceptable salts, solvates or hydrates thereof, wherein the variables are as described elsewhere herein.

In one embodiment, the compounds provided herein have formula VIb:

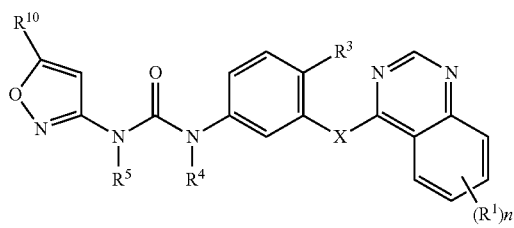

VIb or pharmaceutically acceptable salts, solvates or hydrates thereof, wherein the variables are as described elsewhere herein.

In one embodiment, the compounds provided herein have formula VIc:

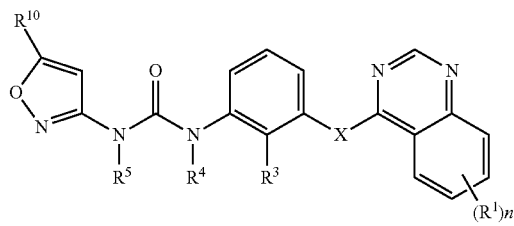

VIc or pharmaceutically acceptable salts, solvates or hydrates thereof, wherein the variables are as described elsewhere herein.

In one embodiment, the compounds provided herein have formula VId:

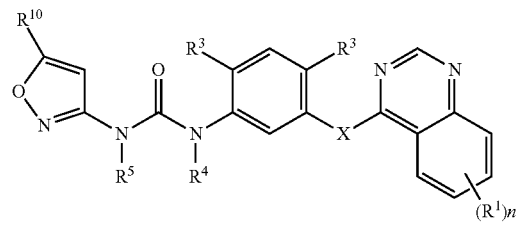

VId or pharmaceutically acceptable salts, solvates or hydrates thereof, wherein the variables are as described elsewhere herein.

In one embodiment, the compounds provided herein have formula VIe:

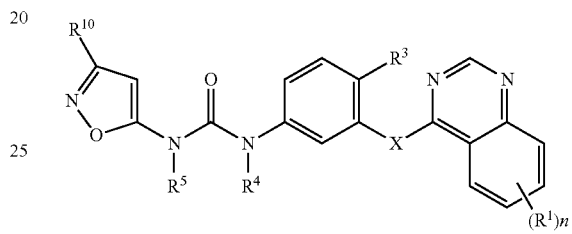

VIe or pharmaceutically acceptable salts, solvates or hydrates thereof, wherein the variables are as described elsewhere herein.

In one embodiment, the compounds provided herein have formula VIf:

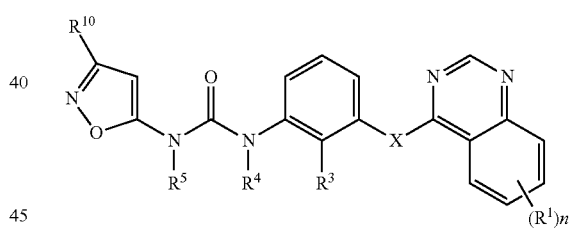

VIf or pharmaceutically acceptable salts, solvates or hydrates thereof, wherein the variables are as described elsewhere herein.

In one embodiment, the compounds provided herein have formula VIg:

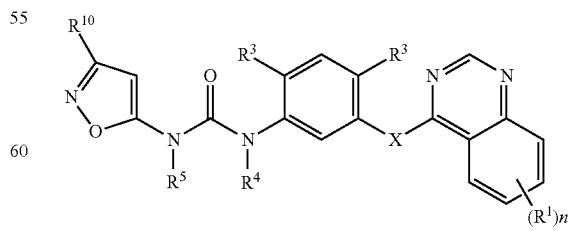

VIg or pharmaceutically acceptable salts, solvates or hydrates thereof, wherein the variables are as described elsewhere herein.

In one embodiment, the compounds provided herein have formula VIIa:

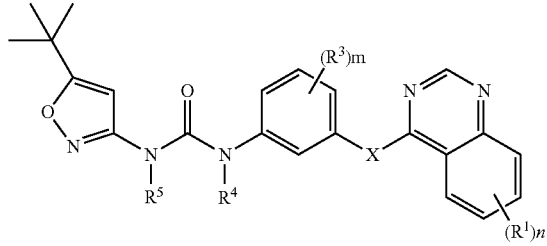

VIIa or pharmaceutically acceptable salts, solvates or hydrates thereof, wherein the variables are as described elsewhere herein.

In one embodiment, the compounds provided herein have formula VIIb:

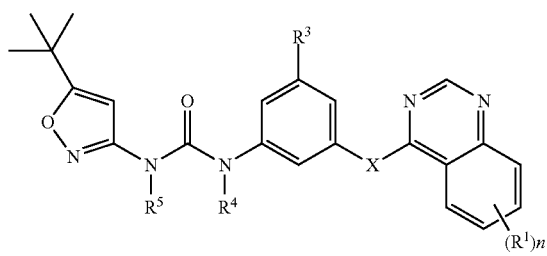

VIIb or pharmaceutically acceptable salts, solvates or hydrates thereof, wherein the variables are as described elsewhere herein.

In one embodiment, $R^{11}$ is

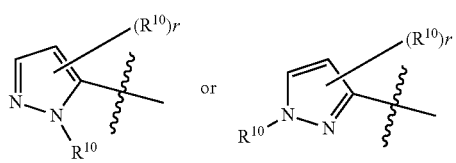

where each $R^{10}$ is independently selected from halo, alkyl, haloalkyl, hydroxyalkyl, cyanoalkyl, alkoxyalkyl, aryl, haloaryl, alkylaryl, heteroaryl and alkoxycarbonylalkyl, and r is 1 or 2. In one embodiment, r is 1, and the $R^{10}$ on the N atom of the pyrazole is phenyl optionally substituted with halo, alkyl, haloalkyl, hydroxyalkyl, alkoxyalkyl, cyanoalkyl, alkoxy or hydroxy and the other $R^{10}$ is selected from hydrogen, halo, alkyl, haloalkyl, hydroxyalkyl, cyanoalkyl and alkoxyalkyl. In one embodiment, r is 1 and the $R^{10}$ on the N atom of the pyrazole is 5 or 6-membered heteroaryl and the other $R^{10}$ is selected from hydrogen, halo, alkyl, haloalkyl, hydroxyalkyl, cyanoalkyl and alkoxyalkyl. In one embodiment, r is 1 and the $R^{10}$ on the N atom of the pyrazole is selected from pyridinyl, pyrimidinyl, pyrazinyl, quinolyl, isoquinolinyl, quinazolinyl, thiazolyl, thiadiazolyl, imidazolyl, thienyl and furanyl and the other $R^{10}$ is selected from hydrogen, halo, alkyl, haloalkyl, hydroxyalkyl, cyanoalkyl and alkoxyalkyl. In one embodiment, each $R^{10}$ is independently selected from hydrogen, tert-butyl, methyl, isopropyl or phenyl; and r is 1.

In one embodiment, $R^{11}$ is

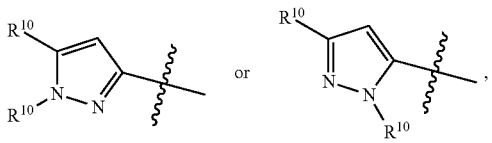

where $R^{10}$ is as defined elsewhere herein. In one embodiment, $R^{10}$ on the N atom of the pyrazole is phenyl optionally substituted with halo, alkyl, haloalkyl, hydroxyalkyl, alkoxyalkyl, cyanoalkyl, alkoxy or hydroxy and the other $R^{10}$ on the carbon atom of the pyrazole is selected from hydrogen, halo, alkyl, haloalkyl, hydroxyalkyl, cyanoalkyl, alkoxyalkyl. In one embodiment, $R^{10}$ on the N atom of the pyrazole is heteroaryl optionally substituted with halo, alkyl, haloalkyl, hydroxyalkyl, alkoxyalkyl, cyanoalkyl, alkoxy or hydroxy and the other $R^{10}$ on the carbon atom of the pyrazole is selected from hydrogen, halo, alkyl, haloalkyl, hydroxyalkyl, cyanoalkyl, alkoxyalkyl.

In one embodiment, each $R^{10}$ of the pyrazole is independently selected from halo, alkyl, haloalkyl, hydroxyalkyl, alkoxyalkyl, cyanoalkyl, cycloalkyl, heterocyclyl, aryl, aralkyl, heteroaryl and heteroaralkyl wherein each cycloalkyl, aryl, aralkyl, heteroaryl and heteroaralkyl is optionally substituted with halo, cyano, alkyl, haloalkyl, hydroxyalkyl, alkoxyalkyl, cyanoalkyl and alkoxyalkyl. In another embodiment, $R^{10}$ on the N atom of the pyrazole is independently selected from halo, alkyl, haloalkyl, hydroxyalkyl, alkoxyalkyl, cyanoalkyl, cycloalkyl, heterocyclyl, aryl, aralkyl, heteroaryl and heteroaralkyl wherein each cycloalkyl, aryl, aralkyl, heteroaryl or heteroaralkyl is optionally substituted with halo, cyano, alkyl, haloalkyl, hydroxyalkyl, alkoxyalkyl, cyanoalkyl and alkoxyalkyl and $R^{10}$ on the C atom of the pyrazole is independently selected from halo, alkyl, haloalkyl, cyanoalkyl and cycloalkyl.

In one embodiment, $R^{11}$ is

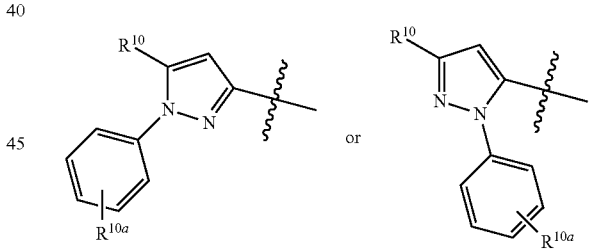

where $R^{10}$ is hydrogen, halo, alkyl, haloalkyl, hydroxyalkyl, cyanoalkyl or alkoxyalkyl; and $R^{10a}$ is hydrogen, halo or alkyl.

In one embodiment, $R^{11}$ is

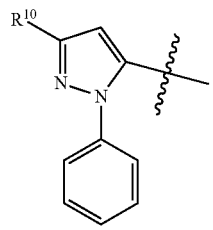

where $R^{10}$ is as defined elsewhere herein.

In one embodiment, $R^{11}$ is

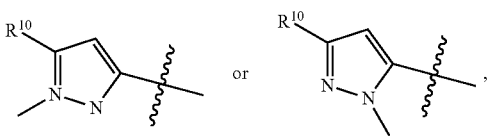

where $R^{10}$ is hydrogen, halo, alkyl, haloalkyl, hydroxyalkyl, cyanoalkyl or alkoxyalkyl.

In one embodiment, $R^{11}$ is

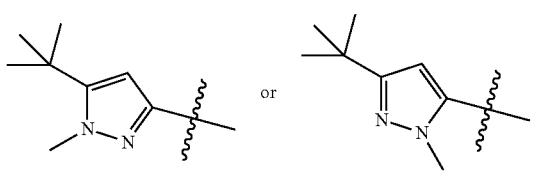

In one embodiment, $R^{11}$ is

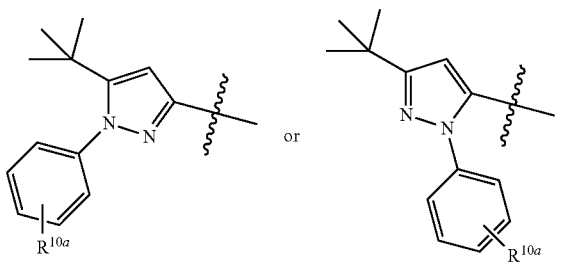

where $R^{10a}$ is hydrogen, halo, haloalkyl, cyano, alkyl, alkoxy, aminoalkoxy, haloalkoxy or alkylsulfonyl.

In one embodiment, the compounds provided herein have formula VIIIA or VIIIB:

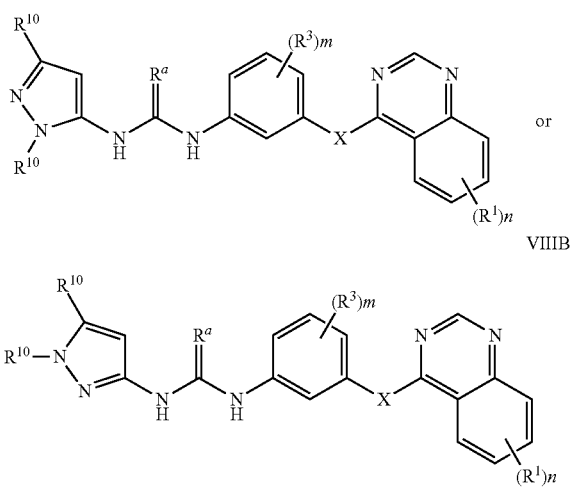

VIIIA

VIIIB or pharmaceutically acceptable salts, solvates or hydrates thereof, wherein the variables are as described elsewhere herein.

In one embodiment, the compounds provided herein have formula VIIIC or VIIID:

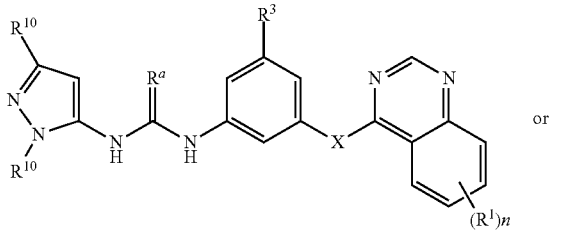

VIIIC

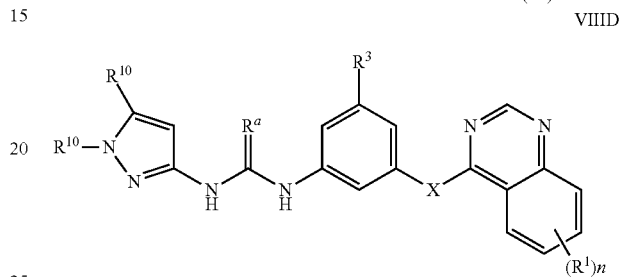

VIIID or pharmaceutically acceptable salts, solvates or hydrates thereof, wherein the variables are as described elsewhere herein.

In one embodiment, $R^{11}$ is

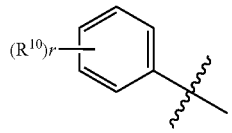

where each $R^{10}$ is independently selected from halo, alkyl, haloalkyl, hydroxyalkyl, haloalkoxy, cycloalkyl, alkoxyalkyl, alkoxyalkoxy, aryl, heterocyclylalkyl and heterocyclylcarbonyl; and r is an integer from 0 to 3. In one embodiment, r is 1, 2 or 3. In one embodiment, r is 1 or 2. In one embodiment, r is 1. In one embodiment, r is 0.

In one embodiment, $R^{11}$ is

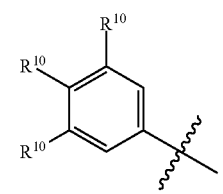

where each $R^{10}$ is absent or is independently selected from halo, alkyl, haloalkyl, hydroxyalkyl, haloalkoxy, cycloalkyl, alkoxyalkyl, alkoxyalkoxy, aryl, heterocyclylalkyl and heterocyclylcarbonyl. In one embodiment, at least one $R^{10}$ is absent and the other two $R^{10}$ are each independently selected from —F, Cl, $C(CH_3)_3$, —$CH(CH_3)_2$, —$C(CH_3)_2CN$, —$C(CH_3)_2CF_3$, —$CF(CH_3)_2$, —$CF_2(CH_3)$, —$C(CH_3)(CH_2F)_2$, —$C(CH_3)_2CH_2OCH_3$, —$C(CH_3)_2CH_2OH$, $CF_3$, —$OCH_3$, —$O(CH_2)_2OCH_3$, —$O(CH_2)_2CH(CH_3)_2OCH_3$, morpholinomethyl, phenyl, cyclopentyl, or

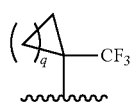

where q is an integer from 1-5.

In one embodiment, $R^{11}$ is

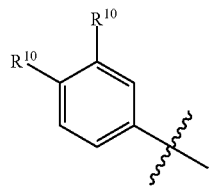

where each $R^{10}$ is independently selected from halo, alkyl, haloalkyl, hydroxyalkyl, haloalkoxy, cycloalkyl, alkoxyalkyl, alkoxyalkoxy, aryl, heterocyclylalkyl and heterocyclylcarbonyl. In one embodiment, each $R^{10}$ is —F, Cl, $C(CH_3)_3$, —$CH(CH_3)_2$, —$C(CH_3)_2CN$, —$C(CH_3)_2CF_3$, —$CF(CH_3)_2$, —$CF_2(CH_3)$, —$C(CH_3)(CH_2F)_2$, —$C(CH_3)_2CH_2OCH_3$, —$C(CH_3)_2CH_2OH$, $CF_3$, —$OCH_3$, —$O(CH_2)_2OCH_3$, —$O(CH_2)_2CH(CH_3)_2OCH_3$, morpholinomethyl, phenyl, cyclopentyl or

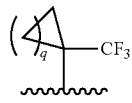

where q is an integer from 1-5.

In one embodiment, $R^{11}$ is

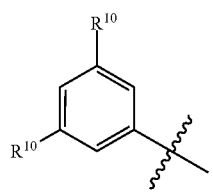

where each $R^{10}$ is independently selected from halo, alkyl, haloalkyl, hydroxyalkyl, haloalkoxy, cycloalkyl, alkoxyalkyl, alkoxyalkoxy, aryl, heterocyclylalkyl and heterocyclylcarbonyl. In one embodiment, $R^{10}$ is —F, Cl, $C(CH_3)_3$, —$CH(CH_3)_2$, —$C(CH_3)_2CN$, —$C(CH_3)_2CF_3$, —$CF(CH_3)_2$, —$CF_2(CH_3)$, —$C(CH_3)(CH_2F)_2$, —$C(CH_3)_2CH_2OCH_3$, —$C(CH_3)_2CH_2OH$, $CF_3$, —$OCH_3$, —$O(CH_2)_2OCH_3$, —$O(CH_2)_2CH(CH_3)_2OCH_3$, morpholinomethyl, phenyl, cyclopentyl or

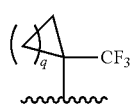

where q is an integer from 1-5.

In one embodiment, $R^{11}$ is

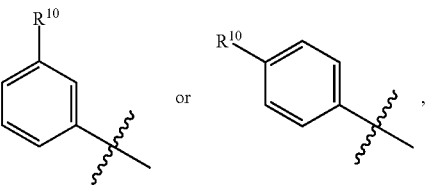

where $R^{10}$ is as defined elsewhere herein. In one embodiment, $R^{10}$ is —F, Cl, $C(CH_3)_3$, —$CH(CH_3)_2$, —$C(CH_3)_2CN$, —$C(CH_3)_2CF_3$, —$CF(CH_3)_2$, —$CF_2(CH_3)$, —$C(CH_3)(CH_2F)_2$, —$C(CH_3)_2CH_2OCH_3$, —$C(CH_3)_2CH_2OH$, $CF_3$, —$OCH_3$, —$O(CH_2)_2OCH_3$, —$O(CH_2)_2CH(CH_3)_2OCH_3$, morpholinomethyl, phenyl, cyclopentyl or

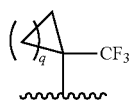

where q is an integer from 1-5.

In one embodiment, the compounds provided herein have formula IX:

IX

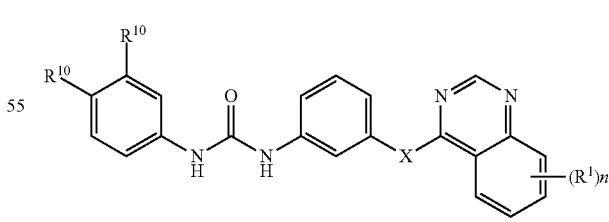

or pharmaceutically acceptable salts, solvates or hydrates thereof, wherein the variables are as described elsewhere herein. In one embodiment, r is 0, 1 or 2. In one embodiment, X is $S(O)_t$ where t is an integer from 0 to 2. In one embodiment, X is S. In one embodiment, X is O.

In one embodiment, compounds provided have formula IXa:

IXa or pharmaceutically acceptable salts, solvates or hydrates thereof, wherein the variables are as described elsewhere herein. In one embodiment, one $R^{10}$ is —$C(CH_3)_3$, —$CH(CH_3)_2$, —$C(CH_3)_2CN$, —$C(CH_3)_2CF_3$, —$CF(CH_3)_2$, —$CF_2(CH_3)$, —$C(CH_3)_2CH_2OH$, —$C(CH_3)(CH_2F)_2$, —$C(CH_3)_2CH_2OCH_3$, $CF_3$, phenyl, cyclopentyl or

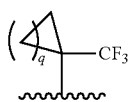

where q is an integer from 1-5 and the other $R^{10}$ is alkoxy, haloalkoxy, alkoxyalkoxy or aminoalkoxy.

In one embodiment, the compounds provided herein have formula X:

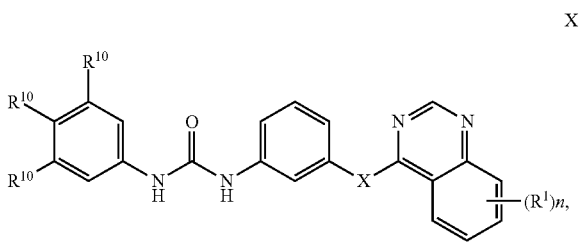

or pharmaceutically acceptable salts, solvates or hydrates thereof, wherein the variables are as described elsewhere herein.

In one embodiment, the compounds provided herein have formula Xa:

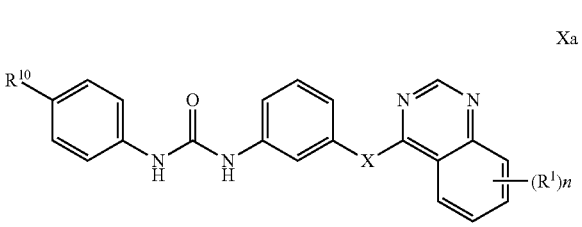

or pharmaceutically acceptable salts, solvates or hydrates thereof, wherein the variables are as described elsewhere herein.

In one embodiment, the compounds provided herein have formula XI:

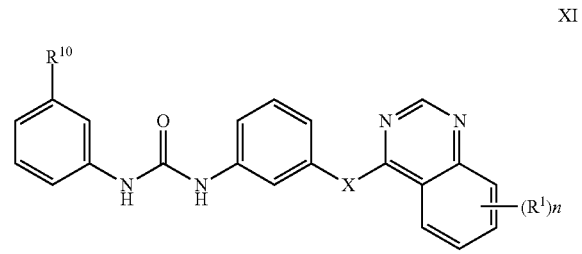

or pharmaceutically acceptable salts, solvates or hydrates thereof, wherein the variables are as described elsewhere herein.

In one embodiment, each $R^1$ is selected as follows:
i) each $R^1$ is absent or is independently selected from the group consisting of halo, nitro, amino, alkyl, alkenyl, alkynyl, cycloalkyl, cycloalkylalkyl, heterocyclyl, heterocyclylalkyl, aryl, aralkyl, heteroaryl, heteroaralkyl, —$R^6OR^7$, —$R^6SR^7$, —$R^6N(R^7)_2$, —$R^6OR^9OR^7$, —$R^6OR^9SR^7$, —$R^6SR^9OR^7$, —$R^6SR^9SR^7$, —$R^6OR^9N(R^7)_2$, —$R^6SR^9N(R^7)_2$, —$R^6CN$, —$R^6C(O)R^7$, —$R^6C(O)OR^7$, —$R^6C(O)OR^9OR^7$, —$R^6C(O)N(R^7)_2$, —$R^6OC(O)N(R^7)_2$ and —$R^6N(R^7)C(O)R^8$; or ii) any two adjacent $R^1$ groups form an alkylenedioxy group, wherein $R^1$, $R^6$, $R^7$ and $R^9$ groups are optionally substituted with one, two or three $Q^1$ groups.

In one embodiment, each $R^1$ is selected as follows:
i) each $R^1$ is absent or is independently selected from the group consisting of halo, nitro, amino, alkyl, alkenyl, alkynyl, cycloalkyl, cycloalkylalkyl, heterocyclyl, heterocyclylalkyl, aryl, aralkyl, heteroaryl, heteroaralkyl, —$R^6OR^7$, —$R^6SR^7$, —$R^6N(R^7)_2$, $R^6OR^9OR^7$, —$R^6OR^9SR^7$, —$R^6SR^9OR^7$, —$R^6SR^9SR^7$, —$R^6CN$, —$R^6C(O)N(R^7)_2$, —$R^6OC(O)N(R^7)_2$ and —$R^6N(R^7)C(O)R^8$; or ii) any two adjacent $R^1$ groups form an alkylenedioxy group, wherein $R^1$, $R^6$, $R^7$ and $R^9$ groups are optionally substituted with one, two or three $Q^1$ groups.

In one embodiment, each $R^1$ is selected as follows:
i) each $R^1$ is absent or is independently selected from the group consisting of halo, nitro, amino, alkyl, cycloalkylalkyl, heterocyclylalkyl, aralkyl, heteroaryl, heteroaralkyl, cycloalkylcarbonylamino, —$R^6OR^7$, —$R^6$ $OR^9$ $OR^7$ and —$R^6$ $OR^9N(R^7)_2$, or ii) any two adjacent $R^1$ groups form an alkylenedioxy group;

each $R^6$ is independently a direct bond, alkylene chain or alkenylene chain;

each $R^7$ is independently selected from (i) or (ii) below:
(i) each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two $R^7$ groups together with the N atom to which they are attached form a heterocyclyl or heteroaryl;

each $R^9$ is independently an alkylene chain or an alkenylene chain, wherein $R^1$, $R^6$, $R^7$ and $R^9$ groups are optionally substituted with one, two or three $Q^1$ groups, wherein each $Q^1$ is independently haloalkyl, alkyl, —$R''OR^x$, —$R''O$-$R''OR^x$, —$R''C(J)OR^x$, —$R''S(O)_2R^w$, —$R''N(R^x)S(O)_2R^w$ or —$R''N(R^x) R''S(O)_2R^w$, wherein $R''$ is direct bond or alkylene, $R^x$ is hydrogen or alkyl; $R^w$ is alkyl and J is O, S or $NR^x$.

In one embodiment, each $R^1$ is absent or is independently selected from the group consisting of halo, amino, alkyl, heteroaryl, alkoxy, hydroxy, alkoxyalkoxy and cycloalkylcarbonylamino, wherein each $R^1$ is optionally substituted with one, two or three $Q^1$ groups, wherein each $Q^1$ is independently haloalkyl, alkyl, —$R''OR^x$, —$R''OR''OR^x$, —$R''C(J)OR^x$, —$R''S(O)_2R^w$, —$R''N(R^x)S(O)_2R^w$ or —$R''N(R^x) R''S(O)_2R^w$, wherein $R''$ is direct bond or alkylene, $R^x$ is hydrogen or alkyl; $R^w$ is alkyl and J is O, S or $NR^x$.

In one embodiment, each $R^1$ is absent or is independently selected from the group consisting of —$R^6OR^7$, —$R^6SR^7$, —$R^6N(R^7)_2$, —$R^6OR^9OR^7$, —$R^6OR^9SR^7$, —$R^6SR^9OR^7$, —$R^6SR^9SR^7$, —$R^6OR^9N(R')_2$, —$R^6SR^9N(R^7)_2$, —$R^6CN$, —$R^6C(O)R^7$, —$R^6C(O)OR^7$, —$R^6C(O)OR^9OR^7$, —$R^6C(O)N(R^7)_2$, —$R^6OC(O)N(R^7)_2$ and —$R^6N(R^7)C(O)R^8$;

each $R^6$ is independently a direct bond, alkylene chain or alkenylene chain;

each $R^7$ is independently selected from (i) or (ii) below:
(i) each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two $R^7$ groups together with the N atom to which they are attached form a heterocyclyl or heteroaryl; and each $R^9$ is independently an alkylene chain or an alkenylene chain;
wherein $R^1$, $R^6$, $R^7$ and $R^9$ groups are optionally substituted with one, two or three $Q^1$ groups.

In one embodiment, each $R^1$ is selected from the group consisting of —$R^6OR^7$, —$R^6OR^9OR^7$ and —$R^6OR^9N(R^7)_2$;

each $R^6$ is independently a direct bond, alkylene chain or alkenylene chain;

each $R^7$ is independently selected from (i) or (ii) below:
(i) each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or
(ii) two $R^7$ groups together with the N atom to which they are attached form a heterocyclyl or heteroaryl;

each $R^9$ is independently an alkylene chain or an alkenylene chain, wherein each $R^1$, $R^6$, $R^7$ and $R^9$ groups are optionally substituted with one, two or three $Q^1$ groups.

In one embodiment, n is 2, and each $R^1$ is independently —$R^6OR^7$ or —$R^6OR^9OR^7$;

each $R^6$ is independently a direct bond, alkylene chain or alkenylene chain;

each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or each $R^9$ is independently an alkylene chain or an alkenylene chain, wherein each $R^1$, $R^6$, $R^7$ and $R^9$ groups are optionally substituted with one, two or three $Q^1$ groups.

In one embodiment, n is 2, one $R^1$ is —$R^6OR^7$ or —$R^6OR^9OR^7$ and the other $R^1$ is heterocylylalkoxy;

each $R^6$ is independently a direct bond, alkylene chain or alkenylene chain;

each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or each $R^9$ is independently an alkylene chain or an alkenylene chain, wherein each $R^1$, $R^6$, $R^7$ and $R^9$ groups are optionally substituted with one, two or three $Q^1$ groups.

In one embodiment, each $R^1$ is absent or is independently selected from the group consisting of fluoro, amino, methyl, methoxy, ethoxy, methoxyethoxy, ethoxyethoxy, cyclopropylcarbonylamino, furyl, and hydroxy, wherein furyl is substituted with —$R^uNH R^uS(O)_2R^w$, wherein $R^u$ is methylene or ethylene and $R^w$ is methyl.

In one embodiment, two adjacent $R^1$ groups form an alkylenedioxy group. In one embodiment, two adjacent $R^1$ groups form an ethylenedioxy group.

In one embodiment, each $R^1$ is independently where each K is independently a direct bond, alkylene, alkenylene or alkynylene;
A is N or $CR^{16}$;
Y is O, —S, —S(O), —S(O)$_2$, —N($R^{14}$), —C(H)$R^{15}$, or —C(O);
p is an integer from 0 to 2;
$R^{14}$ is hydrogen, alkyl, haloalkyl, hydroxy($C_2$-$C_6$)alkyl, cycloalkyl, heteroaryl, heteroarylalkyl, aryl, arylalkyl, S(O)$_t$ $R^{13}$, —C(O)$R^{12}$, —C(O)O$R^{12}$, —C(O)N($R^{12}$)$_2$, or —C(O)S$R^{12}$;

$R^{15}$ is hydrogen, halo, nitro, cyano, alkyl, haloalkyl, hydroxyalkyl, cycloalkyl, heteroaryl, heteroarylalkyl, aryl, arylalkyl, —O$R^{12}$, —S$R^{12}$, —N($R^{12}$)$_2$, —S(O)$_t R^{13}$, —C(O)$R^{12}$, —C(O)O$R^{12}$, —C(O)N($R^{12}$)$_2$, —C(O)S$R^{12}$, or —N($R^{12}$)S(O)$_t R^{13}$;

$R^{16}$ is hydrogen or alkyl;
t is 1 or 2;

each $R^{12}$ is independently selected from a group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl;

each $R^{13}$ is independently selected from a group consisting of alkyl, alkenyl, alkynyl, cycloalkyl, cycloalkylalkyl, aryl, aralkyl, heterocyclyl, heterocyclylalkyl, heteroaryl and heteroaralkyl; and each K is optionally substituted with one, two or three hydroxy or alkyl groups.

In one embodiment, each $R^1$ is independently where K is a direct bond or alkylene, optionally substituted with one or two hydroxy groups;
A is N or CH;
Y is —O, —S(O)$_2$, —N($R^{14}$) or —C(H)$R^{15}$;
p is an integer from 0 to 2;
$R^{14}$ is hydrogen, alkyl, haloalkyl, hydroxy($C_2$-$C_6$)alkyl or S(O)$_t R^{13}$;
$R^{15}$ is hydrogen, halo, alkyl, hydroxyalkyl or —O$R^{12}$;
t is 1 or 2;
$R^{12}$ is hydrogen or alkyl; and
$R^{13}$ is alkyl.

In certain embodiments, K is ethylene or propylene, optionally substituted with hydroxy. In one embodiment, K is a direct bond.

In one embodiment, $R^{13}$ is methyl.

In certain embodiments, $R^{14}$ is —H, —OH, —CH$_3$, —CH$_2$CF$_3$, —CH$_2$CHF$_2$, —CH$_2$CH$_2$OH or S(O)$_2$CH$_3$.

In certain embodiments, $R^{15}$ is —H, —OH, —CH$_3$, CH$_2$OH or —CH$_2$CH$_2$OH.

In one embodiment, p is 0 or 1. In one embodiment, p is 0. In one embodiment, p is 1.

In another aspect, provided herein is a compound of formula XII:

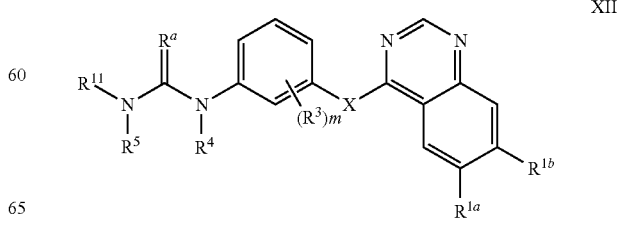

or a pharmaceutically acceptable salt, solvate or hydrate thereof, wherein $R^a$ is O or S;

X is O or S;

$R^{1a}$ and $R^{1b}$ are each independently selected from the group consisting of —$R^6OR^7$, —$R^6SR^7$, —$R^6N(R^7)_2$, —$R^6OR^9OR^7$, —$R^6OR^9SR^7$, —$R^6SR^9OR^7$, —$R^6SR^9SR^7$, —$R^6OR^9N(R^7)_2$, —$R^6SR^9N(R^7)_2$, —$R^6CN$, —$R^6C(O)R^7$, —$R^6C(O)OR^7$, —$R^6C(O)OR^9OR^7$, —$R^6C(O)N(R^7)_2$, —$R^6OC(O)N(R^7)_2$ and —$R^6N(R^7)C(O)R^8$;

each $R^6$ is a direct bond;

each $R^7$ is independently selected from (i) or (ii) below:

(i) each $R^7$ is selected from the group consisting of hydrogen, alkyl, alkenyl, alkynyl, cycloalkyl, cycloalkylalkyl, aryl, aralkyl, heterocyclyl, heterocyclylalkyl, heteroaryl and heteroaralkyl, or (ii) two $R^7$ groups together with the N atom to which they are attached form a heterocyclyl or heteroaryl;

each $R^9$ is independently an alkylene chain or an alkenylene chain;

wherein $R^1$, $R^6$, $R^7$ and $R^9$ groups are optionally substituted with one, two or three $Q^1$ groups; and the other variables are as defined elsewhere herein.

In another aspect, provided herein is a compound of formula XII:

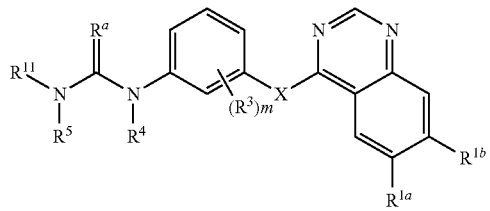

XII or a pharmaceutically acceptable salt, solvate or hydrate thereof, wherein $R^a$ is O or S;

X is O or S;

$R^{1a}$ and $R^{1b}$ are selected as follows:

i) $R^{1a}$ and $R^{1b}$ are each independently selected from hydrogen, halo, amino, alkyl, alkoxy, hydroxy, heteroaryl, alkoxyalkyl, cycloalkylcarbonylamino and a group of formula:

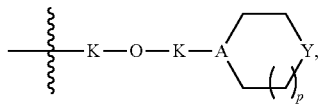

where each K is independently a direct bond or alkylene;

A is N or $CR^{16}$;

Y is —O, —S, —S(O), —S(O)$_2$, —N($R^{14}$), —C(H)$R^{15}$, or —C(O);

p is an integer from 0 to 2;

$R^{14}$ is hydrogen, alkyl, haloalkyl, hydroxy($C_2$-$C_6$)alkyl, cycloalkyl, heteroarylalkyl, arylalkyl, S(O)$_t$$R^{13}$ or —C(O)$R^{12}$;

$R^{15}$ is hydrogen, halo, alkyl, hydroxyalkyl or —$OR^{12}$;

$R^{16}$ is hydrogen or alkyl;

t is 1 or 2;

each $R^{12}$ is independently selected from a group consisting of hydrogen or alkyl;

$R^{13}$ is alkyl;

each K is optionally substituted with one, two or three hydroxy or alkyl groups; or ii) $R^{1a}$ and $R^{1b}$ groups form an alkylenedioxy group;

each $R^{1a}$ and $R^{1b}$ is independently optionally substituted with one or two $Q^1$ groups selected from haloalkyl, alkyl, —$R^uOR^x$, —$R^uC(J)OR^x$, —$R^uS(O)_2R^w$, —$R^uN(R^x)S(O)_2R^w$ and —$R^uN(R^x)R^uS(O)_2R^w$, wherein $R^u$ is direct bond or alkylene, $R^x$ is hydrogen or alkyl; $R^w$ is alkyl and J is O, S or $NR^x$; and the other variables are as defined elsewhere herein.

In one embodiment, at least one of $R^{1a}$ or $R^{1b}$ is other than hydrogen. In one embodiment, A is CH. In one embodiment, p is 0 and A is CH.

In one embodiment, $R^{1b}$ is hydrogen and $R^{1a}$ is heteroaryl group substituted with —$R^uN(R^x)R^uS(O)_2R^w$, wherein $R^u$ is direct bond or alkylene, $R^x$ is hydrogen or alkyl; $R^w$ is alkyl. In one embodiment, $R^{1b}$ is hydrogen and $R^{1a}$ is furyl substituted with —$R^uN(R^x)R^uS(O)_2R^w$, wherein $R^u$ is methylene or ethylene, $R^x$ is hydrogen and $R^w$ is methyl.

In one embodiment, one of $R^{1a}$ and $R^{1b}$ is —OR' where $R^7$ is alkyl, haloalkyl, hydroxyalkyl, cyanoalkyl, alkenyl, alkynyl, cycloalkyl or cycloalkylalkyl; and the other of $R^{1a}$ and $R^{1b}$ is a group of formula

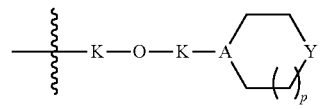

where each K is independently a direct bond or alkylene;

A is N or $CR^{L6}$;

Y is —O, —S, —S(O), —S(O)$_2$, —N($R^{14}$), —C(H)$R^{15}$, or —C(O);

p is an integer from 0 to 2;

$R^{14}$ is hydrogen, alkyl, haloalkyl, hydroxyalkyl, cycloalkyl, heteroarylalkyl, arylalkyl, S(O)$_t$$R^{13}$ or —C(O)$R^{12}$;

$R^{15}$ is hydrogen, halo, alkyl, hydroxyalkyl or —$OR^{12}$;

$R^{16}$ is hydrogen or alkyl;

t is 1 or 2;

each $R^{12}$ is independently selected from a group consisting of hydrogen or alkyl;

$R^{13}$ is alkyl;

each K is optionally substituted with one, two or three hydroxy or alkyl groups; and each $R^{1a}$ and $R^{1b}$ is independently optionally substituted with one or two $Q^1$ groups described elsewhere herein.

In one embodiment, $R^{1a}$ is —$OR^7$ where $R^7$ is alkyl, haloalkyl, hydroxyalkyl, cyanoalkyl, alkenyl, alkynyl, cycloalkyl or cycloalkylalkyl; and $R^{1b}$ is a group of formula

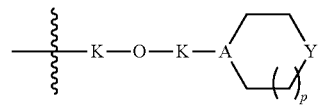

where each K is independently a direct bond or alkylene;

A is N or $CR^{16}$;

Y is —O, —S, —S(O), —S(O)$_2$, —N($R^{14}$), —C(H)$R^{15}$, or —C(O);

p is an integer from 0 to 2;

$R^{14}$ is hydrogen, alkyl, haloalkyl, hydroxyalkyl, cycloalkyl, heteroarylalkyl, arylalkyl, S(O)$_t$$R^{13}$ or —C(O)$R^{12}$;

$R^{15}$ is hydrogen, halo, alkyl, hydroxyalkyl or —$OR^{12}$;

$R^{16}$ is hydrogen or alkyl;

t is 1 or 2;

each $R^{12}$ is independently selected from a group consisting of hydrogen or alkyl;

$R^{13}$ is alkyl;

each K is optionally substituted with one, two or three hydroxy or alkyl groups; and each $R^{1a}$ and $R^{1b}$ is independently optionally substituted with one or two $Q^1$ groups described elsewhere herein.

In one embodiment, $R^{1b}$ is —$R^uOR^x$, and $R^{1a}$ is a group of formula

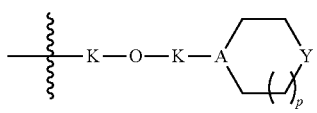

where each K is independently a direct bond or alkylene;

A is N or $CR^{16}$;

Y is —O—, —S—, —S(O), —$S(O)_2$, —$N(R^{14})$, —$C(H)R^{15}$, or —C(O);

p is an integer from 0 to 2;

$R^{14}$ is hydrogen, alkyl, haloalkyl, hydroxyalkyl, cycloalkyl, heteroarylalkyl, arylalkyl, $S(O)_tR^{13}$ or —C(O)$R^{12}$;

$R^{15}$ is hydrogen, halo, alkyl, hydroxyalkyl or —$OR^{12}$;

$R^{16}$ is hydrogen or alkyl;

t is 1 or 2;

each $R^{12}$ is independently selected from a group consisting of hydrogen or alkyl;

$R^{13}$ is alkyl;

each K is optionally substituted with one, two or three hydroxy or alkyl groups; and each $R^{1a}$ and $R^{1b}$ is independently optionally substituted with one or two $Q^1$ groups described elsewhere herein.

In another aspect, provided herein is a compound of formula XIII:

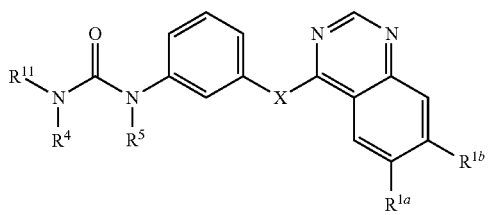

or a pharmaceutically acceptable salt, solvate or hydrate thereof, wherein $R^{1a}$ and $R^{1b}$ are selected as follows:

i) $R^{1a}$ and $R^{1b}$ are each independently hydrogen, alkoxy, alkoxyalkoxy, substituted or unsubstituted heteroaryl, or a group of formula:

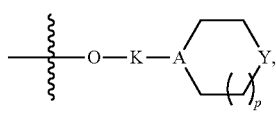

where K is a direct bond or alkylene, optionally substituted with a hydroxy group;

A is N or CH;

Y is —O—, —$S(O)_2$—, —$N(R^{14})$— or —$C(H)R^{15}$—;

p is an integer from 0 to 2;

$R^{14}$ is hydrogen, alkyl, haloalkyl, hydroxy($C_2$-$C_6$)alkyl or $S(O)_tR^{13}$;

$R^{15}$ is hydrogen, halo, alkyl, hydroxyalkyl or —$OR^{12}$;

t is 1 or 2;

$R^{12}$ is hydrogen or alkyl; and $R^{13}$ is alkyl; or ii) $R^{1a}$ and $R^{1b}$ groups together form an alkylenedioxy group;

where the substitutents on the heteroaryl, when present, are selected from one two or three groups selected from halo, alkyl, haloalkyl, hydroxyalkyl, alkoxyalkyl, cyanoalkyl, alkoxy and hydroxyl;

X is O or S;

$R^3$ is halo;

$R^4$ and $R^5$ are each hydrogen; and $R^{11}$ is optionally substituted phenyl, isoxazolyl or pyrazolyl, wherein substituents when present are selected from one or two $R^{10}$ groups, each of which is independently selected from hydrogen, halo, alkyl, alkoxy, haloalkoxy, cycloalkyl, alkoxyalkoxy, aryl, heterocyclyl, heterocyclylcarbonyl, alkoxycarbonyl and heteroaryl, where the alkyl group is optionally substituted with 1 or 2 groups selected from halo, hydroxy, alkoxy, cycloalkyl, heterocyclyl, alkylcarbonyl and alkoxycarbonyl.

In one embodiment, the compound has formula XII or XIII, wherein A is CH and the other variables are as described elsewhere herein. In one embodiment, the compound has formula XII or XIII, wherein p is 0; A is CH and the other variables are as described elsewhere herein.

In another aspect, provided herein is a compound of formula XIV:

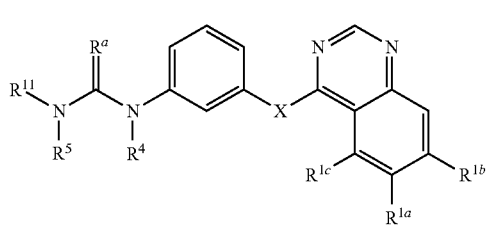

or a pharmaceutically acceptable salt, solvate or hydrate thereof, wherein $R^{1c}$ is hydrogen, halo, alkyl, haloalkyl, alkoxy, alkoxyalkyl, alkoxyalkoxy, heterocyclyloxy or aryl; and the other variables are as described elsewhere herein.

In another aspect, provided herein is a compound of formula XV:

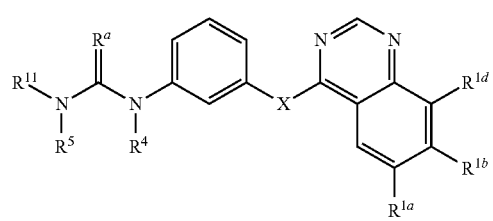

or a pharmaceutically acceptable salt, solvate or hydrate thereof, wherein $R^{1d}$ is hydrogen, halo, alkyl, haloalkyl, alkoxy, alkoxyalkyl, alkoxyalkoxy or aryl; and the other variables are as described elsewhere herein.

In another aspect, provided herein is a compound of formula XVIA or XVIB:

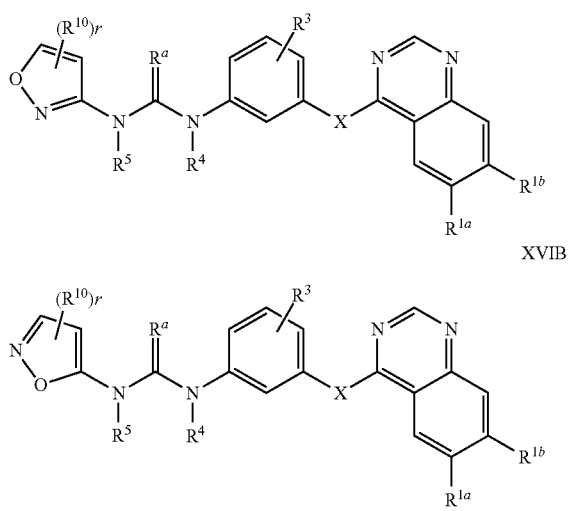

or a pharmaceutically acceptable salt, solvate or hydrate thereof, wherein $R^{1a}$ and $R^{1b}$ are selected from $Q^1$ and the other variables are described elsewhere herein. In one embodiment, the compounds have formula XVIA or XVIB wherein $R^{10}$ is selected from hydrogen, halo, alkyl, cyanoalkyl, haloalkyl or cycloalkyl; and the other variables are as described elsewhere herein.

In another aspect, provided herein is a compound of formula XVII:

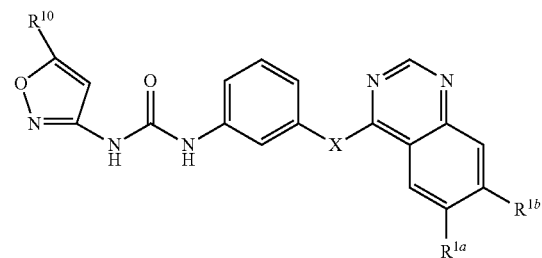

or a pharmaceutically acceptable salt, solvate or hydrate thereof, wherein the variables are as described elsewhere herein. In one embodiment, the compounds have formula XVII, wherein X is O or S;

$R^{1a}$ and $R^{1b}$ are selected as follows:

i) $R^{1a}$ and $R^{1b}$ are each independently methoxy, methoxyethoxy, methylsulfonylpropyloxy, or a group of formula:

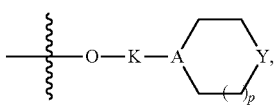

where K is ethylene or propylene, optionally substituted with a hydroxy group;

A is N or CH;
Y is —O—, —S(O)$_2$—, —N(R$^{14}$) or —C(H)R$^{15}$;
p is 1;
R$^{14}$ is hydrogen, methyl, hydroxyethyl, or methylsulfonyl;
R$^{15}$ is hydrogen, hydroxymethyl, hydroxyethyl or hydroxy; and ii) $R^{1a}$ and $R^{1b}$ groups together with the carbon atoms on which they are substituted form an ethylenedioxy group.

In another aspect, provided herein is a compound of formula XVIII:

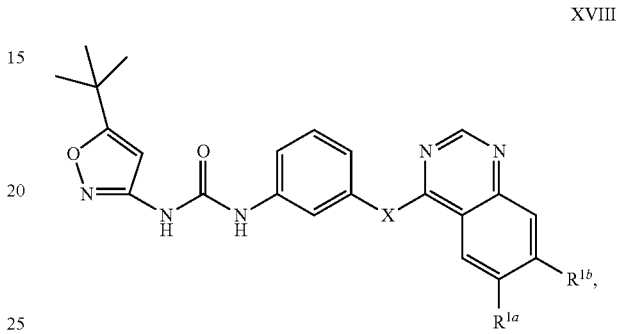

or a pharmaceutically acceptable salt, solvate or hydrate thereof, wherein X is O or S;

$R^{1a}$ and $R^{1b}$ are selected as follows:
i) $R^{1a}$ and $R^{1b}$ are each independently alkoxy, alkoxyalkoxy, alkylsulfonylalkoxy or a group of formula:

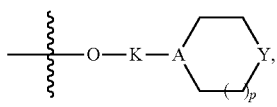

where K is a direct bond or alkylene, optionally substituted with a hydroxy group;
A is N or CH;
Y is —O—, —S(O)$_2$—, —N(R$^{14}$) or —C(H)R$^{15}$;
p is 0 or 1;
R$^{14}$ is hydrogen, alkyl, haloalkyl, hydroxy(C$_2$-C$_6$)alkyl or S(O)$_t$R$^{13}$;
R$^{15}$ is hydrogen, halo, alkyl, hydroxyalkyl or —OR$^{12}$;
t is 1 or 2;
R$^{12}$ is hydrogen or alkyl; and
R$^{13}$ is alkyl; or
ii) $R^{1a}$ and $R^{1b}$ groups together form an alkylenedioxy group.

In one embodiment, the compound is of formula XVIII or a pharmaceutically acceptable salt, solvate or hydrate thereof, wherein X is O or S;

$R^{1a}$ and $R^{1b}$ are selected as follows:
i) $R^{1a}$ and $R^{1b}$ are each independently methoxy, methoxyethoxy, methylsulfonylpropyloxy, or a group of formula:

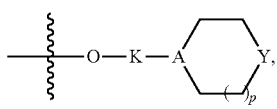

where K is ethylene or propylene, optionally substituted with a hydroxy group;

A is N or CH;

Y is —O—, —S(O)$_2$—, —N(R$^{14}$)— or —C(H)R$^{15}$;

p is 1;

R$^{14}$ is hydrogen, methyl, hydroxyethyl, or methylsulfonyl;

R$^{15}$ is hydrogen, hydroxymethyl, hydroxyethyl or hydroxy; or ii) R$^{1a}$ and R$^{1b}$ groups together with the carbon atoms on which they are substituted form an ethylenedioxy group.

In another aspect, provided herein is a compound of formula XVII or XVIII or a pharmaceutically acceptable salt, solvate or hydrate thereof, wherein X is O or S;

R$^{1a}$ and R$^{1b}$ are each independently hydrogen, fluoro, methoxy, ethoxy, methoxyethoxy, or a group of formula:

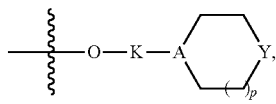

where K is a direct bond or alkylene;

A is CH;

Y is —O—, —S(O)$_2$—, —N(R$^{14}$)— or —C(H)R$^{15}$;

p is 0;

R$^{14}$ is hydrogen, alkyl, haloalkyl, hydroxy(C$_2$-C$_6$)alkyl or S(O)$_t$R$^{13}$;

R$^{15}$ is hydrogen, halo, alkyl, hydroxyalkyl or —OR$^{12}$;

t is 1 or 2;

R$^{12}$ is hydrogen or alkyl; and

R$^{13}$ is alkyl.

In another aspect, provided herein is a compound of formula XVII or XVIII or a pharmaceutically acceptable salt, solvate or hydrate thereof, wherein X is O or S;

at least one of R$^{1a}$ or R$^{1b}$ is hydrogen and the other is hydrogen, fluoro, methoxy, ethoxy, methoxyethoxy or a group of formula:

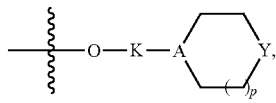

where K is a direct bond or alkylene;

A is CH;

Y is —O—, —S(O)$_2$—, —N(R$^{14}$)— or —C(H)R$^{15}$;

p is 0;

R$^{14}$ is hydrogen, alkyl, haloalkyl, hydroxy(C$_2$-C$_6$)alkyl or S(O)$_t$R$^{13}$;

R$^{15}$ is hydrogen, halo, alkyl, hydroxyalkyl or —OR$^{12}$;

t is 1 or 2;

R$^{12}$ is hydrogen or alkyl; and

R$^{13}$ is alkyl.

In another aspect, provided herein is a compound of formula XIX:

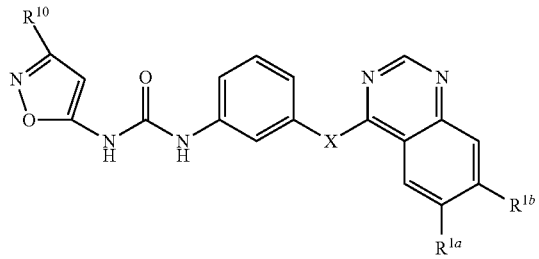

XIX or a pharmaceutically acceptable salt, solvate or hydrate thereof, wherein the variables are as described elsewhere herein. In one embodiment, the compounds have formula XIX, wherein X is O or S;

R$^{1a}$ and R$^{1b}$ are selected as follows:

i) R$^{1a}$ and R$^{1b}$ are each independently methoxy, methoxyethoxy, methylsulfonylpropyloxy, or a group of formula:

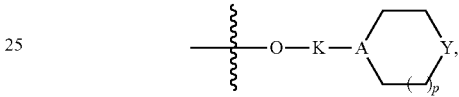

where K is ethylene or propylene, optionally substituted with a hydroxy group;

A is N or CH;

Y is —O—, —S(O)$_2$—, —N(R$^{14}$)— or —C(H)R$^{15}$;

p is 1;

R$^{14}$ is hydrogen, methyl, hydroxyethyl, or methylsulfonyl;

R$^{15}$ is hydrogen, hydroxymethyl, hydroxyethyl or hydroxy; and ii) R$^{1a}$ and R$^{1b}$ groups together with the carbon atoms on which they are substituted form an ethylenedioxy group;

R$^{10}$ is selected from hydrogen, halo, alkyl, cyanoalkyl, haloalkyl or cycloalkyl.

In another aspect, provided herein is a compound of formula XX:

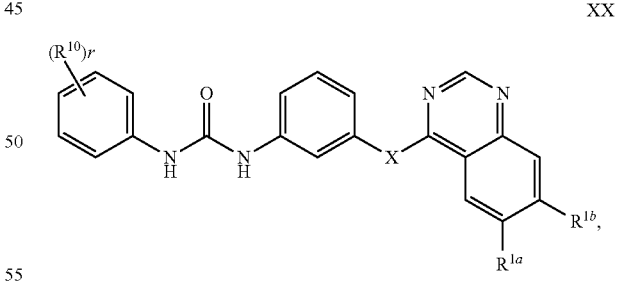

XX or a pharmaceutically acceptable salt, solvate or hydrate thereof, wherein each R$^{10}$ is independently selected from halo, alkyl, haloalkyl, hydroxyalkyl, alkoxy, haloalkoxy, cycloalkyl, alkoxyalkoxy, aryl, heterocyclylalkyl and heterocyclylcarbonyl, where the alkyl group is optionally substituted with 1 or 2 groups selected from halo, hydroxy, alkoxy, cycloalkyl, heterocyclyl, alkylcarbonyl and alkoxycarbonyl; r is an integer from 0 to 3; and the other variables are as described elsewhere herein. In one embodiment, each R$^{10}$ is independently selected from hydrogen, halo, alkyl, haloalkyl, hydroxyalkyl, cycloalkyl and alkoxy and r is 0, 1 or 2.

In another aspect, provided herein is a compound of formula XX or a pharmaceutically acceptable salt, solvate or hydrate thereof,
wherein X is O or S;
$R^{1a}$ and $R^{1b}$ are selected as follows:
i) $R^{1a}$ and $R^{1b}$ are each independently alkoxy, alkoxyalkyl or a group of formula:

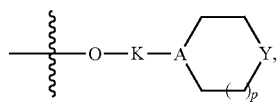

where K is a direct bond or alkylene, optionally substituted with a hydroxy group;
A is N or CH;
Y is —O, —S(O)$_2$, —N(R$^{14}$) or —C(H)R$^{15}$;
p is an integer from 0 to 2;
$R^{14}$ is hydrogen, alkyl, haloalkyl, hydroxy(C$_2$-C$_6$)alkyl or S(O)$_t$R$^{13}$;
$R^{15}$ is hydrogen, halo, alkyl, hydroxyalkyl or —OR$^{12}$;
t is 1 or 2;
$R^{12}$ is hydrogen or alkyl; and
$R^{13}$ is alkyl; or
ii) $R^{1a}$ and $R^{1b}$ groups together form an alkylenedioxy group; and
r is 0, 1, 2 or 3.

In another aspect, provided herein is a compound of formula XXI:

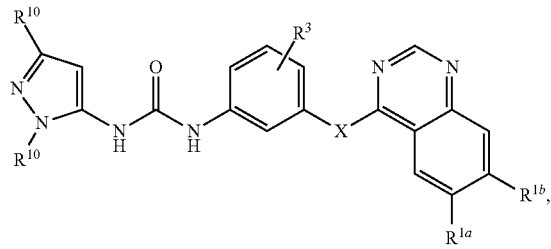

XXI or a pharmaceutically acceptable salt, solvate or hydrate thereof, wherein X is O or S;
$R^{1a}$ and $R^{1b}$ are selected as follows:
i) $R^{1a}$ and $R^{1b}$ are each independently alkoxy, alkoxyalkyl, alkylsulfonylalkoxy or a group of formula:

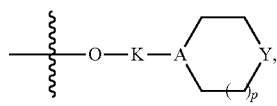

where K is a direct bond or alkylene, optionally substituted with a hydroxy group;
A is N or CH;
Y is —O, —S(O)$_2$, —N(R$^{14}$) or —C(H)R$^{15}$;
p is 0 or 1;
$R^{14}$ is hydrogen, alkyl, haloalkyl, hydroxy(C$_2$-C$_6$)alkyl or S(O)$_t$R$^{13}$;
$R^{15}$ is hydrogen, halo, alkyl, hydroxyalkyl or —OR$^{12}$;
t is 1 or 2;

$R^{12}$ is hydrogen or alkyl; and
$R^{13}$ is alkyl; or
ii) $R^{1a}$ and $R^{1b}$ groups together form an alkylenedioxy group
each $R^{10}$ is independently selected from alkyl, haloalkyl, hydroxyalkyl, aryl, haloaryl, alkylaryl or heteroaryl.

In another aspect, provided herein is a compound of formula XXII:

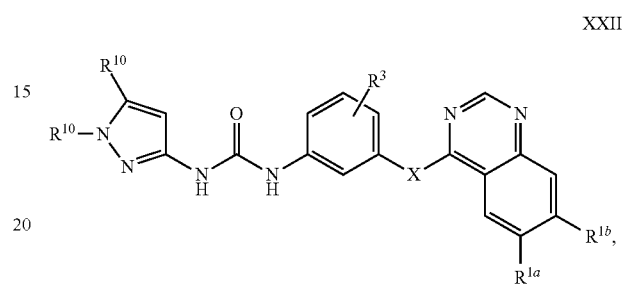

XXII or a pharmaceutically acceptable salt, solvate or hydrate thereof, wherein X is O or S;
$R^{1a}$ and $R^{1b}$ are selected as follows:
i) $R^{1a}$ and $R^{1b}$ are each independently alkoxy, alkoxyalkyl, alkylsulfonylalkoxy or a group of formula:

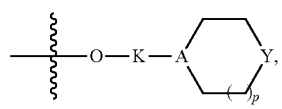

where K is a direct bond or alkylene, optionally substituted with a hydroxy group;
A is N or CH;
Y is —O, —S(O)$_2$, —N(R$^{14}$) or —C(H)R$^{15}$;
p is 0 or 1;
$R^{14}$ is hydrogen, alkyl, haloalkyl, hydroxy(C$_2$-C$_6$)alkyl or S(O)$_t$R$^{13}$;
$R^{15}$ is hydrogen, halo, alkyl, hydroxyalkyl or —OR$^{12}$;
t is 1 or 2;
$R^{12}$ is hydrogen or alkyl; and
$R^{13}$ is alkyl; or
ii) $R^{1a}$ and $R^{1b}$ groups together form an alkylenedioxy group
each $R^{10}$ is independently selected from alkyl, haloalkyl, hydroxyalkyl, aryl, haloaryl, alkylaryl or heteroaryl.

In one embodiment, the compound has formula XXI or XXII or a pharmaceutically acceptable salt, solvate or hydrate thereof, wherein each $R^{10}$ is independently selected from tert-butyl, methyl, trifluoro tert-butyl, phenyl, p-fluorophenyl or p-methylphenyl.

In one embodiment, the compound is selected from formula XVI-XXIII, wherein p is 0; A is CH and the other variables are as described elsewhere herein.

In one embodiment, the compound is selected from a group consisting of the compounds in Table 1.

Certain exemplary compounds are provided in Table 1.

TABLE 1

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 1 1-(5-tert-butylisoxazol-3-yl)-3-(3-(6,7-dimethoxy-quinazolin-4-yloxy)phenyl) urea | A | C | A | D | B | C |
| Ex 2 1-(5-tert-butylisoxazol-3-yl)-3-(3-(6-methoxy-quinazolin-4-yloxyphenyl) urea | ND | ND | ND | ND | ND | ND |
| Ex 3 1-(5-tert-butylisoxazol-3-yl)-3-(3-(7-methoxy-quinazolin-4-yloxy)phenyl) urea | ND | ND | ND | ND | ND | ND |
| Ex 4 1-(5-tert-butylisoxazol-3-yl)-3-(3-(6,7-difluoro-quinazolin-4-yloxy)phenyl) urea | ND | ND | ND | ND | ND | ND |
| Ex 5 1-(5-tert-butylisoxazol-3-yl)-3-(3-(5-methyl-quinazolin-4-yloxy)phenyl) urea | ND | ND | ND | ND | ND | ND |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 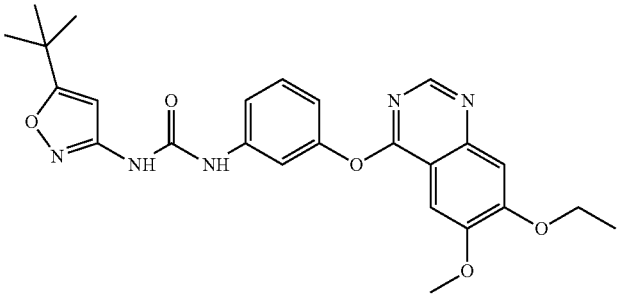 | Ex 6 1-(5-tert-butylisoxazol-3-yl)-3-[3-(7-ethoxy-6-methoxy-quinazolin-4-yloxy)phenyl]urea hydrochloride | A | B | A | D | C | D |
| 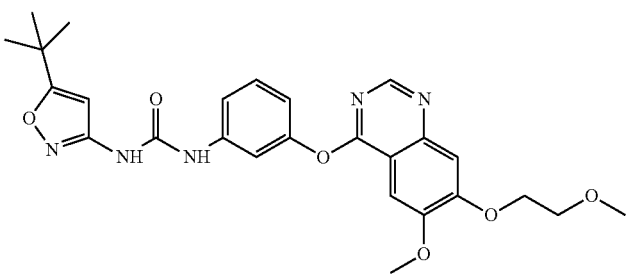 [SMILES: COCCOc1cc2ncnc(Oc3cccc(NC(=O)Nc4cc(C(C)(C)C)on4)c3)c2cc1OC] | Ex 7 1-(5-tert-Butylisoxazol-3-yl)-3-{3-[6-methoxy-7-(2-methoxy-ethoxy)quinazolin-4-yloxy]phenyl}urea hydrochloride | A | B | A | B | B | D |
| 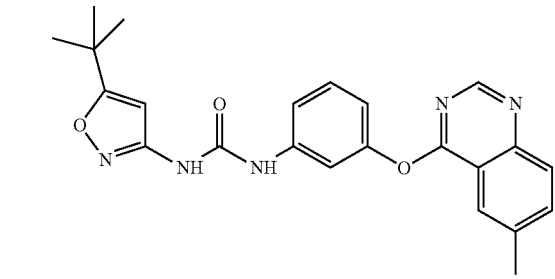 [SMILES: Cc1ccc2ncnc(Oc3cccc(NC(=O)Nc4cc(C(C)(C)C)on4)c3)c2c1] | Ex 8 1-(5-tert-butylisoxazol-3-yl)-3-(3-(6-methyl-quinazolin-4-yloxy)phenyl)urea | ND | ND | ND | ND | ND | ND |
| 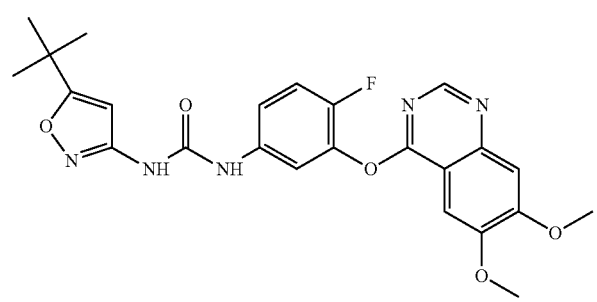 [SMILES: COc1cc2ncnc(Oc3cc(NC(=O)Nc4cc(C(C)(C)C)on4)ccc3F)c2cc1OC] | Ex 9 1-(5-tert-butylisoxazol-3-yl)-3-(3-(6,7-dimethoxy-quinazolin-4-yloxy)-4-fluorophenyl)urea | A | A | A | D | C | D |
| 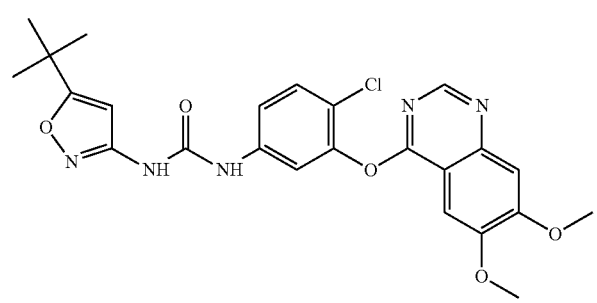 [SMILES: COc1cc2ncnc(Oc3cc(NC(=O)Nc4cc(C(C)(C)C)on4)ccc3Cl)c2cc1OC] | Ex 10 1-(5-tert-butylisoxazol-3-yl)-3-(4-chloro-3-(6,7-dimethoxy-quinazolin-4-yloxy)phenyl)urea | D | D | C | D | C | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 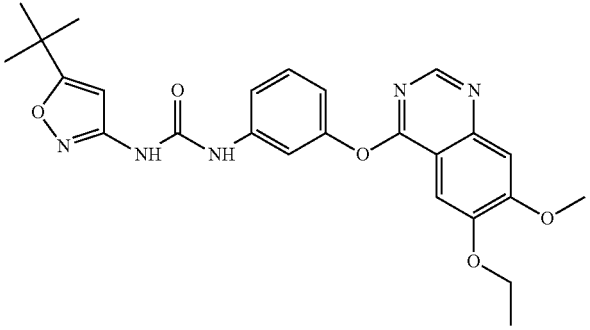 [SMILES: CCOc1cc2c(Oc3cccc(NC(=O)Nc4cc(C(C)(C)C)on4)c3)ncnc2cc1OC] Ex 11 1-(5-tert-butylisoxazol-3-yl)-3-(3-(6-ethoxy-7-methoxy-quinazolin-4-yloxy)phenyl) urea | A | A | A | D | C | C |
| 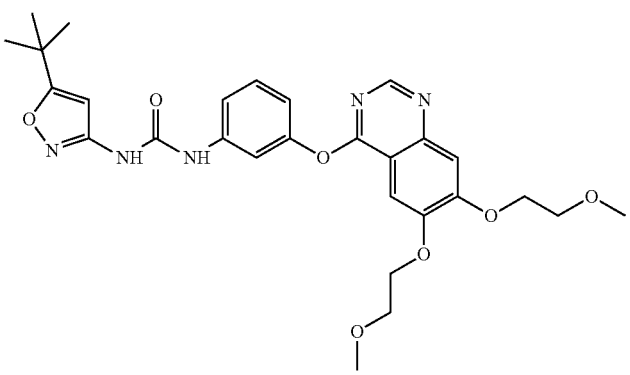 Ex 12 1-{3-[6,7-bis(2-methoxy-ethoxy)-quinazolin-4-yloxy]phenyl}-3-(5-tert-butylisoxazol-3-yl)urea hydrochloride | A | B | A | C | B | C |
| 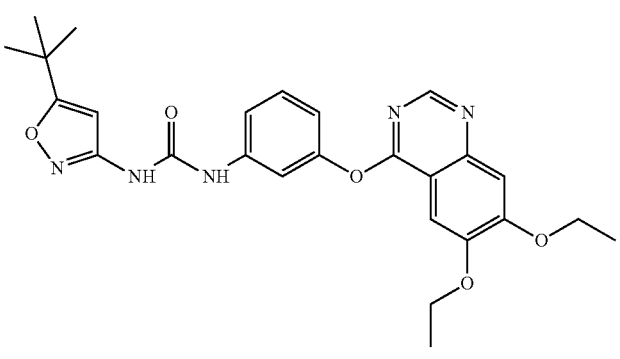 Ex 13 1-(5-tert-Butylisoxazol-3-yl)-3-[3-(6,7-diethoxy-quinazolin-4-yloxy)phenyl] urea hydrochloride | B | C | B | D | D | C |
| 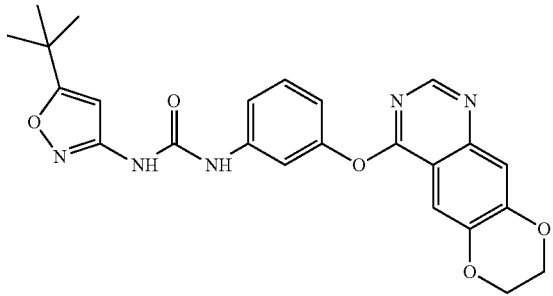 [SMILES: CC(C)(C)c1cc(NC(=O)Nc2cccc(Oc3ncnc4cc5c(cc34)OCCO5)c2)no1] Ex 14 1-(5-tert-Butylisoxazol-3-yl)-3-[3-(7,8-dihydro-[1,4]dioxino[2,3-g]quinazolin-4-yloxy) phenyl]urea hydrochloride | C | D | A | C | B | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 15 1-(5-tert-butylisoxazol-3-yl)-3-{3-[7-methoxy-6-(2-methoxy-ethoxy)quinazolin-4-yloxy]phenyl} urea hydrochloride | A | A | A | B | B | C |
| Ex 16 1-(5-tert-butylisoxazol-3-yl)-3-(3-(7-methoxy-6-(2-(piperidin-1-yl)ethoxy)quinazolin-4-yloxy)phenyl) urea | B | D | A | C | D | C |
| Ex 17 1-(5-tert-butylisoxazol-3-yl)-3-(3-(6-(2-(4-(hydroxy-methyl)piperidin-1-yl)ethoxy)-7-methoxy-quinazolin-4-yloxy)phenyl) urea | B | B | A | C | C | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 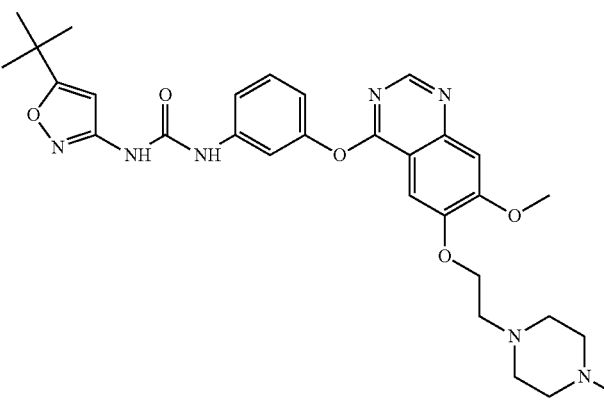 Ex 18 1-(5-tert-butylisoxazol-3-yl)-3-(3-(7-methoxy-6-(2-(4-methylpiperazin-1-yl)ethoxy)quinazolin-4-yloxy)phenyl)urea | A | B | A | B | C | D |
| 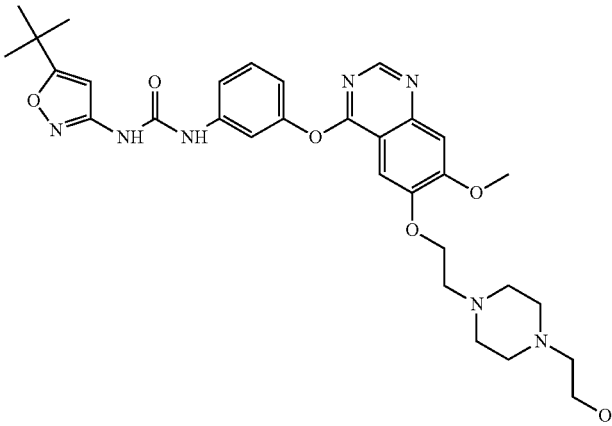 Ex 19 1-(5-tert-butylisoxazol-3-yl)-3-(3-(6-(2-(4-(2-hydroxyethyl)piperazin-1-yl)ethoxy)-7-methoxy-quinazolin-4-yloxy)phenyl)urea | A | B | A | B | B | D |
| 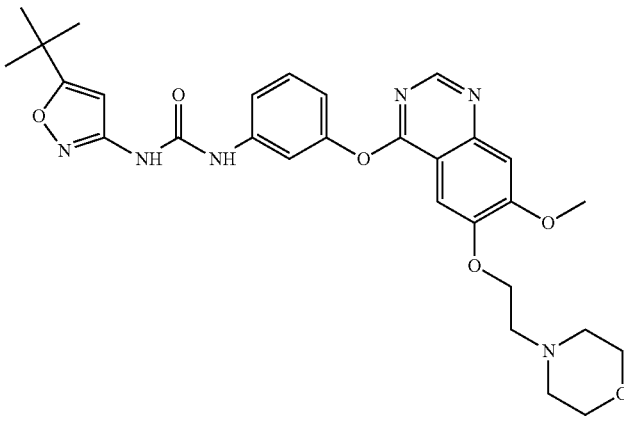 Ex 20 1-(5-tert-butylisoxazol-3-yl)-3-(3-(7-methoxy-6-(2-morpholinoethoxy)quinazolin-4-yloxy)phenyl)urea | A | A | A | B | B | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 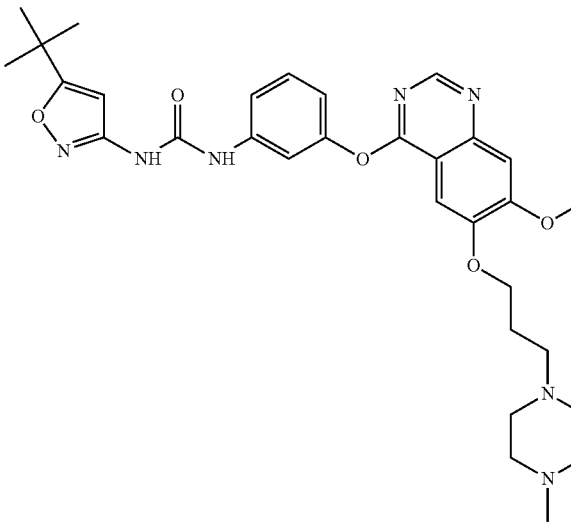 Ex 21 1-(5-tert-butylisoxazol-3-yl)-3-(3-(7-methoxy-6-(3-(4-methyl piperazin-1-yl)propoxy) quinazolin-4-yloxy)phenyl urea | A | B | A | B | B | D |
| 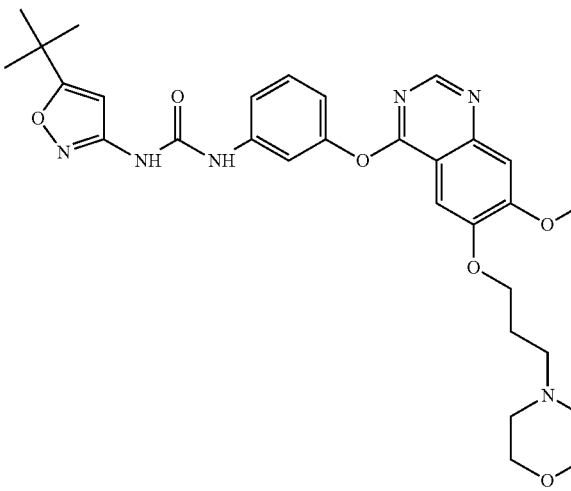 Ex 22 1-(5-tert-butylisoxazol-3-yl)-3-(3-(7-methoxy-6-(3-morpholino-propoxy) quinazolin-4-yloxy)phenyl) urea | A | A | A | A | A | D |
| 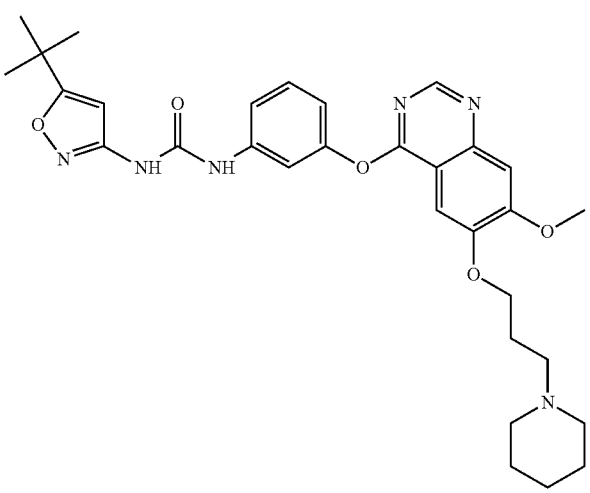 Ex 23 1-(5-tert-butylisoxazol-3-yl)-3-(3-(7-methoxy-6-(3-(piperidin-1-yl)propoxy) quinazolin-4-yloxy)phenyl) urea | A | C | A | C | C | D |

TABLE 1-continued
| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 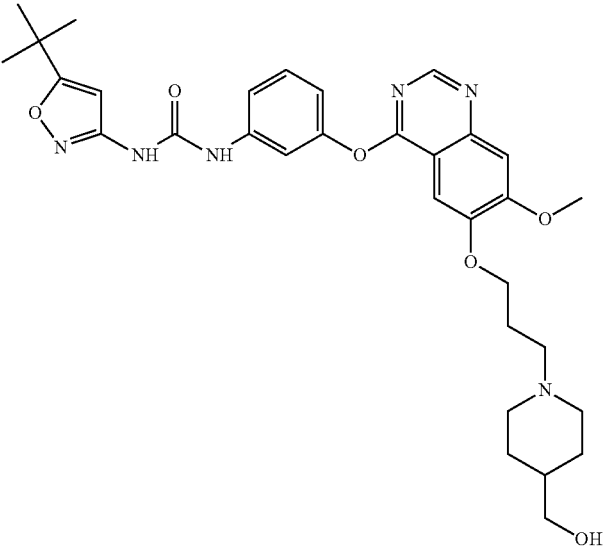 [SMILES: COc1cc2ncnc(Oc3cccc(NC(=O)Nc4cc(C(C)(C)C)on4)c3)c2cc1OCCCN1CCC(CO)CC1] Ex 24 1-(5-tert-butylisoxazol-3-yl)-3-(3-(6-(3-(4-(hydroxymethyl)piperidin-1-yl)propoxy)-7-methoxyquinazolin-4-yloxy)phenyl)urea | A | C | A | C | C | D |
| 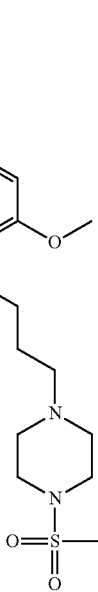 Ex 25 1-(5-tert-butylisoxazol-3-yl)-3-(3-(7-methoxy-6-(3-(4-(methylsulfonyl)piperazin-1-yl)propoxy)quinazolin-4-yloxy)phenyl)urea | A | A | A | B | B | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 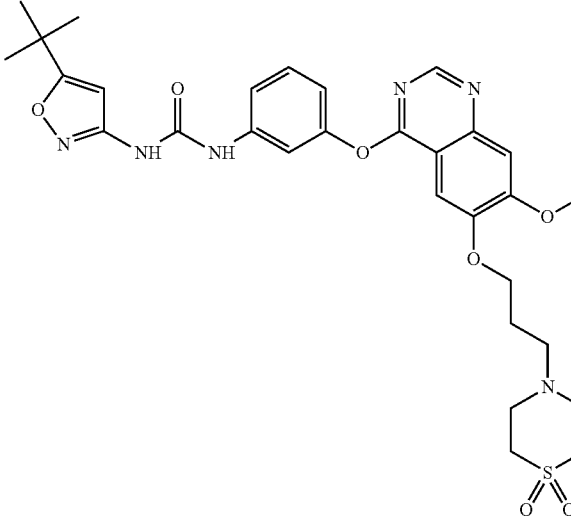 | Ex 26 1-(5-tert-butyl-isoxazol-3-yl)-3-(3-{6-[3-(1,1-dioxo-thiomorpholin-4-yl)-propoxy]-7-methoxy-quinazolin-4-yloxy}-phenyl)-urea | A | A | A | B | A | D |
| 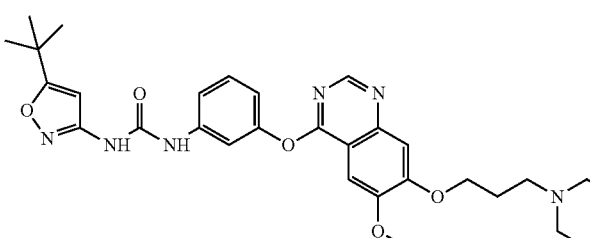 | Ex 27 1-(5-tert-butylisoxazol-3-yl)-3-(3-(6-methoxy-7-(3-morpholino-propoxy)quinazolin-4-yloxy)phenyl)urea | A | A | A | B | B | D |
| 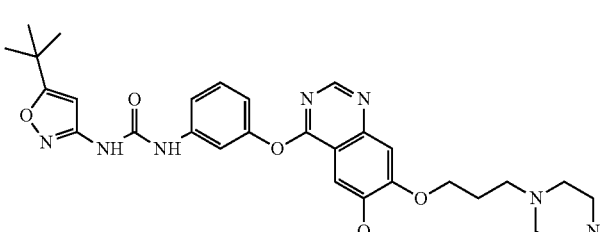 | Ex 28 1-(5-tert-butylisoxazol-3-yl)-3-(3-(6-methoxy-7-(3-(4-methyl-piperazin-1-yl)propoxy)quinazolin-4-yloxy)phenyl)urea | A | A | A | B | A | D |
| 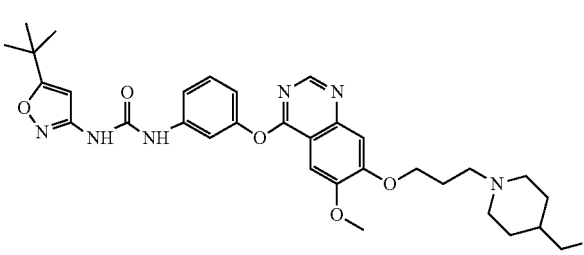 | Ex 29 1-(5-tert-butylisoxazol-3-yl)-3-(3-(7-(3-(4-hydroxy-methyl)piperidin-1-yl)propoxy)-6-methoxy-quinazolin-4-yloxy)phenyl)urea | A | A | A | B | B | D |
| 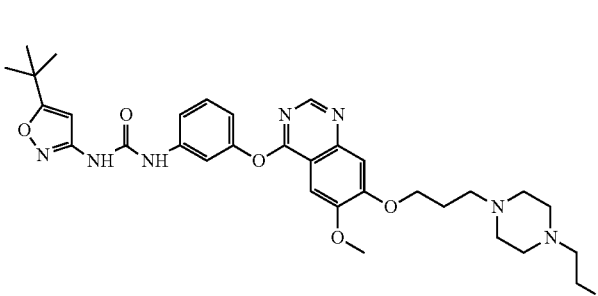 | Ex 30 1-(5-tert-butylisoxazol-3-yl)-3-(3-(7-(3-(4-(2-hydroxyethyl)piperazin-1-yl)propoxy)-6-methoxy quinazolin-4-yloxy)phenyl)urea | A | A | A | A | B | D |

TABLE 1-continued

| | | pMEK IC50 (nM) | A375 Viability EC50 (nM) | BRAF V600E Kd (nM) | BRAF WT Kd nM | RAF1 Kd nM | |
|---|---|---|---|---|---|---|---|
| | Name | | | | | | S35 |
| 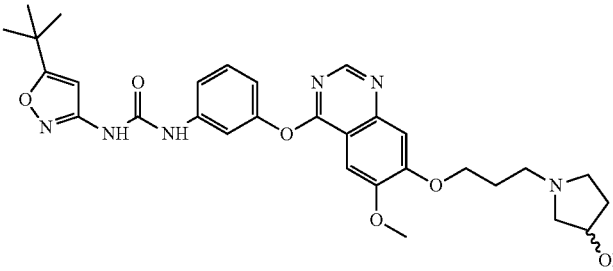 | Ex 31 1-(5-tert-butyl-isoxazol-3-yl)-3-(3-{7-[3-(3-hydroxy-pyrrolidin-1-yl)-propoxy]-6-methoxy-quinazolin-4-yloxy}-phenyl)-urea | A | A | A | B | B | D |
| 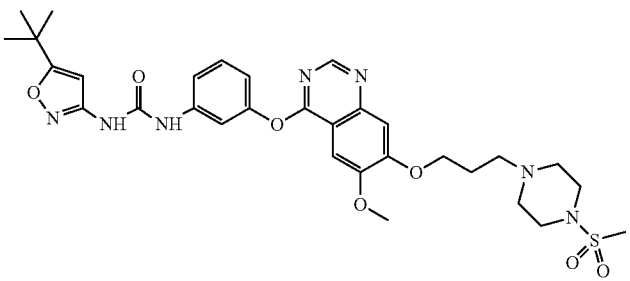 [SMILES: COc1cc2c(Oc3cccc(NC(=O)Nc4cc(C(C)(C)C)on4)c3)ncnc2cc1OCCCN1CCN(S(C)(=O)=O)CC1] | Ex 32 1-(5-tert-butylisoxazol-3-yl)-3-(3-(6-methoxy-7-(3-(4-(methylsulfonyl)piperazin-1-yl)propoxy)quinazolin-4-yloxy)phenyl)urea | A | B | A | C | B | D |
| 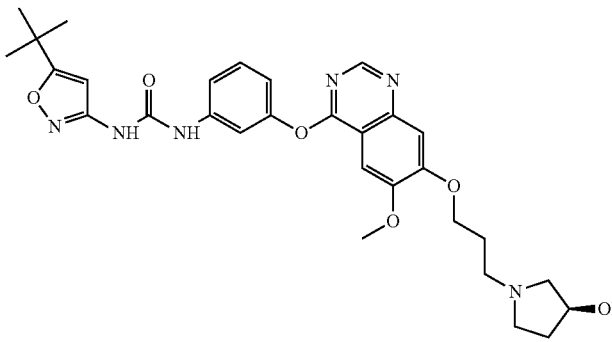 | Ex 33 (S)-1-(5-tert-butylisoxazol-3-yl)-3-(3-(7-(3-(3-hydroxypyrrolidin-1-yl)propoxy)-6-methoxy-quinazolin-4-yloxy)phenyl)urea | A | A | A | B | B | D* |
| 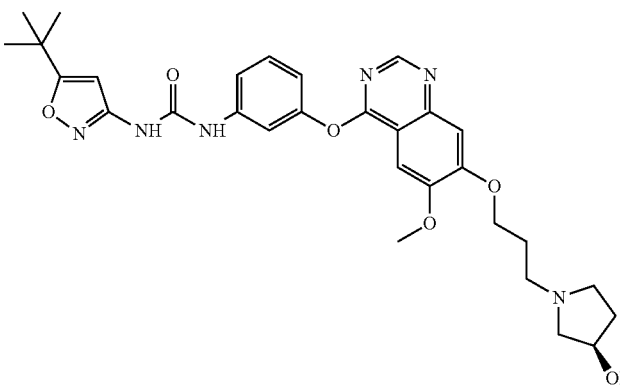 | Ex 34 (R)-1-(5-tert-butylisoxazol-3-yl)-3-(3-(7-(3-(3-hydroxypyrrolidin-1-yl)propoxy)-6-methoxy-quinazolin-4-yloxy)phenyl)urea | A | D | A | B | B | D* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 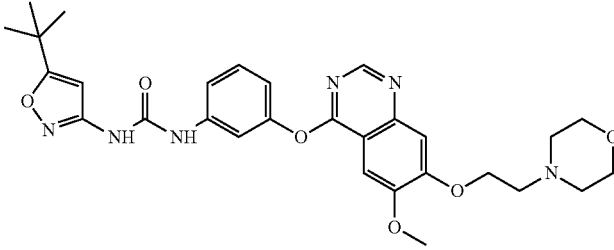 Ex 35 1-(5-tert-butylisoxazol-3-yl)-3-(3-(6-methoxy-7-(2-morpholino-ethoxy)quinazolin-4-yloxy)phenyl)urea | A | C | A | B | B | C |
| 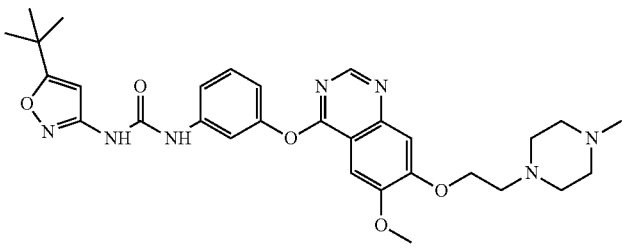 [SMILES: COc1cc2c(Oc3cccc(NC(=O)Nc4cc(C(C)(C)C)on4)c3)ncnc2cc1OCCN1CCN(C)CC1] Ex 36 1-(5-tert-butylisoxazol-3-yl)-3-(3-(6-methoxy-7-(2-(4-methyl piperazin-1-yl)ethoxy)quinazolin-4-yloxy)phenyl)urea | A | B | A | B | B | C |
| 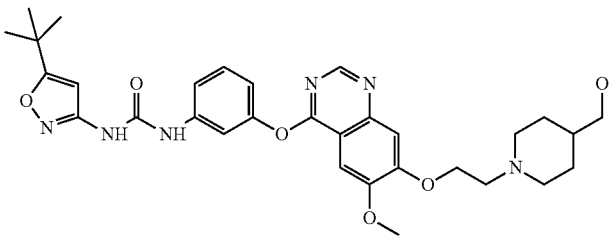 [SMILES: COc1cc2c(Oc3cccc(NC(=O)Nc4cc(C(C)(C)C)on4)c3)ncnc2cc1OCCN1CCS(=O)(=O)CC1] Ex 37 1-(5-tert-Butyl-isoxazol-3-yl)-3-(3-{7-[2-(4-hydroxy-methyl-piperidin-1-yl)-ethoxy]-6-methoxy-quinazolin-4-yloxy}-phenyl)-urea | A | B | A | B | B | C |
| 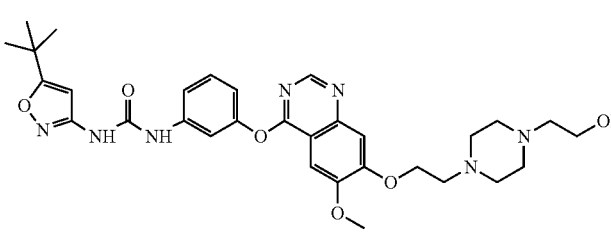 Ex 38 1-(5-tert-butylisoxazol-3-yl)-3-(3-(7-(2-(4-(2-hydroxyethyl)piperazin-1-yl) ethoxy)-6 methoxy quinazolin-4yloxy)phenyl)urea | A | B | A | B | B | D |
| 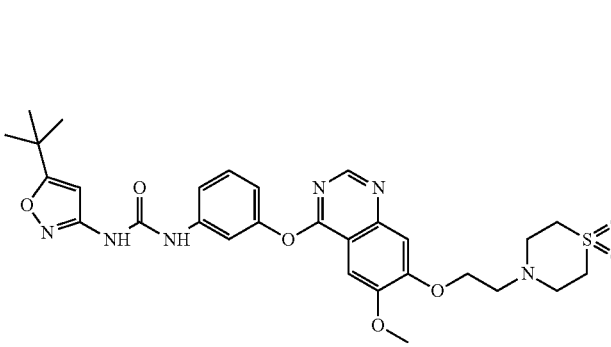 Ex 39 1-(5-tert-Butyl-isoxazol-3-yl)-3-(3-{7-[2-(1,1-dioxo-1l6-thio-morpholin-4-yl)-ethoxy]-6-methoxy-quinazolin-4-yloxy}-phenyl)-urea | A | A | A | B | B | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 40 1-(5-tert-butylisoxazol-3-yl)-3-(3-(6-(2-methoxy-ethoxy)quinazolin-4-yloxy)phenyl)urea | A | C | A | D | B | C |
| Ex 41 1-(5-tert-Butylisoxazol-3-yl)-3-(3-(7-methoxy-6-(3-(methylsulfonyl)propoxy)quinazolin-4-ylthio)phenyl urea | A | A | A | A | A | C |
| Ex 42 1-(3-(2-fluoropropan-2-yl)isoxazol-5-yl)-3-(3-(7-methoxy-6-(3-(methylsulfonyl)propoxy)quinazolin-4-yloxy)phenyl urea | B | C | A | A | A | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 43 1-(5-tert-butylisoxazol-3-yl)-3-(3-(7-(2-methoxyethoxy)quinazolin-4-yloxy)phenyl)urea | B | D | A | C | B | C |
| Ex 44 1-(5-tert-butylisoxazol-3-yl)-3-(3-(7-methoxy-6-(3-(methylsulfonyl)propoxy)quinazolin-4-ylthio)phenyl)urea | A | B | A | A | A | C |
| Ex 45 1-(5-tert-butylisoxazol-3-yl)-3-(3-(7-methoxy-6-(2-methoxyethoxy)quinazolin-4-ylthio)phenyl)urea | A | B | A | C | B | C |
| Ex 46 1-(5-tert-butylisoxazol-3-yl)-3-(3-(6,7-dimethoxy-quinazolin-4-ylthio)phenyl)urea | A | B | A | C | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 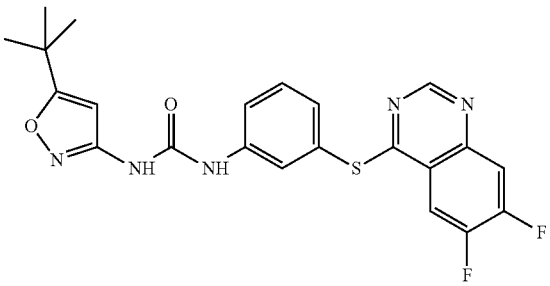 | Ex 47 1-(5-tert-butylisoxazol-3-yl)-3-(3-(6,7-difluoro-quinazolin-4-ylthio)phenyl) urea | D | D | C | D | D | A |
| 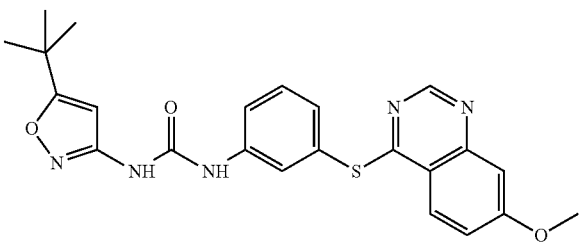 | Ex 48 1-(5-tert-butylisoxazol-3-yl)-3-(3-(7-methoxy-quinazolin-4-ylthio)phenyl) urea | C | D | B | D | D | C |
| 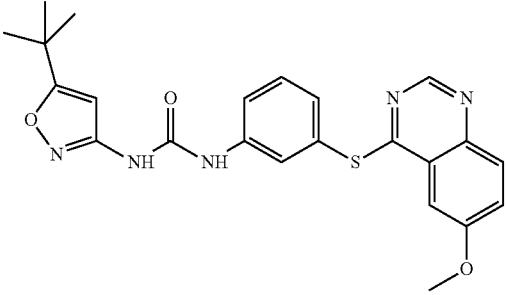 [SMILES: COc1ccc2ncnc(Sc3cccc(NC(=O)Nc4cc(C(C)(C)C)on4)c3)c2c1] | Ex 49 1-(5-tert-butylisoxazol-3-yl)-3-(3-(6-methoxy-quinazolin-4-ylthio)phenyl) urea | C | D | B | D | C | C |
| 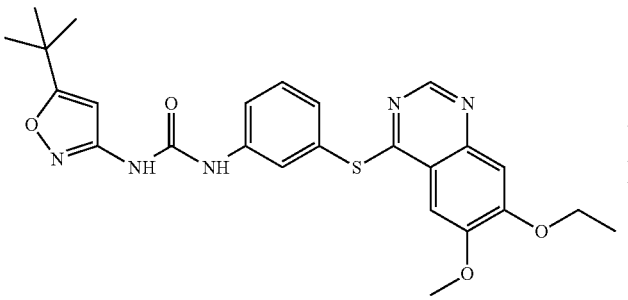 [SMILES: CCOc1cc2ncnc(Sc3cccc(NC(=O)Nc4cc(C(C)(C)C)on4)c3)c2cc1OC] | Ex 50 1-(5-tert-Butylisoxazol-3-yl)-3-[3-(7-ethoxy-6-methoxy-quinazolin-4-ylthio)phenyl] urea | B | D | B | C | B | B |
| 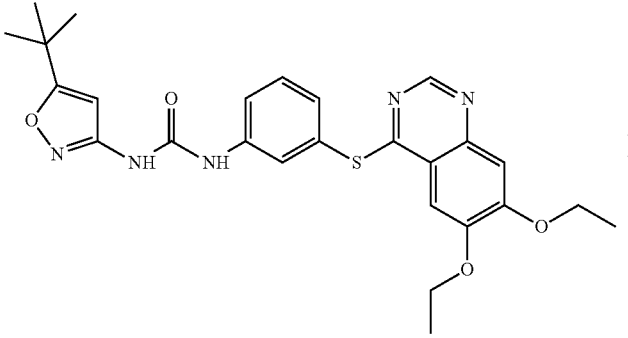 | Ex 51 1-(5-tert-butylisoxazol-3-yl)-3-[3-(6,7-diethoxy-quinazolin-4-ylthio)phenyl] urea | B | D | C | D | D | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 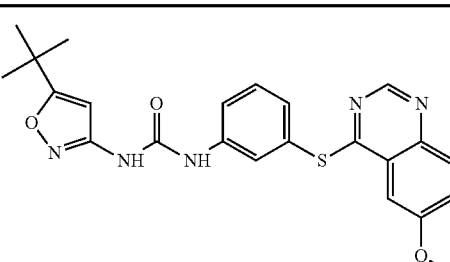 | Ex 52 1-(5-tert-butylisoxazol-3-yl)-3-{3-[6-methoxy-7-(2-methoxy-ethoxy)quinazolin-4-ylthio]phenyl}urea hydrochloride | A | C | A | B | B | C |
| 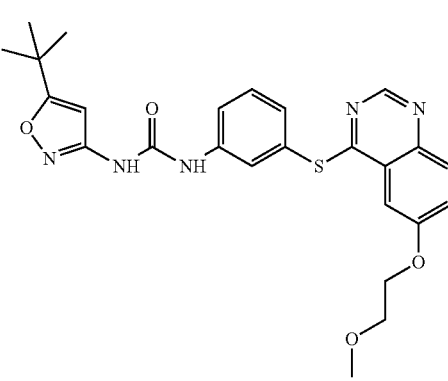 | Ex 53 1-{3-[6,7-bis(2-methoxy-ethoxy)quinazolin-4-ylthio]phenyl}-3-(5-tert-butylisoxazol-3-yl)urea hydrochloride | A | C | A | C | B | C |
| 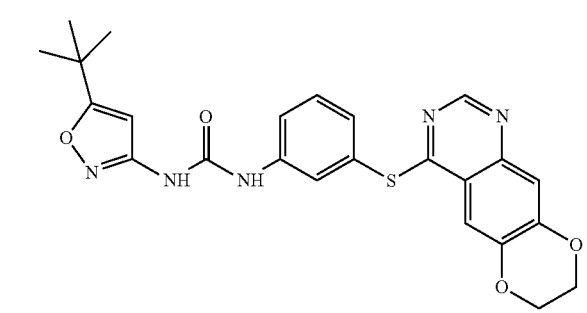 [SMILES: CC(C)(C)c1cc(NC(=O)Nc2cccc(Sc3ncnc4cc5c(cc34)OCCO5)c2)no1] | Ex 54 1-(5-tert-butylisoxazol-3-yl)-3-[3-(7,8-dihydro-[1,4]dioxino[2,3-g]quinazolin-4-ylthio)phenyl]urea hydrochloride | C | D | C | D | D | C |
| 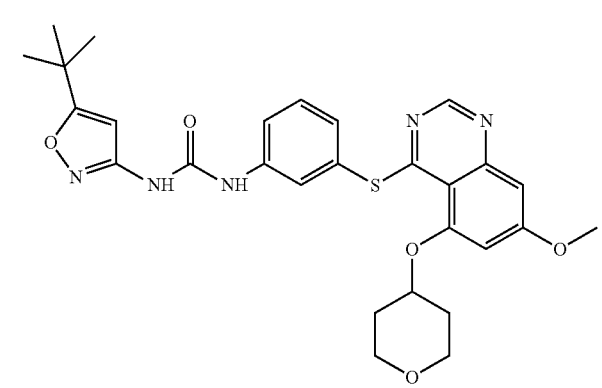 | Ex 55 1-(5-tert-Butylisoxazol-3-yl)-3-{3-[7-methoxy-5-(tetrahydro-2H-pyran-4-ylthio)quinazolin-4-yloxy]phenyl}urea | A | B | A | C | B | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 56 1-(5-tert-butylisoxazol-3-yl)-3-(3-(6-ethoxy-7-methoxy-quinazolin-4-ylthio)phenyl)urea | A | A | A | C | B | B |
| Ex 57 1-(5-tert-butylisoxazol-3-yl)-3-(3-(7-methoxy-6-(3-(piperidin-1-yl)propoxy)quinazolin-4-ylthio)phenyl)urea | A | D | A | C | C | C |
| Ex 58 1-(5-tert-butylisoxazol-3-yl)-3-(3-(6-(3-(4-(hydroxymethyl)piperidin-1-yl)propoxy)-7-methoxy-quinazolin-4-ylthio)phenyl)urea | A | D | A | B | C | D |

TABLE 1-continued
| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 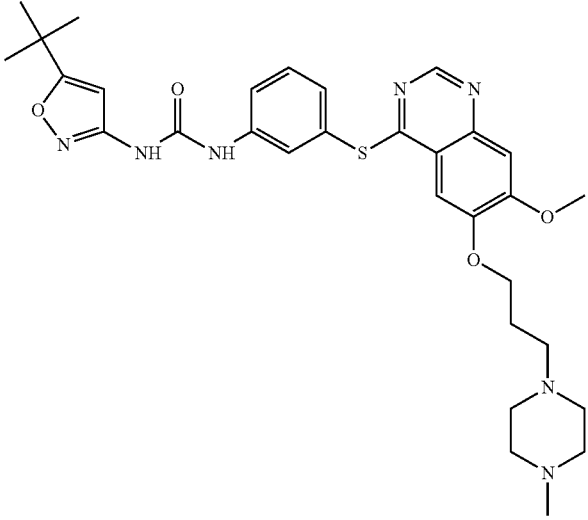 [SMILES: COc1cc2ncnc(Sc3cccc(NC(=O)Nc4cc(C(C)(C)C)on4)c3)c2cc1OCCCN1CCN(C)CC1] Ex 59 1-(5-tert-Butylisoxazol-3-yl)-3-(3-(7-methoxy-6-(3-(4-methyl-piperazin-1-yl)propoxy)quinazolin-4-ylthio)phenyl)urea | A | D | A | B | B | D |
| 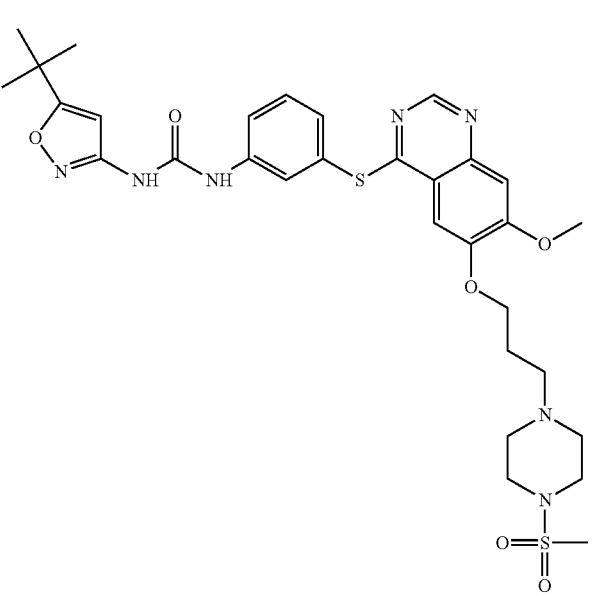 Ex 60 1-(5-tert-butylisoxazol-3-yl)-3-(3-(7-methoxy-6-(3-(4-(methyl-sulfonyl)piperazin-1-yl)propoxy)quinazolin-4-ylthio)phenyl)urea | A | B | A | C | B | C |

TABLE 1-continued
| | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 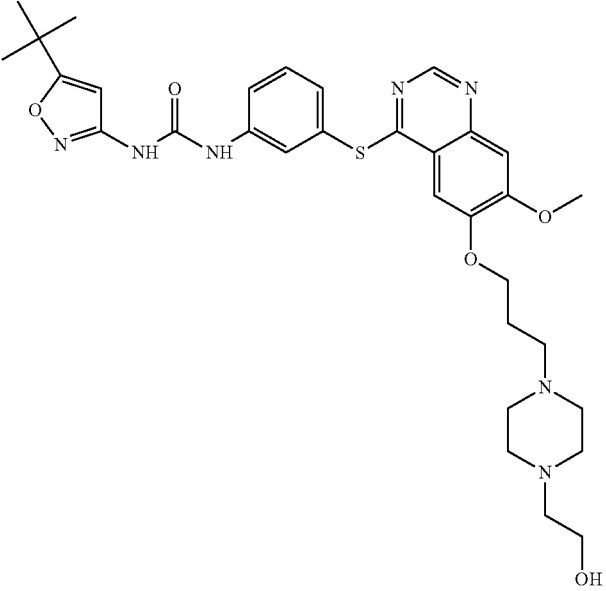 [SMILES: COc1cc2ncnc(Sc3cccc(NC(=O)Nc4cc(C(C)(C)C)on4)c3)c2cc1OCCCN1CCN(CCO)CC1] Ex 61 1-(5-tert-butylisoxazol-3-yl)-3-(3-6-(3-(4-(2-hydroxyethyl)piperazin-1-yl)propoxy)-7-methoxy-quinazolin-4-ylthio)phenyl)urea | D | D | A | B | A | D |
| 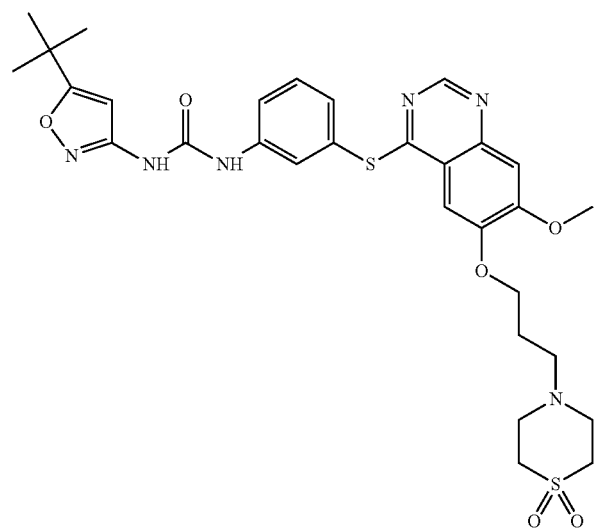 [SMILES: COc1cc2ncnc(Sc3cccc(NC(=O)Nc4cc(C(C)(C)C)on4)c3)c2cc1OCCCN1CCS(=O)(=O)CC1] Ex 62 1-(5-tert-butyl-isoxazol-3-yl)-3-(3-{6-[3-(1,1-dioxo-thiomorpholin-4-yl)-propoxy]-7-methoxy-quinazolin-4-ylsulfanyl}-phenyl)-urea | A | A | A | B | A | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 63 1-(5-tert-butylisoxazol-3-yl)-3-(3-(7-methoxy-6-(3-morpholinopropoxy)quinazolin-4-ylthio)phenyl)urea | A | C | A | B | A | C |
| Ex 64 1-(5-tert-butylisoxazol-3-yl)-3-(3-(7-methoxy-6-(3-(methylsulfonyl)propoxy)quinazolin-4-ylthio)phenyl)urea | A | B | A | A | A | C |
| Ex 65 1-(5-tert-butylisoxazol-3-yl)-3-(3-(7-methoxy-6-(2-(piperidin-1-yl)ethoxy)quinazolin-4-ylthio)phenyl)urea | B | D | A | D | C | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 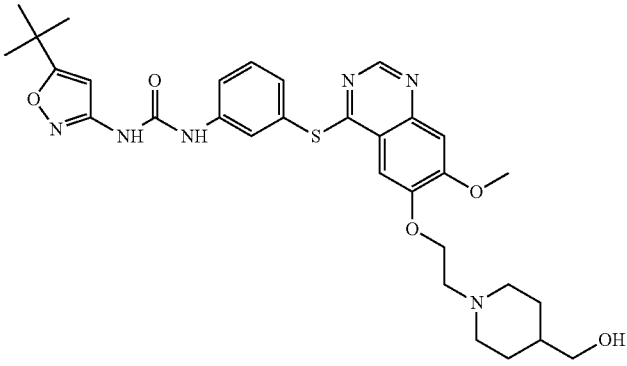 [SMILES: COc1cc2ncnc(Sc3cccc(NC(=O)Nc4cc(C(C)(C)C)on4)c3)c2cc1OCCN1CCC(CO)CC1] Ex 66 1-(5-tert-butylisoxazol-3-yl)-3-(3-(6-(2-(4-(hydroxy-methyl)piperidin-1-yl)ethoxy)-7-methoxy-quinazolin-4-ylthio)phenyl)urea | A | D | A | C | C | C |
| 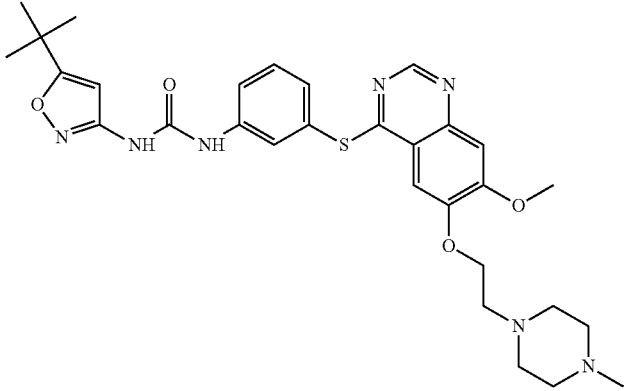 [SMILES: COc1cc2ncnc(Sc3cccc(NC(=O)Nc4cc(C(C)(C)C)on4)c3)c2cc1OCCN1CCN(C)CC1] Ex 67 1-(5-tert-butylisoxazol-3-yl)-3-(3-(7-methoxy-6-(2-(4-methyl piperazin-1-yl)ethoxy)quinazolin-4-ylthio)phenyl)urea | A | D | A | B | B | C |
| 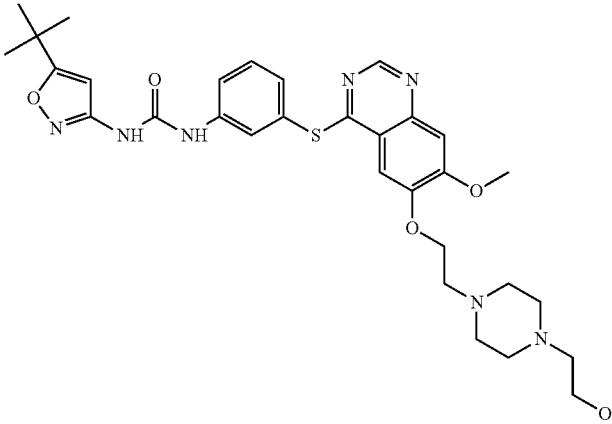 Ex 68 1-(5-tert-butylisoxazol-3-yl)-3-(3-(6-(2-(4-(2-hydroxyethyl)piperazin-1-yl)ethoxy)-7-methoxy-quinazolin-4-ylthio)phenyl)urea | A | C | A | B | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 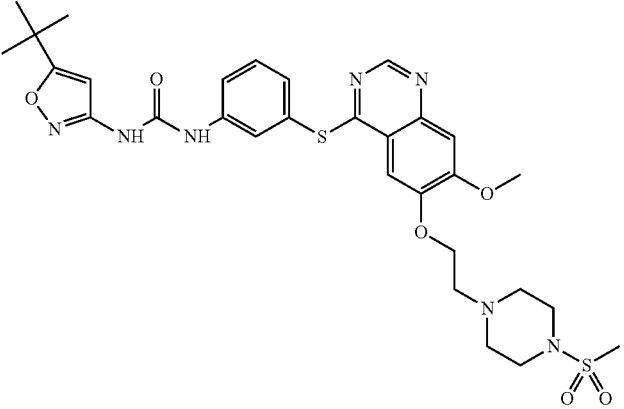 [SMILES: COc1cc2ncnc(Sc3cccc(NC(=O)Nc4cc(C(C)(C)C)on4)c3)c2cc1OCCN1CCN(S(C)(=O)=O)CC1] | Ex 69 1-(5-tert-butylisoxazol-3-yl)-3-(3-(7-methoxy-6-(2-(4-(methyl sulfonyl) piperazin-1-yl)ethoxy) quinazolin-4-ylthio)phenyl) urea | A | B | A | B | B | C |
| 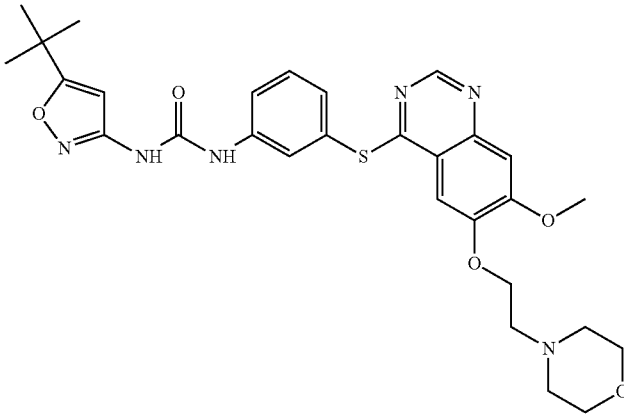 | Ex 70 1-(5-tert-butylisoxazol-3-yl)-3-(3-(7-methoxy-6-(2-morpholino-ethoxy) quinazolin-4-ylthio)phenyl) urea | A | A | A | B | A | C |
| 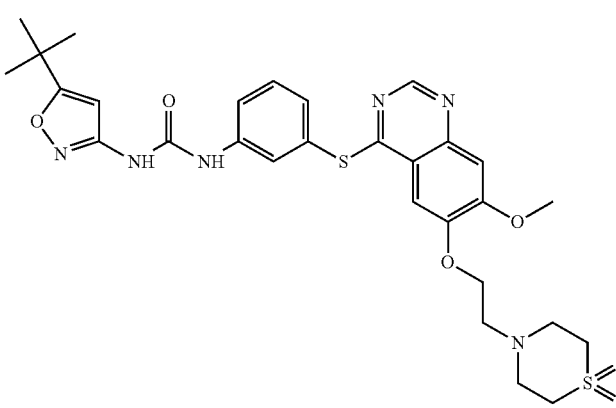 | Ex 71 1-(5-tert-butyl-isoxazol-3-yl)-3-(3-{6-[2-(1,1-dioxo-thiomorpholin-4-yl)-ethoxy]-7-methoxy-quinazolin-4-ylsulfanyl}-phenyl)-urea | A | B | A | A | A | C |
| 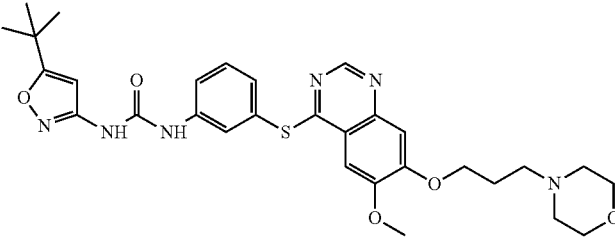 | Ex 72 1-(5-tert-butylisoxazol-3-yl)-3-(3-(6-methoxy-7-(2-morpholino-ethoxy) quinazolin-4-ylthio) phenyl) urea | A | C | A | C | B | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 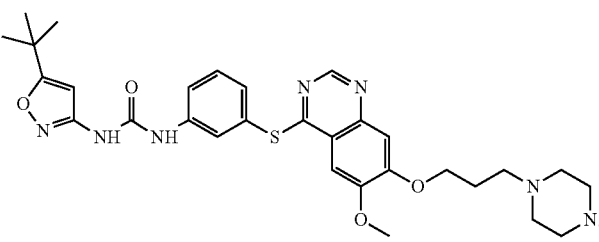 [SMILES: COc1cc2c(Sc3cccc(NC(=O)Nc4cc(C(C)(C)C)on4)c3)ncnc2cc1OCCCN1CCOCC1] Ex 73 1-(5-tert-butylisoxazol-3-yl)-3-(3-(6-methoxy-7-(3-(4-methyl piperazin-1-yl)propoxy) quinazolin-4-ylthio)phenyl) urea | A | C | A | B | B | D |
| 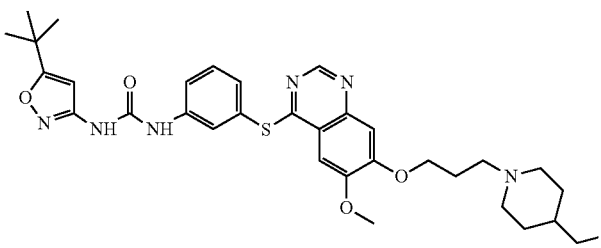 Ex 74 1-(5-tert-butylisoxazol-3-yl)-3-(3-(7-(3-(4-(hydroxyl methyl) piperidin-1-yl)propoxy)-6-methoxy quinazolin-4-ylthio)phenyl) urea | A | B | A | B | A | D |
| 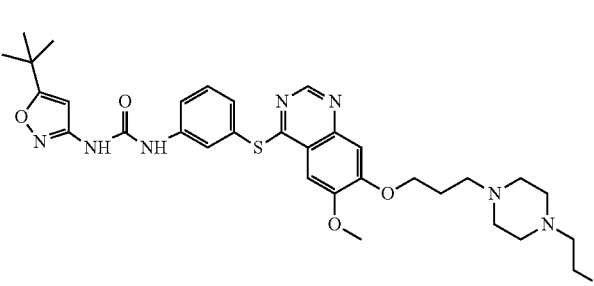 Ex 75 1-(5-tert-butylisoxazol-3-yl)-3-(3-(7-(3-(4-(2-hydroxyethyl) piperazin-1-yl)propoxy)-6-methoxy quinazolin-4-ylthio)phenyl) urea | A | D | A | B | B | D |
| 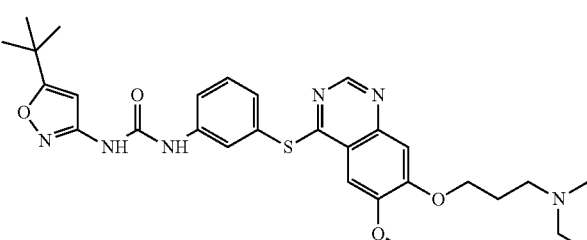 Ex 76 1-(5-tert-butylisoxazol-3-yl)-3-(3-(6-3methoxy-7-(3-(piperidin-1-yl)propoxy) quinazolin-4-ylthio)phenyl) urea | A | D | A | B | C | D |
| 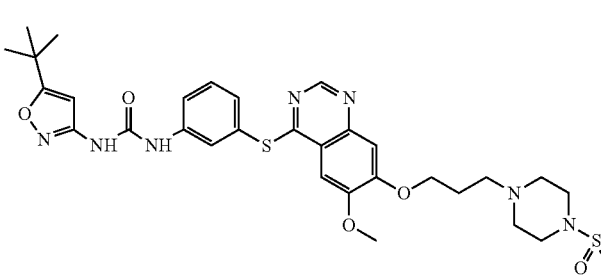 Ex 77 1-(5-tert-butylisoxazol-3-yl)-3-(3-(6-methoxy-7-(3-(4-(methyl sulfonyl) piperazin-1-yl)propoxy) quinazolin-4-ylthio)phenyl) urea | A | B | A | C | C | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 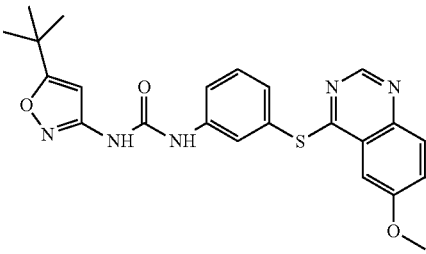 | Ex 79 1-(5-tert-butylisoxazol-3-yl)-3-(3-(6-methoxy-7-(2-morpholino-ethoxy)quinazolin-4-ylthio)phenyl)urea | A | D | A | C | C | D |
| 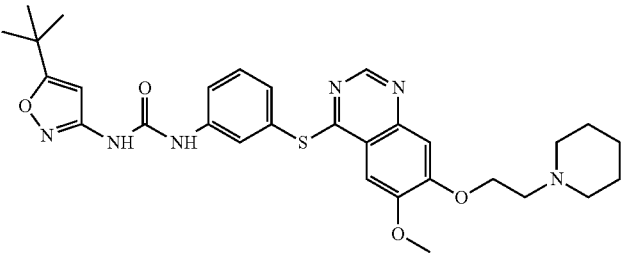 [SMILES: COc1cc2c(Sc3cccc(NC(=O)Nc4cc(C(C)(C)C)on4)c3)ncnc2cc1OCCN1CCCCC1] | Ex 80 1-(5-tert-butylisoxazol-3-yl)-3-(3-(6-methoxy-7-(2-(piperidin-1-yl)ethoxy)quinazolin-4-ylthio)phenyl)urea | B | D | A | B | B | C |
| 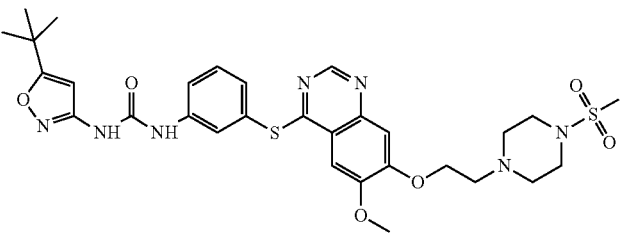 [SMILES: COc1cc2c(Sc3cccc(NC(=O)Nc4cc(C(C)(C)C)on4)c3)ncnc2cc1OCCN1CCN(S(C)(=O)=O)CC1] | Ex 81 1-(5-tert-butylisoxazol-3-yl)-3-(3-(6-methoxy-7-(2-(4-(methylsulfonyl)piperazin-1-yl)ethoxy)quinazolin-4-ylthio)phenyl)urea | A | B | A | C | C | C |
| 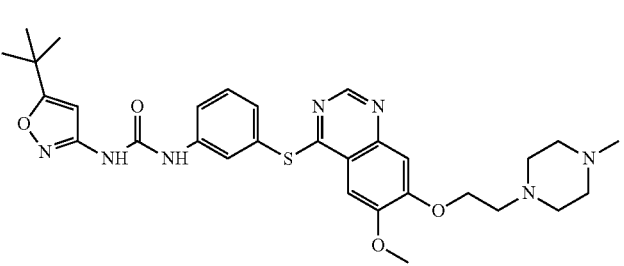 | Ex 83 1-(5-tert-butylisoxazol-3-yl)-3-(3-(6-methoxy-7-(2-(4-methylpiperazin-1-yl)ethoxy)quinazolin-4-ylthio)phenyl)urea | A | D | A | B | B | C |
| 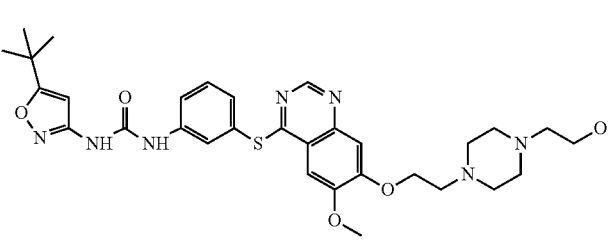 | Ex 84 1-(5-tert-butylisoxazol-3-yl)-3-(3-(7-(2-(4-(2-hydroxyethyl)piperazin-1-yl)ethoxy)-6-methoxyquinazolin-4-ylthio)phenyl)urea | A | D | A | B | B | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 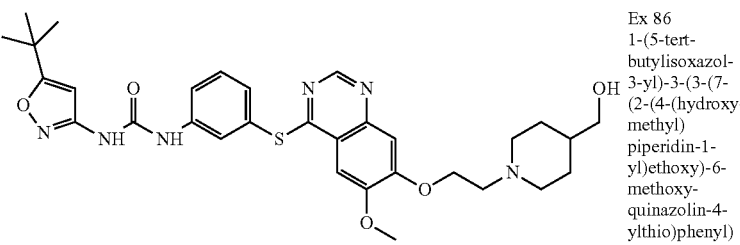 | Ex 86 1-(5-tert-butylisoxazol-3-yl)-3-(3-(7-(2-(4-(hydroxymethyl)piperidin-1-yl)ethoxy)-6-methoxyquinazolin-4-ylthio)phenyl)urea | A | D | B | D | C | C |
| 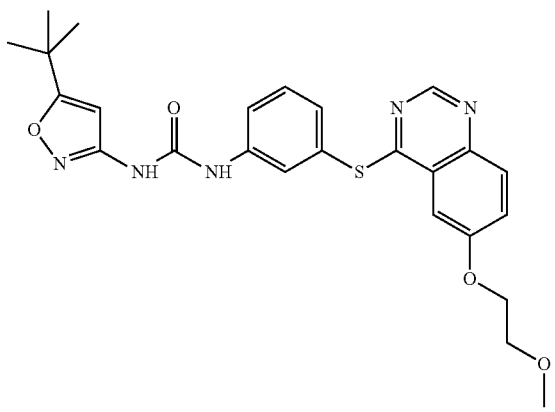 [SMILES: COCCOc1ccc2ncnc(Sc3cccc(NC(=O)Nc4cc(C(C)(C)C)on4)c3)c2c1] | Ex 87 1-(5-tert-butylisoxazol-3-yl)-3-(3-(6-(2-methoxyethoxy)quinazolin-4-ylthio)phenyl)urea | B | D | B | D | C | C |
| 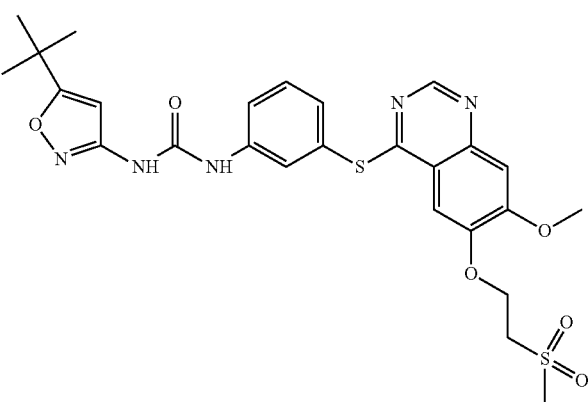 [SMILES: COc1cc2ncnc(Sc3cccc(NC(=O)Nc4cc(C(C)(C)C)on4)c3)c2cc1OCCS(C)(=O)=O] | Ex 88 1-(5-tert-butylisoxazol-3-yl)-3-(3-(7-methoxy-6-(2-(methylsulfonyl)ethoxy)quinazolin-4-ylthio)phenyl)urea | A | C | A | A | A | C |
| 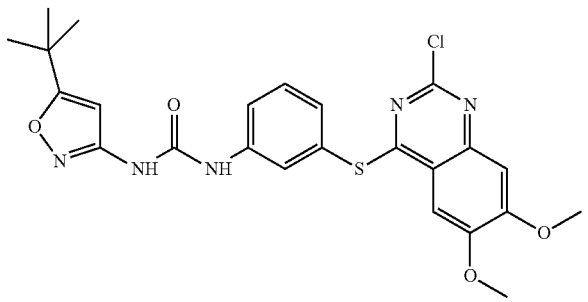 [SMILES: COc1cc2nc(Cl)nc(Sc3cccc(NC(=O)Nc4cc(C(C)(C)C)on4)c3)c2cc1OC] | Ex 89 1-(5-tert-butylisoxazol-3-yl)-3-(3-2-chloro-6,7-dimethoxy-quinazolin-4-ylthio)phenyl urea | D | ND | D | D | D | A |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 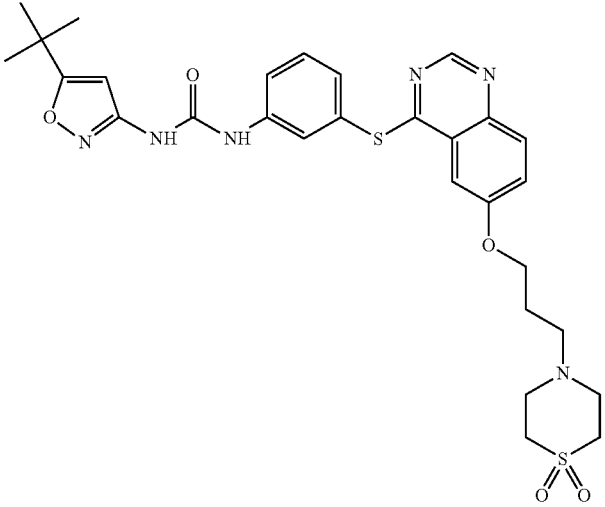 [SMILES: CC(C)(C)c1cc(NC(=O)Nc2cccc(Sc3ncnc4ccc(OCCCN5CCS(=O)(=O)CC5)cc34)c2)no1] | Ex 90 1-(5-tert-Butyl-isoxazol-3-yl)-3-(3-{6-[3-(1,1-dioxo-thiomorpholin-4-yl)-propoxy]-quinazolin-4-ylsulfanyl}-phenyl)-urea | A | D | A | C | B | C |
| 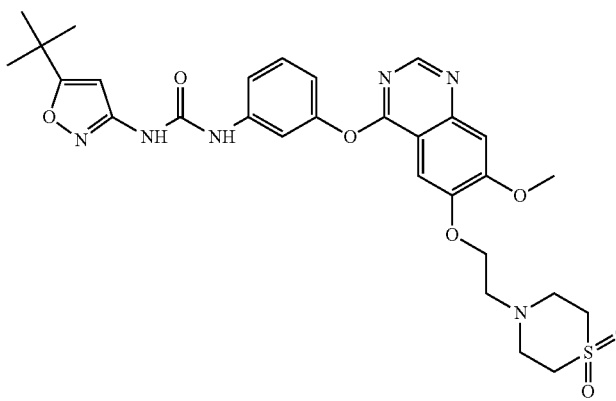 | Ex 91 1-(5-tert-Butyl-isoxazol-3-yl)-3-(3-{6-[2-(1,1-dioxo-1l6-thiomorpholin-4-yl)-ethoxy]-7-methoxy-quinazolin-4-yloxy}-phenyl)-urea | A | A | A | B | B | C |
| 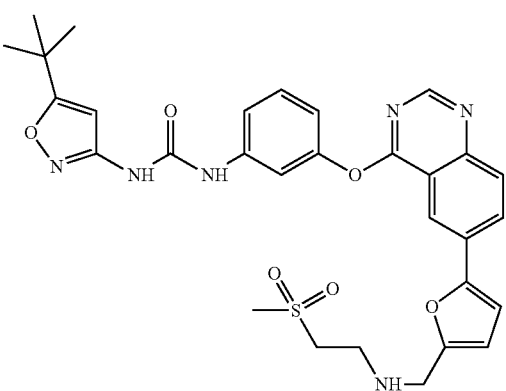 [SMILES: CC(C)(C)c1cc(NC(=O)Nc2cccc(Oc3ncnc4ccc(-c5ccc(CNCCS(C)(=O)=O)o5)cc34)c2)no1] | Ex 92 1-(5-tert-butylisoxazol-3-yl)-3-{3-[6-(5-{[2-(methylsulfonyl)ethylamino]methyl}furan-2-yl)quinazolin-4-yloxy]phenyl}urea | A | A | A | C | B | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 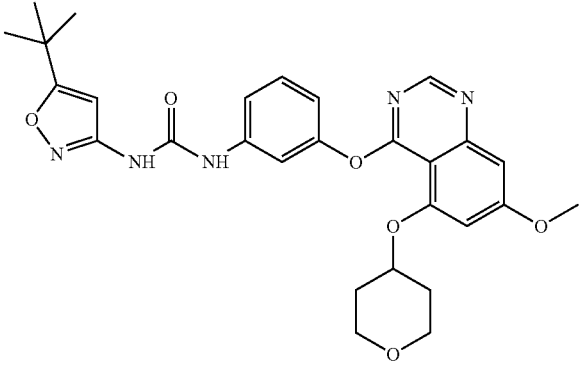 [SMILES: COc1cc(OC2CCOCC2)c2c(Oc3cccc(NC(=O)Nc4cc(C(C)(C)C)on4)c3)ncnc2c1] Ex 94 1-(5-tert-butylisoxazol-3-yl)-3-{3-[7-methoxy-5-(tetrahydro-2H-pyran-4-yloxy)quinazolin-4-yloxy]phenyl}urea | B | D | B | D | B | C |
| 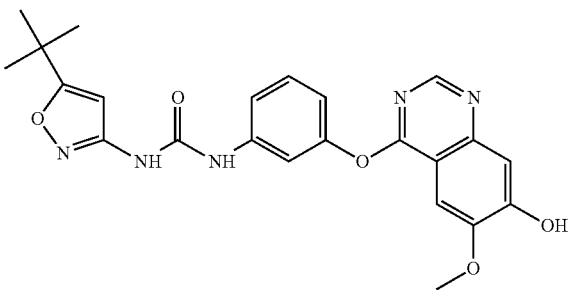 [SMILES: COc1cc2c(Oc3cccc(NC(=O)Nc4cc(C(C)(C)C)on4)c3)ncnc2cc1O] Ex 95 1-(5-tert-butylisoxazol-3-yl)-3-(3-(7-hydroxy-6-methoxy-quinazolin-4-yloxy)phenyl)urea | A | A | A | C | B | C |
| 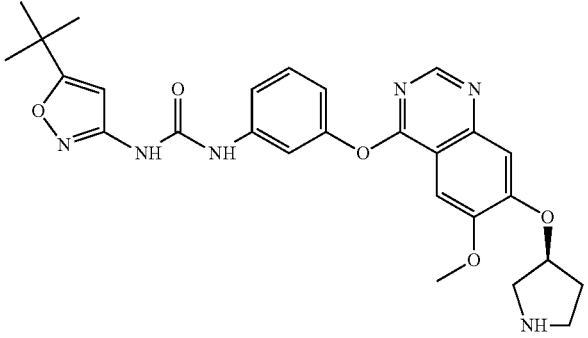 [SMILES: COc1cc2c(Oc3cccc(NC(=O)Nc4cc(C(C)(C)C)on4)c3)ncnc2cc1O[C@H]1CCNC1] Ex 96 (S)-1-(5-tert-butylisoxazol-3-yl)-3-(3-(6-methoxy-7-(pyrrolidin-3-yloxy)quinazolin-4-yloxy)phenyl)urea | B | D | A | B | A | C |
| 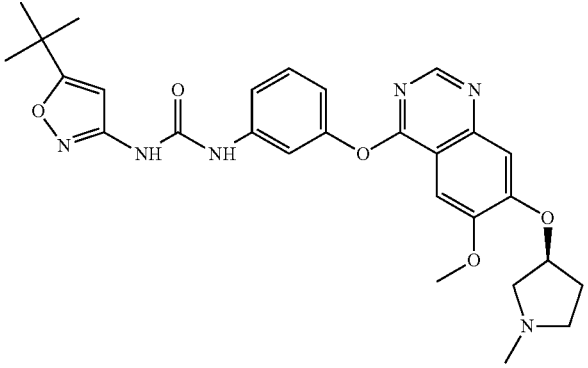 [SMILES: COc1cc2c(Oc3cccc(NC(=O)Nc4cc(C(C)(C)C)on4)c3)ncnc2cc1O[C@H]1CCN(C)C1] Ex 97 (S)-1-(5-tert-butylisoxazol-3-yl)-3-(3-(6-methoxy-7-(1-methyl-pyrrolidin-3-yloxy)quinazolin-4-yloxy)phenyl)urea mono acetate | B | D | A | B | C | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 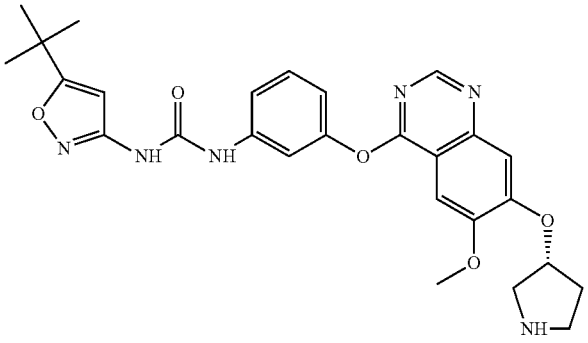 [SMILES: COc1cc2c(Oc3cccc(NC(=O)Nc4cc(C(C)(C)C)on4)c3)ncnc2cc1O[C@@H]1CCNC1] | Ex 98 (R)-1-(5-tert-butylisoxazol-3-yl)-3-(3-(6-methoxy-7-(pyrrolidin-3-yloxy) quinazolin-4-yloxy)phenyl) urea carboxylate | C | D | A | B | A | C |
| 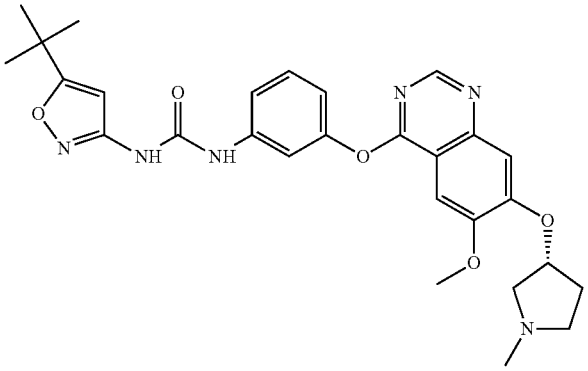 [SMILES: COc1cc2c(Oc3cccc(NC(=O)Nc4cc(C(C)(C)C)on4)c3)ncnc2cc1O[C@@H]1CCN(C)C1] | Ex 99 (R)-1-(5-tert-butylisoxazol-3-yl)-3-(3-(6-methoxy-7-(1-methyl-pyrrolidin-3-yloxy) quinazolin-4-yloxy)phenyl) urea mono acetate | B | D | A | B | B | C |
| 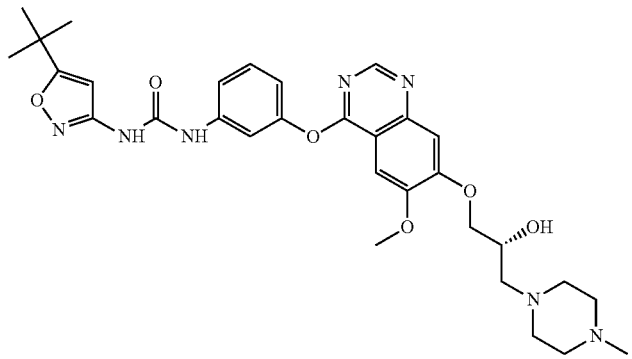 [SMILES: COc1cc2c(Oc3cccc(NC(=O)Nc4cc(C(C)(C)C)on4)c3)ncnc2cc1OC[C@H](O)CN1CCN(C)CC1] | Ex 100 (R)-1-(5-tert-butylisoxazol-3-yl)-3-(3-(7-(2-hydroxy-3-(4-methyl-piperazin-1-yl)propoxy)-6-methoxy quinazolin-4-yloxy)phenyl) urea | A | A | A | A | A | D |
| 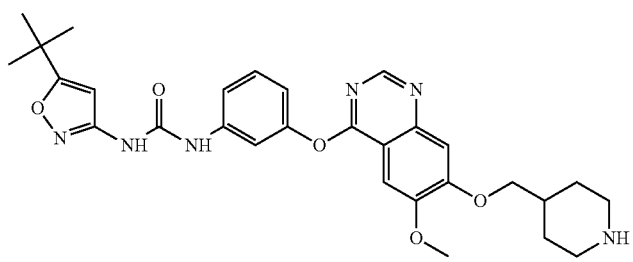 [SMILES: COc1cc2c(Oc3cccc(NC(=O)Nc4cc(C(C)(C)C)on4)c3)ncnc2cc1OCC1CCNCC1] | Ex 101 1-(3-tert-Butylisoxazol-5-yl)-3-(3-(6-methoxy-7-(piperidin-4-ylmethoxy) quinazolin-4-yloxy)phenyl) urea | A | C | A | A | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 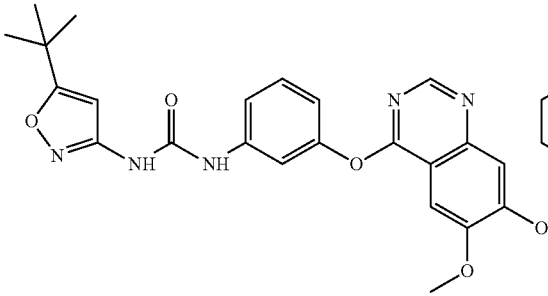 | Ex 102 1-(3-tert-butylisoxazol-5-yl)-3-(3-(6-methoxy-7-((1-methyl-piperidin-4-yl)methoxy)quinazolin-4-yloxy)phenyl)urea | A | A | A | A | B | D |
| 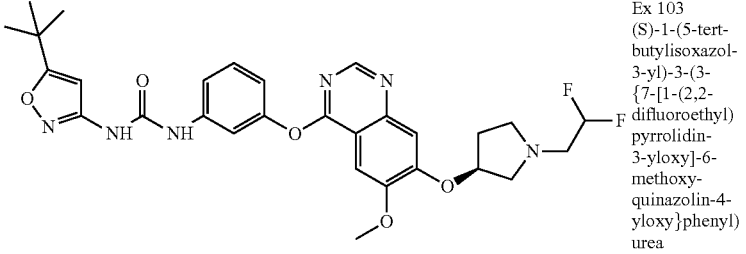 | Ex 103 (S)-1-(5-tert-butylisoxazol-3-yl)-3-(3-{7-[1-(2,2-difluoroethyl)pyrrolidin-3-yloxy]-6-methoxy-quinazolin-4-yloxy}phenyl)urea | C | D | B | D | D | C* |
| 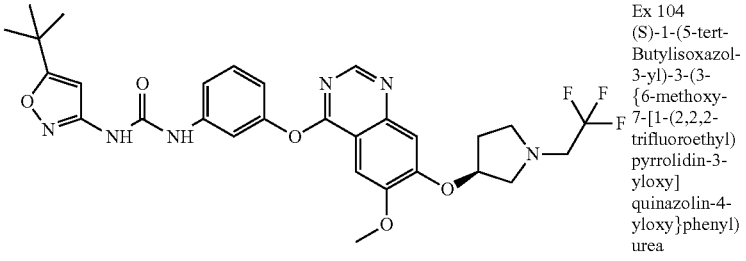 | Ex 104 (S)-1-(5-tert-Butylisoxazol-3-yl)-3-(3-{6-methoxy-7-[1-(2,2,2-trifluoroethyl)pyrrolidin-3-yloxy]quinazolin-4-yloxy}phenyl)urea | C | D | D | D | D | B* |
| 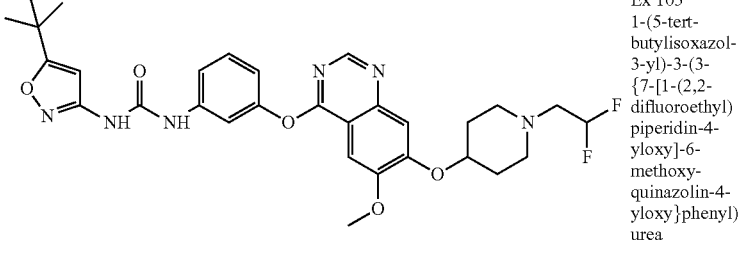 | Ex 105 1-(5-tert-butylisoxazol-3-yl)-3-(3-{7-[1-(2,2-difluoroethyl)piperidin-4-yloxy]-6-methoxy-quinazolin-4-yloxy}phenyl)urea | D | D | D | D | D | C* |
| 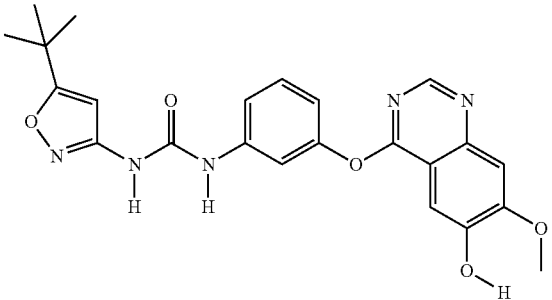 [SMILES: COc1cc2ncnc(Oc3cccc(NC(=O)Nc4cc(C(C)(C)C)on4)c3)c2cc1O] | Ex 107 1-(5-tert-butylisoxazol-3-yl)-3-(3-(6-hydroxy-7-methoxy-quinazolin-4-yloxy)phenyl)urea | A | B | A | B | A | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 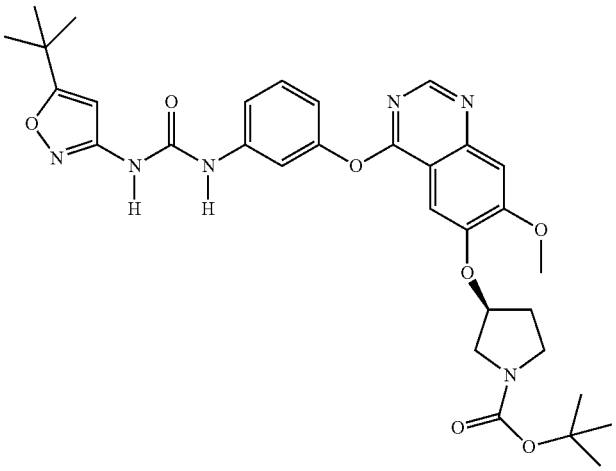 [SMILES: COc1cc2ncnc(Oc3cccc(NC(=O)Nc4cc(C(C)(C)C)on4)c3)c2cc1O[C@H]1CCN(C(=O)OC(C)(C)C)C1] Ex 108 (S)-tert-butyl 3-(4-(3-(3-(5-tert-butylisoxazole-3-yl)ureido) phenoxy)-7-methoxy-quinazolin-6-yloxy) pyrrolidine-1-carboxylate | A | C | C | D | D | C |
| 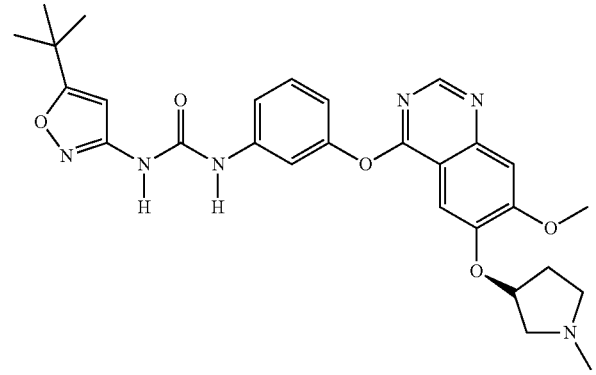 Ex 109 (S)-1-(5-tert-butylisoxazol-3-yl)-3-(3-(7-methoxy-6-(1-methyl-pyrrolidin-3-yloxy)-quinazolin-4-yloxy)phenyl) urea | A | B | A | B | A | D |
| 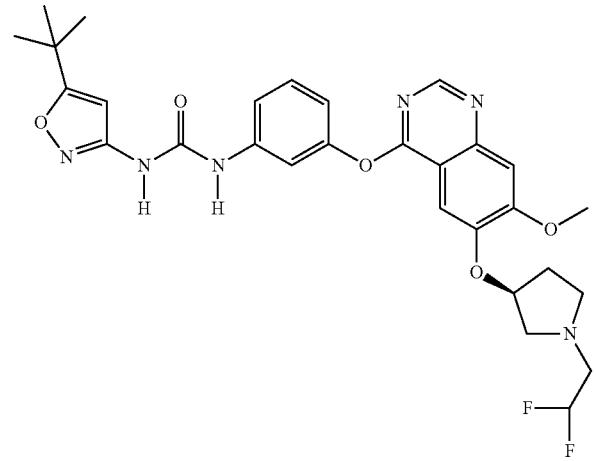 [SMILES: COc1cc2ncnc(Oc3cccc(NC(=O)Nc4cc(C(C)(C)C)on4)c3)c2cc1O[C@H]1CCN(CC(F)F)C1] Ex 110 (S)-1-(5-tert-butylisoxazol-3-yl)-3-(3-(6-(1-(2,2-difluoroethyl) pyrrolidin-3-yloxy)-7-methoxy-quinazolin-4-yloxy)phenyl urea | A | A | A | B | A | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 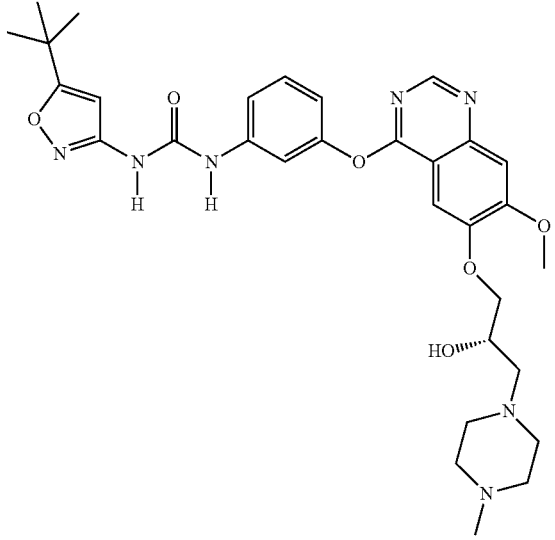 [SMILES: COc1cc2ncnc(Oc3cccc(NC(=O)Nc4cc(C(C)(C)C)on4)c3)c2cc1OC[C@@H](O)CN1CCN(C)CC1] | Ex 111 (S)-1-(5-tert-butylisoxazol-3-yl)-3-(3-(6-(2-hydroxy-3-(4methyl-piperazin-1-yl)propoxy)-7-methoxy-quinazolin-4-yloxy)phenyl)urea | A | B | A | B | A | D |
| 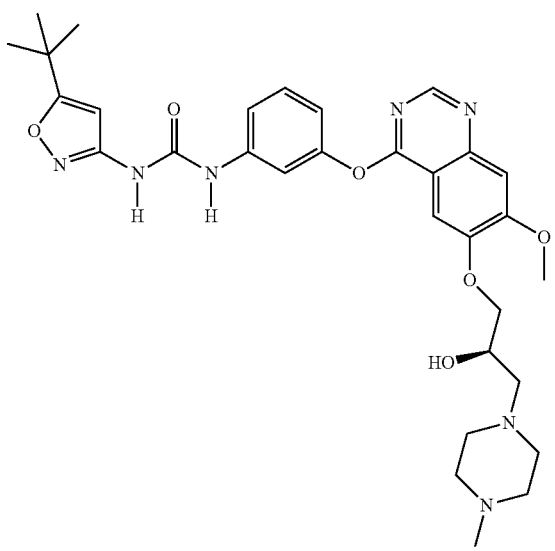 [SMILES: COc1cc2ncnc(Oc3cccc(NC(=O)Nc4cc(C(C)(C)C)on4)c3)c2cc1OC[C@H](O)CN1CCN(C)CC1] | Ex 112 (R)-1-(5-tert-butylisoxazol-3-yl)-3-(3-(6-(2-hydroxy-3-(4methyl-piperazin-1-yl)propoxy)-7-methoxy-quinazolin-4-yloxy)phenyl)urea | B | C | A | C | B | D |
| 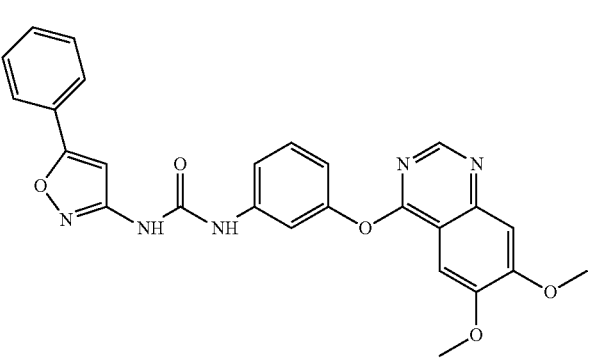 [SMILES: COc1cc2ncnc(Oc3cccc(NC(=O)Nc4cc(-c5ccccc5)on4)c3)c2cc1OC] | Ex 113 1-(3-(6,7-dimethoxy-quinazolin-4-yloxy)phenyl)-3-(5-phenyl-isoxazol-3-yl)urea | C | D | B | C | A | B |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 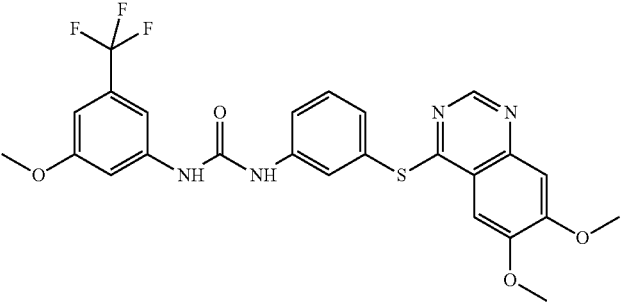 | Ex 115 1-(3-(6,7-dimethoxy-quinazolin-4-ylthio)phenyl)-3-(3-methoxy-5-(trifluoro-methyl)phenyl)urea | D | D | B | C | B | C |
| 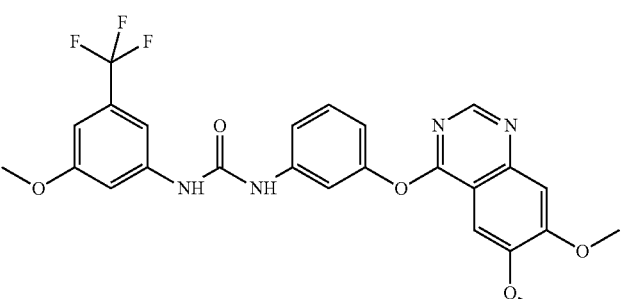 | Ex 116 1-(3-(6,7-dimethoxy-quinazolin-4-yloxy)phenyl)-3-(3-methoxy-5-(trifluoro-methyl)phenyl)urea | D | D | B | C | B | B |
| 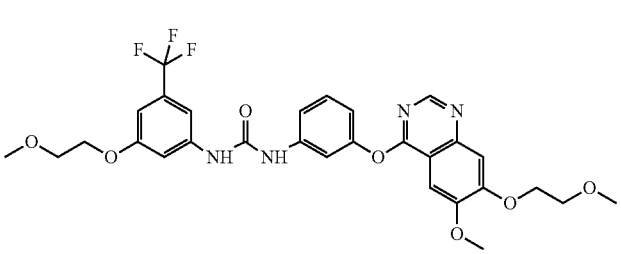 | Ex 117 1-(3-(6-methoxy-7-(2-methoxy-ethoxy)quinazolin-4-yloxy)phenyl)-3-(3-(2-methoxy-ethoxy)-5-(trifluoro-methyl)phenyl)urea | D | D | B | C | B | C |
| 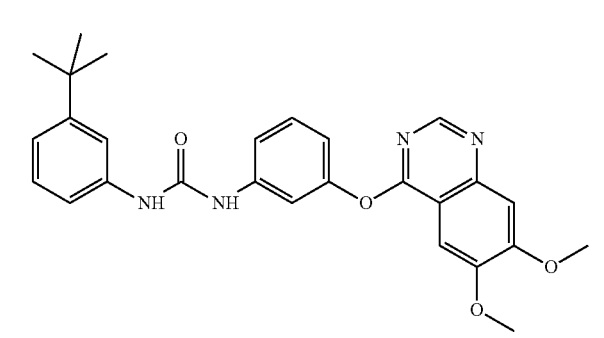 [SMILES: COc1cc2ncnc(Oc3cccc(NC(=O)Nc4cccc(C(C)(C)C)c4)c3)c2cc1OC] | Ex 118 1-(3-tert-butylphenyl)-3-(3-(6,7-dimethoxy-quinazolin-4-yloxy)phenyl)urea | B | D | A | B | A | C* |
| 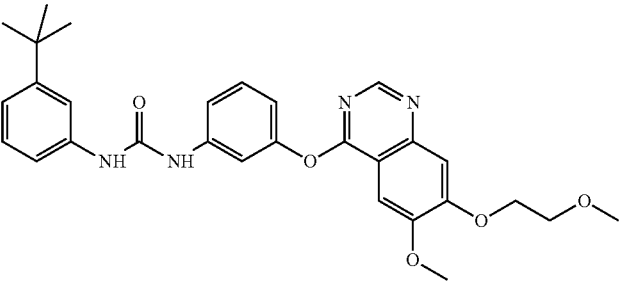 [SMILES: COCCOc1cc2ncnc(Oc3cccc(NC(=O)Nc4cccc(C(C)(C)C)c4)c3)c2cc1OC] | Ex 119 1-(3-tert-butylphenyl)-3-(3-(6-(methoxy-7-(2-methoxy-ethoxy)quinazolin-4-yloxy)phenyl)urea | B | D | A | B | B | C* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 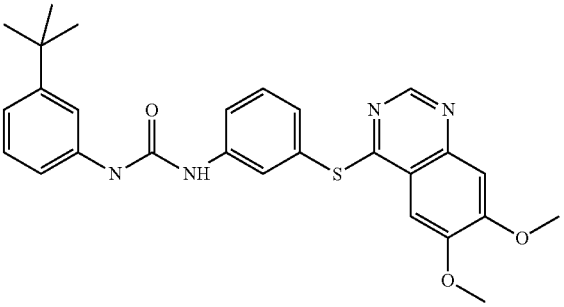 [SMILES: COc1cc2ncnc(Sc3cccc(NC(=O)Nc4cccc(C(C)(C)C)c4)c3)c2cc1OC] | Ex 120 1-(3-tert-butylphenyl)-3-(3-(6,7-dimethoxy-quinazolin-4-yloxy)phenyl) urea | B | D | A | B | A | C* |
| 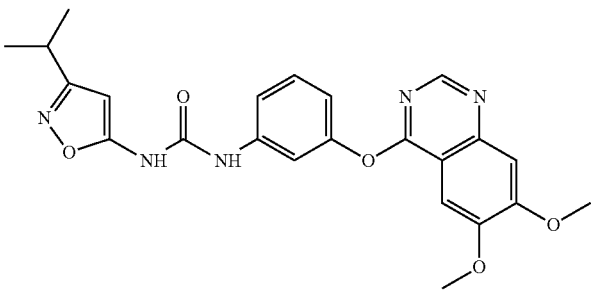 [SMILES: COc1cc2ncnc(Oc3cccc(NC(=O)Nc4cc(C(C)C)no4)c3)c2cc1OC] | Ex 122 1-(3-(6,7-dimethoxy-quinazolin-4-yloxy)phenyl)-3-(3-isopropyl-isoxazol-5-yl)urea | B | D | A | A | A | C |
| 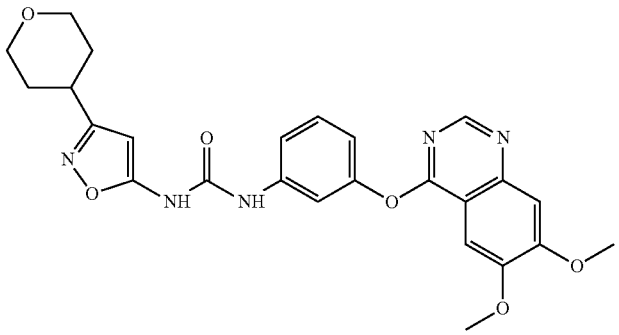 [SMILES: COc1cc2ncnc(Oc3cccc(NC(=O)Nc4cc(C5CCOCC5)no4)c3)c2cc1OC] | Ex 123 1-(3-(6,7-dimethoxy-quinazolin-4-yloxy)phenyl)-3-(3-(tetrahydro-2H-pyran-4-yl)isoxazol-5-yl)urea | D | D | B | D | C | B |
| 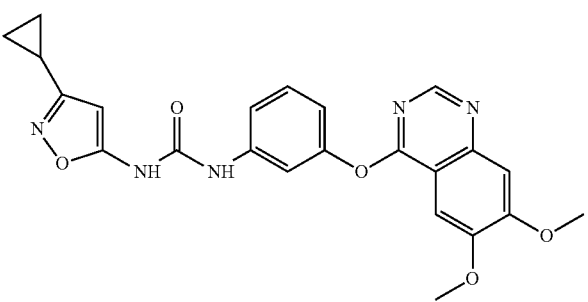 [SMILES: COc1cc2ncnc(Oc3cccc(NC(=O)Nc4cc(C5CC5)no4)c3)c2cc1OC] | Ex 124 1-(3-cyclopropyl-isoxazol-5-yl)-3-(3-(6,7-dimethoxy-quinazolin-4-yloxy)phenyl) urea | D | D | A | A | A | C |
| 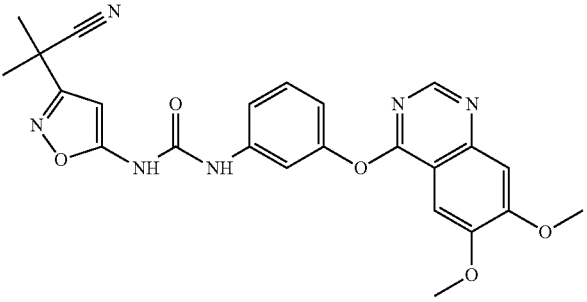 [SMILES: COc1cc2ncnc(Oc3cccc(NC(=O)Nc4cc(C(C)(C)C#N)no4)c3)c2cc1OC] | Ex 125 1-(3-(2-cyanopropan-2-yl)isoxazol-5-yl)-3-(3-(6,7-dimethoxy-quinazolin-4-yloxy)phenyl) urea | B | D | A | B | B | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 126 1-(3-(6,7-dimethoxyquinazolin-4-yloxy)phenyl)-3-(3-(2-fluoropropan-2-yl)isoxazol-5-yl)urea | A | C | A | B | A | C |
| Ex 127 1-(3-(6,7-dimethoxyquinazolin-4-yloxy)phenyl)-3-(5-(1-methylcyclopropyl)isoxazol-3-yl)urea | B | D | A | A | A | C |
| Ex 128 1-(3-(6,7-dimethoxyquinazolin-4-yloxy)phenyl)-3-(3-(1-methoxy-2-methylpropan-2-yl)isoxazol-5-yl)urea | C | D | A | D | D | C* |
| Ex 129 1-(3-(6,7-dimethoxyquinazolin-4-yloxy)phenyl)-3-(3-(2-methoxyethoxy)-5-(trifluoromethyl)phenyl)urea | D | D | B | D | B | B |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 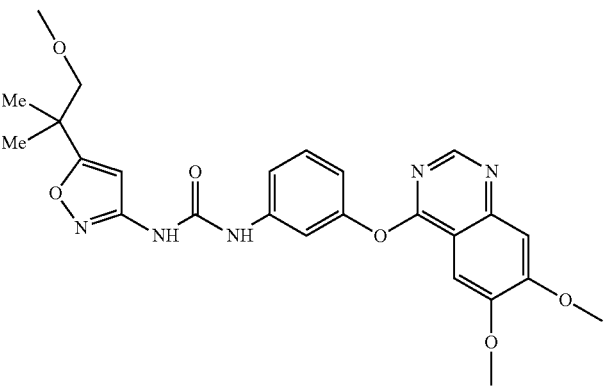 [SMILES: COCC(C)(C)c1cc(NC(=O)Nc2cccc(Oc3ncnc4cc(OC)c(OC)cc34)c2)no1] | Ex 130 1-(3-(6,7-dimethoxy-quinazolin-4-yloxy)phenyl)-3-(5-(1-methoxy-2-methylpropan-2-yl)isoxazol-3-yl)urea | B | D | B | D | D | C |
| 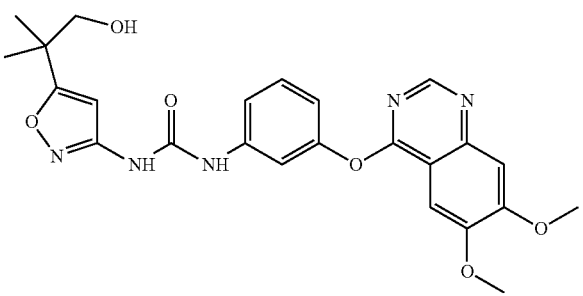 [SMILES: COc1cc2ncnc(Oc3cccc(NC(=O)Nc4cc(C(C)(C)CO)on4)c3)c2cc1OC] | Ex 131 1-(3-(6,7-dimethoxy-quinazolin-4-yloxy)phenyl)-3-(5-(1-hydroxy-2-methylpropan-2-yl)isoxazol-3-yl)urea | C | D | A | B | A | C |
| 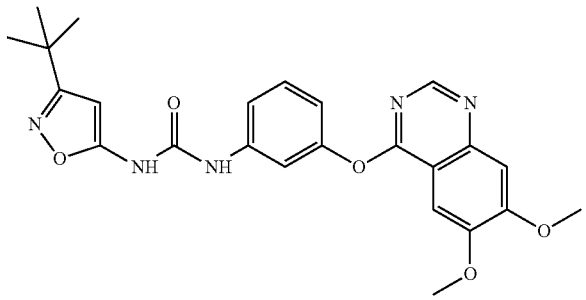 [SMILES: COc1cc2ncnc(Oc3cccc(NC(=O)Nc4cc(C(C)(C)C)no4)c3)c2cc1OC] | Ex 132 1-(3-tert-butylisoxazol-5-yl)-3-(3-(6,7-dimethoxy quinazolin-4-yloxy)phenyl) urea | A | A | A | C | C | C |
| 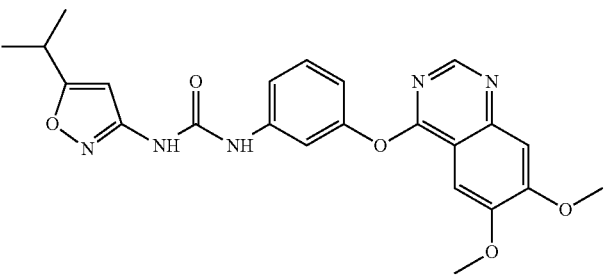 [SMILES: COc1cc2ncnc(Oc3cccc(NC(=O)Nc4cc(C(C)C)on4)c3)c2cc1OC] | Ex 133 1-(3-(6,7-dimethoxy-quinazolin-4-yloxy)phenyl)-3-(5-isopropyl isoxazol-3-yl)urea | B | C | A | A | A | C* |
| 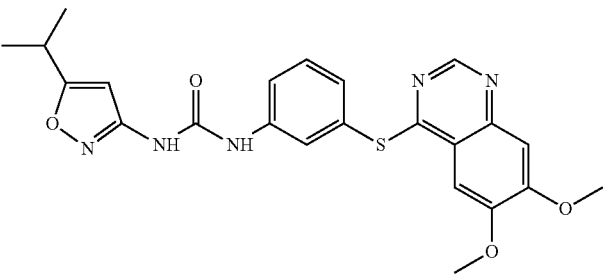 [SMILES: COc1cc2ncnc(Sc3cccc(NC(=O)Nc4cc(C(C)C)on4)c3)c2cc1OC] | Ex 134 1-(3-(6,7-dimethoxy-quinazolin-4-ylthio)phenyl)-3-(5-isopropyl-isoxazol-3-yl)urea | B | D | A | A | A | C* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 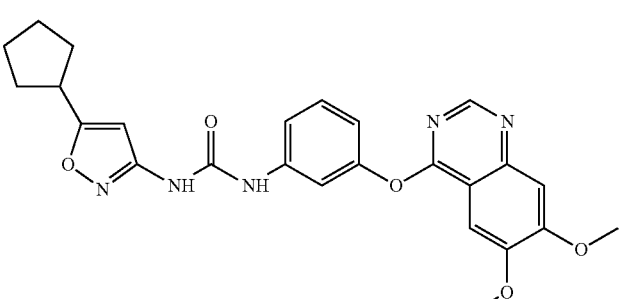 | Ex 135 1-(5-cyclopentyl-isoxazol-3-yl)-3-(3-(6,7-dimethoxy quinazolin-4-yloxy)phenyl) urea | A | B | A | A | A | C* |
| 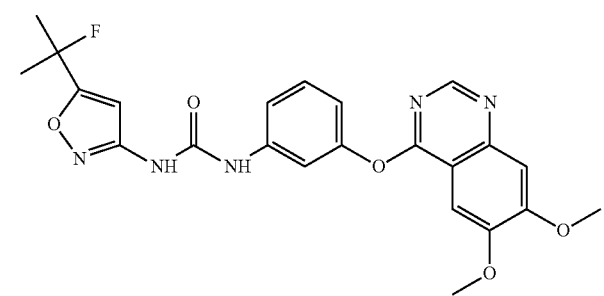 [SMILES: COc1cc2ncnc(Oc3cccc(NC(=O)Nc4cc(C(C)(C)F)on4)c3)c2cc1OC] | Ex 136 1-(3-(6,7-dimethoxy-quinazolin-4-yloxy)phenyl)-3-(5-(2-fluoropropan-2-yl)isoxazol-3-yl)urea | A | B | A | A | A | C* |
| 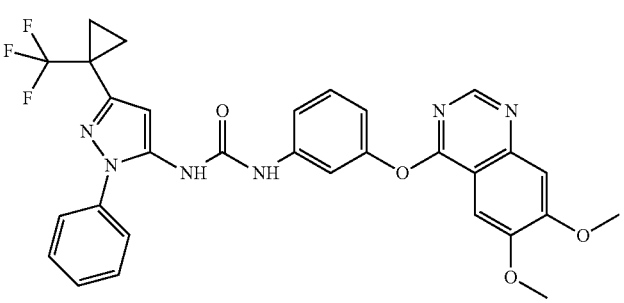 [SMILES: COc1cc2ncnc(Oc3cccc(NC(=O)Nc4cc(C5(C(F)(F)F)CC5)nn4-c4ccccc4)c3)c2cc1OC] | Ex 137 1-(3-(6,7-dimethoxy-quinazolin-4-yloxy)phenyl)-3-(1-phenyl-3-(1-(trifluoro methyl)cyclo propyl)-1H-pyrazol-5-yl) urea | A | C | C | D | D | D* |
| 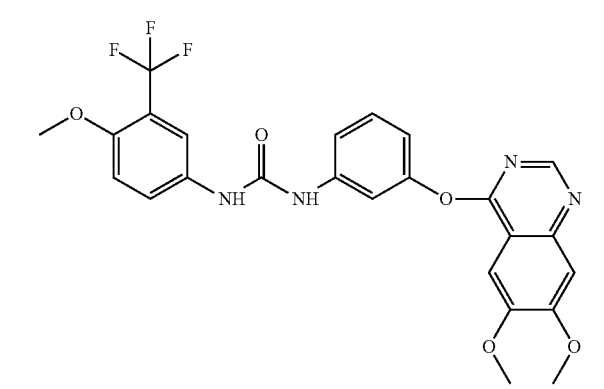 [SMILES: COc1cc2ncnc(Oc3cccc(NC(=O)Nc4ccc(OC)c(C(F)(F)F)c4)c3)c2cc1OC] | Ex 138 1-(3-(6,7-dimethoxy-quinazolin-4-yloxy)phenyl)-3-(4-methoxy-3-(trifluoro methyl)phenyl) urea | B | D | A | B | A | B |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 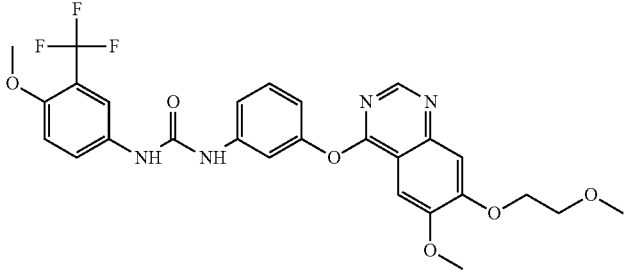 [SMILES: COCCOc1cc2ncnc(Oc3cccc(NC(=O)Nc4ccc(OC)c(C(F)(F)F)c4)c3)c2cc1OC] | Ex 139 1-(4-methoxy-3-(trifluoromethyl)phenyl)-3-(3-(6-methoxy-7-(2-methoxyethoxy)quinazolin-4-yloxy)phenyl)urea | B | D | A | A | A | C* |
| 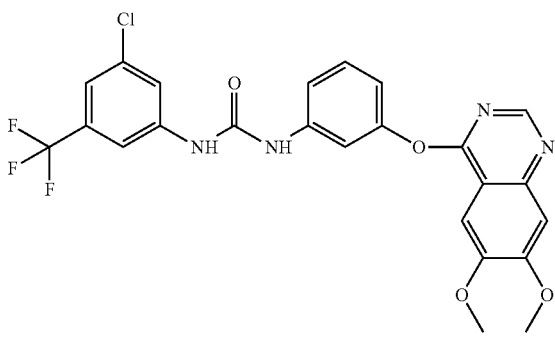 [SMILES: COc1cc2ncnc(Oc3cccc(NC(=O)Nc4cc(Cl)cc(C(F)(F)F)c4)c3)c2cc1OC] | Ex 140 1-(3-chloro-5-(trifluoromethyl)phenyl)-3-(3-(6,7-dimethoxyquinazolin-4-yloxy)phenyl)urea | D | D | C | D | C | B |
| 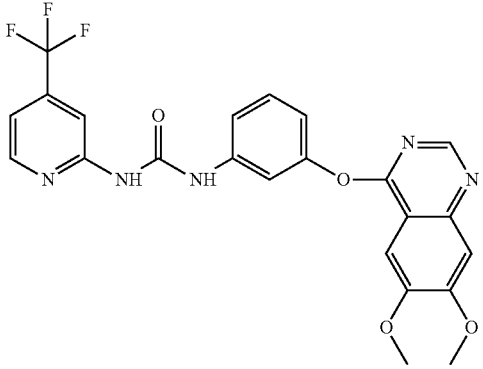 [SMILES: COc1cc2ncnc(Oc3cccc(NC(=O)Nc4cc(C(F)(F)F)ccn4)c3)c2cc1OC] | Ex 141 1-(3-(6,7-dimethoxy-quinazolin-4-yloxy)phenyl)-3-(4-(trifluoromethyl)pyridin-2-yl)urea | C | D | A | A | A | C |
| 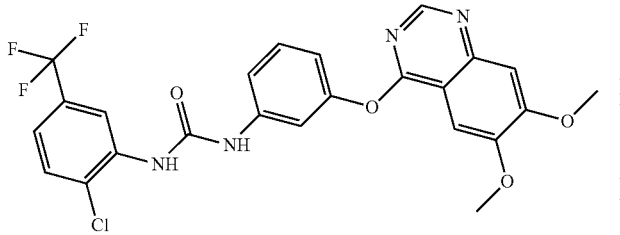 [SMILES: COc1cc2ncnc(Oc3cccc(NC(=O)Nc4cc(C(F)(F)F)ccc4Cl)c3)c2cc1OC] | Ex 142 1-(2-chloro-5-(trifluoromethyl)phenyl)-3-(3-(6,7-dimethoxy-quinazolin-4-yloxy)phenyl)urea | D | D | B | D | B | B |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 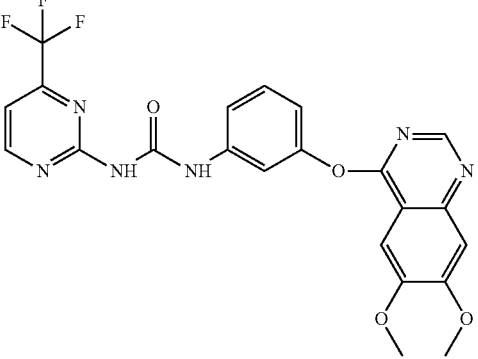 | Ex 143 1-(3-(6,7-dimethoxy-quinazolin-4-yloxy)phenyl)-3-(4-(trifluoromethyl)pyrimidin-2-yl)urea | D | D | B | D | B | A |
| 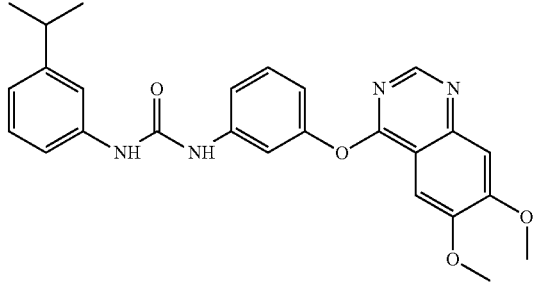 [SMILES: COc1cc2ncnc(Oc3cccc(NC(=O)Nc4cccc(C(C)C)c4)c3)c2cc1OC] | Ex 144 1-(3-(6,7-dimethoxy-quinazolin-4-yloxy)phenyl)-3-(3-isopropyl-phenyl)urea | B | D | A | B | A | C* |
| 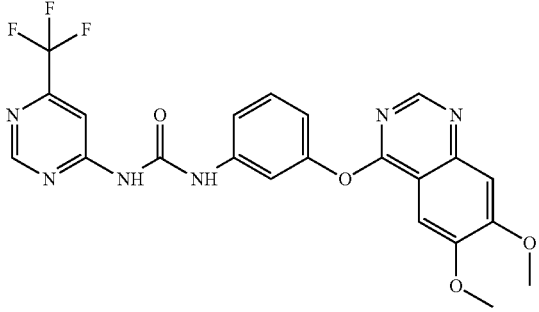 [SMILES: COc1cc2ncnc(Oc3cccc(NC(=O)Nc4cc(C(F)(F)F)ncn4)c3)c2cc1OC] | Ex 146 1-(3-(6,7-dimethoxy-quinazolin-4-yloxy)phenyl)-3-(6-(trifluoromethyl)pyrimidin-4-yl)urea | D | D | A | B | B | B* |
| 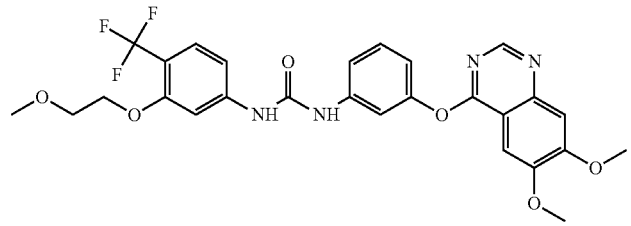 | Ex 147 1-(3-(6,7-dimethoxy-quinazolin-4-yloxy)phenyl)-3-(3-(2-methoxy-ethoxy)-4-(trifluoro-methyl)phenyl)urea | D | D | B | D | C | B* |
| 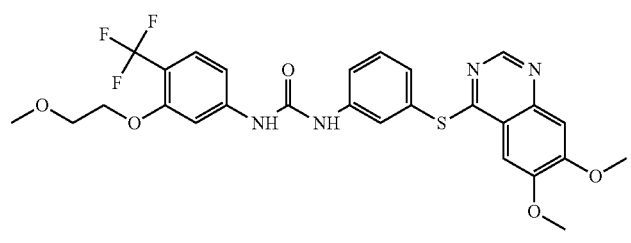 | Ex 148 1-(3-(6,7-Dimethoxy-quinazolin-4-ylthio)phenyl)-3-(3-(2-methoxy-ethoxy)-4-(trifluoro-methyl)phenyl)urea | D | D | C | D | D | B* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 149 1-(3-(6,7-dimethoxy-quinazolin-4-yloxy)phenyl)-3-(3-(morpholine-4-carbonyl)-5-(trifluoro-methyl)phenyl)urea | D | D | C | D | D | B* |
| Ex 150 1-(3-(6,7-dimethoxy-quinazolin-4-yloxy)phenyl)-3-(3-fluoro-4-(trifluoro-methyl)phenyl)urea | D | D | B | C | C | C* |
| Ex 151 1-(3-(6,7-dimethoxy-quinazolin-4-yloxy)phenyl)-3-(3-(morpholino methyl)-5-(trifluoro-methyl)phenyl)urea | D | D | A | D | B | C* |
| Ex 152 1-(3-(1,1-difluoroethyl)isoxazol-5-yl)-3-(3-(6,7-dimethoxy-quinazolin-4-yloxy)phenyl)urea | C | C | A | B | B | C* |
| Ex 153 1-(3-tert-butyl-1-phenyl-1H-pyrazol-5-yl)-3-(3-(6,7-dimethoxy-quinazolin-4-yloxy)phenyl)urea | A | ND | C | D | D | D* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 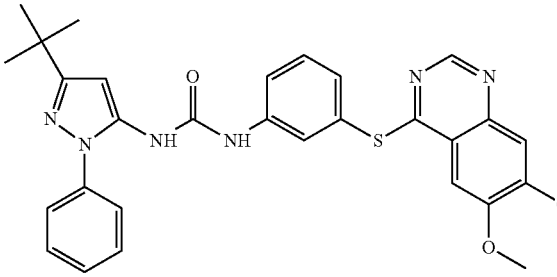 | Ex 154 1-(3-tert-butyl-1-phenyl-1H-pyrazol-5-yl)-3-(3-(6,7-dimethoxy-quinazolin-4-ylthio)phenyl) urea | A | ND | D | D | D | D* |
| 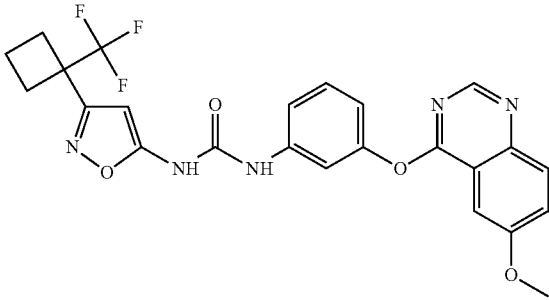 | Ex 155 1-(3-(6,7-dimethoxy-quinazolin-4-yloxy)phenyl)-3-(3-(1-(trifluoro-methyl)cyclo-butyl)isoxazol-5-yl)urea | B | D | B | D | D | C* |
| 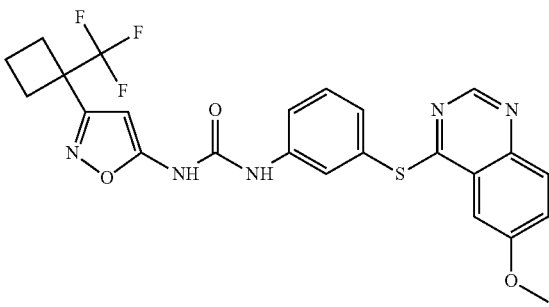 | Ex 156 1-(3-(6,7-dimethoxy-quinazolin-4-ylthio)phenyl)-3-(3-(1-(trifluoro-methyl)cyclo-butyl)isoxazol-5-yl)urea | C | D | C | D | D | C* |
| 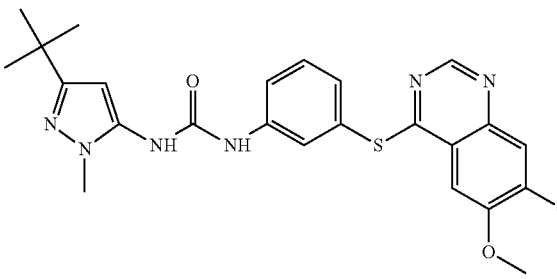 | Ex 157 1-(3-tert-butyl-1-methyl-1H-pyrazol-5-yl)-3-(3-(6,7-dimethoxy-quinazolin-4-ylthio)phenyl) urea | A | D | A | C | B | C* |
| 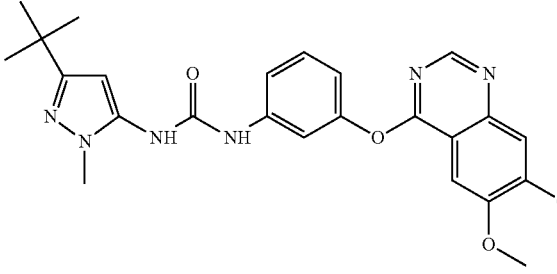 | Ex 158 1-(3-tert-butyl-1-methyl-1H-pyrazol-5-yl)-3-(3-(6,7-dimethoxy-quinazolin-4-yloxy)phenyl) urea | B | D | A | D | C | C* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 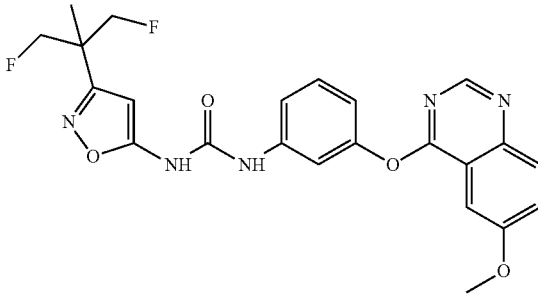 | Ex 159 1-[3-(1,3-difluoro-2-methylpropan-2-yl)isoxazol-5-yl]-3-[3-(6,7-dimethoxy-quinazolin-4-yloxy]phenyl) urea | B | D | B | C | C | D* |
| 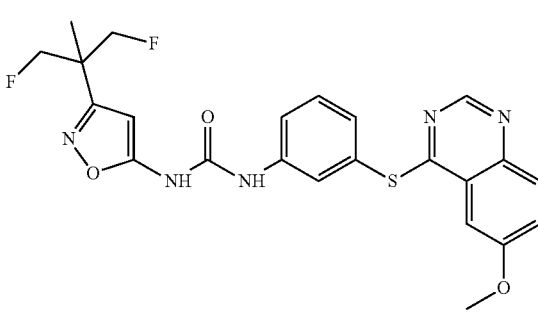 | Ex 160 1-[3-(1,3-difluoro-2-methylpropan-2-yl)isoxazol-5-yl]-3-[3-(6,7-dimethoxy-quinazolin-4-ylthio]phenyl) urea | A | D | A | C | B | C* |
| 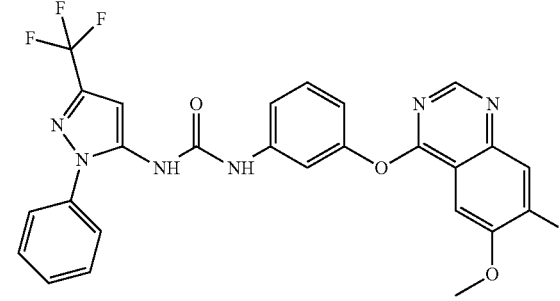 | Ex 161 1-[3-(6,7-dimethoxy-quinazolin-4-yloxy)phenyl]-3-[1-phenyl-3-(trifluoro-methyl)-1H-pyrazol-5-yl]urea | A | B | C | D | D | C* |
| 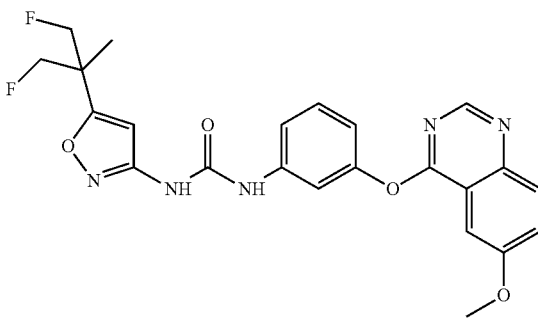 | Ex 162 1-[5-(1,3-difluoro-2-methylpropan-2-yl)isoxazol-3-yl]-3-[3-(6,7-dimethoxy-quinazolin-4-yloxy)phenyl] urea | A | A | A | B | A | C* |
| 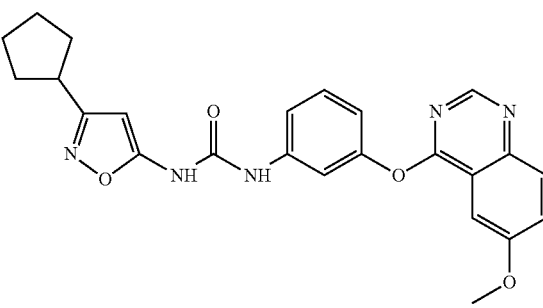 | Ex 163 1-(3-cyclopentyl-isoxazol-5-yl)-3-(3-(6,7-dimethoxy-quinazolin-4-yloxy)phenyl) urea | D | D | B | D | C | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 164 1-[3-(6,7-dimethoxy-quinazolin-4-yloxy)phenyl]-3-[1-methyl-3-(trifluoro-methyl)-1H-pyrazol-5-yl]urea | B | D | A | A | A | C* |
| Ex 165 1-[3-(6,7-dimethoxy-quinazolin-4-yloxy)phenyl]-3-[1-methyl-5-(trifluoro-methyl)-1H-pyrazol-3-yl]urea | B | C | A | A | A | C* |
| Ex 166 ethyl 2-(3-tert-butyl-5-{3-[3-(6,7-dimethoxy-quinazolin-4-yloxy)phenyl]ureido}-1H-pyrazol-1-yl)acetate | C | D | B | D | D | C* |
| Ex 167 1-[3-(1,3-difluoro-2-methylpropan-2-yl)-1-phenyl-1H-pyrazol-5-yl]-3-[3-(6,7-dimethoxy-quinazolin-4-yloxy)phenyl]urea | A | C | D | D | D | D* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 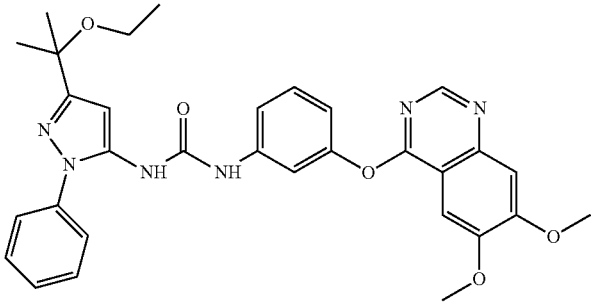 [SMILES: CCOC(C)(C)c1cc(NC(=O)Nc2cccc(Oc3ncnc4cc(OC)c(OC)cc34)c2)n(-c2ccccc2)n1] | Ex 168 1-[3-(6,7-dimethoxy-quinazolin-4-yloxy)phenyl]-3-[3-(2-ethoxypropan-2-yl)-1-phenyl-1H-pyrazol-5-yl]urea | A | D | C | D | D | C* |
| 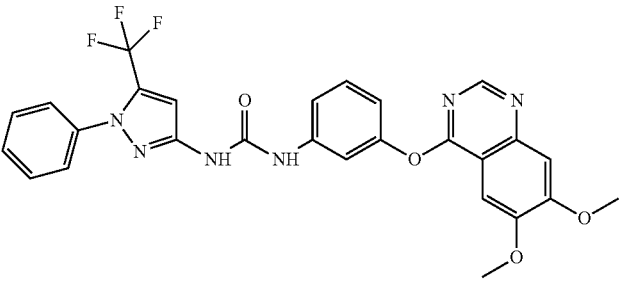 [SMILES: COc1cc2ncnc(Oc3cccc(NC(=O)Nc4cc(C(F)(F)F)n(-c5ccccc5)n4)c3)c2cc1OC] | Ex 169 1-[3-(6,7-dimethoxy-quinazolin-4-yloxy)phenyl]-3-[1-phenyl-5-(trifluoro-methyl)-1H-pyrazol-3-yl]urea | B | D | B | D | C | C* |
| 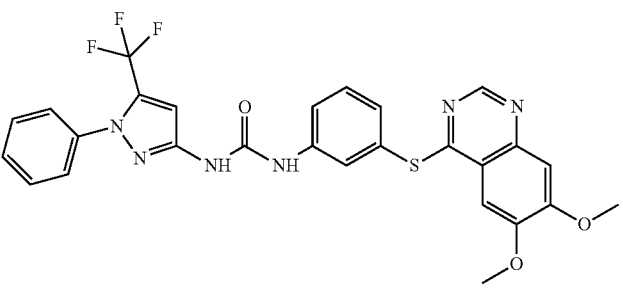 [SMILES: COc1cc2ncnc(Sc3cccc(NC(=O)Nc4cc(C(F)(F)F)n(-c5ccccc5)n4)c3)c2cc1OC] | Ex 170 1-[3-(6,7-dimethoxy-quinazolin-4-ylthio)phenyl]-3-[1-phenyl-5-(trifluoro-methyl)-1H-pyrazol-3-yl]urea | B | B | D | D | D | B* |
| 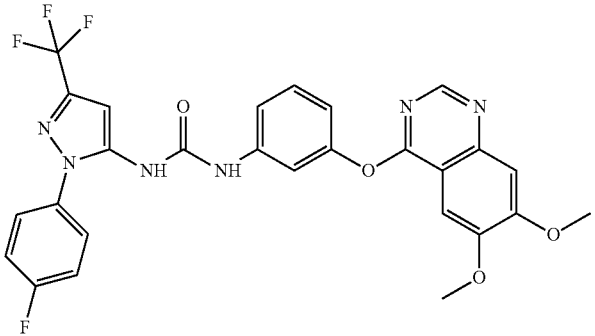 [SMILES: COc1cc2ncnc(Oc3cccc(NC(=O)Nc4cc(C(F)(F)F)nn4-c4ccc(F)cc4)c3)c2cc1OC] | Ex 171 1-[3-(6,7-dimethoxy-quinazolin-4-yloxy)phenyl]-3-[1-(4-fluorophenyl)-3-(trifluoro-methyl)-1H-pyrazol-5-yl]urea | B | B | C | D | D | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 172 1-[3-(6,7-dimethoxy-quinazolin-4-yloxy)phenyl]-3-[1-p-tolyl-3-(trifluoro-methyl)-1H-pyrazol-5-yl]urea | A | A | C | D | D | C* |
| Ex 173 1-(4-tert-butylphenyl)-3-(3-(6,7-dimethoxy-quinazolin-4-yloxy)phenyl)urea | B | D | A | C | B | C |
| Ex 174 1-(4-tert-butylphenyl)-3-(3-(6,7-dimethoxy-quinazolin-4-ylthio)phenyl)urea | D | D | B | D | B | C |
| Ex 175 1-(4-chlorophenyl)-3-(3-(6,7-dimethoxy-quinazolin-4-yloxy)phenyl)urea | D | D | A | A | A | C |
| Ex 176 1-(4-chloro-3-(trifluoro-methyl)phenyl)-3-(3-(6,7-dimethoxy-quinazolin-4-yloxy)phenyl)urea | B | D | A | C | B | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 177 1-(3-(6,7-dimethoxyquinazolin-4-yloxy)phenyl)-3-(4-(trifluoromethoxy)phenyl)urea | D | D | A | B | A | C |
| Ex 178 1-(3-(6,7-dimethoxyquinazolin-4-yloxy)phenyl)-3-(3-methoxyphenyl)urea | D | D | A | C | B | B* |
| Ex 179 1-(3-(6,7-dimethoxyquinazolin-4-yloxy)phenyl)-3-(3-ethoxyphenyl)urea | D | D | A | C | B | B* |
| Ex 180 1-(3-chloro-4-methoxyphenyl)-3-(3-(6,7-dimethoxyquinazolin-4-yloxy)phenyl)urea | D | D | A | A | A | B* |
| Ex 181 1-(3-(6,7-dimethoxyquinazolin-4-yloxy)phenyl)-3-(3-(trifluoromethyl)phenyl)urea | D | D | A | A | A | C* |

TABLE 1-continued

| | | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 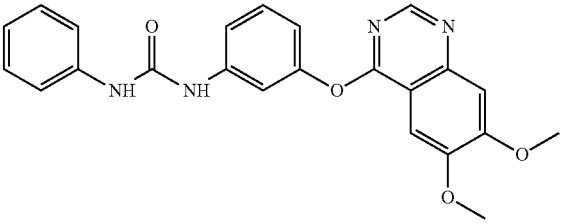 [SMILES: COc1cc2ncnc(Oc3cccc(NC(=O)Nc4ccccc4)c3)c2cc1OC] | Ex 182 1-(3-(6,7-dimethoxy-quinazolin-4-yloxy)phenyl)-3-phenylurea | D | D | D | D | D | B |
| 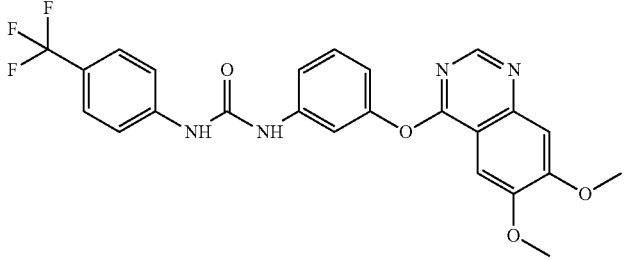 [SMILES: COc1cc2ncnc(Oc3cccc(NC(=O)Nc4ccc(C(F)(F)F)cc4)c3)c2cc1OC] | Ex 183 1-(3-(6,7-dimethoxy-quinazolin-4-yloxy)phenyl)-3-(4-(trifluoro-methyl)phenyl)urea | C | D | A | B | A | C* |
| 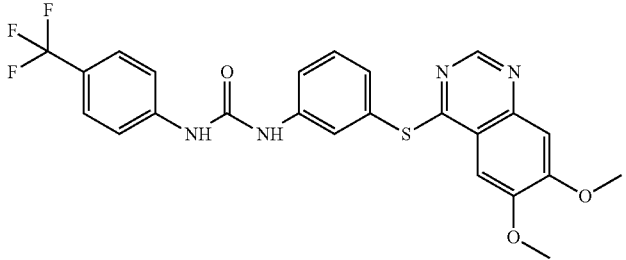 [SMILES: COc1cc2ncnc(Sc3cccc(NC(=O)Nc4ccc(C(F)(F)F)cc4)c3)c2cc1OC] | Ex 184 1-(3-(6,7-dimethoxy-quinazolin-4-ylthio)phenyl)-3-(4-(trifluoro-methyl)phenyl)urea | B | C | B | C | B | C* |
| 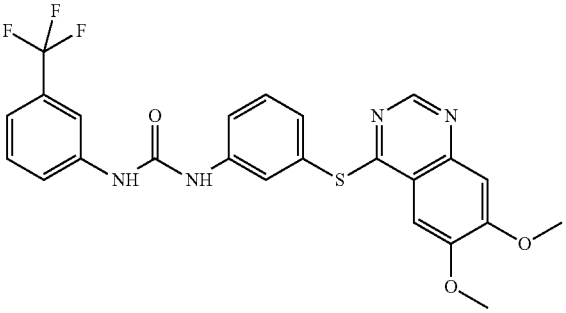 [SMILES: COc1cc2ncnc(Sc3cccc(NC(=O)Nc4cccc(C(F)(F)F)c4)c3)c2cc1OC] | Ex 185 1-(3-(6,7-dimethoxy-quinazolin-4-ylthio)phenyl)-3-(3-(trifluoro-methyl)phenyl)urea | C | D | A | B | A | C* |
| 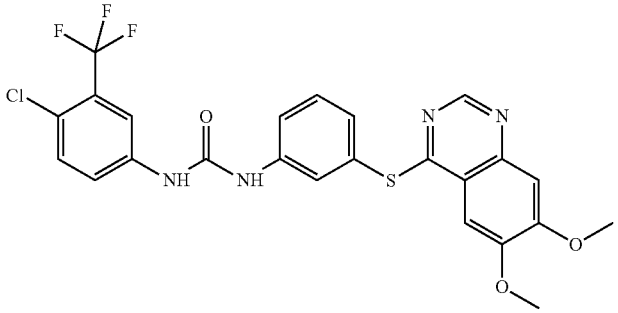 [SMILES: COc1cc2ncnc(Sc3cccc(NC(=O)Nc4ccc(Cl)c(C(F)(F)F)c4)c3)c2cc1OC] | Ex 186 1-(4-chloro-3-(trifluoro-methyl)phenyl)-3-(3-(6,7-dimethoxy-quinazolin-4-ylthio)phenyl urea | B | C | B | D | D | B* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 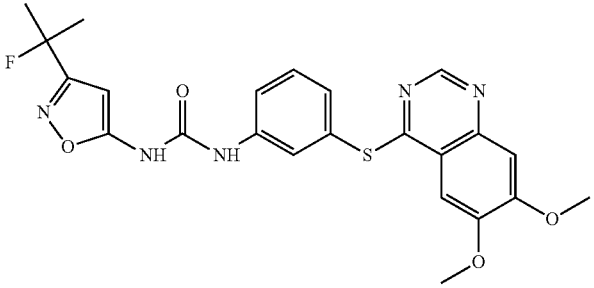 [SMILES: COc1cc2ncnc(Sc3cccc(NC(=O)Nc4cc(C(C)(C)F)no4)c3)c2cc1OC] | Ex 187 1-(3-(6,7-dimethoxy-quinazolin-4-ylthio)phenyl)-3-(3-(2-fluoropropan-2-yl)isoxazol-5-yl)urea | A | D | A | B | A | C* |
| 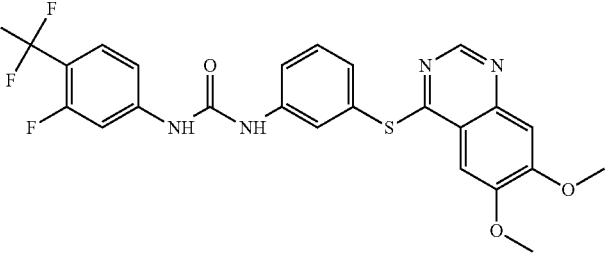 | Ex 188 1-(3-(6,7-dimethoxy-quinazolin-4-ylthio)phenyl)-3-(3-fluoro-4-(trifluoro-methyl)phenyl)urea | D | D | B | D | C | B* |
| 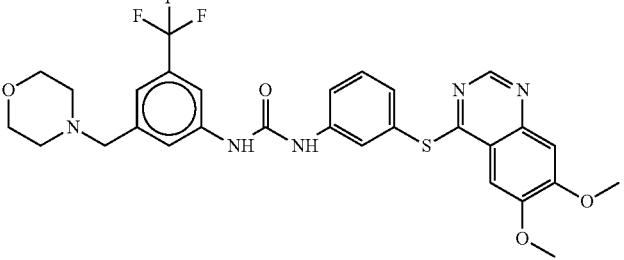 | Ex 189 1-(3-(6,7-dimethoxy-quinazolin-4-ylthio)phenyl)-3-(3-(morpholino methyl)-5-(trifluoro-methyl)phenyl)urea | C | C | B | D | C | C* |
| 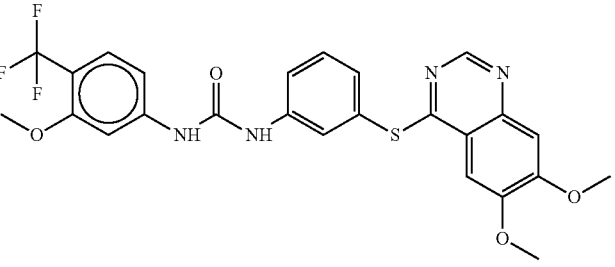 | Ex 190 1-(3-(6,7-dimethoxy-quinazolin-4-ylthio)phenyl)-3-(3-methoxy-4-(trifluoro-methyl)phenyl)urea | D | D | C | D | D | B* |
| 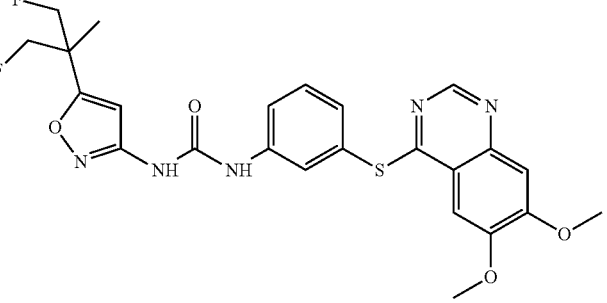 | Ex 191 1-[5-(1,3-difluoro-2-methylpropan-2-yl)isoxazol-3-yl]-3-[3-(6,7-dimethoxy-quinazolin-4-ylthio)phenyl]urea | A | A | A | B | A | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 192 1-[3-(6,7-dimethoxy-quinazolin-4-ylthio)phenyl]-3-[1-phenyl-3-(trifluoro-methyl)-1H-pyrazol-5-yl]urea | A | B | C | D | D | C* |
| Ex 193 1-[3-(6,7-dimethoxy-quinazolin-4-ylthio)phenyl]-3-[1-methyl-3-(trifluoro-methyl)-1H-pyrazol-5-yl]urea | A | C | A | A | A | D* |
| Ex 194 1-[3-(6,7-dimethoxy-quinazolin-4-ylthio)phenyl]-3-[1-methyl-5-(trifluoro-methyl)-1H-pyrazol-3-yl]urea | B | C | A | A | A | C* |
| Ex 195 ethyl 2-(3-text-butyl-5-{3-[3-(6,7-dimethoxy-quinazolin-4-ylthio)phenyl]ureido}-1H-pyrazol-1-yl)acetate | B | D | B | D | D | C* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 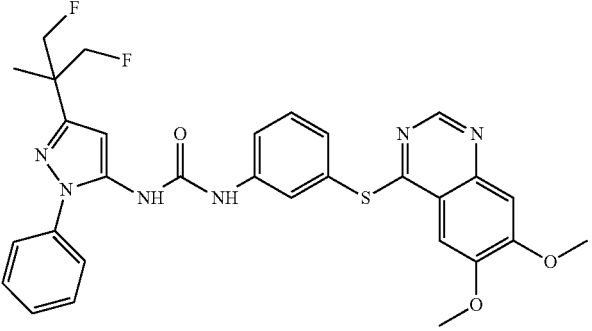 | Ex 196 1-[3-(1,3-difluoro-2-methylpropan-2-yl)-1-phenyl-1H-pyrazol-5-yl]-3-[3-(6,7-dimethoxy-quinazolin-4-ylthio)phenyl]urea | A | D | D | D | D | D* |
| 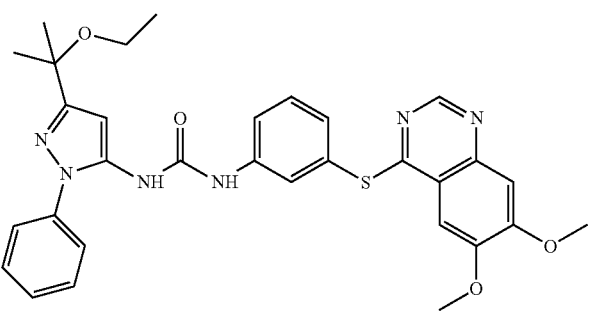 | Ex 197 1-[3-(6,7-dimethoxy-quinazolin-4-ylthio)phenyl]-3-[3-(2-ethoxypropan-2-yl)-1-phenyl-1H-pyrazol-5-yl]urea | B | D | B | D | D | C* |
| 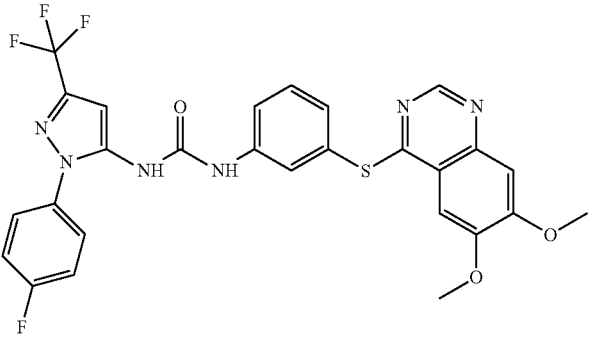 | Ex 198 1-[3-(6,7-dimethoxy-quinazolin-4-ylthio)phenyl]-3-[1-(4-fluorophenyl)-3-(trifluoro-methyl)-1H-pyrazol-5-yl]urea | B | C | C | D | D | C* |
| 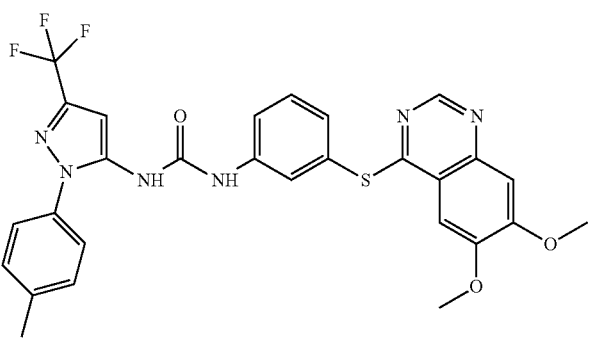 | Ex 199 1-[3-(6,7-dimethoxy-quinazolin-4-ylthio)phenyl]-3-[1-p-tolyl-3-(trifluoro-methyl)-1H-pyrazol-5-yl]urea | A | D | D | D | D | D* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 200 1-(3-(6,7-dimethoxy-quinazolin-4-ylthio)phenyl)-3-(3-(2-methoxy-ethoxy)-5-(trifluoro-methyl)phenyl)urea | D | D | C | C | D | C |
| Ex 201 1-(5-cyclopentyl-isoxazol-3-yl)-3-(3-(6,7-dimethoxy-quinazolin-4-ylthio)phenyl)urea | B | D | A | B | A | C* |
| Ex 202 1-(3-tert-butylisoxazol-5-yl)-3-(3-(6-methoxy-7-(2-methoxy-ethoxy)quinazolin-4-yloxy)phenyl)urea | A | D | A | B | B | C |
| Ex 203 1-(3-(6-Methoxy-7-(2-methoxy-ethoxy)quinazolin-4-yloxy)phenyl)-3-(5-phenyl-isoxazol-3-yl)urea | D | D | D | D | D | B |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 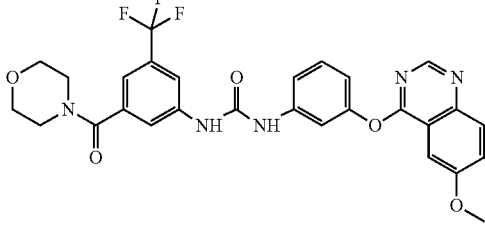 | Ex 205 1-(3-(6-methoxy-7-(2-methoxy-ethoxy) quinazolin-4-yloxy)phenyl)-3-(3-(morpholine-4-carbonyl)-5-(trifluoro-methyl) phenyl)urea | D | D | B | D | D | C* |
| 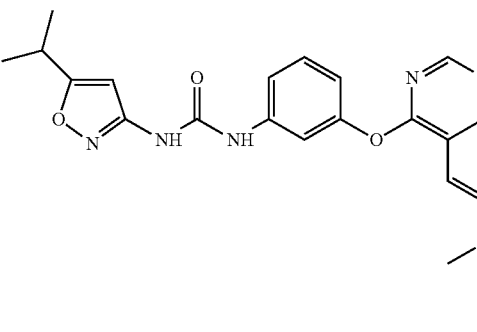 | Ex 206 1-(5-isopropyl-isoxazol-3-yl)-3-(3-(6-methoxy-7-(2-methoxy-ethoxy) quinazolin-4-yloxy)phenyl) urea | C | D | A | A | A | C* |
| 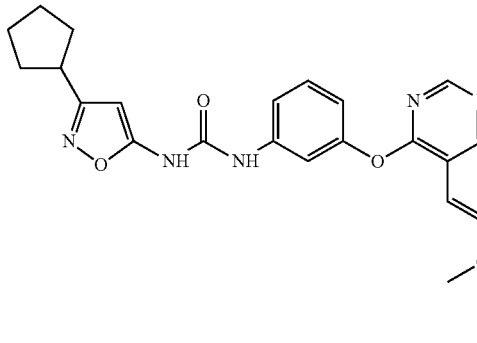 | Ex 207 1-(3-cyclopentyl-isoxazol-5-yl)-3-(3-(6-methoxy-7-(2-methoxy-ethoxy) quinazolin-4-yloxy)phenyl) urea | D | D | A | C | B | C* |
| 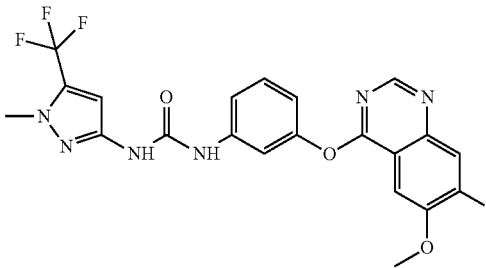 | Ex 208 1-{3-[6-methoxy-7-(2-methoxy-ethoxy) quinazolin-4-yloxy]phenyl}-3-[1-methyl-5-(trifluoro-methyl)-1H-pyrazol-3-yl]urea | D | D | A | A | A | C* |
| 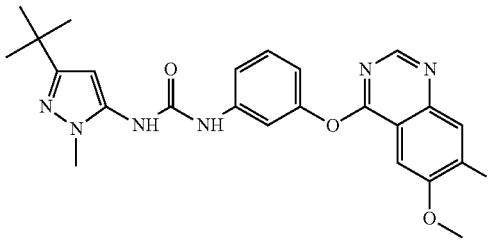 | Ex 209 1-(3-tert-butyl-1-methyl-1H-pyrazol-5-yl)-3-(3-(6-methoxy-7-(2-methoxy-ethoxy) quinazolin-4-yloxy)phenyl) urea | C | D | B | D | D | C* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 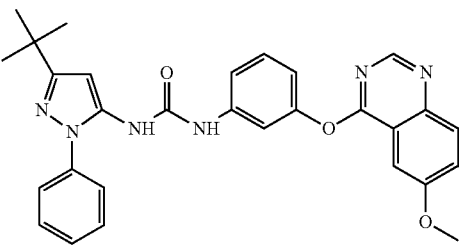 | Ex 210 1-(3-tert-butyl-1-phenyl-1H-pyrazol-5-yl)-3-(3-(6-methoxy-7-(2-methoxyethoxy)quinazolin-4-yloxy)phenyl)urea | A | ND | D | D | D | D* |
| 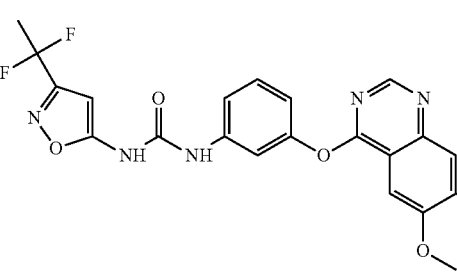 | Ex 211 1-(3-(1,1-difluoroethyl)isoxazol-5-yl)-3-(3-(6-methoxy-7-(2-methoxyethoxy)quinazolin-4-yloxy)phenyl)urea | D | D | B | C | B | C* |
| 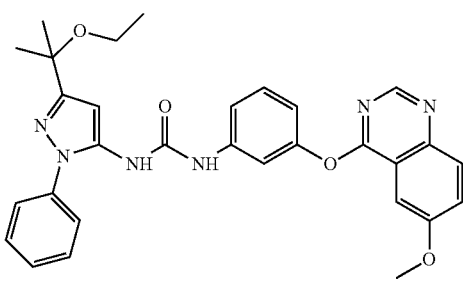 | Ex 212 1-[3-(2-ethoxypropan-2-yl)-1-phenyl-1H-pyrazol-5-yl]-3-{3-[6-methoxy-7-(2-methoxyethoxy)quinazolin-4-yloxy]phenyl}urea | C | D | B | D | D | C* |
| 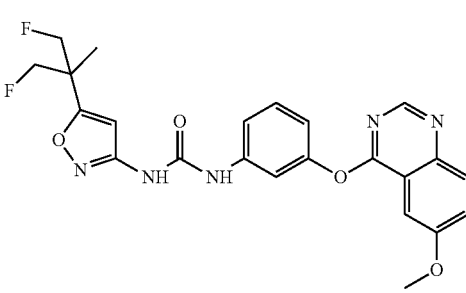 | Ex 213 1-[5-(1,3-difluoro-2-methylpropan-2-yl)isoxazol-3-yl]-3-{3-[6-methoxy-7-(2-methoxyethoxy)quinazolin-4-yloxy]phenyl}urea | A | A | A | B | A | D* |
| 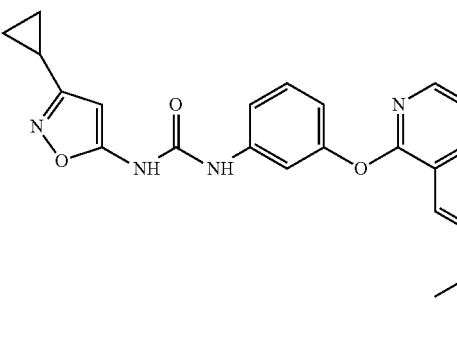 | Ex 214 1-(3-cyclopropylisoxazol-5-yl)-3-(3-(6-methoxy-7-(2-methoxyethoxy)quinazolin-4-yloxy)phenyl)urea | D | D | A | A | A | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 215 1-(3-isopropyl-isoxazol-5-yl)-3-(3-(6-methoxy-7-(2-methoxy-ethoxy)quinazolin-4-yloxy)phenyl)urea | C | D | A | B | B | C* |
| Ex 216 1-(3-(6-methoxy-7-(2-methoxy-ethoxy)quinazolin-4-yloxy)phenyl)-3-(3-(tetrahydro-2H-pyran-4-yl)isoxazol-5-yl)urea | D | D | B | D | D | B* |
| Ex 217 1-(5-(1-methoxy-2-methylpropan-2-yl)isoxazol-3-yl)-3-(3-(6-methoxy-7-(2-methoxy-ethoxy)quinazolin-4-yloxy)phenyl)urea | B | D | A | B | B | C* |
| Ex 218 1-(3-(2-fluoropropan-2-yl)isoxazol-5-yl)-3-(3-(6-methoxy-7-(2-methoxy-ethoxy)quinazolin-4-yloxy)phenyl)urea | B | D | A | B | A | C* |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 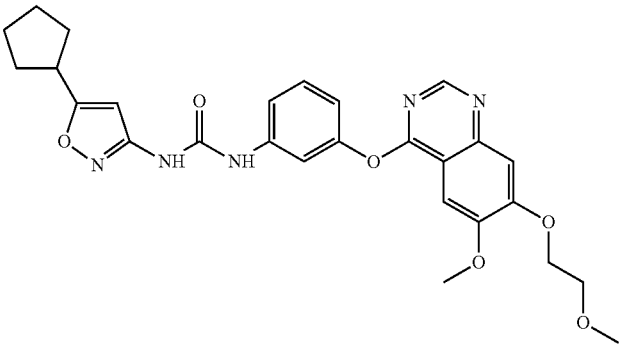 [SMILES: COCCOc1cc2ncnc(Oc3cccc(NC(=O)Nc4cc(C5CCCC5)on4)c3)c2cc1OC] | Ex 219 1-(5-cyclopentyl-isoxazol-3-yl)-3-(3-(6-methoxy-7-(2-methoxy-ethoxy)quinazolin-4-yloxy)phenyl)urea | A | B | A | A | A | C* |
| 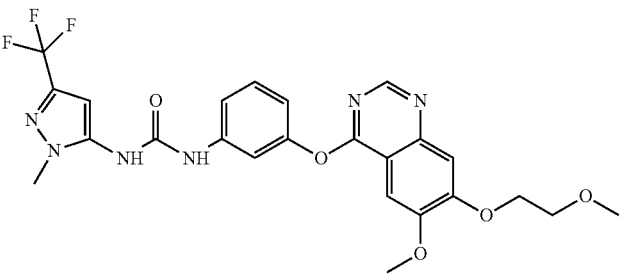 [SMILES: COCCOc1cc2ncnc(Oc3cccc(NC(=O)Nc4cc(C(F)(F)F)nn4C)c3)c2cc1OC] | Ex 220 1-{3-[6-methoxy-7-(2-methoxy-ethoxy)quinazolin-4-yloxy]phenyl}-3-[1-methyl-3-(trifluoro-methyl)-1H-pyrazol-5-yl]urea | C | D | A | A | A | C* |
| 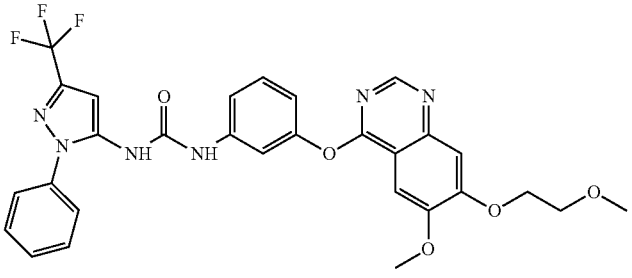 [SMILES: COCCOc1cc2ncnc(Oc3cccc(NC(=O)Nc4cc(C(F)(F)F)nn4-c4ccccc4)c3)c2cc1OC] | Ex 221 1-{3-[6-methoxy-7-(2-methoxy-ethoxy)quinazolin-4-yloxy]phenyl}-3-[1-phenyl-3-(trifluoro-methyl)-1H-pyrazol-5-yl]urea | B | C | B | D | D | C* |
| 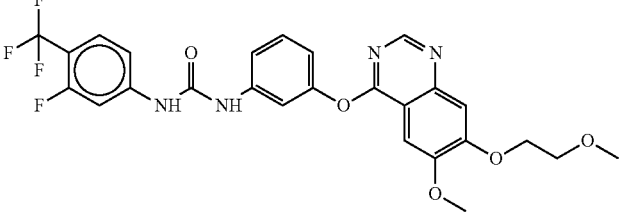 | Ex 222 1-(3-fluoro-4-(trifluoro-methyl)phenyl)-3-(3-(6-methoxy-7-(2-methoxy-ethoxy)quinazolin-4-yloxy)phenyl)urea | D | D | B | C | B | C* |
| 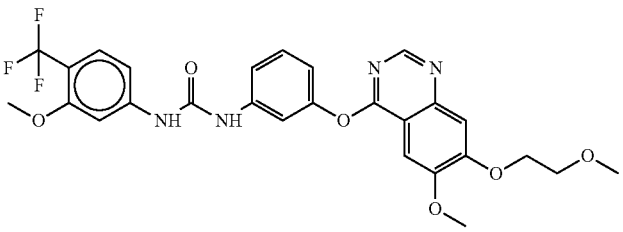 | Ex 223 1-(3-methoxy-4-(trifluoro-methyl)phenyl)-3-(3-(6-methoxy-7-(2-methoxy-ethoxy)quinazolin-4-yloxy)phenyl)urea | D | D | B | D | C | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 224 ethyl 2-[3-text-butyl-5-(3-{3-[6-methoxy-7-(2-methoxy ethoxy) quinazolin-4-yloxy]phenyl} ureido)-1H-pyrazol-1-yl}acetate hydrochloride | D | D | D | D | D | A* |
| Ex 225 1-{3-[6-methoxy-7-(2-methoxy-ethoxy) quinazolin-4-yloxy]phenyl}-3-[1-phenyl-5-(trifluoro-methyl)-1H-pyrazol-3-yl]urea | C | D | B | D | D | C* |
| Ex 226 1-[1-(4-fluorophenyl)-3-(trifluoro methyl)-1H-pyrazol-5-yl]-3-{3-[6-methoxy-7-(2-methoxy ethoxy) quinazolin-4-yloxy]phenyl} urea | B | D | C | D | D | C* |
| Ex 227 1-{3-[6-methoxy-7-(2-methoxy-ethoxy) quinazolin-4-yloxy]phenyl}-3-[1-p-tolyl-3-(trifluoro-methyl)-1H-pyrazol-5-yl}urea | B | B | C | D | D | C* |
| Ex 228 1-[3-(1,3-difluoro-2-methylpropan-2-yl)-1-phenyl-1H-pyrazol-5-yl]-3-{3-[6-methoxy-7-(2-methoxy-ethoxy) quinazolin-4-yloxy]phenyl} urea | A | D | C | D | D | D* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 229 1-(3-(6-methoxy-7-(2-methoxy-ethoxy)quinazlin-4-yloxy)phenyl)-3-(3-(trifluoromethyl)isoxazol-5-yl)urea | D | D | A | B | A | C* |
| Ex 230 1-[5-(1,3-difluoro-2-methylpropan-2-yl)isoxazol-3-yl]-3-{3-[6-methoxy-7-(2-methoxyethoxy)quinazolin-4-ylthio]phenyl}urea | A | B | A | C | B | C* |
| Ex 231 1-(3-fluoro-4-(trifluoromethyl)phenyl)-3-(3-(6-methoxy-7-(2-methoxyethoxy)quinazolin-4-ylthio)phenyl)urea | D | D | C | D | D | B* |
| Ex 232 1-(5-isopropyl-isoxazol-3-yl)-3-(3-(6-methoxy-7-(2-methoxyethoxy)quinazolin-4-ylthio)phenyl)urea | B | D | A | A | A | C* |
| Ex 233 1-(3-methoxy-4-(trifluoromethyl)phenyl)-3-(3-(6-methoxy-7-(2-methoxyethoxy)quinazolin-4-ylthio)phenyl)urea | D | D | C | D | D | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
| --- | --- | --- | --- | --- | --- | --- |
| 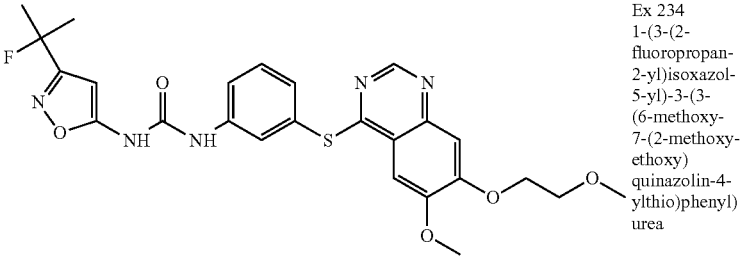 Ex 234 1-(3-(2-fluoropropan-2-yl)isoxazol-5-yl)-3-(3-(6-methoxy-7-(2-methoxy-ethoxy) quinazolin-4-ylthio)phenyl) urea | A | D | A | B | B | C* |
| 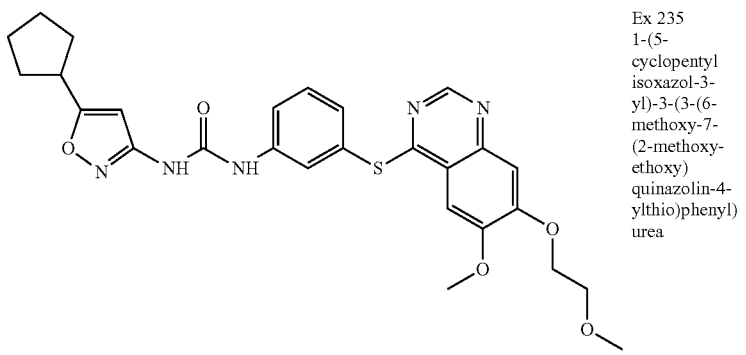 Ex 235 1-(5-cyclopentyl isoxazol-3-yl)-3-(3-(6-methoxy-7-(2-methoxy-ethoxy) quinazolin-4-ylthio)phenyl) urea | B | D | A | B | A | C* |
| 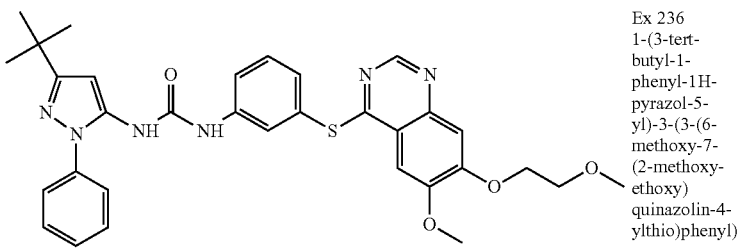 Ex 236 1-(3-tert-butyl-1-phenyl-1H-pyrazol-5-yl)-3-(3-(6-methoxy-7-(2-methoxy-ethoxy) quinazolin-4-ylthio)phenyl) urea | A | ND | D | D | D | D* |
| 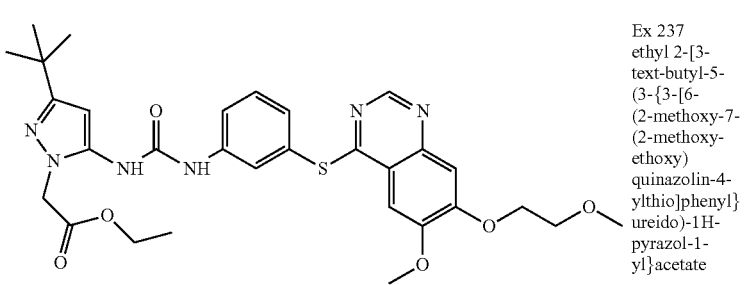 Ex 237 ethyl 2-[3-text-butyl-5-(3-{3-[6-(2-methoxy-7-(2-methoxy-ethoxy) quinazolin-4-ylthio]phenyl} ureido)-1H-pyrazol-1-yl}acetate | C | D | C | D | D | C* |
| 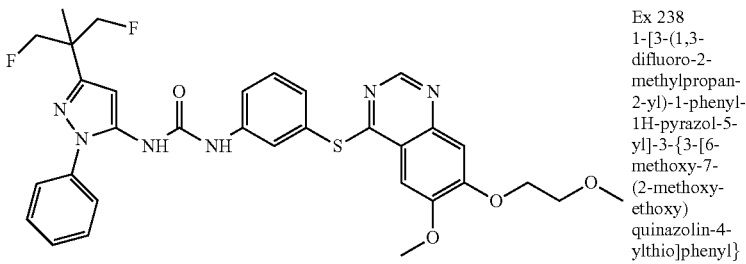 Ex 238 1-[3-(1,3-difluoro-2-methylpropan-2-yl)-1-phenyl-1H-pyrazol-5-yl]-3-{3-[6-methoxy-7-(2-methoxy-ethoxy) quinazolin-4-ylthio]phenyl} urea | A | D | D | D | D | D* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 239 1-{3-[6-methoxy-7-(2-methoxyethoxy)quinazolin-4-ylthio]phenyl}-3-[1-methyl-3-(trifluoromethyl)-1H-pyrazol-5-yl]urea | B | D | A | A | A | D* |
| Ex 240 1-{3-[6-methoxy-7-(2-methoxyethoxy)quinazolin-4-ylthio]phenyl}-3-[1-methyl-3-(trifluoromethyl)-1H-pyrazol-5-yl]urea | B | D | A | A | A | C* |
| Ex 241 1-[3-(2-ethoxypropan-2-yl)-1-phenyl-1H-pyrazol-5-yl]-3-{3-[6-methoxy-7-(2-methoxyethoxy)quinazolin-4-ylthio]phenyl}urea | C | D | B | D | D | C* |
| Ex 242 1-[1-(4-fluorophenyl)-3-(trifluoromethyl)-1H-pyrazol-5-yl]-3-{3-[6-methoxy-7-(2-methoxyethoxy)quinazolin-4-ylthio]phenyl}urea | C | D | D | D | D | C* |
| Ex 243 1-{3-[6-methoxy-7-(2-methoxyethoxy)quinazolin-4-ylthio]phenyl}-3-[1-p-tolyl-3-(trifluoromethyl)-1H-pyrazol-5-yl]urea | B | B | D | D | D | C* |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 244 1-{3-(6-methoxy-7-(2-methoxy-ethoxy)quinazolin-4-ylthio]phenyl}-3-[1-phenyl-5-(trifluoromethyl)-1H-pyrazol-3-yl}urea | D | D | D | D | D | C* |
| Ex 245 1-(3-(2-fluoropropan-2-yl)isoxazol-5-yl)-3-(3-(7-methoxy-6-(4,4-dioxo-3-thiomorpholinopropoxy)quinazolin-4-ylthio)phenyl)urea | A | D | A | A | B | C* |
| Ex 246 1-(4-methoxy-3-(trifluoromethyl)phenyl)-3-(3-(7-methoxy-6-(3-(4,4-dioxothiomorpholino)propoxy)quinazolin-4-ylthio)phenyl)urea | A | C | A | B | B | C* |
| Ex 247 1-(3-(6,7-bis(2-Methoxyethoxy)quinazolin-4-ylthio)phenyl)-3-(3-tert-butylisoxazol-5-yl)urea | A | D | A | B | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 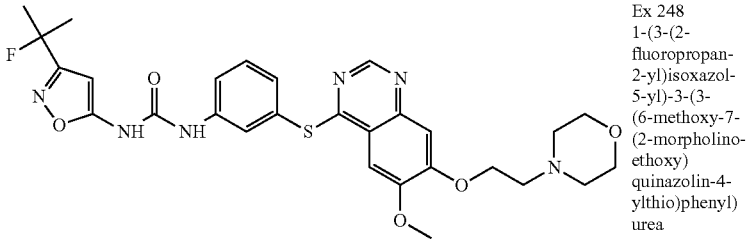 | Ex 248 1-(3-(2-fluoropropan-2-yl)isoxazol-5-yl)-3-(3-(6-methoxy-7-(2-morpholino-ethoxy)quinazolin-4-ylthio)phenyl)urea | B | D | A | B | B | C* |
| 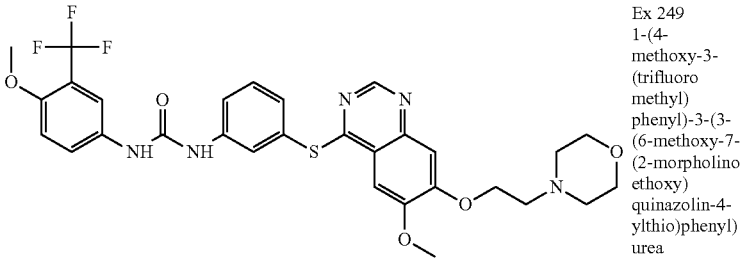 | Ex 249 1-(4-methoxy-3-(trifluoromethyl)phenyl)-3-(3-(6-methoxy-7-(2-morpholino ethoxy)quinazolin-4-ylthio)phenyl)urea | C | D | B | C | C | C* |
| 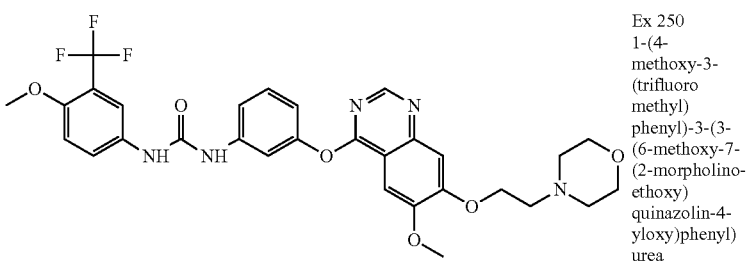 | Ex 250 1-(4-methoxy-3-(trifluoromethyl)phenyl)-3-(3-(6-methoxy-7-(2-morpholino-ethoxy)quinazolin-4-yloxy)phenyl)urea | B | D | A | A | A | C* |
| 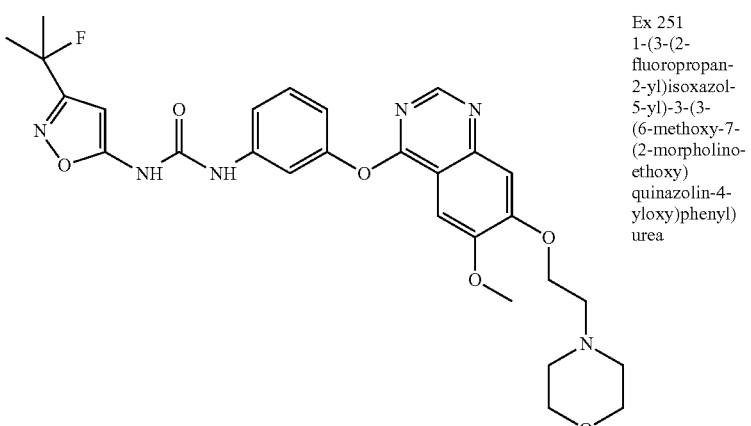 | Ex 251 1-(3-(2-fluoropropan-2-yl)isoxazol-5-yl)-3-(3-(6-methoxy-7-(2-morpholino-ethoxy)quinazolin-4-yloxy)phenyl)urea | B | D | A | A | B | C* |
| 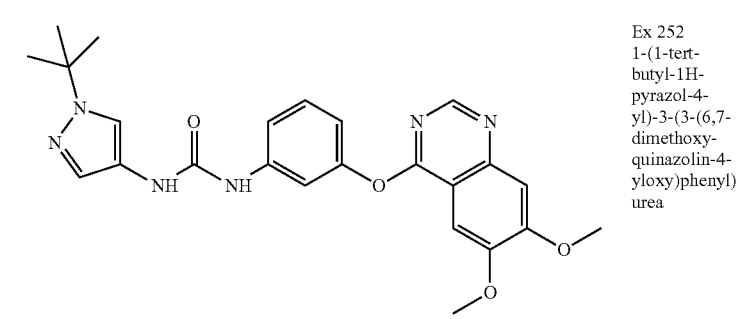 | Ex 252 1-(1-tert-butyl-1H-pyrazol-4-yl)-3-(3-(6,7-dimethoxy-quinazolin-4-yloxy)phenyl)urea | D | D | A | B | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 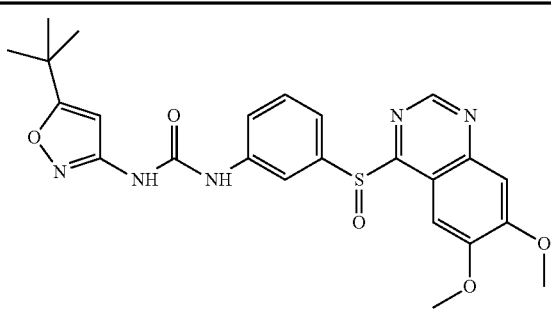 | Ex 253 1-(5-tert-butylisoxazol-3-yl)-3-(3-(6,7-dimethoxy-quinazolin-4-ylsulfinyl)phenyl)urea | C | D | D | D | D | C |
| 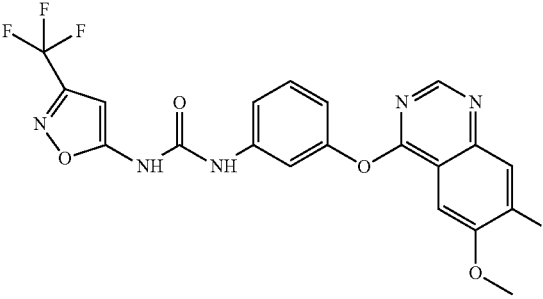 | Ex 254 1-(3-(6,7-dimethoxy-quinazolin-4-yloxy)phenyl)-3-(3-(trifluoro-methyl)isoxazol-5-yl)urea | D | D | A | B | A | C* |
| 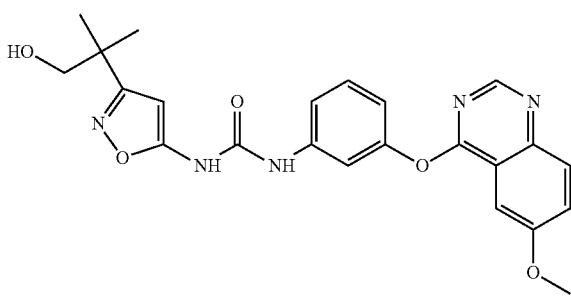 | Ex 255 1-(3-(6,7-dimethoxy-quinazolin-4-yloxy)phenyl)-3-(3-(1-hydroxy-2-methylpropan-2-yl)isoxazol-5-yl)urea | D | D | A | B | B | C |
| 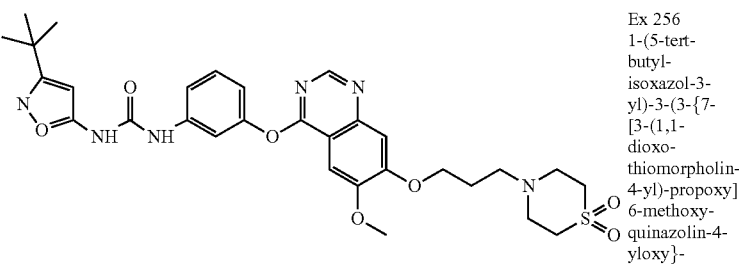 | Ex 256 1-(5-tert-butyl-isoxazol-3-yl)-3-(3-{7-[3-(1,1-dioxo-thiomorpholin-4-yl)-propoxy]-6-methoxy-quinazolin-4-yloxy}-phenyl)-urea | A | A | A | A | A | D |
| 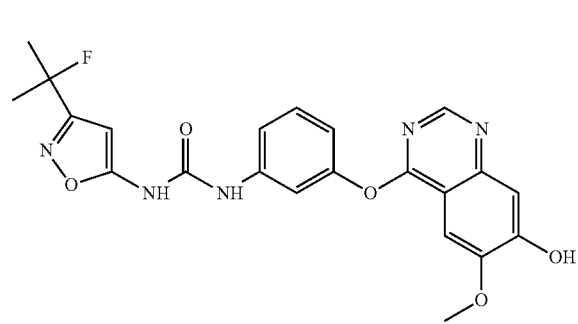 [SMILES: COc1cc2c(Oc3cccc(NC(=O)Nc4cc(C(C)(C)F)no4)c3)ncnc2cc1O] | Ex 257 1-(3-(2-fluoropropan-2-yl)isoxazol-5-yl)-3-(3-(7-hydroxy-6-methoxy-quinazolin-4-yloxy)phenyl)urea | B | C | A | A | A | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 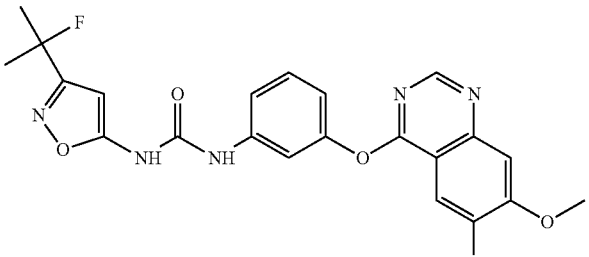 | Ex 258 1-(3-(2-fluoropropan-2-yl)isoxazol-5-yl)-3-(3-(6-hydroxy-7-methoxy-quinazolin-4-yloxy)phenyl) urea | A | B | A | A | A | C |
| 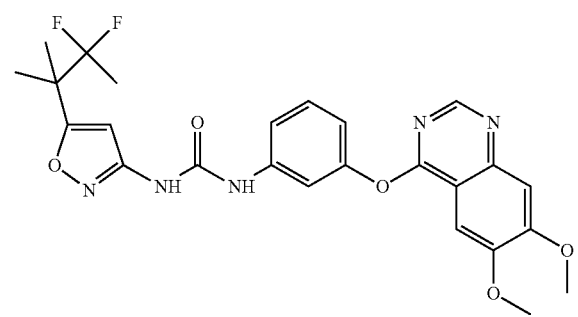 [SMILES: COc1cc2ncnc(Oc3cccc(NC(=O)Nc4cc(C(C)(C)C(C)(F)F)on4)c3)c2cc1OC] | Ex 259 1-(3-(6,7-dimethoxy-quinazolin-4-yloxy)phenyl)-3-(5-(1,1,1 trifluoro-2-methylpropan-2-yl)isoxazol-3-yl)urea | A | A | A | A | A | C |
| 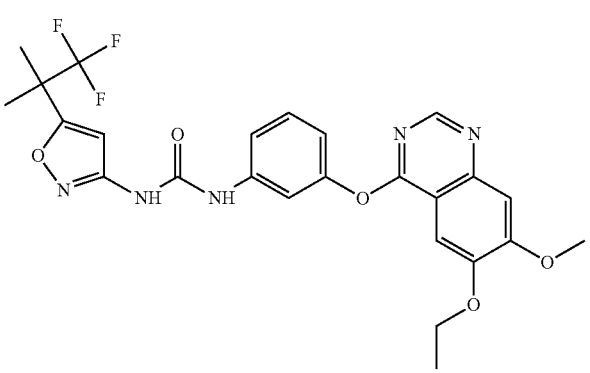 [SMILES: CCOc1cc2c(Oc3cccc(NC(=O)Nc4cc(C(C)(C)C(F)(F)F)on4)c3)ncnc2cc1OC] | Ex 260 1-(3-(6-ethoxy-7-methoxy-quinazolin-4-yloxy)phenyl)-3-(5-(1,1,1-trifluoro-2-methylpropan-2-yl)isoxazol-3-yl)urea | A | A | A | A | A | C |
| 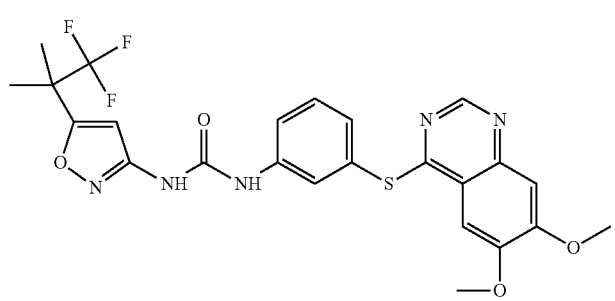 [SMILES: COc1cc2ncnc(Sc3cccc(NC(=O)Nc4cc(C(C)(C)C(F)(F)F)on4)c3)c2cc1OC] | Ex 261 1-(3-(6,7-dimethoxy-quinazolin-4-ylthio)phenyl)-3-(5-(1,1,1-trifluoro-2-methylpropan-2-yl)isoxazol-3-yl)urea | A | D | A | B | A | ND |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 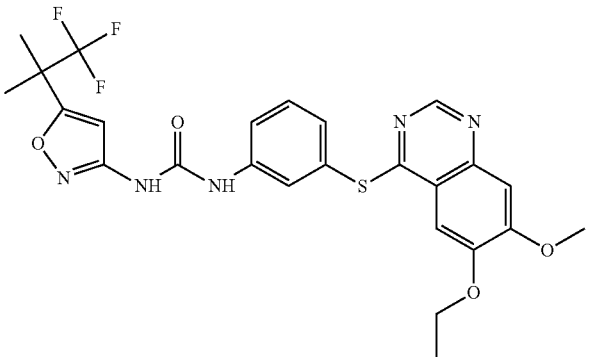 Ex 262 1-(3-(6-ethoxy-7-methoxy-quinazolin-4-ylthio)phenyl)-3-(5-(1,1,1-trifluoro-2-methylpropan-2-yl)isoxazol-3-yl)urea | A | D | A | A | A | C |
| 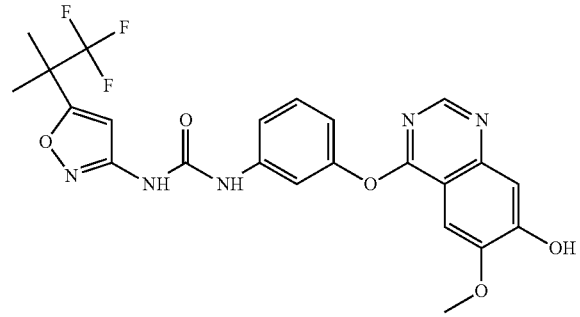 [SMILES: COc1cc2c(Oc3cccc(NC(=O)Nc4cc(C(C)(C)C(F)(F)F)on4)c3)ncnc2cc1O] Ex 263 1-(3-(7-hydroxy-6-methoxy-quinazolin-4-yloxy)phenyl)-3-(5-(1,1,1-trifluoro-2-methylpropan-2-yl)isoxazol-3-yl)urea | A | C | A | A | A | C |
| 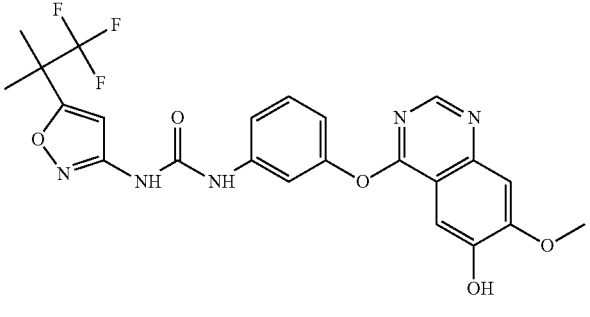 [SMILES: COc1cc2ncnc(Oc3cccc(NC(=O)Nc4cc(C(C)(C)C(F)(F)F)on4)c3)c2cc1O] Ex 264 1-(3-(6-hydroxy-7-methoxy-quinazolin-4-yloxy)phenyl)-3-(5-(1,1,1-trifluoro-2-methylpropan-2-yl)isoxazol-3-yl)urea | A | A | A | A | A | C |
| 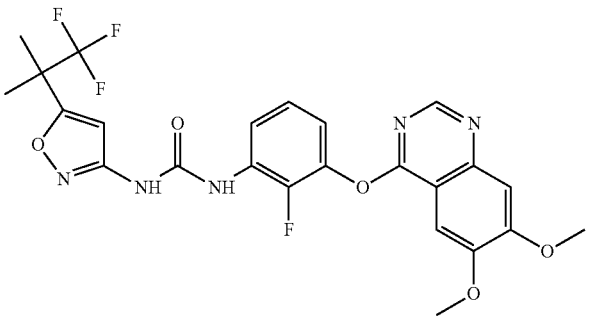 [SMILES: COc1cc2ncnc(Oc3cccc(NC(=O)Nc4cc(C(C)(C)C(F)(F)F)on4)c3F)c2cc1OC] Ex 265 1-(3-(6,7-dimethoxy-quinazolin-4-yloxy)-2-fluorophenyl)-3-(5-(1,1,1-trifluoro-2-methylpropan-2-yl)isoxazol-3-yl)urea | A | B | A | B | A | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 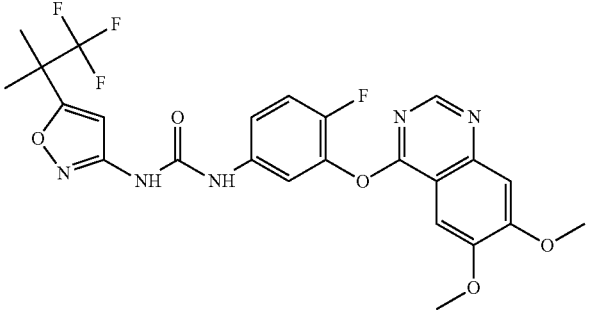 [SMILES: COc1cc2ncnc(Oc3cc(NC(=O)Nc4cc(C(C)(C)C(F)(F)F)on4)ccc3F)c2cc1OC] | Ex 266 1-(3-(6,7-dimethoxy-quinazolin-4-yloxy)-4-fluorophenyl)-3-(5-(1,1,1-trifluoro-2-methylpropan-2-yl)isoxazol-3-yl)urea | A | ND | A | A | A | C |
| 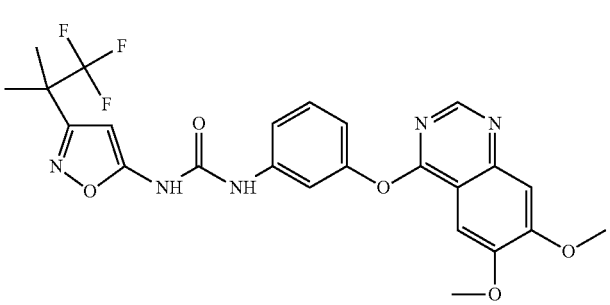 [SMILES: COc1cc2ncnc(Oc3cccc(NC(=O)Nc4cc(C(C)(C)C(F)(F)F)no4)c3)c2cc1OC] | Ex 267 1-(3-(6,7-dimethoxy-quinazolin-4-yloxy)phenyl)-3-(3-(1,1,1-trifluoro-2-methylpropan-2-yl)isoxazol-5-yl)urea | A | C | A | A | A | C |
| 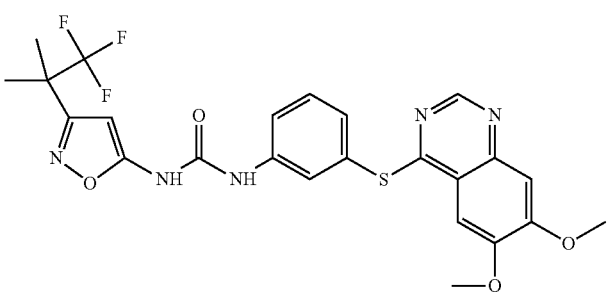 [SMILES: COc1cc2ncnc(Sc3cccc(NC(=O)Nc4cc(C(C)(C)C(F)(F)F)no4)c3)c2cc1OC] | Ex 268 1-(3-(6,7-dimethoxy-quinazolin-4-ylthio)phenyl)-3-(3-(1,1,1-trifluoro-2-methylpropan-2-yl)isoxazol-5-yl)urea | A | C | A | A | A | C |
| 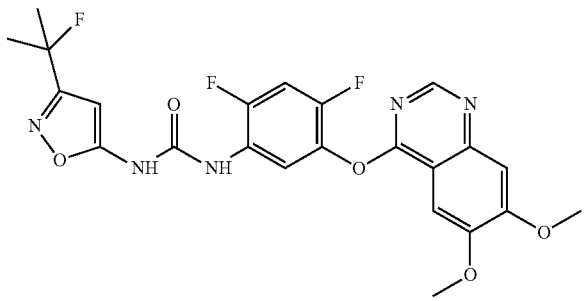 [SMILES: COc1cc2ncnc(Oc3cc(NC(=O)Nc4cc(C(C)(C)F)no4)c(F)cc3F)c2cc1OC] | Ex 269 1-(5-(6,7-dimethoxy-quinazolin-4-yloxy)-2,4-difluoro-phenyl)-3-(3-(2-fluoropropan-2-yl)isoxazol-5-yl)urea | A | A | A | A | A | D |
| 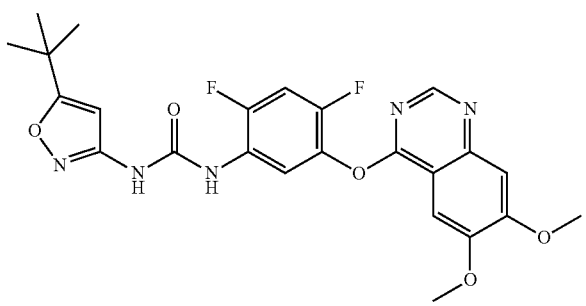 [SMILES: COc1cc2ncnc(Oc3cc(NC(=O)Nc4cc(C(C)(C)C)on4)c(F)cc3F)c2cc1OC] | Ex 270 1-(5-tert-butylisoxazol-3-yl)-3-(5-(6,7-dimethoxy-quinazolin-4-yloxy)-2,4-difluoro-phenyl)urea | A | A | A | A | A | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 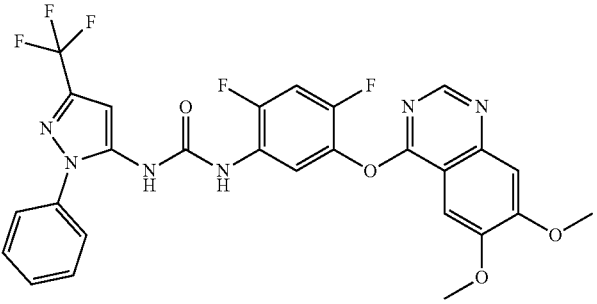 [SMILES: COc1cc2ncnc(Oc3cc(NC(=O)Nc4cc(C(F)(F)F)nn4-c4ccccc4)c(F)cc3F)c2cc1OC] | Ex 271 1-(5-(6,7-dimethoxy-quinazolin-4-yloxy)-2,4-difluoro-phenyl)-3-(1-phenyl-3-(trifluoro-methyl)-1H-pyrazol-5-yl)urea | A | B | B | D | D | D |
| 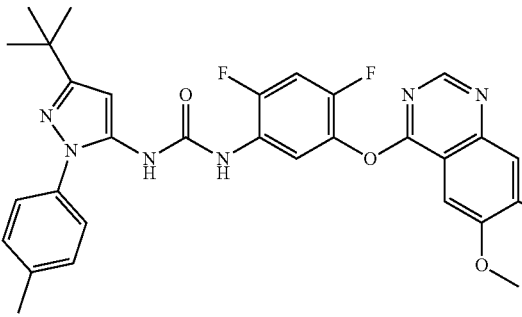 | Ex 272 1-(3-tert-butyl-1-p-tolyl-1H-pyrazol-5-yl)-3-(5-(6,7-dimethoxy-quinazolin-4-yloxy)-2,4-difluoro-phenyl)urea | A | ND | C | D | D | D |
| 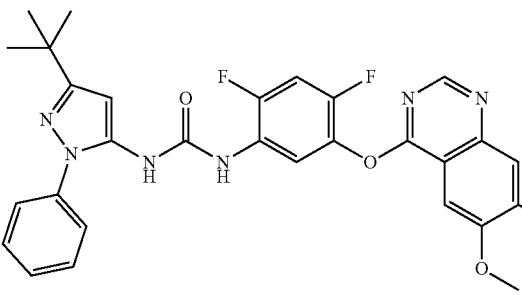 | Ex 273 1-(3-tert-butyl-1-phenyl-1H-pyrazol-5-yl)-3-(5-(6,7-dimethoxy-quinazolin-4-yloxy)-2,4-difluoro-phenyl)urea | A | ND | C | D | D | D |
| 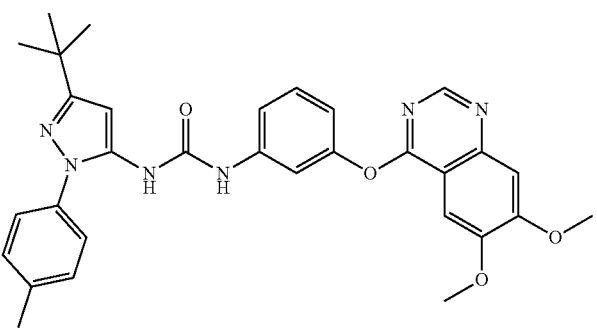 [SMILES: COc1cc2ncnc(Oc3cccc(NC(=O)Nc4cc(C(C)(C)C)nn4-c4ccc(C)cc4)c3)c2cc1OC] | Ex 274 1-(3-tert-butyl-1-p-tolyl-1H-pyrazol-5-yl)-3-(3-(6,7-dimethoxy-quinazolin-4-yloxy)phenyl)urea | A | ND | B | D | D | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 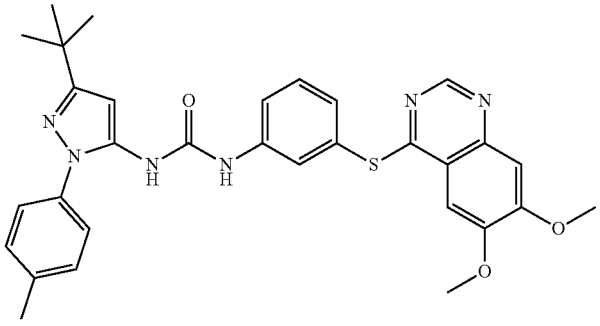 [SMILES: COc1cc2ncnc(Sc3cccc(NC(=O)Nc4cc(C(C)(C)C)nn4-c4ccc(C)cc4)c3)c2cc1OC] | Ex 275 1-(3-tert-Butyl-1-p-tolyl-1H-pyrazol-5-yl)-3-(3-(6,7-dimethoxy-quinazolin-4-ylthio)phenyl) urea | A | ND | B | D | D | D |
| 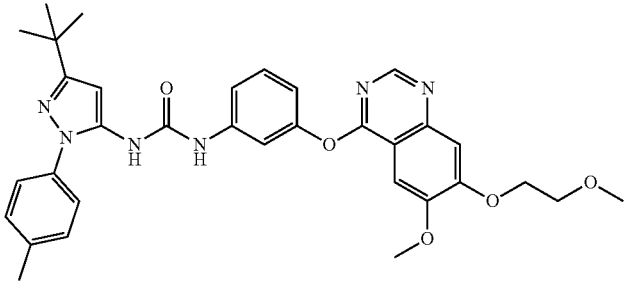 [SMILES: COCCOc1cc2ncnc(Oc3cccc(NC(=O)Nc4cc(C(C)(C)C)nn4-c4ccc(C)cc4)c3)c2cc1OC] | Ex 276 1-(3-tert-butyl-1-p-tolyl-1H-pyrazol-5-yl)-3-(3-(6-methoxy-7-(2-methoxy-ethoxy)quinazolin-4-yloxy)phenyl) urea | A | ND | A | D | D | D |
| 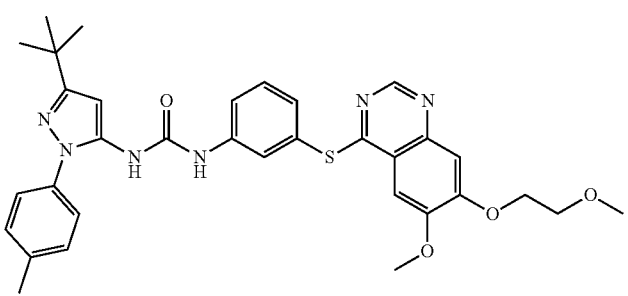 [SMILES: COCCOc1cc2ncnc(Sc3cccc(NC(=O)Nc4cc(C(C)(C)C)nn4-c4ccc(C)cc4)c3)c2cc1OC] | Ex 277 1-(3-tert-Butyl-1-p-tolyl-1H-pyrazol-5-yl)-3-(3-(6-methoxy-7-(2-methoxy-ethoxy)quinazolin-4-ylthio)phenyl) urea | A | ND | B | D | D | D |
| 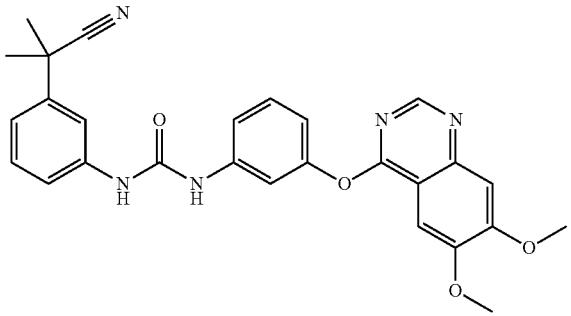 [SMILES: COc1cc2ncnc(Oc3cccc(NC(=O)Nc4cccc(C(C)(C)C#N)c4)c3)c2cc1OC] | Ex 278 1-(3-(2-cyanopropan-2-yl)phenyl)-3-(3-(6,7-dimethoxy-quinazolin-4-yloxy)phenyl) urea | B | C | A | A | A | C |
| 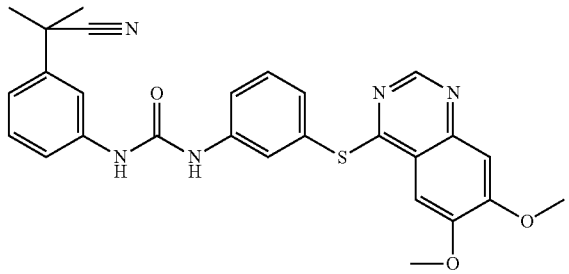 [SMILES: COc1cc2ncnc(Sc3cccc(NC(=O)Nc4cccc(C(C)(C)C#N)c4)c3)c2cc1OC] | Ex 279 1-(3-(2-cyanopropan-2-yl)phenyl)-3-(3-(6,7-dimethoxy-quinazolin-4-ylthio)phenyl) urea | B | D | A | A | A | C |

TABLE 1-continued

| | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 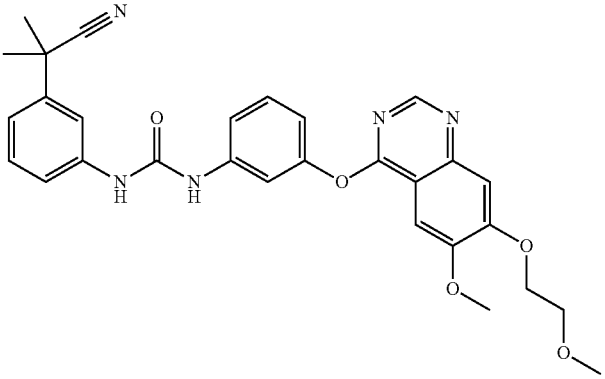 [SMILES: COCCOc1cc2ncnc(Oc3cccc(NC(=O)Nc4cccc(C(C)(C)C#N)c4)c3)c2cc1OC] Ex 280 1-(3-(2-cyanopropan-2-yl)phenyl)-3-(3-(6-methoxy-7-(2-methoxyethoxy)quinazolin-4-yloxy)phenyl)urea | C | D | A | A | A | ND |
| 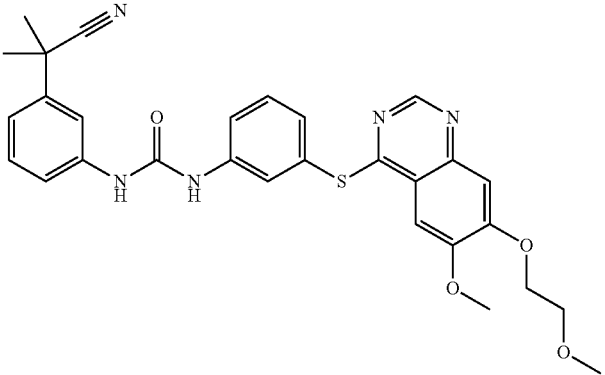 [SMILES: COCCOc1cc2ncnc(Sc3cccc(NC(=O)Nc4cccc(C(C)(C)C#N)c4)c3)c2cc1OC] Ex 281 1-(3-(2-cyanopropan-2-yl)phenyl)-3-(3-(6-methoxy-7-(2-methoxyethoxy)quinazolin-4-ylthio)phenyl)urea | B | D | A | A | A | ND |
| 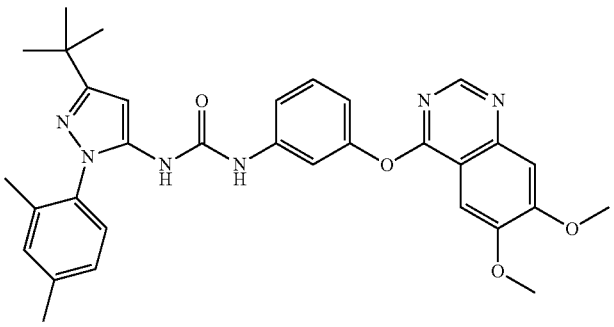 Ex 282 1-(3-tert-butyl-1-(2,4-dimethylphenyl)-1H-pyrazol-5-yl)-3-(3-(6,7-dimethoxyquinazolin-4-yloxy)phenyl)urea | A | ND | C | D | D | C |
| 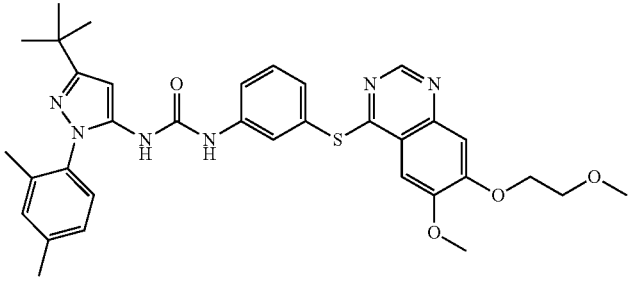 Ex 283 1-(3-tert-butyl-1-(2,4-dimethylphenyl)-1H-pyrazol-5-yl)-3-(3-(6-methoxy-7-(2-methoxyethoxy)quinazolin-4-ylthio)phenyl)urea | A | D | C | D | D | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 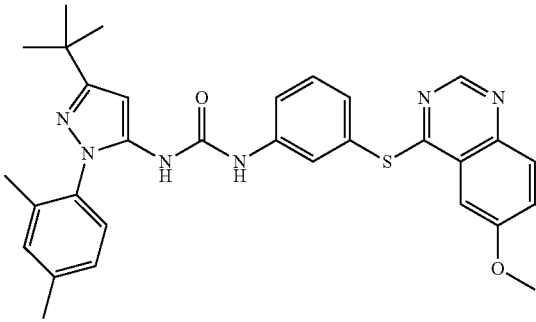 | Ex 284 1-(3-tert-butyl-1-(2,4-dimethyl-phenyl)-1H-pyrazol-5-yl)-3-(3-(6,7-dimethoxy-quinazolin-4-ylthio)phenyl) urea | A | D | D | D | D | C |
| 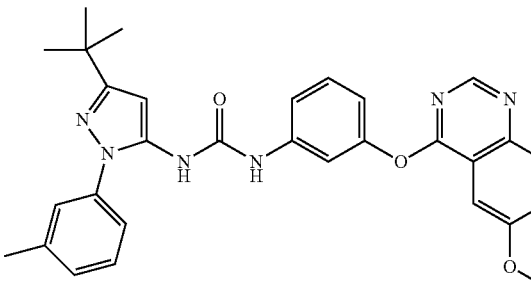 | Ex 285 1-(3-tert-butyl-1-m-tolyl-1H-pyrazol-5-yl)-3-(3-(6,7-dimethoxy-quinazolin-4-yloxy)phenyl) urea | A | ND | B | D | D | D |
| 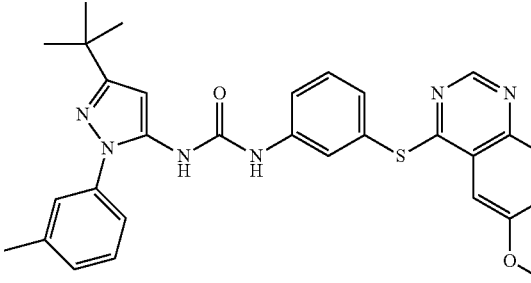 | Ex 286 Preparation of 1-(3-tert-butyl-1-m-tolyl-1H-pyrazol-5-yl)-3-(3-(6,7-dimethoxy-quinazolin-4-ylthio)phenyl) urea | A | ND | B | D | D | D |
| 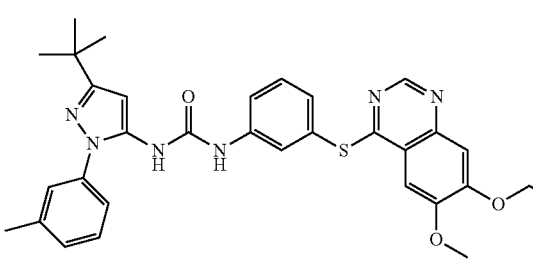 | Ex 287 1-(3-tert-butyl-1-m-tolyl-1H-pyrazol-5-yl)-3-(3-(6-methoxy-7-(2-methoxy-ethoxy) quinazolin-4-ylthio)phenyl) urea | A | ND | C | D | D | D |
| 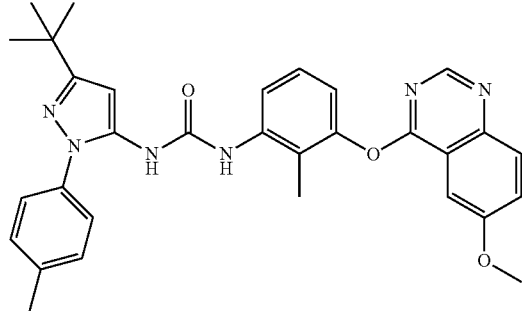 | Ex 288 1-(3-tert-butyl-1-p-tolyl-1H-pyrazol-5-yl)-3-(3-(6,7-dimethoxy-quinazolin-4-yloxy)-2-methylphenyl) urea | A | ND | B | D | D | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 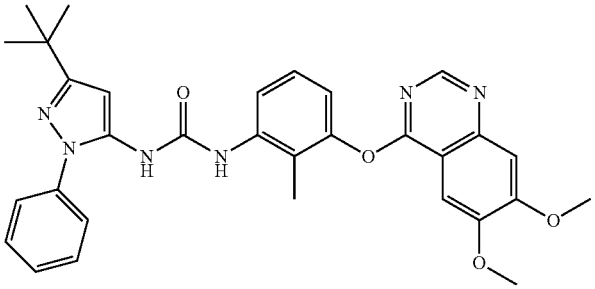 [SMILES: COc1cc2ncnc(Oc3cccc(NC(=O)Nc4cc(C(C)(C)C)nn4-c4ccccc4)c3C)c2cc1OC] | Ex 289 1-(3-tert-butyl-1-phenyl-1H-pyrazol-5-yl)-3-(3-(6,7-dimethoxy-quinazolin-4-yloxy)-2-methylphenyl)urea | A | C | A | D | C | C |
| 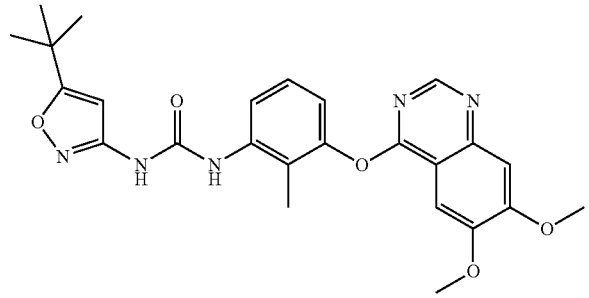 [SMILES: COc1cc2ncnc(Oc3cccc(NC(=O)Nc4cc(C(C)(C)C)on4)c3C)c2cc1OC] | Ex290 1-(5-tert-butylisoxazol-3-yl)-3-(3-(6,7-dimethoxy-quinazolin-4-yloxy)-2-methyl-phenyl)urea | A | B | A | A | A | C |
| 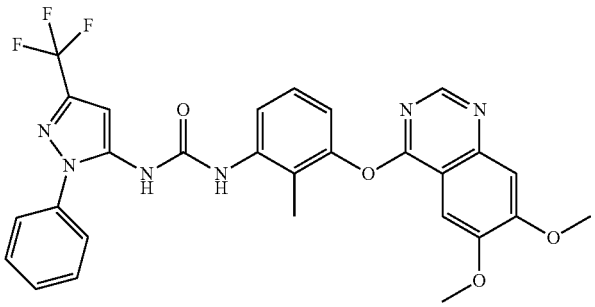 [SMILES: COc1cc2ncnc(Oc3cccc(NC(=O)Nc4cc(C(F)(F)F)nn4-c4ccccc4)c3C)c2cc1OC] | Ex 291 1-(3-(6,7-Dimethoxy-quinazolin-4-yloxy)-2-methyl-phenyl)-3-(1-phenyl-3-(trifluoro-methyl)-1H-pyrazol-5-yl)urea | C | D | A | C | B | B |
| 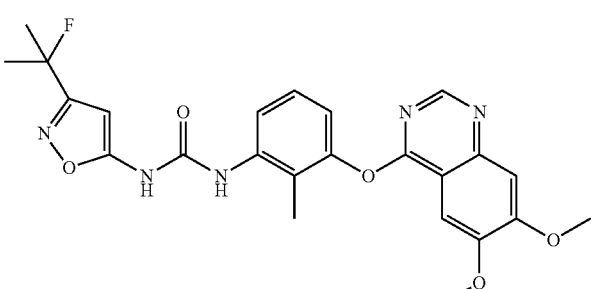 | Ex292 1-(3-(6,7-dimethoxy-quinazolin-4-yloxy)-2-methyl-phenyl)-3-(5-(2-fluoropropan-2-yl)isoxazol-3-yl)urea | C | D | A | A | A | C |
| 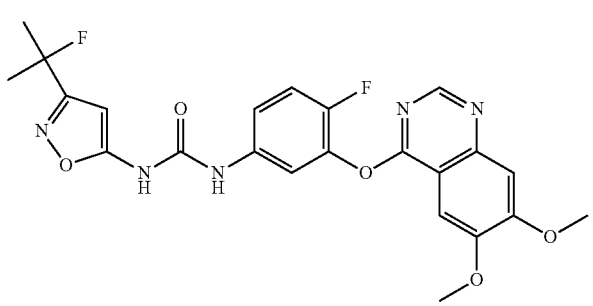 [SMILES: COc1cc2ncnc(Oc3cc(NC(=O)Nc4cc(C(C)(C)F)no4)ccc3F)c2cc1OC] | Ex293 1-(3-(6,7-dimethoxy-quinazolin-4-yloxy)-4-fluorophenyl)-3-(3-(2-fluoropropan-2-yl)isoxazol-5-yl)urea | A | B | A | A | A | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 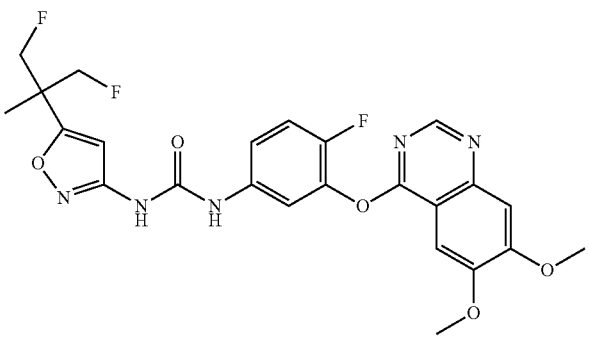 [SMILES: COc1cc2ncnc(Oc3cc(NC(=O)Nc4cc(C(C)(CF)CF)on4)ccc3F)c2cc1OC] | Ex 294 1-(5-(1,3-difluoro-2-methylpropan-2-yl)isoxazol-3-yl)-3-(3-(6,7-dimethoxy-quinazolin-4-yloxy)-4-fluorophenyl) urea | A | ND | A | A | A | D |
| 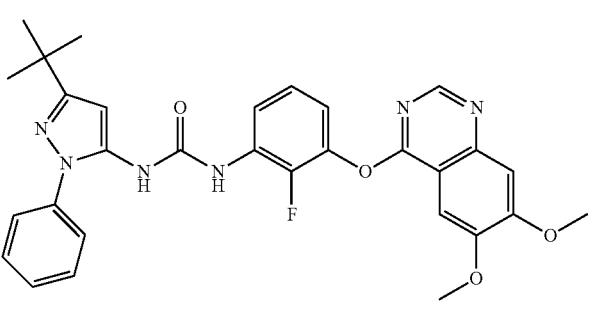 [SMILES: COc1cc2ncnc(Oc3cccc(NC(=O)Nc4cc(C(C)(C)C)nn4-c4ccccc4)c3F)c2cc1OC] | Ex 295 1-(3-tert-butyl-1-phenyl-1H-pyrazol-5-yl)-3-(3-(6,7-dimethoxy-quinazolin-4-yloxy)-2-fluorophenyl) urea | C | D | A | D | C | C |
| 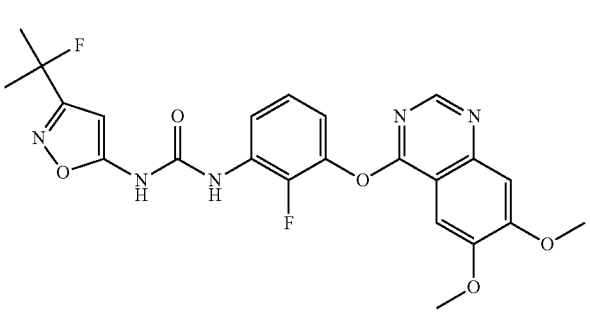 [SMILES: COc1cc2ncnc(Oc3cccc(NC(=O)Nc4cc(C(C)(C)F)no4)c3F)c2cc1OC] | Ex 296 1-(3-(6,7-dimethoxy-quinazolin-4-yloxy)-2-fluorophenyl)-3-(3-(2-fluoropropan-2-yl)isoxazol-5-yl)urea | D | D | A | A | A | B |
| 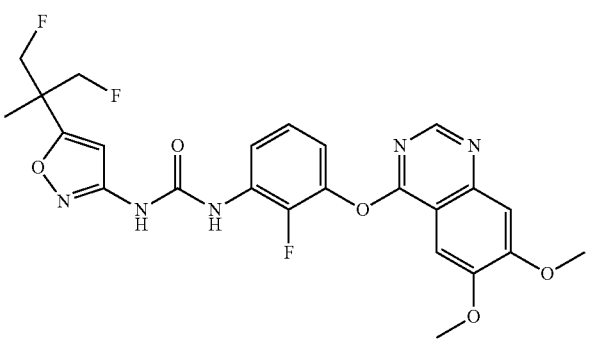 [SMILES: COc1cc2ncnc(Oc3cccc(NC(=O)Nc4cc(C(C)(CF)CF)on4)c3F)c2cc1OC] | Ex 297 1-(5-(1,3-difluoro-2-methylpropan-2-yl)isoxazol-3-yl)-3-(3-(6,7-dimethoxy-quinazolin-4-yloxy)-2-fluorophenyl) urea | B | B | A | A | A | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 298 1-(3-tert-butyl-1-p-tolyl-1H-pyrazol-5-yl)-3-(2-chloro-5-(6,7-dimethoxy-quinazolin-4-yloxy)phenyl)urea | A | A | D | D | D | D |
| Ex 299 1-(5-tert-butylisoxazol-3-yl)-3-(2-chloro-5-(6,7-dimethoxy-quinazolin-4-yloxy)phenyl)urea | A | ND | A | B | A | C |
| Ex 300 1-(2-chloro-5-(6,7-dimethoxy-quinazolin-4-yloxy)phenyl)-3-(1-phenyl-3-(trifluoromethyl)-1H-pyrazol-5-yl)urea | B | D | C | D | D | C |
| Ex 301 1-(3-tert-butyl-1-phenyl-1H-pyrazol-5-yl)-3-(2-chloro-5-(6,7-dimethoxy-quinazolin-4-yloxy)phenyl)urea | A | B | D | D | D | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 302 Preparation of 1-(3-(6,7-dimethoxy-quinazolin-4-yloxy)phenyl)-3-(5-(2-methyl-1-morpholino-propan-2-yl)isoxazol-3-yl)urea | D | D | B | D | D | B |
| Ex 303 1-(3-tert-butyl-1-(4-methylpyridin-3-yl)-1H-pyrazol-5-yl)-3-(3-(6,7-dimethoxy-quinazolin-4-yloxy)phenyl)urea | A | A | A | C | B | D |
| Ex 304 1-(3-(6,7-dimethoxy-quinazolin-4-yloxy)phenyl)-3-(3-(perfluoro-ethyl)-1-phenyl-1H-pyrazol-5-yl)urea | B | A | B | D | D | C |
| Ex 305 1-(3-tert-butyl-1-(2-methylpyridin-3-yl)-1H-pyrazol-5-yl)-3-(3-(6,7-dimethoxy-quinazolin-4-yloxy)phenyl)urea | A | A | A | C | B | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 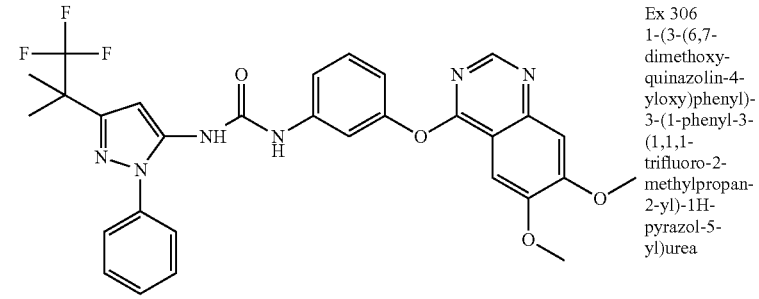 | Ex 306 1-(3-(6,7-dimethoxy-quinazolin-4-yloxy)phenyl)-3-(1-phenyl-3-(1,1,1-trifluoro-2-methylpropan-2-yl)-1H-pyrazol-5-yl)urea | A | ND | B | D | D | D |
| 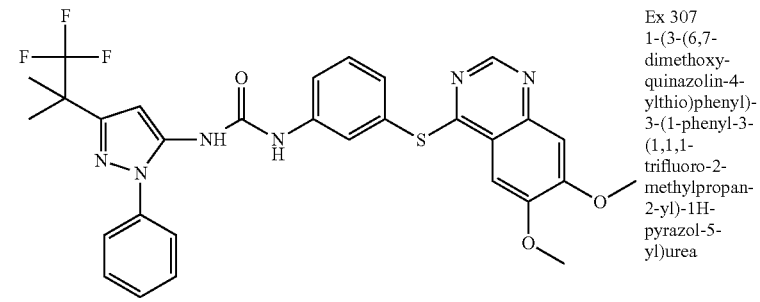 | Ex 307 1-(3-(6,7-dimethoxy-quinazolin-4-ylthio)phenyl)-3-(1-phenyl-3-(1,1,1-trifluoro-2-methylpropan-2-yl)-1H-pyrazol-5-yl)urea | A | ND | B | D | D | D |
| 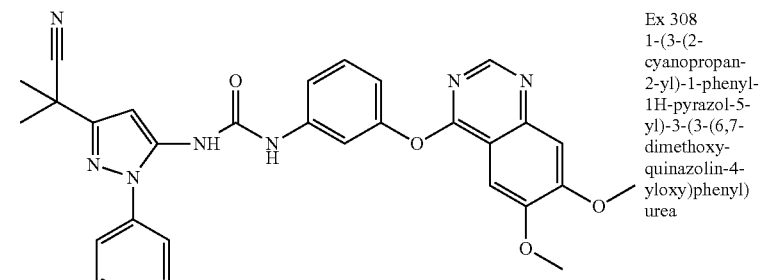 | Ex 308 1-(3-(2-cyanopropan-2-yl)-1-phenyl-1H-pyrazol-5-yl)-3-(3-(6,7-dimethoxy-quinazolin-4-yloxy)phenyl) urea | A | B | A | B | B | D |
| 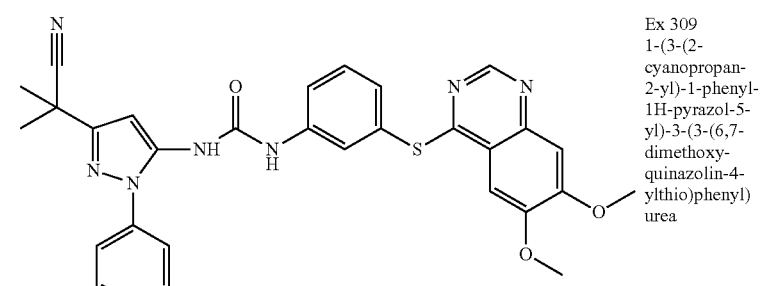 | Ex 309 1-(3-(2-cyanopropan-2-yl)-1-phenyl-1H-pyrazol-5-yl)-3-(3-(6,7-dimethoxy-quinazolin-4-ylthio)phenyl) urea | A | ND | A | C | C | C |
| 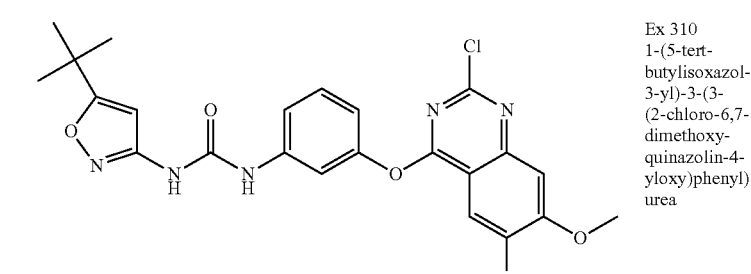 | Ex 310 1-(5-tert-butylisoxazol-3-yl)-3-(3-(2-chloro-6,7-dimethoxy-quinazolin-4-yloxy)phenyl) urea | D | D | C | D | C | A |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 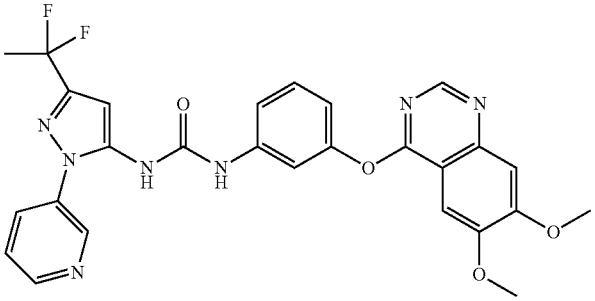 [SMILES: COc1cc2ncnc(Oc3cccc(NC(=O)Nc4cc(C(C)(F)F)nn4-c4cccnc4)c3)c2cc1OC] | Ex 311 1-(3-(1,1-difluoroethyl)-1-(pyridin-3-yl)-1H-pyrazol-5-yl)-3-(3-(6,7-dimethoxy-quinazolin-4-yloxy)phenyl)urea | B | B | A | A | A | C |
| 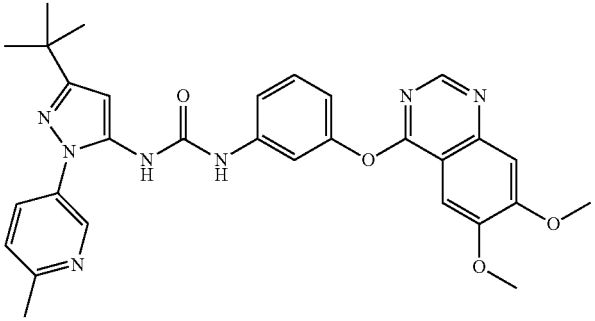 [SMILES: COc1cc2ncnc(Oc3cccc(NC(=O)Nc4cc(C(C)(C)C)nn4-c4ccc(C)nc4)c3)c2cc1OC] | Ex 312 1-(3-tert-butyl-1-(6-methylpyridin-3-yl)-1H-pyrazol-5-yl)-3-(3-(6,7-dimethoxy-quinazolin-4-yloxy)phenyl)urea | A | A | A | C | B | D |
| 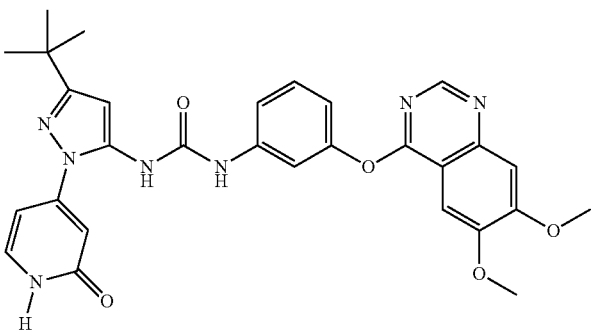 [SMILES: COc1cc2ncnc(Oc3cccc(NC(=O)Nc4cc(C(C)(C)C)nn4-c4cc[nH]c(=O)c4)c3)c2cc1OC] | Ex 313 Preparation of 1-(3-tert-butyl-1-(2-oxo-1,2-dihydropyridin-4-yl)-1H-pyrazol-5-yl)-3-(3-(6,7-dimethoxy-quinazolin-4-yloxy)phenyl)urea | B | C | A | B | B | D |
| 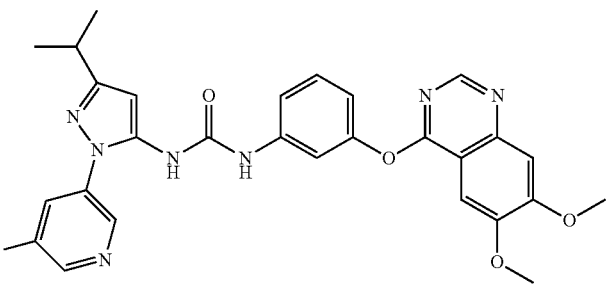 | Ex 314 1-(3-(6,7-dimethoxy-quinazolin-4-yloxy)phenyl)-3-(1-(5-fluoropyridin-3-yl)-3-isopropyl-1H-pyrazol-5-yl)urea | B | A | A | C | B | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 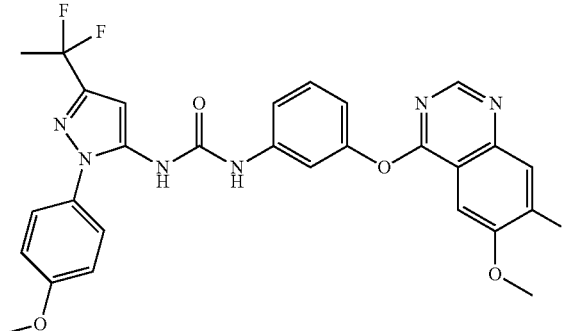 | Ex 315 1-(3-(1,1-difluoroethyl)-1-(4-methoxyphenyl)-1H-pyrazol-5-yl)-3-(3-(6,7-dimethoxyquinazolin-4-yloxy)phenyl)urea | A | A | A | D | C | D |
| 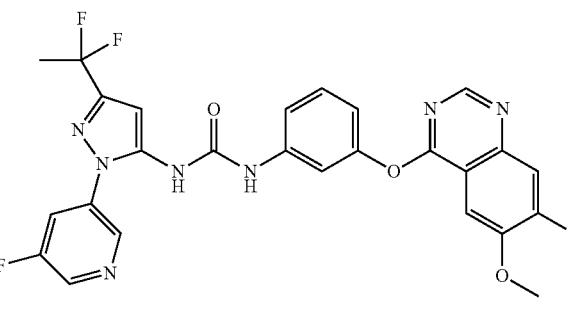 | Ex 316 1-(3-(1,1-difluoroethyl)-1-(5-fluoropyridin-3-yl)-1H-pyrazol-5-yl)-3-(3-(6,7-dimethoxyquinazolin-4-yloxy)phenyl)urea | B | C | A | B | A | C |
| 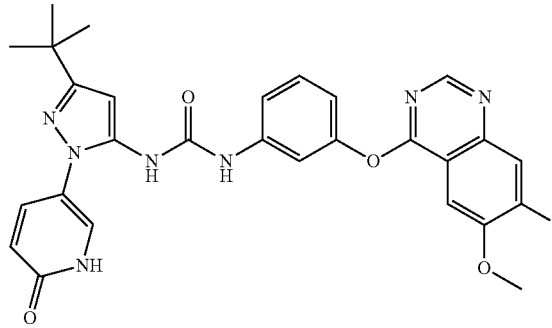 | Ex 317 1-(3-tert-butyl-1-(6-oxo-1,6-dihydropyridin-3-yl)-1H-pyrazol-5-yl)-3-(3-(6,7-dimethoxyquinazolin-4-yloxy)phenyl)urea | D | D | A | D | C | D |
| 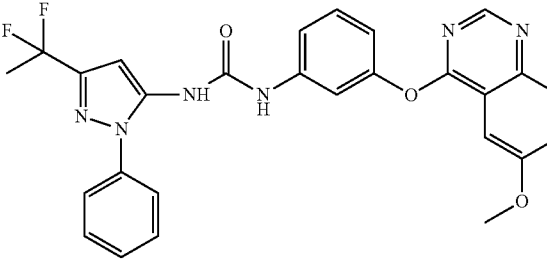 | Ex 318 1-(3-(1,1-difluoroethyl)-1-phenyl-1H-pyrazol-5-yl)-3-(3-(6,7-dimethoxyquinazolin-4-yloxy)phenyl)urea | A | A | A | B | B | C |
| 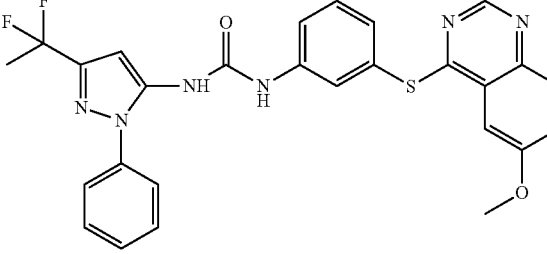 | Ex 319 Preparation of 1-(3-(1,1-difluoroethyl)-1-phenyl-1H-pyrazol-5-yl)-3-(3-(6,7-dimethoxyquinazolin-4-ylthio)phenyl)urea | A | A | A | C | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 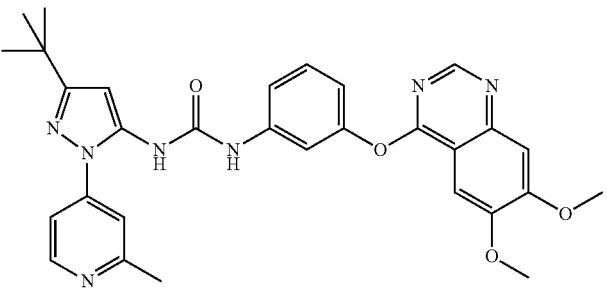 [SMILES: COc1cc2ncnc(Oc3cccc(NC(=O)Nc4cc(C(C)(C)C)nn4-c4ccnc(C)c4)c3)c2cc1OC] | Ex 320 1-(3-tert-butyl-1-(2-methylpyridin-4-yl)-1H-pyrazol-5-yl)-3-(3-(6,7-dimethoxy-quinazolin-4-yloxy)phenyl)urea | A | ND | A | D | D | D |
| 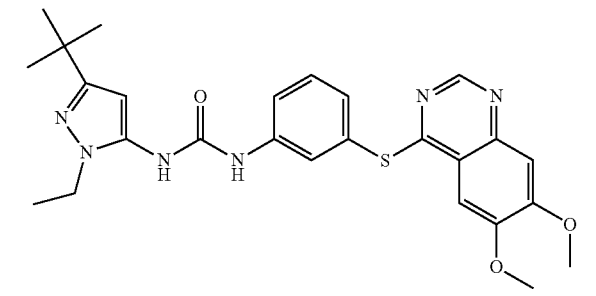 [SMILES: CCn1nc(C(C)(C)C)cc1NC(=O)Nc1cccc(Sc2ncnc3cc(OC)c(OC)cc23)c1] | Ex 321 1-(3-tert-butyl-1-ethyl-1H-pyrazol-5-yl)-3-(3-(6,7-dimethoxy-quinazolin-4-ylthio)phenyl)urea | B | C | A | B | A | C |
| 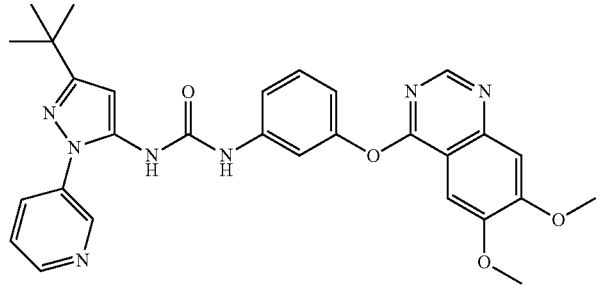 [SMILES: COc1cc2ncnc(Oc3cccc(NC(=O)Nc4cc(C(C)(C)C)nn4-c4cccnc4)c3)c2cc1OC] | Ex 322 1-(3-tert-butyl-1-(pyridin-3-yl)-1H-pyrazol-5-yl)-3-(3-(6,7-dimethoxy-quinazolin-4-yloxy)phenyl)urea | A | ND | A | B | B | D |
| 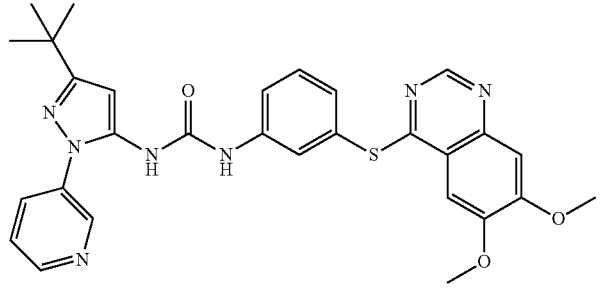 [SMILES: COc1cc2ncnc(Sc3cccc(NC(=O)Nc4cc(C(C)(C)C)nn4-c4cccnc4)c3)c2cc1OC] | Ex 323 1-(3-tert-butyl-1-(pyridin-3-yl)-1H-pyrazol-5-yl)-3-(3-(6,7-dimethoxy-quinazolin-4-ylthio)phenyl)urea | A | B | A | C | C | D |
| 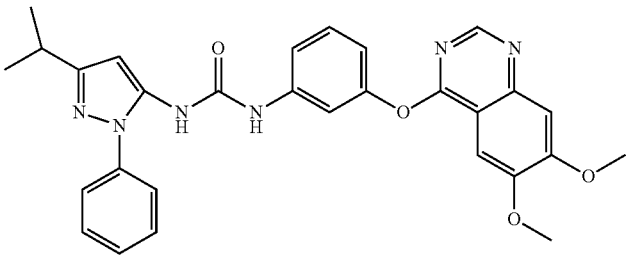 [SMILES: COc1cc2ncnc(Oc3cccc(NC(=O)Nc4cc(C(C)C)nn4-c4ccccc4)c3)c2cc1OC] | Ex 324 Preparation of 1-(3-(6,7-dimethoxy-quinazolin-4-yloxy)phenyl)-3-(3-isopropyl-1-phenyl-1H-pyrazol-5-yl)urea | A | A | A | B | B | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 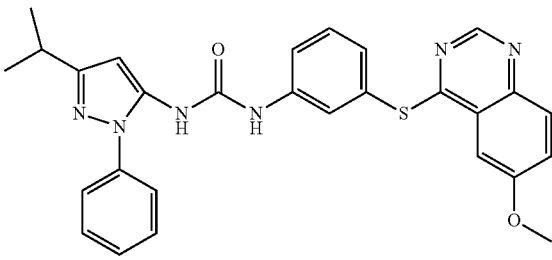 Ex 325 1-(3-(6,7-dimethoxy-quinazolin-4-ylthio)phenyl)-3-(3-isopropyl-1-phenyl-1H-pyrazol-5-yl)urea | A | A | A | B | B | C |
| 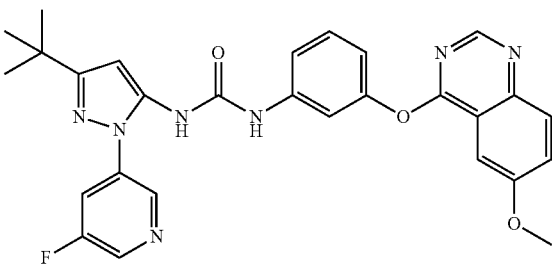 Ex 326 Preparation of 1-(3-tert-butyl-1-(5-fluoropyridin-3-yl)-1H-pyrazol-5-yl)-3-(3-(6,7-dimethoxy-quinazolin-4-yloxy)phenyl)urea | A | ND | A | C | C | D |
| 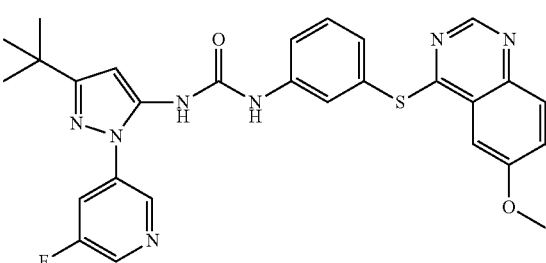 Ex 327 1-(3-tert-butyl-1-(5-fluoropyridin-3-yl)-1H-pyrazol-5-yl)-3-(3-(6,7-dimethoxy-quinazolin-4-ylthio)phenyl)urea | A | ND | A | C | C | D |
| 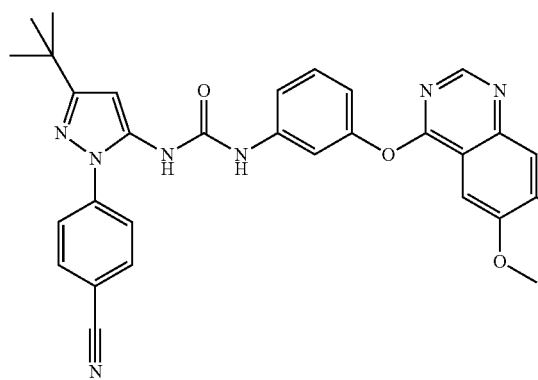 Ex 328 1-(3-tert-butyl-1-(4-cyanophenyl)-1H-pyrazol-5-yl)-3-(3-(6,7-dimethoxy-quinazolin-4-yloxy)phenyl)urea | A | ND | A | B | B | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 329 Preparation of 1-(3-tert-butyl-1-(4-cyanophenyl)-1H-pyrazol-5-yl)-3-(3-(6,7-dimethoxyquinazolin-4-ylthio)phenyl)urea | A | ND | B | B | C | D |
| Ex 330 1-(3-tert-butyl-1-cyclohexyl-1H-pyrazol-5-yl)-3-(3-(6,7-dimethoxyquinazolin-4-yloxy)phenyl)urea | D | D | A | D | D | C |
| Ex 331 1-(3-tert-butyl-1-cyclohexyl-1H-pyrazol-5-yl)-3-(3-(6,7-dimethoxyquinazolin-4-ylthio)phenyl)urea | A | D | B | C | C | B |
| Ex 332 1-(3-tert-butyl-1-isobutyl-1H-pyrazol-5-yl)-3-(3-(6,7-dimethoxyquinazolin-4-yloxy)phenyl)urea | C | D | A | B | B | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 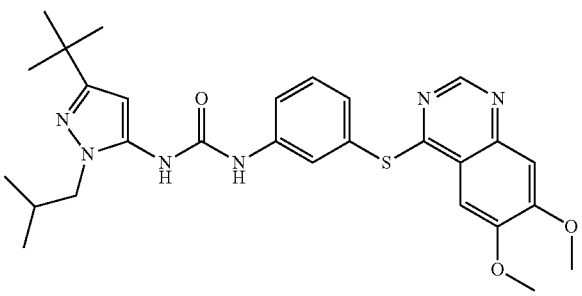 [SMILES: COc1cc2ncnc(Sc3cccc(NC(=O)Nc4cc(C(C)(C)C)nn4CC(C)C)c3)c2cc1OC] | Ex 333 1-(3-tert-butyl-1-isobutyl-1H-pyrazol-5-yl)-3-(3-(6,7-dimethoxy-quinazolin-4-ylthio)phenyl) urea | C | ND | A | B | B | C |
| 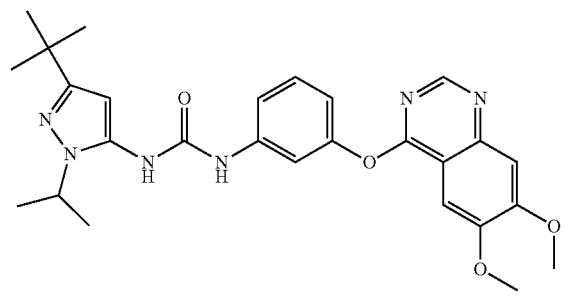 [SMILES: COc1cc2ncnc(Oc3cccc(NC(=O)Nc4cc(C(C)(C)C)nn4C(C)C)c3)c2cc1OC] | Ex 334 1-(3-tert-butyl-1-isopropyl-1H-pyrazol-5-yl)-3-(3-(6,7-dimethoxy-quinazolin-4-yloxy)phenyl) urea | C | C | A | B | B | C |
| 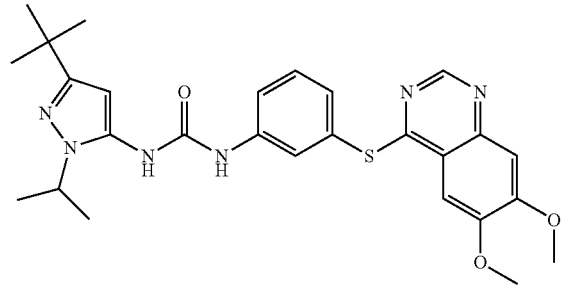 [SMILES: COc1cc2ncnc(Sc3cccc(NC(=O)Nc4cc(C(C)(C)C)nn4C(C)C)c3)c2cc1OC] | Ex 335 1-(3-tert-butyl-1-isopropyl-1H-pyrazol-5-yl)-3-(3-(6,7-dimethoxy-quinazolin-4-ylthio)phenyl) urea | B | D | A | B | B | C |
| 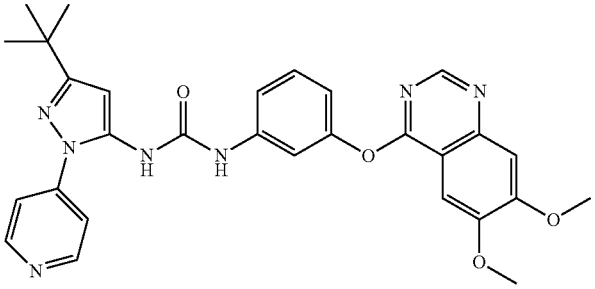 [SMILES: COc1cc2ncnc(Oc3cccc(NC(=O)Nc4cc(C(C)(C)C)nn4-c4ccncc4)c3)c2cc1OC] | Ex 336 1-(3-tert-butyl-1-(pyridin-4-yl)-1H-pyrazol-5-yl)-3-(3-(6,7-dimethoxy-quinazolin-4-yloxy)phenyl) urea | A | ND | A | C | C | D |
| 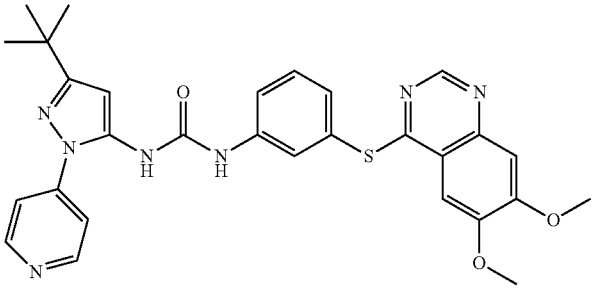 [SMILES: COc1cc2ncnc(Sc3cccc(NC(=O)Nc4cc(C(C)(C)C)nn4-c4ccncc4)c3)c2cc1OC] | Ex 337 1-(3-tert-butyl-1-(pyridin-4-yl)-1H-pyrazol-5-yl)-3-(3-(6,7-dimethoxy-quinazolin-4-ylthio)phenyl) urea | A | ND | A | C | C | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 338 1-(3-(6,7-dimethoxy-quinazolin-4-yloxy)phenyl)-3-(1-m-tolyl-3-(trifluoro-methyl)-1H-pyrazol-5-yl)urea | A | A | A | C | B | C |
| Ex 339 1-(3-(6,7-dimethoxy-quinazolin-4-ylthio)phenyl)-3-(1-m-tolyl-3-(trifluoro-methyl)-1H-pyrazol-5-yl)urea | A | ND | B | D | C | C |
| Ex 340 1-(3-tert-butyl-1-(2-chlorophenyl)-1H-pyrazol-5-yl)-3-(3-(6,7-dimethoxy-quinazolin-4-yloxy)phenyl)urea | A | ND | B | D | D | D |
| Ex 341 1-(3-tert-butyl-1-(2-chlorophenyl)-1H-pyrazol-5-yl)-3-(3-(6,7-dimethoxy-quinazolin-4-ylthio)phenyl)urea | A | ND | B | D | D | C |
| Ex 342 1-(3-tert-butyl-1-o-tolyl-1H-pyrazol-5-yl)-3-(3-(6,7-dimethoxy-quinazolin-4-yloxy)phenyl)urea | A | ND | B | D | D | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 343 1-(3-tert-butyl-1-o-tolyl-1H-pyrazol-5-yl)-3-(3-(6,7-dimethoxy-quinazolin-4-ylthio)phenyl) urea | A | ND | B | D | D | C |
| Ex 344 1-(3-tert-Butyl-1-(pyridin-2-yl)-1H-pyrazol-5-yl)-3-(3-(6,7-dimethoxy-quinazolin-4-yloxy)phenyl) urea | C | ND | C | D | D | C |
| Ex 345 1-(3-tert-butyl-1-(pyridin-2-yl)-1H-pyrazol-5-yl)-3-(3-(6,7-dimethoxy-quinazolin-4-ylthio)phenyl) urea | C | D | D | D | D | B |
| Ex 346 1-(3-(6,7-dimethoxy-quinazolin-4-yloxy)phenyl)-3-(1-p-tolyl-3-(1-(trifluoro-methyl)cyclo-propyl)-1H-pyrazol-5-yl)urea | A | ND | A | D | D | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| 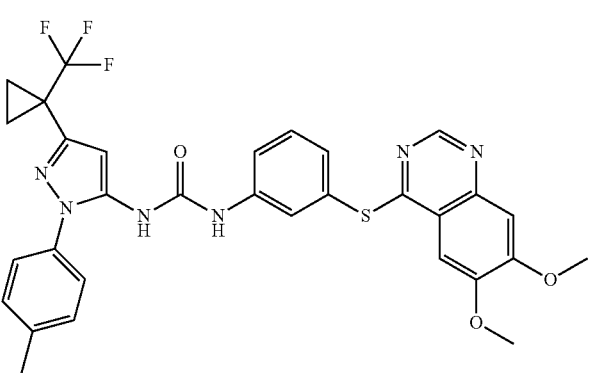 [SMILES: COc1cc2ncnc(Sc3cccc(NC(=O)Nc4cc(C5(C(F)(F)F)CC5)nn4-c4ccc(C)cc4)c3)c2cc1OC] Ex 347 1-(3-(6,7-dimethoxy-quinazolin-4-ylthio)phenyl)-3-(1-p-tolyl-3-(1-(trifluoro-methyl)cyclo-propyl)-1H-pyrazol-5-yl)urea | A | ND | B | D | D | D |
| 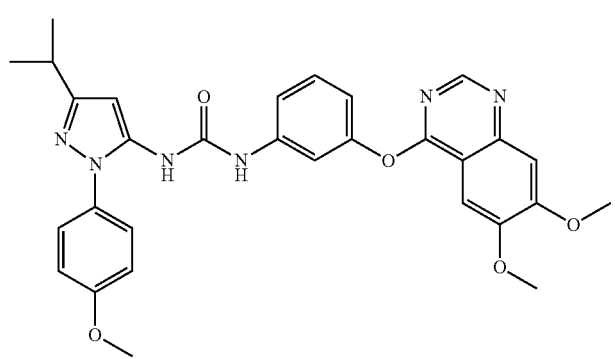 [SMILES: COc1ccc(-n2nc(C(C)C)cc2NC(=O)Nc2cccc(Oc3ncnc4cc(OC)c(OC)cc34)c2)cc1] Ex 348 1-(3-(6,7-dimethoxy-quinazolin-4-yloxy)phenyl)-3-(3-isopropyl-1-(4-methoxy-phenyl)-1H-pyrazol-5-yl)urea | A | A | A | D | C | D |
| 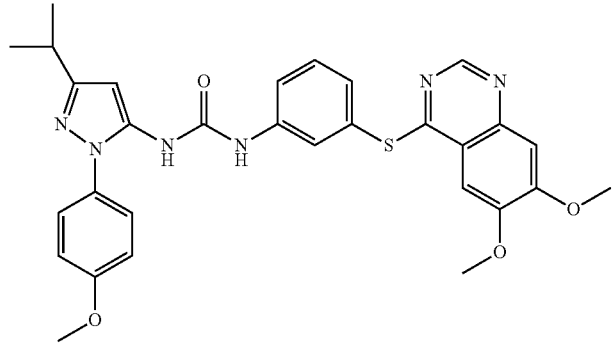 [SMILES: COc1ccc(-n2nc(C(C)C)cc2NC(=O)Nc2cccc(Sc3ncnc4cc(OC)c(OC)cc34)c2)cc1] Ex 349 1-(3-(6,7-dimethoxy-quinazolin-4-ylthio)phenyl)-3-(3-isopropyl-1-(4-methoxy-phenyl)-1H-pyrazol-5-yl)urea | A | A | A | D | C | C |
| 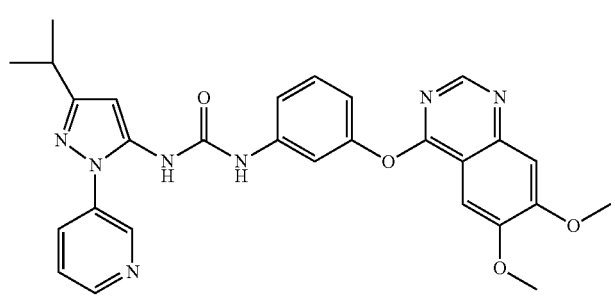 [SMILES: COc1cc2ncnc(Oc3cccc(NC(=O)Nc4cc(C(C)C)nn4-c4cccnc4)c3)c2cc1OC] Ex 350 1-(3-(6,7-dimethoxy-quinazolin-4-yloxy)phenyl)-3-(3-isopropyl-1-(pyridin-3-yl)-1H-pyrazol-5-yl)urea | B | B | A | A | A | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 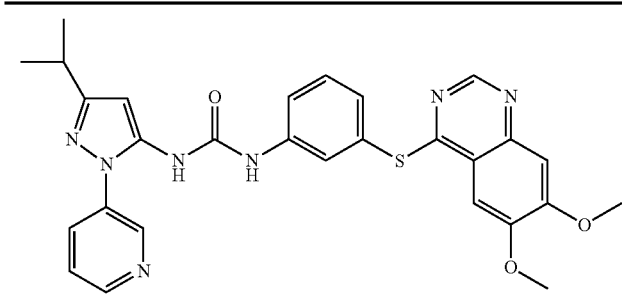 | Ex 351 1-(3-(6,7-dimethoxy-quinazolin-4-ylthio)phenyl)-3-(3-isopropyl-1-(pyridin-3-yl)-1H-pyrazol-5-yl)urea | A | B | A | C | A | C |
| 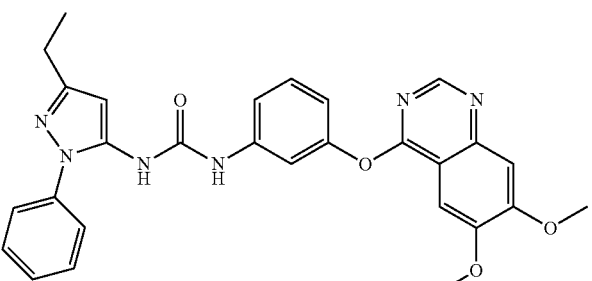 | Ex 352 1-(3-(6,7-dimethoxy-quinazolin-4-yloxy)phenyl)-3-(3-ethyl-1-phenyl-1H-pyrazol-5-yl)urea | C | B | A | A | A | C |
| 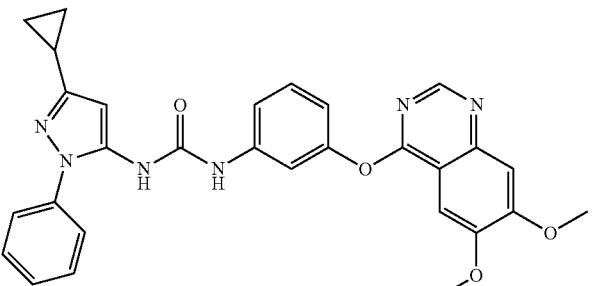 | Ex 353 1-(3-cyclopropyl-1-phenyl-1H-pyrazol-5-yl)-3-(3-(6,7-dimethoxy-quinazolin-4-yloxy)phenyl)urea | B | B | A | B | A | C |
| 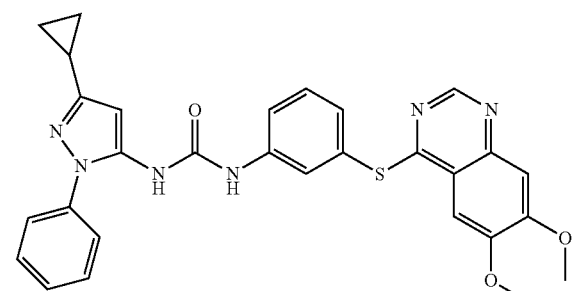 | Ex 354 1-(3-cyclopropyl-1-phenyl-1H-pyrazol-5-yl)-3-(3-(6,7-dimethoxy-quinazolin-4-ylthio)phenyl)urea | B | B | A | A | A | C |
| 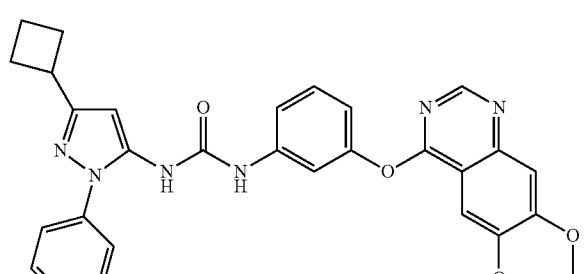 | Ex 355 Preparation of 1-(3-cyclobutyl-1-phenyl-1H-pyrazol-5-yl)-3-(3-(6,7-dimethoxy-quinazolin-4-yloxy)phenyl)urea | A | A | A | C | C | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 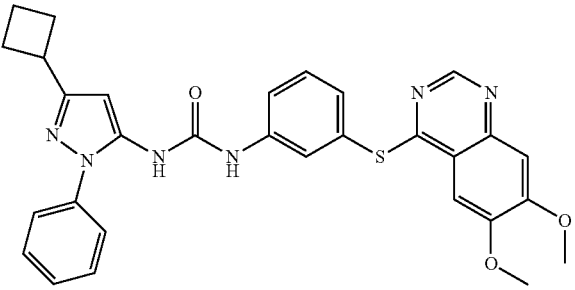 [SMILES: COc1cc2ncnc(Sc3cccc(NC(=O)Nc4cc(C5CCC5)nn4-c4ccccc4)c3)c2cc1OC] | Ex 356 1-(3-cyclobutyl-1-phenyl-1H-pyrazol-5-yl)-3-(3-(6,7-dimethoxy-quinazolin-4-ylthio)phenyl) urea | B | A | A | D | C | C |
| 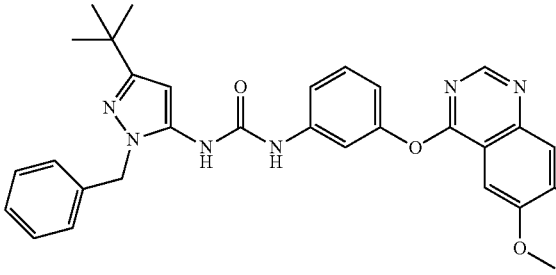 | Ex 357 1-(1-benzyl-3-tert-butyl-1H-pyrazol-5-yl)-3-(3-(6,7-dimethoxy-quinazolin-4-yloxy)phenyl) urea | B | D | A | C | D | C |
| 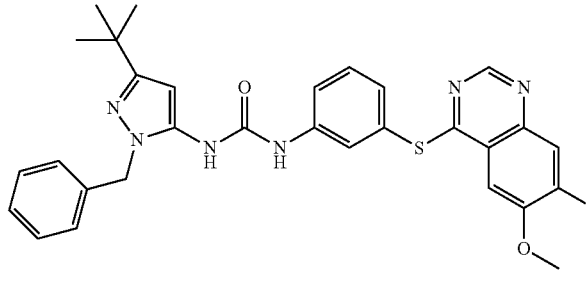 | Ex 358 1-(1-benzyl-3-tert-butyl-1H-pyrazol-5-yl)-3-(3-(6,7-dimethoxy-quinazolin-4-ylthio)phenyl) urea | B | ND | A | D | D | C |
| 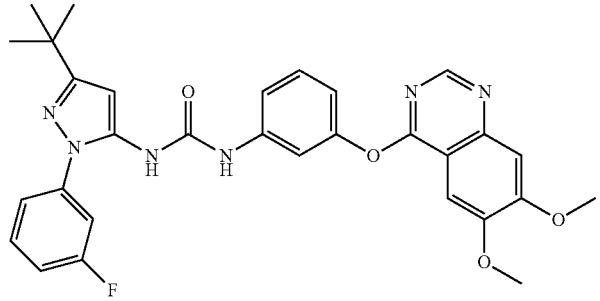 [SMILES: COc1cc2ncnc(Oc3cccc(NC(=O)Nc4cc(C(C)(C)C)nn4-c4cccc(F)c4)c3)c2cc1OC] | Ex 359 1-(3-tert-butyl-1-(3-fluorophenyl)-1H-pyrazol-5-yl)-3-(3-(6,7-dimethoxy-quinazolin-4-yloxy)phenyl) urea | A | ND | A | D | D | D |
| 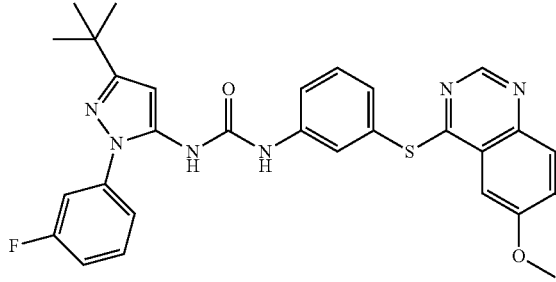 | Ex 360 1-(3-tert-butyl-1-(3-fluorophenyl)-1H-pyrazol-5-yl)-3-(3-(6,7-dimethoxy-quinazolin-4-ylthio)phenyl) urea | A | ND | B | D | D | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 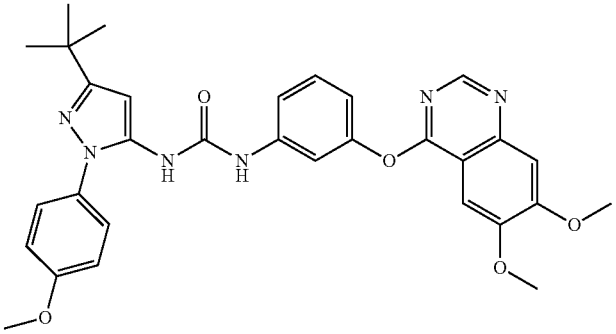 | Ex 361 1-(3-tert-butyl-1-(4-methoxyphenyl)-1H-pyrazol-5-yl)-3-(3-(6,7-dimethoxyquinazolin-4-yloxy)phenyl)urea | A | D | A | B | C | C |
| 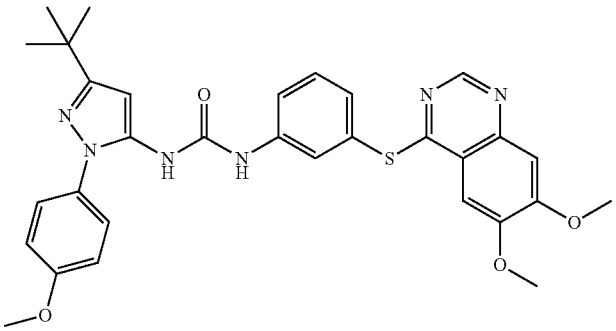 | Ex 362 Preparation of 1-(3-tert-butyl-1-(4-methoxyphenyl)-1H-pyrazol-5-yl)-3-(3-(6,7-dimethoxyquinazolin-4-ylthio)phenyl)urea | A | ND | C | D | D | D |
| 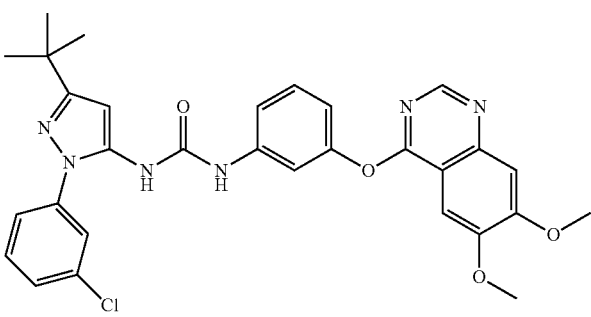 [SMILES: COc1cc2ncnc(Oc3cccc(NC(=O)Nc4cc(C(C)(C)C)nn4-c4cccc(Cl)c4)c3)c2cc1OC] | Ex 363 1-(3-tert-butyl-1-(3-chlorophenyl)-1H-pyrazol-5-yl)-3-(3-(6,7-dimethoxyquinazolin-4-yloxy)phenyl)urea | A | ND | A | B | D | D |
| 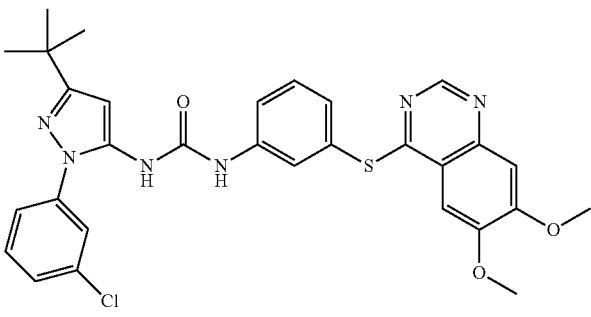 [SMILES: COc1cc2ncnc(Sc3cccc(NC(=O)Nc4cc(C(C)(C)C)nn4-c4cccc(Cl)c4)c3)c2cc1OC] | Ex 364 1-(3-tert-butyl-1-(3-chlorophenyl)-1H-pyrazol-5-yl)-3-(3-(6,7-dimethoxyquinazolin-4-ylthio)phenyl)urea | A | ND | A | C | D | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 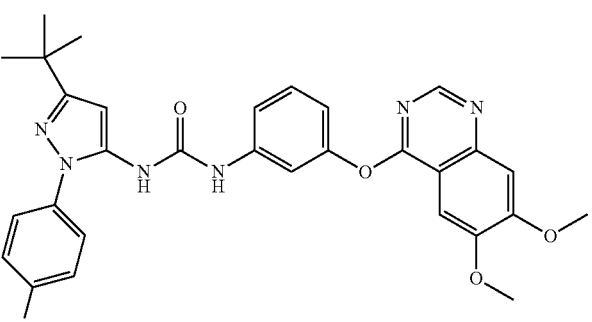 | Ex 365 1-(3-tert-butyl-1-(4-chlorophenyl)-1H-pyrazol-5-yl)-3-(3-(6,7-dimethoxy-quinazolin-4-yloxy)phenyl) urea | A | ND | B | D | D | D |
| 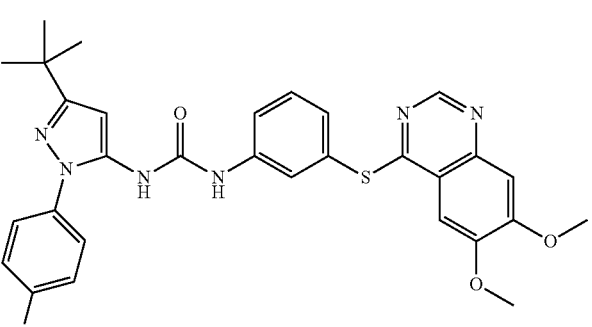 | Ex 366 1-(3-tert-butyl-1-(4-chlorophenyl)-1H-pyrazol-5-yl)-3-(3-(6,7-dimethoxy-quinazolin-4-ylthio)phenyl) urea | A | ND | B | D | D | D |
| 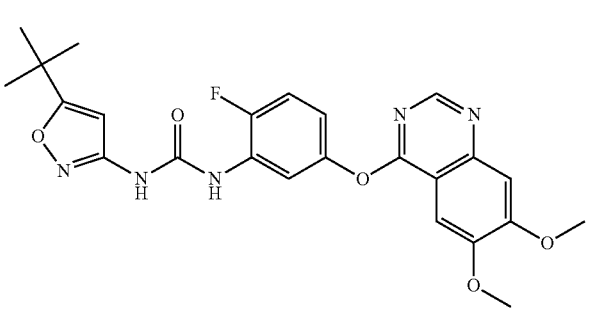 [SMILES: COc1cc2ncnc(Oc3ccc(F)c(NC(=O)Nc4cc(C(C)(C)C)on4)c3)c2cc1OC] | Ex 367 1-(5-tert-butylisoxazol-3-yl)-3-(5-(6,7-dimethoxy-quinazolin-4-yloxy)-2-fluorophenyl) urea | A | B | A | A | A | D |
| 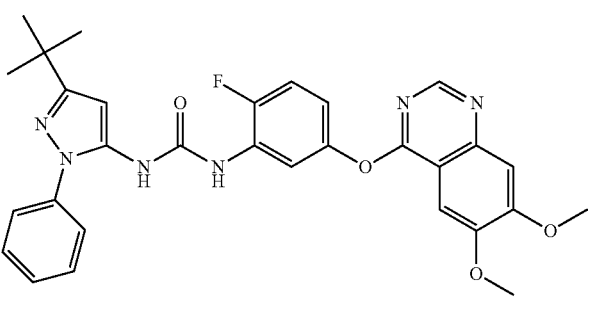 [SMILES: COc1cc2ncnc(Oc3ccc(F)c(NC(=O)Nc4cc(C(C)(C)C)nn4-c4ccccc4)c3)c2cc1OC] | Ex 368 1-(3-tert-butyl-1-phenyl-1H-pyrazol-5-yl)-3-(5-(6,7-dimethoxy-quinazolin-4-yloxy)-2-fluorophenyl) urea | A | ND | C | D | D | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 369 1-(3-tert-butyl-1-(4-tert-butylphenyl)-1H-pyrazol-5-yl)-3-(3-(6,7-dimethoxy-quinazolin-4-yloxy)phenyl) urea | A | D | A | C | D | C |
| Ex 370 1-(3-tert-butyl-1-(4-tert-butylphenyl)-1H-pyrazol-5-yl)-3-(3-(6,7-dimethoxy-quinazolin-4-ylthio)phenyl) urea | A | ND | A | D | D | D |
| Ex 371 1-(3-tert-butyl-1-(2-fluorophenyl)-1H-pyrazol-5-yl)-3-(3-(6,7-dimethoxy-quinazolin-4-ylthio)phenyl) urea | A | ND | B | D | D | D |
| Ex 372 1-(3-tert-butyl-1-(2-fluorophenyl-1H-pyrazol-5-yl)-3-(3-(6,7-dimethoxy-quinazolin-4-yloxy)phenyl) urea | A | ND | A | C | C | D |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 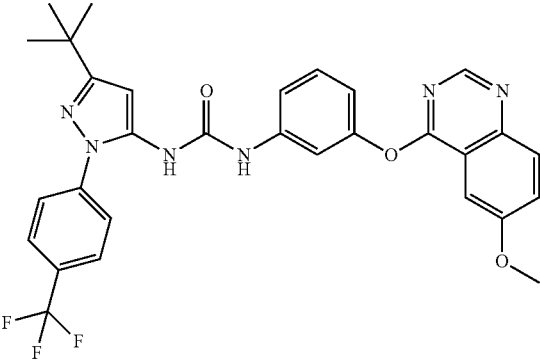 | Ex 373 1-(3-tert-butyl-1-(4-trifluoro-methyl)phenyl)-1H-pyrazol-5-yl)-3-(3-(6,7-dimethoxy-quinazolin-4-yloxy)phenyl)urea | A | ND | C | D | D | C |
| 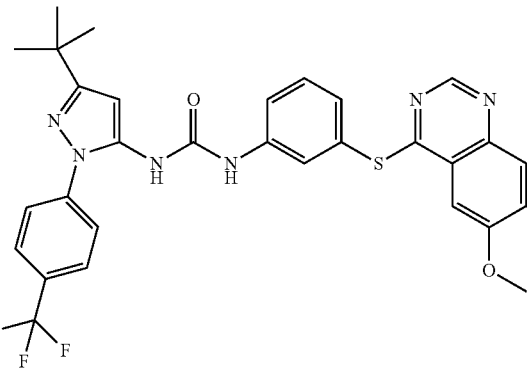 | Ex 374 1-(3-tert-butyl-1-(4-(trifluoro-methyl)phenyl)-1H-pyrazol-5-yl)-3-(3-(6,7-dimethoxy-quinazolin-4-ylthio)phenyl)urea | A | ND | B | D | D | C |
| 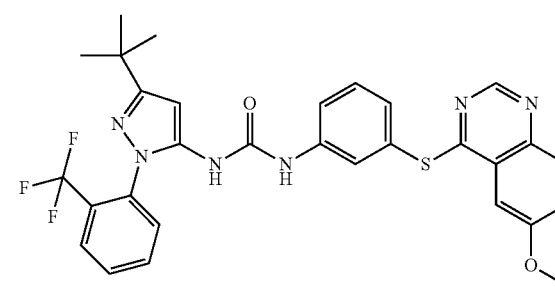 | Ex 375 1-(3-tert-butyl-1-(2-(trifluoro-methyl)phenyl)-1H-pyrazol-5-yl)-3-(3-(6,7-dimethoxy-quinazolin-4-ylthio)phenyl)urea | A | ND | C | D | D | C |
| 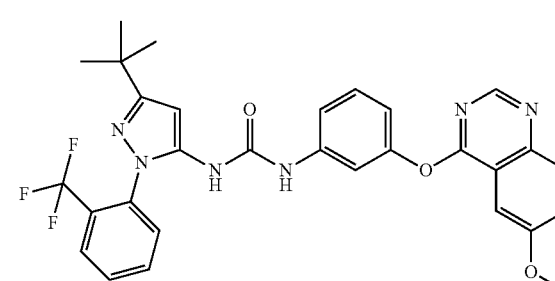 | Ex 376 1-(3-tert-butyl-1-(2-(trifluoro-methyl)phenyl)-1H-pyrazol-5-yl)-3-(3-(6,7-dimethoxy-quinazolin-4-yloxy)phenyl)urea | A | ND | C | D | D | D |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 377 1-(3-(6,7-dimethoxy-quinazolin-4-yloxy)phenyl)-3-(5-(1-trifluoromethyl)cyclopropyl)isoxazol-3-yl)urea | A | A | A | A | A | C |
| Ex 378 1-(3-(6,7-dimethoxy-quinazolin-4-ylthio)phenyl)-3-(5-(1-trifluoromethyl)cyclopropyl)isoxazol-3-yl)urea | B | A | A | A | A | C |
| Ex 379 1-(3-tert-butyl-1-(3-(trifluoromethyl)phenyl)-1H-pyrazol-yl)-3-(3-(6,7-dimethoxy-quinazolin-4-yloxy)phenyl)urea | A | ND | B | D | D | D |
| Ex 380 1-(3-tert-butyl-1-(3-(trifluoromethyl)phenyl)-1H-pyrazol-(5-yl)-3-(3-(6,7-dimethoxy-quinazolin-4-ylthio)phenyl)urea | A | ND | B | D | D | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 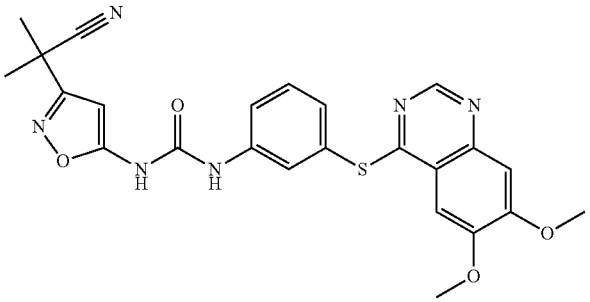 [SMILES: COc1cc2ncnc(Sc3cccc(NC(=O)Nc4cc(C(C)(C)C#N)no4)c3)c2cc1OC] | Ex 381 1-(3-(2-cyanopropan-2-yl)isoxazol-5-yl)-3-(3-(6,7-dimethoxy-quinazolin-4-ylthio)phenyl)urea | A | ND | A | A | A | C |
| 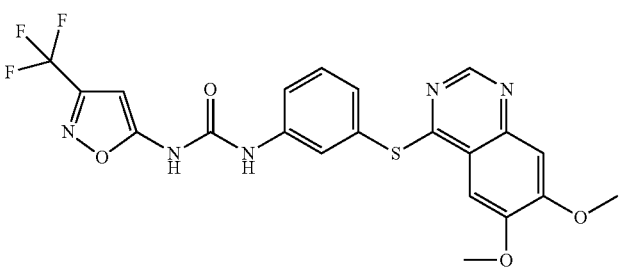 [SMILES: COc1cc2ncnc(Sc3cccc(NC(=O)Nc4cc(C(F)(F)F)no4)c3)c2cc1OC] | Ex 382 1-(3-(6,7-dimethoxy-quinazolin-4-ylthio)phenyl)-3-(3-(trifluoro-methyl)isoxazol-5-yl)urea | D | D | A | A | A | C |
| 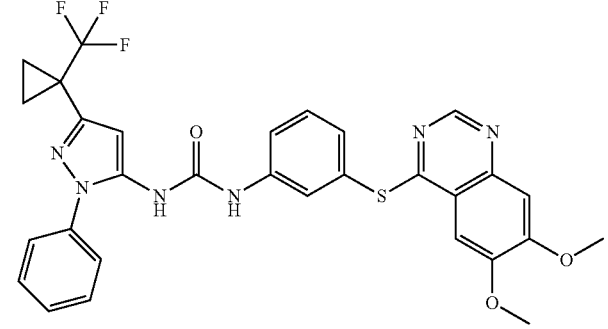 [SMILES: COc1cc2ncnc(Sc3cccc(NC(=O)Nc4cc(C5(C(F)(F)F)CC5)nn4-c4ccccc4)c3)c2cc1OC] | Ex 383 1-(3-(6,7-dimethoxy-quinazolin-4-ylthio)phenyl)-3-(1-phenyl-3-(1-(trifluoro-methyl)cyclo-propyl)-1H-pyrazol-5-yl)urea | A | ND | B | D | D | C |
| 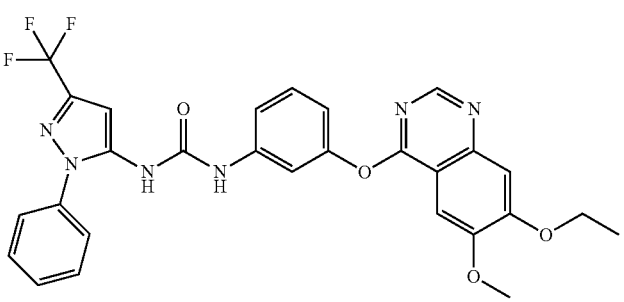 [SMILES: CCOc1cc2ncnc(Oc3cccc(NC(=O)Nc4cc(C(F)(F)F)nn4-c4ccccc4)c3)c2cc1OC] | Example 384 Preparation of 1-(3-(7-ethoxy-6-methoxy-quinazolin-4-yloxy)phenyl)-3-(1-phenyl-3-(trifluoro-methyl)-1H-pyrazol-5-yl)urea | C | B | A | C | B | C |
| 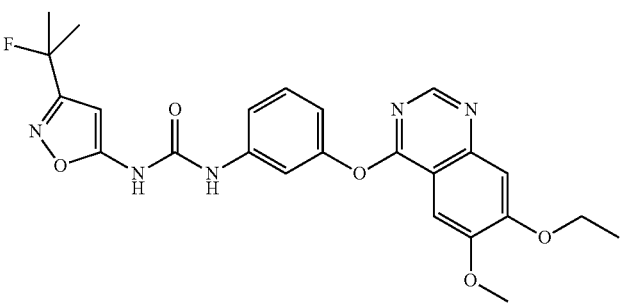 [SMILES: CCOc1cc2ncnc(Oc3cccc(NC(=O)Nc4cc(C(C)(C)F)no4)c3)c2cc1OC] | Ex 385 1-(3-(7-ethoxy-6-methoxy-quinazolin-4-yloxy)phenyl)-3-(3-(2-fluoropropan-2-yl)isoxazol-5-yl)urea | B | B | A | A | A | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 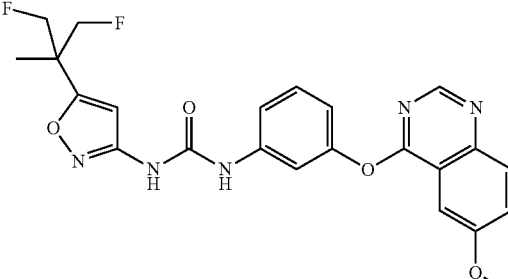 | Ex 386 1-(5-(1,3-difluoro-2-methylpropan-2-yl)isoxazol-3-yl)-3-(3-(7-ethoxy-6-methoxy-quinazolin-4-yloxy)phenyl)urea | A | A | A | A | A | C |
| 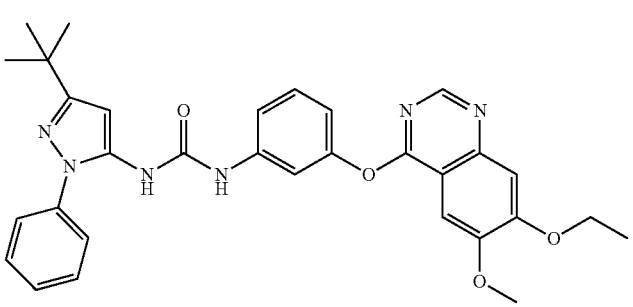 [SMILES: CCOc1cc2ncnc(Oc3cccc(NC(=O)Nc4cc(C(C)(C)C)nn4-c4ccccc4)c3)c2cc1OC] | Ex 387 1-(3-tert-butyl-1-phenyl-1H-pyrazol-5-yl)-3-(3-(7-ethoxy-6-methoxy-quinazolin-4-yloxy)phenyl)urea | A | ND | A | C | C | D |
| 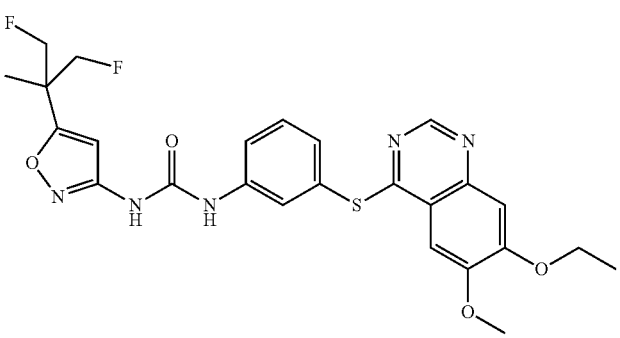 [SMILES: CCOc1cc2ncnc(Sc3cccc(NC(=O)Nc4cc(C(C)(CF)CF)on4)c3)c2cc1OC] | Example 388 Preparation of 1-(5-(1,3-difluoro-2-methylpropan-2-yl)isoxazol-3-yl)-3-(3-(7-ethoxy-6-methoxy-quinazolin-4-ylthio)phenyl)urea | B | B | A | A | A | C |
| 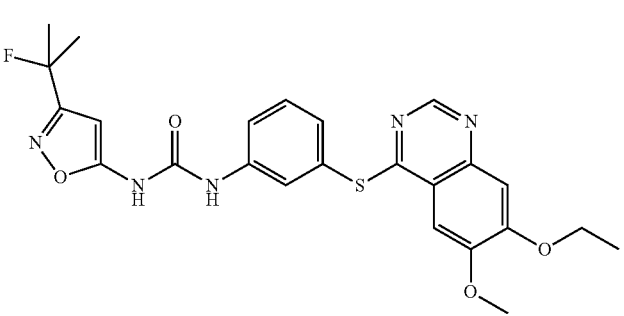 [SMILES: CCOc1cc2ncnc(Sc3cccc(NC(=O)Nc4cc(C(C)(C)F)no4)c3)c2cc1OC] | Ex 389 1-(3-(7-ethoxy-6-methoxy-quinazolin-4-ylthio)phenyl)-3-(3-(2-fluoropropan-2-yl)isoxazol-5-yl)urea | C | B | A | A | A | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 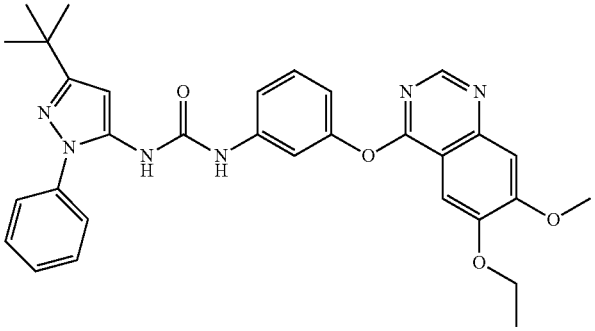 [SMILES: CCOc1cc2c(Oc3cccc(NC(=O)Nc4cc(C(C)(C)C)nn4-c4ccccc4)c3)ncnc2cc1OC] | Ex 390 1-(3-tert-butyl-1-phenyl-1H-pyrazol-5-yl)-3-(3-(6-ethoxy-7-methoxy-quinazolin-4-yloxy)phenyl)urea | A | ND | A | B | C | D |
| 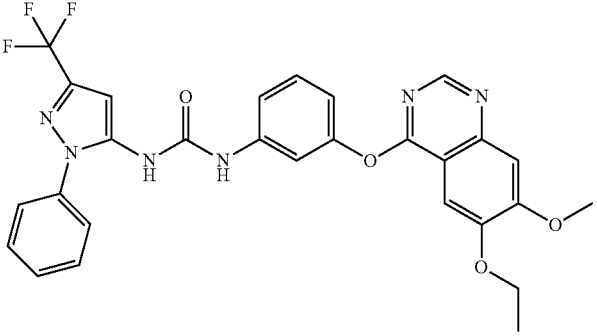 [SMILES: CCOc1cc2c(Oc3cccc(NC(=O)Nc4cc(C(F)(F)F)nn4-c4ccccc4)c3)ncnc2cc1OC] | Ex 391 1-(3-(6-ethoxy-7-methoxy-quinazolin-4-yloxy)phenyl)-3-(1-phenyl-3-(trifluoro-methyl)-1H-pyrazol-5-yl)urea | A | A | A | B | B | C |
| 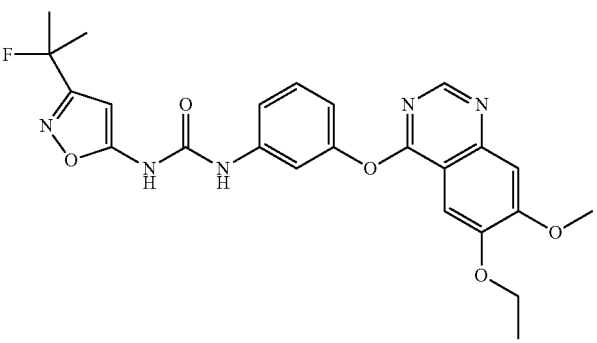 [SMILES: CCOc1cc2c(Oc3cccc(NC(=O)Nc4cc(C(C)(C)F)no4)c3)ncnc2cc1OC] | Ex 392 1-(3-(6-ethoxy-7-methoxy-quinazolin-4-yloxy)phenyl)-3-(3-(2-fluoropropan-2-yl)isoxazol-5-yl)urea | A | A | A | A | A | C |
| 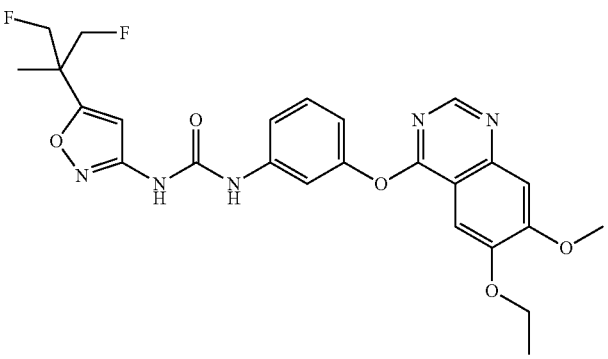 [SMILES: CCOc1cc2c(Oc3cccc(NC(=O)Nc4cc(C(C)(CF)CF)on4)c3)ncnc2cc1OC] | Ex 393 1-(5-(1,3-difluoro-2-methylpropan-2-yl)isoxazol-3-yl)-3-(3-(6-ethoxy-7-methoxy-quinazolin-4-yloxy)phenyl)urea | A | A | A | A | A | C |

TABLE 1-continued

| Name | pMEK IC50 (nM) | A375 Viability EC50 (nM) | BRAF V600E Kd (nM) | BRAF WT Kd nM | RAF1 Kd nM | S35 |
|---|---|---|---|---|---|---|
| Ex 394 1-(3-(6-ethoxy-7-methoxy-quinazolin-4-ylthio)phenyl)-3-(3-(2-fluoropropan-2-yl)isoxazol-5-yl)urea | A | B | A | A | A | C |
| Ex 395 1-(5-(1,3-difluoro-2-methylpropan-2-yl)isoxazol-3-yl)-3-(3-(6-ethoxy-7-methoxy-quinazolin-4-ylthio)phenyl)urea | A | A | A | A | A | C |
| Ex 396 (1-(3-(6-methoxy-7-(2-morpholino-ethoxy)quinazolin-4-yloxy)phenyl)-3-(1-phenyl-3-(trifluoro-methyl)-1H-pyrazol-5-yl)urea | C | C | A | C | C | C |
| Ex 397 1-(3-(6,7-dimethoxy-quinazolin-4-yloxy)-4-fluorophenyl)-3-(1-phenyl-3-(trifluoro-methyl)-1H-pyrazol-5-yl)urea | A | B | A | D | C | C |

TABLE 1-continued

| | Name | pMEK IC50 (nM) | A375 Viability EC50 (nM) | BRAF V600E Kd (nM) | BRAF WT Kd nM | RAF1 Kd nM | S35 |
|---|---|---|---|---|---|---|---|
| 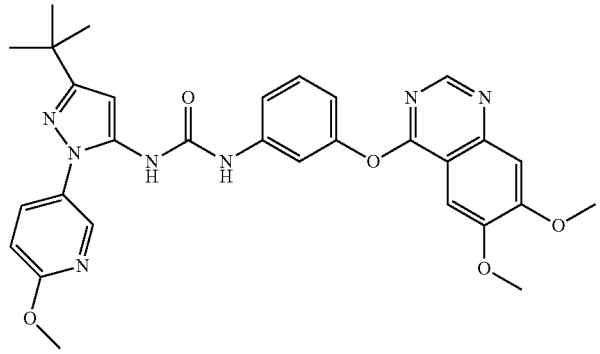 [SMILES: COc1ccc(-n2nc(C(C)(C)C)cc2NC(=O)Nc2cccc(Oc3ncnc4cc(OC)c(OC)cc34)c2)cn1] | Ex 398 1-(3-tert-butyl-1-(4-methoxyphenyl)-1H-pyrazol-5-yl)-3-(3-(6,7-dimethoxyquinazolin-4-yloxy)phenyl)urea | A | ND | A | C | C | D |
| 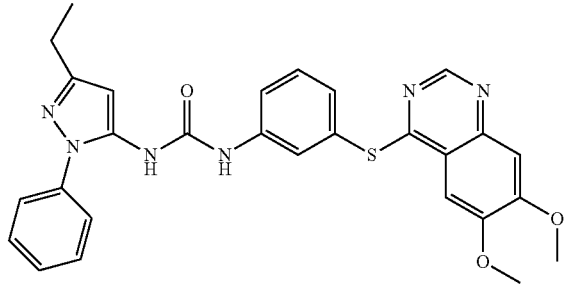 [SMILES: CCc1cc(NC(=O)Nc2cccc(Sc3ncnc4cc(OC)c(OC)cc34)c2)n(-c2ccccc2)n1] | Ex 399 1-(3-(6,7-dimethoxyquinazolin-4-ylthio)phenyl)-3-(3-ethyl-1-phenyl-1H-pyrazol-5-yl)urea | B | B | A | A | A | C | pMEK IC$_{50}$ and A375 Viability EC$_{50}$: A ≤ 250, 250 < B ≤ 500, 500 < C ≤ 1000, D > 1000,
BRAF V600E Kd, BRAF WT Kd and RAF1 Kd: A ≤ 250, 250 < B ≤ 500, 500 < C ≤ 1000, D > 1000
S35: A ≤ 0.10, 0.10 < B ≤ 0.20, 0.20 < C ≤ 0.40, D > 0.40 (Asterisk indicates an S35 score calculated using a panel of 321 distinct kinases, no asterisk indicates an S35 score calculated using a panel of 290 distinct kinases); and
ND = no data.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. NucL Med.*, 27: 388 (1986); Wade D, Chem. *Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a CH bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as T$_2$O. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen, will provide a similar kinetic isotope effects.

In another embodiment, provided herein are methods of using the disclosed compounds and compositions, or pharmaceutically acceptable salts, solvates, or hydrates thereof, for the local or systemic treatment or prophylaxis of human and veterinary diseases, disorders and conditions modulated or otherwise affected mediated via RAF kinase, including BRAF kinase, activity.

C. Formulation of Pharmaceutical Compositions

Provided herein are pharmaceutical compositions comprising a compound provided herein, e.g., a compound of Formula I, as an active ingredient, or a pharmaceutically acceptable salt, solvate or hydrate thereof; in combination with a pharmaceutically acceptable vehicle, carrier, diluent, or excipient, or a mixture thereof The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, e.g., a compound of Formula I, or a pharmaceutically acceptable salt, solvate or hydrate thereof; and one or more pharmaceutically acceptable excipients or carriers.

In another embodiment, the pharmaceutical compositions are provided in a dosage form for parenteral administration, which comprise a compound provided herein, e.g., a compound of Formula I, or a pharmaceutically acceptable salt, solvate or hydrate thereof; and one or more pharmaceutically acceptable excipients or carriers.

In yet another embodiment, the pharmaceutical compositions are provided in a dosage form for topical administration, which comprise a compound provided herein, e.g., a compound of Formula I, or a pharmaceutically acceptable salt, solvateor hydrate thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons. The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Oral Administration

The pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, troches, lozenges, pastilles, cachets, pellets, medicated chewing gum, bulk powders, effervescent or non-effervescent powders or granules, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as *acacia*, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, *acacia*, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, *acacia*, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of nonaqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein can be formulated as immediate or modified release dosage forms, including delayed-, sustained, pulsed-, controlled, targeted-, and programmed-release forms.

The pharmaceutical compositions provided herein can be co-formulated with other active ingredients which do not impair the desired therapeutic action, or with substances that supplement the desired action.

Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained, pulsed-, controlled, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

The pharmaceutical compositions provided herein for topical administration can be formulated to be immediate release or modified release, including delayed-, sustained-, pulsed-, controlled-, targeted, and programmed release.

Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

D. Evaluation of the Activity of the Compounds

Standard physiological, pharmacological and biochemical procedures are available for testing the compounds to identify those that possess biological activities that modulate the activity of BRAF kinases, including wild type and mutant BRAF kinases.

Such assays include, for example, biochemical assays such as binding assays, radioactivity incorporation assays, as well as a variety of cell based assays.

Exemplary cell based assay methodologies include measurement of MEK phosphorylation inhibition in the A375 human melanoma cell line, inhibition of cell proliferation in the A375 human melanoma cell line.

Cells useful in the assays include cells with wildtype or mutated forms. Suitable cells include those derived through cell culture from patient samples as well as cells derived using routine molecular biology techniques, e.g., retroviral transduction, transfection, mutagenesis, etc.

E. Methods of Use of the Compounds and Compositions

Also provided herein are methods of using the disclosed compounds and compositions, or pharmaceutically acceptable salts, solvates, or hydrates thereof, for the treatment, prevention, or amelioration of a disease or disorder that is mediated or otherwise affected via RAF kinase, including BRAF kinase activity or one or more symptoms of diseases or disorders that are mediated or otherwise affected via RAF kinase, including BRAF kinase, activity. BRAF kinase can be wild type and/or mutant form of BRAF kinase. In one embodiment, provided herein are methods for treatment of diseases or disorders including without limitation: cancers, including melanoma, papillary thyroid carcinoma, colorectal, ovarian, breast cancer, endometrial cancer, liver cancer, sarcoma, stomach cancer, Barret's adenocarcinoma, glioma (including ependymoma), lung cancer (including non small cell lung cancer), head and neck cancer, acute lymphoblastic leukemia and non-Hodgkin's lymphoma; and inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD).

In one embodiment, provided herein are methods for treating cancers including blood borne and solid tumors.

F. Combination Therapy

Furthermore, it will be understood by those skilled in the art that compounds provided herein, including pharmaceutical compositions and formulations containing these compounds, can be used in a wide variety of combination therapies to treat the conditions and diseases described above. Thus, also contemplated herein is the use of compounds and pharmaceutically acceptable salts provided herein in combination with other active pharmaceutical agents for the treatment of the disease/conditions described herein.

In one embodiment, such additional pharmaceutical agents include without limitation anti-cancer agents, including chemotherapeutic agents and anti-proliferative agents; anti-inflammatory agents and immunomodulatory agents or immunosuppressive agents.

In certain embodiments, the anti-cancer agents include anti-metabolites (e.g., 5-fluoro-uracil, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (estramustine phosphate, prednimustine), hormones or hormone agonists, antagonists, partial agonists or partial antagonists, kinase inhibitors, and radiation treatment.

In certain embodiments, the anti-inflammatory agents include matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, or glucocorticoid receptor agonists such as corticosteroids, methylprednisone, prednisone, or cortisone.

The compounds or compositions provided herein, or pharmaceutically acceptable salta thereof, may be administered simultaneously with, prior to, or after administration of one or more of the above agents.

Pharmaceutical compositions containing a compound provided herein or pharmaceutically acceptable salt thereof, and one or more of the above agents are also provided.

Also provided is a combination therapy that treats or prevents the onset of the symptoms, or associated complications of cancer and related diseases and disorders comprising the administration to a subject in need thereof, of one of the compounds or compositions disclosed herein, or pharmaceutically acceptable salts, solvates, hydrates or clathrates thereof, with one or more anti-cancer agents.

G. Preparation of the Compounds

Starting materials in the synthesis examples provided herein are either available from commercial sources or via literature procedures (e.g., March *Advanced Organic Chemistry: Reactions, Mechanisms, and Structure*, (1992) 4th Ed.; Wiley Interscience, New York). All commercially available compounds were used without further purification unless otherwise indicated. CDCl$_3$ (99.8% D, Cambridge Isotope Laboratories) was used in all experiments as indicated. Proton ($^1$H) nuclear magnetic resonance (NMR) spectra were recorded on a Bruker Avance 300 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). Preparative HPLC was performed using Varian HPLC systems and Phenomenex columns. Flash chromatography was performed using Merck Silica Gel 60 (230-400 mesh) following standard protocol (Still et al. (1978) *J. Org. Chem.* 43:2923).

It is understood that in the following description, combinations of substituents and/or variables of the depicted formulae are permissible only if such contributions result in stable compounds under standard conditions.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience.

One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is E/Z isomers, enantiomers and/or diastereomers.

Compounds of formula (I) may be generally prepared as depicted in the following schemes, unless otherwise noted, the various substituents are as defined elsewhere herein.

Standard abbreviations and acronyms as defined in *J. Org. Chem.* 2007 72(1): 23A-24A are used herein. Exemplary abbreviations and acronyms used herein are as follows:

DCM—dichloromethane
DIEA—N,N-diisopropylethylamine
EtOAc—ethyl acetate
EDCI—1-ethyl-3-(3'-dimethylaminopropyl)carbodiimide
EtOH—ethanol
FBS—fetal bovine serum
HOAc—acetic acid
MeOH—methanol
min—minute(s)

Activated quinazoline derivatives having one or more $R^1$ substituents (where each $R^1$ substitutent may or may not differ from the other $R^1$ substitutent(s)) are either commercially available or may be prepared according to Scheme 1. Activated quinazoline may be synthesized starting from anthranilic esters (1c, where R is alkyl) which are either commercially available, or are prepared from benzoic ester derivatives (1a, where R is alkyl), which undergoes classical nitration to yield the 2-nitro benzoic ester derivative (1b) which is followed by separation from any undesired regioisomers by crystallization or chromatography. For the reduction step, the 2-nitro intermediate in a suitable solvent such as water, $C_1$-$C_4$ alcohol, ethyl acetate or N,N-dimethylformamide, may be reacted with reducing agents such as hydrogen gas in the presence of noble metal catalyst, sodium dithionite, tin chloride, tin or iron metal in the presence of acid, and the like, to yield the anthranilic ester intermediate (1c).

There are many synthetic routes known to one skilled in the art that may be used to prepare the 4-hydroxy quinazoline derivative (1d). One route that may be used is the condensation of a suitable anthranilic ester derivative with formamide or a suitable formamide derivative such as formamidine hydrochloride in a suitable solvent such as ethanol at a temperature from 100° C. to 130° C., normally in the presence of an acid such as acetic acid (See, for example, Ballard et al. *Bioorganic & Medicinal Chemistry Letters* 2006, 16, 1633-1637) to yield 1d. Following isolation, the intermediate 4-hydroxyquinazoline derivative may be treated with an activating agent such as a phosphoric oxytrihalide or an aryl- or alkyl-sulfonyl halide to produce the activated quinazoline intermediate (1e) (See, for example, Takase et al. *J. Med. Chem.* 1994, 37, 2106-2111).

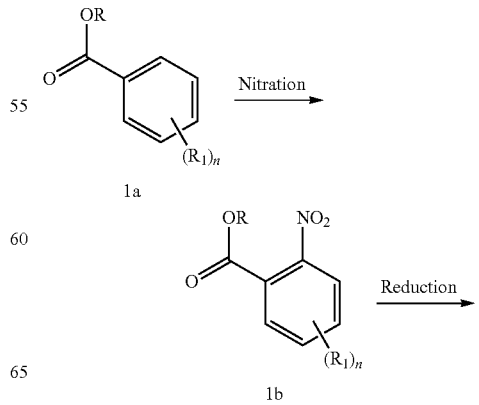

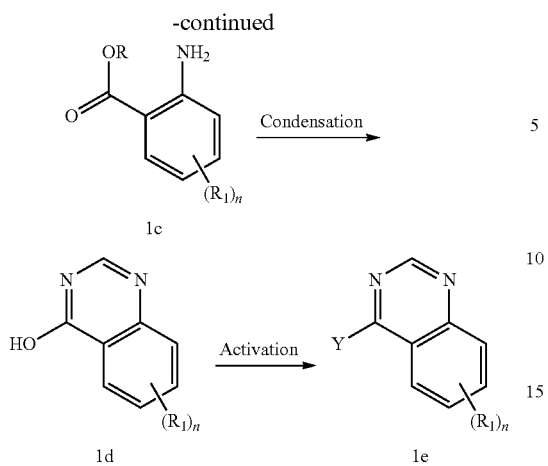

Phenyleneamine derivatives (2b) may be prepared according to Scheme 2 by reaction of corresponding activated quinazoline derivatives (1e) with the unprotected meta-hydroxy- (X=O) or meta-mercapto (X=S) aniline (2a) in a suitable solvent such as tetrahydrofuran or N,N-dimethylformamide at a temperature from 40° C. to 85° C., with formation (preferably preformation) of the oxa or sulfa anion with a base such as sodium hydride or cesium carbonate.

Scheme 2:

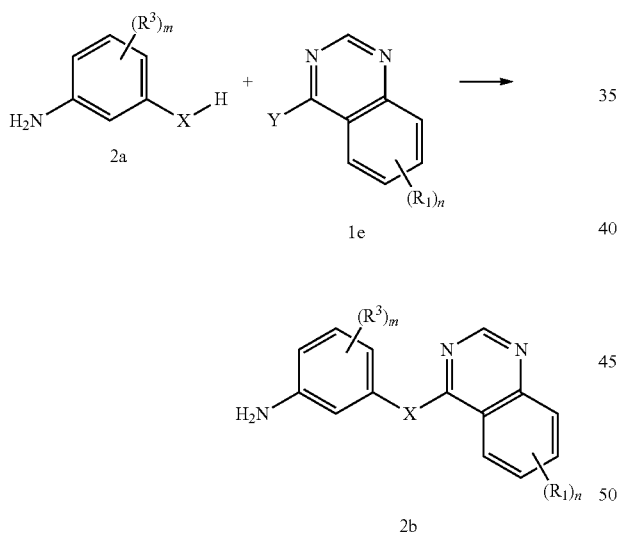

Alternatively, as will be apparent to one skilled in the art, the free amino group of 2a in Scheme 2 may be introduced in the form of an appropriate precursor, for example nitro or protected amino, followed by liberation of the free amine by nitro reduction or amine deprotection, respectively, to furnish 2b.

Diaryl ureas having the Formula I may be prepared according to Scheme 3 by the reaction of a phenyleneamine derivative (2b) (which may be prepared as described in Scheme 2), with an activated arylcarbamic acid derivative (3b, where Ar can be aryl or heteroaryl, which may be prepared as described below), where Z is a leaving group such as halo or optionally substituted phenoxy, for example.

Scheme 3:

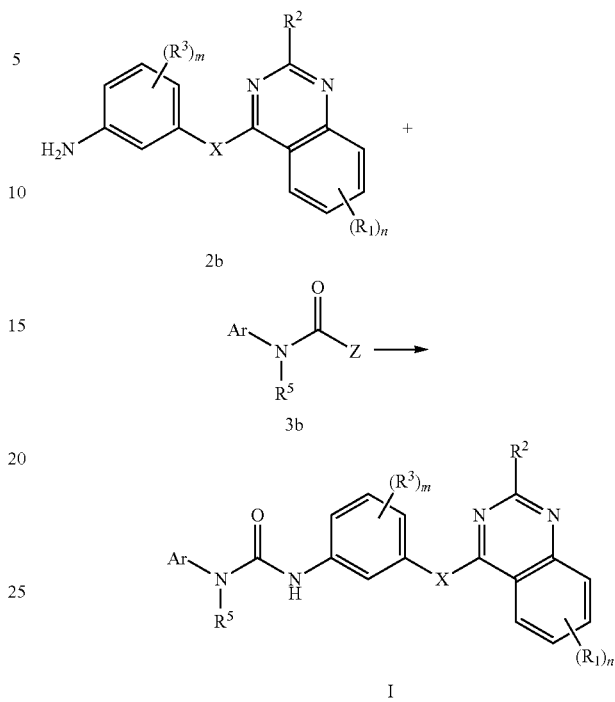

Alternatively, diaryl ureas having the Formula I may be prepared according to Scheme 4 when $R^5$=H. Phenyleneamine (2b) is treated with an aryl isocyanate (4b, where Ar can be aryl or heteroaryl) in a suitable solvent such as tetrahydrofuran at a temperature from 25° C. to 60° C., optionally in the presence of a base.

Scheme 4:

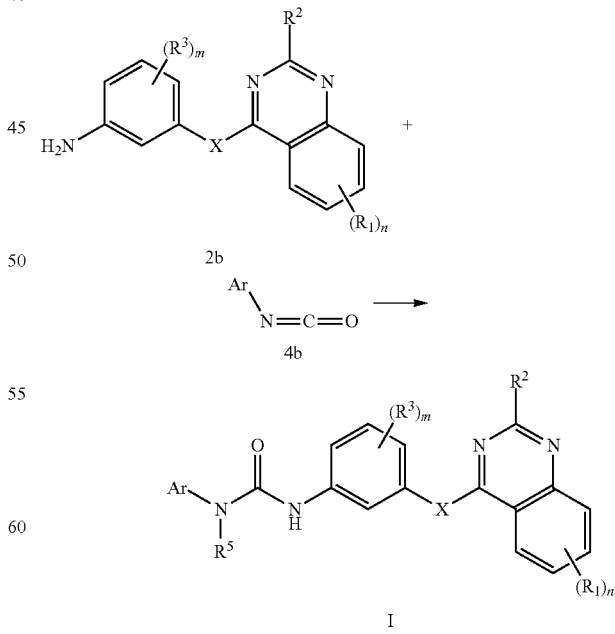

Alternatively, compounds having the Formula I may be prepared according to scheme 5 by the reaction of a hydroxy- (X=O) or mercapto- (X=S) substituted diaryl urea (5a, where Ar can be aryl or heteroaryl, which may be prepared as described below), with an activated quinazoline derivative (1e, where Y is a leaving group such as halo, aryl- or alkyl-sulfonate, which may be prepared as described in Scheme 1), in a suitable solvent such as tetrahydrofuran at a temperature from 40° C. to 80° C., normally in the presence of a base such as sodium hydride or cesium carbonate.

Scheme 5:

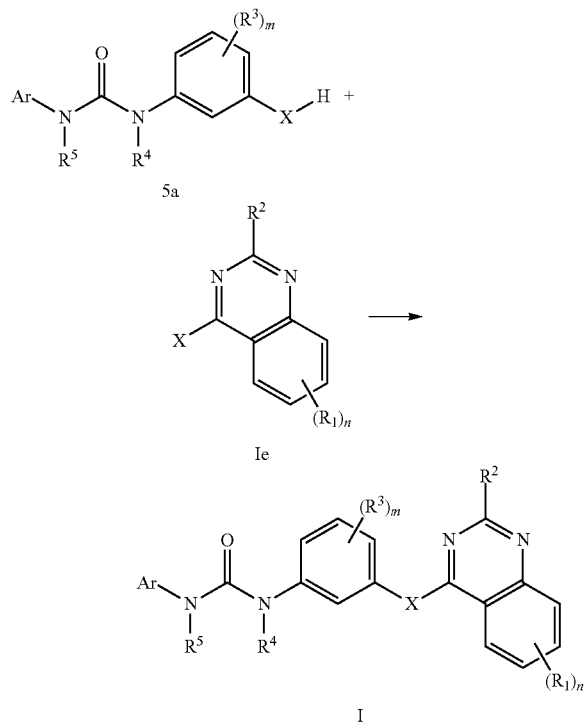

In certain embodiments, $R^1$ substituents of diaryl ureas having the Formula I, prepared as shown in Schemes 3, 4 and 5, may be further modified. For example, $R^1$ containing a haloalkyl moiety may be transformed to, for example, an aminoalkyl, alkoxyalkyl or thioalkyl, by treatment with, respectively, amines, alkoxides or thiolates. Alternatively, $R^1$ containing a carboxylic acid or carboxylic ester group may be transformed to the corresponding amides, amidines, alcohol, aldeyhdes, ketones, and aldehyde or ketone derivatives including oximes, hydrazones and the like. Where $R^1$ contains a hydroxy group, the hydroxy group may be derivatized to form the corresponding ester (by acylation), corresponding carbamate (by carbamylation), corresponding imidate and the like.

Arylcarbamoyl derivatives may be prepared as in Scheme 6 by treatment of corresponding aryl amines (6a, $R^5$=H) with a reagent such as an aryl chloroformate in a solvent such as tetrahydrofuran or dichloromethane in the presence of a base such as potassium carbonate at a temperature from 25° C. to 60° C. to give the corresponding aryl carbamate (6b or 3b, where Z may be, for example, phenoxy). When $R^5 \neq H$, phosgene, trichloromethyl chloroformate, or bis-trichloromethyl carbonate may be used to prepare arylcarbamoyl chloride variants (6c where Hal is halogen, or 3b, where Z may be, for example, halo).

Scheme 6:

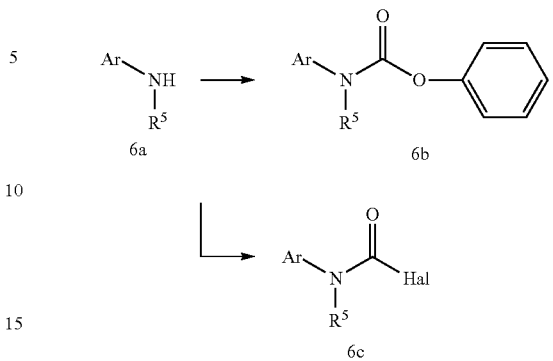

Scheme 7 shows the preparation of isocyanate derivatives (4b) which are prepared by treatment of corresponding primary aryl amines (7a) (where Ar may be aryl or heteroaryl) with phosgene, trichloromethyl chloroformate, or bis-trichloromethyl carbonate in a solvent such as toluene in the presence of a base such as triethylamine at a temperature from 25° C. to 110° C. to give the corresponding isocyanate (4b) (where Ar may be aryl or heteroaryl).

Scheme 7:

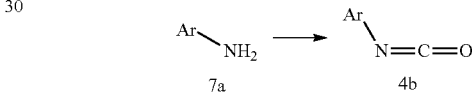

Aryl amine derivatives (7a), wherein Ar is a 5-membered heteroaromatic ring, may be prepared by condensation of appropriate fragments and precursors by methods well known in the art and described in texts such as Gilchrist, T. L., *Heterocyclic Chemistry* (1992), 2nd Ed., Longman Scientific & Technical and John Wiley & Sons. Scheme 8 shows one example where Ar is 5-substituted-3-aminoisoxazole, whereby an appropriate 3-oxonitrile (8a) is treated with hydroxylamine under appropriate conditions of pH and temperature which is described, for example, in Takase et al. *Heterocycles* 1991 32(6), 1153-1158, to afford the desired aryl amine product (8b). This method is particularly applicable for cases in which the atom of $R^{10}$ directly attached to the aromatic ring is highly substituted, for example, is an α,α-dialkyl substituent (See Takase et al. *Heterocycles* 1991 32(6), 1153-1158).

Scheme 8:

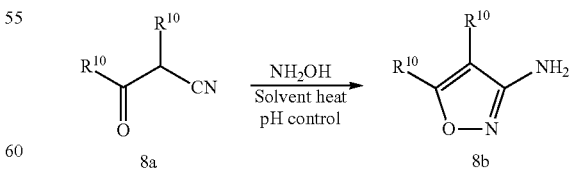

Scheme 9 shows an example for the case where Ar is 3-substituted-5-aminoisoxazole, whereby an appropriate 3-oxonitrile 9a is treated with hydroxylamine under appropriate conditions of pH and temperature, as described again in Takase et al. *Heterocycles* 1991 32(6), 1153-1158, to afford the desired aryl amine product (9b). This method is particularly applicable for cases in which the atom of R¹⁰ directly attached to the aromatic ring is not highly substituted, for example, is not an α,α-dialkyl substituent (See Eddington et al. *Eur. J. Med. Chem.* 2002 37, 635-648), or when R¹⁰ contains one or more highly electron-withdrawing groups, eg, fluorine, or under special conditions of pH and solvent, such as ethanol and water mixtureas described in EP 0220947.

Scheme 9:

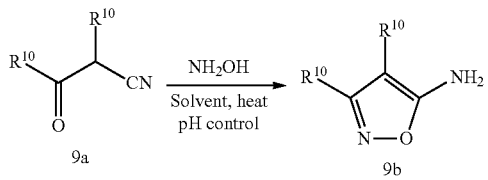

Scheme 10 shows an example for the case where Ar is a 2,5-disubstituted-3-aminopyrazole, whereby an appropriate 3-oxonitrile (10a) is treated with a monosubstituted hydrazine under appropriate conditions of pH and temperature to afford the desired aryl amine product (10b).

Scheme 10:

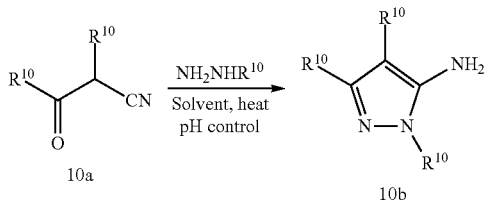

Depending on R¹⁰, in order to influence the yield and regiochemical outcome of the condensation reaction, 3-oxonitrile (10a) may be productively replaced in the foregoing schemes by oxo-protected derivatives of (10a), such as an enol ether derivative (10c, R=lower alkyl or substituted silyl) or a ketal derivative (10d, R=lower alkyl or taken together, an alkylene derivative to form a ketal ring). These derivatives are prepared from 3-oxonitrile under standard conditions, for example as described in Chan et al. *Synthesis* 1983 203-205.

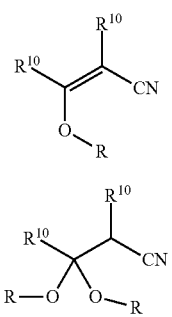

Scheme 11 illustrates preparation of the requisite 3-oxonitriles (10a) by reaction of an R¹⁰-containing carboxylic ester (11a) with an akali metal salt of acetonitrile (11b) (See, for example, U.S. Pat. No. 4,728,743).

Scheme 11:

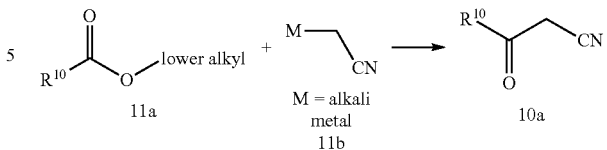

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, 5th ed. (2001). Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

Example 1

Preparation of 1-(5-tert-butylisoxazol-3-yl)-3-(3-(6,7-dimethoxyquinazolin-4-yloxy)phenyl)urea Example 1A preparation of 1-(5-tert-butylisoxazol-3-yl)-3-(3-hydroxyphenyl)urea: to THF (300 ml, degassed w/ argon) was added 3-aminophenol (4.36 g, 40 mmol) and 5-tert-butyl-3-isocyanatoisoxazole (6.64 g, 40 mmol) and the mixture was heated at 50° C. overnight. After cooling to room temperature, the reaction was concentrated in vacuo, and the resulting foam purified by column chromatography (25-75% EtOAc/hexanes) to give 1-(5-tert-butylisoxazol-3-yl)-3-(3-hydroxyphenyl)urea (8.81 g, 32 mmol, 80%). ¹H NMR (300 MHz, DMSO-$d_6$) δ 9.39 (s, 1h), 9.37 (s, 1h), 8.69 (s, 1h), 7.06 (t, 1h), 7.01 (s, 1h), 6.78 (d, 1h), 6.49 (s, 1h), 6.41 (d, 1h), 1.29 (s, 9h); LC-MS (ESI) m/z 275 (M+H)⁺.

Example 1B step 1: preparation of 1-(5-tert-butylisoxazol-3-yl)-3-(3-(6,7-dimethoxyquinazolin-4-yloxy)phenyl)urea: to a slurry of potassium tert-butoxide (6.73 g, 60 mmol) in THF (300 ml) was added the phenol from example 1a (8.25 g, 30 mmol), and the solution stirred at room temperature for 1 hour, at which point 4-chloro-6,7-dimethoxyquinazoline (6.74 g, 30 mmol) was added, followed by K₂CO₃ (4.1 g, 30 mmol). After stirring at room temperature for 72 hours, the reaction was concentrated in vacuo. The resulting solid was diluted with EtOAc, the organic layer washed with water, dried over $MgSO_4$, filtered and concentrated in vacuo. The crude product was purified by column chromatography (15-100% EtOAc/hexanes) to give 1-(5-tert-butylisoxazol-3-yl)-3-(3-(2-chloro-6,7-dimethoxyquinazolin-4-yloxy)phenyl)urea as a white solid.

Example 1B step 2: the compound was dissolved in EtOAc (50 ml) and 4N HCl in dioxane (5 ml, 20 mmol) was added. The mixture was sonicated, stirred and concentrated in vacuo to give the product (6.23 g, 12.5 mmol, 42%) as the mono-hydrochloride. $^1$H NMR (300 MHz, DMSO-$d_6$) δ 9.72 (s, 1h), 9.44 (s, 1h), 8.73 (s, 1h), 7.65-7.60 (m, 2h), 7.45-7.38 (m, 2h), 7.29 (d, 1h), 6.98 (d, 1h), 6.48 (s, 1h), 4.02 (s, 3h), 4.00 (s, 3h), 1.28 (s, 9h); LC-MS (ESI) m/z 464 (M+H)$^+$.

Example 2

Preparation of 1-(5-tert-butylisoxazol-3-yl)-3-(3-(6-methoxyquinazolin-4-yloxy)phenyl)urea To 1-(5-tert-butylisoxazol-3-yl)-3-(3-hydroxyphenyl)urea from Example 1A (275 mg, 1 mmol) was added 4-chloro-6-methoxyquinazoline (194 mg, 1 mmol) according to the procedure described in Example 1B Step 1. The resulting compound was dissolved in EtOAc and 4N HCl in dioxane was added. The mixture was sonicated, stirred and concentrated in vacuo to give 1-(5-tert-butylisoxazol-3-yl)-3-(3-(6-methoxyquinazolin-4-yloxy)phenyl)urea as the mono-hydrochloride (299 mg, 0.64 mmol, 64%). $^1$H NMR (300 MHz, DMSO-$d_6$) δ 9.65 (s, 1H), 9.20 (s, 1H), 8.65 (s, 1H), 7.95 (d, 1H), 7.75-7.60 (m, 3H), 7.42 (t, 1H), 7.29 (d, 1H), 6.98 (d, 1H), 6.48 (s, 1H), 3.98 (s, 3H), 1.29 (s, 9H); LC-MS (ESI) m/z 434 (M+H)$^+$.

Example 3

Preparation of 1-(5-tert-butylisoxazol-3-yl)-3-(3-(7-methoxyquinazolin-4-yloxy)phenyl)urea To 1-(5-tert-butylisoxazol-3-yl)-3-(3-hydroxyphenyl)urea from Example 1A (137 mg, 0.5 mmol) was added 4-chloro-7-methoxyquinazoline (97 mg, 0.5 mmol) according to the procedure described in Example 1B. The resulting compound was dissolved in EtOAc (5 mL) and 4N HCl in dioxane (0.2 mL, 0.8 mmol) was added. The mixture was sonicated, stirred and concentrated in vacuo to give 1-(5-tert-butylisoxazol-3-yl)-3-(3-(7-methoxyquinazolin-4-yloxy)phenyl)urea as the mono-hydrochloride (103 mg, 0.22 mmol, 44%). $^1$H NMR (300 MHz, DMSO-$d_6$) δ 9.63 (s, 1H), 9.15 (s, 1H), 8.69 (s, 1H), 8.28 (d, 1H), 7.58 (s, 1H), 7.45-7.35 (m, 3H), 7.27 (d, 1H), 6.98 (d, 1H), 6.48 (s, 1H), 3.98 (s, 3H), 1.28 (s, 9H); LC-MS (ESI) m/z 434 (M+H)$^+$.

Example 4

Preparation of 1-(5-tert-butylisoxazol-3-yl)-3-(3-(6,7-difluoroquinazolin-4-yloxy)phenyl)urea Example 4A Step 1: To a stirring mixture of formamide (10 mL) and glacial acetic acid (2.5 mL) was added 2-amino-4,5-difluorobenzoic acid (2.0 g, 11.6 mmol) and the solution stirred at 125° C. for 8 hours. After cooling to room temperature, the reaction was diluted with $H_2O$ (100 mL) and the resulting solid filtered and dried under vacuum to give 6,7-difluoro-4-hydroxyquinazoline (1.77 g, 9.7 mmol, 84%). $^1$H NMR (300 MHz, DMSO-$d_6$) δ 12.49 (br s, 1H), 8.15 (s, 1H), 8.04 (dd, 1H), 7.76 (dd, 1H); LC-MS (ESI) m/z 183 (M+H)$^+$.

Example 4A

Step 2: To $POCl_3$ (15 mL) was added 6,7-difluoro-4-hydroxyquinazoline (910 mg, 5 mmol) followed by triethylamine (700 uL, 5 mmol). The solution was then heated at 100° C. for 4 hours and concentrated in vacuo. The resulting sludge was triturated with EtOAc (2×100 mL), and the combined decanted org layers were flushed through a plug of silica gel to give 4-chloro-6,7-difluoroquinazoline (870 mg, 4.35 mmol, 87%). LC-MS (ESI) m/z 201 (M+H)$^+$.

Example 4B

Step 1: To the intermediate 1-(5-tert-butylisoxazol-3-yl)-3-(3-hydroxyphenyl)urea from Example 1A (110 mg, 0.4 mmol) was added 4-chloro-6,7-difluoroquinazoline from the previous step (80 mg, 0.4 mmol) according to the procedure described in Example 1B Step 1, to afford the title compound.

Example 4B

Step 2: The title compound was dissolved in EtOAc and 4N HCl in dioxane was added. The mixture was sonicated, stirred and concentrated in vacuo to give 1-(5-tert-butylisoxazol-3-yl)-3-(3-(6,7-difluoroquinazolin-4-yloxy)phenyl)urea as the mono-hydrochloride (88 mg, 0.18 mmol, 46%). $^1$H NMR (300 MHz, DMSO-$d_6$) δ 9.61 (s, 1H), 9.11 (s, 1H), 8.68 (s, 1H), 8.42 (dd, 1H), 8.11 (dd, 1H), 7.60 (s, 1H), 7.42 (t, 1H), 7.30 (d, 1H), 6.98 (d, 1H), 6.49 (s, 1H), 1.28 (s, 9H); LC-MS (ESI) m/z 440 (M+H)$^+$.

Example 5

Preparation of 1-(5-tert-butylisoxazol-3-yl)-3-(3-(5-methylquinazolin-4-yloxy)phenyl)urea Example 5A Step 1: 2-amino-6-methylbenzoic acid (2.0 g, 13.2 mmol) was reacted using the procedure described in Example 4A Step 1 to give 4-hydroxy-5-methylquinazoline (1.6 g, 10.0 mmol, 76%). $^1$H NMR (300 MHz, DMSO-$d_6$) δ 12.04 (br s, 1H), 8.00 (s, 1H), 7.63 (t, 1H), 7.46 (d, 1H), 7.26 (d, 1H), 2.82 (s, 3H); LC-MS (ESI) m/z 161 (M+H)$^+$.

Example 5A

Step 2: 4-hydroxy-5-methylquinazoline (600 mg, 3.75 mmol) was reacted using the procedure described in Example 4A Step 2 to give 4-chloro-5-methylquinazoline (585 mg, 3.28 mmol, 87%). LC-MS (ESI) m/z 179 (M+H)$^+$.

Example 5B

Step 1: To 1-(5-tert-butylisoxazol-3-yl)-3-(3-hydroxyphenyl)urea from Example 1A (83 mg, 0.3 mmol) was added 4-chloro-5-methylquinazoline from the previous step (53 mg, 0.3 mmol) using the procedure described in Example 1B Step 1, to afford the title compound.

Example 5B

Step 2: Using the procedure described in Example 1B Step 2, the compound from the previous step was dissolved in EtOAc and 4N HCl in dioxane was added. The mixture was sonicated, stirred and concentrated in vacuo to give 1-(5-tert-butylisoxazol-3-yl)-3-(3-(5-methylquinazolin-4-yloxy)phenyl)urea as the mono-hydrochloride (18 mg, 0.04 mmol, 14%). $^1$H NMR (300 MHz, DMSO-$d_6$) δ 9.75 (s, 1H), 9.51 (s, 1H), 8.78 (s, 1H), 7.90 (t, 1H), 7.84 (t, 1H), 7.62-7.55 (m, 2H), 7.42 (t, 1H), 7.28 (d, 1H), 6.99 (d, 1H), 6.49 (s, 1H), 2.92 (s, 3H), 1.28 (s, 9H); LC-MS (ESI) m/z 418 (M+H)$^+$.

Example 6

Preparation of 1-(5-tert-butylisoxazol-3-yl)-3-[3-(7-ethoxy-6-methoxyquinazolin-4-yloxy)phenyl]urea hydrochloride

Example 6A

Step 1: A mixture of methyl vanillate (6.376 g, 35 mmol), bromoethane (4.359 g, 40 mmol), and $K_2CO_3$ (5.528 g, 40 mmol) in DMF (40 mL) was heated at 70° C. for 2 hours. The reaction mixture was quenched with water, filtered, washed with water, and dried under vacuum with $P_2O_5$ to give methyl 4-ethoxy-3-methoxybenzoate as white solid (7.123 g, 97%). $^1$H NMR (300 MHz, CDCl$_3$) δ 7.66 (dd, 1H), 7.55 (d, 1H), 6.88 (d, 1H), 4.17 (q, 2H), 3.93 (s, 3H), 3.89 (s, 3H), 1.50 (t, 3H); LC-MS (ESI) m/z 211 (M+H)$^+$.

Example 6A

Step 2: To a solution of methyl 4-ethoxy-3-methoxybenzoate (7.12 g, 33.9 mmol) and acetic anhydride (40 mL) in acetic acid (40 mL) at room temperature was dropped fume nitric acid (90%, 3.15 g). After stirring at room temperature for 15 minutes, it was heated at 50° C. for 1 hour. The reaction mixture was poured into ice and a solid was formed. It was filtered, washed with water, and dried under vacuum with $P_2O_5$ to give methyl 4-ethoxy-5-methoxy-2-nitrobenzoate as white solid (8.392 g, 97%). $^1$H NMR (300 MHz, CDCl$_3$) δ 7.44 (s, 1H), 7.07 (s, 1H), 4.19 (q, 2H), 3.98 (s, 3H), 3.91 (s, 3H), 1.52 (t, 3H); LC-MS (ESI) m/z 256 (M+H)$^+$.

Example 6A

Step 3: A mixture of methyl 4-ethoxy-5-methoxy-2-nitrobenzoate (8.38 g, 32.8 mmol) and Pd/C (10%, 0.85 g) in MeOH (20 mL) was stirred under 1 atmosphere of hydrogen at room temperature for 6 hours. The reaction mixture was filtered with Celite and washed with MeOH. The filtration was concentrated under reduced pressure to give methyl 2-amino-4-ethoxy-5-methoxybenzoate as solid (6.832 g, 92%). $^1$H NMR (300 MHz, CDCl$_3$) δ 7.30 (s, 1H), 6.13 (s, 1H), 5.56 (br, 2H), 4.08 (q, 2H), 3.85 (s, 3H), 3.82 (s, 3H), 1.48 (t, 3H); LC-MS (ESI) m/z 226 (M+H)$^+$.

Example 6A

Step 4: A mixture of methyl 2-amino-4-ethoxy-5-methoxybenzoate (4.43 g, 19.7 mmol) and formamidine hydrochloride (2.255 g, 28 mmol) in formamide (20 mL) was heated at 130° C. for 8 hours. The reaction mixture was quenched with water, filtered, washed with water, and dried under vacuum with $P_2O_5$ to give 7-ethoxy-6-methoxyquinazolin-4(3H)-one as solid (3.029 g, 70%). $^1$H NMR (300 MHz, DMSO-$d_6$) δ 12.1 (br, 1H), 7.97 (s, 1H), 7.43 (s, 1H), 7.10 (s, 1H), 4.16 (q, 2H), 3.87 (s, 3H), 1.38 (t, 3H); LC-MS (ESI) m/z 221 (M+H)$^+$.

Example 6A

Step 5: A mixture of 7-ethoxy-6-methoxyquinazolin-4 (3M-one (1.20 g, 5.45 mmol) and POCl$_3$ (3 mL), in toluene (10 mL) was heated at 125° C. for 5 hours. It was concentrated under reduced pressure to dryness. To it was added CH$_2$Cl$_2$ and it was washed with saturated NaHCO$_3$. The organic layer was dried over MgSO$_4$ and concentrated to give 4-chloro-7-ethoxy-6-methoxyquinazoline as solid (1.254 g, 96%). $^1$H NMR (300 MHz, CDCl$_3$) δ 8.91 (s, 1H), 7.52 (s, 1H), 7.42 (s, 1H), 4.34 (q, 2H), 4.08 (s, 3H), 1.59 (t, 3H).

Example 6B

Step 1: A mixture of 1-(5-tert-butylisoxazol-3-yl)-3-(3-hydroxyphenyl)urea from Example 1A (0.2 g 0.73 mmol), 4-chloro-7-ethoxy-6-methoxyquinazoline from the previous step (0.18 g, 0.75 mmol), and potassium tert-butoxide (0.252 g, 2.25 mmol) in THF was stirred at room temperature overnight, and then was heated at 60° C. for 5 hours. The reaction was still found to be incomplete and additional 1-(5-tert-butylisoxazol-3-yl)-3-(3-hydroxyphenyl)urea (0.07 g, 0.025 mmol) was added. The mixture was heated further at 60° C. overnight. The reaction was quenched with water and extracted with EtOAc. Extracts were dried over MgSO$_4$ and concentrated under reduced pressure. It was purified by silica gel chromatography with EtOAc/hexane as eluant to afford 1-(5-tert-butylisoxazol-3-yl)-3-[3-(7-ethoxy-6-methoxyquinazolin-4-yloxy)phenyl]urea as a solid (0.078 g). $^1$H NMR (300 MHz, CDCl$_3$) δ 9.12 (br and s, 2H), 8.61 (s, 1H), 7.64 (s, 1H), 7.54 (s, 1H), 7.31 (m, 3H), 7.0 (d, 1H), 6.05 (s, 1H), 4.29 (q, 2H), 4.05 (s, 3H), 1.58 (t, 3H), 1.30 (s, 9H); LC-MS (ESI) m/z 478 (M+H)$^+$.

Example 6B

Step 2: To a solution of 1-(5-tert-butylisoxazol-3-yl)-3-[3-(7-ethoxy-6-methoxyquinazolin-4-yloxy)phenyl]urea in MeOH and CH$_2$Cl$_2$ was added 1.0 M HCl in ethyl ether (2 equivalents). After solvent was concentrated under reduced pressure, to the residue was added ethyl ether and a white solid was formed. It was filtered, washed with ethyl ether, and dried under vacuum with $P_2O_5$ to afford 1-(5-tert-butylisoxazol-3-yl)-3-[3-(7-ethoxy-6-methoxyquinazolin-4-yloxy) phenyl]urea hydrochloride as a white solid (0.067 g, 16%). $^1$H NMR (300 MHz, DMSO-$d_6$) δ 9.64 (s, 1H), 9.19 (s, 1H), 8.62 (s, 1H), 7.59 (s, 2H), 7.40 (m, 2H), 7.26 (d, 1H), 6.98 (d, 1H), 6.48 (s, 1H), 4.27 (q, 2H), 3.99 (s, 3H), 1.44 (t, 3H), 1.27 (s, 9H); LC-MS (ESI) m/z 478 (M+H)$^+$.

Example 7

Preparation of 1-(5-tert-Butylisoxazol-3-yl)-3-{3-[6-methoxy-7-(2-methoxyethoxy)quinazolin-4-yloxy]phenyl}urea hydrochloride

Example 7A

Step 1: A mixture of methyl vanillate (6.376 g, 35 mmol), 1-bromo-2-methoxyethane (5.56 g, 40 mmol), and $K_2CO_3$ (5.528 g, 40 mmol) in DMF (40 mL) were reacted according to the procedure described in Example 6A Step 1, to afford methyl 3-methoxy-4-(2-methoxyethoxyl)benzoate as a solid (8.394 g, 99.8%). $^1$H NMR (300 MHz, CDCl$_3$) δ 7.65 (dd, 1H), 7.54 (d, 1H), 6.92 (d, 1H), 4.23 (q, 2H), 3.91 (s, 3H), 3.89 (s, 3H), 3.81 (t, 2H), 3.45 (s, 3H); LC-MS (ESI) m/z 241 (M+H)$^+$.

Example 7A

Step 2: Using the procedure described in Example 6A Step 2, methyl 3-methoxy-4-(2-methoxyethoxyl)benzoate (8.39 g, 34.9 mmol) was reacted with fuming nitric acid (90%, 3.15 g) in AcOH (60 mL) at 50° C. for 8 hours, to afford methyl 5-methoxy-4-(2-methoxyethoxy)-2-nitrobenzoate as a yellow solid (7.956 g, 80%). $^1$H NMR (300 MHz, CDCl$_3$) δ 7.51 (s, 1H), 7.07 (s, 1H), 4.25 (t, 2H), 3.96 (s, 3H), 3.91 (s, 3H), 3.82 (t, 2H), 3.46 (s, 3H); LC-MS (ESI) m/z 286 (M+H)$^+$.

Example 7A

Step 3: According to the procedure described in Example 6A Step 3, a mixture of methyl 5-methoxy-4-(2-methoxyethoxy)-2-nitrobenzoate (3.19 g, 11.2 mmol) and Pd/C (10%, 0.3 g) in EtOAc (150 mL) was stirred under 1 atmosphere of hydrogen at room temperature for 6 hours, to afford methyl 2-amino-5-methoxy-4-(2-methoxyethoxyl)benzoate as a solid (2.699 g, 95%). $^1$H NMR (300 MHz, CDCl$_3$) δ 7.30 (s, 1H), 6.17 (s, 1H), 5.55 (br, 2H), 4.14 (t, 2H), 3.85 (s, 3H), 3.80 (s, 3H), 3.79 (t. 2H), 3.44 (s, 3H); LC-MS (ESI) m/z 256 (M+H)$^+$.

Example 7A

Step 4: According to the procedure described in Example 6A Step 4, a mixture of methyl 2-amino-5-methoxy-4-(2-methoxyethoxyl)benzoate (2.69 g, 10.5 mmol) and formamidine hydrochloride (1.208 g, 15 mmol) in formamide (10 mL) was heated at 140° C. for 8 hours, to afford 6-methoxy-7-(2-methoxyethoxy)quinazolin-4(3H)-one as a white solid (1.935 g, 74%). $^1$H NMR (300 MHz, DMSO-d$_6$) δ 12.1 (br, 1H), 7.98 (s, 1H), 7.44 (s, 1H), 7.14 (s, 1H), 4.23 (t, 2H), 3.87 (s, 3H), 3.72 (t, 2H), 3.32 (s, 3H); LC-MS (ESI) m/z 251 (M+H)$^+$.

Example 7A

Step 5: According to the procedure described in Example 6A Step 5, a mixture of 6-methoxy-7-(2-methoxyethoxy)quinazolin-4(3H)-one (7.83 g, 31.3 mmol) and POCl$_3$ (20 mL) in toluene (50 mL) was heated at 125° C. for 5 hours, to afford 4-chloro-6-methoxy-7-(2-methoxyethoxy)quinazoline as a solid (8.098 g, 96%). $^1$H NMR (300 MHz, DMSO-d$_6$) δ 8.88 (s, 1H), 7.49 (s, 1H), 7.41 (s, 1H), 4.36 (t, 2H), 4.01 (s, 3H), 3.76 (t, 2H), 3.34 (s, 3H).

Example 7B

According to the procedure described in Example 50, a mixture of 1-(5-tert-butylisoxazol-3-yl)-3-(3-hydroxyphenyl)urea (4.405 g, 16 mmol) from Example 1A, 4-chloro-6-methoxy-7-(2-methoxyethoxy)quinazoline from Example 7A (4.837 g, 18 mmol), and Cs$_2$CO$_3$ (8.145 g, 16 mmol) in isopropanol (80 mL) was heated at 70° C. for 4 hours, to afford 1-(5-tert-butylisoxazol-3-yl)-3-{3-[6-methoxy-7-(2-methoxyethoxy)quinazolin-4-yloxy]phenyl}urea as a solid (5.548 g, 68.3%). $^1$H NMR (300 MHz, DMSO-d$_6$) δ 9.58 (s, 1H), 9.00 (s, 1H), 8.57 (s, 1H), 7.58 (m, 2H), 7.41 (m, 2H), 7.25 (d, 1H), 6.98 (d, 1H), 6.48 (s, 1H), 4.34 (t, 2H), 3.99 (s, 3H), 3.78 (t, 2H), 3.35 (s, 3H), 1.28 (s, 9H); LC-MS (ESI) m/z 508 (M+H)$^+$.

Example 7C

The title compound was prepared as described in Example 6B Step 2 using 1-(5-tert-butylisoxazol-3-yl)-3-{3-[6-methoxy-7-(2-methoxyethoxy)quinazolin-4-yloxy]phenyl}urea (5.545 g, 10.9 mmol) and 1.0 M HCl/Et$_2$O solution (1.3 eq.) in CH$_2$Cl$_2$ (100 mL) and MeOH (10 mL), to afford 1-(5-tert-butylisoxazol-3-yl)-3-{3-[6-methoxy-7-(2-methoxyethoxy)quinazolin-4-yloxy]phenyl}urea hydrochloride as a solid (5.723 g, 96.3%). $^1$H NMR (300 MHz, DMSO-d$_6$) δ 9.58 (s, 1H), 9.68 (s, 1H), 9.28 (s, 1H), 8.65 (s, 1H), 7.60 (m, 2H), 7.41 (m, 2H), 7.27 (d, 1H), 6.98 (d, 1H), 6.48 (s, 1H), 4.35 (t, 2H), 4.00 (s, 3H), 3.78 (t, 2H), 3.35 (s, 3H), 1.27 (s, 9H); LC-MS (ESI) m/z 508 (M+H)$^+$.

Example 8

Preparation of 1-(5-tert-butylisoxazol-3-yl)-3-(3-(6-methylquinazolin-4-yloxy)phenyl)urea Example 8A Step 1: 2-Amino-5-methylbenzoic acid (2.0 g, 13.2 mmol) was reacted according to the procedure described in Example 4A Step 1 to give 4-hydroxy-6-methylquinazoline (1.6 g, 10.0 mmol, 76%). $^1$H NMR (300 MHz, DMSO-d$_6$) δ 12.16 (br s, 1H), 8.03 (d, 1H), 7.92 (s, 1H), 7.65 (dd, 1H), 7.57 (dd, 1H), 2.45 (s, 3H); LC-MS (ESI) m/z 161 (M+H)$^+$.

Example 8A

Step 2: 4-Hydroxy-6-methylquinazoline (500 mg, 3.12 mmol) was reacted according to the procedure described in Example 4A Step 2 to give 4-chloro-6-methylquinazoline (546 mg, 3.05 mmol, 98%). LC-MS (ESI) m/z 179 (M+H)$^+$.

Example 8B

Step 1: The title compound was prepared using 1-(5-tert-butylisoxazol-3-yl)-3-(3-hydroxyphenyl)urea from Example 1A (83 mg, 0.3 mmol) and 4-hydroxy-6-methylquinazoline from the previous step (53 mg, 0.3 mmol) according to the procedure described in Example 1B Step 1 to afford 1-(5-tert-butylisoxazol-3-yl)-3-(3-(6-methylquinazolin-4-yloxy)phenyl)urea.

Example 8B

Step 2: As in Example 1B Step 2, the product from the previous step was dissolved in EtOAc and 4N HCl in dioxane was added. The mixture was sonicated, stirred and concentrated in vacuo to give 1-(5-tert-butylisoxazol-3-yl)-3-(3-(6-methylquinazolin-4-yloxy)phenyl)urea as the mono-hydrochloride (101 mg, 0.24 mmol, 80%). $^1$H NMR (300 MHz, DMSO-d$_6$) δ 9.69 (s, 1H), 9.34 (s, 1H), 8.75 (s, 1H), 8.21 (s, 1H), 7.97-7.91 (m, 2H), 7.60 (d, 1H), 7.42 (t, 1H), 7.31 (d, 1H), 6.99 (d, 1H), 6.48 (s, 1H), 2.61 (s, 3H), 1.28 (s, 9H); LC-MS (ESI) m/z 418 (M+H)$^+$.

Example 9

Preparation of 1-(5-tert-butylisoxazol-3-yl)-3-(3-(6,7-dimethoxyquinazolin-4-yloxy)-4-fluorophenyl)urea Example 9A Step 1: To a mixture of 4-fluoro-3-methoxyaniline (2.0 g, 14.2 mmol) in CH$_2$Cl$_2$ (20 mL) at 0° C. was added 1.0 M solution of BBr₃ in CH₂Cl₂ (40 mL). It was stirred overnight, at which time the temperature was raised to room temperature. To it was added MeOH and the solvents were removed under reduced pressure. To the residue was added water, basified with saturated NaHCO₃, and extracted with EtOAc. Extracts were washed with brine, dried over MgSO₄, and concentrated under reduced pressure to afford 5-amino-2-fluorophenol as solid (1.3 g, 73%). ¹H NMR (300 MHz, DMSO-d₆) δ 9.26 (s, 1H), 6.81 (dd, 1H), 6.34 (dd, 1H), 6.04 (dd, 1H), 4.63 (br, 2H).

Example 9A

Step 2: A mixture of 5-amino-2-fluorophenol (1.3 g, 10.2 mmol) and 5-tert-butyl-3-isocyanatoisoxazole (1.7 g, 10.2 mmol) in toluene (60 mL) was heated at 70° C. overnight. The solid was filtered and dried under vacuum to afford 1-(5-tert-butylisoxazol-3-yl)-3-(4-fluoro-3-hydroxyphenyl)urea as solid.

Example 9B

In a sealed reaction vessel the phenol from the previous step (131 mg, 0.45 mmol) was dissolved in dry THF (2 mL). This was added to a suspension of potassium tert-butoxide (55 mg, 0.49 mmol) in THF (5 mL) at 0° C. The reaction was allowed to slowly warm to room temperature. After stirring for 30 minutes, the 4-chloro-6,7-dimethoxyquinazoline was added and the reaction stirred at room temperature for 2 hours, then at 50° C. overnight. The reaction was still incomplete, so cesium carbonate (320 mg, 0.98 mmol) and the reaction heated to 80° C. for 6 hours. The reaction was partitioned between ethyl acetate and water, and then extracted twice. The extracts were combined, dried over magnesium sulfate, filtered and concentrated. The resulting oil was purified by silica gel chromatography eluting with a gradient of ethyl acetate/dichloromethane 0-25% over 60 minutes. The major peak was collected and concentrated to afford 50 mg of the title compound. This was then dissolved in dry dichloromethane and 1 M HCl in ether (0.5 mL) was added and the solution concentrated to dryness, to give 50 mg of the hydrochloride salt. ¹H NMR (300 MHz, DMSO-d₆) δ 9.80 (s, 1H), 9.70 (s, 1H), 8.73 (s, 1H), 7.71 (m, 1H), 7.64 (s, 1H), 7.47 (s, 1H), 7.37 (m, 2H), 6.48 (s, 1H), 4.00 (s, 6H), 1.30 (s, 9H). LC-MS (ESI) m/z 482 (M+H)⁺.

Example 10

Preparation of 1-(5-tert-butylisoxazol-3-yl)-3-(4-chloro-3-(6,7-dimethoxyquinazolin-4-yloxy)phenyl)urea Example 10A A mixture of 5-amino-2-chlorophenol (1.0 g, 6.97 mmol) and 5-tert-butyl-3isocyanatoisoxazole (1.16 g, 6.97 mmol) in toluene (40 mL) was heated at 70° C. overnight. It was purified by silica gel chromatography with 0-25% EtOAc/hexane as eluants to afford 1-(5-tert-butylisoxazol-3-yl)-3-(4-chloro-3-hydroxyphenyl)urea as solid.

Example 10B

In a sealed reaction vessel the phenol from the previous step (138 mg, 0.44 mmol) was dissolved in 4 mL of dry THF, and cesium carbonate (289 mg, 0.89 mmol) was added. To this mixture 4-chloro-6,7-dimethoxyquinazoline (100 mg, 0.44 mmol) was added and the reaction heated to 60° C. overnight. The reaction was then partitioned between ethyl acetate and water and extracted twice. The extracts combined, dried over magnesium sulfate, filtered, and concentrated. The resulting concentrate was purified by silica gel chromatography eluting with a gradient of ethyl acetate/dichloromethane 0-25% over 60 minutes. The main peak was collected and concentrated to afford 70 mg of the title compound. The compound was then dissolved in anhydrous dichloromethane and 1 M HCl (0.5 mL) was added and the solution evaporated to dryness to give the hydrochloride salt weighing 67 mg. ¹H NMR (300 MHz, DMSO-d₆) δ 9.86 (d, 2H), 8.75 (s, 1H), 7.75 (s, 1H), 7.65 (s, 1H), 7.58 (d, 1H), 7.48 (s, 1H), 7.32 (d, 1H), 6.49 (s, 1H), 4.00 (s, 6H), 1.30 (s, 9H). LC-MS (ESI) m/z 498 (M+H)⁺.

Example 11

Preparation of 1-(5-tert-butylisoxazol-3-yl)-3-(3-(6-ethoxy-7-methoxyquinazolin-4-yloxy)phenyl)urea Example 11A Step 1: A mixture of 4,5-dimethoxy-2-nitrobenzoic acid (20.6 g, 90.7 mmol) in 20% KOH solution (136 mL) was heated at 100° C. for 12 hours. After it was cooled with ice, it was acidified with concentrated HCl to pH 2. It was filtered, washed with CH₂Cl₂ and EtOAc, and dried over vacuum to afford 5-hydroxy-4-methoxy-2-nitrobenzoic acid as solid (18.38 g, 95%). ¹H NMR (300 MHz, DMSO-d₆) δ 7.29 (s, 1H), 6.90 (s, 1H), 4.8 (br, 1H), 3.77 (s, 3H).

Example 11A

Step 2: To a suspension of 5-hydroxy-4-methoxy-2-nitrobenzoic acid (8.0 g, 37.5 mmol) in methanol was added concentrated sulfuric acid (3 drops) and it was heated at 80° C. overnight. After solvent was removed under reduced pressure, to it was added water and EtOAc. The organic layer was washed with saturated NaHCO₃ solution, dried over MgSO₄, and concentrated under reduced pressure to afford methyl 5-hydroxy-4-methoxy-2-nitrobenzoate as a solid (3.86 g, 45%). ¹H NMR (300 MHz, DMSO-d₆) δ 10.96 (s, 1H), 7.63 (s, 1H), 7.08 (s, 1H), 3.91 (s, 3H), 3.81 (s, 3H).

Example 11A

Step 3: According to the procedure described in Example 6A Step 3, a mixture of methyl 5-hydroxy-4-methoxy-2-nitrobenzoate (3.88 g, 17.1 mmol) and Pd/C in EtOAc (100 mL) was stirred under 1 atmosphere of hydrogen at room temperature overnight, to afford methyl 2-amino-5-hydroxy-4-methoxybenzoate as a solid (3.1 g, 92%). ¹H NMR (300 MHz, DMSO-d₆) δ 8.31 (s, 1H), 7.08 (s, 1H), 6.31 (s, 1H), 6.24 (s, 1H), 3.74 (s, 3H), 3.72 (s, 3H).

Example 11A

Step 4: A mixture of methyl 2-amino-5-hydroxy-4-methoxybenzoate (3.1 g, 15.7 mmol) and AcOH (7.1 mL) in formamide (15.5 mL) was heated at 140° C. overnight. To it was added water (20 mL) and filtered to afford 6-hydroxy-7-methoxyquinazoline-4(3H)-one as a solid (2.7 g, 89%). ¹H NMR (300 MHz, DMSO-d₆) δ 9.82 (s, 1H), 7.9 (s, 1H), 7.4 (s, 1H), 7.1 (s, 1H), 3.9 (s, 3H).

Example 11A

Step 5: A mixture of 6-hydroxy-7-methoxyquinazoline-4 (3H)-one (1.0 g, 5.2 mmol) and Cs₂CO₃ (1.69 g, 5.2 mmol) in H₂O:MeCN:MeOH (10:5:1, 20 mL) was stirred at room temperature for 30 minutes and to it was added bromoethane (0.567 g, 5.2 mmol). Then, it was stirred at 60° C. two days. It was filtered to afford 6-ethoxy-7-methoxyquinazolin-4 (3H)-one as a solid (0.550 g, 48%). $^1$H NMR (300 MHz, DMSO-d₆) δ 8.0 (s, 1H), 7.91 (s, 1H), 7.4 (d, 1H), 7.1 (d, 1H), 4.15 (t, 2H), 3.9 (s, 3H), 1.4 (t, 3H).

Example 11A

Step 6: According to the procedure described in Example 6A Step 5, a mixture of 6-ethoxy-7-methoxyquinazolin-4 (3H)-one (0.52 g, 2.36 mmol) and POCl₃ (1 mL) in toluene (10 mL) was heated at 125° C. for 3.5 hours. The residue was purified by silica gel chromatography with 0-25% EtOAc/hexane as eluants to afford 4-chloro-6-ethoxy-7-methoxyquinazoline as a solid (0.19 g, 34%). 1H NMR (300 MHz, CDCl₃) δ 8.9 (s, 1H), 7.4 (s, 1H), 7.3 (s, 1H), 4.3 (t, 2H), 4.1 (s, 3H), 1.6 (t, 3H).

Example 11B

The title compound was prepared using the procedure for Example 10B but using the intermediate 4-chloro-6-ethoxy-7-methoxyquinazoline (97 mg, 0.35 mmol) from the previous step and 1-(5-tert-butylisoxazol-3-yl)-3-(3-hydroxyphenyl) urea from Example 1A (84 mg, 0.35 mmol). To this reaction cesium carbonate (115 mg, 0.35 mmol) was added and the reaction heated to 60° C. overnight. The title compound was purified as above using a gradient of ethyl acetate/dichloromethane 0-50% over 75 minutes. The corresponding hydrochloride salt was prepared using the procedure described in Example 10B. $^1$H NMR (300 MHz, DMSO-d₆) δ 9.81 (s, 1H), 9.69 (s, 1H), 8.84 (s, 1H), 7.64 (m, 2H), 7.43 (m, 2H), 7.29 (m, 1H), 7.01 (m, 1H), 6.49 (s, 1H), 4.30 (m, 2H), 4.04 (s, 3H), 1.46 (m, 3H), 1.16 (s, 9H); LC-MS (ESI) m/z 478 (M+H)⁺.

Example 12

Preparation of 1-{3-[6,7-bis(2-methoxyethoxy) quinazolin-4-yloxy]phenyl}-3-(5-tert-butylisoxazol-3-yl)urea hydrochloride Example 12A Step 1: According to the procedure described in Example 6A Step 1, a mixture of ethyl 3,4-dihydroxybenzoate (5.465 g, 30 mmol), 1-bromo-2-methoxyethane (9.174 g, 66 mmol), and K₂CO₃ (9.122 g, 66 mmol) in DMF (50 mL) was heated at 50° C. for 5 hours, to afford ethyl 3,4-bis(2-methoxyethoxy)benzoate as a solid (7.872 g, 88%). $^1$H NMR (300 MHz, CDCl₃) δ 7.67 (dd, 1H), 7.59 (d, 1H), 6.91 (d, 1H), 4.35 (q, 2H), 4.22 (m, 4H), 3.80 (m, 4H), 3.46 (s, 6H), 1.38 (t, 3H); LC-MS (ESI) m/z 299 (M+H)⁺.

Example 12A

Step 2: According to the procedure described in Example 6A Step 2, to a solution of ethyl 3,4-bis(2-methoxyethoxy) benzoate (7.87 g, 26.4 mmol) in AcOH (50 mL) was added HNO₃ (90%, 4 mL) and the mixture was heated at 50° C. for 5 hours, to afford ethyl 4,5-bis(2-methoxyethoxy)-2-nitrobenzoate as an oil (8.531 g, 94%). $^1$H NMR (300 MHz, CDCl₃) δ 7.51 (s, 1H), 7.12 (s, 1H), 4.37 (q, 2H), 4.25 (m, 4H), 3.80 (m, 4H), 3.45 (s, 6H), 1.35 (t, 3H); LC-MS (ESI) m/z 344 (M+H)⁺.

Example 12A

Step 3: According to the procedure described in Example 6A Step 3, a mixture of ethyl 4,5-bis(2-methoxyethoxy)-2-nitrobenzoate (8.53 g, 24.8 mmol) and Pd/C (10%, 0.85 g) in EtOAc (150 mL) was stirred under 1 atmosphere of hydrogen at room temperature overnight, to afford ethyl 2-amino-4,5-bis(2-methoxyethoxy)benzoate as an oil (7.15 g, 92%). $^1$H NMR (300 MHz, CDCl₃) δ 7.44 (s, 1H), 6.15 (s, 1H), 5.60 (br, 2H), 4.30 (q, 2H), 4.13 (t, 2H), 4.08 (t, 2H), 3.78 (t, 2H), 3.73 (t, 2H), 3.45 (s, 6H), 1.36 (t, 3H); LC-MS (ESI) m/z 314 (M+H)⁺.

Example 12A

Step 4: According to the procedure described in Example 6A Step 4, a mixture of ethyl 2-amino-4,5-bis(2-methoxyethoxy)benzoate (7.15 g, 22.8 mmol) and formamidine hydrochloride (2.012 g, 25 mmol) in formamide (20 mL) was heated at 130° C. for 12 hours, to afford 6,7-bis(2-methoxyethoxy)quinazolin-4(3H)-one as a solid (3.75 g, 56%). $^1$H NMR (300 MHz, CDCl₃) δ 10.89 (br, 1H), 8.00 (s, 1H), 7.62 (s, 1H), 7.16 (s, 1H), 4.29 (t, 4H), 3.86 (t, 4H), 3.48 (s, 6H); LC-MS (ESI) m/z 295 (M+H)⁺.

Example 12A

Step 5: According to the procedure described in Example 6A Step 5, a mixture of 6,7-bis(2-methoxyethoxy)quinazolin-4(3H)-one (2.28 g, 7.7 mmol) and POCl₃ (10 mL) in toluene (30 mL) was heated at 125° C. for 5 hours, to afford 4-chloro-6,7-bis(2-methoxyethoxy)quinazoline as a solid (2.212 g, 91%). $^1$H NMR (300 MHz, CDCl₃) δ 8.86 (s, 1H), 7.44 (s, 1H), 7.34 (s, 1H), 4.34 (t, 4H), 3.89 (t, 4H), 3.50 (s, 3H), 3.49 (s, 3H); LC-MS (ESI) m/z 313 (M+H)⁺.

Example 12B

Step 1: According to the procedure described in Example 13B Step 1, a mixture of 1-(5-tert-butylisoxazol-3-yl)-3-(3-hydroxyphenyl)urea from Example 1A (0.688 g, 2.5 mmol), 4-chloro-6,7-bis(2-methoxyethoxy)quinazoline from the previous step (0.782 g, 2.5 mmol), and Cs₂CO₃ (0.977 g, 3 mmol) in isopropanol (15 mL) was heated at 70° C. for 7 hours, to afford 1-{3-[6,7-bis(2-methoxyethoxy)quinazolin-4-yloxy]phenyl}-3-(5-tert-butylisoxazol-3-yl)urea as solid. $^1$H NMR (300 MHz, DMSO-d₆) δ 9.57 (s, 1H), 8.98 (s, 1H), 8.55 (s, 1H), 7.58 (m, 2H), 7.42 (s, 1H), 7.40 (t, 1H), 7.25 (d, 1H), 6.97 (d 1H), 6.47 (s, 1H), 4.34 (m, 4H), 3.77 (m, 4H), 3.38 (s, 3H), 3.36 (s, 3H), 1.27 (s, 9H).

Example 12B

Step 2: The title compound was prepared as described in Example 6B Step 2 using 1-{3-[6,7-bis(2-methoxyethoxy) quinazolin-4-yloxy]phenyl}-3-(5-tert-butylisoxazol-3-yl) urea and 1.0 M HCl/Et₂O solution (2 eq.) in CH₂Cl₂ and MeOH, to afford 1-{3-[6,7-bis(2-methoxyethoxy)quinazolin-4-yloxy]phenyl}-3-(5-tert-butylisoxazol-3-yl)urea hydrochloride as a solid (1.169 g, 85%). $^1$H NMR (300 MHz, DMSO-d₆) δ 9.71 (s, 1H), 9.39 (s, 1H), 8.70 (s, 1H), 7.66 (s, 1H), 7.60 (m, 1H), 7.46 (s, 1H), 7.44 (t, 1H), 7.28 (d, 1H), 6.98 (d, 1H), 6.48 (s, 1H), 4.37 (m, 4H), 3.78 (m, 4H), 3.37 (s, 3H), 3.36 (s, 3H), 1.27 (s, 9H); LC-MS (ESI) m/z 552 (M+H)⁺.

Example 13

Preparation of 1-(5-tert-butylisoxazol-3-yl)-3-[3-(6,7-diethoxyquinazolin-4-yloxy)phenyl]urea hydrochloride

Example 13A

Step 1: According to the procedure described in Example 6A Step 1, a mixture of ethyl 3,4-dihydroxybenzoate (5.465 g, 30 mmol), bromoethane (7.192 g, 66 mmol), and $K_2CO_3$ (9.122 g, 66 mmol) in DMF (50 mL) was heated at 50° C. for 5 hours, to afford ethyl 3,4-diethoxybenzoate as solid (6.439 g, 90%). $^1$H NMR (300 MHz, $CDCl_3$) δ 7.65 (dd, 1H), 7.55 (d, 1H), 6.87 (d, 1H), 4.35 (q, 2H), 4.15 (q, 4H), 1.48 (m, 6H), 1.38 (t, 3H); LC-MS (ESI) m/z 239 (M+H)$^+$.

Example 13A

Step 2: According to the procedure described in Example 6A Step 2, to a solution of ethyl 3,4-diethoxybenzoate (6.43 g, 27 mmol) in AcOH (50 mL) was dropped fuming nitric acid (90%, 6.3 g) and the reaction was heated at 50° C. overnight, to afford ethyl 4,5-diethoxy-2-nitrobenzoate as a solid (7.175 g, 94%). $^1$H NMR (300 MHz, $CDCl_3$) δ 7.44 (s, 1H), 7.05 (s, 1H), 4.37 (q, 2H), 4.18 (m, 4H), 1.50 (m, 6H), 1.35 (t, 3H); LC-MS (ESI) m/z 284 (M+H)$^+$.

Example 13A

Step 3: According to the procedure described in Example 6A Step 3, a mixture of ethyl 4,5-diethoxy-2-nitrobenzoate (7.17 g, 25.3 mmol) and Pd/C (10%, 0.7 g) in EtOAc (150 mL) was stirred under 1 atmosphere of hydrogen at room temperature overnight, to afford ethyl 2-amino-4,5-diethoxybenzoate as a solid (6.401 g, 99%) $^1$H NMR (300 MHz, $CDCl_3$) δ 7.36 (s, 1H), 6.14 (s, 1H), 5.60 (br, 2H), 4.30 (q, 2H), 4.05 (m, 4H), 1.44 (t, 3H), 1.38 (m, 6H); LC-MS (ESI) m/z 254 (M+H)$^+$.

Example 13A

Step 4: According to the procedure described in Example 6A Step 4, a mixture of ethyl 2-amino-4,5-diethoxybenzoate (2.53 g, 10 mmol) and formamidine hydrochloride (0.966 g, 12 mmol) in formamide (10 mL) was heated at 140° C. for 5 hours, to afford 6,7-diethoxyquinazolin-4(3H)-one as a white solid (1.702 g, 73%). $^1$H NMR (300 MHz, $CDCl_3$) δ 10.49 (br, 1H), 7.98 (s, 1H), 7.60 (s, 1H), 7.14 (s, 1H), 4.24 (m, 4H), 1.54 (m, 6H); LC-MS (ESI) m/z 235 (M+H)$^+$.

Example 13A
Step 5: According to the procedure described in Example 6A Step 5, a mixture of 6,7-diethoxyquinazolin-4(3H)-one (1.70 g, 7.3 mmol) and $POCl_3$ (3 mL) in toluene (10 mL) was heated at 120° C. for 5 hours to afford 4-chloro-6,7-diethoxyquinazoline as a solid (1.794 g, 98%). $^1$H NMR (300 MHz, $CDCl_3$) δ 8.88 (s, 1H), 7.45 (s, 1H), 7.39 (s, 1H), 4.31 (m, 4H), 1.58 (m, 6H); LC-MS (ESI) m/z 253 (M+H)$^+$.

Example 13B

Step 1: A mixture of 1-(5-tert-butylisoxazol-3-yl)-3-(3-hydroxyphenyl)urea from Example 1A (0.137 g, 0.5 mmol), 4-chloro-6,7-diethoxyquinazoline from the previous step (0.126 g, 0.5 mmol), and $Cs_2CO_3$ (0.326 g, 1 mmol) in isopropanol (6 mL) was heated at 90° C. for 4 hours. The reaction was quenched with water and extracted with $CH_2Cl_2$. Extracts were dried over $MgSO_4$ and concentrated under reduced pressure. The residue was purified by silica gel chromatography with EtOAc/hexane as eluant to afford 1-(5-tert-butylisoxazol-3-yl)-3-[3-(6,7-diethoxyquinazolin-4-yloxy) phenyl]urea as a solid. $^1$H NMR (300 MHz, DMSO-$d_6$) δ 9.59 (s, 1H), 9.03 (s, 1H), 8.56 (s, 1H), 7.57 (m, 1H), 7.55 (s, 1H), 7.40 (t, 1H), 7.37 (s, 1H), 7.25 (d, 1H), 6.96 (dd, 1H), 6.47 (s, 1H), 4.26 (m 4H), 1.43 (m, 6H), 1.27 (s, 9H).

Example 13C

The title compound was prepared as described in Example 6B Step 2, using 1-(5-tert-butylisoxazol-3-yl)-3-[3-(6,7-diethoxyquinazolin-4-yloxy)phenyl]urea and 1.0 M $HCl/Et_2O$ solution (2 eq.) in $CH_2Cl_2$ and MeOH, to afford 1-(5-tert-butylisoxazol-3-yl)-3-[3-(6,7-diethoxyquinazolin-4-yloxy) phenyl]urea hydrochloride as a solid (0.053 g, 20%). $^1$H NMR (300 MHz, DMSO-$d_6$) δ 9.67 (s, 1H), 9.27 (s, 1H), 8.66 (s, 1H), 7.68 (m, 2H), 7.40 (m, 2H), 7.26 (d, 1H), 6.97 (d, 1H), 6.48 (s, 1H), 5.78 (br, 1H), 4.28 (m, 4H), 1.43 (m, 6H), 1.27 (s, 9H); LC-MS (ESI) m/z 492 (M+H)$^+$.

Example 14

Preparation of 1-(5-tert-butylisoxazol-3-yl)-3-[3-(7,8-dihydro-[1,4]dioxino[2,3-g]quinazolin-4-yloxy)phenyl]urea hydrochloride Example 14A Step 1: According to the procedure described in Example 6A Step 1, a mixture of ethyl 3,4-dihydroxybenzoate (5.465 g, 30 mmol), 1,2-dibromoethane (5.636 g, 30 mmol), and $K_2CO_3$ (6.219 g, 45 mmol) in DMF (100 mL) was heated at 70° C. overnight. The residue was purified by silica gel chromatography with 20-50% EtOAc/hexane as eluants to afford ethyl 2,3-dihydrobenzo[b][1,4]dioxine-6-carboxylate as an oil (1.423 g, 23%). $^1$H NMR (300 MHz, $CDCl_3$) δ 7.58 (d, 1H), 7.56 (dd, 1H), 6.88 (d, 1H), 4.30 (m, 6H), 1.37 (t, 3H); LC-MS (ESI) m/z 209 (M+H)$^+$.

Example 14A

Step 2: According to the procedure described in Example 6A Step 2, to a solution of ethyl 2,3-dihydrobenzo[b][1,4]dioxine-6-carboxylate (1.42 g, 6.8 mmol) and $Ac_2O$ (3 mL), in AcOH (15 mL) was dropped fuming nitric acid (1 mL). The reaction was heated at 50° C. for 2 hours, to afford ethyl 7-nitro-2,3-dihydrobenzo[b][1,4]dioxine-6-carboxylate as a solid (1.720 g, 99%). $^1$H NMR (300 MHz, $CDCl_3$) δ 7.51 (s, 1H), 7.18 (s, 1H), 4.36 (m, 6H), 1.33 (t, 3H).

Example 14A

Step 3: According to the procedure described in Example 6A Step 3 a mixture of ethyl 7-nitro-2,3-dihydrobenzo[b][1,4]dioxine-6-carboxylate (1.72 g, 6.8 mmol) and Pd/C (10%, 0.2 g) in EtOAc (100 mL) was stirred under 1 atmosphere of hydrogen at room temperature overnight, to afford ethyl 7-amino-2,3-dihydrobenzo[b][1,4]dioxine-6-carboxylate as a solid (1.459 g, 96%). $^1$H NMR (300 MHz, $CDCl_3$) δ 7.41 (s, 1H), 6.18 (s, 1H), 5.41 (br, 2H), 4.30 (m, 4H), 4.19 (q, 2H), 1.38 (t, 3H); LC-MS (ESI) m/z 224 (M+H)$^+$.

Example 14A

Step 4: According to the procedure described in Example 6A Step 4, a mixture of ethyl 7-amino-2,3-dihydrobenzo[b][1,4]dioxine-6-carboxylate (1.45 g, 6.5 mmol) and formamidine hydrochloride (1.208 g, 15 mmol) in formamide (20 mL) was heated at 130° C. for 8 hours, to afford 7,8-dihydro-[1,4]dioxino[2,3-g]quinazolin-4(3H)-one as a solid (1.114 g, 84%). $^1$H NMR (300 MHz, CDCl$_3$ and drops DMSO-d$_6$) δ 11.80 (br, 1H), 7.88 (s, 1H), 7.63 (s, 1H), 7.13 (s, 1H), 4.36 (m, 4H); LC-MS (ESI) m/z 205 (M+H)$^+$.

Example 14A

Step 5: According to the procedure described in Example 6A Step 5, a mixture of 7,8-dihydro-[1,4]dioxino[2,3-g]quinazolin-4(3H)-one (1.114 g, 5.46 mmol) and POCl$_3$ (10 mL) in toluene (10 mL) was heated at 125° C. for 5 hours to afford 4-chloro-7,8-dihydro-[1,4]dioxino[2,3-g]quinazoline as a solid (1.143 g, 94%). $^1$H NMR (300 MHz, CDCl$_3$) δ 8.90 (s, 1H), 7.70 (s, 1H), 7.65 (s, 1H), 4.46 (m, 4H).

Example 14B

According to the procedure described in Example 13B Step 1, a mixture of 1-(5-tert-butylisoxazol-3-yl)-3-(3-hydroxyphenyl)urea from Example 1A (0.138 g, 0.5 mmol), 4-chloro-7,8-dihydro-[1,4]dioxino[2,3-g]quinazoline from the previous step (0.111 g, 0.5 mmol), and Cs$_2$CO$_3$ (0.326 g, 1 mmol) in isopropanol (7 mL) was heated at 70° C. for 13 hours, to afford 1-(5-tert-butylisoxazol-3-yl)-3-[3-(7,8-dihydro-[1,4]dioxino[2,3-g]quinazolin-4-yloxy]phenyl)urea as a solid. $^1$H NMR (300 MHz, CDCl$_3$) δ 9.3 (br, 1H), 9.10 (s, 1H), 8.59 (s, 1H), 7.72 (s, 1H), 7.60 (m, 1H), 7.42 (s, 1H), 7.31 (m, 2H), 6.95 (d, 1H), 6.02 (s, 1H), 4.41 (m 4H), 1.30 (s, 9H).

Example 14C

According to the procedure described in Example 6B Step 2, to a solution of 1-(5-tert-butylisoxazol-3-yl)-3-[3-(7,8-dihydro-[1,4]dioxino[2,3-g]quinazolin-4-yloxy)phenyl]urea in CH$_2$Cl$_2$ and MeOH was added 1.0 M HCl/Et$_2$O solution to afford 1-(5-tert-butylisoxazol-3-yl)-3-[3-(7,8-dihydro-[1,4]dioxino[2,3-g]quinazolin-4-yloxy)phenyl]urea hydrochloride as a solid (0.086 g, 35%). $^1$H NMR (300 MHz, DMSO-d$_6$) δ 9.67 (s, 1H), 9.28 (s, 1H), 8.63 (s, 1H), 7.72 (s, 1H), 7.57 (m, 1H), 7.43 (s, 1H), 7.40 (t, 1H), 7.28 (d, 1H), 6.96 (d, 1H), 6.48 (s, 1H), 5.43 (br, 1H), 4.47 (m, 4H), 1.28 (s, 9H); LC-MS (ESI) m/z 462 (M+H)$^+$.

Example 15

Preparation of 1-(5-tert-butylisoxazol-3-yl)-3-{3-[7-methoxy-6-(2-methoxyethoxy)quinazolin-4-yloxyl]phenyl}urea hydrochloride Example 15A Step 1: According to the procedure described in Example 6A Step 1, a mixture of methyl 3-hydroxy-4-methoxybenzoate (5.00 g, 27.4 mmol), 1-bromo-2-methoxyethane (4.96 g, 35.7 mmol), and K$_2$CO$_3$ (4.6 g, 32.9 mmol) in DMF (20 mL) was heated at 90° C. overnight, to afford methyl 4-methoxy-3-(2-methoxyethoxyl)benzoate as a solid (5.6 g, 85%). $^1$H NMR (300 MHz, DMSO-d$_6$) δ 7.60 (dd, 1H), 7.46 (d, 1H), 7.09 (d, 1H), 4.12 (m, 2H), 3.84 (s, 3H), 3.81 (s, 3H), 3.67 (m, 2H), 3.33 (s, 3H).

Example 15A

Step 2. According to the procedure described in Example 6A Step 2, to a solution of methyl 4-methoxy-3-(2-methoxyethoxyl)benzoate (5.6 g, 23.3 mmol) and Ac$_2$O (12 mL) in AcOH (60 mL) was dropped fuming nitric acid (90%, 4 mL). The reaction was heated at 50° C. for 3 hours, and the residue was purified by silica gel chromatography with 0-15% EtOAc/hexane as eluants to afford methyl 4-methoxy-5-(2-methoxyethoxy)-2-nitrobenzoate as a solid (3.67 g, 56%). $^1$H NMR (300 MHz, DMSO-d$_6$) δ 7.64 (s, 1H), 7.34 (s, 1H), 4.26 (m, 2H), 3.91 (s, 3H), 3.82 (s, 3H), 3.68 (m, 2H), 3.33 (s, 3H).

Example 15A

Step 3. According to the procedure described in Example 6A Step 3, a mixture of methyl 4-methoxy-5-(2-methoxyethoxy)-2-nitrobenzoate (3.67 g, 12.9 mmol) and Pd/C (10%, 0.4 g) in EtOAc (60 mL) was stirred under 1 atmosphere of hydrogen at room temperature overnight, to afford methyl 2-amino-4-methoxy-5-(2-methoxyethoxyl)benzoate as a solid (3.05 g, 93%). $^1$H NMR (300 MHz, DMSO-d$_6$) δ 7.15 (s, 1H), 6.46 (s, 2H), 6.36 (s, 1H), 3.91 (m, 2H), 3.75 (s, 3H), 3.74 (s, 3H), 3.59 (m. 2H), 3.32 (s, 3H).

Example 15A

Step 4. According to the procedure described in Example 6A Step 4, a mixture of methyl 2-amino-4-methoxy-5-(2-methoxyethoxyl)benzoate (3.05 g, 11.9 mmol) and AcOH (5.4 mL) in formamide (15.25 mL) was heated at at 140° C. overnight, to afford 7-methoxy-6-(2-methoxyethoxy)quinazolin-4(3H)-one as a solid (2.07 g, 69%). $^1$H NMR (300 MHz, DMSO-d$_6$) δ 12.0 (br, 1H), 7.99 (s, 1H), 7.45 (s, 1H), 7.14 (s, 1H), 4.19 (t, 2H), 3.91 (s, 3H), 3.71 (t, 2H), 3.32 (s, 3H).

Example 15A

Step 5. According to the procedure described in Example 6A Step 5, a mixture of 7-methoxy-6-(2-methoxyethoxy)quinazolin-4(3H)-one (0.6 g, 2.4 mmol) and POCl$_3$ (1 mL) in toluene (10 mL) was heated at 125° C. for 2 hours, to afford 4-chloro-7-methoxy-6-(2-methoxyethoxy)quinazoline as solid (0.445 g, 69%). $^1$H NMR (300 MHz, DMSO-d$_6$) δ 8.88 (s, 1H), 7.45 (s, 1H), 7.41 (s, 1H), 4.33 (t, 2H), 4.03 (s, 3H), 3.77 (t, 2H), 3.33 (s, 3H).

Example 15B

According to the procedure described in Example 50, a mixture of 1-(5-tert-butylisoxazol-3-yl)-3-(3-hydroxyphenyl)urea (0.201 g, 0.73 mmol) from Example 1A, 4-chloro-7-methoxy-6-(2-methoxyethoxy)quinazoline (0.195 g, 0.73 mmol) from the previous step, and Cs$_2$CO$_3$ (0.261 g, 0.8 mmol) in isopropanol (10 mL) was heated at 70° C. for 7 hours, to afford 1-(5-tert-butylisoxazol-3-yl)-3-{3-[7-methoxy-6-(2-methoxyethoxy)quinazolin-4-yloxy]phenyl}urea as a solid. $^1$H NMR (300 MHz, CDCl$_3$) δ 9.13 (br and s, 2H), 8.61 (s, 1H), 7.62 (s, 1H), 7.55 (s, 1H), 7.31 (m, 3H), 6.97 (dd, 1H), 6.08 (s, 1H), 4.34 (t, 2H), 4.11 (s, 3H), 3.89 (t, 2H), 3.49 (s, 3H), 1.30 (s, 9H); LC-MS (ESI) m/z 508 (M+H)$^+$.

Example 15C

The title compound was prepared as described in Example 6B Step 2 using 1-(5-tert-butylisoxazol-3-yl)-3-{3-[7-methoxy-6-(2-methoxyethoxy)quinazolin-4-yloxy]phenyl}urea and 1.0 M HCl in Et$_2$O solution (1 mL) in CH$_2$Cl$_2$ and MeOH, to afford 1-(5-tert-butylisoxazol-3-yl)-3-{3-[7-methoxy-6-(2-methoxyethoxy)quinazolin-4-yloxy]phenyl}urea hydrochloride as a solid (0.211 g, 53%). ¹H NMR (300 MHz, DMSO-d₆) δ 9.68 (s, 1H), 9.33 (s, 1H), 8.68 (s, 1H), 7.63 (s, 1H), 7.60 (d, 1H), 7.43 (s, 1H), 7.41 (t, 1H), 7.27 (d, 1H), 6.98 (d, 1H), 6.48 (s, 1H), 5.36 (br, 1H), 4.34 (m, 2H), 4.02 (s, 3H), 3.77 (m, 2H), 3.34 (s, 3H), 1.27 (s, 9H); LC-MS (ESI) m/z 508 (M+H)⁺.

Example 16

Preparation of 1-(5-tert-butylisoxazol-3-yl)-3-(3-(7-methoxy-6-(2-(piperidin-1-yl)ethoxy)quinazolin-4-yloxy)phenyl)urea Example 16A Step 1: To DMF (40 mL) was added potassium carbonate (9.1 g, 65.9 mmol) and methyl 3-hydroxy-4-methoxybenzoate (10.0 g, 54.9 mmol) and the mixture stirred 30 minutes at room temperature 1-bromo-2-chloroethane (11.0 g, 76.8 mmol) was added and the mixture was heated at 60° C. overnight at which point excess 1-bromo-2-chloroethane (5.5 g, 38.4 mmol) was added and heating continued for 8 hours. After cooling to room temperature, the mixture was diluted with H₂O, filtered, and the solid washed with EtOAc to give methyl 3-(2-chloroethoxy)-4-methoxybenzoate (4.04 g, 16.6 mmol, 30%). ¹H NMR (300 MHz, DMSO-d₆) δ 7.63 (d, 1H), 7.47 (s, 1H), 7.11 (d, 1H), 4.29 (t, 2H), 3.95 (t, 2H), 3.86 (s, 3H), 3.81 (s, 3H); LC-MS (ESI) m/z 245 (M+H)⁺.

Example 16A

Step 2: To acetic acid (42 mL) and acetic anhydride (8.5 mL) was added methyl 3-(2-chloroethoxy)-4-methoxybenzoate (4.0 g, 16.3 mmol) followed by 70% nitric acid (2.8 mL) and the mixture heated at 50° C. for 1 hour. The mixture was poured into H₂O, filtered, and washed with H₂O to give methyl 5-(2-chloroethoxy)-4-methoxy-2-nitrobenzoate (4.08 g, 14.1 mmol, 86%). ¹H NMR (300 MHz, DMSO-d₆) δ 7.67 (s, 1H), 7.38 (s, 1H), 4.43 (t, 2H), 3.99 (t, 2H), 3.94 (s, 3H), 3.85 (s, 3H).

Example 16A

Step 3: To methyl 5-(2-chloroethoxy)-4-methoxy-2-nitrobenzoate (4.07 g, 14.1 mmol) under argon was added 10% palladium on carbon and in EtOAc (150 mL) and MeOH (50 mL). The flask was flushed with H₂ (g) and stirred under H₂ (1 atm) for 30 minutes. The mixture was filtered through Celite and concentrated in vacuo to give methyl 2-amino-5-(2-chloroethoxy)-4-methoxybenzoate (3.61 g, 13.9 mmol, 99%). ¹H NMR (300 MHz, DMSO-d₆) δ 7.20 (s, 1H), 6.52 (br s, 2H), 6.38 (s, 1H), 4.07 (t, 2H), 3.85 (t, 2H), 3.77 (s, 3H), 3.75 (s, 3H); LC-MS (ESI) m/z 260 (M+H)⁺.

Example 16A

Step 4: To a solution of methyl 2-amino-5-(2-chloroethoxy)-4-methoxybenzoate (3.61 g, 13.9 mmol) in ethanol was added formamidine hydrochloride and the mixture heated in a sealed tube at 130° C. overnight. The reaction was cooled to room temperature and filtered to give 6-(2-chloroethoxy)-4-hydroxy-7-methoxyquinazoline (3.05 g, 12.0 mmol, 86%). ¹H NMR (300 MHz, DMSO-d₆) δ 12.09 (br s, 1H), 8.00 (s, 1H), 7.47 (s, 1H), 7.16 (s, 1H), 4.36 (t, 2H), 4.00 (t, 2H), 3.92 (s, 3H); LC-MS (ESI) m/z 255 (M+H)⁺.

Example 16B

The intermediate 6-(2-chloroethoxy)-4-hydroxy-7-methoxyquinazoline from the previous step (5.0 g, 19.6 mmol) was reacted according to the procedure described in Example 4A Step 2 to give 4-chloro-6-(2-chloroethoxy)-7-methoxyquinazoline (4.3 g, 15.8 mmol, 80%). LC-MS (ESI) m/z 273 (M+H)⁺.

Example 16C

To a slurry of cesium carbonate in THF was added 1-(5-tert-butylisoxazol-3-yl)-3-(3-hydroxyphenyl)urea from Example 1A (2.02 g, 7.3 mmol). After stirring for about 15 minutes at room temperature, the chloride intermediate (2.0 g, 7.3 mmol) from the previous step was added and the reaction mixture was heated at 50° C. overnight. The mixture was diluted with EtOAc and washed with water and brine, dried over MgSO₄, filtered, and concentrated in vacuo. The crude product was purified by column chromatography (10-50% EtOAc/hexanes) to give 1-(5-tert-butylisoxazol-3-yl)-3-(3-(6-(2-chloroethoxy)-7-methoxyquinazolin-4-yloxy)phenyl)urea (2.15 g, 4.2 mmol, 58%). ¹H NMR (300 MHz, DMSO-d₆) δ 9.58 (s, 1H), 9.00 (s, 1H), 8.58 (s, 1H), 7.61 (s, 2H), 7.48-7.37 (m, 2H), 7.26 (d, 1H), 6.98 (d, 1H), 6.49 (s, 1H), 4.53-4.47 (m, 2H), 4.12-4.00 (m, 5H), 1.29 (s, 9H); LC-MS (ESI) m/z 512 (M+H)⁺.

Example 16D 1-(5-tert-butylisoxazol-3-yl)-3-(3-(6-(2-chloroethoxy)-7-methoxyquinazolin-4-yloxy)phenyl)urea (200 mg, 0.39 mmol) from the previous step was treated with piperidine (0.116 mL, 1.17 mmol), tetrabutylammonium iodide (0.39 mmol) and N,N'-diisopropylethylamine (0.78 mmol) in N,N'-dimethylformamide. The mixture was heated to 60° C. for 56h and cooled to room temperature. Water was added and the solid filtered off and dried. The crude solid was purified by preparative HPLC (phenylhexyl reverse phase column) and the obtained solid triturated with water (10 mL) and drops of methanol, then filtered off and dried under high vacuum to afford 1-(5-tert-butylisoxazol-3-yl)-3-(3-(7-methoxy-6-(2-(piperidin-1-yl)ethoxy)quinazolin-4-yloxy)phenyl)urea as a colorless solid (29 mg, 13%). ¹H NMR (300 MHz, DMSO-d₆) δ 9.80 (brs, 1H), 9.10 (brs, 1H), 8.55 (s, 1H), 7.64 (s, 1H), 7.59 (s, 1H), 7.37-7.42 (m, 2H), 7.26 (m, 1H), 6.96 (m, 1H), 6.48 (s, 1H), 4.26-4.30 (m, 2H), 3.99 (s, 3H), 2.72-2.76 (m, 2H), 2.40-2.50 (m, 4H), 1.48-1.52 (m, 4H), 1.37-1.39 (m, 2H), 1.30 (s, 9H); LC-MS (ESI) m/z 561 (M+H)⁺.

Example 17

Preparation of 1-(5-tert-butylisoxazol-3-yl)-3-(3-(6-(2-(4-(hydroxymethyl)piperidin-1-yl)ethoxy)-7-methoxyquinazolin-4-yloxy)phenyl)urea 1-(5-tert-butylisoxazol-3-yl)-3-(3-(6-(2-chloroethoxy)-7-methoxyquinazolin-4-yloxy)phenyl)urea (200 mg, 0.39 mmol) from Example 16C was reacted with 4-piperidinemethanol (135 mg, 1.17 mmol) according to the procedure described in Example 16D to afford 1-(5-tert-butylisoxazol-3-yl)-3-(3-(6-(2-(4-(hydroxymethyl)piperidin-1-yl)ethoxy)-7-methoxyquinazolin-4-yloxy)phenyl)urea as a colorless solid (36 mg, 16%). ¹H NMR (300 MHz, DMSO-d₆) δ 9.70 (brs, 1H), 9.10 (brs, 1H), 8.55 (s, 1H), 7.63 (s, 1H), 7.58 (s, 1H), 7.37-7.43 (m, 2H), 7.27 (m, 1H), 6.97 (m, 1H), 6.48 (s, 1H), 4.20-4.50 (m, 3H), 3.99 (s, 3H), 3.23 (m, 2H), 2.96-3.00 (m, 2H), 2.74-2.78 (m, 2H), 2.01-2.05 (m, 2H), 1.61-1.65 (m, 2H), 1.27 (s, 9H), 1.00-1.15 (m, 2H); LC-MS (ESI) m/z 591 (M+H)⁺.

Example 18

Preparation of 1-(5-tert-butylisoxazol-3-yl)-3-(3-(7-methoxy-6-(2-(4-methylpiperazin-1-yl)ethoxy)quinazolin-4-yloxy)phenyl)urea 1-(5-tert-butylisoxazol-3-yl)-3-(3-(6-(2-chloroethoxy)-7-methoxyquinazolin-4-yloxy)phenyl)urea (200 mg, 0.39 mmol) from Example 16C was reacted with N-methyl piperazine (0.130 mL, 1.17 mmol) according to the procedure described for Example 16D to afford 1-(5-tert-butylisoxazol-3-yl)-3-(3-(7-methoxy-6-(2-(4-methylpiperazin-1-yl)ethoxy)quinazolin-4-yloxy)phenyl)urea as a colorless solid (18 mg, 8%). $^1$H NMR (300 MHz, DMSO-$d_6$) δ 9.58 (brs, 1H), 9.00 (brs, 1H), 8.55 (s, 1H), 7.63 (s, 1H), 7.58 (s, 1H), 7.37-7.42 (m, 2H), 7.25 (m, 1H), 6.96 (m, 1H), 6.47 (s, 1H), 4.26-4.30 (m, 2H), 3.99 (s, 3H), 2.75-2.79 (m, 2H), 2.20-2.50 (m, 8H), 2.13 (s, 3H), 1.27 (s, 9H); LC-MS (ESI) m/z 576 (M+H)$^+$.

Example 19

Preparation of 1-(5-tert-butylisoxazol-3-yl)-3-(3-(6-(2-(4-(2-hydroxyethyl)piperazin-1-yl)ethoxy)-7-methoxyquinazolin-4-yloxy)phenyl)urea Prepared from 1-(5-tert-butylisoxazol-3-yl)-3-(3-(6-(2-chloroethoxy)-7-methoxyquinazolin-4-yloxy)phenyl)urea (200 mg, 0.39 mmol) from Example 16C (200 mg, 0.39 mmol) and 1-(2-hydroxyethyl)piperazine (0.144 mL, 1.17 mmol) according to the procedure described for Example 16D to afford 1-(5-tert-butylisoxazol-3-yl)-3-(3-(6-(2-(4-(2-hydroxyethyl)piperazin-1-yl)ethoxy)-7-methoxyquinazolin-4-yloxy)phenyl)urea as a colorless solid (28 mg, 12%). $^1$H NMR (300 MHz, DMSO-$d_6$) δ 9.59 (brs, 1H), 9.01 (brs, 1H), 8.55 (s, 1H), 7.63 (s, 1H), 7.58 (s, 1H), 7.37-7.42 (m, 2H), 7.26 (m, 1H), 6.96 (m, 1H), 6.47 (s, 1H), 4.26-4.35 (m, 3H), 3.99 (s, 3H), 3.40-3.50 (m, 2H), 2.75-2.79 (m, 2H), 2.30-2.50 (m, 9H), 1.27 (s, 9H); LC-MS (ESI) m/z 606 (M+H)$^+$.

Example 20

Preparation of 1-(5-tert-butylisoxazol-3-yl)-3-(3-(7-methoxy-6-(2-morpholinoethoxy)quinazolin-4-yloxy)phenyl)urea Prepared from 1-(5-tert-butylisoxazol-3-yl)-3-(3-(6-(2-chloro ethoxy)-7-methoxyquinazolin-4-yloxy)phenyl)urea (200 mg, 0.39 mmol) from Example 16C (200 mg, 0.39 mmol) and morpholine (0.102 mL, 1.17 mmol) according to the procedure described for Example 16D to afford 1-(5-tert-butylisoxazol-3-yl)-3-(3-(7-methoxy-6-(2-morpholinoethoxy)quinazolin-4-yloxy)phenyl)urea as a colorless solid (28 mg, 13%). $^1$H NMR (300 MHz, DMSO-$d_6$) δ 9.60 (brs, 1H), 9.08 (brs, 1H), 8.56 (s, 1H), 7.58-7.65 (m, 2H), 7.38-7.43 (m, 2H), 7.25 (m, 1H), 6.97 (m, 1H), 6.48 (s, 1H), 4.30-4.32 (m, 2H), 4.00 (s, 3H), 3.60-3.62 (m, 4H), 2.80 (m, 2H), 2.49-2.52 (m, 4H), 1.27 (s, 9H); LC-MS (ESI) m/z 563 (M+H)$^+$.

Example 21

Preparation of 1-(5-tert-butylisoxazol-3-yl)-3-(3-(7-methoxy-6-(3-(4-methylpiperazin-1-yl)propoxy)quinazolin-4-yloxy)phenyl)urea

Example 21A

Step 1: To DMF (80 mL) was added potassium carbonate (5.7 g, 41.1 mmol) and methyl 3-hydroxy-4-methoxybenzoate (5.0 g, 27.4 mmol). The mixture was cooled to 0° C. and 1-bromo-3-chloropropane (8.64 g, 57.9 mmol) in DMF (10 mL) was added dropwise over 30 minutes. The mixture was allowed to warm to r.t overnight. After removing most of the DMF in vacuo, the remaining oil was diluted with H$_2$O and filtered to give methyl 3-(3-chloropropoxy)-4-methoxybenzoate (6.65 g, 25.8 mmol, 94%). $^1$H NMR (300 MHz, DMSO-$d_6$) δ 7.61 (d, 1H), 7.47 (s, 1H), 7.09 (d, 1H), 4.12 (t, 2H), 3.85 (s, 3H), 3.80 (s, 3H), 3.78 (t, 2H), 2.23-2.15 (m, 2H); LC-MS (ESI) m/z 259 (M+H)$^+$.

Example 21A

Step 2: Methyl 3-(3-chloropropoxy)-4-methoxybenzoate (6.65 g, 25.7 mmol) was reacted with nitric acid as described in Example 16A Step 2 to give methyl 5-(3-chloropropoxy)-4-methoxy-2-nitrobenzoate (6.70 g, 22.1 mmol, 86%). $^1$H NMR (300 MHz, DMSO-$d_6$) δ 7.65 (s, 1H), 7.37 (s, 1H), 4.26 (t, 2H), 3.89 (s, 3H), 3.81 (s, 3H), 3.76 (t, 2H), 2.26-2.18 (m, 2H).

Example 21A Step 3: Methyl 5-(3-chloropropoxy)-4-methoxy-2-nitrobenzoate (6.70 g, 22.1 mmol) in EtOAc (100 mL) was reacted with H$_2$ in the presence of 10% palladium on carbon in the manner described in Example 16A Step 3 to give methyl 2-amino-5-(3-chloropropoxy)-4-methoxybenzoate (6.0 g, 22.0 mmol, 99%). $^1$H NMR (300 MHz, DMSO-$d_6$) δ 7.18 (s, 1H), 6.49 (br s, 2H), 6.37 (s, 1H), 3.93 (t, 2H), 3.82-3.71 (m, 8H), 2.14-2.06 (m, 2H); LC-MS (ESI) m/z 274 (M+H)$^+$.

Example 21A

Step 4: Methyl 2-amino-5-(3-chloropropoxy)-4-methoxybenzoate (6.0 g, 21.9 mmol) in EtOAc was reacted with formamidine hydrochloride in the manner described in Example 16A Step 4 to give 6-(3-chloropropoxy)-4-hydroxy-7-methoxyquinazoline (4.48 g, 16.7 mmol, 76%). $^1$H NMR (300 MHz, DMSO-$d_6$) δ 12.10 (br s, 1H), 8.00 (s, 1H), 7.47 (s, 1H), 7.15 (s, 1H), 4.19 (t, 2H), 3.97 (s, 3H), 3.81 (t, 2H), 2.27-2.19 (m, 2H); LC-MS (ESI) m/z 269 (M+H)$^+$.

Example 21A Step 5: The intermediate 6-(3-chloropropoxy)-4-hydroxy-7-methoxyquinazoline (3.5 g, 13.0 mmol) was reacted with POCl$_3$ in the manner described in Example 4A Step 2 to give 4-chloro-6-(3-chloropropoxy)-7-methoxyquinazoline (3.2 g, 11.2 mmol, 86%). LC-MS (ESI) m/z 287 (M+H)$^+$.

Example 21B 1-(5-tert-butylisoxazol-3-yl)-3-(3-hydroxyphenyl)urea from Example 1A (1.92 g, 6.97 mmol) and 4-chloro-6-(3-chloropropoxy)-7-methoxyquinazoline from the previous step (2.0 g, 6.97 mmol) were reacted in the manner described in Example 16C to give 1-(5-tert-butylisoxazol-3-yl)-3-(3-(6-(3-chloropropoxy)-7-methoxyquinazolin-4-yloxy)phenyl)urea (2.00 g, 3.8 mmol, 55%). $^1$H NMR (300 MHz, DMSO-$d_6$) δ 9.56 (s, 1H), 8.98 (s, 1H), 8.54 (s, 1H), 7.59 (s, 1H), 7.54 (s, 1H), 7.38 (t, 1H), 7.33 (s, 1H), 7.26 (d, 1H), 6.96 (d, 1H), 6.47 (s, 1H), 4.27 (t, 2H), 3.98 (s, 3H), 3.82 (t, 2H), 2.30-2.24 (m, 2H), 1.29 (s, 9H); LC-MS (ESI) m/z 526 (M+H)$^+$.

Example 21C

In a sealed reaction flask 1-(5-tert-butylisoxazol-3-yl)-3-(3-(6-(3-chloropropoxy)-7-methoxyquinazolin-4-yloxy)phenyl)urea (200 mg, 0.38 mmol) was dissolved in 3 mL of anhydrous DMF, to this solution tetrabutylammonium iodide (140 mg, 0.38 mmol) was added followed by N-methylpiperazine (0.127 mL, 1.14 mmol) and the reaction heated at 60° C. for 56 hours. At the end of this time 10 mL of water was added and the resulting solid removed by filtration. The solid was purified by reversed phase HPLC using a phenyl-hexyl reverse phase column with a 30-50% ACN/H$_2$O gradient over 60 minutes. The appropriate peak was concentrated, basified with saturated sodium bicarbonate and extracted twice with ethyl acetate. The extracts were dried with magnesium sulfate, filtered and concentrated to afford 1-(5-tert-butylisoxazol-3-yl)-3-(3-(7-methoxy-6-(3-(4-methylpiperazin-1-yl)propoxy)quinazolin-4-yloxy)phenyl)urea as a solid weighing 15.75 mg. $^1$H NMR (300 MHz, DMSO-d$_6$) δ 9.58 (s, 1H), 9.00 (s, 1H), 8.55 (s, 1H), 7.58 (d, 2H), 7.4 (m, 2H), 7.26 (m, 1H), 6.98 (m, 1H), 6.47 (s, 1H), 4.2 (m, 2H), 3.99 (s, 3H), 2.5-2.2 (m, 9H), 2.11 (s, 3H), 1.99 (m, 2H), 1.27 (s, 9H). LC-MS (ESI) m/z 590 (M+H)$^+$.

Example 22

Preparation of 1-(5-tert-butylisoxazol-3-yl)-3-(3-(7-methoxy-6-(3-morpholinopropoxy)quinazolin-4-yloxy)phenyl)urea In the manner described in Example 21C, 1-(5-tert-butyl-isoxazol-3-yl)-3-(3-(6-(3-chloropropoxy)-7-methoxyquinazolin-4-yloxy)phenyl)urea (200 mg, 0.38 mmol) from Example 21B was reacted with morpholine (99 µL, 1.14 mmol), diisopropylethyl amine (199 µL, 1.14 mmol), and tetrabutyl ammonium iodide (140 mg, 0.38 mmol). After heating at 60° C. overnight the reaction was cooled to room temperature, and 10 mL of water added. The resulting precipitate was collected by filtration and purified by HPLC on a phenyl-hexyl reverse phase column eluting with an acetonitrile/water gradient 35-55% over 60 minutes. The major peak was collected, neutralized to pH-8 with saturated sodium bicarbonate and extracted twice with ethyl acetate. The extracts were combined, dried with magnesium sulfate, and concentrated to a solid. The solid was triturated with 20:1 methanol water and the solid removed by filtration and dried to give 72 mg of the title compound. $^1$H NMR (300 MHz, DMSO-d$_6$) δ 9.57 (s, 1H), 8.99 (s, 1H), 8.55 (s, 1H), 7.58 (m, 2H), 7.39 (m, 2H), 7.26 (m, 1H), 6.99 (m, 1H), 6.47 (s, 1H), 4.25 (m, 2H), 3.99 (s, 3H), 3.58 (m, 4H), 2.5-2.35 (m, 6H), 1.97 (m, 2H), 1.30 (s, 9H). LC-MS (ESI) m/z 577 (M+H)$^+$.

Example 23

Preparation of 1-(5-tert-butylisoxazol-3-yl)-3-(3-(7-methoxy-6-(3-(piperidin-1-yl)propoxy)quinazolin-4-yloxy)phenyl)urea The title compound was prepared using the procedure for Example 21C, substituting piperidine (0.113 mL, 1.14 mmol) for the N-methylpiperazine. The title compound (38.76 mg) was isolated. $^1$H NMR (300 MHz, DMSO-d$_6$) δ 9.64 (s, 1H), 9.07 (s, 1H), 8.55 (s, 1H), 7.58 (d, 2H), 7.40 (m, 2H), 7.25 (m, 1H), 6.98 (m, 1H), 6.48 (s, 1H), 4.23 (m, 2H), 4.00 (s, 3H), 2.4-2.2 (m, 6H), 2.0 (m, 2H), 1.5 (m, 4H), 1.3 (m, 11H). LC-MS (ESI) m/z 575 (M+H)$^+$.

Example 24

Preparation of 1-(5-tert-butylisoxazol-3-yl)-3-(3-(6-(3-(4-(hydroxymethyl)piperidin-1-yl)propoxy)-7-methoxyquinazolin-4-yloxy)phenyl)urea The title compound was prepared using the procedure for Example 21C substituting 4-piperidinemethanol (131 mg, 1.14 mmol) for the N-methyl piperazine. Purification was carried out under identical conditions. The title compound (27.3 mg) was isolated. $^1$H NMR (300 MHz, DMSO-d$_6$) δ 9.58 (s, 1H), 9.00 (s, 1H), 8.55 (s, 1H), 7.57 (d, 2H), 7.38 (m, 2H), 7.27 (m, 1H), 6.95 (m, 1H), 6.47 (s, 1H), 4.39 (m, 1H), 4.2 (m, 2H), 3.95 (s, 3H), 3.20 (m, 2H), 2.90 (m, 2H), 2.49 (m, 2H), 2.1-1.8 (m, 4H), 1.6 (m, 2H), 1.3 (s, 9H), 1.2 (m, 2H); LC-MS (ESI) m/z 605 (M+H)$^+$.

Example 25

Preparation of 1-(5-tert-butylisoxazol-3-yl)-3-(3-(7-methoxy-6-(3-(4-(methylsulfonyl)piperazin-1-yl)propoxy)quinazolin-4-yloxy)phenyl)urea The title compound was prepared using the procedure for Example 21C, substituting 1-methylsulfonyl piperazine (182 mg, 1.14 mmol) for the N-methyl piperazine. Purification was carried out under identical conditions. The title compound (52.69 mg) was isolated. $^1$H NMR (300 MHz, DMSO-d$_6$) δ 9.7 (s, 1H), 9.1 (s, 1H), 8.55 (s, 1H), 7.58 (d, 2H), 7.37 (m, 2H), 7.23 (m, 1H), 6.97 (m, 1H), 6.47 (s, 1H), 4.23 (m, 2H), 4.00 (s, 3H), 3.10 (m, 4H), 2.82 (s, 3H), 2.00 (m, 2H), 1.37 (s, 9H). LC-MS (ESI) m/z 654 (M+H)$^+$.

Example 26

Preparation of 1-(5-tert-butyl-isoxazol-3-yl)-3-(3-{6-[3-(1,1-dioxo-thiomorpholin-4-yl)-propoxy]-7-methoxy-quinazolin-4-yloxy}-phenyl)-urea The intermediate 1-(5-tert-butylisoxazol-3-yl)-3-(3-(6-(3-chloropropoxy)-7-methoxyquinazolin-4-yloxy)phenyl)urea (200 mg, 0.38 mmol) from Example 21B was treated with thiomorpholine-1,1-dioxide (154 mg, 1.14 mmol), tetrabutylammonium iodide (140 mg, 0.38 mmol) and N,N'-diisopropylethylamine (135 µL, 0.76 mmol) in N,N'-dimethylformamide (2 mL). The mixture was heated to 60° C. for 56h and cooled to room temperature. Water was added and the solid filtered off and dried. The crude solid was purified by preparative HPLC (Phenomenex phenylhexyl reverse phase column) and the obtained solid triturated with water and drops of methanol, then filtered off and dried under high vacuum to afford 1-(5-tert-butyl-isoxazol-3-yl)-3-(3-{6-[3-(1,1-dioxo-thiomorpholin-4-yl)-propoxy]-7-methoxy-quinazolin-4-yloxy}-phenyl)-urea (46.40 mg, 20%) as a solid. $^1$H NMR (300 MHz, DMSO-d$_6$) δ 9.62 (bs, 1H), 9.04 (bs, 1H), 8.56 (s, 1H), 7.57 (d, 2H), 7.40-7.37 (m, 2H), 7.25 (d, 1H), 6.97 (d, 1H), 6.47 (s, 1H), 4.25-4.21 (m, 2H), 4.00 (s, 3H), 3.34 (bs, 4H), 2.93 (bs, 4H), 2.68-2.64 (m, 2H), 1.99-1.96 (m, 2H), 1.18 (s, 9H); LC-MS (ESI) m/z 625 (M+H)$^+$.

Example 27

Preparation of 1-(5-tert-butylisoxazol-3-yl)-3-(3-(6-methoxy-7-(3-morpholinopropoxy)quinazolin-4-yloxy)phenyl)urea Example 27A Step 1: To a solution of 4-(3-chloro-propoxy)-3-methoxy-benzoic acid methyl ester (12 g, 65.8 mmol) and potassium carbonate (36.3 g, 263 mmol) in DMF (100 mL) was added 1-bromo-3-chloro-propane (32.5 mL, 329 mmol). The mixture was stirred at ambient temperature for 15 hours. Completion of the reaction was monitored by TLC. The reaction mixture was diluted with ethyl acetate and the ethyl acetate layer was washed with water and brine. The organic layer was dried (Na₂SO₄) and concentrated to afford 4-(3-chloropropoxy)-3-methoxy-benzoic acid methyl ester (15 g, 88%) as a white solid. $^1$H NMR (300 MHz, CDCl₃) δ 7.65 (d, 1H), 7.52 (s, 1H), 6.88 (d, 1H), 4.20 (t, 2H), 3.90 (s, 6H), 3.75 (t, 2H), 2.30 (q, 2H).

Example 27A

Step 2: The intermediate from Step 1 (26.4 g, 102 mmol) was taken in acetic acid (185 mL) and acetic anhydride (15 mL) was added. The solution was cooled to 0° C. and 90% nitric acid (15 mL) was added. The reaction mixture was stirred for 10-15 minutes at ambient temperature, then heated to 50° C. for 3 hours. Completion of the reaction was monitored by LCMS. The reaction mixture was cooled and was diluted with ethyl acetate. The ethyl acetate layer was washed with aq. sodium bicarbonate, and concentrated to afford the pure compound 4-(3-chloro-propoxy)-5-methoxy-2-nitro-benzoic acid methyl ester (29.14 g, 94%) yellow solid. $^1$H NMR (300 MHz, DMSO-d₆) δ 7.68 (s, 1H), 7.33 (s, 1H), 4.24 (t, 2H), 3.92 (s, 3H), 3.82 (s, 3H), 3.77 (t, 2H), 2.21 (q, 2H).

Example 27A

Step 3: To a solution of the intermediate from Step 2 (29.14 g, 95.8 mmol) in ethyl acetate: methanol (3:1, 1 L) was added 10% Pd/C (3 g). The mixture was stirred under H₂ for 12 hours. Completion of the reaction was monitored by LCMS. The reaction mixture was filtered using a celite pad and washed with excess ethyl acetate. The filtrate was evaporated to dryness to afford the pure 2-amino-4-(3-chloro-propoxy)-5-methoxy-benzoic acid methyl ester (24.2 g, 94%) as a solid. $^1$H NMR (300 MHz, DMSO-d₆) δ 7.13 (s, 1H), 6.43 (s, 2H), 6.39 (s, 1H), 4.04 (t, 2H), 3.80 (t, 2H), 3.74 s, 3H), 3.65 (s, 3H), 2.19 (m, 2H), LC-MS (ESI)m/z 274 (M+H)⁺.

Example 27A

Step 4: To a solution of the intermediate from Step 3 (4.2 g, 15.35 mmol) in ethanol was added formamidine hydrochloride (2.97 g, 36.96 mmol). The mixture was heated at 140° C. in sealed tube for 12h. Completion of the reaction was monitored by LCMS. The precipitate formed was filtered and washed with ethanol and dried to afford the pure compound 7-(3-chloro-propoxy)-6-methoxy-quinazolin-4-ol (2.32 g, 56%) as a yellow solid. $^1$H NMR (300 MHz, DMSO-d₆) δ 11.93 (brs, 1H), 7.99 (s, 1H), 7.45 (s, 1H), 7.16 (s, 1H), 4.23 (t, 2H), 3.88 (s, 3H), 3.80 (t, 2H), 2.23 (t, 2H), LC-MS (ESI)m/z 269 (M+H)⁺.

Example 27A

Step 5: To a solution of the intermediate from Step 4 (3.00 g, 11.16 mmol) in toluene (30 mL) in a pressure vessel was added phosphorous oxychloride (8 mL). The mixture was heated to 125° C. for 5 hours. Completion of the reaction was monitored by LCMS. The mixture was concentrated to dryness and excess ethyl acetate was added. The solution was washed with water and brine and was dried (Na₂SO₄) and concentrated to afford the pure compound 4-chloro-7-(3-chloro-propoxy)-6-methoxy-quinazoline (2.51 g, 78%) as a yellow solid. $^1$H NMR (300 MHz, DMSO-d₆) δ 8.85 (s, 1H), 7.48 (s, 1H), 7.35 (s, 1H), 4.35 (t, 2H), 4.00 (s, 3H), 3.75 (t, 2H), 2.25 (q, 2H). LC-MS (ESI)m/z 287 (M+H)⁺.

Example 27B

To a solution of (1-(5-tert-butyl-isoxazol-3-yl)-3-(3-hydroxy-phenyl)-urea, 300 mg, 1.089 mmol) from Example 1A and (4-chloro-7-(3-chloro-propoxy)-6-methoxy-quinazoline (343.96 mg, 1.119 mmol), from the previous step in THF, was added Cs₂CO₃ (532.2 mg, 1.63 mmol) and the mixture was heated at 50° C. for 12 hours. Completion of the reaction was monitored by LCMS. The reaction mixture was diluted with ethyl acetate and the ethyl acetate layer was washed with water and brine successively. The organic layer was dried (Na₂SO₄) and concentrated to dryness. The crude compound was purified by column chromatography to afford the pure compound 1-(5-tert-butyl-isoxazol-3-yl)-3-{3-[7-(3-chloro-propoxy)-6-methoxy-quinazolin-4-yloxy]-phenyl}-urea, (310 mg, 61%) as a white solid. $^1$H NMR (300 MHz, DMSO-d₆) δ 9.55 (s, 1H), 9.00 (s, 1H), 8.55 (s, 1H), 7.55 (m, 2H), 7.40 (m, 2H), 7.25 (d, 1H), 6.95 (d, 1H), 6.45 (s, 1H), 4.35 (t, 2H), 4.00 (s, 3H), 3.85 (2, 2H), 1.30 (s, 9H); LC-MS (ESI)m/z 526 (M+H)⁺.

Example 27C

In a sealed reactor (1-(5-tert-butyl-isoxazol-3-yl)-3-{3-[7-(3-chloro-propoxy)-6-methoxy-quinazolin-4-yloxy]-phenyl}-urea from the previous step (300 mg, 0.57 mmol) was dissolved in 10 mL of dry DMF. To this solution was added diisopropylethyl amine (220 mg, 1.7 mmol), tetrabutylammonium iodide (210 mg, 0.57 mmol) and morpholine (149 mg, 1.7 mmol). The reaction was heated to 60° C. for 48 hours. The solution was then poured into 100 mL of water and extracted three times with ethyl acetate, the extracts combined, washed with brine, dried with magnesium sulfate, filtered and concentrated. The resulting oil was purified using silica gel chromatography eluting with a methanol/dichloromethane gradient 1-12% over 18 column volumes. The appropriate peak was concentrated, then dissolved in 13 mL of dichloromethane. To this was added 3 mL of 1M HCl in ether and the solution concentrated to a solid. The solid was dissolved in a minimal amount of methanol and the salt precipitated by adding ether. The resulting precipitate was collected by vacuum filtration to afford the title compound (264 mg). $^1$H NMR (300 MHz, DMSO-d₆) δ 10.7 (s, 1H), 9.76 (s, 1H), 9.56 (s, 1H), 8.66 (s, 1H), 7.62 (m, 2H), 7.5-7.3 (m, 2H), 7.28 (m, 1H), 6.95 (m, 1H), 6.48 (s, 1H), 4.36 (m, 2H), 4.04 (s, 6H), 3.54 (m, 4H), 3.30 (m, 3H), 3.2 (m, 2H), 2.3 (m, 3H), 1.30 (s, 9H). LCMS (ESI) m/z 577 (M+H)

Example 28

Preparation of 1-(5-tert-butylisoxazol-3-yl)-3-(3-(6-methoxy-7-(3-(4-methylpiperazin-1-yl)propoxy) quinazolin-4-yloxy)phenyl)urea To a solution of (1-(5-tert-butyl-isoxazol-3-yl)-3-{3-[7-(3-chloro-propoxy)-6-methoxy-quinazolin-4-yloxy]-phenyl}-urea (225 mg, 0.427 mmol) from Example 27B in DMF (3 mL) was added N-methyl piperazine (0.142 mL, 1.281 mmol) followed by diisopropyl ethylamine (0.223 mL, 1.281 mmol) and tetrabutyl ammonium iodide (157.72 mg, 0.427 mmol). The reaction mixture was heated at 60° C. for 15 h. Formation of the product was determined by LCMS. The crude reaction mixture was purified by preparative HPLC (using a phenyl-hexyl reverse phase column eluted with gradient of solvent A=0.05% HOAc/H₂O and solvent B=0.05% HOAc/CH₃CN). The appropriate fractions were concentrated followed by trituration with ether to afford 1-(5-tert-butylisoxazol-3-yl)-3-(3-(6-methoxy-7-(3-(4-methylpiperazin-1-yl) propoxy)quinazolin-4-yloxy)phenyl)urea (46 mg, 18%) as a white solid. $^1$H NMR (300 MHz, DMSO-d₆) δ 9.68 (s, 1H), 9.25 (s, 1H), 8.55 (s, 1H), 7.60 (d, 2H), 7.40 (m, 2H), 7.25 (d, 1H), 6.95 (d, 1H), 6.50 (s, 1H), 4.25 (m, 2H), 3.98 (s, 3H), 2.55-2.30 (m, 10H), 2.15 (s, 3H), 1.98 (m, 2H), 1.28 (s, 9H); LC-MS (ESI)m/z 590 (M+H)$^+$.

Example 29

Preparation of 1-(5-tert-butylisoxazol-3-yl)-3-(3-(7-(3-(4-hydroxymethyl) piperidin-1-yl)propoxy)-6-methoxyquinazolin-4-yloxy)phenyl)urea In the manner described in Example 28 (1-(5-tert-butyl-isoxazol-3-yl)-3-{3-[7-(3-chloro-propoxy)-6-methoxy-quinazolin-4-yloxy]-phenyl}-urea (225 mg, 0.427 mmol) from Example 27B was reacted with piperidin-4-yl-methanol (147 mg, 1.281 mmol) to yield 1-(5-tert-butylisoxazol-3-yl)-3-(3-(7-(3-(4-hydroxymethyl) piperidin-1-yl)propoxy)-6-methoxyquinazolin-4-yloxy)phenyl)urea (86 mg, 33%) as a white solid. $^1$H NMR (300 MHz, DMSO-d$_6$) δ 9.60 (s, 1H), 9.05 (s, 1H), 8.55 (s, 1H), 7.55 (d, 2H), 7.35 (m, 2H), 7.25 (d, 1H), 6.95 (d, 1H), 6.45 (s, 1H), 4.40 (m, 1H), 4.22 (m, 2H), 4.00 (s, 3H), 3.22 (m, 2H), 2.80 (d, 2H), 2.45 (m, 2H), 2.10-1.85 (m, 4H), 1.65 (d, 2H), 1.30 (s, 10H), 1.15 (m 2H); LC-MS (ESI)m/z 605 (M+H)$^+$.

Example 30

Preparation of 1-(5-tert-butylisoxazol-3-yl)-3-(3-(7-(3-(4-(2-hydroxyethyl)piperazin-1-yl)propoxy)-6-methoxyquinazolin-4-yloxy)phenyl)urea To a solution of (1-(5-tert-butyl-isoxazol-3-yl)-3-{3-[7-(3-chloro-propoxy)-6-methoxy-quinazolin-4-yloxy]-phenyl}-urea from Example 27B (225 mg, 0.427 mmol) in DMF (3 mL) was added 2-piperazin-1-yl-ethanol (0.157 mL, 1.281 mmol) followed by diisopropylethylamine (0.223 mL, 1.281 mmol) and tetrabutylammonium iodide (157.72 mg, 0.427 mmol). The reaction mixture was heated at 60° C. for 2 days. Formation of the product was determined by LCMS. The crude reaction mixture was purified by preparative HPLC (using phenyl-hexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(7-(3-(4-(2-hydroxyethyl)piperazin-1-yl)propoxy)-6-methoxyquinazolin-4-yloxy)phenyl)urea (68 mg, 26%) as a white solid. $^1$H NMR (300 MHz, DMSO-d$_6$) δ 9.45 (brs, 2H), 8.55 (s, 1H), 7.55 (d, 2H), 7.35 (d, 2H), 7.25 (d, 1H), 6.85 (d, 1H), 6.45 (s, 1H), 4.20 (m, 2H), 3.88 (s, 3H), 3.45 (m, 2H), 2.50-2.25 (m, 12H), 2.00 (m, 2H), 1.25 (s, 9H); LC-MS (ESI)m/z 620 (M+H)$^+$.

Example 31

Preparation of 1-(5-tert-butyl-isoxazol-3-yl)-3-(3-{7-[3-(3-hydroxy-pyrrolidin-1-yl)-propoxy]-6-methoxy-quinazolin-4-yloxy}-phenyl)-urea In the manner described in Example 28 (1-(5-tert-butyl-isoxazol-3-yl)-3-{3-[7-(3-chloro-propoxy)-6-methoxy-quinazolin-4-yloxy]-phenyl}-urea (225 mg, 0.427 mmol) from Example 27B was reacted with pyrrolidin-3-ol (0.103 mL, 1.281 mmol) to yield 1-(5-tert-butyl-isoxazol-3-yl)-3-(3-{7-[3-(3-hydroxy-pyrrolidin-1-yl)-propoxy]-6-methoxy-quinazolin-4-yloxy}-phenyl)-urea (16 mg, 4%) as a white solid. $^1$H NMR (300 MHz, DMSO-d$_6$) δ 9.70 (s, 1H), 9.28 (s, 1H), 8.52 (s, 1H), 7.55 (d, 2H), 7.35 (m, 2H), 7.25 (d, 1H), 6.95 (d, 1H), 6.45 (s, 1H), 4.70 (brs, 1H), 4.25 (m, 3H), 3.95 (s, 3H), 2.80-2.30 (m, 6H), 1.95 (m, 2H), 1.55 (m, 2H), 1.30 (s, 9H); LC-MS (ESI) m/z 577 (M+H)$^+$.

Example 32

Preparation of 1-(5-tert-butylisoxazol-3-yl)-3-(3-(6-methoxy-7-(3-(4-(methylsulfonyl)piperazin-1-yl)propoxy)quinazolin-4-yloxy)phenyl)urea In the manner described in Example 30 (1-(5-tert-butyl-isoxazol-3-yl)-3-{3-[7-(3-chloro-propoxy)-6-methoxy-quinazolin-4-yloxy]-phenyl}-urea from Example 27B (225 mg, 0.427 mmol) was reacted with 1-methanesulfonyl-piperazine (140.2 mg, 0.854 mmol) to yield 1-(5-tert-butylisoxazol-3-yl)-3-(3-(6-methoxy-7-(3-(4-(methyl sulfonyl)piperazin-1-yl)propoxy)quinazolin-4-yloxy)phenyl)urea (51 mg, 18%) as a white solid. $^1$H NMR (300 MHz, DMSO-d$_6$) δ 9.70 (s, 1H), 9.05 (s, 1H), 8.55 (s, 1H), 7.58 (d, 2H), 7.35 (m, 2H), 7.22 (d, 1H), 6.95 (d, 1H), 6.45 (s, 1H), 4.25 (m, 2H), 3.98 (s, 3H), 3.15 (m, 5H), 2.88 (s, 4H), 2.55 (m, 4H), 2.00 (m, 2H), 1.25 (s, 9H); LC-MS (ESI) m/z 654 (M+H)$^+$.

Example 33

Preparation of (S)-1-(5-tert-butylisoxazol-3-yl)-3-(3-(7-(3-(3-hydroxypyrrolidin-1-yl)propoxy)-6-methoxyquinazolin-4-yloxy)phenyl)urea A stirred solution of (1-(5-tert-butyl-isoxazol-3-yl)-3-{3-[7-(3-chloro-propoxy)-6-methoxy-quinazolin-4-yloxy]-phenyl}-urea from Example 27B (102 mg, 0.194 mmol), (S)-3-pyrrolidinol (51 mg, 0.582 mmol), N,N-diisopropylethylamine (75 mg, 0.582 mmol) and tetrabutylammonium iodide (71 mg, 0.194 mmol) in dry N,N-dimethylformamide (5 mL) was heated at 60° C. for 20 h. After cooling to room temperature, the reaction mixture was partitioned between water (50 mL) and ethyl acetate (50 mL) and the organic layer was separated, washed with brine (50 mL), dried (MgSO$_4$) and concentrated under reduced pressure. The residue was purified by preparative HPLC (using a phenyl-hexyl reverse phase column, eluted with gradient of solvent B=0.05% HOAC/CH$_3$CN and solvent A=0.05% HOAc/H$_2$O). The combined fractions were washed with saturated aqueous NaHCO$_3$ and the aqueous layer extracted with a mixture of 20% methanol in dichloromethane (2×50 mL). Concentration under reduced pressureafforded (S)-1-(5-tert-butylisoxazol-3-yl)-3-(3-(7-(3-(3-hydroxypyrrolidin-1-yl) propoxy)-6-methoxyquinazolin-4-yloxy)phenyl)urea as a colorless solid (16 mg, 14%). $^1$H NMR (300 MHz, CDCl$_3$) δ 8.59 (brs, 1H), 7.68 (brs, 1H), 7.52-7.55 (m, 2H), 7.26-7.35 (m, 4H), 6.95 (m, 1H), 6.11 (s, 1H), 4.34-4.40 (m, 3H), 4.04 (s, 3H), 3.00-3.20 (m, 2H), 2.84 (m, 1H), 2.67-2.68 (m, 2H), 2.50 (m, 1H), 2.10-2.30 (m, 3H), 1.80 (m, 1H), 1.51 (m, 1H), 1.26 (s, 9H); LC-MS (ESI) m/z 577 (M+H)$^+$.

Example 34

Preparation of (R)-1-(5-tert-Butylisoxazol-3-yl)-3-(3-(7-(3-(3-hydroxypyrrolidin-1-yl)propoxy)-6-methoxyquinazolin-4-yloxy)phenyl)urea (1-(5-Tert-butyl-isoxazol-3-yl)-3-{3-[7-(3-chloro-propoxy)-6-methoxy-quinazolin-4-yloxy]-phenyl}-urea (210 mg, 0.4 mmol) from Example 27B was treated with (R)-(+)-3-pyrrolidinol (65 μL, 0.8 mmol), tetrabutylammonium iodide (148 mg, 0.4 mmol) and N,N'-diisopropylethylamine (69 μL, 0.4 mmol) in N,N'-dimethylformamide (4 mL). The mixture was stirred at 50° C. for 5h. After cooling to room temperature water (4 mL) was added and the precipitating solid filtered off and dried. The solid residue was purified by preparative HPLC (phenylhexyl reverse phase column). The obtained solid was triturated with water to give (R)-1-(5-tert-butylisoxazol-3-yl)-3-(3-(7-(3-(3-hydroxypyrrolidin-1-yl)propoxy)-6-methoxyquinazolin-4-yloxy)phenyl)urea (37.76 mg, 16%) as a white solid. $^1$H NMR (300 MHz, DMSO-$d_6$) δ 9.60 (s, 1H), 9.10 (s, 1H), 8.55 (s, 1H), 7.58-7.56 (m, 2H), 7.40-7.38 (m, 2H), 7.25 (d, 1H), 6.98 (d, 1H), 6.48 (s, 1H), 4.70 (s, 1H), 4.31-4.20 (m, 3H), 3.99 (s, 3H), 3.32 (s, 1H), 2.81-2.69 (m, 2H), 2.40-2.19 (m, 3H), 2.10-1.98 (m, 3H), 1.67-1.4 (m, 1H), 1.27 (s, 9H); LC-MS (ESI) m/z 577 (M+H)$^+$.

Example 35

Preparation of 1-(5-tert-butylisoxazol-3-yl)-3-(3-(6-methoxy-7-(2-morpholinoethoxy)quinazolin-4-yloxy)phenyl)urea Example 35A Step 1: To a solution of 4-hydroxy-3-methoxy-benzoic acid methyl ester (10 g, 54.8 mmol) and potassium carbonate (22.75 g, 164.4 mmol) in DMF (100 mL) was added 1-bromo-2-chloro-ethane (22.7 mL, 274 mmol). The mixture was heated at 70° C. for 3h and monitored by TLC. The reaction mixture was diluted with ethyl acetate and washed the ethyl acetate layer with water and brine. The organic layer was dried (Na$_2$SO$_4$) and concentrated to afford 4-(2-chloro-ethoxy)-3-methoxy-benzoic acid methyl ester (13.1 gm, 97%) as a white solid. $^1$H NMR (300 MHz, CDCl$_3$) δ 7.65 (d, 1H), 7.55 (s, 1H), 6.90 (d, 1H), 4.35 (t, 2H), 3.90 (m, 8H).

Example 35A

Step 2: The intermediate 4-(2-chloro-ethoxy)-3-methoxy-benzoic acid methyl ester (2.7 g, 11.03 mmol) was taken in acetic acid (30 mL) and acetic anhydride (6 mL) was added. The solution was cooled to 0° C. and 90% nitric acid (2 mL) was added. The reaction mixture was stirred for 10-15 minutes at ambient temperature, then heated to 50° C. for 2h. Completion of the reaction was monitored by TLC. The reaction mixture was cooled and was poured on to crushed ice. The precipitate formed was filtered and was dried to afford the pure 4-(2-chloro-ethoxy)-5-methoxy-2-nitro-benzoic acid methyl ester (2.73 g, 85%) as a yellow solid. $^1$H NMR (300 MHz, DMSO-$d_6$) δ 7.70 (s, 1H), 7.35 (s, 1H), 4.42 (t, 2H), 4.10-3.90 (m, 5H), 3.80 (m, 3H).

Example 35A

Step 3: To a solution of 4-(2-chloro-ethoxy)-5-methoxy-2-nitro-benzoic acid methyl ester (2.7 g, 9.32 mmol) in ethyl acetate (30 mL) was added 10% Pd/C (405 mg) and the mixture was stirred under H$_2$ for 12 h. Completion of the reaction was monitored by LCMS. The reaction mixture was filtered using a celite pad and was washed with excess ethyl acetate and evaporated to dryness to afford the pure 2-amino-4-(2-chloro-ethoxy)-5-methoxy-benzoic acid methyl ester (2.40 g, 99%) as a solid. $^1$H NMR (300 MHz, DMSO-$d_6$) δ 7.15 (s, 1H), 6.40 (s, 2H), 6.35 (s, 1H), 4.18 (t, 2H), 3.95 (t, 2H), 3.70 s, 3H), 3.65 (s, 3H), LC-MS (ESI) m/z 260 (M+H)$^+$.

Example 35A

Step 4: To a solution of 2-amino-4-(2-chloro-ethoxy)-5-methoxy-benzoic acid methyl ester (2.4 g, 9.24 mmol) in ethanol was added formamidine hydrochloride (2.97 g, 36.96 mmol). The mixture was heated at 130° C. in sealed tube for 8 h. The precipitate formed was filterd and washed with ethanol and dried to afford the pure compound 7-(2-chloro-ethoxy)-6-methoxy-quinazolin-4-ol (2.25 g, 96%) as an off-white solid. $^1$H NMR (300 MHz, DMSO-$d_6$) δ 7.95 (s, 1H), 7.45 (s, 2H), 7.15 (s, 1H), 4.40 (t, 2H), 4.00 (t, 2H), 3.88 (s, 3H), LC-MS (ESI) m/z 255 (M+H)$^+$.

Example 35A

Step 5: To a solution of 4-chloro-7-(2-chloro-ethoxy)-6-methoxy-quinazoline 4-chloro-7-(2-chloro-ethoxy)-6-methoxy-quinazoline (3.00 g, 11.77 mmol) in toluene (25 mL) in a pressure vessel was added phosphorous oxychloride (5 mL) and the mixture was heated to 125° C. for 5h. Completion of the reaction was monitored by LCMS. The mixture was evaporated to dryness, then excess ethyl acetate was added. The solution was washed with water and brine, and dried (Na$_2$SO$_4$) then concentrated to afford the pure compound 4-chloro-7-(2-chloro-ethoxy)-6-methoxy-quinazoline (2.5 g, 78%) as a yellow solid. $^1$H NMR (300 MHz, DMSO-$d_6$) δ 8.88 (s, 1H), 7.45 (s, 1H), 7.35 (s, 1H), 4.50 (t, 2H), 4.05 (t, 2H), 3.95 (s, 3H). LC-MS (ESI) m/z 273 (M+H)$^+$.

Example 35B

To a solution of (1-(5-tert-butyl-isoxazol-3-yl)-3-(3-hydroxy-phenyl)-urea, 300.13 mg, 1.098 mmol) from Example 1A and (4-chloro-7-(2-chloro-ethoxy)-6-methoxy-quinazoline from the previous step (300 mg, 1.098 mmol) in THF was added Cs$_2$CO$_3$ (532.7 mg, 1.64 mmol), and the mixture was heated at 50° C. for 12 h. Completion of the reaction was monitored by LCMS. The reaction mixture was diluted with ethyl acetate and the solution was washed with water and brine successively. The organic layer was dried (Na$_2$SO$_4$) and concentrated to dryness to afford the pure compound 1-(5-tert-butyl-isoxazol-3-yl)-3-{3-[7-(2-chloro-ethoxy)-6-methoxy-quinazolin-4-yloxy]-phenyl}-urea (525 mg, 93%) as a white solid. $^1$H NMR (300 MHz, DMSO-$d_6$) δ 9.58 (s, 1H), 9.00 (s, 1H), 8.55 (s, 1H), 7.57 (s, 2H), 7.40 (m, 2H), 7.22 (d, 1H), 6.95 (d, 1H), 6.45 (s, 1H), 4.50 (m, 2H), 4.00 (m, 5H), 1.28 (s, 9H); LC-MS (ESI) m/z 512 (M+H)$^+$.

Example 35C

To a solution of 1-(5-tert-butyl-isoxazol-3-yl)-3-{3-[7-(2-chloro-ethoxy)-6-methoxy-quinazolin-4-yloxy]-phenyl}-urea from Example 35B (225 mg, 0.439 mmol) in DMF (3 mL) was added morpholine (114.86 mg, 1.318 mmol) followed by diisopropylethylamine (0.229 mL, 1.318 mmol) and tetrabutylammonium iodide (162.3 mg, 0.439 mmol). The reaction mixture was heated at 60° C. for 3 days. Formation of product was determined by LCMS. The crude reaction mixture was purified by preparative HPLC (phenomenex phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(2-morpholinoethoxy)quinazolin-4-yloxy)phenyl)urea (51 mg, 21%) as a white solid. $^1$H NMR (300 MHz, DMSO-$d_6$) δ 9.58 (s, 1H), 9.00 (s, 1H), 8.55 (s, 1H), 7.60-7.35 (m, 4H), 7.25 (m, 1H), 6.95 (m, 1H), 6.45 (s, 1H), 4.32 (m, 2H), 3.95 (s, 3H), 3.62 (m, 4H), 2.85 (m, 2H), 2.65-2.45 (m, 4H), 1.28 (s, 9H); LC-MS (ESI) m/z 563 (M+H)$^+$.

Example 36

Preparation of 1-(5-tert-butylisoxazol-3-yl)-3-(3-(6-methoxy-7-(2-(4-methylpiperazin-1-yl)ethoxy)quinazolin-4-yloxy)phenyl)urea To a solution of 1-(5-tert-butyl-isoxazol-3-yl)-3-{3-[7-(2-chloro-ethoxy)-6-methoxy-quinazolin-4-yloxy]-phenyl}-urea from Example 35B (225 mg, 0.439 mmol) in DMF (3 mL) was added N-methyl piperazine (0.146 mL, 1.317 mmol) followed by diisopropyl ethylamine (0.229 mL, 1.317 mmol) and tetrabutyl ammonium iodide (162.15 mg, 0.439 mmol). The reaction mixture was heated at 60° C. for 2 days. Formation of the product was determined by LCMS. The crude reaction mixture was purified by preparative HPLC (phenomenex phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(2-(4-methylpiperazin-1-yl)ethoxy)quinazolin-4-yloxy)phenyl)urea (21 mg, 8%) as a white solid. $^1$H NMR (300 MHz, DMSO-d$_6$) δ 9.80 (s, 1H), 9.32 (s, 1H), 8.55 (s, 1H), 7.55 (d, 2H), 7.40 (m, 2H), 7.25 (s, 1H), 6.98 (m, 1H), 6.48 (s, 1H), 4.30 (m, 2H), 4.00 (s, 3H), 2.82-2.25 (m, 10H), 2.15 (s, 3H), 1.28 (s, 9H); LC-MS (ESI) m/z 576 (M+H)$^+$.

Example 37

Preparation of 1-(5-tert-butyl-isoxazol-3-yl)-3-(3-{7-[2-(4-hydroxymethyl-piperidin-1-yl)-ethoxy]-6-methoxy-quinazolin-4-yloxy}-phenyl)-urea 1-(5-tert-butyl-isoxazol-3-yl)-3-{3-[7-(2-chloro-ethoxy)-6-methoxy-quinazolin-4-yloxy]-phenyl}-urea from Example 35B (225 mg, 0.427 mmol) and piperidin-4-yl-methanol (0.103 mL, 1.281 mmol) were reacted in the manner described in Example 36 to afford 1-(5-tert-butyl-isoxazol-3-yl)-3-(3-{7-[2-(4-hydroxymethyl-piperidin-1-yl)-ethoxy]-6-methoxy-quinazolin-4-yloxy}-phenyl)-urea (41 mg, 16%) as a white solid. $^1$H NMR (300 MHz, DMSO-d$_6$) δ 9.65 (s, 1H), 9.15 (s, 1H), 8.55 (s, 1H), 7.55 (d, 2H), 7.38 (m, 2H), 7.25 (d, 1H), 6.95 (d, 1H), 6.45 (s, 1H), 4.45 (brs, 1H), 4.30 (m, 2H), 3.98 (s, 3H), 3.25 (m, 2H), 3.00 (m, 2H), 2.75 (m, 2H), 2.00 (m, 2H), 1.65 (d, 2H), 1.25 (s, 10H), 1.15 (m, 2H); LC-MS (ESI) m/z 591 (M+H)$^+$.

Example 38

Preparation of 1-(5-tert-butylisoxazol-3-yl)-3-(3-(7-(2-(4-(2-hydroxyethyl)piperazin-1-yl)ethoxy)-6-methoxyquinazolin-4-yloxy)phenyl)urea 1-(5-tert-butyl-isoxazol-3-yl)-3-{3-[7-(2-chloro-ethoxy)-6-methoxy-quinazolin-4-yloxy]-phenyl}-urea from Example 35B (225 mg, 0.427 mmol) and 2-piperazin-1-yl-ethanol (0.161 mL, 1.317 mmol) were reacted in the manner described in Example 36. 1-(5-tert-Butylisoxazol-3-yl)-3-(3-(7-(2-(4-(2-hydroxyethyl)piperazin-1-yl)ethoxy)-6-methoxyquinazolin-4-yloxy)phenyl)urea (33 mg, 13%) was isolated as a white solid. $^1$H NMR (300 MHz, DMSO-d$_6$) δ 9.70 (brs, 1H), 9.25 (brs, 1H), 8.52 (s, 1H), 7.55 (s, 2H), 7.35 (m, 2H), 7.25 (m, 1H), 6.95 (d, 1H), 6.45 (s, 1H), 4.40 (s, 1H), 4.30 (m, 2H), 3.95 (s, 3H), 3.45 (m, 2H), 2.85-2.30 (m, 12H), 1.25 (m, 9H); LC-MS (ESI) m/z 606 (M+H)$^+$.

Example 39

Preparation of 1-(5-tert-butyl-isoxazol-3-yl)-3-(3-{7-(2-(1,1-dioxo-1l6-thiomorpholin-4-yl)-ethoxyl-6-methoxy-quinazolin-4-yloxy}-phenyl)-urea To a solution of 1-(5-tert-butyl-isoxazol-3-yl)-3-{3-[7-(2-chloro-ethoxy)-6-methoxy-quinazolin-4-yloxy]-phenyl}-urea from Example 35B (225 mg, 0.439 mmol) in DMF (3 mL) was added thiomorpholine-1,1-dioxide (178 mg, 1.317 mmol) followed by diisopropylethylamine (0.229 mL, 1.317 mmol) and tetrabutylammonium iodide (162.15 mg, 0.439 mmol). The reaction mixture was heated at 60° C. for 5 days. Formation of the product was determined by LCMS. The crude reaction mixture was purified by preparative HPLC (using phenyl-hexyl reverse phase column eluted with gradient of solvent A=0.05% HOAc/H$_2$O and solvent B=0.05% HOAc/CH$_3$CN) to afford 1-(5-tert-butyl-isoxazol-3-yl)-3-(3-{7-[2-(1,1-dioxo-1l6-thiomorpholin-4-yl)-ethoxy]-6-methoxy-quinazolin-4-yloxy}-phenyl)-urea (29 mg, 11%) as a white solid. $^1$H NMR (300 MHz, DMSO-d$_6$) δ 9.80-9.15 (brs, 2H), 8.52 (s, 1H), 7.55 (d, 2H), 7.35 (m, 2H), 7.25 (d, 1H), 6.92 (d, 1H), 6.45 (s, 1H), 4.30 (m, 2H), 3.95 (s, 3H), 3.20-3.00 (m, 8H), 2.60 (m, 2H), 1.25 (s, 9H); LC-MS (ESI) m/z 611 (M+H)$^+$.

Example 40

Preparation of 1-(5-tert-butylisoxazol-3-yl)-3-(3-(6-(2-methoxyethoxy)quinazolin-4-yloxy)phenyl)urea Example 40A Step 1: To 5-hydroxy-2-nitrobenzaldehyde (1.0 g, 6.0 mmol) in 2.5M NaOH(aq) (10 mL) at 100° C. was added 35% H$_2$O$_2$ (12 mL) dropwise over 10 minutes and the mixture heated at reflux overnight. The solution was acidified with 10% H$_2$SO$_4$, extracted with EtOAc (2×100 mL), and the combined organic layers washed with H$_2$O and brine, dried over MgSO$_4$, filtered and concentrated in vacuo to give 5-hydroxy-2-nitrobenzoic acid (1.03 g, 5.63 mmol, 94%). LC-MS (ESI) m/z 182 (M–H)$^+$.

Example 40A

Step 2: To MeOH (125 mL) was added 5-hydroxy-2-nitrobenzoic acid (1.02 g, 5.6 mmol) followed by dropwise addition of thionyl chloride (~4 mL) and the mixture heated at reflux overnight. The solution was cooled to room temperature, concentrated in vacuo, reconcentrated twice from MeOH, dissolved in EtOAc, washed with H$_2$O and brine, dried over MgSO$_4$, filtered, and concentrated in vacuo to give methyl 5-hydroxy-2-nitrobenzoate (1.09 g, 5.5 mmol, 98%). $^1$H NMR (300 MHz, DMSO-d$_6$) δ 11.38 (s, 1H), 8.05 (d, 1H), 7.03 (d, 1H), 7.01 (s, 1H), 3.82 (s, 3H); LC-MS (ESI) m/z 196 (M–H)$^+$.

Example 40A

Step 3: To methyl 5-hydroxy-2-nitrobenzoate (1.08 g, 5.5 mmol) in DMF (50 mL) was added potassium carbonate (1.52 g, 11 mmol) followed by 1-bromo-2-methoxyethane (1.55 mL, 16.4 mmol) and the mixture heated at 60° C. overnight. After cooling to room temperature, the reaction was diluted with H$_2$O, extracted with EtOAc, and the organic layer washed with H$_2$O and brine, dried over MgSO$_4$, filtered, concentrated in vacuo, and purified by column chromatography (12-100% EtOAc/hexanes) to give methyl 5-(2-methoxyethoxy)-2-nitrobenzoate (1.08 g, 4.2 mmol, 77%). $^1$H NMR (300 MHz, DMSO-$d_6$) δ 8.13 (d, 1H), 7.31 (s, 1H), 7.29 (d, 1H), 4.29 (dd, 2H), 3.86 (s, 3H), 3.68 (dd, 2H), 3.31 (s, 3H); LC-MS (ESI) m/z 256 (M+H)$^+$.

Example 40A

Step 4: To methyl 5-(2-methoxyethoxy)-2-nitrobenzoate (1.08 g, 4.2 mmol) under argon was added 10% Palladium on carbon and MeOH (20 mL). The flask was flushed with H$_2$(g) and stirred under H$_2$ (1 atm) for 30 minutes. The mixture was filtered through Celite and concentrated in vacuo to give methyl 2-amino-5-(2-methoxyethoxyl)benzoate (964 mg, 4.2 mmol, 100%). LC-MS (ESI) m/z 226 (M+H)$^+$.

Example 40A

Step 5: To methyl 2-amino-5-(2-methoxyethoxyl)benzoate (964 mg, 4.2 mmol) in absolute EtOH (25 mL) was added formamidine hydrochloride (1.4 g, 17.2 mmol) and the mixture heated in a sealed tube at 130° C. overnight. The mixture was cooled to room temperature and filtered to give 4-hydroxy-6-(2-methoxyethoxy)quinazoline (871 mg, 4.0 mmol, 95%). $^1$H NMR (300 MHz, DMSO-$d_6$) δ 8.42 (br s, 1H), 7.99 (s, 1H), 7.61 (d, 1H), 7.50 (d, 1H), 7.43 (dd, 1H), 4.21 (dd, 2H), 3.70 (dd, 2H), 3.32 (s, 3H); LC-MS (ESI) m/z 221 (M+H)$^+$.

Example 40A

Step 6: 4-hydroxy-6-(2-methoxyethoxy)quinazoline (870 mg, 3.9 mmol) was reacted with POCl$_3$ as described in Example 4A Step 2 to give 4-chloro-6-(2-methoxyethoxy)quinazoline (662 mg, 2.8 mmol, 71%). LC-MS (ESI) m/z 239 (M+H)$^+$.

Example 40B

The title compound was prepared from 1-(5-tert-butylisoxazol-3-yl)-3-(3-hydroxyphenyl)urea from Example 1A (138 mg, 0.5 mmol) and 4-chloro-6-(2-methoxyethoxy)quinazoline from Example 40A Step 5 (119 mg, 0.5 mmol) using the procedure of Example 16C. The crude product was purified by column chromatography (25-100% EtOAc/hexanes) to give 1-(5-tert-butylisoxazol-3-yl)-3-(3-(6-(2-methoxyethoxy)quinazolin-4-yloxy)phenyl)urea (45 mg, 0.094 mmol, 20%). $^1$H NMR (300 MHz, DMSO-$d_6$) δ 9.59 (s, 1H), 9.01 (s, 1H), 8.62 (s, 1H), 7.94 (d, 1H), 7.74-7.64 (m, 3H), 7.60 (s, 1H), 7.42 (t, 1H), 7.27 (d, 1H), 6.99 (d, 1H), 6.48 (s, 1H), 4.37-4.31 (m, 2H), 3.78-3.71 (m, 2H), 3.34 (s, 3H), 1.28 (s, 9H); LC-MS (ESI) m/z 478 (M+H)$^+$.

Example 41

Preparation of 1-(5-tert-butylisoxazol-3-yl)-3-(3-(7-methoxy-6-(3-(methylsulfonyl)propoxy)quinazolin-4-ylthio)phenyl)urea Example 41A Step 1: To DMF (80 mL) was added potassium carbonate (5.7 g, 41.1 mmol) and methyl 3-hydroxy-4-methoxybenzoate (5.0 g, 27.4 mmol). The mixture was cooled to 0° C. and 1-bromo-3-chloropropane (8.64 g, 57.9 mmol) in DMF (10 mL) was added dropwise over 30 minutes. The mixture was allowed to warm to room temperature overnight. After removing most of the DMF in vacuo, the remaining oil was diluted with H$_2$O and filtered to give methyl 3-(3-chloropropoxy)-4-methoxybenzoate (6.65 g, 25.8 mmol, 94%). $^1$H NMR (300 MHz, DMSO-$d_6$) δ 7.61 (d, 1H), 7.47 (s, 1H), 7.09 (d, 1H), 4.12 (t, 2H), 3.85 (s, 3H), 3.80 (s, 3H), 3.78 (t, 2H), 2.23-2.15 (m, 2H); LC-MS (ESI) m/z 259 (M+H)$^+$.

Example 41A

Step 2: In the manner described in Example 16A Step 2 methyl 3-(3-chloropropoxy)-4-methoxybenzoate (6.65 g, 25.7 mmol) was reacted with nitric acid to give methyl 5-(3-chloropropoxy)-4-methoxy-2-nitrobenzoate (6.70 g, 22.1 mmol, 86%). $^1$H NMR (300 MHz, DMSO-$d_6$) δ 7.65 (s, 1H), 7.37 (s, 1H), 4.26 (t, 2H), 3.89 (s, 3H), 3.81 (s, 3H), 3.76 (t, 2H), 2.26-2.18 (m, 2H).

Example 41A

Step 3: In the manner described in Example 16A Step 3, methyl 5-(3-chloropropoxy)-4-methoxy-2-nitrobenzoate (6.70 g, 22.1 mmol) in EtOAc (100 mL) was reacted with 10% palladium on carbon as described in Example 16A Step 3 to give methyl 2-amino-5-(3-chloropropoxy)-4-methoxybenzoate (6.0 g, 22.0 mmol, 99%). $^1$H NMR (300 MHz, DMSO-$d_6$) δ 7.18 (s, 1H), 6.49 (br s, 2H), 6.37 (s, 1H), 3.93 (t, 2H), 3.82-3.71 (m, 8H), 2.14-2.06 (m, 2H); LC-MS (ESI) m/z 274 (M+H)$^+$.

Example 41A

Step 4: In the manner described in Example 16A Step 4, methyl 2-amino-5-(3-chloropropoxy)-4-methoxybenzoate (6.0 g, 21.9 mmol) in EtOAc from the previous step was reacted with formamidine hydrochloride as in Example 16A Step 4 to give 6-(3-chloropropoxy)-4-hydroxy-7-methoxyquinazoline (4.48 g, 16.7 mmol, 76%). $^1$H NMR (300 MHz, DMSO-$d_6$) δ 12.10 (br s, 1H), 8.00 (s, 1H), 7.47 (s, 1H), 7.15 (s, 1H), 4.19 (t, 2H), 3.97 (s, 3H), 3.81 (t, 2H), 2.27-2.19 (m, 2H); LC-MS (ESI) m/z 269 (M+H)$^+$.

Example 41B

Step 1: To N,N-dimethylformamide (40 mL, purged with argon) was added cesium carbonate (1.43 g, 4.4 mmol) and 6-(3-chloropropoxy)-4-hydroxy-7-methoxyquinazoline from the previous step (1.08 g, 4.0 mmol), at which point methanethiol (g) was bubbled into the reaction for 10 minutes. The mixture was stirred at room temperature for an additional 60 minutes, poured into H$_2$O and filtered to give 4-hydroxy-7-methoxy-6-(3-(methylthio)propoxy)quinazoline (877 mg, 3.13 mmol, 78%). $^1$H NMR (300 MHz, DMSO-$d_6$) δ 12.07 (br s, 1H), 7.99 (s, 1H), 7.45 (s, 1H), 7.13 (s, 1H), 4.14 (t, 2H), 3.91 (s, 3H), 2.64 (t, 2H), 2.05 (s, 3H), 2.04-1.97 (m, 2H); LC-MS (ESI) m/z 281 (M+H)$^+$.

Example 41B

Step 2: To dichloromethane (20 mL) at 0° C. was added 4-hydroxy-7-methoxy-6-(3-(methylthio)propoxy)quinazoline (870 mg, 3.1 mmol) followed by 3-chloroperbenzoic acid (2.7 g, 15.7 mmol). The solution was stirred for 10 minutes, diluted with DCM, and filtered to give 4-hydroxy-7-methoxy-6-(3-(methylsulfonyl)propoxy)quinazoline (710 mg, 2.28 mmol, 73%). $^1$H NMR (300 MHz, DMSO-$d_6$) δ 12.07 (br s, 1H), 8.00 (s, 1H), 7.45 (s, 1H), 7.15 (s, 1H), 4.19 (t, 2H), 3.91 (s, 3H), 3.30 (t, 2H), 3.05 (s, 3H), 2.26-2.15 (m, 2H); LC-MS (ESI) m/z 313 (M+H)+.

Example 41B

Step 3: The intermediate 4-hydroxy-7-methoxy-6-(3-(methylsulfonyl)propoxy)quinazoline (700 mg, 2.24 mmol) from the previous step was reacted with $POCl_3$ in the manner described in Example 4A Step 2 to give 4-chloro-7-methoxy-6-(3-(methylsulfonyl)propoxy)quinazoline (480 mg, 1.45 mmol, 65%). LC-MS (ESI) m/z 331 (M+H)+.

Example 41C 1-(5-tert-butylisoxazol-3-yl)-3-(3-hydroxyphenyl)urea (124 mg, 0.45 mmol) from Example 1A was treated with cesium carbonate (294 mg, 0.90 mmol) in anhydrous tetrahydrofuran (2.5 mL). The mixture was stirred at room temperature for 30 minutes. 4-chloro-7-methoxy-6-(3-(methylsulfonyl)propoxy) quinazoline from the previous step (149 mg, 0.45 mmol) was then added to the suspension and the mixture heated to 60° C. for 2h. After cooling to room temperature the crude mixture was taken in ethyl acetate/water and extracted. The organic fractions were combined, dried ($MgSO_4$) and concentrated under reduced pressure. The residue was purified by preparative HPLC (phenylhexyl reverse phase column) to give 1-(5-tert-butylisoxazol-3-yl)-3-(3-(7-methoxy-6-(3-(methylsulfonyl)propoxy) quinazolin-4-ylthio)phenyl) urea (10.3 mg, 4%). $^1$H NMR (300 MHz, DMSO-$d_6$) δ 9.64 (s, 1H), 9.08 (s, 1H), 8.57 (s, 1H), 7.58 (s, 2H), 7.43-7.38 (m, 2H), 7.27 (d, 1H), 6.97 (d, 1H), 6.48 (s, 1H), 4.34-4.32 (m, 2H), 4.02 (s, 3H), 3.33-3.30 (m, 2H), 3.06 (s, 3H), 3.29-3.27 (m, 2H), 1.30 (s, 9H); LC-MS (ESI) m/z 570 (M+H)+.

Example 42

Preparation of 1-(3-(2-fluoropropan-2-yl)isoxazol-5-yl)-3-(3-(7-methoxy-6-(3-(methylsulfonyl)propoxy) quinazolin-4-yloxy)phenyl)urea Example 42A Step 1: Prepared from ethyl 2-isobutyrate (10 g, 74.62 mmol) according to the method described for 4-methyl-3-oxopentanenitrile in Example 122A Step 1, to afford 4-fluoro-4-methyl-3-oxopentanenitrile as a yellow oil (8 g, 83%) which was used in the next step without further purification. $^1$H NMR (300 MHz, CDCl$_3$) δ 3.82 (s, 2H), 1.54 (d, J=21 Hz, 6H).

Example 42A

Step 2: Prepared from 4-fluoro-4-methyl-3-oxopentanenitrile (6 g, 47 mmol) according to the method described for 3-isopropylisoxazol-5-amine in Example 122A Step 2, to afford 3-(2-fluoropropan-2-yl)isoxazol-5-amine as a light yellow solid (4.83 g, 71%) which was used in the next step without further purification. $^1$H NMR (300 MHz, CDCl$_3$) δ 5.19 (s, 1H), 4.48 (brs, 2H), 1.68 (d, J=21 Hz, 6H); LC-MS (ESI) m/z 145 (M+H)+.

Example 42A

Step 3: Prepared from 3-(2-fluoropropan-2-yl)isoxazol-5-amine (4.83 g, 33.54 mmol) according to the method described for phenyl 3-isopropylisoxazol-5-ylcarbamate in Example 122A Step 3, to afford phenyl 3-(2-fluoropropan-2-yl)isoxazol-5-ylcarbamate as a colorless solid (6.04 g, 68%). $^1$H NMR (300 MHz, CDCl$_3$) δ 7.80 (brs, 1H), 7.39-7.45 (m, 2H), 7.18-7.32 (m, 3H), 6.27 (s, 1H), 1.74 (d, J=21 Hz, 6H); LC-MS (ESI) m/z 265 (M+H)+.

Example 42B

To THF (10 mL) was added phenyl 3-(2-fluoropropan-2-yl)isoxazol-5-ylcarbamate from the previous step (500 mg, 1.9 mmol), 3-aminophenol (207 mg, 1.9 mmol) and dimethylaminopyridine (60 mg, 0.5 mmol) and the mixture stirred overnight at room temperature. The mixture was concentrated in vacuo and purified by chromatography on silica gel (10-50% EtOAc/hexanes) to afford 1-(3-(2-fluoropropan-2-yl)isoxazol-5-yl)-3-(3-hydroxyphenyl)urea (390 mg, 1.4 mmol, 74%). LC-MS (ESI) m/z 280 (M+H)+.

Example 42C

The title compound was prepared from 1-(3-(2-fluoropropan-2-yl)isoxazol-5-yl)-3-(3-hydroxyphenyl)urea (84 mg, 0.3 mmol) and 4-chloro-7-methoxy-6-(3-(methylsulfonyl)propoxy)quinazoline from Example 41B Step 1 (76 mg, 0.23 mmol) using the procedure described in Example 16C. The crude product was purified by chromatography on silica gel (25-100% EtOAc/hexanes) to afford 1-(3-(2-fluoropropan-2-yl)isoxazol-5-yl)-3-(3-(7-methoxy-6-(3-(methylsulfonyl) propoxy)quinazolin-4-yloxy)phenyl)urea (81 mg, 0.14 mmol, 61%). $^1$H NMR (300 MHz, DMSO-$d_6$) δ 10.42 (br s, 1H), 9.11 (s, 1H), 8.57 (s, 1H), 7.63-7.58 (m, 2H), 7.47-7.40 (m, 2H), 7.32 (d, 1H), 7.00 (d, 1H), 6.15 (s, 1H), 4.32 (t, 2H), 4.02 (s, 3H), 3.41-3.29 (m, 2H), 3.06 (s, 3H), 2.31-2.22 (m, 2H), 1.66 (d, 6H); LC-MS (ESI) m/z 574 (M+H)+.

Example 43

Preparation of 1-(5-tert-butylisoxazol-3-yl)-3-(3-(7-(2-methoxyethoxy)quinazolin-4-yloxy)phenyl)urea Example 43A
7-(Benzyloxy)quinazolin-4(3H)-one (5 g, 19.8 mmol) was treated with thionyl chloride (50 mL) and anhydrous N,N'-dimethylformamide (0.5 mL) and heated to 80° C. for 1.5h. The solvent was removed under reduced pressure and the residue dissolved in dichloromethane, cooled to 0° C. and the pH adjusted to basic (pH=8) with a saturated solution of sodium bicarbonate. The organic layer was separated, the water extracted with ethyl acetate and the organics combined, dried ($MgSO_4$) and concentrated under reduced pressure to give 7-(benzyloxy)-4-chloroquinazoline (4.75 g, 89%), which was used directly in the next step without further purification. $^1$H NMR (300 MHz, DMSO-$d_6$) δ 9.13 (s, 1H), 8.18 (d, 1H), 7.97-7.46 (m, 4H), 7.46-7.35 (m, 4H), 5.35 (s, 2H); LC-MS (ESI) m/z 271 (M+H)+.

Example 43B

Step 1: Following to the procedure described in Example 41C, 1-(5-tert-butylisoxazol-3-yl)-3-(3-hydroxyphenyl)urea (1.02 g, 3.7 mmol) from Example 1A was reacted with 7-(benzyloxy)-4-chloroquinazoline (1 g, 3.7 mmol) and cesium carbonate (24 g, 7.4 mmol) in anhydrous tetrahydrofuran (10 mL) and the mixture was heated at 50° C. overnight. The crude product was triturated with dichloromethane to give 1-(3-(7-(benzyloxy)quinazolin-4-yloxy)phenyl)-3-(5-tert-butylisoxazol-3-yl)urea (725 mg, 38%) as a solid. $^1$H NMR (300 MHz, DMSO-d$_6$) δ 9.59 (s, 1H), 9.01 (s, 1H), 8.65 (s, 1H), 8.29 (d, 1H), 7.57-7.38 (m, 9H), 7.28 (d, 1H), 6.98 (d, 1H), 6.48 (s, 1H), 5.37 (s, 2H), 1.27 (s, 9H); LC-MS (ESI) m/z 510 (M+H)$^+$.

Example 43B

Step 2: 1-(3-(7-(Benzyloxy)quinazolin-4-yloxy)phenyl)-3-(5-tert-butylisoxazol-3-yl)urea (725 mg, 1.42 mmol) was treated with trifluoroacetic acid (7 mL) and heated at 85° C. for 3h. The solvent was removed under reduced pressure and the residue dissolved in ethyl acetate/water. The solution was neutralized with saturated sodium bicarbonate (pH=8) and the organic layer separated. After extraction of the aqueous phase with ethyl acetate, the organic fractions were combined, dried (MgSO$_4$) and concentrated under reduced pressure. The solid was triturated with ethyl acetate to afford 1-(5-tert-butylisoxazol-3-yl)-3-(3-(7-hydroxyquinazolin-4-yloxy)phenyl)urea (358 mg, 60%) as a solid. $^1$H NMR (300 MHz, DMSO-d$_6$) δ 10.92 (s, 1H), 9.64 (s, 1H), 9.07 (s, 1H), 8.58 (s, 1H), 8.24 (d, 1H), 7.57 (s, 1H), 7.41 (t, 1H), 7.30 (d, 2H), 7.20 (s, 1H), 6.97 (d, 1H) 6.49 (s, 1H), 1.27 (s, 9H); LC-MS (ESI) m/z 420 (M+H)$^+$.

Example 43B

Step 3: 1-(5-tert-Butylisoxazol-3-yl)-3-(3-(7-hydroxyquinazolin-4-yloxy)phenyl)urea (126 mg, 0.3 mmol) was treated with cesium carbonate (117 mg, 0.36 mmol) in anhydrous N,N'-dimethylformamide (3 mL) and stirred at room temperature for 30 minutes. 2-Bromoethylmethyl ether (50 mg, 0.36 mmol) was added and the mixture was stirred at 50° C. overnight. Cesium carbonate was filtered off and the residue purified by preparative HPLC (phenylhexyl reverse phase column) to afford 1-(5-tert-butylisoxazol-3-yl)-3-(3-(7-(2-methoxyethoxy)quinazolin-4-yloxy)phenyl)urea (21.16 mg, 15%) as a solid. $^1$H NMR (300 MHz, DMSO-d$_6$) δ 9.58 (bs, 1H), 9.00 (bs, 1H), 8.65 (s, 1H), 8.27 (d, 1H), 7.57 (s, 1H), 7.41-7.38 (m, 3H), 7.28 (d, 1H), 6.98 (d, 1H), 6.48 (s, 1H), 4.34 (bs, 2H), 3.76 (bs, 2H), 3.35 (s, 3H), 1.27 (s, 9H); LC-MS (ESI) m/z 478 (M+H)$^+$.

Example 44

Preparation of 1-(5-tert-butylisoxazol-3-yl)-3-(3-(7-methoxy-6-(3-(methylsulfonyl)propoxy)quinazolin-4-ylthio)phenyl)urea Example 44A Step 1: To DMSO (2.75 mL, 38.3 mmol) was added 3-aminothiophenol (4.07 mL, 38.3 mmol) and the mixture was heated at 90° C. for 4 hours and then poured into 6N HCl (40 mL). The yellow solid was filtered and dried under vacuum to give 3,3'-disulfanediyldianiline-xHCl (6.7 g, 17-23 mmol). LC-MS (ESI) m/z 249 (M+H)$^+$.

Example 44A

Step 2: To DMF (50 mL) was added triethylamine (10 mL), 3,3'-disulfanediyldianiline-xHCl (1.98 g) and 5-tert-butyl-3-isocyanatoisoxazole (1.81 g, 11 mmol), and the mixture heated at 50° C. overnight. After cooling to room temperature, the reaction was poured into H$_2$O, extracted with EtOAc (2×250 mL), and the combined org layers were washed with brine, dried over MgSO$_4$, filtered, concentrated in vacuo, and purified by column chromatography (25-100% EtOAc/hexanes) to give 1,1'-(3,3'-disulfanediylbis(3,1-phenylene))bis(3-(5-tert-butylisoxazol-3-yl)urea) (2.2 g, 3.8 mmol). LC-MS (ESI) m/z 581 (M+H)$^+$.

Example 44A

Step 3: To glacial acetic acid (40 mL) was added 1,1'-(3,3'-disulfanediylbis(3,1-phenylene))bis(3-(5-tert-butylisoxazol-3-yl)urea) (2.2 g, 3.8 mmol) and Zinc dust (1.24 g, 19 mmol). The mixture was heated at 50° C. overnight, cooled to r.t, and the AcOH decanted and concentrated. The crude solid was sonicated in 1N aqueous NaHSO$_4$, extracted with EtOAc, the organic layer dried over MgSO$_4$, filtered, concentrated in vacuo, and purified by column chromatography (15-50% EtOAc/hexanes) to give 1-(5-tert-butylisoxazol-3-yl)-3-(3-mercaptophenyl)urea (1.08 g, 3.7 mmol, 49%). $^1$H NMR (300 MHz, DMSO-d$_6$) δ 9.51 (s, 1H), 8.79 (s, 1H), 7.50 (s, 1H), 7.20-7.09 (m, 2H), 6.91 (d, 1H), 6.50 (s, 1H), 5.50 (br s, 1H), 1.28 (s, 9H); LC-MS (ESI) m/z 291 (M+H)$^+$.

Example 44B

To a suspension of sodium hydride (11 mg, 0.44 mmol) in anhydrous tetrahydrofuran (2 mL) cooled to 0° C., was added 1-(5-tert-butylisoxazol-3-yl)-3-(3-mercaptophenyl)urea from the previous step (117 mg, 0.40 mmol) as a solution in tetrahydrofuran (1 mL) and the mixture stirred at 0° C. for 30 minutes. To this suspension 4-chloro-7-methoxy-6-(3-(methylsulfonyl)propoxy)quinazoline from Example 41B Step 1 (133 mg, 0.40 mmol) was added and the resulting mixture was stirred at 0° C. and slowly allowed to reach room temperature. After stirring for additional 1 h, the mixture was taken up in ethyl acetate/water and extracted. The combined organic layers were dried (MgSO$_4$) and concentrated under reduced pressure. The residue was purified by preparative HPLC (Phenomenex phenylhexyl reverse phase column) to afford 1-(5-tert-butylisoxazol-3-yl)-3-(3-(7-methoxy-6-(3-(methylsulfonyl)propoxy)quinazolin-4-ylthio)phenyl)urea (10.30 mg, 4%) as a solid. $^1$H NMR (300 MHz, DMSO-d$_6$) δ 9.73 (bs, 1H), 9.19 (bs, 1H), 8.70 (s, 1H), 7.85 (s, 1H), 7.53-7.27 (m, 5H), 6.49 (s, 1H), 4.32 (bs, 2H), 4.01 (s, 3H), 3.35 (2H), 3.07 (s, 3H), 2.28 (bs, 2H), 1.28 (s, 9H); LC-MS (ESI) m/z 586 (M+H)$^+$.

Example 45

Preparation of 1-(5-tert-butylisoxazol-3-yl)-3-(3-(7-methoxy-6-(2-methoxyethoxy)quinazolin-4-ylthio)phenyl)urea 1-(5-tert-butylisoxazol-3-yl)-3-(3-mercaptophenyl)urea described in Example 44A (223 mg, 0.83 mmol) was treated with cesium carbonate (325 mg, 1.0 mmol) in anhydrous tetrahydrofuran (8 mL). The mixture was stirred at room temperature for 30 minutes. 4-chloro-7-methoxy-6-(2-methoxyethoxy)quinazoline (149 mg, 0.45 mmol) from Example 15A was added to the suspension and the mixture heated to 50° C. overnight. After cooling to room temperature the mixture was concentrated under reduced pressure and the residue purified by silica gel chromatography (ethyl acetate/dichloromethane 1:1) to give 1-(5-tert-butylisoxazol-3-yl)-3-(3-(7-methoxy-6-(2-methoxyethoxy)quinazolin-4-ylthio)phenyl) urea (218 mg, 50%) as a solid. $^1$H NMR (300 MHz, DMSO-d$_6$) δ 9.58 (s, 1H), 9.00 (s, 1H), 8.69 (s, 1H), 7.85 (s, 1H), 7.52-7.27 (m, 5H), 6.49 (s, 1H), 4.32 (bs, 2H), 4.00 (s, 3H), 3.77 (bs, 2H), 3.36 (s, 3H), 1.27 (s, 9H); LC-MS (ESI) m/z 524 (M+H)+.

Example 46

Preparation of 1-(5-tert-butylisoxazol-3-yl)-3-(3-(6,7-dimethoxyquinazolin-4-ylthio)phenyl)urea To a slurry of sodium hydride (53 mg, 2.2 mmol) in THF (20 mL) was added the thiol described in Example 44A (582 mg, 2.0 mmol), prepared as described previously, and the solution stirred at r.t until gas evolution ceased. After an additional 30 minutes of stirring, 4-chloro-6,7-dimethoxyquinazoline (448 mg, 2.0 mmol) was added. After stirring at r.t for 4 hours, the reaction was concentrated in vacuo. The resulting solid was diluted with EtOAc, the organic layer washed with aqueous sat. NaHCO$_3$ and brine, dried over MgSO$_4$, filtered and concentrated in vacuo. The crude product was purified by column chromatography (25-100% EtOAc/hexanes) to give 1-(5-tert-butylisoxazol-3-yl)-3-(3-(2-chloro-6,7-dimethoxyquinazolin-4-ylthio)phenyl)urea as a white solid. The compound was dissolved in EtOAc (5 mL) and 4N HCl in dioxane (0.2 mL, 0.8 mmol) was added. The mixture was sonicated, stirred and concentrated in vacuo to give the product (300 mg, 0.58 mmol, 29%) as the monohydrochloride. $^1$H NMR (300 MHz, DMSO-d$_6$) δ 9.74 (s, 1H), 9.50 (s, 1H), 8.79 (s, 1H), 7.86 (s, 1H), 7.55 (d, 1H), 7.45 (t, 1H), 7.38 (s, 2H), 7.30 (d, 1H), 6.50 (s, 1H), 4.00 (s, 6H), 1.28 (s, 9H); LC-MS (ESI) m/z 480 (M+H)+.

Example 47

Preparation of 1-(5-tert-butylisoxazol-3-yl)-3-(3-(6,7-difluoro quinazolin-4-ylthio)phenyl)urea The title compound was prepared from 1-(5-tert-butylisoxazol-3-yl)-3-(3-mercaptophenyl)urea described in Example 44A (87 mg, 0.3 mmol) and 4-chloro-6,7-difluoroquinazoline (60 mg, 0.3 mmol) from Example 4A Step 2 as described in Example 46 to give 1-(5-tert-butylisoxazol-3-yl)-3-(3-(6,7-difluoro quinazolin-4-ylthio)phenyl)urea (50 mg, 0.11 mmol, 37%). $^1$H NMR (300 MHz, DMSO-d$_6$) δ 9.61 (s, 1H), 9.05 (s, 1H), 8.88 (s, 1H), 8.34 (dd, 1H), 8.09 (dd, 1H), 7.88 (s, 1H), 7.53 (d, 1H), 7.47 (t, 1H), 7.30 (d, 1H), 6.49 (s, 1H), 1.28 (s, 9H); LC-MS (ESI) m/z 478 (M+Na)+.

Example 48

Preparation of 1-(5-tert-butylisoxazol-3-yl)-3-(3-(7-methoxyquinazolin-4-ylthio)phenyl)urea The title compound was prepared from 1-(5-tert-butylisoxazol-3-yl)-3-(3-mercaptophenyl)urea described in Example 44A (116 mg, 0.4 mmol) and 4-chloro-7-methoxyquinazoline (78 mg, 0.4 mmol) as described in Example 46 and its corresponding hydrochloride salt was prepared as described in Example X4 Step 2 to give 1-(5-tert-butylisoxazol-3-yl)-3-(3-(7-methoxyquinazolin-4-ylthio)phenyl)urea as the mono-hydrochloride (143 mg, 0.30 mmol, 75%). $^1$H NMR (300 MHz, DMSO-d$_6$) δ 9.77 (s, 1H), 9.55 (s, 1H), 8.85 (s, 1H), 8.20 (d, 1H), 7.87 (s, 1H), 7.55 (d, 1H), 7.48-7.42 (m, 2H), 7.38 (s, 1H), 7.29 (d, 1H), 6.50 (s, 1H), 3.99 (s, 3H), 1.28 (s, 9H); LC-MS (ESI) m/z 450 (M+H)+.

Example 49

Preparation of 1-(5-tert-butylisoxazol-3-yl)-3-(3-(6-methoxyquinazolin-4-ylthio)phenyl)urea The title compound was prepared from 1-(5-tert-butylisoxazol-3-yl)-3-(3-mercaptophenyl)urea described in Example 44A (87 mg, 0.3 mmol) and 4-chloro-6-methoxyquinazoline (59 mg, 0.3 mmol) as described in Example 46 and its corresponding hydrochloride salt was prepared as described in Example 4B Step 2 to give 1-(5-tert-butylisoxazol-3-yl)-3-(3-(6-methoxyquinazolin-4-ylthio)phenyl)urea as the monohydrochloride (76 mg, 0.15 mmol, 50%). $^1$H NMR (300 MHz, DMSO-d$_6$) δ 9.75 (s, 1H), 9.49 (s, 1H), 8.80 (s, 1H), 7.95 (d, 1H), 7.87 (s, 1H), 7.71 (dd, 1H), 7.55 (d, 1H), 7.49-7.42 (m, 2H), 7.29 (d, 1H), 6.50 (s, 1H), 4.00 (s, 3H), 1.28 (s, 9H); LC-MS (ESI) m/z 450 (M+H)+.

Example 50

Preparation of 1-(5-tert-butylisoxazol-3-yl)-3-[3-(7-ethoxy-6-methoxyquinazolin-4-ylthio)phenyl]urea A mixture of 1-(5-tert-butylisoxazol-3-yl)-3-(3-mercaptophenyl)urea described in Example 44A (0.146 g 0.5 mmol), 4-chloro-7-ethoxy-6-methoxyquinazoline from Example 6B Step 1 (0.12 g, 0.5 mmol), and Cs$_2$CO$_3$ (0.161 mg, 0.5 mmol) in isopropanol (10 mL) was heated at 70° C. for 7 hours. It was quenched with water and extracted with CH$_2$Cl$_2$. Extracts were dried over MgSO$_4$ and concentrated under reduced pressure. It was purified by silica gel chromatography with EtOAc/hexane as eluant to afford 1-(5-tert-butylisoxazol-3-yl)-3-[3-(7-ethoxy-6-methoxyquinazolin-4-ylthio)phenyl] urea as solid (0.118 g, 48%). $^1$H NMR (300 MHz, CDCl$_3$) δ 9.3 (br, 1H), 8.74 (s, 1H), 8.05 (s, 1H), 7.86 (s, 1H), 7.62 (d, 1H), 7.37 (m, 3H), 7.25 (1H), 5.91 (s, 1H), 4.29 (q, 2H), 4.06 (s, 3H), 1.58 (t, 3H), 1.32 (s, 9H); LC-MS (ESI) m/z 494 (M+H)+.

Example 51

Preparation of 1-(5-tert-butylisoxazol-3-yl)-3-[3-(6,7-diethoxyquinazolin-4-ylthio)phenyl]urea As described in Example 50 the intermediate 1-(5-tert-butylisoxazol-3-yl)-3-(3-mercaptophenyl)urea described in Example 44A (0.117 g, 0.4 mmol) was reacted with 4-chloro-6,7-diethoxyquinazoline (0.101 g, 0.4 mmol) from Example 13A, and Cs$_2$CO$_3$ (0.130 g, 0.4 mmol) in isopropanol (10 mL) at 70° C. for 4 hours, to afford 1-(5-tert-butylisoxazol-3-yl)-3-[3-(6,7-diethoxyquinazolin-4-ylthio)phenyl]urea as solid (0.131 g, 65%). $^1$H NMR (300 MHz, DMSO-d$_6$) δ 9.59 (s, 1H), 9.03 (s, 1H), 8.68 (s, 1H), 7.84 (s, 1H), 7.50 (d, 1H), 7.44 (t, 1H), 7.33 (m, 2H), 7.29 (d, 1H), 6.49 (s, 1H), 4.26 (m 4H), 1.45 (m, 6H), 1.28 (s, 9H); LC-MS (ESI) m/z 508 (M+H)+.

Example 52

Preparation of 1-(5-tert-butylisoxazol-3-yl)-3-{3-[6-methoxy-7-(2-methoxyethoxy)quinazolin-4-ylthio] phenyl}urea hydrochloride Example 52A As described in Example 50 the intermediate 1-(5-tert-butylisoxazol-3-yl)-3-(3-mercaptophenyl)urea described in Example 44A (0.105 g, 0.36 mmol) was reacted with 4-chloro-6-methoxy-7-(2-methoxyethoxy)quinazoline from Example 7A (0.134 g, 0.5 mmol), and Cs$_2$CO$_3$ (0.325 g, 1 mmol) in isopropanol (8 mL) at 70° C. for 4 hours, to afford 1-(5-tert-butylisoxazol-3-yl)-3-{3-[6-methoxy-7-(2-methoxyethoxy)quinazolin-4-ylthio]phenyl}urea as solid. $^1$H NMR (300 MHz, DMSO-d$_6$) δ 9.58 (s, 1H), 9.00 (s, 1H), 8.69 (s, 1H), 7.84 (m, 1H), 7.51 (m, 1H), 7.44 (t, 1H), 7.37 (s, 1H), 7.34 (s, 1H), 7.28 (m 1H), 6.49 (s, 1H), 4.33 (t, 2H), 4.00 (s, 3H), 3.76 (t, 2H), 3.34 (s, 3H), 1.28 (s, 9H).

Example 52B

To 1-(5-tert-butylisoxazol-3-yl)-3-{3-[6-methoxy-7-(2-methoxyethoxy)quinazolin-4-ylthio]phenyl}urea was added 1.0 M HCl in Et$_2$O solution (2 eq.) in the manner described in Example 6B Step 2 to afford 1-(5-tert-butylisoxazol-3-yl)-3-{3-[6-methoxy-7-(2-methoxyethoxy)quinazolin-4-ylthio]phenyl}urea hydrochloride as solid (0.16 g, 80%). $^1$H NMR (300 MHz, DMSO-d$_6$) δ 9.65 (s, 1H), 9.23 (s, 1H), 8.72 (s, 1H), 7.85 (s, 1H), 7.52 (d, 1H), 7.44 (t, 1H), 7.38 (s, 1H), 7.36 (s, 1H), 7.28 (d, 1H), 6.49 (s, 1H), 4.34 (t, 2H), 4.01 (s, 3H), 3.76 (t, 2H), 3.34 (s, 3H), 1.28 (s, 9H); LC-MS (ESI) m/z 524 (M+H)$^+$.

Example 53

Preparation of 1-{3-[6,7-bis(2-methoxyethoxy)quinazolin-4-ylthio]phenyl}-3-(5-tert-butylisoxazol-3-yl)urea hydrochloride Example 53A As described in Example 50, a mixture of the intermediate 1-(5-tert-butylisoxazol-3-yl)-3-(3-mercaptophenyl)urea described in Example 44A (0.117 g, 0.4 mmol), 4-chloro-6,7-bis(2-methoxyethoxy)quinazoline (0.125 g, 0.4 mmol) from Example 12A, and Cs$_2$CO$_3$ (0.20 g, 0.6 mmol) in isopropanol (5 mL) was heated at 90° C. overnight, to afford 1-{3-[6,7-bis(2-methoxyethoxy)quinazolin-4-ylthio]phenyl}-3-(5-tert-butylisoxazol-3-yl)urea. as solid. $^1$H NMR (300 MHz, DMSO-d$_6$) δ 9.58 (s, 1H), 8.99 (s, 1H), 8.68 (s, 1H), 7.84 (m, 1H), 7.51 (m, 1H), 7.46 (t, 1H), 7.39 (s, 1H), 7.38 (s, 1H), 7.28 (dd 1H), 6.49 (s, 1H), 4.34 (m 4H), 3.78 (m, 4H), 3.37 (s, 3H), 3.35 (s, 3H), 1.28 (s, 9H).

Example 53B

As described in Example 6B Step 2, to a solution of 1-{3-[6,7-bis(2-methoxyethoxy)quinazolin-4-ylthio]phenyl}-3-(5-tert-butylisoxazol-3-yl)urea in CH$_2$Cl$_2$ and MeOH was added 1.0 M HCl/Et$_2$O solution (2 eq.), to afford 1-{3-[6,7-bis(2-methoxyethoxy)quinazolin-4-ylthio]phenyl}-3-(5-tert-butylisoxazol-3-yl)urea hydrochloride as solid (0.098 g, 40%). $^1$H NMR (300 MHz, DMSO-d$_6$) δ 9.66 (s, 1H), 9.23 (s, 1H), 8.72 (s, 1H), 7.85 (s, 1H), 7.52 (d, 1H), 7.44 (t, 1H), 7.44 (s, 1H), 7.38 (s, 1H), 7.28 (d, 1H), 6.49 (s, 1H), 4.35 (m, 4H), 3.78 (m, 4H), 3.37 (s, 3H), 3.35 (s, 3H), 1.28 (s, 9H); LC-MS (ESI) m/z 568 (M+H)$^+$.

Example 54

Preparation of 1-(5-tert-butylisoxazol-3-yl)-3-[3-(7,8-dihydro-[1,4]dioxino[2,3-g]quinazolin-4-ylthio)phenyl]urea hydrochloride Example 54A According to the procedure described in Example 50, a mixture of the intermediate 1-(5-tert-butylisoxazol-3-yl)-3-(3-mercaptophenyl)urea described in Example 44A (0.105 g, 0.36 mmol), 4-chloro-7,8-dihydro-[1,4]dioxino[2,3-g]quinazoline described in Example 14A (0.111 g, 0.5 mmol), and Cs$_2$CO$_3$ (0.326 g, 1 mmol) in isopropanol (7 mL) was heated at 60° C. for 2 hours, to afford 1-(5-tert-butylisoxazol-3-yl)-3-[3-(7,8-dihydro-[1,4]dioxino[2,3-g]quinazolin-4-ylthio]phenyl)urea as solid.

Example 54B

According to the procedure described in Example 6B Step 2, to a solution of 1-(5-tert-butylisoxazol-3-yl)-3-[3-(7,8-dihydro-[1,4]dioxino[2,3-g]quinazolin-4-ylthio)phenyl]urea in CH$_2$Cl$_2$ and MeOH was added 1.0 M HCl/Et$_2$O solution, to afford 1-(5-tert-butylisoxazol-3-yl)-3-[3-(7,8-dihydro-[1,4]dioxino[2,3-g]quinazolin-4-ylthio)phenyl]urea hydrochloride as solid (0.113 g, 61%). $^1$H NMR (300 MHz, DMSO-d$_6$) δ 9.66 (s, 1H), 9.23 (s, 1H), 8.69 (s, 1H), 7.83 (m, 1H), 7.56 (s, 1H), 7.51 (d, 1H), 7.44 (t, 1H), 7.38 (s, 1H), 7.27 (d, 1H), 6.49 (s, 1H), 4.47 (m, 4H), 1.28 (s, 9H); LC-MS (ESI) m/z 478 (M+H)$^+$.

Example 55

Preparation of 1-(5-tert-butylisoxazol-3-yl)-3-{3-[7-methoxy-5-(tetrahydro-2H-pyran-4-ylthio)quinazolin-4-yloxy]phenyl}urea According to the procedure described in Example 50, a mixture of the intermediate 1-(5-tert-butylisoxazol-3-yl)-3-(3-mercaptophenyl)urea described in Example 44A (0.204 g, 0.7 mmol), 4-chloro-7-methoxy-5-(tetrahydro-2H-pyran-4-yloxy)quinazoline from Example 94A (0.212 g, 0.72 mmol), and Cs$_2$CO$_3$ (0.326 g, 1 mmol) in isopropanol (10 mL) was heated at 60° C. for 4 hours, to afford 1-(5-tert-butylisoxazol-3-yl)-3-{3-[7-methoxy-5-(tetrahydro-2H-pyran-4-yloxy)quinazolin-4-ylthio]phenyl}urea as solid (0.086 g, 22%). $^1$H NMR (300 MHz, CDCl$_3$) δ 9.3 (s, 1H), 8.60 (s, 1H), 7.82 (s, 1H), 7.76 (s, 1H), 7.65 (d, 1H), 7.41 (t, 1H), 7.33 (d, 1H), 6.86 (d, 1H), 6.54 (d, 1H), 5.90 (s, 1H), 4.78 (m 1H), 4.18 (m, 2H), 3.94 (s, 3H), 3.69 (m, 2H), 2.19 (m, 2H), 2.11 (m, 2H), 1.33 (s, 9H); LC-MS (ESI) m/z 550 (M+H)$^+$.

Example 56

Preparation of 1-(5-tert-butylisoxazol-3-yl)-3-(3-(6-ethoxy-7-methoxyquinazolin-4-ylthio)phenyl)urea In a sealed reaction vessel 1-(5-tert-butylisoxazol-3-yl)-3-(3-mercaptophenyl)urea described in Example 44A (333 mg, 1.14 mmol) was dissolved in 11 mL of THF. To this solution was added cesium carbonate (447 mg, 1.37 mmol), and the solution stirred for 30 minutes. At the end of this time 4-chloro-6-ethoxy-7-methoxyquinazoline (273 mg, 1.14 mmol) from Example 10A and the reaction heated to 50° C. for 48 hours. The reaction was concentrated and purified by silica gel chromatography eluting with an ethyl acetate/dichloromethane gradient 0-50% over 75 minutes. Concentration of the main peak gave the title compound (374 mg, 66.5% yield). $^1$H NMR (300 MHz, DMSO-d$_6$) δ 9.58 (s, 1H), 9.01 (s, 1H), 8.69 (s, 1H), 7.48 (s, 1H), 7.55-7.25 (m, 5H), 6.49 (s, 1H), 4.25 (m, 2H), 3.99 (s, 3H), 1.47 (m, 3H), 1.32 (s, 9H). LCMS (ESI) m/z 494 (M+H)

Example 57

Preparation of 1-(5-tert-butylisoxazol-3-yl)-3-(3-(7-methoxy-6-(3-(piperidin-1-yl)propoxy)quinazolin-4-ylthio)phenyl)urea Example 57A The intermediate 1-(5-tert-butylisoxazol-3-yl)-3-(3-mercaptophenyl)urea described in Example 44A (1.01 g, 3.5 mmol) was reacted with 4-chloro-6-(3-chloropropoxy)-7-methoxyquinazoline (1.0 g, 3.5 mmol) from Example 21 A Step 5 as described in Example 46 to afford 1-(5-tert-butylisoxazol-3-yl)-3-(3-(6-(3-chloropropoxy)-7-methoxyquinazolin-4-ylthio)phenyl)urea (1.69 g, 3.12 mmol, 89%). $^1$H NMR (300 MHz, DMSO-$d_6$) δ 9.59 (s, 1H), 9.01 (s, 1H), 8.70 (s, 1H), 7.85 (s, 1H), 7.51 (d, 1H), 7.44 (t, 1H), 7.36 (s, 2H), 7.28 (d, 1H), 6.49 (s, 1H), 4.31 (t, 2H), 4.00 (s, 3H), 3.85 (t, 2H), 2.37-2.25 (m, 2H), 1.29 (s, 9H); LC-MS (ESI) m/z 542 (M+H)$^+$.

Example 57B

The urea from the previous step (200 mg, 0.37 mmol) was treated with piperidine (109 μL, 1.11 mmol), tetrabutylammonium iodide (136 mg, 0.37 mmol) and N,N'-diisopropylethylamine (129 μL, 0.74 mmol) in N,N'-dimethylformamide (3 mL). The mixture was heated to 60° C. for 56h and cooled to room temperature. Water (10 mL) was added and the solid filtered off and dried. The crude solid was purified by preparative HPLC (phenylhexyl reverse phase column) and the obtained solid triturated with water (10 mL) and drops of methanol, then filtered off and dried under high vacuum to afford 1-(5-tert-butylisoxazol-3-yl)-3-(3-(7-methoxy-6-(3-(piperidin-1-yl)propoxy)quinazolin-4-ylthio)phenyl)urea (24.05 mg, 11%) as a solid. $^1$H NMR (300 MHz, DMSO-$d_6$) δ 9.59 (s, 1H), 9.01 (s, 1H), 8.69 (s, 1H), 7.85 (s, 1H), 7.52-7.41 (m, 2H), 7.35-7.26 (m, 3H), 6.49 (s, 1H), 4.22-4.18 (m, 2H), 3.99 (s, 3H), 2.51-2.36 (m, 6H), 1.99-1.95 (m, 2H), 1.51-1.49 (m, 4H), 1.39-1.38 (m, 2H), 1.27 (s, 9H); LC-MS (ESI) m/z 591 (M+H)$^+$.

Example 58

Preparation of 1-(5-tert-butylisoxazol-3-yl)-3-(3-(6-(3-(4-(hydroxymethyl)piperidin-1-yl)propoxy)-7-methoxyquinazolin-4-ylthio)phenyl)urea The title compound was prepared as described in Example 57B by using 1-(5-tert-butylisoxazol-3-yl)-3-(3-(6-(3-chloropropoxy)-7-methoxyquinazolin-4-ylthio)phenyl)urea from Example 57B (200 mg, 0.37 mmol) and 4-piperidinemethanol (127 mg, 1.11 mmol) to afford 1-(5-tert-butylisoxazol-3-yl)-3-(3-(6-(3-(4-(hydroxymethyl)piperidin-1-yl)propoxy)-7-methoxyquinazolin-4-ylthio)phenyl)urea (35.75 mg, 58%) as a solid. $^1$H NMR (300 MHz, DMSO-$d_6$) δ 9.60 (s, 1H), 9.02 (s, 1H), 8.69 (s, 1H), 7.85 (s, 1H), 7.53-7.43 (m, 2H), 7.34-7.26 (m, 3H), 6.49 (s, 1H), 4.42-4.40 (m, 1H), 4.22-4.18 (m, 2H), 4.18 (s, 3H), 3.25-3.21 (m, 2H), 2.91 (d, 2H), 2.50-2.47 (m, 2H), 2.00-1.88 (m, 4H), 1.64 (d, 2H), 1.27 (s, 9H), 1.16-1.12 (m, 2H); LC-MS (ESI) m/z 621 (M+H)$^+$.

Example 59

Preparation of 1-(5-tert-butylisoxazol-3-yl)-3-(3-(7-methoxy-6-(3-(4-methylpiperazin-1-yl)propoxy)quinazolin-4-ylthio)phenyl)urea The title compound was prepared as described in Example 57B by using 1-(5-tert-butylisoxazol-3-yl)-3-(3-(6-(3-chloropropoxy)-7-methoxyquinazolin-4-ylthio)phenyl)urea from Example 57B (200 mg, 0.37 mmol) and N-methyl piperazine (123 μL, 1.11 mmol) to afford 1-(5-tert-butylisoxazol-3-yl)-3-(3-(7-methoxy-6-(3-(4-methylpiperazin-1-yl)propoxy)quinazolin-4-ylthio)phenyl)urea (15.75 mg, 7%) as a solid. $^1$H NMR (300 MHz, DMSO-$d_6$) δ 9.59 (s, 1H), 9.01 (s, 1H), 8.69 (s, 1H), 7.85 (s, 1H), 7.52-7.43 (m, 2H), 7.34-7.26 (m, 3H), 6.49 (s, 1H), 4.20 (bs, 2H), 3.99 (s, 3H), 2.46-2.34 (m, 10H), 2.14 (s, 3H), 1.99-1.97 (m, 2H), 1.27 (s, 9H); LC-MS (ESI) m/z 606 (M+H)$^+$.

Example 60

Preparation of 1-(5-tert-butylisoxazol-3-yl)-3-(3-(7-methoxy-6-(3-(4-(methylsulfonyl)piperazin-1-yl)propoxy)quinazolin-4-ylthio)phenyl)urea The title compound was prepared as described in Example 57B by using 1-(5-tert-butylisoxazol-3-yl)-3-(3-(6-(3-chloropropoxy)-7-methoxyquinazolin-4-ylthio)phenyl)urea from Example 57B (200 mg, 0.37 mmol) and N-methylsulfonyl-piperazine (182 mg, 1.11 mmol) to afford 1-(5-tert-butylisoxazol-3-yl)-3-(3-(7-methoxy-6-(3-(4-(methylsulfonyl)piperazin-1-yl)propoxy)quinazolin-4-ylthio)phenyl)urea (54.17 mg, 22%) as a solid. $^1$H NMR (300 MHz, DMSO-$d_6$) δ 9.59 (s, 1H), 9.00 (s, 1H), 9.69 (s, 1H), 7.85 (s, 1H), 7.51-7.26 (m, 5H), 6.49 (s, 1H), 4.22 (bs, 2H), 3.99 (s, 3H), 3.14 (s, 4H), 2.86 (s, 3H), 2.20-1.90 (m, 2H), 1.28 (s, 9H); LC-MS (ESI) m/z 670 (M+H)$^+$.

Example 61

Preparation of 1-(5-tert-butylisoxazol-3-yl)-3-(3-(6-(3-(4-(2-hydroxyethyl)piperazin-1-yl)propoxy)-7-methoxyquinazolin-4-ylthio)phenyl)urea The title compound was prepared as described in Example 57B by using 1-(5-tert-butylisoxazol-3-yl)-3-(3-(6-(3-chloropropoxy)-7-methoxyquinazolin-4-ylthio)phenyl)urea from Example 57B (200 mg, 0.37 mmol) and 1-(2-hydroxyethyl)piperazine (136 μL, 1.11 mmol) to afford 1-(5-tert-butylisoxazol-3-yl)-3-(3-(6-(3-(4-(2-hydroxyethyl)piperazin-1-yl)propoxy)-7-methoxyquinazolin-4-ylthio)phenyl)urea (17.86 mg, 7%) as a solid. $^1$H NMR (300 MHz, DMSO-$d_6$) δ 9.62 (bs, 1H), 9.05 (bs, 1H), 8.69 (s, 1H), 7.85 (s, 1H), 7.65-7.36 (m, 5H), 6.49 (s, 1H), 4.21 (bs, 2H), 3.99 (s, 3H), 3.70-3.19 (m, 6H), 2.50-2.29 (m, 8H), 1.98 (bs, 2H), 1.27 (s, 9H); LC-MS (ESI) m/z 636 (M+H)$^+$.

Example 62

1-(5-tert-butyl-isoxazol-3-yl)-3-(3-{6-[3-(1,1-dioxo-thiomorpholin-4-yl)-propoxy]7-methoxy-quinazolin-4-ylsulfanyl}-phenyl)-urea The title compound was prepared as described in Example 57B by using 1-(5-tert-butylisoxazol-3-yl)-3-(3-(6-(3-chloropropoxy)-7-methoxyquinazolin-4-ylthio)phenyl)urea from Example 57B (200 mg, 0.37 mmol) and thiomorpholine 1,1-dioxide (150 mg, 1.11 mmol) to afford 1-(5-tert-butyl-isoxazol-3-yl)-3-(3-{6-[3-(1,1-dioxo-thiomorpholin-4-yl)-propoxy]-7-methoxy-quinazolin-4-ylsulfanyl}-phenyl)-urea (54.51 mg, 23%) as a solid. $^1$H NMR (300 MHz, DMSO-d$_6$) δ 9.59 (s, 1H), 9.01 (s, 1H), 8.69 (s, 1H), 7.85 (s, 1H), 7.52-7.27 (m, 5H), 6.49 (s, 1H), 4.25-4.21 (m, 2H), 3.99 (s, 3H), 3.11 (bs, 4H), 2.95 (bs, 4H), 2.70-2.65 (m, 2H), 2.01-1.97 (m, 2H), 1.27 (s, 9H); LC-MS (ESI) m/z 641 (M+H)$^+$.

Example 63

Preparation of 1-(5-tert-butylisoxazol-3-yl)-3-(3-(7-methoxy-6-(3-morpholinopropoxy)quinazolin-4-ylthio)phenyl)urea In the manner described in Example 21C 1-(5-tert-butyl-isoxazol-3-yl)-3-(3-(6-(3-chloropropoxy)-7-methoxyquinazolin-4-ylthio)phenyl)urea from Example 57B (200 mg, 0.37 mmol) was reacted with morpholine (96 μL, 1.11 mmol), diisopropylethyl amine (193 μL, 1.11 mmol), and tetrabutyl ammonium iodide (136 mg, 0.37 mmol). The purification and isolation steps afforded 1-(5-tert-butylisoxazol-3-yl)-3-(3-(7-methoxy-6-(3-morpholinopropoxy)quinazolin-4-ylthio)phenyl)urea (49 mg, 22% yield). $^1$H NMR (300 MHz, DMSO-d$_6$) δ 9.58 (s, 1H), 9.01 (s, 1H), 8.69 (s, 1H), 7.48 (s, 1H), 7.55-7.25 (m, 5H), 6.47 (s, 1H), 4.25 (m, 2H), 3.99 (s, 3H), 3.59 (m, 4H), 2.5-2.35 (m, 6H), 2.01 (m, 2H), 1.37 (s, 9H); LCMS (ESI) m/z 593 (M+H).

Example 64

Preparation of 1-(5-tert-butylisoxazol-3-yl)-3-(3-(7-methoxy-6-(3-(methylsulfonyl)propoxy)quinazolin-4-ylthio)phenyl)urea To a suspension of sodium hydride (11 mg, 0.44 mmol) in anhydrous tetrahydrofuran (2 mL) cooled to 0° C., was added compound 1-(5-tert-butylisoxazol-3-yl)-3-(3-mercaptophenyl)urea described in Example 44A (117 mg, 0.40 mmol) as a solution in tetrahydrofuran (1 mL) and the mixture stirred at 0° C. for 30 minutes. To this suspension 4-chloro-7-methoxy-6-(3-(methylsulfonyl)propoxy)quinazoline from Example 41B Step 1 (133 mg, 0.40 mmol) was added and the resulting mixture was stirred at 0° C. and slowly allowed to reach room temperature. After stirring for additional 1 h, the mixture was taken up in ethyl acetate/water and extracted. The combined organic layers were dried (MgSO$_4$) and concentrated under reduced pressure. The residue was purified by preparative HPLC (Phenomenex phenylhexyl reverse phase column) to afford 1-(5-tert-butylisoxazol-3-yl)-3-(3-(7-methoxy-6-(3-(methylsulfonyl)propoxy)quinazolin-4-ylthio)phenyl)urea (10.30 mg, 4%) as a solid. $^1$H NMR (300 MHz, DMSO-d$_6$) δ 9.73 (bs, 1H), 9.19 (bs, 1H), 8.70 (s, 1H), 7.85 (s, 1H), 7.53-7.27 (m, 5H), 6.49 (s, 1H), 4.32 (bs, 2H), 4.01 (s, 3H), 3.35 (2H), 3.07 (s, 3H), 2.28 (bs, 2H), 1.28 (s, 9H); LC-MS (ESI) m/z 586 (M+H)$^+$.

Example 65

Preparation of 1-(5-tert-butylisoxazol-3-yl)-3-(3-(7-methoxy-6-(2-(piperidin-1-yl)ethoxy)quinazolin-4-ylthio)phenyl)urea Example 65A To 1-(5-tert-butylisoxazol-3-yl)-3-(3-mercaptophenyl)urea described in Example 44A (1.07 g, 3.70 mmol) was added 4-chloro-6-(2-chloroethoxy)-7-methoxyquinazoline (1.0 g, 3.70 mmol) from Example 16B according to the procedure described in Example 46 to give 1-(5-tert-butylisoxazol-3-yl)-3-(3-(6-(2-chloroethoxy)-7-methoxyquinazolin-4-ylthio)phenyl)urea (1.54 g, 2.92 mmol, 79%). $^1$H NMR (300 MHz, DMSO-d$_6$) δ 9.59 (s, 1H), 9.02 (s, 1H), 8.71 (s, 1H), 7.85 (s, 1H), 7.51 (d, 1H), 7.44 (t, 1H), 7.38 (s, 2H), 7.28 (d, 1H), 6.49 (s, 1H), 4.50 (t, 2H), 4.07 (t, 2H), 4.01 (s, 3H), 1.29 (s, 9H); LC-MS (ESI) m/z 528 (M+H)$^+$.

Example 65B

The urea intermediate from the previous step (200 mg, 0.38 mmol) and piperidine (0.112 mL, 1.14 mmol) were reacted as described in Example 57B to afford 1-(5-tert-butylisoxazol-3-yl)-3-(3-(7-methoxy-6-(2-(piperidin-1-yl)ethoxy)quinazolin-4-ylthio)phenyl)urea as a colorless solid (28 mg, 13%). $^1$H NMR (300 MHz, DMSO-d$_6$) δ 9.59 (brs, 1H), 9.01 (brs, 1H), 8.69 (s, 1H), 7.86 (s, 1H), 7.25-7.53 (m, 5H), 6.49 (s, 1H), 4.25-4.29 (m, 2H), 3.99 (s, 3H), 2.73-2.77 (m, 2H), 1.50-1.54 (m, 8H), 1.38-1.40 (m, 2H), 1.27 (s, 9H); LC-MS (ESI) m/z 577 (M+H)$^+$.

Example 66

Preparation of 1-(5-tert-butylisoxazol-3-yl)-3-(3-(6-(2-(4-(hydroxymethyl)piperidin-1-yl)ethoxy)-7-methoxyquinazolin-4-ylthio)phenyl)urea The urea intermediate from Example 65A (200 mg, 0.38 mmol) and 4-piperidinemethanol (131 mg, 1.14 mmol) were reacted as described in Example 16D to afford 1-(5-tert-butylisoxazol-3-yl)-3-(3-(6-(2-(4-(hydroxymethyl)piperidin-1-yl)ethoxy)-7-methoxyquinazolin-4-ylthio)phenyl)urea as a colorless solid (28 mg, 12%). $^1$H NMR (300 MHz, DMSO-d$_6$) δ 9.60 (brs, 1H), 9.04 (brs, 1H), 8.69 (s, 1H), 7.85 (s, 1H), 7.26-7.52 (m, 5H), 6.49 (s, 1H), 4.41 (m, 1H), 4.27 (m, 2H), 3.99 (s, 3H), 3.24 (m, 2H), 2.96-3.00 (m, 2H), 2.74-2.78 (m, 2H), 1.99-2.06 (m, 2H), 1.61-1.65 (m, 2H), 1.27 (s, 9H), 1.00-1.15 (m, 2H); LC-MS (ESI) m/z 607 (M+H)$^+$.

Example 67

Preparation of 1-(5-tert-butylisoxazol-3-yl)-3-(3-(7-methoxy-6-(2-(4-methylpiperazin-1-yl)ethoxy)quinazolin-4-ylthio)phenyl)urea The urea intermediate from Example 65A (200 mg, 0.38 mmol) and N-methyl piperazine (0.126 mL, 1.14 mmol) were reacted as described in Example 57B to afford 1-(5-tert-butylisoxazol-3-yl)-3-(3-(7-methoxy-6-(2-(4-methylpiperazin-1-yl)ethoxy)quinazolin-4-ylthio)phenyl)urea as a colorless solid (49 mg, 22%). $^1$H NMR (300 MHz, DMSO-d$_6$) δ 9.58 (brs, 1H), 9.00 (brs, 1H), 8.69 (s, 1H), 7.85 (s, 1H), 7.26-7.49 (m, 5H), 6.49 (s, 1H), 4.25-4.29 (m, 2H), 3.98 (s, 3H), 2.75-2.79 (m, 2H), 2.20-2.60 (m, 8H), 2.15 (s, 3H), 1.27 (s, 9H); LC-MS (ESI) m/z 592 (M+H)$^+$.

Example 68

Preparation of 1-(5-tert-butylisoxazol-3-yl)-3-(3-(6-(2-(4-(2-hydroxyethyl)piperazin-1-yl)ethoxy)-7-methoxyquinazolin-4-ylthio)phenyl)urea The urea intermediate from Example 65A (200 mg, 0.38 mmol) and 1-(2-hydroxyethyl)piperazine (0.139 mL, 1.14 mmol) in the manner described in Example 57B to afford 1-(5-tert-butylisoxazol-3-yl)-3-(3-(6-(2-(4-(2-hydroxyethyl)piperazin-1-yl)ethoxy)-7-methoxyquinazolin-4-ylthio)phenyl)urea as a colorless solid (32 mg, 14%). $^1$H NMR (300 MHz, DMSO-d$_6$) δ 9.58 (brs, 1H), 9.00 (brs, 1H), 8.69 (s, 1H), 7.84 (s, 1H), 7.26-7.49 (m, 5H), 6.49 (s, 1H), 4.26-4.37 (m, 3H), 3.99 (s, 3H), 3.40-3.50 (m, 2H), 2.75-2.79 (m, 2H), 2.30-2.50 (m, 9H), 1.27 (s, 9H); LC-MS (ESI) m/z 622 (M+H)$^+$.

Example 69

Preparation of 1-(5-tert-butylisoxazol-3-yl)-3-(3-(7-methoxy-6-(2-(4-(methylsulfonyl)piperazin-1-yl)ethoxy)quinazolin-4-ylthio)phenyl)urea The urea intermediate from Example 65A (200 mg, 0.38 mmol) and 1-methylsulfonyl-piperazine (187 mg, 1.14 mmol) in the manner described in Example 57B to afford 1-(5-tert-butylisoxazol-3-yl)-3-(3-(7-methoxy-6-(2-(4-(methylsulfonyl)piperazin-1-yl)ethoxy)quinazolin-4-ylthio)phenyl)urea as a colorless solid (53 mg, 21%). $^1$H NMR (300 MHz, DMSO-d$_6$) δ 9.58 (brs, 1H), 8.99 (brs, 1H), 8.69 (s, 1H), 7.85 (s, 1H), 7.29-7.51 (m, 5H), 6.48 (s, 1H), 4.30-4.32 (m, 2H), 3.99 (s, 3H), 3.14-3.15 (m, 4H), 2.86-2.87 (m, 5H), 2.66-2.67 (m, 4H), 1.27 (s, 9H); LC-MS (ESI) m/z 656 (M+H)$^+$.

Example 70

Preparation of 1-(5-tert-butylisoxazol-3-yl)-3-(3-(7-methoxy-6-(2-morpholinoethoxy)quinazolin-4-ylthio)phenyl)urea The urea intermediate from Example 65A (200 mg, 0.38 mmol) and morpholine (0.099 mL, 1.14 mmol) in the manner described in Example 57B to afford 1-(5-tert-butylisoxazol-3-yl)-3-(3-(7-methoxy-6-(2-morpholinoethoxy)quinazolin-4-ylthio)phenyl)urea as a colorless solid (29 mg, 13%). $^1$H NMR (300 MHz, DMSO-d$_6$) δ 9.58 (brs, 1H), 9.02 (brs, 1H), 8.69 (s, 1H), 7.84 (s, 1H), 7.26-7.49 (m, 5H), 6.48 (s, 1H), 4.30-4.32 (m, 2H), 3.99 (s, 3H), 3.60-3.62 (m, 4H), 2.80 (m, 2H), 2.49-2.52 (m, 4H), 1.27 (s, 9H); LC-MS (ESI) m/z 579 (M+H)$^+$.

Example 71

Preparation of 1-(5-tert-butyl-isoxazol-3-yl)-3-(3-{6-[2-(1,1-dioxo-thiomorpholin-4-yl)-ethoxy]-7-methoxy-quinazolin-4-ylsulfany}-phenyl)-urea The title compound was prepared as described in Example 57B by using 1-(5-tert-butylisoxazol-3-yl)-3-(3-(6-(2-chloroethoxy)-7-methoxyquinazolin-4-ylthio)phenyl)urea from Example 65A (200 mg, 0.38 mmol), thiomorpholine 1,1-dioxide (154 mg, 1.14 mmol), tetrabutylammonium iodide (140 mg, 0.38 mmol) and N,N'-diisopropylethylamine (135 µL, 0.76 mmol) in N,N'-dimethylformamide (2 mL) to afford 1-(5-tert-butyl-isoxazol-3-yl)-3-(3-{6-[2-(1,1-dioxo-thiomorpholin-4-yl)-ethoxy]-7-methoxy-quinazolin-4-ylsulfanyl}-phenyl)-urea (56.27 mg, 24%) as a solid. $^1$H NMR (300 MHz, DMSO-d$_6$) δ 9.59 (s, 1H), 9.01 (s, 1H), 8.69 (s, 1H), 7.85 (s, 1H), 7.52-7.27 (m, 5H), 6.49 (s, 1H), 4.30 (bs, 2H), 3.99 (s, 3H), 3.12-3.04 (m, 10H), 1.27 (s, 9H); LC-MS (ESI) m/z 627 (M+H)$^+$.

Example 72

Preparation of (1-(5-tert-butylisoxazol-3-yl)-3-(3-(6-methoxy-7-(2-morpholinoethoxy) quinazolin-4-ylthio)phenyl)urea)

Example 72A

To a solution of (1-(5-tert-butyl-isoxazol-3-yl)-3-(3-mercapto-phenyl)-urea described in Example 44A (303.02 mg, 1.04 mmol) in THF: DMF (2:1, 6 mL) was added NaH (95%, 28.9 mg, 1.144 mmol), stirred for 5-10 min at ambient temperature. Then (4-chloro-7-(3-chloro-propoxy)-6-methoxyquinazoline, (300 mg, 1.04 mmol) described in Example 27A was added as solution in DMF:THF (2:1). The reaction mixture was then stirred overnight. Completion of the reaction was monitored by LCMS. The reaction mixture was diluted with ethyl acetate and washed the ethyl acetate layer with water and brine successively. The organic layer was dried (Na$_2$SO$_4$) concentrated to dryness to afford the pure 1-(5-tert-butyl-isoxazol-3-yl)-3-{3-[7-(3-chloro-propoxy)-6-methoxy-quinazolin-4-ylsulfanyl]-phenyl}-urea (480 mg, 85%) as a white solid. $^1$H NMR (300 MHz, DMSO-d$_6$) δ 9.60 (s, 1H), 9.05 (s, 1H), 8.68 (s, 1H), 7.85 (s, 1H), 7.60-7.28 (m, 5H), 6.50 (s, 1H), 4.35 (t, 2H), 4.05 (s, 3H), 3.82 (t, 2H), 1.30 (s, 9H); LC-MS (ESI) m/z 542 (M+H)$^+$.

Example 72B

To a solution of urea from the previous step (250 mg, 0.461 mmol) in DMF (3 mL) was added morpholine (120.5 mg, 1.383 mmol) followed by diisopropyl ethylamine (0.241 mL, 1.383 mmol) and tetrabutyl ammonium iodide (170.35 mg, 0.461 mmol). The reaction mixture was heated at 60° C. for 15 h. Formation of product was determined by LCMS. The crude reaction was diluted with ethyl acetate (50 mL), washed successively with water and brine, dried (MgSO$_4$) and concentrated in vacuo. The crude reaction mixture was purified by column chromatography (DCM/MeOH) to afford (1-(5-tert-butylisoxazol-3-yl)-3-(3-(6-methoxy-7-(2-morpholinoethoxy) quinazolin-4-ylthio)phenyl) urea) (40 mg, 15%) as a white solid. $^1$H NMR (300 MHz, DMSO-d$_6$) δ 9.65 (s, 1H), 9.12 (s, 1H), 8.72 (s, 1H), 7.85 (s, 1H), 7.61-7.21 (m, 5H), 6.45 (s, 1H), 3.95 (s, 3H), 3.62 (s, 3H), 2.75-2.25 (m, 6H), 2.01 (m, 2H), 1.25 (s, 9H); LC-MS (ESI) m/z 593 (M+H)$^+$.

Example 73

Preparation of 1-(5-tert-butylisoxazol-3-yl)-3-(3-(6-methoxy-7-(3-(4-methylpiperazin-1-yl)propoxy) quinazolin-4-ylthio)phenyl)urea To a solution of 1-(5-tert-butyl-isoxazol-3-yl)-3-{3-[7-(3-chloro-propoxy)-6-methoxy-quinazolin-4-ylsulfanyl]-phenyl}-urea from Example 72A (200 mg, 0.368 mmol) in DMF (3 mL) was added N-methyl piperazine (0.122 mL, 1.104 mmol) followed by diisopropyl ethylamine (0.192 mL, 1.104 mmol) and tetrabutyl ammonium iodide (136.2 mg, 0.368 mmol). The reaction mixture was heated at 60° C. for 24 h. Formation of the product was determined by LCMS. The crude reaction mixture was purified by preparative HPLC (phenomenex phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(3-(4-methylpiperazin-1-yl)propoxy)quinazolin-4-ylthio)phenyl)urea (72 mg, 32%) as a white solid. $^1$H NMR (300 MHz, DMSO-d$_6$) δ 9.60 (s, 1H), 9.00 (s, 1H), 8.68 (s, 1H), 7.85 (s, 1H), 7.60-7.20 (m, 5H), 6.45 (s, 1H), 4.25 (m, 2H), 3.88 (s, 3H), 2.50-2.25 (m, 10H), 2.15 (s, 3H), 1.95 (m, 2H), 1.23 (s, 9H); LC-MS (ESI) m/z 606 (M+H)$^+$.

Example 74

Preparation of 1-(5-tert-butylisoxazol-3-yl)-3-(3-(7-(3-(4-(hydroxymethyl)piperidin-1-yl)propoxy)-6-methoxyquinazolin-4-ylthio)phenyl)urea 1-(5-tert-butyl-isoxazol-3-yl)-3-{3-[7-(3-chloro-propoxy)-6-methoxy-quinazolin-4-ylsulfanyl]-phenyl}-urea from Example 72A (200 mg, 0.368 mmol) and piperidin-4-yl-methanol (127 mg, 1.104 mmol) were reacted as described in Example 73. Isolated yield of 1-(5-tert-butylisoxazol-3-yl)-3-(3-(7-(3-(4-(hydroxymethyl)piperidin-1-yl)propoxy)-6-methoxyquinazolin-4-ylthio)phenyl)urea (47 mg, 21%) as a white solid. $^1$H NMR (300 MHz, DMSO-d$_6$) δ 9.60 (s, 1H), 9.05 (s, 1H), 8.70 (s, 1H), 7.60-7.20 (m, 5H), 6.45 (s, 1H), 4.40 (m, 1H), 4.20 (m, 2H), 3.98 (s, 3H), 3.25 (m, 2H), 2.87 (d, 2H), 2.45 (m, 2H), 2.10-1.80 (m, 4H), 1.65 (d, 2H), 1.30 (s, 10H), 1.15 (m, 2H); LC-MS (ESI) m/z 621 (M+H)$^+$.

Example 75

Preparation of 1-(5-tert-butylisoxazol-3-yl)-3-(3-(7-(3-(4-(2-hydroxyethyl)piperazin-1-yl)propoxy)-6-methoxyquinazolin-4-ylthio)phenyl)urea 1-(5-tert-butyl-isoxazol-3-yl)-3-{3-[7-(3-chloro-propoxy)-6-methoxy-quinazolin-4-ylsulfanyl]-phenyl}-urea from Example 72A (200 mg, 0.368 mmol) and 2-piperazin-1-yl-ethanol (135 mL, 1.104 mmol) were reacted as described in Example 73. Isolated yield of 1-(5-tert-butylisoxazol-3-yl)-3-(3-(7-(3-(4-(2-hydroxyethyl)piperazin-1-yl)propoxy)-6-methoxyquinazolin-4-ylthio)phenyl)urea (75 mg, 32%) as a white solid. $^1$H NMR (300 MHz, DMSO-d$_6$) δ 9.80 (s, 1H), 9.55 (s, 1H), 8.65 (s, 1H), 7.85 (s, 1H), 7.60-7.25 (m, 5H), 6.50 (s, 1H), 4.40 (s, 1H), 4.25 (m, 2H), 4.00 (s, 3H), 3.45 (m, 2H), 2.50-2.25 (m, 12H), 1.95 (m, 2H), 1.25 (s, 9H); LC-MS (ESI) m/z 636 (M+H)$^+$.

Example 76

Preparation of 1-(5-tert-butylisoxazol-3-yl)-3-(3-(6-methoxy-7-(3-(piperidin-1-yl)propoxy)quinazolin-4-ylthio)phenyl)urea 1-(5-tert-butyl-isoxazol-3-yl)-3-{3-[7-(3-chloro-propoxy)-6-methoxy-quinazolin-4-ylsulfanyl]-phenyl}-urea from Example 72A (200 mg, 0.368 mmol) and piperidine (0.109 mL, 1.104 mmol) were reacted as described in Example 73. Isolated yield of 1-(5-tert-butylisoxazol-3-yl)-3-(3-(6-methoxy-7-(3-(piperidin-1-yl)propoxy)quinazolin-4-ylthio)phenyl)urea (57 mg, 26%) as a white solid. $^1$H NMR (300 MHz, DMSO-d$_6$) δ 9.60 (s, 1H), 9.05 (s, 1H), 8.65 (s, 1H), 7.85 (s, 1H), 7.60-7.20 (m, 5H), 6.45 (s, 1H), 4.20 (m, 2H), 4.00 (s, 3H), 2.50-2.25 (m, 6H), 1.95 (m, 2H), 1.60-1.30 (m, 6H), 1.25 (s, 9H); LC-MS (ESI) m/z 591 (M+H)$^+$.

Example 77

Preparation of 1-(5-tert-butylisoxazol-3-yl)-3-(3-(6-methoxy-7-(3-(4-(methylsulfonyl)piperazin-1-yl)propoxy)quinazolin-4-ylthio)phenyl)urea To a solution of 1-(5-tert-butyl-isoxazol-3-yl)-3-{3-[7-(3-chloro-propoxy)-6-methoxy-quinazolin-4-ylsulfanyl]-phenyl}-urea from Example 72A (200 mg, 0.368 mmol) in DMF (3 mL) was added 1-methane sulfonyl piperazine (181 mg, 1.104 mmol) followed by diisopropyl ethylamine (0.192 mL, 1.104 mmol) and tetrabutyl ammonium iodide (136.2 mg, 0.368 mmol). The reaction mixture was heated at 60° C. for 2 days. Formation of the product was determined by LCMS. The crude reaction mixture was purified by preparative HPLC (phenomenex phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(3-(4-(methylsulfonyl)piperazin-1-yl)propoxy)quinazolin-4-ylthio)phenyl)urea (85 mg, 35%) as a white solid. $^1$H NMR (300 MHz, DMSO-d$_6$) δ 9.60 (s, 1H), 9.05 (s, 1H), 8.70 (s, 1H), 7.85 (s, 1H), 7.55-7.20 (m, 5H), 6.50 (s, 1H), 4.25 (m, 1H), 3.95 (s, 3H), 3.15 (m, 4H), 2.55 (m, 6H), 2.00 (m, 2H), 1.30 (s, 9H); LC-MS (ESI) m/z 670 (M+H)$^+$.

Example 78

Preparation of 1-(5-tert-butylisoxazol-3-yl)-3-(3-(6-methoxy-7-(3-(pyrrolidin-1-yl)propoxy)quinazolin-4-ylthio)phenyl)urea 1-(5-tert-butyl-isoxazol-3-yl)-3-{3-[7-(3-chloro-propoxy)-6-methoxy-quinazolin-4-ylsulfanyl]-phenyl}-urea from Example 72A (200 mg, 0.368 mmol) and pyrrolidine (91 µL 1.104 mmol) were reacted in the manner described in Example 73 to yield 1-(5-tert-butylisoxazol-3-yl)-3-(3-(6-methoxy-7-(3-(pyrrolidin-1-yl)propoxy)quinazolin-4-ylthio)phenyl)urea (12 mg, 6%) as a white solid. $^1$H NMR (300 MHz, DMSO-d$_6$) δ 9.50 (s, 1H), 8.85 (s, 1H), 8.30 (s, 1H), 7.25 (m, 2H), 7.35-7.00 (m, 4H), 6.45 (s, 1H), 4.20 (m, 2H), 3.85 (m, 7H), 3.15 (m, 2H), 2.20-1.85 (m, 6H), 1.30 (s, 9H); LC-MS (ESI) m/z 577 (M+H)$^+$.

Example 79

Preparation of (1-(5-tert-butylisoxazol-3-yl)-3-(3-(6-methoxy-7-(2-morpholinoethoxy)quinazolin-4-ylthio)phenyl)urea)

Example 79A

To a solution of 1-(5-tert-butyl-isoxazol-3-yl)-3-(3-mercapto-phenyl)-urea (319 mg, 1.098 mmol) described in Example 44A in THF: DMF (2:1, 6 mL) was added NaH (95%, 30.5 mg, 1.207 mmol), stirred for 5-10 min at ambient temperature. Then 4-chloro-7-(2-chloro-ethoxy)-6-methoxy-quinazoline from Example 35A (300 mg, 1.098 mmol) was added as a solution in DMF:THF (2:1). The reaction mixture was then stirred overnight. Completion of the reaction was monitored by LCMS. The reaction mixture was diluted with ethyl acetate and washed the ethyl acetate layer with water and brine successively. The organic layer was dried (Na$_2$SO$_4$) concentrated to dryness to get the pure compound 1-(5-tert-Butyl-isoxazol-3-yl)-3-{3-[7-(2-chloro-ethoxy)-6-methoxy-quinazolin-4-ylsulfanyl]-phenyl}-urea (550 mg, 95%) as a white solid. $^1$H NMR (300 MHz, DMSO-d$_6$) δ 9.60 (s, 1H), 9.05 (s, 1H), 8.68 (s, 1H), 7.85 (s, 1H), 7.55-7.25 (m, 5H), 6.45 (s, 1H), 4.50 (m, 2H), 4.05 (m, 5H), 1.25 (s, 9H); LC-MS (ESI) m/z 528 (M+H)$^+$.

Example 79B

To a solution of the urea from the previous step (100 mg, 0.189 mmol) in DMF (2 mL) was added morpholine (49.3 mg, 0.567 mmol) followed by diisopropyl ethylamine (98.7 µL, 0.567 mmol) and tetrabutyl ammonium iodide (69.8 mg, 0.189 mmol). The reaction mixture was heated at 60° C. for 3 days. Formation of product was determined by LCMS. The crude reaction mixture was purified by preparative HPLC (using phenylhexyl reverse phase column eluted with gradient of solvent A=0.05% HOAc/H$_2$O and solvent B=0.05% HOAc/CH$_3$CN) to afford (1-(5-tert-butylisoxazol-3-yl)-3-(3-(6-methoxy-7-(2-morpholino ethoxy) quinazolin-4-ylthio)phenyl)urea) (23 mg, 23%) as a white solid. $^1$H NMR (300 MHz, DMSO-d$_6$) δ 9.85 (s, 1H), 9.70 (s, 1H), 8.70 (s, 1H), 7.85 (s, 1H), 7.70-7.25 (m, 5H), 6.50 (s, 1H), 4.40 (s, 2H), 4.05 (s, 3H), 3.85 (m, 4H), 2.75-2.35 (m, 6H), 1.35 (s, 9H); LC-MS (ESI) m/z 579 (M+H)$^+$.

Example 80

Preparation of 1-(5-tert-butylisoxazol-3-yl)-3-(3-(6-methoxy-7-(2-(piperidin-1-yl)ethoxy)quinazolin-4-ylthio)phenyl)urea To a solution of 1-(5-tert-butyl-isoxazol-3-yl)-3-{3-[7-(2-chloro-ethoxy)-6-methoxy-quinazolin-4-ylsulfanyl]-phenyl}-urea from Example 79A (225 mg, 0.426 mmol) in DMF (3 mL) was added piperidine (0.126 mL, 1.278 mmol) followed by diisopropyl ethylamine (0.222 mL, 1.278 mmol) and tetrabutyl ammonium iodide (157.35 mg, 0.426 mmol). The reaction mixture was heated at 60° C. for 2 days. Formation of product was determined by LCMS. The crude reaction mixture was purified by preparative HPLC (using phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(2-(piperidin-1-yl)ethoxy)quinazolin-4-ylthio)phenyl)urea (42 mg, 17%) as a white solid. $^1$H NMR (300 MHz, DMSO-d$_6$) δ 9.60 (s, 1H), 9.20 (s, 1H), 8.65 (s, 1H), 7.85 (s, 1H), 7.60-7.22 (m, 5H), 6.45 (s, 1H), 4.30 (m, 2H), 3.95 (s, 3H), 2.85-2.30 (m, 6H), 1.70-1.30 (m, 6H), 1.25 (s, 9H); LC-MS (ESI) m/z 577 (M+H)$^+$.

Example 81

Preparation of 1-(5-tert-butylisoxazol-3-yl)-3-(3-(6-methoxy-7-(2-(4-(methylsulfonyl)piperazin-1-yl)ethoxy)quinazolin-4-ylthio)phenyl)urea To a solution of 1-(5-tert-butyl-isoxazol-3-yl)-3-{3-[7-(2-chloro-ethoxy)-6-methoxy-quinazolin-4-ylsulfanyl]-phenyl}-urea from Example 79A (225 mg, 0.426 mmol) in DMF (3 mL) was added 1-methane sulfonyl pyperazine (139.9 mg, 0.852 mmol) followed by diisopropyl ethylamine (0.222 mL, 1.278 mmol) and tetrabutyl ammonium iodide (157.35 mg, 0.426 mmol). The reaction mixture was heated at 60° C. for 3 days. Formation of the product was determined by LCMS. The crude reaction mixture was purified by preparative HPLC (phenomenex phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(2-(4-(methylsulfonyl)piperazin-1-yl)ethoxy)quinazolin-4-ylthio)phenyl)urea (47 mg, 17%) as a white solid. $^1$H NMR (300 MHz, DMSO-d$_6$) δ 9.60 (s, 1H), 9.05 (s, 1H), 8.65 (s, 1H), 7.85 (s, 1H), 7.62-7.25 (m, 5H), 6.45 (s, 1H), 4.30 (m, 2H), 3.15 (m, 4H), 2.85 (m, 5H), 2.60 (m, 4H), 1.25 (s, 9H); LC-MS (ESI) m/z 656 (M+H)$^+$.

Example 82

Preparation of 1-(5-tert-butylisoxazol-3-yl)-3-(3-(7-(2-(3-hydroxypyrrolidin-1-yl)ethoxy)-6-methoxyquinazolin-4-ylthio)phenyl)urea The intermediate 1-(5-tert-butyl-isoxazol-3-yl)-3-{3-[7-(2-chloro-ethoxy)-6-methoxy-quinazolin-4-ylsulfanyl]-phenyl}-urea from Example 79A and pyrrolidin-3-ol were reacted as described in Example 80 to yield 1-(5-tert-butyl-isoxazol-3-yl)-3-(3-(7-(2-(3-hydroxypyrrolidin-1-yl)ethoxy)-6-methoxyquinazolin-4-ylthio)phenyl)urea (59 mg, 24%) as a white solid. $^1$H NMR (300 MHz, DMSO-d$_6$) δ 9.55 (s, 1H), 8.85 (s, 1H), 8.30 (s, 1H), 7.65-7.50 (m, 2H), 7.35-7.05 (m, 4H), 6.50 (s, 1H), 5.05 (s, 1H), 4.45-4.25 (m, 3H), 4.15-3.85 (m, 6H), 3.75-3.65 (d, 1H), 3.45 (m, 2H), 2.00 (m, 2H), 1.25 (s, 9H); LC-MS (ESI) m/z 579 (M+H)$^+$.

Example 83

Preparation of 1-(5-tert-butylisoxazol-3-yl)-3-(3-(6-methoxy-7-(2-(4-methylpiperazin-1-yl)ethoxy)quinazolin-4-ylthio)phenyl)urea To a solution of 1-(5-tert-butyl-isoxazol-3-yl)-3-{3-[7-(2-chloro-ethoxy)-6-methoxy-quinazolin-4-ylsulfanyl]-phenyl}-urea from Example 79A (225 mg, 0.426 mmol) in DMF (3 mL) was added N-methyl piperazine (0.141 mL, 1.278 mmol) followed by diisopropyl ethylamine (0.222 mL, 1.278 mmol) and tetrabutyl ammonium iodide (157.35 mg, 0.426 mmol). The reaction mixture was heated at 60° C. for 24 h. Formation of the product was determined by LCMS. The crude reaction mixture was purified by preparative HPLC (using phenylhexyl reverse phase column eluted with gradient of solvent A=0.05% HOAc/H$_2$O and solvent B=0.05% HOAc/CH$_3$CN) to afford 1-(5-tert-butylisoxazol-3-yl)-3-(3-(6-methoxy-7-(2-(4-methylpiperazin-1-yl)ethoxy)quinazolin-4-ylthio)phenyl)urea (21 mg, 8.3%) as a white solid. $^1$H NMR (300 MHz, DMSO-d$_6$) δ 9.60 (s, 1H), 9.05 (s, 1H), 8.65 (s, 1H), 7.85 (s, 1H), 7.60-7.25 (m, 5H), 6.45 (s, 1H), 4.35 (m, 2H), 4.00 (m, 3H), 2.80-2.25 (m, 10H), 2.15 (s, 3H), 1.25 (s, 9H); LC-MS (ESI) m/z 592 (M+H)$^+$.

Example 84

Preparation of 1-(5-tert-butylisoxazol-3-yl)-3-(3-(7-(2-(4-(2-hydroxyethyl)piperazin-1-yl)ethoxy)-6-methoxyquinazolin-4-ylthio)phenyl)urea To the intermediate 1-(5-tert-butyl-isoxazol-3-yl)-3-{3-[7-(2-chloro-ethoxy)-6-methoxy-quinazolin-4-ylsulfanyl]-phenyl}-urea (225 mg, 0.426 mmol) from Example 79A was added 2-piperazin-1-yl-ethanol (0.157 mL, 1.278 mmol) followed by diisopropyl ethylamine (1.3 mmol) and tetrabutyl ammonium iodide (0.43 mmol). The reaction mixture was heated at 60° C. for 3 days. Formation of product was determined by LCMS. The crude reaction mixture was purified by preparative HPLC (using phenylhexyl reverse phase column eluted with gradient of solvent A=0.05% HOAc/H$_2$O and solvent B=0.05% HOAc/CH$_3$CN) to afford 1-(5-tert-butyl-isoxazol-3-yl)-3-(3-(7-(2-(4-(2-hydroxyethyl)piperazin-1-yl)ethoxy)-6-methoxyquinazolin-4-ylthio)phenyl)urea (34 mg, 13%) as a white solid. $^1$H NMR (300 MHz, DMSO-d$_6$) δ 9.60 (s, 1H), 9.05 (s, 1H), 8.65 (s, 1H), 7.85 (s, 1H), 7.60-7.20

(m, 5H), 6.45 (s, 1H), 4.45-4.25 (m, 3H), 4.00 (s, 3H), 3.45 (m, 2H), 2.80-2.30 (m, 12H), 1.25 (s, 9H); LC-MS (ESI)m/z 622 (M+H)+.

Example 85

Preparation of 1-(5-tert-butylisoxazol-3-yl)-3-(3-(6-methoxy-7-(2-(pyrrolidin-1-yl)ethoxy)quinazolin-4-ylthio)phenyl)urea To the intermediate 1-(5-tert-butyl-isoxazol-3-yl)-3-{3-[7-(2-chloro-ethoxy)-6-methoxy-quinazolin-4-ylsulfanyl]-phenyl}-urea (225 mg, 0.426 mmol) from Example 79A was added pyrrolidine (0.105 mL, 1.278 mmol) in the manner described in Example 80 to yield 1-(5-tert-butylisoxazol-3-yl)-3-(3-(6-methoxy-7-(2-(pyrrolidin-1-yl)ethoxy)quinazolin-4-ylthio)phenyl)urea (41 mg, 18%) as a white solid. $^1$H NMR (300 MHz, DMSO-$d_6$) δ 9.55 (s, 1H), 8.85 (s, 1H), 8.30 (s, 1H), 7.65-7.50 (m, 2H), 7.35-7.05 (m, 4H), 6.50 (s, 1H), 4.30 (m, 2H), 4.00-3.75 (m, 7H), 2.55 (m, 2H), 1.98 (m, 4H), 1.30 (s, 9H); LC-MS (ESI)m/z 563 (M+H)+.

Example 86

Preparation of 1-(5-tert-butylisoxazol-3-yl)-3-(3-(7-(2-(4-(hydroxymethyl)piperidin-1-yl)ethoxy)-6-methoxyquinazolin-4-ylthio)phenyl)urea The intermediate 1-(5-tert-butyl-isoxazol-3-yl)-3-{3-[7-(2-chloro-ethoxy)-6-methoxy-quinazolin-4-ylsulfanyl]-phenyl}-urea (225 mg, 0.426 mmol) from Example 79A and piperidin-4-yl-methanol (147 mg, 1.278 mmol) were reacted using the procedure described in Example 80 to yield of 1-(5-tert-butylisoxazol-3-yl)-3-(3-(7-(2-(4-(hydroxymethyl)piperidin-1-yl)ethoxy)-6-methoxyquinazolin-4-ylthio)phenyl)urea (61 mg, 24%) as a white solid. $^1$H NMR (300 MHz, DMSO-$d_6$) δ 10.55-10.05 (m, 2H), 8.68 (s, 1H), 7.85 (s, 1H), 7.65-7.20 (m, 5H), 6.50 (s, 1H), 4.50 (s, 1H), 4.30 (s, 2H), 4.02 (s, 3H), 3.25 (m, 2H), 3.00 (m, 2H), 2.80-2.65 (m, 4H), 2.05 (m, 2H), 1.70-1.50 (m, 2H), 1.30 (s, 10H); LC-MS (ESI)m/z 607 (M+H)+.

Example 87

Preparation of 1-(5-tert-butylisoxazol-3-yl)-3-(3-(6-(2-methoxyethoxy)quinazolin-4-ylthio)phenyl)urea The title compound was prepared from 1-(5-tert-butylisoxazol-3-yl)-3-(3-mercaptophenyl)urea described in Example 44A (146 mg, 0.5 mmol) and 4-chloro-6-(2-methoxyethoxy)quinazoline from Example 40A (119 mg, 0.5 mmol) using the procedure described in Example 46 to give 1-(5-tert-butylisoxazol-3-yl)-3-(3-(6-(2-methoxyethoxy)quinazolin-4-ylthio)phenyl)urea (160 mg, 0.32 mmol, 64%). $^1$H NMR (300 MHz, DMSO-$d_6$) δ 9.61 (s, 1H), 9.03 (s, 1H), 8.76 (s, 1H), 7.96-7.85 (m, 2H), 7.70 (dd, 1H), 7.58-7.42 (m, 3H), 7.30 (d, 1H), 6.50 (s, 1H), 4.37-4.30 (m, 2H), 3.79-3.74 (m, 2H), 3.38 (s, 3H), 1.28 (s, 9H); LC-MS (ESI) m/z 494 (M+H)+.

Example 88

Preparation of 1-(5-tert-butylisoxazol-3-yl)-3-(3-(7-methoxy-6-(2-(methylsulfonyl)ethoxy)quinazolin-4-ylthio)phenyl)urea Example 88A Step 1: 6-(2-Chloroethoxy)-4-hydroxy-7-methoxyquinazoline (1.12 g, 4.4 mmol) from Example 16A was reacted using the procedure described in Example 41B Step 1 to give 4-hydroxy-7-methoxy-6-(2-(methylthio)ethoxy)quinazoline (1.02 g, 3.83 mmol, 87%). $^1$H NMR (300 MHz, DMSO-$d_6$) δ 12.09 (br s, 1H), 7.99 (s, 1H), 7.46 (s, 1H), 7.14 (s, 1H), 4.24 (t, 2H), 3.91 (s, 3H), 3.89 (t, 2H), 2.20 (s, 3H); LC-MS (ESI) m/z 267 (M+H)+.

Example 88A

Step 2: 4-Hydroxy-7-methoxy-6-(2-(methylthio)ethoxy) quinazoline (800 mg, 3.0 mmol) was reacted using the procedure described in Example 41B Step 2 to give 4-hydroxy-7-methoxy-6-(2-(methylsulfonyl)ethoxy)quinazoline (880 mg, 2.95 mmol, 98%). $^1$H NMR (300 MHz, DMSO-$d_6$) δ 12.13 (br s, 1H), 8.02 (s, 1H), 7.51 (s, 1H), 7.18 (s, 1H), 4.43 (t, 2H), 3.92 (s, 3H), 3.68 (t, 2H), 3.17 (s, 3H); LC-MS (ESI) m/z 299 (M+H)+.

Example 88A

Step 3: 4-Hydroxy-7-methoxy-6-(2-(methylsulfonyl) ethoxy)quinazoline (880 mg, 2.95 mmol) was reacted using the procedure described in Example 41B Step 3, to give 4-chloro-7-methoxy-6-(2-(methylsulfonyl)ethoxy)quinazoline (405 mg, 1.28 mmol, 43%). LC-MS (ESI) m/z 317 (M+H)+.

Example 88B 1-(5-tert-butylisoxazol-3-yl)-3-(3-mercaptophenyl)urea described in Example 44A (92 mg, 0.32 mmol) was treated with cesium carbonate (113 mg, 0.35 mmol) in anhydrous tetrahydrofuran (2 mL) and the suspension stirred at 40° C. for 20 minutes. 4-Chloro-7-methoxy-6-(2-(methylsulfonyl) ethoxy) quinazoline from the previous step (100 mg, 0.32 mmol) was carefully added in portions and the resulting mixture heated at 40° C. for 2h. Cesium carbonate was filtered off, the filtrate concentrated under reduced pressure and the residue purified by preparative HPLC (Phenomenex phenylhexyl reverse phase column) to afford 1-(5-tert-butylisoxazol-3-yl)-3-(3-(7-methoxy-6-(2-(methylsulfonyl)ethoxy)quinazolin-4-ylthio)phenyl)urea (36.88 mg, 20%) as a solid. $^1$H NMR (300 MHz, DMSO-$d_6$) δ 9.59 (s, 1H), 9.01 (s, 1H), 8.72 (s, 1H), 7.85 (s, 1H), 7.53-7.40 (m, 4H), 7.30-7.28 (d, 1H), 6.49 (s, 1H), 4.59-4.56 (m, 2H), 4.00 (s, 3H), 3.78-3.74 (m, 2H), 3.20 (s, 3H), 1.27 (s, 9H); LC-MS (ESI) m/z 572 (M+H)+.

Example 89

Preparation of 1-(5-tert-butylisoxazol-3-yl)-3-(3-(2-chloro-6,7-dimethoxyquinazolin-4-ylthio)phenyl) urea To a slurry of sodium hydride (7.5 mg, 0.3 mmol) in DMF (3 mL) was added 1-(5-tert-butylisoxazol-3-yl)-3-(3-mercaptophenyl)urea described in Example 44A (90 mg, 0.3 mmol), and the solution stirred at room temperature When gas evolution ceased, 2,4-dichloro-6,7-dimethoxyquinazoline (78 mg, 0.3 mmol) was added and the solution heated at 50° C. overnight, cooled to room temperature, and diluted with H$_2$O. The mixture was extracted with EtOAc, the organic layer washed with aqueous sat. NaHCO$_3$ and brine, dried over MgSO$_4$, filtered and concentrated in vacuo. The crude solid was purified by HPLC to give 1-(5-tert-butylisoxazol-3-yl)-3-(3-(2-chloro-6,7-dimethoxyquinazolin-4-ylthio)phenyl) urea (20 mg, 0.04 mmol, 13%). $^1$H NMR (300 MHz, DMSO-$d_6$) δ 9.79 (s, 1H), 9.53 (s, 1H), 7.90 (s, 1H), 7.62 (d, 1H), 7.44

(t, 1H), 7.36 (s, 2H), 7.27 (d, 1H), 6.49 (s, 1H), 4.00 (s, 6H), 1.28 (s, 9H); LC-MS (ESI) m/z 514 (M+H)+.

Example 90

Preparation of 1-(5-tert-butyl-isoxazol-3-yl)-3-(3-{6-[3-(1,1-dioxo-thiomorpholin-4-yl)-propoxy]-quinazolin-4-ylsulfanyl}-phenyl)-urea Example 90A Step 1: Methyl 5-hydroxy-2-nitrobenzoate (4.37 g, 22.17 mmol, prepared as previously described), and 1-bromo-3-chloropropane (6.58 mL, 66.5 mmol) were reacted using the procedure described in Example 40A Step 3 to give methyl 5-(3-chloropropoxy)-2-nitrobenzoate (5.70 g, 20.8 mmol, 94%). $^1$H NMR (300 MHz, DMSO-$d_6$) δ 8.14 (d, 1H), 7.33 (d, 1H), 7.30 (dd, 1H), 4.27 (dt, 2H), 3.86 (s, 3H), 3.68 (t, 2H), 2.21 (t, 2H); LC-MS (ESI) m/z 274 (M+H)+.

Example 90A

Step 2: Methyl 5-(3-chloropropoxy)-2-nitrobenzoate (5.7 g, 20.8 mmol) was reacted using the procedure described in Example 40A Step 4 to give methyl 2-amino-5-(3-chloropropoxyl)benzoate (4.83 mg, 19.8 mmol, 95%). LC-MS (ESI) m/z 244 (M+H)+.

Example 90A

Step 3: Methyl 2-amino-5-(3-chloropropoxyl)benzoate (4.83 g, 19.8 mmol) was reacted using the procedure described in Example 40A Step 5. The product was purified by column chromatography (25-100% EtOAc/hexanes) to give 6-(3-chloropropoxy)-4-hydroxyquinazoline (1.04 g, 4.3 mmol, 22%). $^1$H NMR (300 MHz, DMSO-$d_6$) δ 12.20 (br s, 1H), 7.99 (s, 1H), 7.62 (d, 1H), 7.52 (d, 1H), 7.44 (dd, 1H), 4.17 (dt, 2H), 3.82 (t, 2H), 2.22 (t, 2H); LC-MS (ESI) m/z 239 (M+H)+.

Example 90A

Step 4: 6-(3-chloropropoxy)-4-hydroxyquinazoline (540 mg, 2.26 mmol) was reacted using the procedure described in Example 40A Step 6 to give 4-chloro-6-(3-chloropropoxy) quinazoline (485 mg, 1.9 mmol, 83%). LC-MS (ESI) m/z 258 (M+H)+.

Example 90B

Using the procedure described in Example 46, 1-(5-tert-butylisoxazol-3-yl)-3-(3-mercaptophenyl)urea described in Example 44A (181 mg, 0.62 mmol) was reacted with 4-chloro-6-(3-chloropropoxy)-quinazoline from the previous step (160 mg, 0.62 mmol) to give 1-(5-tert-butylisoxazol-3-yl)-3-(3-(6-(3-chloropropoxy)-7-methoxyquinazolin-4-ylthio)phenyl)urea (230 mg, 0.45 mmol, 72%). $^1$H NMR (300 MHz, DMSO-$d_6$) δ 9.60 (s, 1H), 9.02 (s, 1H), 8.76 (s, 1H), 7.94 (d, 1H), 7.86 (s, 1H), 7.72 (d, 1H), 7.58-7.42 (m, 3H), 7.30 (d, 1H), 6.49 (s, 1H), 4.33 (t, 2H), 3.87 (t, 2H), 2.32-2.25 (m, 2H), 1.28 (s, 9H); LC-MS (ESI) m/z 512 (M+H)+.

Example 90C

The title compound was prepared as described in Example 57B by using 1-(5-tert-butylisoxazol-3-yl)-3-(3-(6-(3-chloropropoxy)-7-methoxyquinazolin-4-ylthio)phenyl)urea from the previous step (230 mg, 0.45 mmol), thiomorpholine 1,1-dioxide (182 mg, 1.35 mmol), tetrabutylammonium iodide (166 mg, 0.45 mmol) and N,N'-diisopropylethylamine (160 µL, 0.89 mmol) in N,N'-dimethylformamide (3 mL) to afford 1-(5-tert-Butyl-isoxazol-3-yl)-3-(3-{6-[3-(1,1-dioxo-thiomorpholin-4-yl)-propoxy]-quinazolin-4-ylsulfanyl}-phenyl)-urea (117 mg, 43%) as solid. $^1$H NMR (300 MHz, DMSO-$d_6$) δ 9.61 (s, 1H), 9.03 (s, 1H), 8.75 (s, 1H), 7.94-7.86 (m, 2H), 7.68 (d, 1H), 7.51-7.41 (m, 3H), 7.30 (d, 1H), 6.49 (s, 1H), 4.26-4.23 (m, 2H), 3.11 (bs, 4H), 2.95 (bs, 4H), 2.71-2.67 (m, 2H), 2.00-1.96 (m, 2H), 1.27 (s,m 9H); LC-MS (ESI) m/z 611 (M+H)+.

Example 91

Preparation of 1-(5-tert-butyl-isoxazol-3-yl)-3-(3-{6-[2-(1,1-dioxo-thiomorpholin-4-yl)-ethoxy]-7-methoxy-quinazolin-4-yloxy}-phenyl)-urea The title compound was prepared as described in Example 57B by using compound 1-(5-tert-butylisoxazol-3-yl)-3-(3-(6-(2-chloroethoxy)-7-methoxyquinazolin-4-yloxy)phenyl) urea from Example 16C (200 mg, 0.39 mmol), thiomorpholine 1,1-dioxide (158 mg, 1.17 mmol), tetrabutylammonium iodide (144 mg, 0.39 mmol) and N,N'-diisopropylethylamine (139 µL, 0.78 mmol) in N,N'-dimethylformamide (2 mL) to afford 1-(5-tert-butyl-isoxazol-3-yl)-3-(3-{6-[2-(1,1-dioxothiomorpholin-4-yl)-ethoxy]-7-methoxy-quinazolin-4-yloxy}-phenyl)-urea (52.75 mg, 23%) as a solid. $^1$H NMR (300 MHz, DMSO-$d_6$) δ 9.58 (s, 1H), 9.00 (s, 1H), 8.56 (s, 1H), 7.61 (d, 2H), 7.40-7.37 (m, 2H), 7.25 (d, 1H), 6.97 (d, 1H), 6.47 (s, 1H), 4.31 (m, 2H), 4.00 (s, 3H), 3.10-3.03 (m, 10H), 1.27 (s, 9H); LC-MS (ESI) m/z 611 (M+H)+.

Example 92

Preparation of 1-(5-tert-butylisoxazol-3-yl)-3-{3-[6-(5-{[2-(methylsulfonyl)ethylamino]methyl}furan-2-yl)quinazolin-4-yloxy]phenyl}urea Example 92A Step 1: A mixture of 2-amino-5-iodobenzoic acid (9.00 g, 34.2 mmol) and formamidine acetate (18.00 g, 173 mmol) in acetic acid (50 mL) was heated at 130° C. for 3 hours. After it was cooled down to room temperature, it was quenched with water, filtered, washed with water, and dried under vacuum with $P_2O_5$ to afford 6-iodoquinazolin-4(3H)-one as solid (9.289 g, 99.8%). $^1$H NMR (300 MHz, DMSO-$d_6$) δ 8.38 (d, 1H), 8.13 (s, 1H), 8.09 (dd, 1H), 7.46 (d, 1H); LC-MS (ESI) m/z 273 (M+H)+.

Example 92A

Step 2: To a mixture of 6-iodoquinazolin-4(3H)-one (1.70 g, 6.25 mmol) in $SOCl_2$ (10 mL) was dropped a few drops of DMF, and then it was heated at 90° C. for 5 hours. After excess $SOCl_2$ was removed under reduced pressure, to it was added $CH_2Cl_2$ and water, and neutralized with saturated $NaHCO_3$ solution. The aqueous was extracted with $CH_2Cl_2$ three times. Extracts were dried over $MgSO_4$ and concentrated under reduced pressure to afford 4-chloro-6-iodoquinazoline as solid (1.266 g, 70%). $^1$H NMR (300 MHz, $CDCl_3$) δ 9.07 (s, 1H), 8.67 (d, 1H), 8.22 (dd, 1H), 7.81 (d, 1H).

Example 92A

Step 3: A mixture of 1-(5-tert-butylisoxazol-3-yl)-3-(3-hydroxyphenyl)urea (0.413 g, 1.5 mmol) from Example 1A, 4-chloro-6-iodoquinazoline (0.436 g, 1.5 mmol), and Cs$_2$CO$_3$ (0.489 g, 1.5 mmol) in isopropanol (10 mL) was heated at 50° C. for 2 hours. It was quenched with water and extracted with CH$_2$Cl$_2$. Extracts were dried over MgSO$_4$ and concentrated under reduced pressure. It was purified by silica gel chromatography with EtOAc/hexane as eluant to afford 1-(5-tert-butylisoxazol-3-yl)-3-[3-(6-iodoquinazolin-4-yloxy)phenyl]urea as solid (0.551 g, 69%). $^1$H NMR (300 MHz, DMSO-d$_6$) δ 9.66 (s, 1H), 9.08 (s, 1H), 8.84 (s, 1H), 8.78 (m, 1H), 8.40 (dd, 1H), 7.87 (d, 1H), 7.67 (d, 1H), 7.49 (t, 1H), 7.38 (d, 1H), 7.09 (d, 1H), 6.55 (s, 1H), 1.35 (s, 9H); LC-MS (ESI) m/z 530 (M+H)$^+$.

Example 92B

A mixture of 1-(5-tert-butylisoxazol-3-yl)-3-[3-(6-iodoquinazolin-4-yloxy)phenyl]urea from the previous step (0.21 g, 0.4 mmol), 5-formylfuran-2-ylboronic acid (0.07 g, 0.51 mmol), bis(triphenylphosphine)palladium(II) dichloride (0.035 g, 0.05 mmol), and 1.0 M Na$_2$CO$_3$ solution (3 mL) in EtOH (2 mL) and 1,2-dimethoxyethane (3 mL) was heated at 55° C. for 1 hour. It was quenched with water and extracted with CH$_2$Cl$_2$. Extracts were dried over MgSO$_4$ and concentrated under reduced pressure. It was purified by silica gel chromatography with 30-60% EtOAc/hexane as eluants to afford 1-(5-tert-butylisoxazol-3-yl)-3-{3-[6-(5-formylfuran-2-yl)quinazolin-4-yloxy]phenyl}urea as solid (0.172 g, 87%). $^1$H NMR (300 MHz, CDCl$_3$) δ 9.75 (s, 1H), 9.53 (br, 1H), 8.80 (d, 1H), 8.78 (s, 1H), 7.32 (dd, 1H), 8.07 (d, 1H), 7.67 (m, 2H), 7.34-7.54 (m, 3H), 7.07 (d, 1H), 7.01 (d, 1H), 5.94 (s, 1H), 1.32 (s, 9H); LC-MS (ESI) m/z 498 (M+H)$^+$.

Example 92C

Step 1. To a 1.0 M solution of BH$_3$.THF in THF (40 mL) at −40° C. was added 2-(methylsulfonyl)acetonitrile (2.383 g, 20 mmol) in several small portions. After addition it was stirred at room temperature overnight. It was poured into MeOH (40 mL) and concentrated under reduced pressure. To the residue was added MeOH (60 mL) and 1.0 M HCl/Et$_2$O solution (30 mL), and then it was heated to reflux for 1 hour. After it was concentrated under reduced pressure to about 40 mL, to it was added a 7 N NH$_3$/MeOH solution until it was basic. It was concentrated under reduced pressure to dryness and dried under vacuum, to afford 2-(methylsulfonyl)ethanamine as solid (2.41 g). It was used in next step without further purification.

Example 92C

Step 2. To a mixture of 1-(5-tert-butylisoxazol-3-yl)-3-{3-[6-(5-formylfuran-2-yl)quinazolin-4-yloxy]phenyl}urea (0.17 g. 0.34 mmol), 2-(methylsulfonyl)ethanamine (0.15 g. 1.2 mmol), and MgSO$_4$ in CH$_2$Cl$_2$ was added acetic acid (4 drops), followed by MeOH (1 mL). After the mixture was stirred at room temperature for 1 hour, NaBH(OAc)$_3$ (0.212 g, 1 mmol) was added. After stirring the mixture at room temperature for more 2 hours, more NaBH(OAc)$_3$ (0.212 g, 1 mmol) was added and stirred at room temperature overnight. The reaction was quenched with water, basified with saturated NaHCO$_3$, and extracted with CH$_2$Cl$_2$. The extracts were dried over MgSO$_4$ and concentrated under reduced pressure. The crude product was purified by silica gel chromatography with 2-6% MeOH/EtOAc as eluants to afford 1-(5-tert-butylisoxazol-3-yl)-3-{3-[6-(5-{[2-(methylsulfonyl)ethylamino]methyl}furan-2-yl)quinazolin-4-yloxy]phenyl}urea as solid (0.052 g, 25%). $^1$H NMR (300 MHz, DMSO-d$_6$) δ 9.59 (s, 1H), 9.02 (s, 1H), 8.70 (s, 1H), 8.52 (s, 1H), 8.38 (d, 1H), 8.03 (d, 1H), 7.61 (s, 1H), 7.43 (t, 1H), 7.31 (d, 1H), 7.23 (d, 1H), 7.03 (d, 1H), 6.48 (m, 2H), 3.83 (br, 2H), 3.24 (t, 2H), 3.02 (s, 3H), 2.97 (br, 2H), 1.27 (s, 9H); LC-MS (ESI) m/z 605 (M+H)$^+$.

Example 93

Preparation of 1-(5-tert-butylisoxazol-3-yl)-3-[3-(6-morpholinoquinazolin-4-yloxy)phenyl]urea A mixture of 1-(5-tert-butylisoxazol-3-yl)-3-[3-(6-iodoquinazolin-4-yloxy)phenyl]urea from Example 92A (0.225 g, 0.425 mmol), morpholine (0.5 mL), xamtphhos (0.087 g, 0.15 mmol), tris(dibenzylideneacetone)dipalladium (0) (0.046 g, 0.05 mmol), and Cs$_2$CO$_3$ (0.489 g, 1.5 mmol) in 1,2-dimethoxyethane (8 mL) was heated at 70° C. for 4 hours. It was quenched with water and extracted with CH$_2$Cl$_2$. Extracts were dried over MgSO$_4$ and concentrated under reduced pressure. It was purified by silica gel chromatophraphy with 30-100% EtOAc/hexane and 5% MeOH/EtOAc as eluants, and by preparative HPLC (C$_{18}$) with 60-80% CH$_3$CN/H$_2$O (0.05% AcOH) to afford 1-(5-tert-butylisoxazol-3-yl)-3-[3-(6-morpholinoquinazolin-4-yloxy)phenyl]urea as a solid (0.007 g, 3.4%). $^1$H NMR (300 MHz, CD$_3$CN) δ 9.48 (br, 1H), 8.39 (s, 1H), 7.78 (m, 4H), 7.67 (dd, 1H), 7.44 (m, 3H), 7.03 (d, 1H), 3.76 (t, 4H), 3.23 (t, 4H), 1.11 (s, 9H); LC-MS (ESI) m/z 489 (M+H)$^+$.

Example 94

Preparation of 1-(5-tert-butylisoxazol-3-yl)-3-{3-[7-methoxy-5-(tetrahydro-2H-pyran-4-yloxy)quinazolin-4-yloxy]phenyl}urea

Example 94A

Step 1: To a solution of 3,5-dimethoxyaniline (15.00 g, 97.9 mmol) in diethyl ether (300 mL) was added 1.0 M HCl solution in diethyl ether (100 mL). A white solid was formed, filtered, washed with Et$_2$O, and dried under vacuum. The solid was mixed with oxalyl chloride (30 mL) and it was heated at 165° C. for 30 minutes to form a green solid. The excess oxalyl chloride was evaporated under reduced pressure. To the solid was added MeOH (150 mL) and heated to reflux. After it was cooled down to room temperature, it was filtered, washed with MeOH, and dried under vacuum, to afford 4,6-dimethoxyindoline-2,3-dione as a solid (20.285 g, 100%). $^1$H NMR (300 MHz, DMSO-d$_6$) δ 10.92 (s, 1H), 6.17 (d, 1H), 6.01 (d, 1H), 3.88 (s, 3H), 3.86 (s, 3H); LC-MS (ESI) m/z 208 (M+H)$^+$.

Example 94A

Step 2: To a mixture of 4,6-dimethoxyindoline-2,3-dione (20.28 g, 97.9 mmol) in 30% NaOH solution (100 mL) at 100° C. was carefully dropped a 50% H$_2$O$_2$ solution. It was heated at 100° C. for 20 minutes. It was cooled down and neutralized by concentrated HCl to pH 8, followed by acetic acid to pH 5 to form a solid. It was filtered, washed with water, and dried under vacuum with P$_2$O$_5$ to afford 2-amino-4,6-dimethoxybenzoic acid as a yellow solid (15.034 g, 78%). $^1$H NMR (300 MHz, DMSO-d$_6$) δ 6.00 (d, 1H), 5.85 (d, 1H), 3.83 (s, 3H), 3.77 (s, 3H), 3.41 (br, 2H); LC-MS (ESI) m/z 198 (M+H)$^+$.

Example 94A

Step 3: To a mixture of 2-amino-4,6-dimethoxybenzoic acid (7.888 g, 40 mmol) in MeOH (40 mL) and THF (40 mL)

at room temperature was dropped 2.0 M solution of (trimethylsilyl)diazomethane in diethyl ether. The mixture was stirred at room temperature overnight. After the solvent was evaporated under reduced pressure, water and EtOAc was added to the residue. The organic layer was separated, dried (MgSO$_4$) and concentrated under reduced pressure. The crude product was purified by silica gel chromatography with 20-40% EtOAc/hexane as eluants to afford methyl 2-amino-4,6-dimethoxybenzoate as a solid (6.462 g, 76%). $^1$H NMR (300 MHz, CDCl$_3$) δ 5.83 (d, 1H), 5.78 (d, 1H), 5.53 (br, 2H), 3.86 (s, 3H), 3.80 (s, 3H), 3.77 (s, 3H); LC-MS (ESI) m/z 212 (M+H)$^+$.

Example 94A

Step 4: A mixture of methyl 2-amino-4,6-dimethoxybenzoate (6.46 g, 30.6 mmol), formamidine acetate (15.92 g, 153 mmol) in 2-methoxyethanol (50 mL) was heated at 130° C. for 4 hours. After the solvent was removed under reduced pressure, the reaction was quenched with water, filtered, washed with water, and dried under vacuum with P$_2$O$_5$ to afford 5,7-dimethoxyquinazolin-4(3H)-one as a solid (4.805 g, 76%). $^1$H NMR (300 MHz, DMSO-d$_6$) δ 11.7 (br, 1H), 7.98 (s, 1H), 6.72 (d, 1H), 6.60 (d, 1H), 3.92 (s, 3H), 3.88 (s, 3H); LC-MS (ESI) m/z 207 (M+H)$^+$.

Example 94A

Step 5: To a mixture of 5,7-dimethoxyquinazolin-4(3H)-one (4.80 g, 23.3 mmol) in pyridine (50 mL) at room temperature was slowly added MgBr$_2$ (4.29 g, 23.3 mmol). It was heated to reflux for 1.5 hour. After solvent was evaporated under reduced pressure, to the residue was added a solution of AcOH (10 mL) in water (50 mL). A solid was precipitated. It was filtered, washed with water, and dried under vacuum with P$_2$O$_5$ to afford 5-hydroxy-7-methoxyquinazolin-4(3H)-one as solid (4.398 g, 98%). $^1$H NMR (300 MHz, DMSO-d$_6$) δ 11.95 (br, 1H), 8.08 (s, 1H), 6.63 (s, 1H), 6.50 (s, 1H), 3.85 (s, 3H); LC-MS (ESI) m/z 193 (M+H)$^+$.

Example 94A

Step 6: To a suspension of 5-hydroxy-7-methoxyquinazolin-4(3H)-one (4.395 g, 22.9 mmol) in DMF (50 mL) at 0° C. was added 1.0 M solution of lithium bis(trimethylsilyl)amide in THF (55 mL, 55 mmol). After it was stirred at room temperature for 1 hour, it was cooled again with an ice-water bath and to it was added chloromethyl pivalate (4.14 g, 27.5 mmol). After it was stirred at room temperature for another hour, it was quenched with a solution of AcOH (10 mL) in water (150 mL) and extracted with CH$_2$Cl$_2$. Extracts were dried over MgSO$_4$ and concentrated to afford the (5-hydroxy-7-methoxy-4-oxoquinazolin-3(4H)-yl)methyl pivalate solid (5.674 g, 81%). $^1$H NMR (300 MHz, CDCl$_3$) δ 11.36 (s, 1H), 8.16 (s, 1H), 6.69 (d, 1H), 6.51 (d, 1H), 5.88 (s, 2H), 3.89 (s, 3H), 1.21 (s, 9H); LC-MS (ESI) m/z 307 (M+H)$^+$.

Example 94A

Step 7: To a solution of (5-hydroxy-7-methoxy-4-oxoquinazolin-3(4H)-yl)methyl pivalate (2.50 g, 8.16 mmol), tetrahydro-4H-pyran-4-ol (1.02 g, 10 mmol), and Ph$_3$P (3.41 g, 13 mmol) in CH$_2$Cl$_2$ (40 mL) at 0° C. was added di t-butyl azodicarboxylate (3.993 g, 13 mmol). It was stirred at room temperature for 2 hour. After solvent was evaporated under reduced pressure, to the residue was added 7 N NH$_3$/MeOH (80 mL) and stirred at room temperature overnight. A solid was precipitated. It was filtered, washed with MeOH, and dried under vacuum to afford 7-methoxy-5-(tetrahydro-2H-pyran-4-yloxy)quinazolin-4(3H)-one as solid (1.091 g, 76%). $^1$H NMR (300 MHz, DMSO-d$_6$) δ 10.6 (br, 1H), 7.98 (s, 1H), 6.74 (d, 1H), 6.69 (d, 1H), 4.79 (m, 1H), 3.97 (m, 2H), 3.91 (s, 3H), 3.57 (m, 2H), 1.98 (m, 2H), 1.74 (m, 2H); LC-MS (ESI) m/z 277 (M+H)$^+$.

Example 94A

Step 8: A mixture of 7-methoxy-5-(tetrahydro-2H-pyran-4-yloxy)quinazolin-4(3H)-one (0.60 g, 2.17 mmol), POCl$_3$ (0.5 mL), and N,N-diisopropylethylamine (1.5 mL) in ClCH$_2$CH$_2$Cl (6 mL) was heated at 100° C. for 4 hours. After the solvent and reagents were evaporated under reduced pressure, toluene was added to the residue, and the solution was evaporated under reduced pressure. The residue was dried under vacuum to afford 4-chloro-7-methoxy-5-(tetrahydro-2H-pyran-4-yloxy)quinazoline as a brown solid. LC-MS (ESI) m/z 295 (M+H)$^+$.

Example 94B

Using the procedure described in Example 92A Step 3, using 1-(5-tert-butylisoxazol-3-yl)-3-(3-hydroxyphenyl)urea (0.193 g, 0.7 mmol) from Example 1A, 4-chloro-7-methoxy-5-(tetrahydro-2H-pyran-4-yloxy)quinazoline from the previous step (0.212 g, 0.72 mmol), and Cs$_2$CO$_3$ (0.326 g, 1 mmol) in isopropanol (10 mL) at 60° C. for 4 hours, to afford 1-(5-tert-butylisoxazol-3-yl)-3-{3-[7-methoxy-5-(tetrahydro-2H-pyran-4-yloxy)quinazolin-4-yloxy]phenyl}urea as solid (0.104 g, 28%). $^1$H NMR (300 MHz, CDCl$_3$) δ 9.4 (s, 1H), 8.58 (s, 1H), 7.94 (s, 1H), 7.56 (s, 1H), 7.37 (d and s, 2H), 6.95 (d and s, 2H), 6.59 (s, 1H), 5.89 (s, 1H), 4.76 (m 1H), 3.99 (m, 2H), 3.96 (s, 3H), 3.66 (m, 2H), 2.06 (m, 2H), 1.95 (m, 2H), 1.33 (s, 9H); LC-MS (ESI) m/z 534 (M+H)$^+$.

Example 95

Preparation of 1-(5-tert-butylisoxazol-3-yl)-3-(3-(7-hydroxy-6-methoxyquinazolin-4-yloxy)phenyl)urea Example 95A Step 1: A stirred mixture of 7-(benzyloxy)-6-methoxyquinazolin-4-ol (5.10 g, 18.09 mmol) and phosphorous oxychloride (10 mL, 109 mmol) in dry toluene (30 mL), was heated to 120° C. for 2 h. After cooling to room temperature the mixture was concentrated under reduced pressure. The residue was dissolved in ethyl acetate (200 mL) and washed with sat aqueous NaHCO$_3$ solution (2×100 mL). The organic layer was separated and dried over MgSO$_4$ then concentrated under reduced pressure to afford 7-(benzyloxy)-4-chloro-6-methoxyquinazoline as a cream solid (3.89 g, 72%) which was taken into the next step without further purification. $^1$H NMR (300 MHz, CDCl$_3$) δ 8.85 (s, 1H), 7.49 (m, 2H), 7.33-7.43 (m, 5H), 5.33 (s, 2H), 4.07 (s, 3H); LC-MS (ESI) m/z 301 (M+H)$^+$.

Example 95A

Step 2: To a stirred solution of 3-aminophenol (1.41 g, 12.93 mmol) in dry tetrahydrofuran (70 mL) at room temperature, was added cesium carbonate (6.32 g, 19.39 mmol). After stirring for a further 75 mins, added 7-(benzyloxy)-4-chloro-6-methoxyquinazoline from the previous step (3.89 g, 12.93 mmol) in one portion and the reaction mixture was heated at 75° C. for 24 h. After cooling to room temperature the mixture was concentrated under reduced pressure. The residue was partitioned between water (200 mL) and a mixture of dichloromethane (160 mL) and 2-propanol (60 mL). The mixture was filtered through a celite plug and the organic layer was separated and dried over MgSO$_4$ and concentrated under reduced pressure. Trituration with diethyl ether, followed by filtration and drying under reduced pressure, afforded 3-(7-(benzyloxy)-6-methoxyquinazolin-4-yloxy)aniline as a cream solid (3.57 g, 74%) which was taken into the next step without further purification. $^1$H NMR (300 MHz, CDCl$_3$) δ 8.62 (s, 1H), 7.21-7.55 (m, 8H), 6.57-6.63 (m, 3H), 5.33 (s, 2H), 4.03 (s, 3H), 3.73 (brs, 2H); LC-MS (ESI) m/z 374 (M+H)$^+$.

Example 95A

Step 3: A stirred mixture of 3-(7-(benzyloxy)-6-methoxyquinazolin-4-yloxy)aniline from the previous step (2.52 g, 6.76 mmol) and palladium (10% wt on activated carbon) (200 mg) in ethanol (100 mL), under 1 atmosphere of hydrogen gas, was heated at 50° C. for 45 mins. The reaction mixture was filtered through a celite plug and concentrated under reduced pressure. The residue was purified via silica gel chromatography eluting with 1% to 10% methanol in dichloromethane to afford 4-(3-aminophenoxy)-6-methoxyquinazolin-7-ol as a colorless solid (840 mg, 44%). $^1$H NMR (300 MHz, DMSO-d$_6$) δ 10.73 (brs, 1H), 8.47 (s, 1H), 7.50 (s, 1H), 7.21 (s, 1H), 7.08 (m, 1H), 6.35-6.50 (m, 3H), 5.28 (brs, 2H), 3.97 (s, 3H); LC-MS (ESI) m/z 284 (M+H)$^+$.

Example 95B

A stirred mixture of 4-(3-aminophenoxy)-6-methoxyquinazolin-7-ol from the previous step (500 mg, 1.77 mmol) and phenyl 5-tert-butylisoxazol-3-ylcarbamate (460 mg, 1.77 mmol) in dry N,N-dimethylformamide (10 mL) was heated at 60° C. for 5 h. After cooling to room temperature the mixture was concentrated under reduced pressure. The residue was triturated with diethyl ether and filtered and dried under reduced pressure to afford 1-(5-tert-butylisoxazol-3-yl)-3-(3-(7-hydroxy-6-methoxyquinazolin-4-yloxy)phenyl)urea as a cream solid (650 mg, 82%) which did not require further purification. $^1$H NMR (300 MHz, DMSO-d$_6$) δ 10.78 (brs, 1H), 9.58 (brs, 1H), 9.00 (brs, 1H), 8.48 (s, 1H), 7.55-7.57 (m, 2H), 7.40 (m, 1H), 7.24-7.26 (m, 2H), 6.97 (m, 1H), 6.48 (s, 1H), 3.99 (s, 3H), 1.28 (s, 9H); LC-MS (ESI) m/z 450 (M+H)$^+$.

Example 96

Preparation of (S)-1-(5-tert-Butyl-isoxazol-3-yl)-3-{3-[6-methoxy-7-(pyrrolidin-3-yloxy)-quinazolin-4-yloxy]-phenyl}-urea (S)-tert-butyl 3-(4-(3-(3-(5-tert-butylisoxazol-3-yl)ureido)phenoxy)-6-methoxyquinazolin-7-yloxy)pyrrolidine-1-carboxylate Example 96A A solution of 1-(5-tert-butylisoxazol-3-yl)-3-(3-(7-hydroxy-6-methoxyquinazolin-4-yloxy)phenyl)urea from Example 95B (50 mg, 0.111 mmol), (R)-3-hydroxy-1-tert-butoxycarbonylpyrrolidine (31 mg, 0.167 mmol), triphenylphosphine (44 mg, 0.167 mmol) and diisopropylazodicarboxylate (34 mg, 0.167 mmol) in dry tetrahydrofuran (1 mL) was stirred at room temperature for 15 h. The reaction mixture was partitioned between aqueous 1M sodium hydroxide solution (20 mL) and 10% methanol in dichloromethane (50 mL) and the organic layer was separated and washed with brine (50 mL), dried over MgSO$_4$, and concentrated under reduced pressure. The residue was purified via silica gel chromatography eluting with 100% dichloromethane to 10% methanol in dichloromethane to afford (S)-tert-butyl 3-(4-(3-(3-(5-tert-butylisoxazol-3-yl)ureido)phenoxy)-6-methoxyquinazolin-7-yloxy)pyrrolidine-1-carboxylate as a colorless oil (35 mg, 51%). $^1$H NMR (300 MHz, CDCl$_3$) δ 9.30 (brs, 1H), 8.62 (s, 1H), 8.30 (brs, 1H), 7.66 (s, 1H), 7.56 (s, 1H), 7.26-7.39 (m, 2H), 7.00 (m, 1H), 5.95 (s, 1H), 5.12 (s, 1H), 4.02 (s, 3H), 3.50-3.80 (m, 5H), 2.20-2.40 (m, 2H), 1.50 (s, 9H), 1.30 (s, 9H); LC-MS (ESI) m/z 619 (M+H)$^+$.

Example 96B

A solution of (S)-tert-butyl 3-(4-(3-(3-(5-tert-butylisoxazol-3-yl)ureido)phenoxy)-6-methoxyquinazolin-7-yloxy)pyrrolidine-1-carboxylate from the previous step (35 mg, 0.0566 mmol) and hydrochloric acid (0.1 mL of a 4N solution in 1,4-dioxane, 0.40 mmol) in dry dichloromethane (0.01 mL) was stirred at room temperature for 2 h. Concentrated under reduced pressure to afford (S)-1-(5-tert-butylisoxazol-3-yl)-3-(3-(6-methoxy-7-(pyrrolidin-3-yloxy)quinazolin-4-yloxy)phenyl)urea dihydrochloride as a colorless solid (22 mg, 67%), which did not require further purification. $^1$H NMR (300 MHz, MeOH-d$_4$) δ 9.02 (brs, 1H), 7.82 (s, 1H), 7.73 (brs, 1H), 7.54 (s, 1H), 7.41 (m, 1H), 7.29 (m, 1H), 7.06 (m, 1H), 6.32 (s, 1H) 5.56 (brs, 1H), 4.04 (s, 3H), 3.50-3.85 (m, 5H), 2.50-2.60 (m, 2H), 1.35 (s, 9H); LC-MS (ESI) m/z 519 (M+H)$^+$.

Example 97

Preparation of (S)-1-(5-tert-butylisoxazol-3-yl)-3-(3-(6-methoxy-7-(1-methylpyrrolidin-3-yloxy)quinazolin-4-yloxy)phenyl)urea mono acetate A solution of (S)-1-(5-tert-butylisoxazol-3-yl)-3-(3-(6-methoxy-7-(pyrrolidin-3-yloxy)quinazolin-4-yloxy)phenyl)urea dihydrochloride from Example 96B (100 mg, 0.193 mmol) and formaldehyde (0.08 mL of a 37 wt % solution in water, 0.987 mmol) in a mixture of dry 1,2-dichloroethane (1.5 mL) and dry N,N-dimethylformamide (0.8 mL) was stirred at room temperature for 20 mins. Sodium triacetoxyborohydride (135 mg, 0.640 mmol) was added in one portion and stirring continued for a further 45 mins. The reaction mixture was partitioned between aqueous 1M sodium hydroxide solution (20 mL) and 10% methanol in dichloromethane (50 mL) and the organic layer was separated and washed with brine (50 mL), dried over MgSO$_4$, and concentrated under reduced pressure. The residue was purified by preparative HPLC (using phenylhexyl reverse phase column, eluted with gradient of solvent B=0.05% HOAc/CH$_3$CN and solvent A=0.05% HOAc/H$_2$O) to afford (S)-1-(5-tert-butylisoxazol-3-yl)-3-(3-(6-methoxy-7-(1-methylpyrrolidin-3-yloxy)quinazolin-4-yloxy)phenyl)urea mono acetate as a colorless solid (29 mg, 25%). $^1$H NMR (300 MHz, CDCl$_3$) δ 9.50 (brs, 1H), 9.00 (brs, 1H), 8.60 (s, 1H), 7.65 (s, 1H), 7.52 (s, 1H), 7.30-7.40 (m, 2H), 7.22 (s, 1H), 6.99 (m, 1H), 6.05 (s, 1H), 5.10 (s, 1H), 4.01 (s, 3H), 3.37 (m, 1H), 2.96-3.12 (m, 3H), 2.59 (s, 3H), 2.50 (m, 1H), 2.25 (m, 1H), 2.10 (s, 3H), 1.30 (s, 9H); LC-MS (ESI) m/z 533 (M+H)$^+$.

Example 98

Preparation of (R)-tert-butyl 3-(4-(3-(3-(5-tert-butyl-isoxazol-3-yl)ureido)phenoxy)-6-methoxyquinazolin-7-yloxy)pyrrolidine-1-carboxylate

Example 98A

Prepared from 1-(5-tert-butylisoxazol-3-yl)-3-(3-(7-hydroxy-6-methoxyquinazolin-4-yloxy)phenyl)urea from Example 95B (350 mg, 0.780 mmol) and (S)-3-hydroxy-1-tert-butoxycarbonylpyrrolidine (219 mg, 1.17 mmol) according to the procedure described for (S)-tert-butyl 3-(4-(3-(3-(5-tert-butylisoxazol-3-yl)ureido)phenoxy)-6-methoxyquinazolin-7-yloxy)pyrrolidine-1-carboxylate in Example 96A to afford (R)-tert-butyl 3-(4-(3-(3-(5-tert-butylisoxazol-3-yl)ureido)phenoxy)-6-methoxyquinazolin-7-yloxy)pyrrolidine-1-carboxylate as a colorless oil (109 mg, 23%). $^1$H NMR (300 MHz, DMSO-d$_6$) δ 9.58 (brs, 1H), 9.00 (brs, 1H), 8.57 (s, 1H), 7.50-7.70 (m, 2H), 7.40-7.50 (m, 2H), 7.30 (m, 1H), 7.00 (m, 1H), 6.48 (s, 1H), 5.30 (brs, 1H), 4.00 (s, 3H), 3.70 (m, 1H), 3.40-3.50 (m, 2H), 3.25 (m, 1H), 2.20-2.40 (m, 2H), 1.40 (s, 9H), 1.30 (s, 9H); LC-MS (ESI) m/z 619 (M+H)$^+$.

Example 98B

Prepared from (R)-tert-butyl 3-(4-(3-(3-(5-tert-butylisoxazol-3-yl)ureido)phenoxy)-6-methoxyquinazolin-7-yloxy)pyrrolidine-1-carboxylate from the previous step (109 mg, 0.176 mmol) according to the procedure described for (S)-1-(5-tert-butylisoxazol-3-yl)-3-(3-(6-methoxy-7-(pyrrolidin-3-yloxy)quinazolin-4-yloxy)phenyl)urea dihydrochloride in Example 96B to afford (R)-1-(5-tert-butylisoxazol-3-yl)-3-(3-(6-methoxy-7-(pyrrolidin-3-yloxy)quinazolin-4-yloxy)phenyl)urea dihydrochloride as a colorless solid (42 mg, 40%). $^1$H NMR (300 MHz, CDCl$_3$) δ 9.30 (brs, 1H), 8.61 (brs, 1H), 7.65 (s, 1H), 7.52 (s, 1H), 7.20-7.40 (m, 4H), 6.99 (m, 1H), 6.02 (s, 1H), 5.05 (m, 1H), 4.01 (s, 3H), 3.10-3.40 (m, 2H), 3.00 (m, 1H), 2.00-2.40 (m, 4H), 1.40 (s, 9H); LC-MS (ESI) m/z 519 (M+H)$^+$.

Example 99

Preparation of (R)-1-(5-tert-butylisoxazol-3-yl)-3-(3-(6-methoxy-7-(1-methylpyrrolidin-3-yloxy)quinazolin-4-yloxy)phenyl)urea mono acetate A solution of (R)-1-(5-tert-butylisoxazol-3-yl)-3-(3-(6-methoxy-7-(pyrrolidin-3-yloxy)quinazolin-4-yloxy)phenyl) urea dihydrochloride from Example 98B (110 mg, 0.212 mmol) and formaldehyde (0.08 mL of a 37 wt % solution in water, 0.987 mmol) in a mixture of dry 1,2-dichloroethane (1.5 mL) and dry N,N-dimethylformamide (0.8 mL) was stirred at room temperature for 20 mins. Sodium triacetoxyborohydride (135 mg, 0.640 mmol) was added in one portion and stirring continued for a further 45 mins. The reaction mixture was partitioned between aqueous 1M sodium hydroxide solution (20 mL) and 10% methanol in dichloromethane (50 mL) and the organic layer was separated and washed with brine (50 mL), dried over MgSO$_4$, and concentrated under reduced pressure. The residue was purified by preparative HPLC (Phenomenex phenylhexyl reverse phase column, eluted with gradient of solvent B=0.05% HOAc/CH$_3$CN and solvent A=0.05% HOAc/H$_2$O) to afford (R)-1-(5-tert-butylisoxazol-3-yl)-3-(3-(6-methoxy-7-(1-methylpyrrolidin-3-yloxy)quinazolin-4-yloxy)phenyl)urea mono acetate as a colorless solid (48 mg, 38%). $^1$H NMR (300 MHz, CDCl$_3$) δ 9.50 (brs, 1H), 9.00 (brs, 1H), 8.60 (s, 1H), 7.65 (s, 1H), 7.52 (s, 1H), 7.30-7.40 (m, 2H), 7.22 (s, 1H), 6.99 (m, 1H), 6.05 (s, 1H), 5.11 (s, 1H), 4.01 (s, 3H), 3.49 (s, 3H), 3.38 (m, 1H), 2.97-3.06 (m, 3H), 2.59 (s, 3H), 2.50 (m, 1H), 2.20 (m, 1H), 1.30 (s, 9H); LC-MS (ESI) m/z 533 (M+H)$^+$.

Example 100

Preparation of (R)-1-(5-tert-butylisoxazol-3-yl)-3-(3-(7-(2-hydroxy-3-(4-methylpiperazin-1-yl)propoxy)-6-methoxyquinazolin-4-yloxy)phenyl)urea

Example 100

Step 1: A stirred mixture of 1-(5-tert-butylisoxazol-3-yl)-3-(3-(7-hydroxy-6-methoxyquinazolin-4-yloxy)phenyl)urea from Example 95B (160 mg, 0.356 mmol), (R)-(−)-epichlorohydrin (65 mg, 0.702 mmol), cesium carbonate (120 mg, 0.356 mmol) and potassium iodide (40 mg, 0.241 mmol) in dry N,N-dimethylformamide (4 mL) was heated in a sealed vial at 80° C. in a Biotage microwave synthesizer for 90 mins. After cooling to room temperature, the mixture was partitioned between water (50 mL) and a mixture of ethyl acetate (40 mL) and tetrahydrofuran (10 mL). The organic layer was separated, washed with brine (50 mL), dried over MgSO$_4$ and concentrated under reduced pressure. Purification via silica gel chromatography eluting with 100% dichloromethane to 5% methanol in dichloromethane to afford (R)-1-(5-tert-butylisoxazol-3-yl)-3-(3-(6-methoxy-7-(oxiran-2-ylmethoxy)quinazolin-4-yloxy)phenyl)urea as a colorless solid (27 mg, 15%). LC-MS (ESI) m/z 506 (M+H)$^+$.

Example 100

Step 2: A stirred solution of (R)-1-(5-tert-butylisoxazol-3-yl)-3-(3-(6-methoxy-7-(oxiran-2-ylmethoxy)quinazolin-4-yloxy)phenyl)urea from the previous step (25 mg, 0.0495 mmol) and N-methylpiperazine (10 mg, 0.0998 mmol) in dry N,N-dimethylformamide (1 mL) was heated at 70° C. for 15 h. Concentration under reduced pressure gave a residue that was triturated with diethyl ether and further purified via silica gel chromatography eluting with 10% methanol in dichloromethane to afford (R)-1-(5-tert-butylisoxazol-3-yl)-3-(3-(7-(2-hydroxy-3-(4-methylpiperazin-1-yl)propoxy)-6-methoxyquinazolin-4-yloxy)phenyl)urea as a colorless solid (5 mg, 17%). $^1$H NMR (300 MHz, CDCl$_3$) δ 9.40 (brs, 1H), 8.62 (s, 1H), 8.30 (brs, 1H), 7.64 (s, 1H), 7.52 (s, 1H), 7.27-7.39 (m, 3H), 7.00 (m, 1H), 5.96 (s, 1H), 4.20-4.28 (m, 3H), 4.02 (s, 3H), 2.00-2.80 (m, 14H), 1.29 (s, 9H); LC-MS (ESI) m/z 606 (M+H)$^+$.

Example 101

Preparation of 1-(3-tert-butylisoxazol-5-yl)-3-(3-(6-methoxy-7-(piperidin-4-ylmethoxy)quinazolin-4-yloxy)phenyl)urea

Example 101A

The intermediate from Example 95B (102 mg, 0.23 mmol) was treated with cesium carbonate (89 mg, 0.27 mmol) in N,N'-dimethylformamide (4 mL) and stirred at room temperature for 30 minutes. tert-Butyl 4-(tosyloxymethyl)piperidine-1-carboxylate (84.3 mg, 0.23 mmol) was added and the mixture stirred at 70° C. for 17h. After cooling to room temperature the solid was filtered off and washed with diethyl ether. The filtrate was concentrated under reduced pressure and the resulting residue purified by silica gel chromatography (dichloromethane/methanol 9:1) to afford 4-((4-(3-(3-(3-tert-butylisoxazol-5-yl)ureido)phenoxy)-6-methoxyquinazolin-7-yloxy)methyl)piperidine-1-carboxylate (71 mg, 48%) as a solid. $^1$H NMR (300 MHz, CDCl$_3$) δ 9.2 (bs, 1H), 8.80 (bs, 1H), 8.62 (s, 1H), 7.64 (s, 1H), 7.53 (s, 1H), 7.37-7.27 (m, 3H), 6.98 (d, 1H), 6.04 (s, 1H), 4.30-4.05 (m, 2H), 4.05 (s, 5H), 2.79 (t, 3H), 2.25-2.05 (m, 1H), 1.99-1.89 (m, 3H), 1.46 (s, 9H), 1.28 (2, 9H); LC-MS (ESI) m/z 647 (M+H)$^+$.

Example 101B

To a solution of 4-((4-(3-(3-(3-tert-butylisoxazol-5-yl)ureido)phenoxy)-6-methoxyquinazolin-7-yloxy)methyl)piperidine-1-carboxylate (49 mg, 0.062 mmol) in dichloromethane (0.31 mL) was added hydrochloric acid (0.31 mL, 4M in dioxane) and the mixture stirred at room temperature for 30 minutes. The solid was filtered off, dissolved in methanol and concentrated under reduced pressure. The residue was taken in ethyl acetate and a saturated solution of sodium bicarbonate was added until the solution became basic. The solid was filtered off, washed thoroughly with water and dried to afford 1-(3-tert-butylisoxazol-5-yl)-3-(3-(6-methoxy-7-(piperidin-4-ylmethoxy)quinazolin-4-yloxy)phenyl)urea as a white solid (23.31 mg, 69%). $^1$H NMR (300 MHz, DMSO-d$_6$) δ 10.10 (bs, 1H), 9.65 (bs, 1H), 8.56 (s, 1H), 7.61-7.21 (m, 5H), 6.95 (d, 1H), 6.56 (s, 1H), 4.25-3.90 (m, 6H), 3.00 (d, 2H), 2.45 (d, 2H), 2.20-1.79 (m, 1H), 1.78-1.51 (m, 4H), 1.25 (s, 9H); LC-MS (ESI) m/z 547 (M+H)$^+$.

Example 102

Preparation of 1-(3-tert-butylisoxazol-5-yl)-3-(3-(6-methoxy-7-((1-methylpiperidin-4-yl)methoxy)quinazolin-4-yloxy)phenyl)urea To a solution of 1-(3-tert-butylisoxazol-5-yl)-3-(3-(6-methoxy-7-(piperidin-4-ylmethoxy)quinazolin-4-yloxy)phenyl)urea (82.5 mg, 0.15 mmol) in 1,2-dichloroethane/N,N'-dimethylacetamide (1.3 mL, 3:1) was added 37% formaldehyde (24 mL, 0.3 mmol) and acetic acid (10 μL, 0.18 mmol). The mixture was stirred at room temperature for 20 minutes. Sodium triacetoxyborohydride (48 mg, 0.23 mmol) was added in portions and the resulting mixture stirred at room temperature for 2h. Ethyl acetate and 1N sodium hydroxide were added to the mixture, the organic layer was separated and the water phase extracted three times. The organics were combined, dried (MgSO$_4$) and concentrated under reduced pressure. The crude material was purified by preparative HPLC (Phenomenex phenylhexyl reverse phase column) to afford 1-(3-tert-butylisoxazol-5-yl)-3-(3-(6-methoxy-7-((1-methylpiperidin-4-yl)methoxy)quinazolin-4-yloxy)phenyl)urea (57 mg, 68%) as a white solid. $^1$H NMR (300 MHz, DMSO-d$_6$) δ 9.75 (bs, 1H), 9.21 (bs, 1H), 8.55 (s, 1H), 7.57 (d, 2H), 7.37-7.26 (m, 3H), 6.96 (d, 1H), 6.47 (s, 1H), 4.07-3.99 (m, 5H), 2.83-2.79 (m, 2H), 2.17 (s, 3H), 1.93-1.76 (m, 5H), 1.39-1.35 (m, 2H), 1.27 (s, 9H); LC-MS (ESI) m/z 561 (M+H)$^+$.

Example 103

Preparation of (5)-1-(5-tert-butylisoxazol-3-yl)-3-(3-{7-[1-(2,2-difluoroethyl)pyrrolidin-3-yloxy]-6-methoxyquinazolin-4-yloxy}phenyl)urea Example 103A To a suspension of 1-(5-tert-butylisoxazol-3-yl)-3-[3-(7-hydroxy-6-methoxyquinazolin-4-yloxy)phenyl]urea from Example 95B (0.45 g, 1 mmol), (S)-tert-butyl 3-hydroxypyrrolidine-1-carboxylate (0.225 g, 1.2 mmol), and Ph$_3$P (0.393 g, 1.5 mmol) in THF (10 mL) was added di t-butyl azodicarboxylate (0.345 g, 1.5 mmol). After it was stirred at room temperature overnight, it was quenched with saturated NaHCO$_3$ solution and extracted with CH$_2$Cl$_2$. Extracts were dried over MgSO$_4$ and concentrated under reduced pressure. It was purified by silica gel chromatography with 70-90% EtOAc/hexane as eluants to afford (S)-tert-butyl 3-(4-{3-[3-(5-tert-Butylisoxazol-3-yl)ureido]phenoxy}-6-methoxyquinazolin-7-yloxy)pyrrolidine-1-carboxylate as solid (0.609 g, 98%). $^1$H NMR (300 MHz, CDCl$_3$) δ 9.4 (s, 1H), 8.8 (s, 1H), 8.61 (s, 1H), 7.67 (m, 1H), 7.50 (m, 2H), 7.34 (t, 1H), 7.31 (m, 1H), 6.96 (d, 1H), 6.13 (s, 1H), 5.12 (m, 1H), 4.06 (s, 3H), 3.61-3.80 (m, 4H), 2.34 (m, 2H), 1.47 (s, 9H), 1.31 (s, 9H); LC-MS (ESI) m/z 619 (M+H)$^+$.

Example 103B

To a solution of (S)-tert-butyl 3-(4-{3-[3-(5-tert-butylisoxazol-3-yl)ureido]phenoxy}-6-methoxyquinazolin-7-yloxy)pyrrolidine-1-carboxylate (0.609 g, 0.98 mmol) in CH$_2$Cl$_2$ (10 mL) was dropped 4.0 M solution of HCl in 1,4-dioxane (2 mL) and it was stirred at room temperature for 4 hours. After solvents were concentrated under reduced pressure, it was dissolved in CH$_2$Cl$_2$ with a few milliliters of MeOH and washed with saturated NaHCO$_3$ solution. The organic layer was dried over MgSO$_4$ and concentrated to dryness under reduced pressure to afford (S)-1-(5-tert-butylisoxazol-3-yl)-3-{3-[6-methoxy-7-(pyrrolidin-3-yloxy)quinazolin-4-yloxy]phenyl}urea as a white solid (0.396 g, 77%). $^1$H NMR (300 MHz, CDCl$_3$) δ 9.4 (s, 1H), 8.61 (s, 1H), 8.5 (s, 1H), 7.67 (m, 2H), 7.49 (m, 2H), 7.38 (t, 1H), 6.99 (d, 1H), 5.99 (s, 1H), 5.05 (m, 1H), 4.01 (s, 3H), 3.40 (m, 1H), 3.21 (m, 2H), 3.0 (m, 1H), 2.3 (m, 1H), 2.1 (m, 2H), 1.32 (s, 9H); LC-MS (ESI) m/z 519 (M+H)$^+$.

Example 103C

To a solution of (5)-1-(5-tert-butylisoxazol-3-yl)-3-{3-[6-methoxy-7-(pyrrolidin-3-yloxy)quinazolin-4-yloxy]phenyl}urea (0.198 g, 0.38 mmol) and N,N-diisopropylethylamine (0.5 mL) in CH$_2$Cl$_2$ (10 mL) was added 2,2-difluoroethyl trifluoromethanesulfonate (0.128 g. 0.6 mmol) and it was stirred at 40° C. for 1 hour. It was quenched with saturated NaHCO$_3$ and extracted with CH$_2$Cl$_2$. Extracts were dried over MgSO$_4$ and concentrated under reduced pressure. It was purified by silica gel chromatography with 70-85% EtOAc/hexane as eluants to afford (S)-1-(5-tert-Butylisoxazol-3-yl)-3-(3-{7-[1-(2,2-difluoroethyl)pyrrolidin-3-yloxy]-6-methoxyquinazolin-4-yloxy}phenyl)urea as solid (0.098 g, 44%). $^1$H NMR (300 MHz, CDCl$_3$) δ 9.4 (s, 1H), 8.62 (s, 1H), 7.81 (s, 1H), 7.65 (t, 1H), 7.54 (s, 1H), 7.40 (t, 1H), 7.33 (m, 1H), 7.19 (s, 1H), 7.00 (d, 1H), 5.93 (tt, 1H), 5.87 (s, 1H), 5.05 (m, 1H), 4.03 (s, 3H), 3.20 (m, 1H), 3.89-3.09 (m, 4H), 2.8 (m, 1H), 2.5 (m, 1H), 2.15 (m, 1H), 1.33 (s, 9H); LC-MS (ESI) m/z 583 (M+H)$^+$.

Example 104

Preparation of (S)-1-(5-tert-butylisoxazol-3-yl)-3-(3-{6-methoxy-7-[1-(2,2,2-trifluoroethyl)pyrrolidin-3-yloxy]quinazolin-4-yloxy}phenyl)urea The title compound was prepared as described in Example 103C using (S)-1-(5-tert-butylisoxazol-3-yl)-3-{3-[6-methoxy-7-(pyrrolidin-3-yloxy)quinazolin-4-yloxy]phenyl}urea (0.198 g, 0.38 mmol), 2,2,2-trifluoroethyl trifluoromethanesulfonate (0.139 g, 0.6 mmol), and N,N-diisopropylethylamine (0.5 mL) in CH$_2$Cl$_2$ (10 mL) at 40° C. for 3 hours, which was purified by silica gel chromatography with 70-85% EtOAc/hexane as eluants to afford (5)-1-(5-tert-butylisoxazol-3-yl)-3-(3-{6-methoxy-7-[1-(2,2,2-trifluoroethyl)pyrrolidin-3-yloxy]quinazolin-4-yloxy}phenyl)urea as solid (0.108 g, 47%). $^1$H NMR (300 MHz, CDCl$_3$) δ 9.4 (s, 1H), 8.62 (s, 1H), 7.93 (s, 1H), 7.65 (t, 1H), 7.54 (s, 1H), 7.39 (t, 1H), 7.32 (m, 1H), 7.20 (s, 1H), 7.01 (d, 1H), 5.89 (s, 1H), 5.06 (m, 1H), 4.03 (s, 3H), 3.41 (m, 1H), 3.18 (q, 2H), 2.9-3.08 (m, 3H), 2.44 (m, 1H), 2.2 (m, 1H), 1.33 (s, 9H); LC-MS (ESI) m/z 601 (M+H)$^+$.

Example 105

Preparation of 1-(5-tert-butylisoxazol-3-yl)-3-(3-{7-[1-(2,2-difluoroethyl)piperidin-4-yloxy]-6-methoxyquinazolin-4-yloxy}phenyl)urea Example 105A Using the procedure described in Example 103A, 1-(5-tert-butylisoxazol-3-yl)-3-[3-(7-hydroxy-6-methoxyquinazolin-4-yloxy)phenyl]urea from Example 95B (0.45 g, 1 mmol) was reacted with tert-butyl 4-hydroxypiperidine-1-carboxylate (0.242 g, 1.2 mmol) in the presence of Ph$_3$P (0.393 g, 1.5 mmol), and di t-butyl azodicarboxylate (0.345 g, 1.5 mmol) in THF (10 mL) at room temperature overnight, to afford tert-butyl 4-(4-{3-[3-(5-tert-butylisoxazol-3-yl)ureido]phenoxy}-6-methoxyquinazolin-7-yloxy)piperidine-1-carboxylate as a crude product. LC-MS (ESI) m/z 633 (M+H)$^+$.

Example 105B

Using the procedure described in Example 103B, tert-butyl 4-(4-{3-[3-(5-tert-butylisoxazol-3-yl)ureido]phenoxy}-6-methoxyquinazolin-7-yloxy)piperidine-1-carboxylate was reacted with 4.0 M HCl/1,4-dioxane at room temperature for 6 hours, to afford 1-(5-tert-butylisoxazol-3-yl)-3-{3-[6-methoxy-7-(piperidin-4-yloxy)quinazolin-4-yloxy]phenyl}urea as a crude product. LC-MS (ESI) m/z 533 (M+H)$^+$.

Example 105C

The title compound was prepared as described in Example 103C, using 1-(5-tert-butylisoxazol-3-yl)-3-{3-[6-methoxy-7-(piperidin-4-yloxy)quinazolin-4-yloxy]phenyl}urea (0.213 g, 0.4 mmol), 2,2-difluoroethyl trifluoromethanesulfonate (0.128 g. 0.6 mmol), and N,N-diisopropylethylamine (0.5 mL) in CH$_2$Cl$_2$ (10 mL) at room temperature for 4 hours, which was purified by silica gel chromatography with EtOAc/hexane as eluants to afford 1-(5-tert-butylisoxazol-3-yl)-3-(3-{7-[1-(2,2-difluoroethyl)piperidin-4-yloxy]-6-methoxyquinazolin-4-yloxy}phenyl)urea as a solid (0.011 g, 4%). $^1$H NMR (300 MHz, CDCl$_3$) δ 9.45 (s, 1H), 8.61 (s, 1H), 7.66 (t, 1H), 7.55 (s, 1H), 7.31-7.44 (m, 4H), 7.01 (d, 1H), 5.90 (tt, 1H), 5.81 (s, 1H), 4.58 (m, 1H), 4.04 (s, 3H), 2.93 (m, 2H), 2.80 (td, 2H), 2.53 (m, 2H), 2.15 (m, 2H), 2.00 (m, 2H), 1.33 (s, 9H); LC-MS (ESI) m/z 597 (M+H)$^+$.

Example 106

Preparation of 1-(5-tert-butylisoxazol-3-yl)-3-(3-{6-methoxy-7-[1-(2,2,2-trifluoroethyl)piperidin-4-yloxy]quinazolin-4-yloxy}phenyl)urea The title compound was prepared as described in Example 103C, using 1-(5-tert-butylisoxazol-3-yl)-3-{3-[6-methoxy-7-(piperidin-4-yloxy)quinazolin-4-yloxy]phenyl}urea (0.213 g, 0.4 mmol), 2,2,2-trifluoroethyl trifluoromethanesulfonate (0.139 g, 0.6 mmol), and N,N-diisopropylethylamine (0.5 mL) in CH$_2$Cl$_2$ (10 mL) at room temperature for 4 hours, which was purified by silica gel chromatography with EtOAc/hexane as eluants and preparative HPLC (C$_{18}$ column and 60-90% MeCN/H$_2$O with 0.05% AcOH) to afford 1-(5-tert-butylisoxazol-3-yl)-3-(3-{6-methoxy-7-[1-(2,2,2-trifluoroethyl)piperidin-4-yloxy]quinazolin-4-yloxy}phenyl)urea as a solid (0.027 g, 11%). $^1$H NMR (300 MHz, CDCl$_3$) δ 9.42 (s, 1H), 8.61 (s, 1H), 7.66 (t, 1H), 7.59 (m, 1H), 7.55 (s, 1H), 7.40 (t, 1H), 7.31 (m, 2H), 7.02 (d, 1H), 5.83 (s, 1H), 4.60 (m, 1H), 4.04 (s, 3H), 3.04 (q, 2H), 3.00 (m, 2H), 2.67 (m, 2H), 2.15 (m, 2H), 2.02 (m, 2H), 1.33 (s, 9H); LC-MS (ESI) m/z 615 (M+H)$^+$.

Example 107

Preparation of 1-(5-tert-butylisoxazol-3-yl)-3-(3-(6-hydroxy-7-methoxyquinazolin-4-yloxy)phenyl)urea Example 107A Step 1: A suspension of 5,4-dimethoxy-2-nitrobenzoic acid (15.0 g, 0.066 mol) in 20% potassium hydroxide solution (99 mL) was heated at 100° C. for 12 h. The reaction mixture was cooled down to 0° C. and 6N HCl was added to bring the solution to pH 3. The yellow solid was filtered and the cake washed with cold water. LC/MS: M-1: 212. The solid was dissolved in MeOH (400 mL) and HCl gas was bubbled for 2-3 min. After stirring at 65° C. for 16 h, the solvent was evaporated under vacuum. The solid was taken up in ethyl acetate and washed with sat'd NaHCO$_3$ solution. The organic phase was washed with brine and dried over MgSO$_4$ to yield methyl 5-hydroxy-4-methoxy-2-nitrobenzoate (13.01 g, 87% yield). LC-MS (ESI) m/z 228 (M+H)$^+$.

Example 107A

Step 2: To solution of methyl 5-hydroxy-4-methoxy-2-nitrobenzoate (13.0 g, 0.0572 mol) in DMF (120 mL) and benzyl chloride (7.23 ml, 0.0629 mol), K$_2$CO$_3$ (8.69 g, 0.0629 mol) and potassium iodide (0.949 g, 0.0057 mol) were added. The reaction mixture was heated at 90-95° C. overnight. The solvent was evaporated under vacuum and the residue was taken in ethyl acetate and washed with water and brine. After drying over MgSO$_4$, the solution was concentrated ad purified on silica gel column to yield methyl 5-(benzyloxy)-4-methoxy-2-nitrobenzoate (13.99 g, 77% yield). $^1$HNMR (DMSO-d$_6$): δ 7.66 (1H, s), 7.40 (6H, m), 5.27 (2H, s), 3.83 (3H, s), 3.80 (3H, s). LC-MS (ESI) m/z 318 (M+H)$^+$.

Example 107A

Step 3: To a solution of methyl 5-(benzyloxy)-4-methoxy-2-nitrobenzoate (13.48 g, 0.0425 mol) in MeOH (700 mL) at 55° C., a concentrated solution of Na$_2$S$_2$O$_4$ in water was added slowly until no more starting material was observed on TLC. The heterogeneous solution was concentrated under vacuum. The residue was treated with water (100 ml) and the mixture extracted with ethyl acetate (2×200 mL). The combined organic layers were washed with water and brine. After drying over MgSO$_4$, the solvent was evaporated and the residue was purified on silica gel column, using ethyl acetate/DCM (1/9) as eluent to yield methyl 2-amino-5-(benzyloxy)-4-methoxybenzoate. Yield: 7.36 g (60%). $^1$HNMR (DMSO-d$_6$): δ 7.34 (5H, m), 7.25 (1H, s), 6.48 (2H, s), 6.39 (1H, s), 4.91 (2H, s), 3.80 (3H, s), 3.73 (3H, s). LC-MS (ESI) m/z 288 (M+H)$^+$.

Example 107A

Step 4: A mixture of methyl 2-amino-5-(benzyloxy)-4-methoxybenzoate (7.36 g, 0.025 mol), formamide (25 mL) and acetic acid (6.25 mL) was heated at 130° C. for 24 hr. After letting cooling down to room temperature, water was added and the resulting solid was filtered and washed with plenty of cold water. The solid was dried under vacuum at 120° C. for 3 hr to yield 6-(benzyloxy)-7-methoxyquinazolin-4(3H)-one. Yield: 7.45 g (100%). $^1$HNMR (DMSO-d$_6$): δ 12.15 (1H, s), 8.05 (1H, s), 7.66 (1H, s), 7.44 (5H, m), 7.23 (1H, s), 5.28 (2H, s), 3.92 (3H, s). LC-MS (ESI) m/z 207 (M+H)$^+$.

Example 107A

Step 5: A solution of 6-(benzyloxy)-7-methoxyquinazolin-4(3H)-one (7.45 g, 0.026 mol) was heated at 4 hr under argon. The reaction mixture was concentrated to dryness, the residue taken in toluene (150 mL) and evaporated to dryness again. The solid was taken in ethyl acetate and washed with cold sat'd solution of NaHCO$_3$. The organic layer was washed with brine and dried over MgSO$_4$. After solvent evaporation the titled compound was obtained 6-(benzyloxy)-4-chloro-7-methoxyquinazoline as a light yellow solid. Yield: 6.34 g (79.8%). $^1$HNMR (DMSO-d$_6$): δ 8.89 (s, 1H), 7.40 (m, 7H), 5.34 (s, 2H), 4.00 (s, 3H).

Example 107A

Step 6: To a solution of 6-(benzyloxy)-4-chloro-7-methoxyquinazoline (3.3 g, 0.01097 mol) and 3-aminophenol (1.2 g, 0.01097 mol) in THF (70 mL), Cs$_2$CO$_3$ (5.36 g, 0.0164 mol) was added at room temperature. The reaction mixture was stirred at 75° C. for 25 hr. The mixture was filtered and the solid was washed with ethyl acetate (100 mL). The organic phase was washed with water, brine and dried over MgSO$_4$. The solvent was evaporated under vacuum and the solid was triturated with ethyl ether (20 mL). The solid was filtered and washed with ethyl ether to afford 3-(6-(benzyloxy)-7-methoxyquinazolin-4-yloxy)aniline (3.72 g, 90% yield). $^1$HNMR (DMSO-d$_6$): δ 8.55 (s, 1H), 7.66 (s, 1H,), 7.46 (m, 8H), 7.08 (t, 1H), 6.49 (d, 1H), 6.40 (m, 2H), 5.30 (s, 2H), 4.02 (s, 3H). LC-MS (ESI) m/z 508 (M+H)$^+$.

Example 107A

Step 7: A mixture of 3-(6-(benzyloxy)-7-methoxyquinazolin-4-yloxy)aniline (3.64 g, 0.00974 mol) and Pd/C (10%) in ethanol/THF (400 mL, 3/1) was hydrogenated at 1 atm. of H$_2$, at 50-55° C. for 3 h. The mixture was filtered through Celite and the filtrate was concentrated to about 100 mL. The crude was left in the fridge overnight. The solid was filtered and washed with small portion of cold ethanol to afford 4-(3-aminophenoxy)-7-methoxyquinazolin-6-ol (2.05 g, 74.3% yield). $^1$HNMR (DMSO-d$_6$): δ 10.30 (1H, s), 8.49 (1H, s), 7.46 (1H, s), 7.34 (1H, s), 7.07 (1H, m), 6.48 (1H, m), 6.40 (2H, m), 5.29 (2H, s), 3.90 (3H, s). LC-MS (ESI) m/z 284 (M+H)$^+$.

Example 107B

To a solution of 4-(3-aminophenoxy)-7-methoxyquinazolin-6-ol (2.0 g, 0.0070 mol) in DMF (10 mL), phenyl 5-tert-butylisoxazol-3-ylcarbamate (1.74 g, 0.0067 mol) was added. The reaction mixture was stirred at 60° C., overnight. The solvent was evaporated under vacuum and the residue was sonicated in the presence of ethyl ether (60 mL). The solid was filtered and washed with ethyl ether to afford 1-(5-tert-butylisoxazol-3-yl)-3-(3-(6-hydroxy-7-methoxyquinazolin-4-yloxy)phenyl)urea (2.75 g, 87.5% yield). $^1$HNMR (DMSO-d$_6$): δ 10.53 (s, 1H), 9.57 (s, 1H), 8.99 (s, 1H), 8.50 (s, 1H), 7.52 (d, 2H), 7.37 (m, 2H), 7.25 (d, 1H), 6.95 (d, 1H), 6.18 (s, 1H), 4.00 (s, 3H), 1.30 (s, 9H); LC-MS (ESI) m/z 450 (M+H)$^+$.

Example 108

Preparation of (S)-tert-butyl 3-(4-(3-(3-(5-tert-butyl-isoxazole-3-yl)ureido)phenoxy)-7-methoxyquinazolin-6-yloxy)pyrrolidine-1-carboxylate To a stirred solution of diisopropylazodicarboxylate (155 μL, 0.80 mmol) in THF (5 mL) under argon, triphenylphosphine (209 mg, 0.80 mmol) was added. After stirring 15 at room temperature, a solution of (R)-tert-butyl pyrrolidinol carboxylate (150 mg, 0.80 mmol) 1-(5-tert-butylisoxazol-3-yl)-3-(3-(6-hydroxy-7-methoxyquinazolin-4-yloxy)phenyl) urea (300 mg, 0.668 mmol) in THF (3 mL) was added. Reaction mixture was left stirring at room temperature overnight. The solvent was evaporated and the residue was purified on silica gel column, using ethyl acetate/hexane as eluent. The titled compound was obtained as a foam. Yield: 330 mg (80%). $^1$HNMR (dmso-d6): δ 9.58 (1H, s), 9.00 (1H, s), 8.57 (1H, s), 7.60 (2H, m), 7.40 (2H, m), 7.26 (1H, m), 6.98 (1H, m), 6.48 (1H, s), 5.30 (1H, m), 3.99 (3H, s), 3.50 (4H, m), 2.20 (2H, m), 1.27 (9H, s), 1.02 (H, s). LC-MS (ESI) m/z 619 (M+H)$^+$.

Example 109

Preparation of (S)-1-(5-tert-butylisoxazol-3-yl)-3-(3-(7-methoxy-6-(1-methylpyrrolidin-3-yloxy)quinazolin-4-yloxy)phenyl)urea Example 109A To a solution of (S)-tert-butyl 3-(4-(3-(3-(5-tert-butylisoxazole-3-yl)ureido)phenoxy)-7-methoxyquinazolin-6-yloxy) pyrrolidine-1-carboxylate (300 mg, ~0.40 mmol), a 4N solution of HCl in dioxane (1 ml, 4 mmol) was added. The reaction mixture was stirred at room temperature overnight. The resulting solid was filtered and washed with plenty of ethyl ether to yield (S)-1-(5-tert-butylisoxazol-3-yl)-3-(3-(7-methoxy-6-(pyrrolidin-3-yloxy)quinazolin-4-yloxy)phenyl) urea dihydrochloride (215 mg, 91%). LC-MS (ESI) m/z 519 (M+H)$^+$.

Example 109B

To a solution of (S)-1-(5-tert-butylisoxazol-3-yl)-3-(3-(7-methoxy-6-(pyrrolidin-3-yloxy)quinazolin-4-yloxy)phenyl) urea dihydrochloride (110 mg, 0.18 mmol) and acetic acid (12 μL, 0.2 mmol) in DMA (1.5 mL), a 37% aqueous solution of formaldehyde (29 μL, 0.36 mmol) and NaBH(OAc)$_3$ (57 mg, 0.27 mmol) were added at room temperature. After 2 h, the reaction mixture was diluted with water and extracted with a mixture 8/2 of ethyl acetate/THF. After drying over MgSO$_4$, the solution was evaporated and concentrated to dryness. The crude product was purified on HPLC. Yield: 82 mg (85%). $^1$HNMR (dmso-d6): δ 10.62 (1H, s), 10.10 (1H, s), 8.55 (1H, s), 7.59 (1H, s), 7.45 (1H, s), 7.37 (3H, m), 6.93 (1H, d), 6.47 (1H, s), 5.12 (1H, m), 3.99 (3H, s), 2.76 (4H, m), 2.35 (2H, m), 2.28 (3H, s), 1.25 (9H, s). LC-MS (ESI) m/z 533 (M+H)$^+$.

Example 110

Preparation of (S)-1-(5-tert-butylisoxazol-3-yl)-3-(3-(6-(1-(2,2-difluoroethyl)pyrrolidin-3-yloxy)-7-methoxyquinazolin-4-yloxy)phenyl)urea To a mixture of a solution of NaHCO$_3$ (47 mg in 1.5 mL, 0.561 mmol) and ethyl acetate (3 mL), 2,2-difluoroethyl trifluoromethanesulfonate (48 µL, 0.22 mmol) was added. After heating at 40 C, (S)-1-(5-tert-butylisoxazol-3-yl)-3-(3-(7-methoxy-6-(pyrrolidin-3-yloxy)quinazolin-4-yloxy)phenyl)urea dihydrochloride (110 mg, 0.187 mmol) was added. The reaction mixture was stirred at 40° C. for 1 h. The mixture was diluted with ethyl acetate and organic layer was washed with brine. After drying over MgSO$_4$, the solvent was evaporated and the crude product purified on silica gel, using dichloromethane/methanol as mobile phase. Yield: 40 mg (37%). $^1$HNMR (dmso-d6): δ 9.58 (1H, s), 9.00 (1H, s), 8.56 (1H, s), 7.59 (1H, s), 7.47 (1H, s), 7.40 (2H, m), 7.25 (1H, d), 6.97 (1H, d), 6.48 (1H, s), 5.15 (1H, m), 5.15 (1H, m), 3.99 (3H, s), 2.91 (6H, m), 2.40 (1H, m), 1.90 (1H, m), 1.27 (9H, s). LC-MS (ESI) m/z 583 (M+H)$^+$.

Example 111

Preparation of (S)-1-(5-tert-butylisoxazol-3-yl)-3-(3-(6-(2-hydroxy-3-(4methylpiperazin-1-yl)propoxy)-7-methoxyquinazolin-4-yloxy)phenyl)urea Example 111A Synthesis of (S)-1-(5-tert-butylisoxazol-3-yl)-3-(3-(7-methoxy-6-(oxiran-2-ylmethoxy)quinazolin-4-yloxy)phenyl)urea To a solution of 1-(5-tert-butylisoxazol-3-yl)-3-(3-(6-hydroxy-7-methoxyquinazolin-4-yloxy)phenyl)urea (120 mg, 0.267 mmol) in DMF (4 mL), Cs$_2$CO$_3$ (0.32 mmol) and (S) (+) epichlorohydrin (104 µL, 1.33 mmol) was added. The reaction mixture was reacted at 80 C under microwave condition for 2 h. The mixture was diluted with a ethyl acetate/THF (15/5) mixture and washed with water, brine and dried over MgSO4. After removal of the solvent, the titled compound was obtained as an off-white solid. Yield: 135 mg (100%). LC-MS (ESI) m/z 506 (M+H)$^+$.

Example 111B

To a solution of (S)-1-(5-tert-butylisoxazol-3-yl)-3-(3-(7-methoxy-6-(oxiran-2-ylmethoxy)quinazolin-4-yloxy)phenyl)urea (129 mg, 0.260 mmol) in DMF (2 mL), 1-methylpiperazine (144 µL, 1.30 mmol) added. The reaction mixture was stirred at 70 C for 8 h. The mixture was purified on HPLC. Yield: 28 mg (17%). $^1$HNMR (dmso-d6): δ 9.74 (1H, s), 9.18 (1H, s), 8.55 (1H, s), 7.58 (2H, s), 7.41 (2H, m), 7.26 (1H, d), 6.97 (1H, d), 6.48 (1H, s), 4.90 (1H, bs), 4.15 (2H, m), 4.00 (3H, s), 2.40 (10H, m), 2.06 (3H, s), 1.29 (9H, s). LC-MS (ESI) m/z 606 (M+H)$^+$.

Example 112

Preparation of (R)-1-(5-tert-butylisoxazol-3-yl)-3-(3-(6-(2-hydroxy-3-(4methylpiperazin-1-yl)propoxy)-7-methoxyquinazolin-4-yloxy)phenyl)urea Example 112A 1-(5-tert-butylisoxazol-3-yl)-3-(3-(6-hydroxy-7-methoxyquinazolin-4-yloxy)phenyl)urea (320 mg, 0.712 mol) and (R) (−) epichlorohydrin (288 µL, 3.56 mmol) were reacted using the same procedureas described before from Example 111A to afford (R)-1-(5-tert-butylisoxazol-3-yl)-3-(3-(7-methoxy-6-(oxiran-2-ylmethoxy)quinazolin-4-yloxy)phenyl)urea (160 mg, 44%). LC-MS (ESI) m/z 506 (M+H)$^+$.

Example 112B

Starting from (R)-1-(5-tert-butylisoxazol-3-yl)-3-(3-(7-methoxy-6-(oxiran-2-ylmethoxy)quinazolin-4-yloxy)phenyl)urea, followed the same procedure as described in Example 111B to yield (R)-1-(5-tert-butylisoxazol-3-yl)-3-(3-(6-(2-hydroxy-3-(4methylpiperazin-1-yl)propoxy)-7-methoxyquinazolin-4-yloxy)phenyl)urea (18 mg, 12%). $^1$HNMR (dmso-d6): δ 9.74 (1H, s), 9.18 (1H, s), 8.55 (1H, s), 7.58 (2H, s), 7.41 (2H, m), 7.26 (1H, d), 6.97 (1H, d), 6.48 (1H, s), 4.90 (1H, bs), 4.15 (2H, m), 4.00 (3H, s), 2.40 (10H, m), 2.06 (3H, s), 1.29 (9H, s). LC/MS: M+1: 606.

Example 113

Preparation of 1-(3-(6,7-dimethoxyquinazolin-4-yloxy)phenyl)-3-(5-phenylisoxazol-3-yl)urea Example 113A To a slurry of cesium carbonate (13.3 mmol) in THF was added 3-aminophenol (1.45 g, 13.3 mmol). After stirring 15 minutes at room temperature, 4-chloro-6,7-dimethoxyquinazoline (3.0 g, 13.3 mmol) was added and the reaction mixture heated at 50° C. overnight. The mixture was diluted with EtOAc and washed with water and brine, dried over MgSO$_4$, filtered, and concentrated in vacuo. to give 3-(6,7-dimethoxyquinazolin-4-yloxy)aniline (3.62 g, 12.2 mmol, 91%). $^1$H NMR (300 MHz, DMSO-d$_6$) δ 8.55 (s, 1H), 7.51 (s, 1H), 7.37 (s, 1H), 7.09 (t, 1H), 6.50 (d, 1H), 6.43 (s, 1H), 6.38 (d, 1H), 5.30 (br s, 2H), 3.99 (s, 3H), 3.97 (s, 3H); LC-MS (ESI) m/z 298 (M+H)$^+$.

Example 113B

5-Phenylisoxazol-3-amine (428 mg, 2.67 mmol) in tetrahydrofuran (4.8 mL) was treated with potassium carbonate (481 mg, 3.47 mmol) and phenyl choloroformate (0.67 mL, 5.3 mmol). The reaction mixture was stirred at room temperature overnight. The mixture was filtered through a celite pad, washed with ethyl acetate and concentrated to dryness. The residue was taken into chloroform, washed with brine, and the organics dried (MgSO$_4$) and concentrated. The residue was purified by silica gel chromatography (hexane/ethyl acetate 8:2) to give phenyl 5-phenylisoxazol-3-ylcarbamate (599 mg, 80%) as a white solid. $^1$H NMR (300 MHz, CDCl$_3$) δ 7.92 (bs, 1H), 7.78 (d, 2H), 7.45 (m, 6H), 7.26 (m, 2H), 7.12 (s, 1H); LC-MS (ESI) m/z 281 (M+H)$^+$.

Example 113C 3-(6,7-dimethoxyquinazolin-4-yloxy)aniline from Example 113A (90 mg, 0.3 mmol), in tetrahydrofuran (1.5 mL) was treated with N,N-diisopropylethylamine (78 µl, 0.45 mmol), 4-(dimethylamino)pyridine (1.8 mg, 0.015 mmol) and phenyl 5-phenylisoxazol-3-ylcarbamate from the previous step (126 mg, 0.45 mmol). The reaction mixture was heated to 50° C. for 2.5 h. After cooling to room temperature, the mixture was partitioned between dichloromethane and a saturated solution of sodium bicarbonate. The water phase was back extracted three times with dichloromethane and the organics combined and dried (MgSO$_4$). Concentration under reduced pressure gave a residue which was purified by preparative HPLC (phenylhexyl reverse phase column). The obtained solid was triturated with anhydrous diethyl ether to afford 1-(3-(6,7-dimethoxyquinazolin-4-yloxy)phenyl)-3-(5-phenylisoxazol-3-yl)urea as a white solid (47.16 mg, 32%). $^1$H NMR (300 MHz, DMSO-d$_6$) δ 9.75 (s, 1H), 9.08 (s, 1H), 8.58 (s, 1H), 7.86 (d, 2H), 7.87-7.51 (m, 4H), 7.51-7.40 (m, 2H), 7.31-7.21 (m, 3H), 7.00 (d, 1H), 4.00 (s, 6H); LC-MS (ESI) m/z 484 (M+H)$^+$.

Example 114

Preparation of 1-(3-(6,7-dimethoxyquinazolin-4-yloxy)phenyl)-3-(3-phenylisoxazol-5-yl)urea Example 114A 3-Phenylisoxazol-5-amine (456 mg, 2.85 mmol) was prepared according to the procedure described in Example 113B by using an excess of phenyl chloroformate (10.2 mmol). Purification by silica gel chromatography (hexane/ethyl acetate 8:2) gave phenyl 3-phenylisoxazol-5-ylcarbamate (675 mg, 84%) as a white solid. $^1$H NMR (300 MHz, CDCl$_3$) δ 7.80 (d, 2H), 7.47-7.40 (m, 5H), 7.32-7.19 (m, 3H), 6.54 (s, 1H); LC-MS (ESI) m/z 281 (M+H)$^+$.

Example 114B

The title compound was prepared according to the procedure described in Example 113C, by using compound 3-(6,7-dimethoxyquinazolin-4-yloxy)aniline from Example 113A (90 mg, 0.3 mmol) and compound phenyl 3-phenylisoxazol-5-ylcarbamate from the previous step (126 mg, 0.45 mmol) to afford 1-(3-(6,7-dimethoxyquinazolin-4-yloxy)phenyl)-3-(3-phenylisoxazol-5-yl)urea as a white solid (63.34 mg, 44%). $^1$H NMR (300 MHz, DMSO-d$_6$) δ 10.4 (s, 1H), 9.14 (s, 1H), 8.5 (s, 1H), 7.83 (d, 2H), 7.83-7.48 (m, 7H), 7.42 (d, 1H), 7.00 (d, 1H), 6.56 (s, 1H), 4.00 (s, 6H); LC-MS (ESI) m/z 484 (M+H)$^+$.

Example 115

Preparation of 1-(3-(6,7-dimethoxyquinazolin-4-ylthio)phenyl)-3-(3-methoxy-5-(trifluoromethyl)phenyl)urea Example 115A
Step 1: 1-Methoxy-3-nitro-5-(trifluoromethyl)benzene (1.33 g, 6.0 mmol) was reacted according to the procedure in Example 16A Step 3 to give 3-methoxy-5-(trifluoromethyl)aniline (1.11 g, 5.8 mmol, 97%). LC-MS (ESI) m/z 192 (M+H)$^+$.

Example 115A

Step 2: To THF was added 3-methoxy-5-(trifluoromethyl)aniline (1.10 g, 5.7 mmol), potassium carbonate (2 equivalents), phenyl chloroformate (3 equivalents) and 4-dimethylaminopyridine (0.1 equivalent) and the reaction was stirred at room temperature overnight. The mixture was diluted with EtOAc, filtered, concentrated in vacuo, and purified by silica gel column chromatography (5-15% EtOAc/hexanes) to give phenyl 3-methoxy-5-(trifluoromethyl)phenylcarbamate (1.02 g, 3.28 mmol, 57%). $^1$H NMR (300 MHz, DMSO-d$_6$) δ 10.59 (s, 1H), 7.50-7.35 (m, 4H), 7.31-7.22 (m, 3H), 6.94 (s, 1H), 3.81 (s, 3H); LC-MS (ESI) m/z 312 (M+H)$^+$.

Example 115B

3-Aminothiophenol (1.42 mL, 13.3 mmol) and 4-chloro-6,7-dimethoxyquinazoline (3.0 g, 13.3 mmol) were reacted using the procedure described in Example 46 to give 3-(6,7-dimethoxyquinazolin-4-ylthio)aniline (4.32 g, 13.8 mmol, 100% (wet with H$_2$O)). $^1$H NMR (300 MHz, DMSO-d$_6$) δ 8.70 (s, 1H), 7.33 (s, 1H), 7.31 (s, 1H), 7.13 (t, 1H), 6.80 (s, 1H), 6.73 (d, 1H), 6.68 (d, 1H), 5.34 (br s, 2H), 3.98 (s, 3H), 3.97 (s, 3H); LC-MS (ESI) m/z 314 (M+H)$^+$.

Example 115C

To 3-(6,7-dimethoxyquinazolin-4-ylthio)aniline from the previous step (94 mg, 0.3 mmol) in THF (3 mL) was added phenyl 3-methoxy-5-(trifluoromethyl)phenylcarbamate from Example 115A (140 mg, 0.45 mmol), diisopropylethylamine (80 uL, 0.45 mmol), and 4-dimethylaminopyridine (4 mg, 0.03 mmol). The solution was stirred at 50° C. overnight, allowed to cool to room temperature, and diluted with EtOAc. The solid was then filtered to give 14346,7-dimethoxyquinazolin-4-ylthio)phenyl)-3-(3-methoxy-5-(trifluoromethyl)phenyl)urea (89 mg, 0.17 mmol, 56%). $^1$H NMR (300 MHz, DMSO-d$_6$) δ 9.12 (s, 1H), 9.02 (s, 1H), 8.70 (s, 1H), 7.84 (s, 1H), 7.55 (d, 1H), 7.48 (s, 1H), 7.44 (t, 1H), 7.35 (s, 1H), 7.34 (s, 1H), 7.29-7.24 (m, 2H), 6.85 (s, 1H), 3.99 (s, 6H), 3.81 (s, 3H); LC-MS (ESI) m/z 531 (M+H)$^+$.

Example 116

Preparation of 1-(3-(6,7-dimethoxyquinazolin-4-yloxy)phenyl)-3-(3-methoxy-5-(trifluoromethyl)phenyl)urea 3-(6,7-dimethoxyquinazolin-4-yloxy)aniline from Example 113A (89 g, 0.3 mmol) and phenyl 3-methoxy-5-(trifluoromethyl)phenylcarbamate from Example 115A (140 mg, 0.45 mmol) were reacted using the procedure in Example 115C to give 1-(3-(6,7-dimethoxyquinazolin-4-yloxy)phenyl)-3-(3-methoxy-5-(trifluoromethyl)phenyl)urea (71 mg, 0.14 mmol, 46%). $^1$H NMR (300 MHz, DMSO-d$_6$) δ 9.19 (s, 1H), 9.08 (s, 1H), 8.56 (s, 1H), 7.62-7.55 (m, 2H), 7.48 (s, 1H), 7.45-7.37 (m, 2H), 7.31-7.24 (m, 2H), 6.95 (d, 1H), 6.84 (s, 1H), 4.00 (s, 3H), 3.99 (s, 3H), 3.80 (s, 3H); LC-MS (ESI) m/z 515 (M+H)$^+$.

Example 117

Preparation of 1-(3-(6-methoxy-7-(2-methoxyethoxy)quinazolin-4-yloxy)phenyl)-3-(3-(2-methoxyethoxy)-5-(trifluoromethyl)phenyl)urea Example 117A Step 1: To 1-methoxy-3-nitro-5-(trifluoromethyl)benzene (2.21 g, 10.0 mmol) in DCM at 0° C. was added BBr$_3$ (10 equivalents) dropwise over 5 minutes. The solution was allowed to warm to r.t overnight at which point it was quenched with sat. aqueous NaHCO₃ and extracted with EtOAc. The organic layer was washed with H₂O and brine, dried over MgSO₄, filtered, and concentrated in vacuo to give 3-nitro-5-(trifluoromethyl)phenol (778 mg, 3.76 mmol, 37%), ¹H NMR (300 MHz, DMSO-d₆) δ 11.22 (s, 1H), 7.90 (s, 1H), 7.81 (s, 1H), 7.51 (s, 1H); LC-MS (ESI) m/z 208 (M+H)⁺.

Example 117A

Step 2: 3-nitro-5-(trifluoromethyl)phenol (770 mg, 3.72 mmol) and 1-bromo-2-methoxyethane (1.75 mL, 19 mmol) were reacted using the procedure described in Example 40A Step 3 to give 1-(2-methoxyethoxy)-3-nitro-5-(trifluoromethyl)benzene (456 mg, 1.72 mmol, 46%). ¹H NMR (300 MHz, DMSO-d₆) δ 8.05 (s, 1H), 8.02 (s, 1H), 7.80 (s, 1H), 4.36 (dd, 2H), 3.71 (dd, 2H), 3.31 (s, 3H); LC-MS (ESI) m/z 266 (M+H)⁺.

Example 117A

Step 3: The procedure described in Example 16A Step 3 was used, but substituting the benzoate with 1-(2-methoxyethoxy)-3-nitro-5-(trifluoromethyl)benzene (450 mg, 1.70 mmol) to give 3-(2-methoxyethoxy)-5-(trifluoromethyl)aniline (419 mg, 1.76 mmol, 100%), ¹H NMR (300 MHz, DMSO-d₆) δ 6.49 (s, 1H), 6.39 (s, 1H), 6.36 (s, 1H), 5.73 (br s, 2H), 4.05 (dd, 2H), 3.63 (dd, 2H), 3.29 (s, 3H); LC-MS (ESI) m/z 236 (M+H)⁺.

Example 117A

Step 4: 3-(2-methoxyethoxy)-5-(trifluoromethyl)aniline (415 mg, 1.75 mmol) was reacted as described in Example 115A Step 2 to give phenyl 3-(2-methoxyethoxy)-5-(trifluoromethyl)phenylcarbamate (524 mg, 1.48 mmol, 84%). LC-MS (ESI) m/z 356 (M+H)⁺.

Example 117B

Using the procedure described in Example 46, 3-aminophenol (1.21 g, 11.1 mmol) and 4-chloro-6-methoxy-7-(2-methoxyethoxy)quinazoline (2.85 g, 10.6 mmol) were reacted to give 3-(6-methoxy-7-(2-methoxyethoxy)quinazolin-4-yloxy)aniline (1.22 g, 3.58 mmol, 34%). ¹H NMR (300 MHz, DMSO-d₆) δ 8.54 (s, 1H), 7.52 (s, 1H), 7.39 (s, 1H), 7.09 (t, 1H), 6.50 (d, 1H), 6.53 (s, 1H), 6.40 (d, 1H), 5.30 (br s, 2H), 4.33 (t, 2H), 3.97 (s, 3H), 3.77 (t, 2H), 3.31 (s, 3H); LC-MS (ESI) m/z 342 (M+H)⁺.

Example 117C 3-(6-methoxy-7-(2-methoxyethoxy)quinazolin-4-yloxy) aniline from the previous step (102 mg, 0.3 mmol) was reacted with phenyl 3-(2-methoxyethoxy)-5-(trifluoromethyl)phenylcarbamate from Example 117A (160 mg, 0.45 mmol) in the manner described in Example 115C. The final product was purified by column chromatography (25-100% EtOAc/hexanes then 5-10% MeOH/DCM) to give 1-(3-(6-methoxy-7-(2-methoxyethoxy)quinazolin-4-yloxy)phenyl)-3-(3-(2-methoxyethoxy)-5-(trifluoromethyl)phenyl)urea (137 mg, 0.23 mmol, 76%). ¹H NMR (300 MHz, DMSO-d₆) δ 9.10 (s, 1H), 9.04 (s, 1H), 8.56 (s, 1H), 7.61 (s, 1H), 7.57 (s, 1H), 7.49 (s, 1H), 7.45-7.38 (m, 2H), 7.32-7.26 (m, 2H), 6.96 (d, 1H), 6.87 (s, 1H), 4.37-4.31 (m, 2H), 4.19-4.12 (m, 2H), 4.00 (s, 3H), 3.80-3.73 (m, 2H), 3.70-3.63 (m, 2H), 3.36 (s, 3H), 3.31 (s, 3H); LC-MS (ESI) m/z 603 (M+H)⁺.

Example 118

Preparation of 1-(3-tert-butylphenyl)-3-(3-(6,7-dimethoxyquinazolin-4-yloxy)phenyl)urea Example 118A To THF (15 mL) was added 3-tert-butylaniline (447 mg, 3 mmol), potassium carbonate (828 mg, 6 mmol), phenyl chloroformate (1.13 mL, 9 mmol), and dimethylaminopyridine (36 mg, 0.30 mmol) and the reaction stirred at room temperature overnight. The mixture was diluted with EtOAc, filtered, concentrated in vacuo, and purified by silica gel column chromatography (5-15% EtOAc/hexanes) to give phenyl 3-tert-butylphenylcarbamate (458 mg, 1.70 mmol, 57%). ¹H NMR (300 MHz, DMSO-d₆) δ 10.14 (s, 1H), 7.59 (s, 1H), 7.49-7.10 (m, 7H), 7.08 (d, 1H), 1.25 (s, 9H); LC-MS (ESI) m/z 270 (M+H)⁺.

Example 118B

The title compound was prepared from 3-(6,7-dimethoxyquinazolin-4-yloxy)aniline from Example 113A (90 mg, 0.3 mmol) and phenyl 3-tert-butylphenylcarbamate from the previous step (114 mg, 0.42 mmol) using Example 115C. The final product was purified by silica gel column chromatography (25-100% EtOAc/hexanes) to give 1-(3-tert-butylphenyl)-3-(3-(6,7-dimethoxyquinazolin-4-yloxy)phenyl)urea (83 mg, 0.18 mmol, 58%). ¹H NMR (300 MHz, DMSO-d₆) δ 8.83 (s, 1H), 8.70 (s, 1H), 8.57 (s, 1H), 7.61 (s, 1H), 7.57 (s, 1H), 7.50-7.36 (m, 3H), 7.31-7.14 (m, 3H), 7.05-6.86 (m, 2H), 4.00 (s, 6H), 1.28 (s, 9H); LC-MS (ESI) m/z 473 (M+H)⁺.

Example 119

Preparation of 1-(3-tert-butylphenyl)-3-(3-(6-methoxy-7-(2-methoxyethoxy)quinazolin-4-yloxy)phenyl)urea The title compound was prepared from 3-(6-methoxy-7-(2-methoxyethoxy)quinazolin-4-yloxy)aniline from Example 117B (103 mg, 0.3 mmol) and phenyl 3-tert-butylphenylcarbamate from Example 118A (114 mg, 0.42 mmol) using Example 115C. The final product was purified by silica gel column chromatography (25-100% EtOAc/hexanes) to give 1-(3-tert-butylphenyl)-3-(3-(6-methoxy-7-(2-methoxyethoxy)quinazolin-4-yloxy)phenyl)urea (74 mg, 0.14 mmol, 48%). ¹H NMR (300 MHz, DMSO-d₆) δ 8.83 (s, 1H), 8.70 (s, 1H), 8.56 (s, 1H), 7.61-7.58 (m, 2H), 7.49-7.36 (m, 3H), 7.27-7.16 (m, 3H), 7.03 (d, 1H), 6.92 (d, 1H), 4.38-4.32 (m, 2H), 4.00 (s, 3H), 3.81-3.73 (m, 2H), 3.33 (s, 3H), 1.26 (s, 9H); LC-MS (ESI) m/z 517 (M+H)⁺.

Example 120

Preparation of 1-(3-tert-butylphenyl)-3-(3-(6,7-dimethoxyquinazolin-4-ylthio)phenyl)urea 3-(6,7-dimethoxyquinazolin-4-ylthio)aniline from Example 115B (94 mg, 0.3 mmol) and phenyl 3-tert-butylphenylcarbamate from Example 118A (114 mg, 0.42 mmol) were reacted as described in Example 115C to give 1-(3-tert-butylphenyl)-3-(3-(6,7-dimethoxyquinazolin-4- ylthio)phenyl)urea (71 mg, 0.14 mmol, 48%). $^1$H NMR (300 MHz, DMSO-$d_6$) δ 8.84 (s, 1H), 8.70 (s, 2H), 7.84 (s, 1H), 7.53-7.39 (m, 3H), 7.35 (s, 2H), 7.28-7.17 (m, 3H), 7.02 (d, 1H), 3.99 (s, 6H), 1.27 (s, 9H); LC-MS (ESI) m/z 489 (M+H)$^+$.

Example 121

Preparation of 1-(3-(6,7-dimethoxyquinazolin-4-yloxy)phenyl)-3-(5-methylisoxazol-3-yl)urea Example 121A: 5-methylisoxazol-3-amine (490 mg, 5.0 mmol) was reacted as described in Example 118A to give phenyl 5-methylisoxazol-3-ylcarbamate (425 mg, 1.95 mmol, 39%). $^1$H NMR (300 MHz, DMSO-$d_6$) δ 11.14 (s, 1H), 7.45 (t, 2H), 7.29 (d, 1H), 7.21 (d, 2H), 6.47 (s, 1H), 2.38 (s, 3H); LC-MS (ESI) m/z 219 (M+H)$^+$.

Example 121B 3-(6,7-dimethoxyquinazolin-4-yloxy)aniline from Example 113A (89 mg, 0.3 mmol) and phenyl 5-methylisoxazol-3-ylcarbamate from the previous step (98 mg, 0.42 mmol) were reacted using Example 115C to give 1-(3-(6,7-dimethoxyquinazolin-4-yloxy)phenyl)-3-(5-methylisoxazol-3-yl)urea (31 mg, 0.074 mmol, 25%). $^1$H NMR (300 MHz, DMSO-$d_6$) δ 9.53 (s, 1H), 9.01 (s, 1H), 8.56 (s, 1H), 7.57 (s, 1H), 7.55 (s, 1H), 7.45-7.35 (m, 2H), 7.26 (d, 1H), 6.97 (d, 1H), 6.51 (s, 1H), 3.99 (s, 6H), 2.35 (s, 3H); LC-MS (ESI) m/z 422 (M+H)$^+$.

Example 122

Preparation of 1-(3-(6,7-dimethoxyquinazolin-4-yloxy)phenyl)-3-(3-isopropylisoxazol-5-yl)urea Example 122A Step 1: A stirred suspension of sodium hydride (1.95 g, 60% dispersion in mineral oil, 48.75 mmol) in dry tetrahydrofuran (25 mL), was heated to 75° C. To this was added a mixture of methyl isobutyrate (3.19 g, 31.25 mmol) and dry acetonitrile (2.56 mL, 48.75 mmol), dropwise over the course of 45 mins. The resulting pale yellow suspension was heated at 70° C. for a further 15 h. After cooling to room temperature, the reaction mixture was poured into water (150 mL) and the resulting solution was extracted with diethyl ether (2×100 mL). The aqueous layer was separated, acidified to pH 2 with aqueous 2N hydrochloric acid and extracted with diethyl ether (2×100 mL). The combined ether layers were dried over MgSO$_4$ then concentrated under reduced pressure to afford 4-methyl-3-oxopentanenitrile as a yellow oil (2.71 g, 78%) which was used in the next step without further purification. $^1$H NMR (300 MHz, CDCl$_3$) δ 3.53 (s, 2H), 2.81 (septet, J=6 Hz, 1H), 1.21 (d, J=6 Hz, 6H).

Example 122A

Step 2: To a stirred solution of sodium hydroxide (238 mg, 5.95 mmol) and 4-methyl-3-oxopentanenitrile from the previous step (600 mg, 5.41 mmol) in a mixture of water (5 mL) and ethanol (5 mL), was added hydroxylamine sulfate (977 mg, 5.95 mmol). The reaction mixture was adjusted to pH 7.5 with aqueous 1N sodium hydroxide solution, then heated to 80° C. for 15 h. After cooling to room temperature the solvent was removed under reduced pressure. The resulting solid was partitioned between water (50 mL) and dichloromethane (50 mL). The organic layer was separated, washed with brine (50 mL), dried over MgSO$_4$, then concentrated under reduced pressure to afford 3-isopropylisoxazol-5-amine as a cream solid (530 mg, 78%) which was used in the next step without further purification. $^1$H NMR (300 MHz, CDCl$_3$) δ 5.00 (s, 1H), 4.39 (brs, 2H), 2.89 (septet, J=6 Hz, 1H), 1.23 (d, J=6 Hz, 6H); LC-MS (ESI) m/z 127 (M+H)$^+$.

Example 122A

Step 3: To a stirred mixture of 3-isopropylisoxazole-5-amine (250 mg, 1.98 mmol) and potassium carbonate (634 mg, 4.59 mmol) in dry tetrahydrofuran (6 mL) was added phenyl chloroformate (341 mg, 2.18 mmol). The reaction mixture was stirred at room temperature for 3.5 h, then additional phenyl chloroformate (341 mg, 2.18 mmol) was added and stirring was continued for a further 15 h. The resulting mixture was partitioned between water (50 mL) and dichloromethane (50 mL). The organic layer was separated, washed with brine (50 mL), dried over MgSO$_4$, then concentrated under reduced pressure to give a yellow oil. Purification via silica gel chromatography eluting with 4% to 40% ethyl acetate in hexanes afforded phenyl 3-isopropylisoxazol-5-ylcarbamate as a colorless solid (330 mg, 68%). $^1$H NMR (300 MHz, CDCl$_3$) δ 7.76 (brs, 1H), 7.40-7.45 (m, 2H), 7.18-7.31 (m, 3H), 6.07 (s, 1H), 3.02 (septet, J=6 Hz, 1H), 1.28 (d, J=6 Hz, 6H); LC-MS (ESI) m/z 247 (M+H)$^+$.

Example 122B

A stirred solution of 3-(6,7-dimethoxyquinazolin-4-yloxy)aniline from Example 113A (89 mg, 0.30 mmol), phenyl 3-isopropylisoxazol-5-ylcarbamate from the previous step (89 mg, 0.36 mmol), N,N-diisopropylethylamine (58 mg, 0.45 mmol) and 4-(dimethylamino)pyridine (1.8 mg, 0.015 mmol) in dry tetrahydrofuran (1.5 mL), was heated at 50° C. for 30 mins. After cooling to room temperature, concentration under reduced pressure gave a residue which was partitioned between water (50 mL) and dichloromethane (50 mL). The organic layer was separated, washed with brine (50 mL), dried over MgSO$_4$ and concentrated under reduced pressure. The residue was purified by preparative HPLC (using phenylhexyl reverse phase column, eluted with gradient of solvent B=0.05% HOAC/CH$_3$CN and solvent A=0.05% HOAc/H$_2$O) to afford 1-(3-(6,7-dimethoxyquinazolin-4-yloxy)phenyl)-3-(3-isopropylisoxazol-5-yl)urea as a colorless solid (25 mg, 19%). $^1$H NMR (300 MHz, DMSO-$d_6$) δ 10.30 (brs, 1H), 9.14 (s, 1H), 8.56 (s, 1H), 7.57 (s, 2H), 7.39-7.44 (m, 2H), 7.31 (m, 1H), 6.99 (m, 1H), 5.99 (s, 1H), 4.00 (s, 6H), 2.90 (septet, J=6 Hz, 1H), 1.19 (d, J=6 Hz, 6H); LC-MS (ESI) m/z 450 (M+H)$^+$.

Example 123

Preparation of 1-(3-(6,7-dimethoxyquinazolin-4-yloxy)phenyl)-3-(3-(tetrahydro-2H-pyran-4-yl)isoxazol-5-yl)urea Example 123A Step 1: Prepared from methyl tetrahydropyran-4-carboxylate (3 g, 20.80 mmol) according to the method described for 4-methyl-3-oxopentanenitrile in Example 122A Step 1, to afford 3-oxo-3-(tetrahydro-2H-pyran-4-yl)propanenitrile as a yellow oil (760 mg, 24%) which was used in the next step without further purification. $^1$H NMR (300 MHz, CDCl$_3$) δ

3.96-4.05 (m, 2H), 3.52 (s, 1H), 3.42-3.50 (m, 2H), 2.82 and 2.59 (2×m, 1H), 1.67-1.90 (m, 4H).

Example 123A

Step 2: Prepared from 3-oxo-3-(tetrahydro-2H-pyran-4-yl)propanenitrile (350 mg, 2.29 mmol) according to the method described for 3-isopropylisoxazol-5-amine in Example 122A Step 2, to afford 3-(tetrahydro-2H-pyran-4-yl)isoxazol-5-amine as a colorless solid (170 mg, 44%) which was used in the next step without further purification. $^1$H NMR (300 MHz, CDCl$_3$) δ 5.01 (s, 1H), 4.40 (brs, 2H), 4.02-4.05 (m, 2H), 3.46-3.55 (m, 2H), 2.87 (m, 1H), 1.71-1.84 (m, 4H); LC-MS (ESI) m/z 169 (M+H)$^+$.

Example 123A

Step 3: Prepared from 3-(tetrahydro-2H-pyran-4-yl)isoxazol-5-amine (170 mg, 1.01 mmol) according to the method described for phenyl 3-isopropylisoxazol-5-ylcarbamate in Example 122A Step 3, to afford phenyl 3-(tetrahydro-2H-pyran-4-yl)isoxazol-5-ylcarbamate as a colorless solid (164 mg, 56%). $^1$H NMR (300 MHz, CDCl$_3$) δ 7.93 (brs, 1H), 7.39-7.45 (m, 2H), 7.18-7.32 (m, 3H), 6.09 (s, 1H), 4.02-4.08 (m, 2H), 3.48-3.57 (m, 2H), 2.96 (m, 1H), 1.78-1.89 (m, 4H); LC-MS (ESI) m/z 289 (M+H)$^+$.

Example 123B 3-(6,7-dimethoxyquinazolin-4-yloxy)aniline from Example 113A (89 mg, 0.3 mmol) was reacted with phenyl 3-(tetrahydro-2H-pyran-4-yl)isoxazol-5-ylcarbamate (104 mg, 0.36 mmol) according to the method described for 1-(3-(6,7-dimethoxyquinazolin-4-yloxy)phenyl)-3-(3-isopropylisoxazol-5-yl)urea in Example 122B to afford 1-(3-(6,7-dimethoxyquinazolin-4-yloxy)phenyl)-3-(3-(tetrahydro-2H-pyran-4-yl)isoxazol-5-yl)urea as a cream solid (68 mg, 46%). $^1$H NMR (300 MHz, DMSO-d$_6$) δ 10.25 (brs, 1H), 9.07 (s, 1H), 8.56 (s, 1H), 7.56-7.58 (m, 2H), 7.39-7.44 (m, 2H), 7.31 (m, 1H), 6.99 (m, 1H), 6.01 (s, 1H), 3.99-4.00 (2×s, 6H), 3.86-3.90 (m, 2H), 3.40-3.46 (m, 2H), 2.90 (m, 1H), 1.69-1.76 (m, 2H), 1.60-1.69 (m, 2H); LC-MS (ESI) m/z 492 (M+H)$^+$.

Example 124

Preparation of 1-(3-cyclopropylisoxazol-5-yl)-3-(3-(6,7-dimethoxyquinazolin-4-yloxy)phenyl)urea Example 124A Step 1: Prepared from methyl cyclopropane carboxylate (3.13 g, 31.25 mmol) according to the method described for 4-methyl-3-oxopentanenitrile Example 122A Step 1, to afford 3-cyclopropyl-3-oxopentanenitrile as a yellow oil (2.12 g, 62%) which was used in the next step without further purification. $^1$H NMR (300 MHz, CDCl$_3$) δ 3.63 (s, 2H), 2.12 (m, 1H), 1.18-1.25 (m, 2H), 1.10-1.16 (m, 2H).

Example 124A

Step 2: Prepared from 3-cyclopropyl-3-oxopentanenitrile (1 g, 9.17 mmol) according to the method described for 3-isopropylisoxazol-5-amine in Example 122A Step 2, to afford 3-cyclopropylisoxazol-5-amine as a yellow oil (760 mg, 67%) which was used in the next step without further purification. $^1$H NMR (300 MHz, CDCl$_3$) δ 4.78 (s, 1H), 4.37 (brs, 2H), 1.85 (m, 1H), 0.93-0.99 (m, 2H), 0.75-0.81 (m, 2H); LC-MS (ESI) m/z 125 (M+H)$^+$.

Example 124A

Step 3: Prepared from 3-cyclopropylisoxazol-5-amine (300 mg, 2.42 mmol) according to the method described for phenyl 3-isopropylisoxazol-5-ylcarbamate in Example 122A Step 3, to afford phenyl 3-cyclopropylisoxazol-5-ylcarbamate as a yellow oil (420 mg, 71%). $^1$H NMR (300 MHz, CDCl$_3$) δ 7.99 (brs, 1H), 7.39-7.44 (m, 2H), 7.29 (m, 1H), 7.15-7.20 (m, 2H), 5.84 (s, 1H), 1.98 (m, 1H), 1.01-1.05 (m, 2H), 0.82-0.88 (m, 2H); LC-MS (ESI) m/z 245 (M+H)$^+$.

Example 124B 3-(6,7-dimethoxyquinazolin-4-yloxy)aniline from Example 113A (89 mg, 0.3 mmol) and phenyl 3-cyclopropylisoxazol-5-ylcarbamate from the previous step (88 mg, 0.36 mmol) were reacted according to the method described for 1-(3-(6,7-dimethoxyquinazolin-4-yloxy)phenyl)-3-(3-isopropylisoxazol-5-yl)urea in Example 122B to afford 1-(3-cyclopropylisoxazol-5-yl)-3-(3-(6,7-dimethoxyquinazolin-4-yloxy)phenyl)urea as a colorless solid (65 mg, 49%). $^1$H NMR (300 MHz, DMSO-d$_6$) δ 10.17 (brs, 1H), 9.05 (brs, 1H), 8.56 (s, 1H), 7.56 (s, 2H), 7.38-7.44 (m, 2H), 7.29 (m, 1H), 6.99 (m, 1H), 5.77 (s, 1H), 3.98-4.00 (2×s, 6H), 1.91 (m, 1H), 0.94-0.99 (m, 2H), 0.71-0.75 (m, 2H); LC-MS (ESI) m/z 448 (M+H)$^+$.

Example 125

Preparation of 1-(3-(2-cyanopropan-2-yl)isoxazol-5-yl)-3-(3-(6,7-dimethoxyquinazolin-4-yloxy)phenyl)urea Example 125A Step 1: Prepared from ethyl 2-cyano-2-methylpropanoate (3 g, 21.25 mmol) according to the method described for 4-methyl-3-oxopentanenitrile in Example 122A Step 1, to afford 2,2-dimethyl-3-oxopentanedinitrile as a yellow oil (1.40 g, 48%) which was used in the next step without further purification. $^1$H NMR (300 MHz, CDCl$_3$) δ 3.98 (s, 2H), 1.60 (s, 6H).

Example 125A

Step 2: Prepared from 2,2-dimethyl-3-oxopentanedinitrile (500 mg, 3.68 mmol) and hydroxylamine sulfate (332 mg, 2.02 mmol) according to the method described for 3-isopropylisoxazol-5-amine in Example 122A Step 2. Purification via silica gel chromatography eluting with 5% to 60% ethyl acetate in hexanes, afforded 2-(5-aminoisoxazol-3-yl)-2-methylpropanenitrile as a colorless solid (130 mg, 23%). $^1$H NMR (300 MHz, CDCl$_3$) δ 5.22 (s, 1H), 4.58 (brs, 2H), 1.72 (s, 6H); LC-MS (ESI) m/z 152 (M+H)$^+$.

Example 125A

Step 3: Prepared from 2-(5-aminoisoxazol-3-yl)-2-methylpropanenitrile (130 mg, 0.861 mmol) according to the method described for phenyl 3-isopropylisoxazol-5-ylcarbamate in Example 122A Step 3, to afford phenyl 3-(2-cyanopropan-2-yl)isoxazol-5-ylcarbamate as a colorless solid (93 mg, 40%). $^1$H NMR (300 MHz, CDCl$_3$) δ 7.82 (brs, 1H), 7.41-7.46 (m, 2H), 7.32 (m, 1H), 7.18-7.21 (m, 2H), 6.29 (s, 1H), 1.83 (s, 6H); LC-MS (ESI) m/z 272 (M+H)$^+$.

Example 125B

Prepared from 3-(6,7-dimethoxyquinazolin-4-yloxy)aniline from Example 113A (89 mg, 0.30 mmol) and the carbamate from the previous step (90 mg, 0.332 mmol) according to the method described for 1-(3-(6,7-dimethoxyquinazolin-4-yloxy)phenyl)-3-(3-isopropylisoxazol-5-yl)urea in Example 122B, except the reaction mixture was stirred at room temperature for 3 h. Purification via silica gel chromatography eluting with 100% dichloromethane to 10% methanol in dichloromethane afforded 1-(3-(2-cyanopropan-2-yl)isoxazol-5-yl)-3-(3-(6,7-dimethoxyquinazolin-4-yloxy)phenyl)urea as a colorless solid (55 mg, 39%). $^1$H NMR (300 MHz, DMSO-d$_6$) δ 10.51 (brs, 1H), 9.12 (brs, 1H), 8.57 (s, 1H), 7.56-7.57 (m, 2H), 7.31-7.45 (m, 3H), 7.01 (m, 1H), 6.27 (s, 1H), 4.00 (s, 6H), 1.68 (s, 6H); LC-MS (ESI) m/z 475 (M+H)$^+$.

Example 126

Preparation of 1-(3-(6,7-dimethoxyquinazolin-4-yloxy)phenyl)-3-(3-(2-fluoropropan-2-yl)isoxazol-5-yl)urea 3-(6,7-dimethoxyquinazolin-4-yloxy)aniline from Example 113A (89 mg, 0.3 mmol) and phenyl 3-(2-fluoropropan-2-yl)isoxazol-5-ylcarbamate from Example 42A (95 mg, 0.36 mmol) were reacted according to the method described for 143-(6,7-dimethoxyquinazolin-4-yloxy)phenyl)-3-(3-isopropylisoxazol-5-yl)urea in Example 122B to afford 1-(3-(6,7-dimethoxyquinazolin-4-yloxy)phenyl)-3-(3-(2-fluoropropan-2-yl)isoxazol-5-yl)urea as a colorless solid (63 mg, 45%). $^1$H NMR (300 MHz, DMSO-d$_6$) δ 10.50 (brs, 1H), 9.15 (s, 1H), 8.56 (s, 1H), 7.57-7.58 (m, 2H), 7.40-7.45 (m, 2H), 7.32 (m, 1H), 7.00 (m, 1H), 6.14 (s, 1H), 3.99-4.00 (2×s, 6H), 1.67 (d, J=21 Hz, 6H); LC-MS (ESI) m/z 468 (M+H)$^+$.

Example 127

Preparation of 1-(3-(6,7-dimethoxyquinazolin-4-yloxy)phenyl)-3-(5-(1-methylcyclopropyl)isoxazol-3-yl)urea Example 127A Step 1: Prepared from methyl 1-methylcyclopropane-1-carboxylate (3 g, 26.28 mmol) according to the method described in Example 122A Step 1 for 4-methyl-3-oxopentanenitrile to afford 3-(1-methylcyclopropyl)-3-oxopentanenitrile as a yellow oil (2.28 g, 71%) which was taken onto the next step without further purification. $^1$H NMR (300 MHz, CDCl$_3$) δ 3.59 (s, 2H), 1.40 (s, 3H), 1.33-1.37 (m, 2H), 0.89-0.91 (m, 2H).

Example 127A Step 2: Prepared from 3-(1-methylcyclopropyl)-3-oxopentanenitrile (1 g, 8.13 mmol) according to the method described for 5-(1-methoxy-2-methylpropan-2-yl)isoxazol-3-amine. Purification via silica gel chromatography eluting with 12% to 60% ethyl acetate in hexanes afforded 5-(1-methylcyclopropyl)isoxazol-3-amine as a colorless solid (80 mg, 7%). $^1$H NMR (300 MHz, CDCl$_3$) δ 5.51 (s, 1H), 3.90 (brs, 2H), 1.40 (s, 3H), 1.17 (m, 2H), 0.79 (m, 2H); LC-MS (ESI) m/z 139 (M+H)$^+$.

Example 127A

Step 3: Prepared from 5-(1-methylcyclopropyl)isoxazol-3-amine (80 mg, 0.58 mmol) according to the method described for phenyl 3-isopropylisoxazol-5-ylcarbamate in Example 122A Step 3, to afford phenyl 5-(1-methylcyclopropyl)isoxazol-3-ylcarbamate as a colorless solid (105 mg, 70%). $^1$H NMR (300 MHz, CDCl$_3$) δ 7.87 (brs, 1H), 7.39-7.44 (m, 2H), 7.18-7.29 (m, 3H), 6.52 (s, 1H), 1.58 (s, 3H), 1.20-1.24 (m, 2H), 0.84-0.87 (m, 2H); LC-MS (ESI) m/z 259 (M+H)$^+$.

Example 127B 3-(6,7-dimethoxyquinazolin-4-yloxy)aniline from Example 113A (89 mg, 0.3 mmol) and phenyl 5-(1-methylcyclopropyl)isoxazol-3-ylcarbamate (93 mg, 0.36 mmol) were reacted according to the method described for 1-(3-(6,7-dimethoxyquinazolin-4-yloxy)phenyl)-3-(3-isopropylisoxazol-5-yl)urea in Example 122B to afford 1-(3-(6,7-dimethoxyquinazolin-4-yloxy)phenyl)-3-(5-(1-methylcyclopropyl)isoxazol-3-yl)urea as a colorless solid (80 mg, 58%). $^1$H NMR (300 MHz, DMSO-d$_6$) δ 9.57 (brs, 1H), 9.01 (brs, 1H), 8.56 (s, 1H), 7.56-7.58 (m, 2H), 7.38-7.43 (m, 2H), 7.25 (m, 1H), 6.97 (m, 1H), 6.47 (s, 1H), 3.99-4.00 (2×s, 6H), 1.39 (s, 3H), 1.06-1.10 (m, 2H), 0.86-0.90 (m, 2H); LC-MS (ESI) m/z 462 (M+H)$^1$.

Example 128

Preparation of 1-(3-(6,7-dimethoxyquinazolin-4-yloxy)phenyl)-3-(3-(1-methoxy-2-methylpropan-2-yl)isoxazol-5-yl)urea Example 128A Step 1: Prepared from methyl 3-methoxy-2,2-dimethylpropanoate (8 g, 54.7 mmol) according to the method described in Example 122A Step 1 for 4-methyl-3-oxopentanenitrile. Purification via silica gel chromatography eluting with mixtures of petroleum ether and ethyl acetate afforded 5-methoxy-4,4-dimethyl-3-oxopentanenitrile as a yellow oil (2.5 g, 29%). $^1$H NMR (300 MHz, CDCl$_3$) δ 3.72 (s, 2H), 3.32-3.33 (m, 5H), 1.18 (s, 6H).

Example 128A

Step 2: Prepared from 5-methoxy-4,4-dimethyl-3-oxopentanenitrile (500 mg, 3.22 mmol) according to the method described for 3-isopropylisoxazol-5-amine in Example 122A Step 2, to afford 3-(1-methoxy-2-methylpropan-2-yl)isoxazol-5-amine as a orange oil (380 mg, 69%) which was used in the next step without further purification. $^1$H NMR (300 MHz, CDCl$_3$) δ 5.08 (s, 1H), 4.41 (brs, 2H), 3.39 (s, 2H), 3.35 (s, 3H), 1.28 (s, 6H).

Example 128A

Step 3: Prepared from 3-(1-methoxy-2-methylpropan-2-yl)isoxazol-5-amine (100 mg, 0.59 mmol) according to the method described for phenyl 3-isopropylisoxazol-5-ylcarbamate in Example 122A Step 3, to afford phenyl 3-(1-methoxy-2-methylpropan-2-yl)isoxazol-5-ylcarbamate as an oil that was not purified further.

Example 128B 3-(6,7-dimethoxyquinazolin-4-yloxy)aniline from Example 113A (40 mg, 0.13 mmol) and phenyl 3-(1-methoxy-2-methylpropan-2-yl)isoxazol-5-ylcarbamate from the previous step (50 mg, 0.18 mmol) were reacted according to the method described for 1-(3-(6,7-dimethoxyquinazolin-4-yloxy)phenyl)-3-(3-isopropylisoxazol-5-yl)urea in Example 122B. Purification via preparative silica gel thin layer chromatography eluting with 10% methanol in dichloromethane afforded 1-(3-(6,7-dimethoxyquinazolin-4-yloxy)phenyl)-3-(3-(1-methoxy-2-methylpropan-2-yl)isoxazol-5-yl)urea as a pale yellow solid (35 mg, 54%). $^1$H NMR (300 MHz, DMSO-$d_6$) δ 10.17 (brs, 1H), 9.05 (brs, 1H), 8.56 (s, 1H), 7.56 (s, 2H), 7.38-7.44 (m, 2H), 7.30 (m, 1H), 7.00 (m, 1H), 6.03 (s, 1H), 3.98-4.00 (2×s, 6H), 3.34 (s, 3H), 3.22 (s, 2H), 1.20 (s, 6H); LC-MS (ESI) m/z 494 (M+H)$^+$.

Example 129

Preparation of 1-(3-(6,7-dimethoxyquinazolin-4-yloxy)phenyl)-3-(3-(2-methoxyethoxy)-5-(trifluoromethyl)phenyl)urea Example 129B The title compound was prepared from 3-(6,7-dimethoxyquinazolin-4-yloxy)aniline from Example 113A (89 g, 0.3 mmol) and phenyl 3-(2-methoxyethoxy)-5-(trifluoromethyl)phenylcarbamate from Example 117A (160 mg, 0.45 mmol) in the manner described in Example 115C. The final product was purified by column chromatography (25-100% EtOAc/hexanes then 5-10% MeOH/DCM) to give 1-(3-(6,7-dimethoxyquinazolin-4-yloxy)phenyl)-3-(3-(2-methoxyethoxy)-5-(trifluoromethyl)phenyl)urea (150 mg, 0.27 mmol, 90%). $^1$H NMR (300 MHz, DMSO-$d_6$) δ 9.09 (s, 1H), 9.03 (s, 1H), 8.57 (s, 1H), 7.61-7.57 (m, 2H), 7.49 (s, 1H), 7.43-7.38 (m, 2H), 7.31-7.24 (m, 2H), 6.95 (d, 1H), 6.86 (s, 1H), 4.19-4.11 (m, 2H), 4.00 (s, 3H), 3.99 (s, 3H), 3.70-3.63 (m, 2H), 3.31 (s, 3H); LC-MS (ESI) m/z 559 (M+H)$^+$.

Example 130

Preparation of 1-(3-(6,7-dimethoxyquinazolin-4-yloxy)phenyl)-3-(5-(1-methoxy-2-methylpropan-2-yl)isoxazol-3-yl)urea Example 130A Step 1: To a mixture of 5-methoxy-4,4-dimethyl-3-oxopentanenitrile (1 g, 6.5 mmol) in ethanol (100 mL), was added 96% sodium hydroxide (308 mg, 7.70 mmol). To this was added a solution of hydroxylamine hydrochloride (537 mg, 7.70 mmol) in water (100 mL). The resulting solution (pH 7.8) was stirred at 60° C. for 22 h, then cooled to room temperature. To this was added concentrated hydrochloric acid (3 mL, 36 mmol) and the mixture refluxed (80° C.) for 1 h. The reaction mixture was concentrated under reduced pressure to remove ethanol and the residue was mixed with 30% sodium hydroxide (2.1 g). The mixture was shaken with chloroform. The chloroform layer was washed with water, dried over anhydrous sodium sulfate and concentrated under reduced pressure to give an oil. Purification via silica gel chromatography afforded 5-(1-methoxy-2-methylpropan-2-yl)isoxazol-3-amine as a colorless solid (350 mg, 32%). $^1$H NMR (300 MHz, CDCl$_3$) δ 5.60 (s, 1H), 3.39 (s, 2H), 3.32 (s, 3H), 2.94 (brs, 2H), 1.28 (s, 6H); LC-MS (ESI) m/z 171 (M+H)$^+$.

Example 130A

Step 2: Prepared from 5-(1-methoxy-2-methylpropan-2-yl)isoxazol-3-amine (30 mg, 0.176 mmol) according to the method described for phenyl 3-isopropylisoxazol-5-ylcarbamate in Example 122A Step 3, to afford phenyl 5-(1-methoxy-2-methylpropan-2-yl)isoxazol-3-ylcarbamate as an oil (50 mg, 98%). $^1$H NMR (300 MHz, CDCl$_3$) δ 8.04 (brs, 1H), 7.42-7.43 (m, 2H), 7.31 (m, 1H), 7.18-7.21 (m, 2H), 6.63 (s, 1H), 3.45 (s, 2H), 3.33 (s, 3H), 1.35 (s, 6H).

Example 130B

Prepared from 3-(6,7-dimethoxyquinazolin-4-yloxy)aniline from Example 113A (50 mg, 0.16 mmol) and phenyl 5-(1-methoxy-2-methylpropan-2-yl)isoxazol-3-ylcarbamate from Example 130A (50 mg, 0.17 mmol) according to the method described for 1-(3-(6,7-dimethoxyquinazolin-4-yloxy)phenyl)-3-(3-isopropylisoxazol-5-yl)urea in Example 122B. Purification via preparative silica gel TLC eluting with 10% methanol in dichloromethane afforded 1-(3-(6,7-dimethoxyquinazolin-4-yloxy)phenyl)-3-(5-(1-methoxy-2-methylpropan-2-yl)isoxazol-3-yl)urea as a colorless solid (38 mg, 44%). $^1$H NMR (300 MHz, DMSO-$d_6$) δ 9.57 (brs, 1H), 9.01 (brs, 1H), 8.56 (s, 1H), 7.57-7.58 (m, 2H), 7.38-7.42 (m, 2H), 7.25 (m, 1H), 6.97 (m, 1H), 6.50 (s, 1H), 3.99 (s, 6H), 3.38 (s, 2H), 3.23 (s, 3H), 1.24 (s, 6H); LC-MS (ESI) m/z 494 (M+H)$^+$.

Example 131

Preparation of 1-(3-(6,7-dimethoxyquinazolin-4-yloxy)phenyl)-3-(5-(1-hydroxy-2-methylpropan-2-yl)isoxazol-3-yl)urea Example 131A Step 1: A solution of methyl 3-hydroxy-2,2-dimethylpropanoate (5.00 g, 38 mmol), N,N-diisopropylethylamine (7.30 g, 57 mmol) and tert-butyldimethylchlorosilane (6.80 g, 45 mmol) in dry DMF (70 mL) was stirred at room temperature for 12 h. The reaction solution was quenched with water (225 mL) and extracted with diethyl ether (3×50 mL). The combined organic extracts were washed with water (100 mL), brine (100 mL), then dried over MgSO$_4$. Concentration under reduced pressure afforded methyl 3-(tert-butyldimethylsilyloxy)-2,2-dimethylpropanoate as colorless oil (9.36 g, 100%). It was used in the next step without further purification. $^1$H NMR (300 MHz, CDCl$_3$) δ 3.64 (s, 3H), 3.55 (s, 2H), 1.13 (s, 6H), 0.85 (s, 9H), 0.0 (s, 6H).

Example 131A

Step 2: Prepared from methyl 3-(tert-butyldimethylsilyloxy)-2,2-dimethylpropanoate (6 g, 24.39 mmol) according to the method described for 4-methyl-3-oxopentanenitrile Example XA Step 1. Purification via silica gel chromatography eluting with 33% ethyl acetate in petroleum ether afforded 5-hydroxy-4,4-dimethyl-3-oxopentanenitrile as a yellow oil (1 g, 29%). $^1$H NMR (300 MHz, CDCl$_3$) δ 3.76 (s, 2H), 3.61 (s, 2H), 1.19 (s, 6H).

Example 131A

Step 3: Prepared from 5-hydroxy-4,4-dimethyl-3-oxopentanenitrile (1 g, 7.90 mmol) according to the method described for 5-(1-methoxy-2-methylpropan-2-yl)isoxazol-3-amine. Purification via recrystallisation from diethyl ether afforded 2-(3-aminoisoxazol-5-yl)-2-methylpropan-1-ol as a colorless solid (600 mg, 49%). $^1$H NMR (300 MHz, CDCl$_3$) δ 5.64 (s, 1H), 3.65 (s, 2H), 2.30 (brs, 2H), 1.31 (s, 6H).

Example 131A

Step 4: Prepared from 2-(3-aminoisoxazol-5-yl)-2-methylpropan-1-ol (100 mg, 0.60 mmol) according to the method described for phenyl 3-isopropylisoxazol-5-ylcarbamate in Example 122A Step 3, to afford phenyl 5-(1-hydroxy-2-methylpropan-2-yl)isoxazol-3-ylcarbamate as a colorless solid (120 mg, 72%). $^1$H NMR (300 MHz, CDCl$_3$) δ 8.30 (brs, 1H), 7.42-7.43 (m, 2H), 7.26 (m, 1H), 7.18-7.21 (m, 2H), 6.65 (s, 1H), 3.67 (s, 2H), 1.98 (brs, 1H), 1.32 (s, 6H).

Example 131B

Preparation of final product: Prepared from 3-(6,7-dimethoxyquinazolin-4-yloxy)aniline from Example 113A (30 mg, 0.10 mmol) and phenyl 5-(1-hydroxy-2-methylpropan-2-yl)isoxazol-3-ylcarbamate from the previous step (41 mg, 0.15 mmol) according to the method described for 14346,7-dimethoxyquinazolin-4-yloxy)phenyl)-3-(3-isopropylisoxazol-5-yl)urea in Example 122B. Purification via preparative TLC eluting with 10% methanol in dichloromethane afforded 1-(3-(6,7-dimethoxyquinazolin-4-yloxy)phenyl)-3-(5-(1-hydroxy-2-methylpropan-2-yl)isoxazol-3-yl)urea as a colorless solid (30 mg, 61%). $^1$H NMR (300 MHz, DMSO-d$_6$) δ 9.57 (brs, 1H), 8.99 (brs, 1H), 8.56 (s, 1H), 7.56-7.58 (m, 2H), 7.38-7.42 (m, 2H), 7.23-7.26 (m, 1H), 6.95-6.98 (m, 1H), 6.49 (s, 1H), 4.95 (brs, 1H), 3.98-3.99 (2×s, 6H), 3.43 (s, 2H), 1.20 (s, 6H); LC-MS (ESI) m/z 480 (M+H)$^+$.

Example 132

Preparation of 1-(3-tert-butylisoxazol-5-yl)-3-(3-(6,7-dimethoxyquinazolin-4-yloxy)phenyl)urea

Example 132A

Using the procedure described in Example 113B 3-tert-butylisoxazol-5-amine (620 mg, 4.4 mmol) was reacted to afford phenyl 3-tert-butylisoxazol-5-ylcarbamate (1.02 g, 89%) as a white solid. $^1$H NMR (300 MHz, CDCl$_3$) δ 11.81 (bs, 1H), 7.47-7.42 (m, 2H), 7.32-7.23 (m, 3H), 6.05 (s, 1H), 1.27 (s, 9H); LC-MS (ESI) m/z 261 (M+H)$^+$.

Example 132B

The title compound was prepared as described in Example 113C with 3-(6,7-dimethoxyquinazolin-4-yloxy)aniline from Example 113A (90 mg, 0.3 mmol) and phenyl 3-tert-butylisoxazol-5-ylcarbamate from the previous step (118 mg, 0.45 mmol) to give 1-(3-tert-butylisoxazol-5-yl)-3-(3-(6,7-dimethoxyquinazolin-4-yloxy)phenyl)urea (41 mg, 29%) as a white solid. $^1$H NMR (300 MHz, DMSO-d$_6$) δ 10.19 (s, 1H), 9.04 (s, 1H), 8.57 (s, 1H), 7.59-7.56 (m, 2H), 7.44-7.39 (m, 2H), 7.30 (d, 1H), 6.98 (d, 1H), 6.04 (s, 1H), 3.99 (s, 6H), 1.25 (s, 9H); LC-MS (ESI) m/z 464 (M+H)$^+$.

Example 133

Preparation of 1-(3-(6,7-dimethoxyquinazolin-4-yloxy)phenyl)-3-(5-isopropylisoxazol-3-yl)urea

Example 133A

Step 1: In an oven dried flask equipped with a condenser and an Argon inlet, sodium hydride, 60% in mineral oil, (2.4 g, 61.10 mmol) was suspended in anhydrous tetrahydrofuran (26 mL). The suspension was refluxed under Argon and a mixture of anhydrous acetonitrile (3.2 mL, 61.10 mmol) and methylisobutyrate (4 g, 39.16 mmol) was added dropwise over fifty minutes. After the addition was complete, the mixture was heated at reflux overnight. After cooling to room temperature, the mixture was poured into water (150 mL). Diethyl ether (150 mL) was added and the two phases separated. The aqueous layer was acidified to pH=1 with 10% aqueous hydrochloric acid and the organics extracted twice with diethyl ether (2×100 mL). The combined organic layers were dried (MgSO$_4$), filtered and concentrated under reduced pressure to afford 4-methyl-3-oxopentanenitrile (3.12 g, 72%) as a yellow oil, which was used directly in the next step without further purification. $^1$H NMR (300 MHz, CDCl$_3$) δ 3.54 (s, 2H), 2.86-2.77 (m, 1H), 1.19 (d, 6H).

Example 133A

Step 2: 4-Methyl-3-oxopentanenitrile was added to a mixture of ethylene glycol (4.7 mL, 84 mmol) and chlorotrimethylsilane (10.6 mL, 84 mmol) in anhydrous dichloromethane (50 mL). The mixture was stirred at 40° C. overnight. After cooling to room temperature a solution of 5% sodium bicarbonate (50 mL) was added, the layer were separated and the water phase back extracted three times with diethyl ether. The organics were combined, dried (MgSO$_4$), filtered and concentrated under reduced pressure. The resulting residue was purified by silica gel chromatography (hexane/ethyl acetate 8:2) to afford 2-(2-isopropyl-1,3-dioxolan-2-yl)acetonitrile (3.38 g, 78%) as a colorless oil. $^1$H NMR (300 MHz, CDCl$_3$) δ 4.21-4.16 (m, 2H), 4.07-3.99 (m, 2H), 2.69 (s, 2H), 2.08-2.01 (m, 1H), 0.96 (d, 6H).

Example 133A

Step 3: To a solution of hydroxylamine hydrochloride (6.3 g, 91.7 mmol) in methanol (2.5 mL), liquid ammonia (15.7 mL, 7N in methanol) was added and the suspension stirred for 30 minutes at room temperature. A catalytic amount of 8-hydroxyquinoline was added to the mixture, followed by 2-(2-isopropyl-1,3-dioxolan-2-yl)acetonitrile (3.38 g, 22 mmol) as a solution in methanol (2.5 mL). The mixture was stirred at 70° C. overnight. After cooling to room temperature, the suspension was filtered off and washed with dichloromethane. The solution was concentrated under reduced pressure, and reconcentrated three times from toluene to afford N'-hydroxy-2-(2-isopropyl-1,3-dioxolan-2-yl)acetimidamide (3.9 g, 94%) as a yellow solid, which was used directly in the next step without further purification. $^1$H NMR (300 MHz, CDCl$_3$) δ 5.01 (bs, 2H), 4.05-3.94 (m, 4H), 2.44 (s, 2H), 2.03-1.94 (m, 1H), 0.95 (d, 6H); LC-MS (ESI) m/z 189 (M+H)$^+$.

Example 133A

Step 4: N'-Hydroxy-2-(2-isopropyl-1,3-dioxolan-2-yl)acetimidamide (1.8 g, 9.57 mmol) was dissolved in ethanol (12 ml) and acidified to pH=1 with 37% aqueous hydrochloric acid. The mixture was subjected to microwave heating at 120° C. for 30 minutes. After concentration under reduced pressure the residue was diluted with dichloromethane, a solution of saturated sodium bicarbonate was added until the solution became basic (pH=11) and the organic layer separated. After multiple extractions of the water phase with dichloromethane, the organic layers were combined, dried (MgSO$_4$), filtered and concentrated under reduced pressure. The crude material was purified by silica gel chromatography (hexane/ethyl acetate 1:1) to afford 5-isopropylisoxazol-3- amine (819 mg, 68%). 1H NMR (300 MHz, CDCl$_3$) δ 5.52 (s, 1H), 3.89 (bs, 2H), 2.96-2.91 (m, 1H), 1.27 (d, 6H); LC-MS (ESI) m/z 127 (M+H)$^+$.

Example 133A

Step 5: The procedure described in Example 113B was used, but using 5-isopropylisoxazol-3-amine (816 mg, 6.5 mmol) as the amine, to afford phenyl 5-isopropylisoxazol-3-ylcarbamate (1.24 g, 77%). $^1$H NMR (300 MHz, CDCl$_3$) δ 8.05 (bs, 1H), 7.41 (t, 2H), 7.30-7.18 (m, 3H), 6.55 (s, 1H), 3.09-3.02 (m, 1H), 1.3 (d, 6H); LC-MS (ESI) m/z 247 (M+H)$^+$.

Example 133B

The title compound was prepared as described in Example 113C using 3-(6,7-dimethoxyquinazolin-4-yloxy)aniline from Example 113A (90 mg, 0.3 mmol) and phenyl 5-isopropylisoxazol-3-ylcarbamate from the previous step (110 mg, 0.45 mmol) to give 1-(3-(6,7-dimethoxyquinazolin-4-yloxy) phenyl)-3-(5-isopropylisoxazol-3-yl)urea (79 mg, 59%) as a white solid after purification by preparative HPLC (phenyl-hexyl reverse phase column). $^1$H NMR (300 MHz, DMSO-d$_6$) δ 9.57 (s, 1H), 9.01 (s, 1H), 8.56 (s, 1H), 7.57 (s, 2H), 7.41 (t, 2H) 7.27 (d, 1H), 6.99 (d, 1H), 6.49 (s, 1H), 4.00 (s, 6H), 3.01-2.99 (m, 1H), 1.22 (d, 6H); LC-MS (ESI) m/z 450 (M+H)$^+$.

Example 134

Preparation of 1-(3-(6,7-dimethoxyquinazolin-4-ylthio)phenyl)-3-(5-isopropylisoxazol-3-yl)urea The title compound was prepared using the procedure described in Example 113C with 3-(6,7-dimethoxyquinazolin-4-ylthio)aniline described in Example 115B (94 mg, 0.3 mmol) and phenyl 5-isopropylisoxazol-3-ylcarbamate described in Example 133A (110 mg, 0.45 mmol). Precipitation of the desired product detected completion of reaction. The solid was filtered off and washed with diethyl ether to give 1-(3-(6,7-dimethoxyquinazolin-4-ylthio)phenyl)-3-(5-isopropylisoxazol-3-yl)urea (96.26 mg, 69%) as a solid. $^1$H NMR (300 MHz, DMSO-d$_6$) δ 9.57 (s, 1H), 9.02 (s, 1H), 8.70 (s, 1H), 7.84 (s, 1H), 7.53-7.42 (m, 2H), 7.36-7.27 (m, 3H), 6.51 (s, 1H), 3.99 (s, 6H), 3.04-3.00 (m, 1H), 1.23 (d, 6H); LC-MS (ESI) m/z 466 (M+H)$^+$.

Example 135

Preparation of 1-(5-cyclopentylisoxazol-3-yl)-3-(3-(6,7-dimethoxyquinazolin-4-yloxy)phenyl)urea Example 135A Step 1: According to the procedure described in Example 133A Step 1 methyl cyclopentanecarboxylate (4 g, 31.25 mmol), anhydrous acetonitrile (2.55 mL, 48.75 mmol) and sodium hydride, 60% in mineral oil, (1.95 g, 48.75 mmol) in anhydrous tetrahydrofuran (25 mL) were reacted to afford 3-cyclopentyl-3-oxopropanenitrile (3.97 g, 93%) as yellow oil, which was used directly in the next step without further purification. $^1$H NMR (300 MHz, CDCl$_3$) δ 3.5 (s, 2H), 3.13-3.02 (m, 1H), 1.95-1.62 (m, 8H).

Example 135A

Step 2: According to the procedure described in Example 133A Step 2,3-cyclopentyl-3-oxopropanenitrile (2 g, 14 mmol) was added to a mixture of ethylene glycol (2.4 mL, 44 mmol) and chlorotrimethylsilane (5.5 mL, 44 mmol) to give 2-(2-cyclopentyl-1,3-dioxolan-2-yl)acetonitrile (1.5 g, 60%). $^1$H NMR (300 MHz, CDCl$_3$) δ 4.23-4.15 (m, 2H), 4.12-4.01 (m, 2H), 2.72 (s, 2H), 2.42-2.30 (m, 1H), 1.81-1.45 (m, 8H).

Example 135A

Step 3: According to the procedure described in Example 133A Step 3, 2-(2-cyclopentyl-1,3-dioxolan-2-yl)acetonitrile (1.5 g, 8.3 mmol) was reacted with hydroxylamine hydrochloride (3.17 g, 45.5 mmol) and liquid ammonia (7.8 mL, 7N in methanol), to afford 2-(2-cyclopentyl-1,3-dioxolan-2-yl)-N'-hydroxyacetimidamide, which was used directly in the next step without further purification. $^1$H NMR (300 MHz, CDCl$_3$) δ 5.11 (bs, 2H), 4.20-3.95 (m, 4H), 2.38 (s, 2H), 2.33-2.22 (m, 1H), 1.73-1.41 (m, 8H); LC-MS (ESI) m/z 215 (M+H)$^+$ Example 135A Step 4: According to the procedure described for 5-isopropylisoxazol-3-amine in Example 133A Step 4, 2-(2-cyclopentyl-1,3-dioxolan-2-yl)-N'-hydroxyacetimidamide (1.99 g, 93 mmol) was dissolved in ethanol (2 mL) and acidified with 37% aq. hydrochloric acid to give 5-cyclopentylisoxazol-3-amine (875 mg, 62%) as a white solid. $^1$H NMR (300 MHz, CDCl$_3$) δ 5.52 (s, 1H), 3.86 (bs, 2H), 3.09-3.04 (m, 1H), 2.04 (d, 2H), 1.75-1.62 (m, 6H); LC-MS (ESI) m/z 153 (M+H)'

Example 135A

Step 5: 5-Cyclopentylisoxazol-3-amine (875 mg, 5.75 mmol) was reacted according to the procedure described in Example 113B to afford phenyl 5-isopropylisoxazol-3-ylcarbamate (1.4 g, 89%) as a white solid. $^1$H NMR (300 MHz, CDCl$_3$) δ 7.97 (bs, 1H), 7.42 (t, 2H), 7.29-7.18 (m, 3H), 6.54 (s, 1H), 3.19-3.12 (m, 1H), 2.10-2.04 (m, 2H), 1.78-1.58 (m, 6H); LC-MS (ESI) m/z 273 (M+H)'

Example 135B

The title compound was prepared as described in Example 113C by using compound 3-(6,7-dimethoxyquinazolin-4-yloxy)aniline from Example 113A (95 mg, 0.32 mmol) and the phenyl 5-isopropylisoxazol-3-ylcarbamate intermediate from the previous step (130 mg, 0.48 mmol) to give 1-(5-cyclopentylisoxazol-3-yl)-3-(3-(6,7-dimethoxyquinazolin-4-yloxy)phenyl)urea (80.60 mg, 53%) as a white solid. $^1$H NMR (300 MHz, DMSO-d$_6$) δ 9.58 (s, 1H), 9.03 (s, 1H), 8.56 (s, 1H), 7.57 (s, 2H), 7.41 (t, 2H), 7.26 (d, 1H), 6.97 (d, 1H), 6.50 (s, 1H), 4.00 (s, 6H), 3.21-3.00 (m, 1H), 1.66-1.64 (m, 2H), 1.20-1.18 (m, 6H); LC-MS (ESI) m/z 476 (M+H)$^+$.

Example 136

Preparation of 1-(3-(6,7-dimethoxyquinazolin-4-yloxy)phenyl)-3-(5-(2-fluoropropan-2-yl)isoxazol-3-yl)urea Example 136A Step 1: To a stirred solution of 4-fluoro-4-methyl-3-oxopentanenitrile (1 g, 7.75 mmol) in dry diethyl ether (150 mL) at 0° C., was added dropwise (trimethylsilyl)diazomethane (4.65 mL of a 2.0 M solution in diethyl ether, 9.30 mmol). After warming to room temperature the reaction mixture was stirred for a further 15 h. The reaction mixture was concentrated under reduced pressure to afford 4-fluoro-3-methoxy-4-methylpent-2-enenitrile as a yellow oil (1 g, 91%) which was taken on to the next step without further purification. $^1$H NMR (300 MHz, CDCl$_3$) δ 4.89 (s, 1H), 4.23 (s, 3H), 1.47 (d, J=21 Hz, 6H).

Example 136A

Step 2: To dry methanol (10 mL) at room temperature, was added portionwise sodium metal (145 mg, 6.30 mmol). After all metal had dissolved, the reaction mixture was cooled to 0° C. and hydroxylamine hydrochloride (438 mg, 6.30 mmol) was added in one portion. The reaction mixture was stirred for 15 mins before adding a solution of 4-fluoro-3-methoxy-4-methylpent-2-enenitrile (500 mg, 3.50 mmol) in dry methanol (3 mL). The mixture was heated at 70° C. for 16 h. Concentrated hydrochloric acid (0.8 mL, 9.6 mmol) was added and the reaction mixture stirred at 80° C. for 30 mins. After cooling to room temperature, the reaction was concentrated under reduced pressure to give an orange foam which was dissolved in water (50 mL) and adjusted to pH 10 using aq 1M NaOH solution. The aqueous layer was then extracted with dichloromethane (3×50 mL) and the combined organic layers were washed with brine (50 mL), dried over MgSO$_4$ and concentrated under reduced pressure to give a yellow oil. The crude product was purified by silica gel chromatography eluting with 12% ethyl acetate in hexanes to 100% ethyl acetate to afford 5-(2-fluoropropan-2-yl)isoxazol-3-amine as a cream solid (64 mg, 13%). $^1$H NMR (300 MHz, CDCl$_3$) δ 5.82 (s, 1H), 4.08 (brs, 2H), 1.71 (d, J=21 Hz, 6H); LC-MS (ESI) m/z 145 (M+H)$^+$.

Example 136A

Step 3: Prepared from 5-(2-fluoropropan-2-yl)isoxazol-3-amine (40 mg, 0.278 mmol) and 4-chlorophenyl chloroformate (54 mg, 0.28 mmol) according to the procedure described in Example 122A Step 3, to afford 4-chlorophenyl 5-(2-fluoropropan-2-yl)isoxazol-3-ylcarbamate as a colorless solid (83 mg, 100%). $^1$H NMR (300 MHz, CDCl$_3$) δ 8.11 (brs, 1H), 7.36-7.40 (m, 2H), 7.12-7.17 (m, 2H), 6.83 (s, 1H), 1.76 (d, J=21 Hz, 6H); LC-MS (ESI) m/z 299 (M+H)$^+$.

Example 136B: 3-(6,7-Dimethoxyquinazolin-4-yloxy)aniline from Example 113A (90 mg, 0.302 mmol) and 4-chlorophenyl 5-(2-fluoropropan-2-yl)isoxazol-3-ylcarbamate from the previous step (90 mg, 0.302 mmol) were reacted according to the procedure described in Example 122B, except the reaction mixture was stirred at room temperature for 3 h. The crude material was purified via silica gel chromatography (0%-10% methanol in dichloromethane) to afford 1-(3-(6,7-dimethoxyquinazolin-4-yloxy)phenyl)-3-(5-(2-fluoropropan-2-yl)isoxazol-3-yl)urea as a colorless solid (37 mg, 26%). $^1$H NMR (300 MHz, DMSO-d$_6$) δ 9.75 (brs, 1H), 9.04 (brs, 1H), 8.56 (s, 1H), 7.56-7.58 (m, 2H), 7.40-7.41 (m, 2H), 7.29 (m, 1H), 7.00 (m, 1H), 6.86 (s, 1H), 4.00 (s, 6H), 1.72 (d, J=21 Hz, 6H); LC-MS (ESI) m/z 468 (M+H)$^+$.

Example 137

Preparation of 1-(3-(6,7-dimethoxyquinazolin-4-yloxy)phenyl)-3-(1-phenyl-3-(1-(trifluoromethyl) cyclopropyl)-1H-pyrazol-5-yl)urea Example 137A Step 1: To a slurry of NaH (432 mg, 18 mmol) in THF (40 mL) heated at reflux was added dropwise over 10 minutes a solution of methyl 1-(trifluoromethyl)cyclopropanecarboxylate (2.0 g, 11.9 mmol) in acetonitrile (940 uL, 12 mmol) and the mixture heated at reflux overnight. After cooling to room temperature, the reaction was partitioned between ether and H$_2$O, the aqueous layer acidified with 1N HCl$_{(aq)}$, extracted with ether, and the combined org layers washed with brine, dried over MgSO$_4$, filtered, concentrated in vacuo, and purified by column chromatography (5-40% EtOAc/hexanes) to give 3-oxo-3-(1-(trifluoromethyl)cyclopropyl)propanenitrile (1.04 g, 5.88 mmol, 49%). LC-MS (ESI) m/z 178 (M+H)$^+$.

Example 137A

Step 2: To 3-oxo-3-(1-(trifluoromethyl)cyclopropyl) propanenitrile (230 mg, 1.3 mmol) in EtOH (5 mL, 200 proof) was added H$_2$O (3.7 mL), 1N NaOH$_{(aq)}$ (1.3 mL), and phenylhydrazine hydrochloride (188 mg, 1.3 mmol) and the mixture heated at 90° C. overnight. After cooling to room temperature, the mixture was diluted with H2O, extracted with EtOAc, the org layer concentrated in vacuo, and purified by column chromatography (5-25% EtOAc/hexanes) to give 1-phenyl-3-(1-(trifluoromethyl)cyclopropyl)-1H-pyrazol-5-amine (150 mg, 0.56 mmol, 43%). LC-MS (ESI) m/z 268 (M+H)$^+$.

Example 137A

Step 3: Using the procedure described in Example 118A, 1-phenyl-3-(1-(trifluoromethyl)cyclopropyl)-1H-pyrazol-5-amine (150 mg, 0.56 mmol) was used in place of the aniline to give phenyl 1-phenyl-3-(1-(trifluoromethyl)cyclopropyl)-1H-pyrazol-5-ylcarbamate (129 mg, 0.33 mmol, 59%). LC-MS (ESI) m/z 388 (M+H)$^+$.

Example 137B

The title compound was prepared from phenyl 1-phenyl-3-(1-(trifluoromethyl) cyclopropyl)-1H-pyrazol-5-ylcarbamate described in Example 137A (129 mg, 0.33 mmol) and 3-(6,7-dimethoxyquinazolin-4-yloxy)aniline described in Example 113A (100 mg, 0.33 mmol) using the procedure described in Example 115C. The crude product was purified by column chromatography (25-100% EtOAc/hexanes) to give 1-(3-(6,7-dimethoxyquinazolin-4-yloxy)phenyl)-3-(1-phenyl-3-(1-(trifluoromethyl)cyclopropyl)-1H-pyrazol-5-yl)urea (139 mg, 0.24 mmol, 71%). $^1$H NMR (300 MHz, DMSO-d$_6$) δ 9.28 (s, 1H), 8.61 (s, 1H), 8.55 (s, 1H), 7.63-7.51 (m, 6H), 7.48 (d, 1H), 7.39 (s, 1H), 7.37 (t, 1H), 7.17 (d, 1H), 6.93 (d, 1H), 6.55 (s, 1H), 4.00 (s, 3H), 3.98 (s, 3H), 1.31 (d, 4H); LC-MS (ESI) m/z 591 (M+H)$^+$.

Example 138

Preparation of 1-(3-(6,7-dimethoxyquinazolin-4-yloxy)phenyl)-3-(4-methoxy-3-(trifluoromethyl) phenyl)urea Example 138A To a solution of 4-methoxy-3-trifluoromethyl aniline (500 mg, 2.62 mmol) in 20 mL of tetrahydrofuran was added potassium carbonate (470 mg, 3.4 mmol), followed by phenyl chloroformate (532 mg, 3.4 mmol). This solution was stirred overnight at room temperature, then concentrated and purified by silica gel chromatography using a gradient of ethyl acetate/hexanes 0-20% to afford phenyl 4-methoxy-3-(trifluoromethyl)phenylcarbamate as a white solid. $^1$H NMR (300

MHz, CDCl$_3$) 7.75-7.65 (m, 2H), 7.60-7.40 (m, 2H), 7.27-7.19 (m, 3H), 7.00-6.93 (m, 2H), 3.89 (s, 3H).

Example 138B

In a sealed reaction vessel 3-(6,7-dimethoxyquinazolin-4-yloxy)aniline from Example 113A (100 mg, 0.34 mmol) was dissolved in 10 ml of dry THF and diisopropylethyl amine (90 µL, 0.51 mmol) and DMAP (50 mg, 0.40 mmol) was added followed by carbamate from the previous step (159 mg, 0.51 mmol) and the reaction heated to 80° C. overnight. The reaction was concentrated to dryness and then triturated with ethyl acetate, and filtered to afford 1-(3-(6,7-dimethoxyquinazolin-4-yloxy)phenyl)-3-(4-methoxy-3-(trifluoromethyl)phenyl) urea (67.5 mg, 34% yield). $^1$H (DMSO-d$_6$) δ 8.97 (d, 2H), 8.56 (s, 1H), 7.83 (s, 1H), 7.70-7.60 (m, 3H), 7.5-7.2 (m, 4H), 6.93 (m, 1H), 3.98 (s, 6H), 3.83 (s, 3H) LCMS (ESI) m/z 582 (M+H)$^+$.

Example 139

Preparation of 1-(4-methoxy-3-(trifluoromethyl) phenyl)-3-(3-(6-methoxy-7-(2-methoxyethoxy) quinazolin-4-yloxy)phenyl)urea According to the procedure for Example 138B, 4-methoxy-3-(trifluoromethyl)phenylcarbamate described in Example 138A (104 mg, 0.34 mmol) was reacted with 3-(6-methoxy-7-(2-methoxyethoxy)quinazolin-4-yloxy)aniline described in Example 117B (100 mg, 0.28 mmol). To this solution was added diisopropylethyl amine (74 µL, 0.42 mmol) and DMAP (20.0 mg, 0.16 mmol). The reaction was concentrated to dryness and partitioned between water and dichloromethane, and extracted twice. The combined extracts were washed with brine, dried over magnesium sulfate, filtered and concentrated. The crude oil was purified by silica gel chromatography (methanol/dichloromethane 0-5%) to give 1-(4-methoxy-3-(trifluoromethyl)phenyl)-3-(3-(6-methoxy-7-(2-methoxyethoxy)quinazolin-4-yloxy)phenyl) urea as a white solid (18.6 mg, 10% yield). $^1$H (DMSO-d$_6$) 8.90 (s, 1H), 8.80 (s, 1H), 8.60 (s, 1H), 7.85 (s, 1H), 7.60 (m, 3H), 7.40 (m, 2H), 7.25 (m, 2H), 6.90 (d, 1H), 4.35 (m, 2H), 3.99 (s, 3H), 3.80 (s, 3H), 3.75 (m, 2H), 3.30 (s, 3H). LCMS (ESI) m/z 559 (M+H)$^+$.

Example 140

Preparation of 1-(3-chloro-5-(trifluoromethyl)phenyl)-3-(3-(6,7-dimethoxyquinazolin-4-yloxy)phenyl) urea Example 140A According to the procedure described in Example 113B, 3-chloro-5-trifluoromethylaniline (500 mgs, 2.56 mmoles) in 20 ml of tetrahydrofuran was treated with potassium carbonate (460 mgs, 3.33 mmoles) and phenyl chloroformate (521 mgs, 3.33 mmoles). After stirring overnight at room temperature the solution was filtered, and concentrated to a solid. Trituration with ethyl acetate gave phenyl 3-chloro-5-(trifluoromethyl)phenyl carbamate as a white solid used without further purification.

$^1$H NMR (300 MHz, CDCl$_3$) δ 7.75 (s, 1H), 7.64 (s, 1H), 7.45 (m, 2H), 7.35 (s, 1H), 7.2-7.1 (m, 2H), 7.0 (m, 1H)

Example 140B

The resulting carbamate was reacted as described in Example 138B and isolated and purified to give the title compound (26 mg, 15%). $^1$H (DMSO-d$_6$) 9.30 (s, 1H), 9.15 (s, 1H), 8.56 (s, 1H), 7.83 (d, 2H), 7.59 (m, 2H), 7.40 (m, 3H), 7.30 (m, 1H), 6.9 (m, 1H), 4.0 (s, 6H) LCMS (ESI) m/z 519 (M+H)$^+$.

Example 141

Preparation of 1-(3-(6,7-dimethoxyquinazolin-4-yloxy)phenyl)-3-(4-(trifluoromethyl)pyridin-2-yl) urea Example 141A According to the procedure described in Example 113B, 2-amino-4-trifluoromethylpyridine (462 mg, 2.85 mmoles) was dissolved in 20 ml of tetrahydrofuran. To this solution was added potassium carbonate (511 mgs, 3.7 mmoles) followed by phenyl chloroformate (521 mgs, 3.33 mmoles). The mixture was concentrated and purified according to the procedure in in Example 138 to afford phenyl 4-(trifluoromethyl) pyridin-2-ylcarbamate. $^1$H NMR (300 MHz, CDCl$_3$) δ 9.53 (s, 1H), 8.56 (m, 1H), 8.38 (s, 1H), 7.6-7.4 (m, 2H), 7.3-7.2 (m, 2H), 6.8 (m, 1H).

Example 141B

The resulting carbamate (144 mg, 0.51 mmol) was reacted as described in Example 138B and isolated and purified to give 55 mg of final product. $^1$H (DMSO-d$_6$) 9.95 (s, 1H), 9.76 (s, 1H), 8.56 (m, 2H) 8.01 (s, 1H), 7.64 (d, 2H), 7.5-7.3 (m, 4H), 6.98 (m, 1H), 3.98 (s, 6H) LCMS (ESI) m/z 486 (M+H)$^+$.

Example 142

Preparation of 1-(2-chloro-5-(trifluoromethyl)phenyl)-3-(3-(6,7-dimethoxyquinazolin-4-yloxy)phenyl) urea Example 142A According to the procedure described in Example 113B, 2-chloro-5-trifluoromethylaniline (500 mg, 2.56 mmoles) was dissolved in 20 mL of tetrahydrofuran. To this solution was added potassium carbonate (460 mg, 3.33 mmoles) followed by phenyl chloroformate (521 mg, 3.33 mmoles). This was isolated and purified according to the procedure in Example 140A to afford 2-chloro-5-(trifluoromethyl)phenyl-carbamate. $^1$H NMR (300 MHz, CDCl$_3$) δ 8.58 (s, 1H), 7.7-7.3 (m, 7H)

Example 142B

The resulting carbatmate (160 mg, 0.51 mmol) was reacted as described in the procedure for Example 138Band isolated and purified to give 83 mg of final product. $^1$H NMR (300 MHz, DMSO-d$_6$) δ 9.76 (s, 1H), 8.7-8.5 (m, 3H), 7.74 (d, 1H), 7.64 (m, 1H), 7.57 (s, 1H), 7.5-7.3 (m, 3H), 7.24 (m, 1H), 7.00 (m, 1H), 4.00 (s, 6H). LCMS (ESI) m/z 519 (M+H)$^+$.

Example 143

Preparation of 1-(3-(6,7-dimethoxyquinazolin-4-yloxy)phenyl)-3-(4-(trifluoromethyl)pyrimidin-2-yl) urea Example 143A According to the procedure described in Example 113B, to a solution of 4-(trifluoromethyl)pyrimidin-2-amine (500 mg, 3.1 mmoles) in 20 mL of tetrahydrofuran was added potassium carbonate (533 mg, 4 mmoles) followed by phenyl chloroformate (626 mg, 4 mmoles). The mixture was stirred at room temperature overnight. After 24 hours, and additional portion of phenyl chloroformate was added and the reaction heated to 60° C. for 3 days. This solution was concentrated to dryness and purified by silica chromatography (eluted with a gradient of 0-5% ethyl acetate/dichloromethane) to afford phenyl 4-(trifluoromethyl)pyrimidin-2-ylcarbamate. $^1$H NMR (300 MHz, DMSO-$d_6$) δ 11.50 (s, 1H), 9.05 (s, 1H), 7.69 (m, 1H), 7.46 (m, 2H), 7.25 (m, 3H).

Example 143B

The resulting carbamate (144 mg, 0.51 mmol) was reacted as described in Example 138B to give 93 mg of final product. $^1$H NMR (300 MHz, DMSO-$d_6$) δ 11.13 (s, 1H), 10.72 (s, 1H), 9.03 (s, 1H), 8.56 (s, 1H), 7.7-7.4 (m, 6H), 7.04 (m, 1H), 3.99 (s, 6H). LCMS (ESI) m/z 487 (M+H)$^+$.

Example 144

Preparation of 1-(3-(6,7-dimethoxyquinazolin-4-yloxy)phenyl)-3-(3-isopropylphenyl)urea Example 144A According to the procedure described in Example 113B, 4-(trifluoromethyl)pyrimidin-2-amine (500 mg, 3.1 mmoles) in 20 mL of tetrahydrofuran. To this solution was added potassium carbonate (533 mg, 4 mmoles) followed by phenyl chloroformate (626 mg, 4 mmoles). This was stirred at room temperature overnight. After 24 hours, and additional portion of phenyl chloroformate was added and the reaction heated to 60 C for 3 days. This solution was concentrated to dryness and purified by silica chromatography (eluting with a gradient of 0-5% ethyl acetate/dichloromethane) to afford phenyl 3-isopropylphenylcarbamate as a solid. $^1$H NMR (300 MHz, CDCl$_3$) δ 7.6-7.0 (m, 9H), 2.9 (m,1H), 1.35 (m, 6H).

Example 144B

The resulting carbamate (144 mg, 0.51 mmol) was reacted as in Example 138B to give 24 mg of final product. $^1$H NMR (300 MHz, DMSO-$d_6$) δ 8.61 (s, 1H), 7.9 (s, 1H), 7.7-7.5 (m, 3H), 7.5-7.2 (m, 3H), 7.15 (m, 1H), 7.1-6.8 (m, 4H), 4.05 (s, 6H), 2.80 (m, 1H), 1.17 (m, 6H). LCMS (ESI) m/z 459 (M+H)$^+$.

Example 145

Preparation of 1-(3-(6,7-dimethoxyquinazolin-4-yloxy)phenyl)-3-(443-methoxy-3-methylbutoxy)-3-(trifluoromethyl)phenyl)urea Example 145A According to the procedure described in Example 113B, 4-(3-methoxy-3-methylbutoxy)-3-(trifluoromethyl)aniline (490 mg, 1.77 mmoles) was dissolved in 20 mL of dry tetrahydrofuran. To this solution was added potassium carbonate (318 mg, 2.30 mmoles) followed by phenyl chloroformate (360 mg, 2.30 mmoles). The mixture was stirred overnight at room temperature, then purified with silica gel chromatography (using a gradient of 0-30% ethyl acetate/hexanes) to afford phenyl 4-(3-methoxy-3-methylbutoxy)-3-(trifluoromethyl)-phenylcarbamate as a yellow oil. $^1$H NMR (300 MHz, CDCl$_3$) δ 7.58 (m, 2H), 7.40 (m, 2H), 7.35-7.1 (m, 4H), 6.9 (m, 1H), 4.10 (m, 2H), 3.22 (s, 3H), 2.1 (m, 2H), 2.1 (m, 2H).

Example 145B

The resulting carbamate (202 mg, 0.51 mmol) was reacted as in Example 138B, isolated and purified by HPLC (using a reversed phase phenyl hexyl column and a gradient of 40-70% ACN/water over 60 minutes) to afford 82.5 mg of the title compound as a solid. $^1$H NMR (300 MHz, DMSO-$d_6$) δ 9.05 (s, 1H), 8.95 (s, 1H), 8.55 (s, 1H), 7.85 (s, 1H), 7.55 (m, 3H), 7.35 (m, 2H), 7.25 (m, 2H), 6.90 (m, 1H), 4.15 (m, 2H) 4.00 (s, 6H), 3.10 (s, 3H), 1.9 (m, 2H) 1.16 (s, 6H). LCMS (ESI) m/z 601 (M+H)

Example 146

Preparation of 1-(3-(6,7-dimethoxyquinazolin-4-yloxy)phenyl)-3-(6-(trifluoromethyl)pyrimidin-4-yl)urea Example 146A According to the procedure described in Example 113B, 6-(trifluoromethyl)pyrimidin-4-amine (480 mg, 2.94 mmoles) was dissolved in 20 mL of tetrahydrofuran. To this solution was added potassium carbonate (528 mg, 3.82 mmoles), followed by phenyl chloroformate (598 mg, 3.82 mmoles). An additional equivalent of phenyl chloroformate was added after stirring overnight and the reaction heated to 60° C. for 2 days. The crude product was purified to afford phenyl 6-(trifluoromethyl)pyrimidin-4-ylcarbamate as a white solid. $^1$H NMR (300 MHz, CDCl$_3$) δ 10.12 (s, 1H), 9.13 (s, 1H), 8.46 (s, 1H), 7.7-7.2 (m, 5H)

Example 146B

The resulting carbamate (144 mg, 0.51 mmol) was reacted as described in Example 138B, and isolated and purified to give 15 mg of final product. $^1$H NMR (300 MHz, DMSO-$d_6$) δ 10.26 (s, 1H), 9.80 (s, 1H), 9.01 (s, 1H), 8.56 (s, 1H), 7.62 (m, 2H), 7.5-7.3 (m, 3H), 7.08 (m, 1H), 3.99 (s, 6H). LCMS (ESI) m/z 487 (M+H)

Example 147

Preparation of 1-(3-(6,7-dimethoxyquinazolin-4-yloxy)phenyl)-3-(3-(2-methoxyethoxy)-4-(trifluoromethyl)phenyl)urea Example 147A Step 1: In a round bottomed flask sodium hydride (138 mg, 5.7 mmol) was suspended in 20 mL of dry tetrahydrofuran and cooled to 0° C. To this suspension was added 2-methoxyethanol (364 mg, 4.8 mmol) dropwise and the reaction stirred for 30 minutes. A solution of 2-fluoro-4-nitro-1-trifluoromethyl-benzene (1.0 g, 4.8 mmol) was prepared with 1 mL of dry tetrahydrofuran and added to the sodium hydride solution dropwise. This was stirred overnight while warming to room temperature. The solution was then concentrated to dryness and partitioned between ethyl acetate and water, then extracted twice. The organic layers were dried over magnesium sulfate, filtered and concentrated. The crude oil was purified by silica gel chromatography (using a gradient of 0-10% ethyl acetate/hexane). The major peak was collected, concentrated to a solid, and then triturated with hexane, and filtered to give 2-(2-methoxy-ethoxy)-4-nitro-1-trifluoromethyl-benzene (711 mg, 47% yield). $^1$H (300 MHz, DMSO-d$_6$) δ 8.0 (s, 1H), 7.9 (s, 2H), 4.4 (m, 2H), 3.7 (m, 2H), 3.3 (s, 3H)

Example 147A

Step 2: The 2-(2-methoxy-ethoxy)-4-nitro-1-trifluoromethyl-benzene from the previous step was dissolved in 5 ml of ethyl acetate to which 10% palladium on carbon was added. The flask was evacuated three times and flushed with hydrogen. After stirring under hydrogen overnight at room temperature the solution was filtered and concentrated to afford 3-fluoro-4-trifluoromethyl-phenylamine (610 mg, 97%). $^1$H NMR (300 MHz, DMSO-d$_6$) δ 7.18 (d, 1H), 6.3 (s, 1H), 6.1 (d, 1H), 5.8 (s, 2H), 4.0 (m, 2H), 3.6 (m, 2H), 3.3 (s, 3H).

Example 147A

Step 3: The amine from the previous step (610 mg, 2.6 mmol) was dissolved in tetrahydrofuran and potassium carbonate (466 mg, 3.4 mmol) was added. To this solution was added phenyl chloroformate (447 mg, 2.9 mmol) and the solution was stirred overnight at room temperature. The solution was then filtered through celite, concentrated, and then partitioned between dichloromethane and water, then extracted with an additional portion of dichloromethane. The extracts were combined, dried over magnesium sulfate, filtered and concentrated to give phenyl 3-(2-methoxyethoxy)-4-(trifluoromethyl)phenylcarbamate as a solid (820 mg, 88%). $^1$H NMR (300 MHz, DMSO-d$_6$) δ 10.6 (s, 1H), 7.6 (d, 1H), 7.4 (m, 3H), 7.3 (m, 3H), 7.1 (d, 1H), 4.1 (m, 2H), 3.7 (m, 2H), 3.3 (d, 3H)

Example 147B

As described in Example 113C, 3-(6,7-dimethoxyquinazolin-4-yloxy)aniline from Example 113A (90 mg, 0.3 mmol) in THF (5 mL) was treated with N,N-diisopropylethylamine (78 µl, 0.45 mmol), 4-(dimethylamino)pyridine (4 mg, 0.03 mmol) and phenyl 3-(2-methoxyethoxy)-4-(trifluoromethyl)phenylcarbamate (161 mg, 0.45 mmol). The reaction mixture was heated to 50° C. for 3h. After removal of the solvent, the crude material was purified by silica gel chromatography (ethyl acetate/dichloromethane 1:1) to afford 1-(3-(6,7-dimethoxyquinazolin-4-yloxy)phenyl)-3-(3-(2-methoxyethoxy)-4-(trifluoromethyl)phenyl)urea (109.5 mg, 65%) as a solid. $^1$H NMR (300 MHz, DMSO-d$_6$) δ 9.14 (s, 1H), 9.02 (s, 1H), 8.57 (s, 1H), 7.59 (d, 2H), 7.50-7.38 (m, 2H), 7.43-7.38 (m, 2H), 7.27 (d, 1H), 7.04 (d, 1H), 6.96 (d, 1H), 4.17-4.14 (m, 2H), 4.04 (s, 6H), 3.69-3.67 (m, 2H), 3.34 (s, 3H); LC-MS (ESI) m/z 559 (M+H)$^+$.

Example 148

Preparation of 1-(3-(6,7-dimethoxyquinazolin-4-ylthio)phenyl)-3-(3-(2-methoxyethoxy)-4-(trifluoromethyl)phenyl)urea The title compound was prepared according to the procedure described in Example 147B by using 3-(6,7-dimethoxyquinazolin-4-ylthio)aniline from Example 115B (95 mg, 0.3 mmol) and phenyl 3-(2-methoxyethoxy)-4-(trifluoromethyl)phenylcarbamate described in Example 147A (161 mg, 0.45 mmol). The reaction was stirred at 50° C. overnight. After removal of the solvent, dichloromethane was added and the precipitating solid filtered off, washed with DCM and dried to give 1-(3-(6,7-dimethoxyquinazolin-4-ylthio)phenyl)-3-(3-(2-methoxyethoxy)-4-(trifluoromethyl)phenyl)urea (78 mg, 45%) as a solid. $^1$H NMR (300 MHz, DMSO-d$_6$) δ 9.15 (s, 1H), 9.03 (s, 1H), 8.70 (s, 1H), 7.86 (s, 1H), 7.55-7.42 (m, 4H), 7.35 (d, 2H), 7.28 (d, 1H), 7.05 (d, 1H), 4.18-4.15 (m, 2H), 4.00 (s, 6H), 3.69-3.68 (m, 2H), 3.31 (s, 3H); LC-MS (ESI) m/z 575 (M+H)$^+$.

Example 149

Preparation of 1-(3-(6,7-dimethoxyquinazolin-4-yloxy)phenyl)-3-(3-(morpholine-4-carbonyl)-5-(trifluoromethyl)phenyl)urea Example 149A Step 1. In a round bottomed flask, 3-nitro-5-trifluoromethylbenzoic acid (5.0 g, 21.3 mmoles) was dissolved in 40 mL of dry DMF, to this solution was added hydoxybenzotriazole (5.8 g, 42.5 mmoles) and EDCI (8.2 g, 42.5 mmoles) and the solution stirred for 1 hour at room temperature. At the end of this time morpholine (2.2 g. 25.5 mmoles) was added and the reaction stirred overnight. The solution was then concentrated to dryness, and partitioned between water and ethyl acetate. The aqueous layer was extracted with ethyl acetate and the combined extracts dried with magnesium sulfate, filtered and concentrated. Chromatography with silica gel and eluting with a ethyl acetate/hexane gradient of 0-35% over 80 minutes gave morpholin-4-yl-(3-nitro-5-trifluoromethyl-phenyl)-methanone (1.8 g). $^1$H NMR (300 MHz, DMSO-d$_6$) δ 8.6 (d, 2H), 8.3 (s, 1H), 3.8-3.6 (bm, 4H), 3.56 (b, 2H), 3.33 (bs, 2H).

Example 149A

Step 2. Morpholin-4-yl-(3-nitro-5-trifluoromethyl-phenyl)-methanone (800 mg, 2.6 mmoles) from the previous step was dissolved in 40 mL of ethyl acetate. To this solution was added 10% palladium on carbon, the reaction was stirred under hydrogen at room temperature overnight. The solution filtered through celite and concentrated to give 3-(morpholine-4-carbonyl)-5-(trifluoromethyl)phenylamine (688 mg). $^1$H NMR (300 MHz, DMSO-d$_6$) δ 6.90 (s, 1H), 6.75 (d, 2H), 5.6 (b, 6H).

Example 149A

Step 3: 3-(Morpholine-4-carbonyl)-5-(trifluoromethyl)phenylamine (688 mg, 2.5 mmoles) was dissolved in tetrahydrofuran and potassium carbonate (451 mg, 3.3 mmoles) was added followed by phenyl chloroformate (432 mg, 2.76 mmoles) and the solution stirred overnight at room temperature. This solution was filtered through celite and concentrated to a solid. This was partitioned between dichloromethane and brine, extracted twice. The extracts were combined and dried with magnesium sulfate, filtered and concentrated to a solid. The solid was triturated with ether, the solid collected by filtration to afford phenyl 3-(morpholine-4-carbonyl)-5-(trifluoromethyl)phenyl carbamate. $^1$H NMR (300 MHz, DMSO-d$_6$) δ 10.7 (s, 1H), 7.98 (s, 1H), 7.77 (s, 1H), 7.3 (m, 3H), 7.2 (m, 3H), 3.6 (bm, 6H)

Example 149B

The resulting carbamate (180 mg, 0.45 mmol) was reacted as described in Example 138B. Isolation and purification was accomplished using silica gel chromatography (0-100% ethyl acetate/hexane) to afford the title compound (78 mg, 29% yield). $^1$H NMR (300 MHz, DMSO-d$_6$) δ 9.25 (s, 1H), 9.13 (s, 1H), 8.57 (s, 1H), 8.00 (s, 1H), 7.66 (s, 1H), 7.60 (d, 2H), 7.38 (m, 2H), 7.30 (m, 2H), 6.95 (m, 1H), 4.10 (s, 6H), 3.63 (m, 6H), 3.2 (d, 2H). LCMS (ESI) m/z 598 (M+H)$^+$.

Example 150

Preparation of 1-(3-(6,7-dimethoxyquinazolin-4-yloxy)phenyl)-3-(3-fluoro-4-(trifluoromethyl)phenyl)urea Example 150A Step 1: In a round bottomed flask, 2-fluoro-4-nitro-1-trifluoromethyl-benzene (1.00 g, 4.78 mmol) was dissolved in 10 mL of methanol. To this solution was added 10% palladium on carbon (100 mg) and the solution was stirred overnight at room temperature under hydrogen (1 atm). The solution was filtered and concentrated to afford 3-fluoro-4-trifluoromethyl-phenylamine. $^1$H NMR (300 MHz, DMSO-d$_6$) δ 7.3 (m, 1H), 6.6 (d, 2H), 6.2 (s, 2H)

Example 150A

Step 2: The above amine (600 mg, 3.35 mmol) was dissolved in 10 ml of dry DMF. To this solution was added potassium carbonate (603 mg, 4.36 mmol) followed by the addition of phenyl chloroformate (577 mg, 3.69 mmol) as a DMF solution dropwise, and the reaction stirred overnight at room temperature. The solution was filtered and concentrated to an oil. The oil was purified by silica gel chromatography (using a 10-50% ethyl acetate/hexane gradient) to give 584 mg of phenyl 3-fluoro-4-(trifluoromethyl)phenylcarbamate. $^1$H NMR (300 MHz, DMSO-d$_6$) δ 10.9 (s, 1H), 7.7 (m, 1H), 7.6 (d, 1H) 7.4 (m, 3H), 7.2 (m, 2H)

Example 150B

The procedure described in Example 138B was used to react the carbamate intermediate from above (135 mg, 0.45 mmol) with 3-(6,7-dimethoxyquinazolin-4-yloxy)aniline from Example 113A (89 mg, 0.3 mmol). To this solution was added diisopropylethyl amine (58 mg, 0.45 mmol) and DMAP (3.7 mg, 0.03 mmol). Isolation and purification was accomplished using silica gel chromatography eluting with a 10-50% ethyl acetate/dichloromethane gradient to give the title compound (112 mg, 74% yield). $^1$H NMR (300 MHz, DMSO-d$_6$) δ 9.43 (s, 1H), 9.32 (s, 1H), 8.57 (s, 1H), 7.70 (m, 4H), 7.40 (m, 2H), 7.30 (m, 2H), 6.9 (m, 1H), 4.00 (s, 6H). LCMS (ESI) m/z 503 (M+H)$^+$.

Example 151

Preparation of 1-(3-(6,7-dimethoxyquinazolin-4-yloxy)phenyl)-3-(3-(morpholinomethyl)-5-(trifluoromethyl)phenyl)urea Example 151A Step 1: In a round bottomed flask morpholino(3-nitro-5-(trifluoromethyl)phenyl)methanone (1.60 g, 5.25 mmol) was dissolved in 8 mL of anhydrous THF and cooled to 0 C. To this solution, a 2 M solution of Borane-dimethyl sulfide (10.5 mL, 21 mmol) in THF was added dropwise. The reaction was stirred overnight while warming to room temperature. The solution was then concentrated to an oil. This was partitioned between dichloromethane and water, then basified with 1 M sodium hydroxide solution, and extracted twice. The extracts were combined, washed with water and brine. They were then dried over magnesium sulfate, filtered and concentrated and purified by silica gel chromatography (using a 0-50% ethyl acetate/hexane gradient) to afford 4-(3-nitro-5-trifluoromethyl-benzyl)-morpholine (409 mg, 27% yield). $^1$H NMR (DMSO-d$_6$) δ 8.46 (s, 1H), 8.4 (s, 1H), 8.15 (s, 1H), 3.7 (s, 2H), 3.6 (m, 4H), 2.4 (s, 4H).

Example 151A

Step 2: The nitro compound from the previous step was dissolved in 6 ml of ethyl acetate, to this solution 10% palladium on carbon was added. The solution was evacuated and purged with hydrogen three times and stirred overnight at room temperature. The reaction was filtered and concentrated to give 3-morpholin-4-ylmethyl-5-trifluoromethyl-phenylamine (350 mg, 95% yield). $^1$H NMR (DMSO-d$_6$) δ 6.78 (s, 1H), 6.70 (m, 2H), 5.6 (s, 2H), 4.0 (m, 4H), 3.58 (d, 2H), 2.22 (m, 4H); LCMS (ESI) m/z 233 (M+H)$^+$.

Example 151A

Step 3: The amine (350 mg, 1.3 mmol) was dissolved in 8 ml of dry THF, and potassium carbonate (242 mg, 1.7 mmol) was added followed by phenyl chloroformate (232 mg, 1.8 mmol). The reaction was stirred overnight at room temperature. The reaction was filtered through celite and concentrated to dryness. The resulting oil was partitioned between ethyl acetate and water and extracted twice. The resulting extracts were combined and dried over magnesium sulfate, filtered and concentrated to give phenyl 3-(morpholinomethyl)-5-(trifluoromethyl)phenylcarbamate. $^1$H NMR (DMSO-d$_6$) δ 10.58 (s, 1H), 7.8 (d, 2H), 7.4 (m, 2H), 7.3 (m, 4H), 3.6 (m, 6H), 2.37 (s, 4H).

Example 151B

The procedure described in Example 138B was used to react phenyl 3-(morpholinomethyl)-5-(trifluoromethyl)phenylcarbamate (140 mg, 0.37 mmol) with 3-(6,7-dimethoxyquinazolin-4-yloxy)aniline from Example 113A (78 mg, 0.25 mmol). To this solution was added diisopropylethyl amine (64 μL, 0.37 mmol) and DMAP (3.0 mg, 0.03 mmol). The reaction was concentrated to dryness and triturated with methanol to give 1-(3-(6,7-dimethoxyquinazolin-4-yloxy)phenyl)-3-(3-(morpholinomethyl)-5-(trifluoromethyl)phenyl)urea (47 mg, 32% yield). $^1$H NMR (DMSO-d$_6$) δ 9.15 (s, 1H), 8.97 (s, 1H), 8.57 (s, 1H), 7.92 (s, 1H), 7.60 (m, 3H), 7.40 (m, 2H), 7.28 (m, 2H), 6.96 (m, 1H), 4.00 (s, 6H), 3.51 (s, 4H), 3.38 (s, 2H), 2.35 (s, 4H). LCMS (ESI) m/z 584 (M+H)$^+$.

Example 152

Preparation of 1-(3-(1,1-difluoroethyl)isoxazol-5-yl)-3-(3-(6,7-dimethoxyquinazolin-4-yloxy)phenyl)urea Example 152A Step 1: In a round bottomed flask flushed with argon, a suspension of sodium hydride 60% in mineral oil (1.30 g, 34 mmoles) was rinsed twice with hexane, and suspended in 20 mL of dry THF. The solution was heated to 75° C., and ethyl difluoropropionate (3.00 g, 22 mmoles) and acetonitrile (1.78 mL) in 5 ml of dry THF was added dropwise over 30 minutes.

The temperature of the reaction was lowered to 65° C. and stirred overnight. The mixture was then concentrated to an oil and partitioned between water and ether, and extracted twice to remove any mineral oil and other impurities. The aqueous layer was acidified to pH=1 with 10% HCl, and the solution extracted twice. These extracts were dried over magnesium sulfate, filtered and concentrated to a crude oil. The crude product was purified using silica gel chromatography using a gradient of 10-40% ethyl acetate/hexane to afford 4,4-difluoro-3-oxo-pentanenitrile $^1$H(300 MHz, CDCl$_3$) δ 3.95 (s, 2H), 1.86 (m, 3H).

Example 152A

Step 2: The above ketonitrile (100 mg, 0.75 mmoles) was dissolved in 2 mL of ethanol, to this solution an aqueous solution of sodium hydroxide (33 mg, 0.82 mmoles) in 2 ml of water was added and stirred for 10 minutes. To this solution hydroxylamine sulfate (135 mg, 0.82 mmoles) was added in a single portion and stirred at room temperature for 15 minutes. The reaction was then heated to 80 C overnight. The solution was concentrated to one half the volume, diluted with water and extracted twice with ether. The ether extracts were dried over magnesium sulfate, filtered, and concentrated to give 3-(1,1-difluoro-ethyl)-isoxazol-5-ylamine (100 mg). $^1$H NMR (300 MHz, CDCl$_3$) δ 5.3 (s, 1H), 4.7 (s, 2H), 2.0 (m, 3H); LCMS (ESI) m/z 149 (M+H)$^+$.

Example 152A

Step 3: 3-(1,1-Difluoro-ethyl)-isoxazol-5-ylamine (100 mg, 0.68 mmoles) from the previous step was dissolved in 6 mL of dry THF. To this solution was added potassium carbonate (122 mg, 0.88 mmoles) and phenyl chloroformate (138 mg, 0.88 mmoles) and the reaction stirred overnight at room temperature. The reaction was filtered and concentrated to a yellow oil, and purified using silica gel chromatography with and ethyl acetate/hexane gradient 0-20% over 70 minutes to give phenyl 3-(1,1-difluoroethyl)isoxazol-5-ylcarbamate (141 mg) as an oil. $^1$H NMR (300 MHz, CDCl$_3$) δ 8.1 (s, 1H), 7.4-7.1 (m, 5H), 6.9 (m, 1H), 6.4 (s, 1H), 4.9 (s, 1H), 2.0 (m, 3H).

Example 152B

The carbamate from the previous step (141 mg, 0.52 mmol) was reacted as described in Example 138B with the 3-(6,7-dimethoxyquinazolin-4-yloxy)aniline from Example 113A (156 mg, 0.52 mmol). To this solution was added diisopropylethyl amine (136 μL, 0.78 mmol) and DMAP (5.0 mg, 0.04 mmol). The reaction was concentrated to dryness and partitioned between water and dichloromethane, and extracted twice. The combined extracts were washed with brine, dried over magnesium sulfate, filtered and concentrated. The oil was purified by reversed phase HPLC using a phenyl hexyl column eluting with a gradient of 40-70% acetonitrile/water over 60 minutes. The main peak was collected, concentrated, and lyophilized to afford the title compound (66 mg, 27% yield). $^1$H NMR (300 MHz, DMSO-d$_6$) δ 10.70 (s, 1H), 9.15 (s, 1H), 8.58 (s, 1H), 7.56 (s, 1H), 7.45 (m, 2H), 7.40 (m, 1H), 7.00 (m, 1H), 6.25 (s, 1H), 3.99 (s, 3H), 3.80 (s, 6H), 2.0 (m, 3H). LCMS (ESI) m/z 472 (M+H)

Example 153

Preparation of 1-(3-tert-butyl-1-phenyl-1H-pyrazol-5-yl)-3-(3-(6,7-dimethoxyquinazolin-4-yloxy)phenyl)urea Example 153A Using the procedure described in Example 161C, 3-tert-butyl-1-phenyl-1H-pyrazol-5-amine (2.00 g, 9.3 mmol) was reacted with phenyl chloroformate (1.6 g, 10.2 mmol) and K$_2$CO$_3$ (1.7 g, 12.1 mmol) in THF (20 mL), which was purified by silica gel chromatography (0-50% EtOAc/hexane) to afford phenyl 3-tert-butyl-1-phenyl-1H-pyrazol-5-ylcarbamate as solid (1.3 g, 42%). $^1$H NMR (300 MHz, DMSO-d$_6$) δ 10.0 (s, 1H), 7.55 (m, 4H), 7.40 (m, 3H), 7.08-7.23 (m, 3H), 6.37 (s, 1H), 1.3 (s, 9H); LC-MS (ESI) m/z 336 (M+H)$^+$.

Example 153B

The resulting carbamate (151 mg, 0.45 mmol) was reacted as described in Example 138B with 3-(6,7-dimethoxyquinazolin-4-yloxy)aniline from Example 113A (89 mg, 0.30 mmol) using diisopropylethyl amine (80 μL/45 mmol) and DMAP (4 mg, 0.03 mmol). After heating for 2 hours at 50° C. the reaction was concentrated to dryness. The resulting solid purified by silica gel chromatography (eluting with 0-85% ethyl acetate/hexane) to afford the title compound (68 mg, 42% yield). $^1$H NMR (DMSO-d$_6$) δ 9.13 (s, 1H), 8.55 (s, 1H), 8.47 (s, 1H), 7.55 (m, 6H), 7.40 (m, 3H), 7.15 (s, 1H), 6.95 (m, 1H), 6.36 (s, 1H), 4.00 (s, 6H), 1.25 (s, 9H). LCMS (ESI) m/z 539 (M+H).

Example 154

Preparation of 1-(3-tert-butyl-1-phenyl-1H-pyrazol-5-yl)-3-(3-(6,7-dimethoxyquinazolin-4-ylthio)phenyl)urea According to the procedure described in Example 138B, phenyl 3-tert-butyl-1-phenyl-1H-pyrazol-5-ylcarbamate (151 mg, 0.45 mmol) from Example 153A was reacted with 3-(6,7-dimethoxyquinazolin-4-ylthio)aniline from Example 115B (89 mg, 0.30 mmol). To this solution was added diisopropylethyl amine (80 μL, 0.45 mmol) and DMAP (4 mg, 0.03 mmol). After heating for 2 hours at 50° C., the reaction was concentrated to dryness. The resulting solid was triturated with 1:1 dichloromethane/hexane and the solid removed by filtration to afford the title compound (83 mg, 50% yield). $^1$H NMR (300 MHz, DMSO-d$_6$) δ 9.24 (s, 1H), 8.68 (s, 1H), 8.47 (s, 1H), 7.55 (m, 4H), 7.40 (m, 5H), 7.20 (s, 1H), 6.95 (m, 1H), 6.36 (s, 1H), 3.98 (s, 6H), 1.25 (s, 9H); LCMS (ESI) m/z 555 (M+H)$^+$.

Example 155

Preparation of 1-(3-(6,7-dimethoxyquinazolin-4-yloxy)phenyl)-3-(3-(1-(trifluoromethyl)cyclobutyl)isoxazol-5-yl)urea Example 155A Step 1: Methyl 1-(trifluoromethyl)cyclobutanecarboxylate (2 g, 11 mmol) was reacted according to the procedure described in Example 122A Step 1, to afford 3-oxo-3-(1-(trifluoromethyl)cyclobutyl)propanenitrile as a yellow oil (1.68 g, 80%) which was used in the next step without further purification. ¹H NMR (300 MHz, CDCl₃) δ 3.70 (s, 2H), 2.39-2.65 (m, 4H), 1.95-2.15 (m, 2H).

Example 155A

Step 2: 3-Oxo-3-(1(trifluoromethyl)cyclobutyl)propanenitrile (500 mg, 2.6 mmol) was reacted according to the procedure described in Example 122A Step 2 to afford 341-(trifluoromethyl)cyclobutyl)isoxazol-5-amine as a colorless solid (210 mg, 39%). ¹H NMR (300 MHz, CDCl₃) δ 5.04 (s, 1H), 4.55 (brs, 2H), 2.40-2.60 (m, 4H), 1.90-2.10 (m, 2H).

Example 155A

Step 3: 3-(1-(Trifluoromethyl)cyclobutyl)isoxazol-5-amine (210 mg, 1.0 mmol) was reacted according to the procedure described in Example 12A Step 3, to afford phenyl 3-(1-(trifluoromethyl)cyclobutyl)isoxazol-5-ylcarbamate as a colorless solid (320 mg, 98%). ¹H NMR (300 MHz, DMSO-d₆) δ 12.17 (brs, 1H), 7.10-7.54 (m, 5H), 6.08 (s, 1H), 2.50-2.70 (m, 4H), 1.90-2.10 (m, 2H); LC-MS (ESI) m/z 327 (M+H)⁺.

Example 155B

The resulting carbamate intermediate (147 mg, 0.45 mmol) from the previous step was reacted as described in Example 138B with 3-(6,7-dimethoxyquinazolin-4-yloxy)aniline from Example 113A (89 mg, 0.30 mmol) and diisopropylethyl amine (80 µL, 0.45 mmol) and DMAP (4 mg, 0.03 mmol). After heating for 2 hours the reaction was concentrated to dryness. The resulting solid was purified by silica gel chromatography eluting with a 0-100% ethyl acetate/hexane gradient over 60 minutes. The appropriate fractions were concentrated to a solid weighing 74 mg. ¹H NMR (300 MHz, DMSO-d₆) δ 10.48 (s, 1H), 9.11 (s, 1H), 8.56 (s, 1H), 7.79 (s, 1H), 7.57 (m, 2H), 7.40 (m, 2H), 7.39 (s, 1H), 7.01 (m, 1H), 6.08 (s, 1H), 3.99 (s, 6H), 2.58 (m, 4H), 2.03 (s, 2H). LCMS (ESI) m/z 530 (M+H)⁺.

Example 156

Preparation of 1-(3-(6,7-dimethoxyquinazolin-4-ylthio)phenyl)-3-(3-(1-(trifluoromethyl)cyclobutyl)isoxazol-5-yl)urea The procedure for Example 138B was used to react phenyl-3-(1-(trifluoromethyl)cyclobutyl)isoxazol-5-y carbamate (147 mg, 0.45 mmol) with 3-(6,7-dimethoxyquinazolin-4-ylthio)aniline from Example 115B (94 mg, 0.30 mmol). To this solution was added diisopropylethyl amine (80 µL, 0.45 mmol) and DMAP (4 mg, 0.03 mmol). After heating for 2 hours the reaction was concentrated to dryness. The resulting solid was purified by silica gel chromatography (eluting with a 0-100% ethyl acetate/hexane gradient) to afford the title compound (42 mg). ¹H NMR (300 MHz, DMSO-d₆) δ 10.49 (s, 1H), 9.13 (s, 1H), 8.69 (s, 1H), 7.84 (s, 1H), 7.7-7.2 (m, 5H), 6.08 (s, 1H), 3.99 (s, 6H), 2.58 (m, 4H), 2.03 (s, 2H); LCMS (ESI) m/z 546 (M+H)⁺.

Example 157

Preparation of 1-(3-tert-butyl-1-methyl-1H-pyrazol-5-yl)-3-(3-(6,7-dimethoxyquinazolin-4-ylthio)phenyl)urea Example 157A According to the procedure described in Example 161C, 3-tert-butyl-1-methyl-1H-pyrazol-5-amine (1.0 g, 6.5 mmol), and K₂CO₃ (1.17 g, 8.5 mmol) in THF (15 mL) were reacted with phenyl chloroformate (1.12 g, 7.2 mmol). The crude product was purified by silica gel chromatography with 0-50% EtOAc/hexane gradient to afford phenyl 3-tert-butyl-1-methyl-1H-pyrazol-5-ylcarbamate as solid (0.53 g, 31%). ¹H NMR (300 MHz, DMSO-d₆) δ 10.2 (s, 1H), 7.43 (m, 2H), 7.25 (m, 3H), 6.06 (s, 1H), 3.66 (s, 3H), 1.25 (s, 9H); LC-MS (ESI) m/z 274 (M+H)⁺.

Example 157B

The procedure for Example 138B was used to react phenyl 3-tert-butyl-1-methyl-1H-pyrazol-5-ylcarbamate (123 mg, 0.45 mmol) with 3-(6,7-dimethoxyquinazolin-4-ylthio) aniline from Example 115B (94 mg, 0.30 mmol). To this solution was added diisopropylethyl amine (80 µL, 0.45 mmol) and DMAP (4 mg, 0.03 mmol). After heating for 2 hours the reaction was concentrated to dryness. The resulting solid was purified by silica gel chromatography eluting with an ethyl acetate/hexane gradient 0-100% over 60 minutes. The appropriate fractions were concentrated to a solid weighing 102 mg. ¹H NMR (300 MHz, DMSO-d₆) δ 9.15 (s, 1H), 8.75 (s, 1H), 8.56 (s, 1H), 7.85 (s, 1H), 7.65-7.15 (m, 5H), 6.08 (s, 1H), 4.00 (s, 6H), 3.65 (s, 3H), 1.25 (s, 9H). LCMS (ESI) m/z 493 (M+H)⁺.

Example 158

Preparation of 1-(3-tert-butyl-1-methyl-1H-pyrazol-5-yl)-3-(3-(6,7-dimethoxyquinazolin-4-yloxy)phenyl)urea Example 158A According to the procedure described in Example 161C, to a suspension of 3-tert-butyl-1-methyl-1H-pyrazol-5-amine (1.0 g, 6.5 mmol) and K₂CO₃ (1.17 g, 8.5 mmol) in THF (15 mL) was added phenyl chloroformate (1.12 g, 7.2 mmol). The crude product was purified by silica gel chromatography with 0-50% EtOAc/hexane as eluants to afford phenyl 3-tert-butyl-1-methyl-1H-pyrazol-5-ylcarbamate as solid (0.53 g, 31%). ¹H NMR (300 MHz, DMSO-d₆) δ 10.2 (s, 1H), 7.43 (m, 2H), 7.25 (m, 3H), 6.06 (s, 1H), 3.66 (s, 3H), 1.25 (s, 9H); LC-MS (ESI) m/z 274 (M+H)⁺.

Example 158B

The resulting carbamate (123 mg, 0.45 mmol) was reacted as described in Example 138B with the intermediate amine (89 mg, 0.30 mmol) using diisopropylethyl amine (80 µL, 0.45 mmol) and DMAP (4 mg, 0.03 mmol). After heating for 2 hours at 50° C., the reaction was concentrated to dryness. The resulting solid was purified by silica gel chromatography eluting with a gradient of 0-100% ethyl acetate/hexane to afford the title compound (102 mg, 71% yield). ¹H NMR (300 MHz, DMSO-d₆) δ 9.20 (s, 1H), 8.56 (s, 1H), 7.53 (m, 2H), 7.50 (m, 2H), 7.30 (m, 1H), 6.95 (m, 1H), 6.08 (s, 1H), 3.99 (s, 6H), 3.54 (s, 3H), 1.25 (s, 9H). LC-MS (ESI) m/z 477 (M+H)⁺.

Example 159

Preparation of 1-[3-(1,3-difluoro-2-methylpropan-2-yl)isoxazol-5-yl]-3-[3-(6,7-dimethoxyquinazolin-4-yloxy]phenyl)urea Example 159A Step 1: To a solution of 5-fluoro-4-(fluoromethyl)-4-methyl-3-oxopentanenitrile (1.00 g, 6.2 mmol) and NaOH (0.272 g, 6.8 mmol) in EtOH (5 mL) and water (5 mL) at room temperature was added a solution of hydroxylamine sulfate (1.12 g, 6.8 mmol) in water (5 mL). To the mixture was added additional NaOH until the pH was about 8. After heating at 100° C. for 2 hours, it was quenched with water and extracted with $CH_2Cl_2$. Extracts were washed with water, dried over $MgSO_4$, and concentrated under reduced pressure. The residue was purified by silica gel chromatography eluted with with gradient of 0-50% EtOAc/hexane to afford 3-(1,3-difluoro-2-methylpropan-2-yl)isoxazol-5-amine as a solid (0.191 g, 17%). $^1$H NMR (300 MHz, $CDCl_3$) δ 5.16 (s, 1H), 4.63 (q, 2H), 4.5 (q and br, 4H), 1.37 (s, 3H); LC-MS (ESI) m/z 177 (M+H)$^+$.

Example 159A

Step 2: Using the procedure described in Example 161C, 3-(1,3-difluoro-2-methylpropan-2-yl)isoxazol-5-amine (0.19 g, 1.08 mmol) was reacted with phenyl chloroformate (0.235 g, 1.5 mmol) in the presence of $K_2CO_3$ (0.276 g, 2 mmol) in THF (10 mL), and purified by silica gel chromatography with 10-25% EtOAc/hexane as eluants to afford phenyl 3-(1,3-difluoro-2-methylpropan-2-yl)isoxazol-5-ylcarbamate as solid (0.319 g, 100%). $^1$H NMR (300 MHz, $CDCl_3$) δ 7.83 (s, 1H), 7.17-7.45 (m, 5H), 6.23 (s, 1H), 4.69 (dq, 2H), 4.50 (dq, 2H), 1.40 (s, 3H); LC-MS (ESI) m/z 297 (M+H)$^+$.

Example 159B

A mixture of phenyl 3-(1,3-difluoro-2-methylpropan-2-yl)isoxazol-5-ylcarbamate (0.158 g, 0.5 mmol), 3-(6,7-dimethoxyquinazolin-4-yloxy)aniline from Example 113A (0.119 g, 0.4 mmol), and N,N-diisopropylethylamine (0.8 mL) in THF (6 mL) was heated at 50° C. for 5 hours. It was quenched with saturated $NaHCO_3$ and extracted with $CH_2Cl_2$. Extracts were dried over $MgSO_4$ and concentrated under reduced pressure. It was purified by silica gel chromatography with 40-95% EtOAc/hexane as eluants to afford 1-[3-(1,3-difluoro-2-methylpropan-2-yl)isoxazol-5-yl]-3-[3-(6,7-dimethoxyquinazolin-4-yloxy]phenyl)urea as solid (0.115 g, 58%). $^1$H NMR (300 MHz, DMSO-$d_6$) δ 10.33 (s, 1H), 9.00 (s, 1H), 8.55 (s, 1H), 7.56 (m, 3H), 7.39 (s, 1H), 7.27 (s and d, 2H), 6.24 (s, 1H), 4.73 (m, 2H), 4.56 (m, 2H), 3.99 (s, 3H), 3.98 (s, 3H), 1.30 (s, 3H); LC-MS (ESI) m/z 500 (M+H)$^+$.

Example 160

Preparation of 1-[3-(1,3-difluoro-2-methylpropan-2-yl)isoxazol-5-yl]-3-[3-(6,7-dimethoxyquinazolin-4-ylthio]phenyl)urea Using the procedure described in Example 159B, a mixture of phenyl 3-(1,3-difluoro-2-methylpropan-2-yl)isoxazol-5-ylcarbamate described in Example 159A (0.158 g, 0.5 mmol), 3-(6,7-dimethoxyquinazolin-4-ylthio)aniline from Example 115B (0.125 g, 0.4 mmol), and N,N-diisopropylethylamine (0.8 mL) in THF (6 mL) were heated at 50° C. for 5 hours, to afford 1-[3-(1,3-difluoro-2-methylpropan-2-yl)isoxazol-5-yl]-3-[3-(6,7-dimethoxyquinazolin-4-ylthio)phenyl]urea as solid (0.114 g, 55%). $^1$H NMR (300 MHz, DMSO-$d_6$) δ 10.38 (s, 1H), 9.10 (s, 1H), 8.70 (s, 1H), 7.85 (s, 1H), 7.56 (d, 1H), 7.46 (t, 1H), 7.34 (m, 3H), 6.22 (s, 1H), 4.70 (m, 2H), 4.55 (m, 2H), 3.99 (s, 6H), 1.28 (s, 3H); LC-MS (ESI) m/z 516 (M+H)$^+$.

Example 161

1-[3-(6,7-dimethoxyquinazolin-4-yloxy)phenyl]-3-[1-phenyl-3-(trifluoromethyl)-1H-pyrazol-5-yl]urea Example 161A Step 1: To a solution of triethyl orthoacetate (8.11 g, 50 mmol) and pyridine (9.10 g, 115 mmol) in $CH_2Cl_2$ (50 mL) at 0° C. was dropped 2,2,2-trifluoroacetic anhydride (21.00 g, 100 mmol). After stirred at room temperature overnight, it was quenched with cold saturated $NaHCO_3$ solution and washed with water. The organic layer was dried over $MgSO_4$, concentrated under reduced pressure, and dried under vacuum to afford 4,4-diethoxy-1,1,1-trifluorobut-3-en-2-one as an oil (10.116 g, 95%). $^1$H NMR (300 MHz, $CDCl_3$) δ 4.94 (s, 1H), 4.37 (q, 2H), 4.15 (q, 2H), 1.46 (t, 3H), 1.42 (t, 3H); LC-MS (ESI) m/z 213 (M+H)$^+$.

Example 161A

Step 2: To a solution of 4,4-diethoxy-1,1,1-trifluorobut-3-en-2-one (7.94 g, 37.4 mmol) in MeCN (30 mL) at room temperature was dropped 28% solution of $NH_4OH$ in water (7 mL). It was stirred at room temperature overnight. After solvent was removed under reduced pressure, to it was added $CH_2Cl_2$ and washed with water. The organic layer was dried over $MgSO_4$ and concentrated under reduced pressure to afford (E)-4-amino-4-ethoxy-1,1,1-trifluorobut-3-en-2-one as solid (6.371 g, 93%). $^1$H NMR (300 MHz, $CDCl_3$) δ 9.79 (br, 1H), 5.66 br, 1H), 5.13 (s, 1H), 4.15 (q, 2H), 1.38 (t, 3H); LC-MS (ESI) m/z 184 (M+H)$^+$.

Example 161A

Step 3: A mixture of (E)-4-amino-4-ethoxy-1,1,1-trifluorobut-3-en-2-one (2.93 g, 16 mmol) and phenylhydrazine (1.947 g, 18 mmol) in EtOH (15 mL) was heated at 95° C. for 8 hours. The reaction was quenched with water and extracted with $CH_2Cl_2$. Extracts were dried over $MgSO_4$ and concentrated under reduced pressure. The crude product was purified by silica gel chromatography with 5-25% EtOAc/hexane as eluants to afford 1-phenyl-3-(trifluoromethyl)-1H-pyrazol-5-amine as a yellow solid (2.23 g, 66%). $^1$H NMR (300 MHz, $CDCl_3$) δ 7.51 (m, 5H), 5.87 (s, 1H), 3.93 (br, 2H); LC-MS (ESI) m/z 228 (M+H)$^+$.

Alternative Preparation of 1-phenyl-3-(trifluoromethyl)-1H-pyrazol-5-amine

Step 161B Step 1: To a suspension of NaH (2.88 g, 120 mmol) in THF (70 mL) at 80° C. was dropped a solution of methyl 2,2,2-trifluoroacetate (10.244 g, 80 mmol) in MeCN (5.377 g, 130 mmol) over 40 minutes. The mixture was heated at 70° C. for 2 hours and stirred at room temperature overnight. The reaction was quenched with water, acidified with 10% HCl solution to pH 1, and extracted with $CH_2Cl_2$. Extracts were dried over $MgSO_4$, concentrated under reduced pressure, and dried under vacuum to afford 4,4,4-trifluoro-3-oxobutanenitrile as an oil (9.084 g, 83%). $^1$H NMR (300 MHz, $CDCl_3$) δ 2.93 (s, 2H).

Example 161B

Step 2: A mixture of 4,4,4-trifluoro-3-oxobutanenitrile (2.056 g, 15 mmol) and phenylhydrazine hydrochloride (2.169 g, 15 mmol) in EtOH was heated at 90° C. for 8 hours.

The reaction was quchened with water, basified with saturated NaHCO$_3$ solution, and extracted with CH$_2$Cl$_2$. Extracts were dried over MgSO$_4$, concentrated under reduced pressure, and dried under vacuum to afford 1-phenyl-3-(trifluoromethyl)-1H-pyrazol-5-amine as yellow solid (3.089 g, 91%). $^1$H NMR (300 MHz, CDCl$_3$) δ 7.54 (m, 5H), 5.85 (s, 1H), 3.95 (br, 2H); LC-MS (ESI) m/z 228 (M+H)$^+$.

Example 161C

To a suspension of 1-phenyl-3-(trifluoromethyl)-1H-pyrazol-5-amine (1.136 g, 5 mmol) and K$_2$CO$_3$ (1.035 g, 7.5 mmol) in THF (20 mL) was dropped a solution of phenyl chloroformate (0.939 g, 6 mmol) in THF (10 mL). After stirred at room temperature overnight, the mixture was quenched with water and extracted with CH$_2$Cl$_2$. Extracts were dried over MgSO$_4$, concentrated under reduced pressure, and dried under vacuum to afford phenyl 1-phenyl-3-(trifluoromethyl)-1H-pyrazol-5-ylcarbamate as solid (1.714 g, 99%). $^1$H NMR (300 MHz, CDCl$_3$) δ 7.55 (m, 5H), 7.39 (m, 2H), 7.28 (m, 2H), 7.14 (m, 2H), 6.86 (m, 1H); LC-MS (ESI) m/z 348 (M+H)$^+$.

Example 161D

The title compound was prepared as described in Example 159B, using phenyl 1-phenyl-3-(trifluoromethyl)-1H-pyrazol-5-ylcarbamate from the previous step (0.139 g, 0.4 mmol), 3-(6,7-dimethoxyquinazolin-4-yloxy)aniline from Example 113A (0.119 g, 0.4 mmol), and N,N-diisopropylethylamine (0.3 mL) in THF (6 mL) at 50° C. for 6 hours, to afford 1-[3-(6,7-dimethoxyquinazolin-4-yloxy)phenyl]-3-[1-phenyl-3-(trifluoromethyl)-1H-pyrazol-5-yl]urea as solid (0.116 g, 53%). $^1$H NMR (300 MHz, DMSO-d$_6$) δ 9.32 (s, 1H), 8.80 (s, 1H), 8.55 (s, 1H), 7.54-7.62 (m, 7H), 7.39 (m, 2H), 7.19 (d, 1H), 6.96 (d, 1H), 6.86 (s, 1H), 3.99 (s, 3H), 3.98 (s, 3H); LC-MS (ESI) m/z 551 (M+H)$^+$.

Example 162

Preparation of 1-[5-(1,3-difluoro-2-methylpropan-2-yl)isoxazol-3-yl]-3-[3-(6,7-dimethoxyquinazolin-4-yloxy)phenyl]urea Example 162A Step 1: To a mixture of hydroxylamine sulfate (0.59 g, 3.6 mmol) and NaHCO$_3$ (0.700 g, 8.3 mmol) in MeOH (1 mL) and water (10 mL) was added 5-fluoro-4-(fluoromethyl)-4-methyl-3-oxopentanenitrile (0.483 g, 3 mmol). After heated at 60° C. for 8 hours, to it was added 10% HCl until pH 1. It was heated at 60° C. for 3 hours, basified with saturated NaHCO$_3$, and extracted with CH$_2$Cl$_2$. Extracts were dried over MgSO$_4$ and concentrated under reduced pressure to afford 5-(1,3-difluoro-2-methylpropan-2-yl)isoxazol-3-amine as needles (0.289 g, 55%). $^1$H NMR (300 MHz, CDCl$_3$) δ 5.76 (s, 1H), 4.59 (q, 2H), 4.50 (q and br, 4H), 1.37 (s, 3H); LC-MS (ESI) m/z 177 (M+H)$^+$.

Example 162A

Step 2: Using the procedure described in Example 161C, using 5-(1,3-difluoro-2-methylpropan-2-yl)isoxazol-3-amine (0.287 g, 1.6 mmol), phenyl chloroformate (0.313 g, 2 mmol) were reacted in the presence of K$_2$CO$_3$ (0.345 g, 2.5 mmol) in THF (15 mL), and purified by silica gel chromatography (using 5-25% EtOAc/hexane as eluants) to afford phenyl 5-(1,3-difluoro-2-methylpropan-2-yl)isoxazol-3-ylcarbamate as a solid (0.358 g, 76%). $^1$H NMR (300 MHz, CDCl$_3$) δ 8.17 (br, 1H), 7.42 (m, 2H), 7.26 (m, 1H), 7.20 (m, 2H), 6.81 (s, 1H), 4.67 (q, 2H), 4.51 (q, 2H), 1.42 (s, 3H); LC-MS (ESI) m/z 297 (M+H)$^+$.

Example 162B

A mixture of phenyl 5-(1,3-difluoro-2-methylpropan-2-yl)isoxazol-3-ylcarbamate from the previous step (0.089 g, 0.3 mmol), 3-(6,7-dimethoxyquinazolin-4-yloxy)aniline from Example 113A (0.089 g, 0.3 mmol), and 4-(dimethylamino)pyridine (0.03 g) in THF (6 mL) was stirred at room temperature overnight. The reaction was quenched with water and extracted with CH$_2$Cl$_2$. Extracts were dried over MgSO$_4$ and concentrated under reduced pressure. The crude product was purified by silica gel chromatography (eluting with 70-95% EtOAc/hexane) to afford 1-[5-(1,3-difluoro-2-methylpropan-2-yl)isoxazol-3-yl]-3-[3-(6,7-dimethoxyquinazolin-4-yloxy)phenyl]urea as solid (0.055 g, 31%). $^1$H NMR (300 MHz, DMSO-d$_6$) δ 9.70 (s, 1H), 9.02 (s, 1H), 8.57 (s, 1H), 7.57 (m, 2H), 7.40 (m, 2H), 7.27 (d, 1H), 6.98 (d, 1H), 6.77 (s, 1H), 4.71 (s, 2H), 4.56 (s, 2H), 4.00 (s, 3H), 3.98 (s, 3H), 1.28 (s, 3H); LC-MS (ESI) m/z 500 (M+H)$^+$.

Example 163

Preparation of 1-(3-cyclopentylisoxazol-5-yl)-3-(3-(6,7-dimethoxyquinazolin-4-yloxy)phenyl)urea Example 163A Using the procedure described in Example 113B but substituting 3-cyclopentylisoxazol-5-amine (675 mg, 4.44 mmol) for the 5-phenylisoxazole-3-amine, phenyl 3-cyclopentylisoxazol-5-ylcarbamate (528 mg, 50%) was afforded as a white solid. $^1$H NMR (300 MHz, CDCl$_3$) δ 8.21 (bs, 1H), 7.44-7.39 (m, 2H), 7.30-7.26 (m, 1H), 7.21 (d, 2H), 6.06 (s, 1H), 3.17-3.07 (m, 1H), 2.06-1.99 (m, 2H), 1.76-1.63 (m, 6H); LC-MS (ESI) m/z 273 (M+H)$^+$.

Example 163B

Using the procedure described in Example 113C, 3-(6,7-dimethoxyquinazolin-4-yloxy)aniline from Example 113A (104 mg, 0.35 mmol) and the carbamate from the previous step (124 mg, 0.45 mmol) were reacted in the presence of N,N-diisopropylethylamine (73 μl, 0.42 mmol) to give 143-cyclopentylisoxazol-5-yl)-3-(3-(6,7-dimethoxyquinazolin-4-yloxy)phenyl)urea (75.22 mg, 45%) as a white solid. $^1$H NMR (300 MHz, DMSO-d$_6$) δ 10.18 (s, 1H), 9.05 (s, 1H), 8.56 (s, 1H) 7.57 (s, 2H), 7.56-7.39 (t, 2H) 7.29 (d, 1H), 6.98 (d, 1H), 5.95 (s, 1H), 4.00 (s, 6H), 3.04-3.01 (m, 1H), 1.99-1.93 (m, 2H), 1.69-1.61 (m, 6H)); LC-MS (ESI) m/z 476 (M+H)$^+$.

Example 164

Preparation of 1-[3-(6,7-dimethoxyquinazolin-4-yloxy)phenyl]-3-[1-methyl-3-(trifluoromethyl)-1H-pyrazol-5-yl]urea Example 164A Step 1: Using the procedure described in Example 161A Step 3, (E)-4-amino-4-ethoxy-1,1,1-trifluorobut-3-en-2-one (2.34 g, 12.78 mmol) and methylhydrazine (0.645 g, 14 mmol) were reacted in EtOH (10 mL) at 95° C. for 8 hours, and purified by silica gel chromatography with 30-40% EtOAc/hexane as eluants to afford 1-methyl-3-(trifluoromethyl)-1H-pyrazol-5-amine as solid (1.733 g, 68.3%). MP: 100-101° C.; $^1$H NMR (300 MHz, CDCl$_3$) δ 5.80 (s, 1H), 3.71 (s, 3H), 3.62 (br, 2H); LC-MS (ESI) m/z 166 (M+H)$^+$.

Example 164B

Using the procedure described in Example 161C, 1-methyl-3-(trifluoromethyl)-1H-pyrazol-5-amine (1.70 g, 10.3 mmol) and phenyl chloroformate (1.88 g, 12 mmol) were reacted to afford phenyl 1-methyl-3-(trifluoromethyl)-1H-pyrazol-5-ylcarbamate as solid (0.760 g, 26%). LC-MS (ESI) m/z 286 (M+H)$^+$.

Example 164C

Using the procedure described in Example 159B, phenyl 1-methyl-3-(trifluoromethyl)-1H-pyrazol-5-ylcarbamate from the previous step (0.114 g, 0.4 mmol), 3-(6,7-dimethoxyquinazolin-4-yloxy)aniline from Example 113A (0.119 g, 0.4 mmol), and N,N-diisopropylethylamine (0.3 mL) in THF (6 mL) were heated at 50° C. for 3 hours, to afford 1-[3-(6,7-Dimethoxyquinazolin-4-yloxy)phenyl]-3-[1-methyl-3-(trifluoromethyl)-1H-pyrazol-5-yl]urea as solid (0.047 g, 24%). $^1$H NMR (300 MHz, CDCl$_3$) δ 9.6 (br, 1H), 8.64 (s, 1H), 7.63 (m, 1H), 7.57 (s, 1H), 7.43 (t, 1H), 7.33 (m, 2H), 7.01 (d, 1H), 6.94 (s, 1H), 6.26 (s, 1H), 4.08 (s, 6H), 3.93 (s, 3H); LC-MS (ESI) m/z 489 (M+H)$^+$.

Example 165

Preparation of 1-[3-(6,7-dimethoxyquinazolin-4-yloxy)phenyl]-3-[1-methyl-5-(trifluoromethyl)-1H-pyrazol-3-yl]urea Example 165A Step 1: Using the procedure described in Example 161A Step 3, (E)-4-amino-4-ethoxy-1,1,1-trifluorobut-3-en-2-one (1.83 g, 10 mmol) and methylhydrazine sulfate (1.586 g, 11 mmol) were reacted and the crude product purified by silica gel chromatography (with 0-10% EtOAc/CH$_2$Cl$_2$ as eluants) to afford 1-methyl-5-(trifluoromethyl)-1H-pyrazol-3-amine as solid (0.381 g, 23%). $^1$H NMR (300 MHz, CDCl$_3$) δ 5.94 (s, 1H), 3.78 (s, 3H), 3.67 (br, 2H); LC-MS (ESI) m/z 166 (M+H)$^+$.

Example 165A

Step 2: Using the procedure described in Example 161C, 1-methyl-5-(trifluoromethyl)-1H-pyrazol-3-amine (0.38 g, 2.3 mmol) and phenyl chloroformate (0.438 g, 2.8 mmol) were reacted in the presence of K$_2$CO$_3$ (0.415 g, 3 mmol) in THF (10 mL), to afford phenyl 1-methyl-5-(trifluoromethyl)-1H-pyrazol-3-ylcarbamate as solid (0.465 g, 71%). $^1$H NMR (300 MHz, CDCl$_3$) δ 8.05 (s, 1H), 7.17-7.45 (m, 5H), 6.93 (s, 1H), 3.91 (s, 3H); LC-MS (ESI) m/z 286 (M+H)$^+$.

Example 165B

Using the procedure described in Example 159B, phenyl 1-methyl-5-(trifluoromethyl)-1H-pyrazol-3-ylcarbamate from the previous step (0.114 g, 0.4 mmol), 3-(6,7-dimethoxyquinazolin-4-yloxy)aniline from Example 113A (0.119 g, 0.4 mmol), and N,N-diisopropylethylamine (0.5 mL) in THF (6 mL) were heated at 50° C. for 3 hours, to afford 1-[3-(6,7-dimethoxyquinazolin-4-yloxy)phenyl]-3-[1-methyl-5-(trifluoromethyl)-1H-pyrazol-3-yl]urea as solid (0.041 g, 21%). $^1$H NMR (300 MHz, CDCl$_3$) δ 9.6 (br, 1H), 8.65 (s, 1H), 7.63 (m, 1H), 7.61 (s, 1H), 7.43 (t, 1H), 7.33 (m, 2H), 7.02 (dd, 1H), 6.92 (s, 1H), 6.25 (s, 1H), 4.08 (s, 6H), 3.93 (s, 3H); LC-MS (ESI) m/z 489 (M+H)$^+$.

Example 166

Preparation of ethyl 2-(3-tert-butyl-5-{3-[3-(6,7-dimethoxyquinazolin-4-yloxy)phenyl]ureido}-1H-pyrazol-1-yl)acetate Example 166A Step 1: A mixture of ethyl 2-hydrazinylacetate hydrochloride (0.309 g, 2 mmol), NaHCO$_3$ (0.185 g, 2.2 mmol), and 4,4-dimethyl-3-oxopentanenitrile (0.250 g, 2 mmol) in EtOH (10 mL) was heated at 60° C. overnight. The reaction was quenched with water and extracted with CH$_2$Cl$_2$. Extracts were dried over MgSO$_4$ and concentrated under reduced pressure to afford ethyl 2-(5-amino-3-tert-butyl-1H-pyrazol-1-yl)acetate as solid (0.369 g, 82%). $^1$H NMR (300 MHz, CDCl$_3$) δ 5.50 (s, 1H), 4.75 (s, 2H), 4.23 (q, 2H), 3.57 (br, 2H), 1.29 (t, 3H), 1.25 (s, 9H); LC-MS (ESI) m/z 226 (M+H)$^+$.

Example 166A

Step 2: In the manner described in Example 161C, using ethyl 2-(5-amino-3-tert-butyl-1H-pyrazol-1-yl)acetate (1.68 g, 7.46 mmol), phenyl chloroformate (1.284 g, 8.2 mmol), and K$_2$CO$_3$ (1.52 g, 11 mmol) in THF (20 mL), which was purified by silica gel chromatography with 0-40% EtOAc/hexane as eluants to afford ethyl 2-[3-tert-butyl-5-(phenoxycarbonylamino)-1H-pyrazol-1-yl]acetate as solid (1.115 g, 43%). $^1$H NMR (300 MHz, CDCl$_3$) δ 7.37-7.43 (m, 2H), 7.25-7.27 (m, 2H), 7.21 (m, 2H), 6.25 (s, 1H), 4.88 (s, 2H), 4.28 (q, 2H), 1.33 (t, 3H), 1.28 (s, 9H); LC-MS (ESI) m/z 346 (M+H)$^+$.

Example 166B

In the manner described in Example 159B, ethyl 2-[3-tert-butyl-5-(phenoxycarbonylamino)-1H-pyrazol-1-yl]acetate from the previous step (0.138 g, 0.4 mmol) was reacted with 3-(6,7-dimethoxyquinazolin-4-yloxy)aniline from Example 113A (0.119 g, 0.4 mmol), and N,N-diisopropylethylamine (0.5 mL) in THF (6 mL) at 50° C. for 7 hours, to afford ethyl 2-(3-tert-butyl-5-{3-[3-(6,7-dimethoxyquinazolin-4-yloxy)phenyl]ureido}-1H-pyrazol-1-yl)acetate as solid (0.145 g, 66%). $^1$H NMR (300 MHz, DMSO-d$_6$) δ 8.97 (s, 1H), 8.59 (s, 1H), 8.56 (s, 1H), 7.59 (m, 1H), 7.56 (s, 1H), 7.39 (m, 2H), 7.22 (d, 1H), 6.94 (d, 1H), 6.11 (s, 1H), 4.85 (s, 2H), 4.16 (q, 2H), 3.99 (s, 6H), 1.19 (t and s, 12H); LC-MS (ESI) m/z 549 (M+H)$^+$.

Example 167

Preparation of 1-[3-(1,3-difluoro-2-methylpropan-2-yl)-1-phenyl-1H-pyrazol-5-yl]-3-[3-(6,7-dimethoxyquinazolin-4-yloxy)phenyl]urea Example 167A Step 1: To a suspension of 3-hydroxy-2-(hydroxymethyl)-2-methylpropanoic acid (10.06 g, 75 mmol) in MeOH was dropped 2.0 M solution of (trimethylsilyl)diazomethane in diethyl ether and stirred at room temperature overnight. After solvent was concentrated under reduced pressure, the reaction was quenched with saturated NaHCO$_3$ solution and extracted with CH$_2$Cl$_2$. Extracts were dried over MgSO$_4$ and concentrated under reduced pressure to afford methyl 3-hydroxy-2-(hydroxymethyl)-2-methylpropanoate as an oil (3.79 g, 34%). $^1$H NMR (300 MHz, CDCl$_3$) δ 3.81 (d, 2H), 3.67 (s, 3H), 3.60 (d, 2H), 2.89 (br, 2H), 0.96 (s, 3H).

Example 167A

Step 2: To a solution of methyl 3-hydroxy-2-(hydroxymethyl)-2-methylpropanoate (13.04 g, 88 mmol) and 2,6-lutidine (26.79 g, 250 mmol) in CH$_2$Cl$_2$ at −78° C. under argon was dropped neat trifluoroacetic anhydride (50.00 g, 177 mmol). It was stirred for 2 hours, at which time the temperature was raised to room temperature and the mixture was stirred for 2 more hours at room temperature. The reaction was quenched with CH$_2$Cl$_2$ (200 mL), washed with 3% HCl solution (200 mL), dried over MgSO$_4$, and concentrated to dryness to provide an oil.

The oil was dissolved in THF (50 mL) and cooled with ice bath. To it was added 1.0 M solution of tetrabutylammonum fluoride in THF (200 mL). The solution was stirred at room temperature overnight. After solvent was concentrated under reduced pressure, CH$_2$Cl$_2$ (400 mL) was added, and the solution was washed with brine twice (200 mL×2), dried over MgSO$_4$, and concentrated under reduced pressure. It was distilled under reduced pressure and the fraction was collected at about 60° C. to afford methyl 3-fluoro-2-(fluoromethyl)-2-methylpropanoate as an oil (2.89 g, 22%). $^1$H NMR (300 MHz, CDCl$_3$) δ 4.33-4.66 (m, 4H), 3.67 (s, 3H), 1.14 (s, 3H).

Example 167A

Step 3: According to the procedure described in Example 161B Step 1, methyl 3-fluoro-2-(fluoromethyl)-2-methylpropanoate (5.21 g, 34.2 mmol), NaH (1.248 g, 52 mmol), and MeCN (2.791 g, 68 mmol) in THF (40 mL) were heated at 70° C. overnight, to afford 5-fluoro-4-(fluoromethyl)-4-methyl-3-oxopentanenitrile as oil (4.412 g, 80%). $^1$H NMR (300 MHz, CDCl$_3$) δ 4.67 (m, 2H), 4.52 (m, 2H), 3.80 (s, 2H), 1.27 (s, 3H).

Example 167A

Step 4: According to the procedure described in Example 161B Step 2, 5-fluoro-4-(fluoromethyl)-4-methyl-3-oxopentanenitrile (0.81 g, 5 mmol) and phenylhydrazine hydrochloride (0.868 g, 14 mmol) in EtOH were heated at 95° C. for 2 hours, to afford 3-(1,3-difluoro-2-methylpropan-2-yl)-1-phenyl-1H-pyrazol-5-amine as solid (0.75 g, 52%). LC-MS (ESI) m/z 252 (M+H)$^+$.

Example 167B

According to the procedure described in Example 161C, to a solution of 3-(1,3-difluoro-2-methylpropan-2-yl)-1-phenyl-1H-pyrazol-5-amine (0.75 g, 2.98 mmol) in THF (25 mL) and K$_2$CO$_3$ (1.037 g, 7.5 mmol), was added phenyl chloroformate (0.548 g, 3.5 mmol). The crude product was purified by silica gel chromatography (with 10-25% EtOAc/hexane as eluants) to afford phenyl 3-(1,3-difluoro-2-methylpropan-2-yl)-1-phenyl-1H-pyrazol-5-ylcarbamate as solid (1.143 g, 100%). $^1$H NMR (300 MHz, CDCl$_3$) δ 7.5 (m, 3H), 7.4 (m, 4H), 7.2 (m, 4H), 6.6 (s, 1H), 4.75 (q, 2H), 4.55 (q, 2H), 1.4 (s, 3H); LC-MS (ESI) m/z 372 (M+H)$^+$.

Example 167C

Using the procedure described in Example 159B, phenyl 3-(1,3-difluoro-2-methylpropan-2-yl)-1-phenyl-1H-pyrazol-5-ylcarbamate from the previous step (0.186 g, 0.5 mmol) was reacted with 3-(6,7-dimethoxyquinazolin-4-yloxy) aniline from Example 113A (0.119 g, 0.4 mmol), and N,N-diisopropylethylamine (0.8 mL) in THF (6 mL) at 50° C. for 6 hours, to afford 1-[3-(1,3-difluoro-2-methylpropan-2-yl)-1-phenyl-1H-pyrazol-5-yl]-3-[3-(6,7-dimethoxyquinazolin-4-yloxy)phenyl]urea as solid (0.037 g, 16%). $^1$H NMR (300 MHz, DMSO-d$_6$) δ 9.16 (s, 1H), 8.54 (s, 2H), 7.56 (m, 7H), 7.50 (d, 1H), 7.38 (s, 1H), 7.22 (m, 2H), 6.54 (s, 1H), 4.73 (m, 2H), 4.58 (m, 2H), 3.99 (s, 3H), 3.97 (s, 3H), 1.33 (s, 3H); LC-MS (ESI) m/z 575 (M+H)$^+$.

Example 168

Preparation of 1-[3-(6,7-dimethoxyquinazolin-4-yloxy)phenyl]-3-[3-(2-ethoxypropan-2-yl)-1-phenyl-1H-pyrazol-5-yl]urea Example 168A Using the procedure described in Example 161B Step 2, using 4-fluoro-4-methyl-3-oxopentanenitrile (0.77 g, 6 mmol) and phenylhydrazine hydrochloride (0.954 g, 6.6 mmol) in EtOH at 95° C. for 3 hours, which was purified by silica gel chromatography with 10-35% EtOAc/hexane to afford 3-(2-ethoxypropan-2-yl)-1-phenyl-1H-pyrazol-5-amine as solid (0.315 g, 24%). $^1$H NMR (300 MHz, CDCl$_3$) δ 7.54 (m, 2H), 7.43 (m, 2H), 7.27 (m, 1H), 5.60 (s, 1H), 3.83 (br, 2H), 3.35 (q, 2H), 1.63 (s, 6H), 1.15 (t, 3H); LC-MS (ESI) m/z 246 (M+H)$^+$.

Example 168B

Using the procedure described in Example 161C, 3-(2-ethoxypropan-2-yl)-1-phenyl-1H-pyrazol-5-amine (0.429 g, 1.75 mmol) and phenyl chloroformate (0.329 g, 2.1 mmol) were reacted in the presence of K$_2$CO$_3$ (0.415 g, 3 mmol) in THF (15 mL), and purified by silica gel chromatography with 15-35% EtOAc/hexane as eluants to afford phenyl 3-(2-ethoxypropan-2-yl)-1-phenyl-1H-pyrazol-5-ylcarbamate as solid (0.594 g, 93%). $^1$H NMR (300 MHz, CDCl$_3$) δ 7.53 (m, 5H), 7.41-7.48 (m, 4H), 7.14-7.38 (m, 2H), 6.6 (s, 1H), 3.37 (q, 2H), 1.59 (s, 6H), 1.14 (t, 3H); LC-MS (ESI) m/z 320 (M-OEt)$^+$.

Example 168C

Using the procedure described in Example 159B, phenyl 3-(2-ethoxypropan-2-yl)-1-phenyl-1H-pyrazol-5-ylcarbamate (0.115 g, 0.33 mmol), 3-(6,7-dimethoxyquinazolin-4-yloxy)aniline from Example 113A (0.098 g, 0.33 mmol), and N,N-diisopropylethylamine (0.8 mL) in THF (6 mL) were heated at 50° C. for 5 hours, to afford 1-[3-(6,7-dimethoxyquinazolin-4-yloxy)phenyl]-3-[3-(2-ethoxypropan-2-yl)-1-phenyl-1H-pyrazol-5-yl]urea as solid (0.113 g, 60%). $^1$H NMR (300 MHz, DMSO-d$_6$) δ 9.25 (br, 1H), 8.55 (s, 1H), 8.54 (s, 1H), 7.54 (m, 6H), 7.39 (m, 3H), 7.18 (d, 1H), 6.93 (d, 1H), 6.41 (s, 1H), 3.77 (s, 3H), 3.98 (s, 3H), 3.25 (q, 2H), 1.45 (s, 6H), 1.03 (t, 3H); LC-MS (ESI) m/z 523 (M-OEt)$^+$.

Example 169

Preparation of 1-[3-(6,7-dimethoxyquinazolin-4-yloxy)phenyl]-3-[1-phenyl-5-(trifluoromethyl)-1H-pyrazol-3-yl]urea

Example 169A

Step 1. To a solution of NaOEt (10.893 g, 160 mmol) in EtOH (60 mL) was added phenylhydrazine (4.466 g, 41.3 mmol). After stirring for 10 minutes, (Z)-4,4,4-trifluorobut-2-enenitrile (5.00 g, 41.3 mmol) was added to the solution. The solution was heated at 95° C. overnight. The solvent was removed under reduced pressure, and the reaction was quenched with water and extracted with $CH_2Cl_2$. Extracts were dried over $MgSO_4$ and concentrated under reduced pressure to about 1/10 volume. To it was added hexane to form a brown solid, which was filtered to give the product (5.401 g). The filtrate was purified by silica gel chromatography (with 30-45% EtOAc/hexane) to give 1-phenyl-5-(trifluoromethyl)-4,5-dihydro-1H-pyrazol-3-amine the product (1.517 g). Both solids were then combined. (6.918 g, 73%). $^1$H NMR (300 MHz, $CDCl_3$) δ 7.24 (m, 2H), 7.09 (m, 2H), 6.92 (m, 1H), 4.39 (m, 1H), 4.22 (br, 2H), 3.46 (dd, 1H), 2.87 (q, 1H); LC-MS (ESI) m/z 230 $(M+H)^+$.

Example 169A

Step 2. A mixture of 1-phenyl-5-(trifluoromethyl)-4,5-dihydro-1H-pyrazol-3-amine (1.47 g, 6.41 mmol) and DDQ (1.748 g, 7.7 mmol) in $CH_2Cl_2$ (30 mL) was stirred at room temperature for 4 hours. The crude product was purified by silica gel chromatography twice (with 15-35% and 10-30% EtOAc/hexane as eluants) to afford 1-phenyl-5-(trifluoromethyl)-1H-pyrazol-3-amine as an oil (0.666 g, 46%). $^1$H NMR (300 MHz, $CDCl_3$) δ 7.42 (m, 5H), 6.18 (s, 1H), 3.82 (br, 2H); LC-MS (ESI) m/z 228 $(M+H)^+$.

Example 169B

Using the procedure described in Example 161C, 1-phenyl-5-(trifluoromethyl)-1H-pyrazol-3-amine (0.665 g, 2.9 mmol) and phenyl chloroformate (0.548 g, 3.5 mmol) were reacted in the presence of $K_2CO_3$ (0.691 g, 5 mmol) in THF (20 mL) and purified by silica gel chromatography with 10-20% EtOAc/hexane as eluents to afford phenyl 1-phenyl-5-(trifluoromethyl)-1H-pyrazol-3-ylcarbamte as a solid (0.794 g, 79%). $^1$H NMR (300 MHz, $CDCl_3$) δ 7.97 (br, 1H), 7.38-7.46 (m, 7H), 7.14-7.29 (m, 4H); LC-MS (ESI) m/z 348 $(M+H)^+$.

Example 169C

A mixture of phenyl 1-phenyl-5-(trifluoromethyl)-1H-pyrazol-3-ylcarbamate (0.115 g, 0.33 mmol), 3-(6,7-dimethoxyquinazolin-4-yloxy)aniline from Example 113A (0.098 g, 0.33 mmol), and N,N-diisopropylethylamine (0.8 mL) in THF (6 mL) was heated at 50° C. for 12 hours and 60° C. for 6 hours. LC-MS showed the reaction was not complete. Therefore, to it was added 4-(dimethylamino)pyridine (0.03 g) and heated at 60° C. for 5 hours. The crude product was purified by silica gel chromatography with EtOAc/hexane as eluants to afford the title compound as solid (0.061 g, 34%). $^1$H NMR (300 MHz, DMSO-$d_6$) δ 9.47 (s, 1H), 8.99 (s, 1H), 8.57 (s, 1H), 7.57 (m, 7H), 7.40 (m, 2H), 7.26 (d, 1H), 7.12 (s, 1H), 6.96 (d, 1H), 4.00 (s, 3H), 3.99 (s, 3H); LC-MS (ESI) m/z 551 $(M+H)^+$.

Example 170

Preparation of 1-[3-(6,7-dimethoxyquinazolin-4-ylthio)phenyl]-3-[1-phenyl-5-(trifluoromethyl)-1H-pyrazol-3-yl]urea The title compound was prepared as described in Example 169C, using phenyl 1-phenyl-5-(trifluoromethyl)-1H-pyrazol-3-ylcarbamate described in Example 169B (0.115 g, 0.33 mmol), 3-(6,7-dimethoxyquinazolin-4-ylthio)aniline from Example 115B (0.103 g, 0.33 mmol), and N,N-diisopropylethylamine (0.8 mL) in THF (6 mL), to afford 1-[3-(6,7-dimethoxyquinazolin-4-ylthio)phenyl]-3-[1-phenyl-5-(trifluoromethyl)-1H-pyrazol-3-yl]urea as solid (0.084 g, 45%). $^1$H NMR (300 MHz, DMSO-$d_6$) δ 9.47 (s, 1H), 9.01 (s, 1H), 8.70 (s, 1H), 7.86 (s, 1H), 7.55 (m, 6H), 7.45 (t, 1H), 7.36 (s, 1H), 7.35 (s, 1H), 7.28 (s, 1H), 7.14 (s, 1H), 4.00 (s, 6H); LC-MS (ESI) m/z 567 $(M+H)^+$.

Example 171

Preparation of 1-[3-(6,7-dimethoxyquinazolin-4-yloxy)phenyl]-3-[1-(4-fluorophenyl)-3-(trifluoromethyl)-1H-pyrazol-5-yl]ure

Example 171A

According to the procedure described in Example 161A Step 3, using (E)-4-amino-4-ethoxy-1,1,1-trifluorobut-3-en-2-one (2.747 g, 15 mmol), (4-fluorophenyl)hydrazine hydrochloride (2.439 g, 15 mmol), and triethylamine (2.03 g, 20 mmol) at 95° C. for 8 hours, which was purified by silica gel chromatography with 5-25% EtOAc/hexane as eluants to afford 1-(4-fluorophenyl)-3-(trifluoromethyl)-1H-pyrazol-5-amine as solid (2.346 g, 64%). $^1$H NMR (300 MHz, $CDCl_3$) 67.55 (m, 2H), 7.20 (m, 2H), 5.87 (s, 1H), 3.87 (br, 2H); LC-MS (ESI) m/z 246 $(M+H)^+$.

Example 171B

According to the procedure described in Example 161C, to a solution of 1-(4-fluorophenyl)-3-(trifluoromethyl)-1H-pyrazol-5-amine (2.346 g, 9.57 mmol) in THF (25 mL) and $K_2CO_3$ (2.63 g, 19 mmol) was added phenyl chloroformate (1.948 g, 12.4 mmol). The crude product was purified by silica gel chromatography (with 5-20% EtOAc/hexane as eluants) to afford phenyl 1-(4-fluorophenyl)-3-(trifluoromethyl)-1H-pyrazol-5-ylcarbamate as solid (2.772 g, 79%). $^1$H NMR (300 MHz, $CDCl_3$) δ 7.54 (m, 2H), 7.40 (m, 2H), 7.27 (m, 3H), 7.14 (m, 2H), 6.97 (br, 1H), 6.85 (s, 1H); LC-MS (ESI) m/z 366 $(M+H)^+$.

Example 171C

The title compound was prepared as described in Example 162B, using phenyl 1-(4-fluorophenyl)-3-(trifluoromethyl)-1H-pyrazol-5-ylcarbamate described in Example 171B (0.146 g, 0.4 mmol), 3-(6,7-dimethoxyquinazolin-4-yloxy)aniline from Example 113A (0.119 g, 0.4 mmol), and 4-(dimethylamino)pyridine (0.025 g) in THF (6 mL), to afford 1-[3-(6,7-dimethoxyquinazolin-4-yloxy)phenyl]-3-[1-(4-fluorophenyl)-3-(trifluoromethyl)-1H-pyrazol-5-yl]urea as solid (0.203 g, 89%). $^1$H NMR (300 MHz, DMSO-$d_6$) δ 9.28 (s, 1H), 8.79 (s, 1H), 8.55 (d, 1H), 7.68 (m, 2H), 7.55 (m, 2H), 7.41 (m, 4H), 7.20 (d, 1H), 6.96 (d, 1H), 6.85 (s, 1H), 3.99 (s, 3H), 3.98 (s, 3H); LC-MS (ESI) m/z 569 $(M+H)^+$.

Example 172

Preparation of 1-[3-(6,7-dimethoxyquinazolin-4-yloxy)phenyl]-3-[(1-p-tolyl-3-(trifluoromethyl)-1H-pyrazol-5-yl]urea

Example 172A

According to the procedure described in Example 161A Step 3, (E)-4-amino-4-ethoxy-1,1,1-trifluorobut-3-en-2-one (2.747 g, 15 mmol), p-tolylhydrazine hydrochloride (2.379 g, 15 mmol) and triethylamine (2.03 g, 20 mmol) were heated at 95° C. for 8 hours. The crude product was purified by silica gel chromatography with 5-25% EtOAc/hexane as eluants to afford 1-p-tolyl-3-(trifluoromethyl)-1H-pyrazol-5-amine as solid (2.237 g, 62%). $^1$H NMR (300 MHz, CDCl$_3$) δ 7.42 (d, 2H), 7.30 (d, 2H), 5.84 (s, 1H), 3.88 (br, 2H), 2.41 (s, 3H); LC-MS (ESI) m/z 242 (M+H)$^+$.

Example 172B

According to the procedure described in Example 161C, to a solution of 1-p-tolyl-3-(trifluoromethyl)-1H-pyrazol-5-amine (2.237 g, 9.57 mmol) in THF (25 mL) and K$_2$CO$_3$ (2.48 g, 18.5 mmol) was added phenyl chloroformate (1.887 g, 12.1 mmol). The crude product was purified by silica gel chromatography with 5-20% EtOAc/hexane as eluants to afford phenyl 1-p-Tolyl-3-(trifluoromethyl)-1H-pyrazol-5-ylcarbamate as solid (3.614 g, 94%). $^1$H NMR (300 MHz, CDCl$_3$) δ 7.40 (m, 6H), 7.26 (m, 2H), 7.24 (m, 2H), 6.86 (s, 1H), 2.46 (s, 3H); LC-MS (ESI) m/z 362 (M+H)$^+$.

Example 172C

According to the procedure described in Example 162B, the intermediate phenyl 1-p-tolyl-3-(trifluoromethyl)-1H-pyrazol-5-ylcarbamate from the previous step (0.145 g, 0.4 mmol) was reacted with 3-(6,7-dimethoxyquinazolin-4-yloxy)aniline from Example 113A (0.119 g, 0.4 mmol), and 4-(dimethylamino)pyridine (0.025 g) in THF (6 mL), to afford 1-[3-(6,7-dimethoxyquinazolin-4-yloxy)phenyl]-3-[1-p-tolyl-3-(trifluoromethyl)-1H-pyrazol-5-yl]urea as a solid (0.134 g, 59%). $^1$H NMR (300 MHz, DMSO-d$_6$) δ 9.32 (s, 1H), 8.75 (s, 1H), 8.55 (d, 1H), 7.55 (m, 2H), 7.39 (m, 6H), 7.19 (d, 1H), 6.95 (d, 1H), 6.84 (s, 1H), 3.99 (s, 3H), 3.98 (s, 3H), 2.41 (s, 3H); LC-MS (ESI) m/z 565 (M+H)$^+$.

Example 173

Preparation of 1-(4-tert-butylphenyl)-3-(3-(6,7-dimethoxyquinazolin-4-yloxy)phenyl)urea To 3-(6,7-dimethoxyquinazolin-4-yloxy)aniline from Example 113A (89 mg, 0.3 mmol) in DMF (3 mL) was added 4-tert-butylphenyl isocyanate (54 µL, 0.3 mmol) and the solution stirred at 50° C. for 4h. The reaction was allowed to cool to room temperature, diluted with H$_2$O, and extracted with EtOAc. The organic layer was washed with brine, dried over MgSO$_4$, filtered, concentrated in vacuo, and purified by column chromatography (25-100% EtOAc/hexanes) to give 1-(4-tert-butylphenyl)-3-(3-(6,7-dimethoxyquinazolin-4-yloxy)phenyl)urea (54 mg, 0.11 mmol, 38%). $^1$H NMR (300 MHz, DMSO-d$_6$) δ 8.83 (s, 1H), 8.65 (s, 1H), 8.57 (s, 1H), 7.60 (s, 1H), 7.56 (s, 1H), 7.40-7.21 (m, 7H), 6.91 (d, 1H), 3.99 (s, 6H), 1.25 (s, 9H); LC-MS (ESI) m/z 473 (M+H)$^+$.

Example 174

Preparation of 1-(4-tert-butylphenyl)-3-(3-(6,7-dimethoxyquinazolin-4-ylthio)phenyl)urea 3-(6,7-dimethoxyquinazolin-4-ylthio)aniline from Example 115B (94 mg, 0.3 mmol) was reacted with 4-tert-butylphenyl isocyanate (54 uL, 0.3 mmol) as described in Example 173 to give 1-(4-tert-butylphenyl)-3-(3-(6,7-dimethoxyquinazolin-4-ylthio)phenyl)urea (40 mg, 0.08 mmol, 27%). $^1$H NMR (300 MHz, DMSO-d$_6$) δ 8.84 (s, 1H), 8.70 (s, 1H), 8.65 (s, 1H), 7.84 (s, 1H), 7.51 (d, 1H), 7.45-7.20 (m, 8H), 3.99 (s, 6H), 1.25 (s, 9H); LC-MS (ESI) m/z 489 (M+H)$^+$.

Example 175

Preparation of 1-(4-chlorophenyl)-3-(3-(6,7-dimethoxyquinazolin-4-yloxy)phenyl)urea In a sealed reaction vessel, 3-(6,7-dimethoxyquinazolin-4-yloxy)aniline from Example 113A (100 mg, 0.34 mmol) was dissolved in 10 mL of dry THF. To this solution was added 4-chlorophenyl isocyanate (61 mg, 0.4 mmol). The reaction was heated to 80° C. for 2 hours. The solution was then concentrated to dryness and purified by silica gel chromatography eluting with an ethyl acetate/dichloromethane gradient 5-30% over 16 column volumes. The major peak was concentrated and recrystallized with ethyl acetate/hexanes, and the solid collected by vacuum filtration to give 26.53 mg. $^1$H (DMSO-d6) 8.9 (m, 2H), 8.5 (s, 1H), 7.8-7.2 (m, 9H), 6.9 (m, 1H), 4.1 (s, 6H)
LCMS (ESI) m/z 515 (M+H)

Example 176

Preparation of 1-(4-chloro-3-(trifluoromethyl)phenyl)-3-(3-(6,7-dimethoxyquinazolin-4-yloxy)phenyl)urea Using the procedure for Example 175 the title compound was synthesized substituting 4-chloro-3-trifluoromethylphenyl isocyanate (89 mg, 0.40 mmol) for 4-chlorophenyl isocyanate. Isolation and purification was accomplished using the identical procedure to give 21.7 mg. $^1$H (DMSO-d6) 9.35 (s, 1H), 9.15 (s, 1H), 8.60 (s, 1H), 8.10 (s, 1H), 7.60 (m, 4H), 7.5-7.2 (m, 3H), 6.95 (m, 1H), 3.99 (s, 6H). LCMS (ESI) m/z 519 (M+H)

Example 177

Preparation of 1-(3-(6,7-dimethoxyquinazolin-4-yloxy)phenyl)-3-(4-(trifluoromethoxy)phenyl)urea Using the procedure for Example 175 the title compound was synthesized substituting 4-trifluoromethoxy phenyl isocyanate (82 mg, 0.40 mmol) for 4-chlorophenyl isocyanate. Isolation and purification was accomplished using the identical procedure to give 21.7 mg. $^1$H (DMSO-d6) 8.98 (s, 1H), 8.56 (s, 1H), 7.7-7.2 (m, 9H), 6.95 (m, 1H), 3.99 (s, 6H). LCMS (ESI) m/z 501 (M+H)

Example 178

Preparation of 1-(3-(6,7-dimethoxyquinazolin-4-yloxy)phenyl)-3-(3-methoxyphenyl)urea Using the procedure for Example 175 the title compound was synthesized substituting 3-methoxy phenyl isocyanate (60 mg, 0.40 mmol) for 4-chlorophenyl isocyanate. Isolation and purification was accomplished using the identical procedure to give 13.4 mg. $^1$H (DMSO-d6) 8.88 (s, 1H), 8.76 (s, 1H), 8.57 (s, 1H), 7.59 (m, 2H), 7.40 (m, 2H), 7.18 (m, 3H), 9.93 (m, 2H), 6.55 (m, 1H), 4.00 (s, 6H), 3.71 (s, 3H). LCMS (ESI) m/z 447 (M+H).

Example 179

Preparation of 1-(3-(6,7-dimethoxyquinazolin-4-yloxy)phenyl)-3-(3-ethoxyphenyl)urea Using the procedure for Example 175 the title compound was synthesized substituting 3-ethoxyphenyl isocyanate (56 mg, 0.34 mmol) for 4-chlorophenyl isocyanate. Isolation and purification was accomplished by silica gel chromatography eluting with a methanol-dichloromethane 0-15% over 70 minutes to give 47 mg. $^1$H (DMSO-d6) 8.85 (s, 1H), 8.71 (s, 1H), 8.55 (s, 1H), 7.60 (m, 2H), 7.39 (m, 2H), 7.21 (m, 3H), 6.9 (m, 2H), 5.75 (m, 1H), 4.0 (m, 8H), 1.30 (m, 3H). LCMS (ESI) m/z 461 (M+H).

Example 180

Preparation of 1-(3-chloro-4-methoxyphenyl)-3-(3-(6,7-dimethoxyquinazolin-4-yloxy)phenyl)urea Using the procedure for Example 175 the title compound was synthesized substituting 3-chloro-4-methoxyphenyl isocyanate (63 mg, 0.34 mmol) for 4-chlorophenyl isocyanate. Isolation and purification was accomplished by silica gel chromatography eluting with a methanol-dichlromethane 0-15% over 70 minutes to give 107 mg. $^1$H (DMSO-d6) 8.87 (s, 1H), 8.70 (s, 1H), 8.56 (s, 1H), 7.65 (s, 1H), 7.56 (s, 2H), 7.40 (m, 2H), 7.2 (m, 2H), 7.1 (d, 1H), 6.90 (d, 1H), 4.0 (s, 6H), 3.80 (s, 3H). LCMS (ESI) m/z 481 (M+H)

Example 181

Preparation of 1-(3-(6,7-dimethoxyquinazolin-4-yloxy)phenyl)-3-(3-(trifluoromethyl)phenyl)urea Using the procedure for Example 175 the title compound was synthesized substituting 3-trifluoromethyl phenyl isocyanate (60 μL, 0.34 mmol) for 4-chlorophenyl isocyanate. Isolation and purification was accomplished by trituration with hexane to give 112 mg. $^1$H (DMSO-d6) 9.13 (s, 1H), 9.02 (s, 1H), 8.56 (s, 1H), 8.01 (s, 1H), 7.7-7.5 (m, 4H), 7.5-7.2 (m, 4H), 6.93 (1H), 3.99 (s, 6H). LCMS (ESI) m/z 485 (M+H)

Example 182

Preparation of 1-(3-(6,7-dimethoxyquinazolin-4-yloxy)phenyl)-3-phenylurea

To 3-(6,7-dimethoxyquinazolin-4-yloxy)aniline from Example 113A (89 mg, 0.3 mmol) in THF (3 mL) was added phenyl isocyanate (33 uL, 0.3 mmol) and the solution stirred at room temperature overnight. The reaction was concentrated in vacuo, diluted with EtOAc, and filtered to give 14346,7-dimethoxyquinazolin-4-yloxy)phenyl)-3-phenylurea (63 mg, 0.15 mmol, 50%). $^1$H NMR (300 MHz, DMSO-d$_6$) δ 8.88 (s, 1H), 8.74 (s, 1H), 8.57 (s, 1H), 7.61-7.56 (m, 2H), 7.48-7.35 (m, 4H), 7.32-7.21 (m, 3H), 7.02-7.89 (m, 2H), 3.99 (s, 6H); LC-MS (ESI) m/z 417 (M+H)$^+$.

Example 183

Preparation of 1-(3-(6,7-dimethoxyquinazolin-4-yloxy)phenyl)-3-(4-(trifluoromethyl)phenyl)urea The title compound was prepared from 3-(6,7-dimethoxyquinazolin-4-yloxy)aniline from Example 113A (89 mg, 0.3 mmol) and 4-(trifluoromethyl)phenyl isocyanate (42 uL, 0.3 mmol) using the procedure in Example 182 to give 14346,7-dimethoxyquinazolin-4-yloxy)phenyl)-3-(4-(trifluoromethyl)phenyl)urea (119 mg, 0.25 mmol, 82%). $^1$H NMR (300 MHz, DMSO-d$_6$) δ 9.18 (s, 1H), 9.03 (s, 1H), 8.57 (s, 1H), 7.68-7.62 (m, 4H), 7.61-7.55 (m, 2H), 7.44-7.37 (m, 2H), 7.28 (d, 1H), 6.95 (d, 1H), 3.99 (s, 6H); LC-MS (ESI) m/z 485 (M+H)$^+$.

Example 184

Preparation of 1-(3-(6,7-dimethoxyquinazolin-4-ylthio)phenyl)-3-(4-(trifluoromethyl)phenyl)urea The title compound was prepared from 3-(6,7-dimethoxyquinazolin-4-ylthio)aniline from Example 115B (94 mg, 0.3 mmol) and 4-(trifluoromethyl)phenyl isocyanate (42 uL, 0.3 mmol) using the procedure in Example 182 to give 14346,7-dimethoxyquinazolin-4-ylthio)phenyl)-3-(4-(trifluoromethyl)phenyl)urea (130 mg, 0.26 mmol, 87%). $^1$H NMR (300 MHz, DMSO-d$_6$) δ 9.19 (s, 1H), 9.03 (s, 1H), 8.70 (s, 1H), 7.83 (s, 1H), 7.68-7.60 (m, 4H), 7.56 (d, 1H), 7.44 (t, 1H), 7.35 (d, 2H), 7.27 (d, 1H), 3.99 (s, 6H); LC-MS (ESI) m/z 501 (M+H)$^+$.

Example 185

Preparation of 1-(3-(6,7-dimethoxyquinazolin-4-ylthio)phenyl)-3-(3-(trifluoromethyl)phenyl)urea The title compound was prepared from 3-(6,7-dimethoxyquinazolin-4-ylthio)aniline from Example 115B (94 mg, 0.3 mmol) and 3-(trifluoromethyl)phenyl isocyanate (42 uL, 0.3 mmol) using the procedure in Example 182 to give 14346,7-dimethoxyquinazolin-4-ylthio)phenyl)-3-(3-(trifluoromethyl)phenyl)urea (109 mg, 0.22 mmol, 73%). $^1$H NMR (300 MHz, DMSO-d$_6$) δ 9.13 (s, 1H), 9.03 (s, 1H), 8.70 (s, 1H), 8.01 (s, 1H), 7.84 (s, 1H), 7.62-7.41 (m, 4H), 7.39-7.24 (m, 4H), 3.99 (s, 6H); LC-MS (ESI) m/z 501 (M+H)$^+$.

Example 186

Preparation of 1-(4-chloro-3-(trifluoromethyl)phenyl)-3-(3-(6,7-dimethoxyquinazolin-4-ylthio)phenyl)urea The title compound was prepared from 3-(6,7-dimethoxyquinazolin-4-ylthio)aniline from Example 115B (94 mg, 0.3 mmol) and 4-chloro-3-(trifluoromethyl)phenyl isocyanate (66 mg, 0.3 mmol) using the procedure in Example 182 to give 1-(4-chloro-3-(trifluoromethyl)phenyl)-3-(3-(6,7-dimethoxyquinazolin-4-ylthio)phenyl)urea (113 mg, 0.21 mmol, 70%). $^1$H NMR (300 MHz, DMSO-d$_6$) δ 9.25 (s, 1H), 9.08 (s, 1H), 8.70 (s, 1H), 8.10 (s, 1H), 7.83 (s, 1H), 7.66-7.54 (m, 3H), 7.44 (t, 1H), 7.35 (s, 1H), 7.34 (s, 1H), 7.28 (d, 1H), 3.99 (s, 6H); LC-MS (ESI) m/z 535 (M+H)$^+$.

Example 187

Preparation of 1-(3-(6,7-dimethoxyquinazolin-4-ylthio)phenyl)-3-(3-(2-fluoropropan-2-yl)isoxazol-5-yl)urea 3-(6,7-dimethoxyquinazolin-4-ylthio)aniline from Example 115B (200 mg, 0.639 mmol) was reacted with phenyl 3-(2-fluoropropan-2-yl)isoxazol-5-ylcarbamate from Example 42A (253 mg, 0.959 mmol) according to the method described for 1-(3-(6,7-dimethoxyquinazolin-4-yloxy)phenyl)-3-(3-isopropylisoxazol-5-yl)urea in Example 122B, except the reaction mixture was stirred at room temperature for 72 h. Purification via trituration with methanol afforded 14346,7-dimethoxyquinazolin-4-ylthio)phenyl)-3-(3-(2-fluoropropan-2-yl)isoxazol-5-yl)urea as a colorless solid (142 mg, 46%). $^1$H NMR (300 MHz, DMSO-$d_6$) δ 10.43 (brs, 1H), 9.13 (brs, 1H), 8.70 (s, 1H), 7.84 (s, 1H), 7.57 (m, 1H), 7.46 (m, 1H), 7.30-7.35 (m, 3H), 6.16 (s, 1H), 3.99 (s, 6H), 1.67 (d, J=21 Hz, 6H); LC-MS (ESI) m/z 484 (M+H)$^+$.

Example 188

Preparation of 1-(3-(6,7-dimethoxyquinazolin-4-ylthio)phenyl)-3-(3-fluoro-4-(trifluoromethyl)phenyl)urea Following the procedure described in Example 138B with 3-fluoro-4-(trifluoromethyl)phenylcarbamate as described in Example 150 (135 mg, 0.45 mmol) and using 3-(6,7-dimethoxyquinazolin-4-ylthio)aniline from Example 115B (94 mg, 0.3 mmol). To this mixture diisopropylethyl amine (58 mg, 0.45 mmol) and DMAP (3.7 mg, 0.03 mmol) the reaction was heated at 50° C. overnight. The reaction was concentrated to dryness and triturated with dichloromethane. The resulting solid was collected by vacuum filtration to give 156 mg. $^1$H NMR (300 MHz, DMSO-$d_6$) δ 9.45 (s, 1H), 9.10 (s, 1H), 8.79 (s, 1H), 7.8 (s, 1H), 7.6 (m, 2H), 7.5 (m, 1H), 7.35 (m, H), 7.25 (m, 4H), 4.00 (s, 6H). LCMS (ESI) m/z 519 (M+H)

Example 189

Preparation of 1-(3-(6,7-dimethoxyquinazolin-4-ylthio)phenyl)-3-(3-(morpholinomethyl)-5-(trifluoromethyl)phenyl)urea The procedure described in Example 138B was used to react phenyl 3-(morpholinomethyl)-5-(trifluoromethyl)phenylcarbamate described in example 151A (140 mg, 0.37 mmol) with 3-(6,7-dimethoxyquinazolin-4-ylthio)aniline from Example 115B (77 mg, 0.25 mmol). To this solution was added diisopropylethyl amine (64 μL, 0.37 mmol) and DMAP (3.0 mg, 0.03 mmol). The reaction was concentrated to dryness and triturated with methanol to give 47 mg. $^1$H NMR (300 MHz, DMSO-$d_6$) δ 9.15 (s, 1H), 8.98 (s, 1H), 8.70 (s, 1H), 7.88 (d, 2H), 7.55 (m, 2H), 7.44 (m, 1H), 7.35 (s, 2H), 7.25 (m, 2H), 4.00 (s, 6H), 3.58 (s, 4H), 3.34 (s, 2H), 2.39 (s, 4H). LCMS (ESI) m/z 600 (M+H)

Example 190

Preparation of 1-(3-(6,7-dimethoxyquinazolin-4-ylthio)phenyl)-3-(3-methoxy-4-(trifluoromethyl)phenyl)urea

Example 190A

Step 1: Using the procedure for Example 113C, in a 100 mL round bottomed flask, sodium hydride (276 mg. 11.5 mmol) was suspended in 30 ml, of a dry THF and cooled to 0° C. To this solution methanol (427 μL, 10.56 mmol) was added and stirred for 30 minutes. This solution 2-fluoro-4-nitro-1-trifluoromethyl-benzene (2.0 g, 9.6 mmol) was added as a 2 mL THF solution. The reaction was allowed to warm to room temperature overnight with stirring. The reaction was concentrated and then partitioned between ethyl acetate and water, extracting twice. The extracts were dried with magnesium sulfate, filtered and concentrated. The nitro compound was purified by silica gel chromatography using a gradient of ethyl acetate/hexane 0-50% over 60 minutes. The main peak was collected, and concentrated to afford 2-methoxy-4-nitro-1-trifluoromethyl-benzene as an oil weighing 1.16 g. $^1$H NMR (300 MHz, DMSO-$d_6$) δ 8.0-7.9 (m, 3H), 3.9 (s, 3H)

Example 190A

Step 2: The nitro compound (1.16 g, 5.24 mmol) from the previous was dissolved in 30 mL of methanol and 10% palladium on carbon (100 mg) was added. The solution was evacuated and purged with hydrogen three times, then stirred under hydrogen overnight. This solution was then filtered through celite, and concentrated to an oil to give 3-methoxy-4-trifluoromethyl-phenylamine; $^1$H NMR (300 MHz, DMSO-$d_6$) δ 7.1 (d, 1H), 6.4 (s, 1H), 6.1 (m, 1H), 5.8 (s, 2H), 3.7 (s, 3H).

Example 190B

The amine from the previous step (831 mg, 3.75 mmol) was dissolved in 15 ml of THF, to this solution potassium carbonate (674 mg, 4.88 mmol) was added followed by phenyl chloroformate (647 mg, 4.13 mmol) dropwise as a THF solution. The reaction was stirred overnight at room temperature, then filtered through celite, concentrated and partitioned between ethyl acetate and water, and extracted twice. The extracts were combined and dried with magnesium sulfate, filtered and concentrated to a solid. The solid was triturated with 10% ether in hexane. The resulting solid weighing 684 mg was found to be phenyl 3-methoxy-4-(trifluoromethyl)phenyl carbamate. $^1$H NMR (300 MHz, DMSO-$d_6$) δ 10.6 (s, 1H), 7.58 (d, 1H), 7.48 (m, 3H), 7.2 (m, 3H), 7.1 (d, 1H), 3.8 (s, 3H)

Example 190C

The procedure described in Example 138B was used to react phenyl 3-methoxy-4-(trifluoromethyl)phenylcarbamate from the previous step (140 mg, 0.45 mmol) with 3-(6,7-dimethoxyquinazolin-4-ylthio)aniline from Example 115B (94 mg, 0.30 mmol). To this solution was added diisopropylethyl amine (80 μL, 0.46 mmol) and DMAP (4.0 mg, 0.03 mmol). The reaction was concentrated to dryness and triturated with dichloromethane to give 44 mg of final compound. $^1$H NMR (300 MHz, DMSO-$d_6$) δ 9.29 (s, 1H), 8.93 (s, 1H), 8.70 (s, 1H), 7.90 (s, 1H), 7.6-7.40 (m, 4H), 7.35 (m, 3H), 7.00 (m, 1H), 4.00 (s, 6H), 3.84 (s, 3H). LCMS (ESI) m/z 531 (M+H)

Example 191

Preparation of 1-[5-(1,3-difluoro-2-methylpropan-2-yl)isoxazol-3-yl]-3-[3-(6,7-dimethoxyquinazolin-4-ylthio)phenyl]urea Using the procedure described in Example 162B, phenyl 5-(1,3-difluoro-2-methylpropan-2-yl)isoxazol-3-ylcarbamate as described in Example 162A (0.089 g, 0.3 mmol) was reacted with 3-(6,7-dimethoxyquinazolin-4-ylthio)aniline from Example 115B (0.094 g, 0.3 mmol), and 4-(dimethylamino)pyridine (0.03 g) in THF (6 mL), to afford 1-[5-(1,3-difluoro-2-methylpropan-2-yl)isoxazol-3-yl]-3-[3-(6,7-dimethoxyquinazolin-4-ylthio)phenyl]urea as solid (0.048 g, 31%). $^1$H NMR (300 MHz, DMSO-d$_6$) δ 9.71 (s, 1H), 9.02 (s, 1H), 8.70 (s, 1H), 7.85 (d, 1H), 7.52 (d, 1H), 7.46 (t, 1H), 7.35 (d, 2H), 7.29 (d, 1H), 6.78 (s, 1H), 4.72 (s, 2H), 4.56 (s, 2H), 3.99 (s, 6H), 1.29 (s, 3H); LC-MS (ESI) m/z 516 (M+H)$^+$.

Example 192

Preparation of 1-[3-(6,7-dimethoxyquinazolin-4-ylthio)phenyl]-3-[1-phenyl-3-(trifluoromethyl)-1H-pyrazol-5-yl]urea Using the procedure described in Example 159B, using phenyl 1-phenyl-3-(trifluoromethyl)-1H-pyrazol-5-ylcarbamate described in Example 161C (0.139 g, 0.4 mmol), 3-(6,7-dimethoxyquinazolin-4-ylthio)aniline from Example 115B (0.125 g, 0.4 mmol), and N,N-diisopropylethylamine (0.3 mL) in THF (6 mL) at 50° C. for 6 hours, to afford 1-[3-(6,7-dimethoxyquinazolin-4-ylthio)phenyl]-3-[1-phenyl-3-(trifluoromethyl)-1H-pyrazol-5-yl]urea as solid (0.100 g, 44%). $^1$H NMR (300 MHz, DMSO-d$_6$) δ 9.33 (s, 1H), 8.80 (s, 1H), 8.70 (s, 1H), 7.78 (s, 1H), 7.53 (m, 5H), 7.25-7.48 (m, 5H), 6.81 (s, 1H), 3.99 (s, 6H); LC-MS (ESI) m/z 567 (M+H)$^+$.

Example 193

Preparation of 1-[3-(6,7-dimethoxyquinazolin-4-ylthio)phenyl]-3-[1-methyl-3-(trifluoromethyl)-1H-pyrazol-5-yl]urea Using the procedure described in Example 159B, phenyl 1-methyl-3-(trifluoromethyl)-1H-pyrazol-5-ylcarbamate as described in Example 164B (0.114 g, 0.4 mmol), 3-(6,7-dimethoxyquinazolin-4-ylthio)aniline from Example 115B (0.125 g, 0.4 mmol), and N,N-diisopropylethylamine (0.3 mL) in THF (6 mL) at 50° C. for 3 hours, to afford 1-[3-(6,7-dimethoxyquinazolin-4-ylthio)phenyl]-3-[1-methyl-3-(trifluoromethyl)-1H-pyrazol-5-yl]urea as solid (0.035 g, 17%). $^1$H NMR (300 MHz, CDCl$_3$) δ 9.45 (br, 1H), 8.77 (s, 1H), 7.80 (s, 1H), 7.63 (d, 1H), 7.44 (t, 1H), 7.35 (m, 2H), 7.28 (s, 1H), 7.21 (s, 1H), 6.31 (s, 1H), 4.08 (s, 3H), 4.06 (s, 3H), 3.91 (s, 3H); LC-MS (ESI) m/z 505 (M+H)$^+$.

Example 194

Preparation of 1-[3-(6,7-dimethoxyquinazolin-4-ylthio)phenyl]-3-[1-methyl-5-(trifluoromethyl)-1H-pyrazol-3-yl]urea Using the procedure described in Example 159B, phenyl 1-methyl-5-(trifluoromethyl)-1H-pyrazol-3-ylcarbamate described in Example 165A (0.114 g, 0.4 mmol) was reacted with 3-(6,7-dimethoxyquinazolin-4-ylthio)aniline from Example 115B (0.125 g, 0.4 mmol), and N,N-diisopropylethylamine (0.5 mL) in THF (6 mL) at 50° C. for 3 hours, to afford 1-[3-(6,7-dimethoxyquinazolin-4-ylthio)phenyl]-3-[1-methyl-5-(trifluoromethyl)-1H-pyrazol-3-yl]urea as solid (0.035 g, 17%). $^1$H NMR (300 MHz, CDCl$_3$) δ 9.43 (br, 1H), 8.77 (s, 1H), 7.80 (m, 1H), 7.63 (d, 1H), 7.44 (t, 1H), 7.38 (m, 2H), 7.28 (s, 1H), 7.20 (s, 1H), 6.31 (s, 1H), 4.08 (s, 3H), 4.06 (s, 3H), 3.91 (s, 3H); LC-MS (ESI) m/z 505 (M+H)$^+$.

Example 195

Preparation of ethyl 2-(3-tert-butyl-5-{3-[3-(6,7-dimethoxyquinazolin-4-ylthio)phenyl]ureido}-1H-pyrazol-1-yl)acetate Using the procedure described in Example 159B, using ethyl 2-[3-tert-butyl-5-(phenoxycarbonylamino)-1H-pyrazol-1-yl]acetate described in Example 166A (0.138 g, 0.4 mmol), 3-(6,7-dimethoxyquinazolin-4-ylthio)aniline from Example 115B (0.125 g, 0.4 mmol), and N,N-diisopropylethylamine (0.5 mL) in THF (6 mL) at 50° C. for 7 hours, to afford ethyl 2-(3-tert-butyl-5-{3-[3-(6,7-dimethoxyquinazolin-4-ylthio)phenyl]ureido}-1H-pyrazol-1-yl)acetate as solid (133 mg, 59%). $^1$H NMR (300 MHz, DMSO-d$_6$) δ 8.98 (s, 1H), 8.70 (s, 1H), 8.60 (m, 1H), 7.83 (s, 1H), 7.51 (d, 1H), 7.43 (t, 1H), 7.35 (s, 1H), 7.34 (s, 1H), 7.25 (d, 1H), 6.12 (s, 1H), 4.85 (s, 2H), 4.15 (q, 2H), 3.99 (s, 6H), 1.20 (s and t, 12H); LC-MS (ESI) m/z 565 (M+H)$^+$.

Example 196

Preparation of 1-[3-(1,3-difluoro-2-methylpropan-2-yl)-1-phenyl-1H-pyrazol-5-yl]-3-[3-(6,7-dimethoxyquinazolin-4-ylthio)phenyl]urea Using the procedure described in Example 159B, phenyl 341,3-difluoro-2-methylpropan-2-yl)-1-phenyl-1H-pyrazol-5-ylcarbamate as described in Example 167B (0.186 g, 0.5 mmol), 3-(6,7-dimethoxyquinazolin-4-ylthio)aniline from Example 115B (0.125 g, 0.4 mmol), and N,N-diisopropylethylamine (0.8 mL) in THF (6 mL) at 50° C. for 6 hours, to afford 1-[3-(1,3-difluoro-2-methylpropan-2-yl)-1H-pyrazol-5-yl]-3-[3-(6,7-dimethoxyquinazolin-4-ylthio)phenyl]urea as solid (95 mg, 40%). $^1$H NMR (300 MHz, DMSO-d$_6$) δ 9.27 (s, 1H), 8.69 (s, 1H), 8.56 (s, 1H), 7.80 (s, 1H), 7.23-7.80 (m, 10H), 6.51 (s, 1H), 4.71 (m, 2H), 4.55 (m, 2H), 3.99 (s, 6H), 1.31 (s, 3H); LC-MS (ESI) m/z 591 (M+H)$^+$.

Example 197

Preparation of 1-[3-(6,7-dimethoxyquinazolin-4-ylthio)phenyl]-3-[3-(2-ethoxypropan-2-yl)-1-phenyl-1H-pyrazol-5-yl]urea Example 197A Using the procedure described in Example 159B, using phenyl 3-(2-ethoxypropan-2-yl)-1-phenyl-1H-pyrazol-5-ylcarbamate described in Example 168B (0.115 g, 0.33 mmol), 3-(6,7-dimethoxyquinazolin-4-ylthio)aniline from Example 115B (0.103 g, 0.33 mmol), and N,N-diisopropylethylamine (0.8 mL) in THF (6 mL) at 50° C. for 5 hours, to afford 1-[3-(6,7-dimethoxyquinazolin-4-ylthio)phenyl]-3-[3-(2-ethoxypropan-2-yl)-1-phenyl-1H-pyrazol-5-yl]urea as solid (123 mg, 64%). $^1$H NMR (300 MHz, DMSO-d$_6$) δ 9.26 (br, 1H), 8.69 (s, 1H), 8.54 (s, 1H), 7.80 (s, 1H), 7.54 (m, 4H), 7.23-7.45 (m, 5H), 7.24 (d, 1H), 6.42 (s, 1H), 3.99 (s, 6H), 3.25 (q, 2H), 1.46 (s, 6H), 1.04 (t, 3H); LC-MS (ESI) m/z 539 (M-OEt)$^+$.

Example 198

Preparation of 1-[3-(6,7-dimethoxyquinazolin-4-ylthio)phenyl]-3-[1-(4-fluorophenyl)-3-(trifluoromethyl)-1H-pyrazol-5-yl]urea The title compound was prepared as described in Example 162B, using phenyl 1-(4-fluorophenyl)-3-(trifluoromethyl)-1H-pyrazol-5-ylcarbamate described in Example 171B (0.146 g, 0.4 mmol), 3-(6,7-dimethoxyquinazolin-4-ylthio) aniline from Example 115B (0.125 g, 0.4 mmol), and 4-(dimethylamino)pyridine (0.025 g) in THF (6 mL), to afford 1-[3-(6,7-dimethoxyquinazolin-4-ylthio)phenyl]-3-[1-(4-fluorophenyl)-3-(trifluoromethyl)-1H-pyrazol-5-yl]urea as solid (184 mg, 79%). $^1$H NMR (300 MHz, DMSO-d$_6$) δ 9.28 (s, 1H), 8.79 (s, 1H), 8.69 (d, 1H), 7.79 (s, 1H), 7.68 (m, 2H), 7.46 (m, 4H), 7.42 (s, 1H), 7.35 (s, 1H), 7.27 (d, 1H), 6.87 (s, 1H), 3.99 (s, 6H); LC-MS (ESI) m/z 585 (M+H)$^+$.

Example 199

Preparation of 1-[3-(6,7-dimethoxyquinazolin-4-ylthio)phenyl]-3-[1-p-tolyl-3-(trifluoromethyl)-1H-pyrazol-5-yl]urea The title compound was prepared as described in Example 162B, using phenyl 1-p-tolyl-3-(trifluoromethyl)-1H-pyrazol-5-ylcarbamate described in Example 172B (0.145 g, 0.4 mmol), 3-(6,7-dimethoxyquinazolin-4-ylthio)aniline from Example 115B (0.125 g, 0.4 mmol), and 4-(dimethylamino)pyridine (0.025 g) in THF (6 mL), to afford 1-[3-(6,7-dimethoxyquinazolin-4-ylthio)phenyl]-3-[1-p-tolyl-3-(trifluoromethyl)-1H-pyrazol-5-yl]urea as solid (0.192 g, 83%). $^1$H NMR (300 MHz, DMSO-d$_6$) δ 9.32 (s, 1H), 8.74 (s, 1H), 8.69 (d, 1H), 7.78 (s, 1H), 7.45 (m, 6H), 7.35 (s, 1H), 7.33 (s, 1H), 7.25 (d, 1H), 6.85 (s, 1H), 3.99 (s, 6H), 2.41 (s, 3H); LC-MS (ESI) m/z 581 (M+H)$^+$.

Example 200

Preparation of 1-(3-(6,7-dimethoxyquinazolin-4-ylthio)phenyl)-3-(3-(2-methoxyethoxy)-5-(trifluoromethyl)phenyl)urea The title compound was prepared from 3-(6,7-dimethoxyquinazolin-4-ylthio)aniline from Example 115B (94 mg, 0.3 mmol) and 3-(2-methoxyethoxy)-5-(trifluoromethyl)phenylcarbamate from Example 117A (160 mg, 0.45 mmol) using Example 115C to give 1-(3-(6,7-dimethoxyquinazolin-4-ylthio)phenyl)-3-(3-(2-methoxyethoxy)-5-(trifluoromethyl)phenyl)urea (118 mg, 0.21 mmol, 69%). $^1$H NMR (300 MHz, DMSO-d$_6$) δ 9.09 (s, 1H), 9.04 (s, 1H), 8.70 (s, 1H), 7.84 (s, 1H), 7.55 (d, 1H), 7.50-7.41 (m, 2H), 7.35 (s, 1H), 7.34 (s, 1H), 7.29-7.23 (m, 2H), 6.87 (s, 1H), 4.19-4.11 (m, 2H), 4.00 (s, 6H), 3.70-3.63 (m, 2H), 3.31 (s, 3H); LC-MS (ESI) m/z 575 (M+H)$^+$.

Example 201

Preparation of 1-(5-Cyclopentylisoxazol-3-yl)-3-(3-(6,7-dimethoxyquinazolin-4-ylthio)phenyl)urea The title compound was prepared as described in Example 113C by using 3-(6,7-dimethoxyquinazolin-4-ylthio)aniline described in Example 115B (114 mg, 0.32 mmol) and phenyl 5-isopropylisoxazol-3-ylcarbamate described in Example 135A (130 mg, 0.48 mmol). Precipitation of the desired product detected completion of reaction. The solid was filtered off and washed with diethyl ether to give 1-(5-cyclopentylisoxazol-3-yl)-3-(3-(6,7-dimethoxyquinazolin-4-ylthio)phenyl)urea (126 mg, 80%) as a white solid. $^1$H NMR (300 MHz, DMSO-d$_6$) δ 9.58 (s, 1H), 9.04 (s, 1H), 8.69 (s, 1H), 7.84 (s, 1H), 7.50-7.44 (m, 2H), 7.36-7.28 (m, 3H), 6.51 (s, 1H), 3.99 (s, 6H), 3.21-3.01 (m, 1H), 2.02-2.00 (m, 2H), 1.67-1.64 (m, 6H); LC-MS (ESI) m/z 492 (M+H)$^+$.

Example 202

Preparation of 1-(3-tert-butylisoxazol-5-yl)-3-(3-(6-methoxy-7-(2-methoxyethoxy)quinazolin-4-yloxy)phenyl)urea The title compound was prepared as described in Example 113C by using 3-(6-methoxy-7-(2-methoxyethoxy)quinazolin-4-yloxy)aniline described in Example 117B (102 mg, 0.3 mmol) and phenyl 3-tert-butylisoxazol-5-ylcarbamate described in Example 132A (101 mg, 0.39 mmol) to give 1-(3-tert-butylisoxazol-5-yl)-3-(3-(6-methoxy-7-(2-methoxyethoxy)quinazolin-4-yloxy)phenyl)urea (103 mg, 68%) as a white solid. $^1$H NMR (300 MHz, DMSO-d$_6$) δ 10.19 (s, 1H), 9.03 (s, 1H), 8.56 (s, 1H), 7.58 (s, 2H), 7.42 (t, 2H), 7.30 (d, 1H), 6.99 (d, 1H), 6.04 (s, 1H), 4.34 (bs, 2H), 3.99 (s, 3H), 3.77 (bs, 2H), 3.36 (s, 3H), 1.25 (s, 9H); LC-MS (ESI) m/z 508 (M+H)$^+$.

Example 203

Preparation of 1-(3-(6-methoxy-7-(2-methoxyethoxy)quinazolin-4-yloxy)phenyl)-3-(5-phenylisoxazol-3-yl)urea According to the procedure described in Example 113C, 3-(6-methoxy-7-(2-methoxyethoxy)quinazolin-4-yloxy) aniline from Example 117B (102 mg, 0.3 mmol) in THF (1.5 mL) was treated with N,N-diisopropylethylamine (68 μl, 0.39 mmol), 4-(dimethylamino)pyridine (1.8 mg, 0.015 mmol) and phenyl 5-phenylisoxazol-3-ylcarbamate from Example 113B (109 mg, 0.39 mmol). The reaction mixture was heated to 50° C. for 4h. After cooling to room temperature, the mixture was partitioned between chloroform and a saturated solution of sodium bicarbonate. The water phase was back extracted three times with chloroform and the organics combined and dried (MgSO$_4$). Concentration under reduced pressure gave a residue which was purified by preparative HPLC (phenylhexyl reverse phase column). The obtained solid was triturated with anhydrous diethyl ether to afford 1-(3-(6-methoxy-7-(2-methoxyethoxy)quinazolin-4-yloxy)phenyl)-3-(5-phenylisoxazol-3-yl)urea as a white solid (110 mg, 70%). $^1$H NMR (300 MHz, DMSO-d$_6$) δ 9.74 (s, 1H), 9.06 (s, 1H), 8.57 (s, 1H), 7.86 (d, 2H), 7.62-7.53 (m, 5H), 7.51 (t, 2H), 7.28 (m, 2H), 6.99 (d, 1H), 4.34 (bs, 2H), 4.00 (s, 3H), 3.77 (bs, 2H), 3.35 (s, 3H); LC-MS (ESI) m/z 528 (M+H)$^+$.

Example 204

Preparation of 1-(3-(6,7-dimethoxyquinazolin-4-yloxy)phenyl)-3-(3-phenylisoxazol-5-yl)urea The title compound was prepared according to the procedure described in Example 207 by using 3-(6-methoxy-7-(2-methoxyethoxy)quinazolin-4-yloxy)aniline from Example 117B (102 mg, 0.3 mmol) and phenyl 3-phenylisoxazol-5-ylcarbamate from Example 114B (109 mg, 0.45 mmol) to afford 1-(3-(6,7-dimethoxyquinazolin-4-yloxy)phenyl)-3-

(3-phenylisoxazol-5-yl)urea as a white solid upon trituration with methanol (26 mg, 16%). $^1$H NMR (300 MHz, DMSO-d$_6$) δ 10.41 (s, 1H), 9.13 (s, 1H), 9.13 (s, 1H), 7.83 (m, 2H), 7.59 (d, 2H), 7.50-7.41 (m, 5H), 7.33 (d, 2H), 7.00 (d, 1H), 6.56 (s, 1H), 4.34 (bs, 2H), 4.00 (s, 3H), 3.35 (s, 3H); LC-MS (ESI) m/z 528 (M+H)$^+$.

Example 205

Preparation of 1-(3-(6-methoxy-7-(2-methoxy-ethoxy)quinazolin-4-yloxy)phenyl)-3-3-(morpholine-4-carbonyl)-5-(trifluoromethyl)phenyl)urea 3-(6-methoxy-7-(2-methoxyethoxy)quinazolin-4-yloxy) aniline from Example 117B (103 mg, 0.3 mmol) was reacted with phenyl 3-(morpholine-4-carbonyl)-5-(trifluoromethyl) phenyl) carbamate described in Example 149A (114 mg, 0.42 mmol) using the procedure in Example 115C. The final product was purified by column chromatography (2-10% MeOH/DCM) to give 1-(3-(6-methoxy-7-(2-methoxyethoxy) quinazolin-4-yloxy)phenyl)-3-(3-(morpholine-4-carbonyl)-5-(trifluoromethyl)phenyl)urea (115 mg, 0.18 mmol, 60%). $^1$H NMR (300 MHz, DMSO-d$_6$) δ 9.25 (s, 1H), 9.13 (s, 1H), 8.56 (s, 1H), 8.00 (s, 1H), 7.67 (s, 1H), 7.60 (s, 1H), 7.57 (s, 1H), 7.43-7.37 (m, 2H), 7.35-7.36 (m, 2H), 6.96 (d, 1H), 4.38-4.32 (m, 2H), 4.00 (s, 3H), 3.80-3.51 (m, 10H), 3.33 (s, 3H); LC-MS (ESI) m/z 642 (M+H)$^+$.

Example 206

Preparation of 1-(5-isopropylisoxazol-3-yl)-3-(3-(6-methoxy-7-(2-methoxyethoxy)quinazolin-4-yloxy) phenyl)urea The title compound was prepared as described in Example 113C by using 3-(6-methoxy-7-(2-methoxyethoxy)quinazolin-4-yloxy)aniline from Example 117B (102 mg, 0.3 mmol) and phenyl 5-isopropylisoxazol-3-ylcarbamate described in Example 133A (110 mg, 0.45 mmol) to give 1-(5-isopropyl-isoxazol-3-yl)-3-(3-(6-methoxy-7-(2-methoxyethoxy) quinazolin-4-yloxy)phenyl)urea (69.5 mg, 47%) as a white solid. $^1$H NMR (300 MHz, DMSO-d$_6$) δ 9.52 (s, 1H), 9.05 (s, 1H), 8.55 (s, 1H), 7.52 (s, 2H), 7.45-7.36 (m, 2H), 7.25 (d, 1H), 6.99 (d, 1H), 6.5 (s, 1H), 4.35 (bs, 2H), 4.00 (s, 3H), 3.89 (bs, 2H), 3.36 (s, 3H), 3.01-2.99 (m, 1H), 1.22 (d, 6H); LC-MS (ESI) m/z 494 (M+H)$^+$.

Example 207

Preparation of 1-(3-cyclopentylisoxazol-5-yl)-3-(3-(6-methoxy-7-(2-methoxyethoxy)quinazolin-4-yloxy)phenyl)urea The title compound was prepared as described in Example 113C by using 3-(6-methoxy-7-(2-methoxyethoxy)quinazolin-4-yloxy)aniline from Example 117B (104 mg, 0.35 mmol), phenyl 3-cyclopentylisoxazol-5-ylcarbamate described in Example 163A (124 mg, 0.45 mmol) and N,N-diisopropylethylamine (73 µl, 0.42 mmol) to give 1-(3-cyclopentylisoxazol-5-yl)-3-(3-(6-methoxy-7-(2-methoxyethoxy) quinazolin-4-yloxy)phenyl)urea (51.72 mg, 28%) as a white solid. $^1$H NMR (300 MHz, DMSO-d$_6$) δ 10.18 (s, 1H), 9.05 (s, 1H), 8.56 (s, 1H), 7.57 (s, 1H), 7.50-7.35 (m, 2H), 7.30 (s, 1H), 7.00 (d, 1H), 5.95 (s, 1H), 4.34 (bs,2H), 3.99 (s, 3H), 3.77 (bs, 2H), 3.34 (s, 3H), 3.11-2.99 (m, 1H), 2.10-1.80 (m, 2H), 1.75-1.50 (m, 6H); LC-MS (ESI) m/z 520 (M+H)$^+$.

Example 208

1-{3-[6-methoxy-7-(2-methoxyethoxy)quinazolin-4-yloxy]phenyl}-3-[1-methyl-5-(trifluoromethyl)-1H-pyrazol-3-yl]urea Using the procedure described in Example 159B, phenyl 1-methyl-5-(trifluoromethyl)-1H-pyrazol-3-ylcarbamate described in Example 165A (0.114 g, 0.4 mmol) was reacted with 3-(6-methoxy-7-(2-methoxyethoxy)quinazolin-4-yloxy)aniline from Example 117B (0.137 g, 0.4 mmol), and N,N-diisopropylethylamine (0.5 mL) in THF (6 mL) at 50° C. for 3 hours, to afford 1-{3-[6-methoxy-7-(2-methoxyethoxy) quinazolin-4-yloxy]phenyl}-3-[1-methyl-5-(trifluoromethyl)-1H-pyrazol-3-yl]urea as solid (0.028 g, 13%). $^1$H NMR (300 MHz, CDCl$_3$) δ 9.53 (br, 1H), 8.63 (s, 1H), 7.61 (s, 1H), 7.55 (s, 1H), 7.41 (t, 1H), 7.32 (m, 2H), 7.12 (s, 1H), 7.01 (d, 1H), 6.28 (s, 1H), 4.36 (t, 2H), 4.04 (s, 3H), 3.92 (s and t, 5H), 3.50 (s, 3H); LC-MS (ESI) m/z 533 (M+H)$^+$.

Example 209

Preparation of 1-(3-tert-butyl-1-methyl-1H-pyrazol-5-yl)-3-(3-(6-methoxy-7-(2-methoxyethoxy)quinazolin-4-yloxy)phenyl)urea The procedure in 138B was used to react the carbamate from Example 157A (123 mg, 0.45 mmol) with 3-(6-methoxy-7-(2-methoxyethoxy)quinazolin-4-yloxy)aniline from Example 117B (103 mg, 0.30 mmol). To this solution was added diisopropylethyl amine (78 µL, 0.45 mmol) and DMAP (3.6 mg, 0.03 mmol). The reaction was concentrated to dryness. The resulting oil purified by silica gel chromatography eluting with ethyl acetate/dichloromethane 10-50% over 60 minutes. The main peak concentrated to a solid weighing 126 mg. $^1$H (DMSO-d6) 9.10 (s, 1H), 8.70 (s, 2H), 7.65 (m, 2H), 7.50 (m, 2H), 7.30 (m, 1H), 7.15 (s, 1H), 6.95 (m, 1H), 6.00 (s, 1H), 4.40 (s, 2H), 4.00 (s, 3H), 3.85 (s, 2H), 3.60 (s, 3H), 3.40 (s, 3H), 1.25 (s, 9H). LCMS (ESI) m/z 521 (M+H)

Example 210

Preparation of 1-(3-tert-butyl-1-phenyl-1H-pyrazol-5-yl)-3-(3-(6-methoxy-7-(2-methoxyethoxy)quinazolin-4-yloxy)phenyl)urea The procedure for Example 138B was used to react phenyl 3-tert-butyl-1-phenyl-1H-pyrazol-5-ylcarbamate described in Example 154A (151 mg, 0.45 mmol) with 3-(6-methoxy-7-(2-methoxyethoxy)quinazolin-4-yloxy)aniline from Example 117B (103 mg, 0.30 mmol). To this solution was added diisopropylethyl amine (80 µL, 0.45 mmol) and DMAP (4 mg, 0.03 mmol). After heating for 2 hours the reaction was concentrated to dryness. The resulting solid was chromatographed using silica gel (eluting with an ethyl acetate/hexane gradient 0-85%). The main peak was concentrated to give 59 mg. $^1$H (DMSO-d6) 9.23 (s, 1H), 8.54 (s, 1H), 8.47 (s, 1H), 7.55 (m, 6H), 7.40 (m, 3H), 7.18 (s, 1H), 6.95 (m, 1H), 6.35 (s, 1H), 4.34 (m, 2H), 3.98 (s, 3H), 3.77 (m, 2H), 3.34 (s, 3H), 1.25 (s, 9H). LCMS (ESI) m/z 583 (M+H)

Example 211

Preparation of 1-(3-(1,1-difluoroethyl)isoxazol-5-yl)-3-(3-(6-methoxy-7-(2-methoxyethoxy)quinazolin-4-yloxy)phenyl)urea The procedure for Example 138B was used substituting phenyl 3-(1,1-difluoroethyl)isoxazol-5-yl carbamate described in Example 152A (80 mg, 0.30 mmol) and 3-(6-methoxy-7-(2-methoxyethoxy)quinazolin-4-yloxy)aniline from Example 117B (100 mg, 0.29 mmol). To this solution was added diisopropylethyl amine (75 µL, 0.43 mmol) and DMAP (5 mg, 0.04 mmol). After heating for 1 hour the reaction was concentrated to dryness. The resulting solid was purified by reversed phase HPLC using a phenyl hexyl column and eluting with an acetonitrile/water gradient 40-75% over 60 minutes. The major peak was concentrated and then lypholyzed to give 33 mg. $^1$H (DMSO-d6) 10.08 (s, 1H), 8.59 (s, 1H), 7.60 (m, 2H), 7.57 (m, 3H), 6.95 (m, 1H), 6.24 (s, 1H), 4.35 (m, 2H), 4.00 (s, 3H), 3.85 (m, 2H), 3.35 (s, 3H), 2.00 (t, 3H); LCMS (ESI) m/z 516 (M+H).

Example 212

Preparation of 1-[3-(2-ethoxypropan-2-yl)-1-phenyl-1H-pyrazol-5-yl]-3-{3-[6-methoxy-7-(2-methoxyethoxy)quinazolin-4-yloxy]phenyl}urea Using the procedure described in Example 159B, phenyl 342-ethoxypropan-2-yl)-1-phenyl-1H-pyrazol-5-ylcarbamate described in Example 168B (0.115 g, 0.33 mmol), 3-(6-methoxy-7-(2-methoxyethoxy)quinazolin-4-yloxy)aniline from Example 117B (0.112 g, 0.33 mmol), and N,N-diisopropylethylamine (0.8 mL) in THF (6 mL) at 50° C. for 5 hours, to afford 1-[3-(2-ethoxypropan-2-yl)-1-phenyl-1H-pyrazol-5-yl]-3-{3-[6-methoxy-7-(2-methoxyethoxy)quinazolin-4-yloxy]phenyl}urea as solid (0.116 g, 57%). $^1$H NMR (300 MHz, DMSO-d$_6$) δ 9.25 (br, 1H), 8.55 (s, 2H), 7.56 (m, 6H), 7.41 (m, 3H), 7.18 (d, 1H), 6.94 (d, 1H), 6.41 (s, 1H), 4.34 (m, 2H), 3.98 (s, 3H), 3.77 (m, 2H), 3.35 (s, 3H), 3.24 (q, 2H), 1.46 (s, 6H), 1.03 (t, 3H); LC-MS (ESI) m/z 567 (M-OEt)$^+$.

Example 213

Preparation of 1-[5-(1,3-difluoro-2-methylpropan-2-yl)isoxazol-3-yl]-3-{3-[6-methoxy-7-(2-methoxyethoxy)quinazolin-4-yloxy]phenyl}urea The title compound was prepared as described in Example 162B, using phenyl 5-(1,3-difluoro-2-methylpropan-2-yl)isoxazol-3-ylcarbamate as described in Example 162A (0.089 g, 0.3 mmol), 3-(6-methoxy-7-(2-methoxyethoxy)quinazolin-4-yloxy)aniline from Example 117B (0.102 g, 0.3 mmol), and 4-(dimethylamino)pyridine (0.03 g) in THF (6 mL), to afford 1-[5-(1,3-difluoro-2-methylpropan-2-yl)isoxazol-3-yl]-3-{3-[6-methoxy-7-(2-methoxyethoxy)quinazolin-4-yloxy]phenyl}urea as solid (0.061 g, 37%). $^1$H NMR (300 MHz, DMSO-d$_6$) δ 9.71 (s, 1H), 9.01 (s, 1H), 8.56 (s, 1H), 7.58 (m, 2H), 7.42 (m, 2H), 7.27 (d, 1H), 6.98 (d, 1H), 6.77 (s, 1H), 4.71 (s, 2H), 4.56 (s, 2H), 4.35 (m, 2H), 3.99 (s, 3H), 3.77 (m, 2H), 3.56 (s 3H), 1.28 (s, 3H); LC-MS (ESI) m/z 544 (M+H)$^+$.

Example 214

Preparation of 1-(3-cyclopropylisoxazol-5-yl)-3-(3-(6-methoxy-7-(2-methoxyethoxy)quinazolin-4-yloxy)phenyl)urea Prepared from 3-(6-methoxy-7-(2-methoxyethoxy)quinazolin-4-yloxy)aniline from Example 117B (90 mg, 0.264 mmol) and phenyl 3-cyclopropylisoxazol-5-ylcarbamate from Example 124A (78 mg, 0.317 mmol) according to the method described for 1-(3-(6,7-dimethoxyquinazolin-4-yloxy)phenyl)-3-(3-isopropylisoxazol-5-yl)urea in Example 122B to afford 143-cyclopropylisoxazol-5-yl)-3-(3-(6-methoxy-7-(2-methoxyethoxy)quinazolin-4-yloxy)phenyl)urea as a colorless solid (68 mg, 52%). $^1$H NMR (300 MHz, DMSO-d$_6$) δ 10.21 (brs, 1H), 9.08 (brs, 1H), 8.55 (s, 1H), 7.56 (s, 2H), 7.38-7.44 (m, 2H), 7.29 (m, 1H), 6.99 (m, 1H), 5.77 (s, 1H), 4.35 (m, 2H), 3.99 (s, 3H), 3.78 (m, 2H), 3.30 (s, 3H), 1.90 (m, 1H), 0.94-0.98 (m, 2H), 0.71-0.73 (m, 2H); LC-MS (ESI) m/z 492 (M+H)$^+$.

Example 215

Preparation of 1-(3-isopropylisoxazol-5-yl)-3-(3-(6-methoxy-7-(2-methoxyethoxy)quinazolin-4-yloxy)phenyl)urea 3-(6-methoxy-7-(2-methoxyethoxy)quinazolin-4-yloxy)aniline from Example 117B (90 mg, 0.264 mmol) was reacted with phenyl 3-isopropylisoxazol-5-ylcarbamate as prepared in Example 122A (78 mg, 0.317 mmol) to afford 1-(3-isopropylisoxazol-5-yl)-3-(3-(6-methoxy-7-(2-methoxyethoxy)quinazolin-4-yloxy)phenyl)urea as a colorless solid (70 mg, 54%). $^1$H NMR (300 MHz, DMSO-d$_6$) δ 10.30 (brs, 1H), 9.14 (brs, 1H), 8.56 (s, 1H), 7.57 (s, 2H), 7.38-7.44 (m, 2H), 7.31 (m, 1H), 6.99 (m, 1H), 5.99 (s, 1H), 4.32-4.35 (m, 2H), 3.99 (s, 3H), 3.77-3.78 (m, 2H), 3.35 (s, 3H), 2.90 (septet, J=9 Hz, 1H), 1.19 (d, J=9 Hz, 6H); LC-MS (ESI) m/z 494 (M+H)$^+$.

Example 216

Preparation of 1-(3-(6-methoxy-7-(2-methoxyethoxy)quinazolin-4-yloxy)phenyl)-3-(3-(tetrahydro-2H-pyran-4-yl)isoxazol-5-yl)urea Prepared from 3-(6-methoxy-7-(2-methoxyethoxy)quinazolin-4-yloxy)aniline from Example 117B (60 mg, 0.176 mmol) and phenyl 3-(tetrahydro-2H-pyran-4-yl)isoxazol-5-ylcarbamate from Example 123A (56 mg, 0.194 mmol) according to the method described for 1-(3-(6,7-dimethoxyquinazolin-4-yloxy)phenyl)-3-(3-isopropylisoxazol-5-yl)urea in Example 122B to afford 14346-methoxy-7-(2-methoxyethoxy)quinazolin-4-yloxy)phenyl)-3-(3-(tetrahydro-2H-pyran-4-yl)isoxazol-5-yl)urea as a colorless solid (19 mg, 20%). $^1$H NMR (300 MHz, DMSO-d$_6$) δ 10.70 (brs, 1H), 9.38 (brs, 1H), 8.55 (s, 1H), 7.57 (s, 2H), 7.38-7.42 (m, 2H), 7.32 (m, 1H), 6.98 (m, 1H), 6.00 (s, 1H), 4.34-4.35 (m, 2H), 3.99 (s, 3H), 3.87-3.90 (m, 2H), 3.77-3.78 (m, 2H), 3.42-3.46 (m, 2H), 3.35 (s, 3H), 2.88 (m, 1H), 1.76-1.81 (m, 2H), 1.60-1.65 (m, 2H); LC-MS (ESI) m/z 536 (M+H)$^+$.

Example 217

Preparation of 1-(5-(1-methoxy-2-methylpropan-2-yl)isoxazol-3-yl)-3-(3-(6-methoxy-7-(2-methoxyethoxy)quinazolin-4-yloxy)phenyl)urea Prepared from 3-(6-methoxy-7-(2-methoxyethoxy)quinazolin-4-yloxy)aniline from Example 117B (100 mg, 0.293 mmol) and phenyl 3-(1-methoxy-2-methylpropan-2-yl)isoxazol-5-ylcarbamate described in Example 128A (118 mg, 0.407 mmol) according to the method described for 1-(3-(6,7-dimethoxyquinazolin-4-yloxy)phenyl)-3-(3-isopropylisoxazol-5-yl)urea in Example 122B to afford 1-(5-(1-methoxy-2-methylpropan-2-yl)isoxazol-3-yl)-3-(3-(6-methoxy-7-(2-methoxyethoxy)quinazolin-4-yloxy)phenyl)urea as a colorless solid (72 mg, 46%). $^1$H NMR (300 MHz, DMSO-d$_6$) δ 9.61 (brs, 1H), 9.03 (brs, 1H), 8.56 (s, 1H), 7.57-7.58 (m, 2H), 7.38-7.43 (m, 2H), 7.26 (m, 1H), 6.98 (m, 1H), 6.51 (s, 1H), 4.35 (m, 2H), 3.99 (s, 3H), 3.78 (m, 2H), 3.38 (s, 2H), 3.35 (s, 3H), 3.23 (s, 3H), 1.20 (s, 6H); LC-MS (ESI) m/z 538 (M+H)$^+$.

Example 218

Preparation of 1-(3-(2-fluoropropan-2-yl)isoxazol-5-yl)-3-(3-(6-methoxy-7-(2-methoxyethoxy)quinazolin-4-yloxy)phenyl)urea Prepared from 3-(6-methoxy-7-(2-methoxyethoxy)quinazolin-4-yloxy)aniline from Example 117B (72 mg, 0.212 mmol) and phenyl 3-(2-fluoropropan-2-yl)isoxazol-5-ylcarbamate from Example 42A (56 mg, 0.212 mmol) according to the method described for 1-(3-(6,7-dimethoxyquinazolin-4-yloxy)phenyl)-3-(3-isopropylisoxazol-5-yl)urea in Example 122B to afford 1-(3-(2-fluoropropan-2-yl)isoxazol-5-yl)-3-(3-(6-methoxy-7-(2-methoxyethoxy)quinazolin-4-yloxy)phenyl)urea as a colorless solid (46 mg, 43%). $^1$H NMR (300 MHz, DMSO-d$_6$) δ 10.45 (brs, 1H), 9.12 (brs, 1H), 8.56 (s, 1H), 7.57-7.58 (m, 2H), 7.39-7.45 (m, 2H), 7.32 (m, 1H), 7.00 (m, 1H), 6.14 (s, 1H), 4.32-4.35 (m, 2H), 3.99 (s, 3H), 3.75-3.78 (m, 2H), 3.35 (s, 3H), 1.67 (d, J=21 Hz, 6H); LC-MS (ESI) m/z 512 (M+H)$^+$.

Example 219

Preparation of 1-(5-cyclopentylisoxazol-3-yl)-3-(3-(6-methoxy-7-(2-methoxyethoxy)quinazolin-4-yloxy)phenyl)urea The title compound was prepared as described in Example 113C by using 3-(6-methoxy-7-(2-methoxyethoxy)quinazolin-4-yloxy)aniline described in Example 117B (109 mg, 0.32 mmol) and phenyl 5-isopropylisoxazol-3-ylcarbamate described in Example 135A (130 mg, 0.48 mmol) to give 1-(5-cyclopentylisoxazol-3-yl)-3-(3-(6-methoxy-7-(2-methoxyethoxy)quinazolin-4-yloxy)phenyl)urea (87.11 mg, 52%) as a white solid. $^1$H NMR (300 MHz, DMSO-d$_6$) δ 9.59 (s, 1H), 9.04 (s, 1H), 8.56 (s, 1H), 7.57 (s, 2H), 7.41 (t, 2H), 7.26 (d, 1H), 6.98 (d, 1H), 6.50 (s, 1H), 4.34 (bs, 2H), 3.99 (s, 3H), 3.77 (bs, 2H), 3.34 (s, 3H), 3.18-3.05 (m, 1H), 2.09-1.99 (m, 2H), 1.70-1.64 (m, 6H); LC-MS (ESI) m/z 520 (M+H)$^+$.

Example 220

Preparation of 1-{3-[6-methoxy-7-(2-methoxyethoxy)quinazolin-4-yloxy]phenyl}-3-[1-methyl-3-(trifluoromethyl)-1H-pyrazol-5-yl]urea Using the procedure described in Example 159B, using phenyl 1-methyl-3-(trifluoromethyl)-1H-pyrazol-5-ylcarbamate described in Example 164B (0.114 g, 0.4 mmol), 3-(6-methoxy-7-(2-methoxyethoxy)quinazolin-4-yloxy)aniline from Example 117B (0.137 g, 0.4 mmol), and N,N-diisopropylethylamine (0.3 mL) in THF (6 mL) at 50° C. for 3 hours, to afford 1-{3-[6-methoxy-7-(2-methoxyethoxy)quinazolin-4-yloxy]phenyl}-3-[1-methyl-3-(trifluoromethyl)-1H-pyrazol-5-yl]urea as solid (0.033 g, 15%). $^1$H NMR (300 MHz, CDCl$_3$) δ 9.5 (br, 1H), 8.63 (s, 1H), 7.60 (m, 1H), 7.55 (s, 1H), 7.32-7.43 (m, 4H), 7.00 (dd, 1H), 6.31 (s, 1H), 4.36 (t, 2H), 4.04 (s, 3H), 3.91 (s and t, 5H), 3.50 (s, 3H); LC-MS (ESI) m/z 533 (M+H)$^+$.

Example 221

Preparation of 1-{3-[6-methoxy-7-(2-methoxyethoxy)quinazolin-4-yloxy]phenyl}-3-[1-phenyl-3-(trifluoromethyl)-1H-pyrazol-5-yl]urea Using the procedure described in Example 159B, using phenyl 1-phenyl-3-(trifluoromethyl)-1H-pyrazol-5-ylcarbamate from Example 161C (0.139 g, 0.4 mmol), 3-(6-methoxy-7-(2-methoxyethoxy)quinazolin-4-yloxy)aniline from Example 117B (0.137 g, 0.4 mmol), and N,N-diisopropylethylamine (0.3 mL) in THF (6 mL) at 50° C. for 6 hours, to afford 1-{3-[6-methoxy-7-(2-methoxyethoxy)quinazolin-4-yloxy]phenyl}-3-[1-phenyl-3-(trifluoromethyl)-1H-pyrazol-5-yl]urea as solid (0.115 g, 48%). $^1$H NMR (300 MHz, DMSO-d$_6$) δ 9.32 (s, 1H), 8.81 (s, 1H), 8.54 (s, 1H), 7.49-7.62 (m, 7H), 7.38 (m, 2H), 7.20 (d, 1H), 6.95 (d, 1H), 6.87 (s, 1H), 4.38 (m, 2H), 3.98 (s, 3H), 3.78 (m, 2H), 3.35 (s, 3H); LC-MS (ESI) m/z 595 (M+H)$^+$.

Example 222

Preparation of 1-(3-fluoro-4-(trifluoromethyl)phenyl)-3-(3-(6-methoxy-7-(2-methoxyethoxy)quinazolin-4-yloxy)phenyl)urea The procedure for Example 138B was used reacting 3-fluoro-4-(trifluoromethyl)phenylcarbamate carbamate as described in Example 150 (135 mg, 0.45 mmol) with amine 3-(6-methoxy-7-(2-methoxyethoxy)quinazolin-4-yloxy) aniline from Example 117B (102 mg, 0.30 mmol). To this solution was added diisopropylethyl amine (80 μL, 0.46 mmol) and DMAP (4.0 mg, 0.03 mmol). The reaction was concentrated to dryness and triturated with dichloromethane to give 126 mg of _1-(3-fluoro-4-(trifluoromethyl)phenyl)-3-(3-(6-methoxy-7-(2-methoxyethoxy)quinazolin-4-yloxy) phenyl)urea. $^1$H (DMSO-d6) 9.50 (s, 1H), 9.15 (s, 1H), 8.60 (s, 1H), 7.70 (m, 2H), 7.60 (s, 2H), 7.35 (m, 2H), 7.30 (m, 2H), 7.00 (m, 1H), 4.30 (m, 2H), 4.00 (s, 3H), 3.84 (m, 2H), 3.40 (s, 3H). LCMS (ESI) m/z 547 (M+H)

Example 223

Preparation of 1-(3-methoxy-4-(trifluoromethyl) phenyl)-3-(3-(6-methoxy-7-(2-methoxyethoxy) quinazolin-4-yloxy)phenyl)urea The procedure for Example 138B was used to react with phenyl 3-methoxy-4-(trifluoromethyl)phenylcarbamate described in Example 190B (140 mg, 0.45 mmol) with 3-(6-methoxy-7-(2-methoxyethoxy)quinazolin-4-yloxy)aniline from Example 117B (103 mg, 0.30 mmol). To this solution was added diisopropylethyl amine (80 μL, 0.46 mmol) and DMAP (4.0 mg, 0.03 mmol). The reaction was concentrated to dryness and triturated with dichloromethane to give 52 mg. $^1$H (DMSO-d6) 9.30 (s, 1H), 9.15 (s, 1H), 8.60 (s, 1H), 7.60 (m, 2H), 7.50 (s, 2H), 7.35 (m, 2H), 7.25 (m, 1H), 7.00 (m, 2H), 4.35 (m, 2H), 4.00 (s, 3H), 3.84 (s, 3H), 3.70 (m, 2H), 3.40 (m, 3H). LCMS (ESI) m/z 559 (M+H)

Example 224

Preparation of ethyl 2-[3-tert-butyl-5-(3-{3-[6-methoxy-7-(2-methoxyethoxy)quinazolin-4-yloxy] phenyl}ureido)-1H-pyrazol-1-yl]acetate hydrochloride

Example 224A

Using the procedure described in Example 159B, ethyl 2-[3-tert-butyl-5-(phenoxycarbonylamino)-1H-pyrazol-1- yl]acetate described in Example 166A (0.138 g, 0.4 mmol) was reacted with 3-(6-methoxy-7-(2-methoxyethoxy)quinazolin-4-yloxy)aniline from Example 117B (0.137 g, 0.4 mmol), and N,N-diisopropylethylamine (0.5 mL) in THF (6 mL) at 50° C. for 7 hours, to afford ethyl 243-tert-butyl-5-(3-{3-[6-methoxy-7-(2-methoxyethoxy)quinazolin-4-yloxy]phenyl}ureido)-1H-pyrazol-1-yl]acetate as solid.

Example 224B

The title compound was prepared as described in Example 6, Step B, using ethyl 2-[3-tert-butyl-5-(3-{3-[6-methoxy-7-(2-methoxyethoxy)quinazolin-4-yloxy]phenyl}ureido)-1H-pyrazol-1-yl]acetate and 1.0 M HCl/Et$_2$O solution in CH$_2$Cl$_2$ and MeOH, to afford ethyl 243-tert-butyl-5-(3-{3-[6-methoxy-7-(2-methoxyethoxy)quinazolin-4-yloxy]phenyl}ureido)-1H-pyrazol-1-yl]acetate hydrochloride as solid (0.185 g, 73%). $^1$H NMR (300 MHz, DMSO-d$_6$) δ 9.30 (s, 1H), 8.99 (s, 1H), 8.64 (s, 1H), 7.60 (m, 2H), 7.43 (s, 1H), 7.40 (t, 1H), 7.24 (d, 1H), 6.95 (d, 1H), 6.13 (s, 1H), 4.89 (s, 2H), 4.5 (br, 3H), 4.36 (m, 2H), 4.15 (q, 2H), 4.00 (s, 3H), 3.78 (m, 2H), 1.20 (s and t, 12H); LC-MS (ESI) m/z 593 (M+H)$^+$.

Example 225

Preparation of 1-{3-[6-methoxy-7-(2-methoxyethoxy)quinazolin-4-yloxy]phenyl}-3-[1-phenyl-5-(trifluoromethyl)-1H-pyrazol-3-yl]urea The title compound was prepared as described in Example 169C using phenyl 1-phenyl-5-(trifluoromethyl)-1H-pyrazol-3-ylcarbamate described in Example 169B (0.115 g, 0.33 mmol), 3-(6-methoxy-7-(2-methoxyethoxy)quinazolin-4-yloxy)aniline from Example 117B (0.112 g, 0.33 mmol), to afford 1-{3-[6-methoxy-7-(2-methoxyethoxy)quinazolin-4-yloxy]phenyl}-3-[1-phenyl-5-(trifluoromethyl)-1H-pyrazol-3-yl]urea as solid (0.114 g, 58%). $^1$H NMR (300 MHz, DMSO-d$_6$) δ 9.47 (s, 1H), 8.99 (s, 1H), 8.56 (s, 1H), 7.58 (m, 7H), 7.42 (m, 2H), 7.27 (d, 1H), 7.13 (s, 1H), 6.97 (d, 1H), 4.35 (m, 2H), 4.00 (s, 3H), 3.78 (m, 2H), 3.35 (s, 3H); LC-MS (ESI) m/z 595 (M+H)$^+$.

Example 226

Preparation of 1-[1-(4-fluorophenyl)-3-(trifluoromethyl)-1H-pyrazol-5-yl]-3-{3-[6-methoxy-7-(2-methoxyethoxy)quinazolin-4-yloxy]phenyl}urea The title compound was prepared as described in Example 162B, using phenyl 1-(4-fluorophenyl)-3-(trifluoromethyl)-1H-pyrazol-5-ylcarbamate described in Example 171B (0.146 g, 0.4 mmol), 3-(6-methoxy-7-(2-methoxyethoxy)quinazolin-4-yloxy)aniline from Example 117B (0.137 g, 0.4 mmol), and 4-(dimethylamino)pyridine (0.025 g) in THF (6 mL), to afford 1-[1-(4-fluorophenyl)-3-(trifluoromethyl)-1H-pyrazol-5-yl]-3-{3-[6-methoxy-7-(2-methoxyethoxy)quinazolin-4-yloxy]phenyl}urea as solid (0.166 g, 68%). $^1$H NMR (300 MHz, DMSO-d$_6$) δ 9.28 (s, 1H), 8.79 (s, 1H), 8.55 (d, 1H), 7.67 (m, 2H), 7.54 (m, 2H), 7.44 (m, 4H), 7.20 (d, 1H), 6.97 (d, 1H), 6.86 (s, 1H), 4.35 (m, 2H), 3.98 (s, 3H), 3.77 (m, 2H), 3.35 (s, 3H); LC-MS (ESI) m/z 613 (M+H)$^+$.

Example 227

Preparation of 1-{3-[6-methoxy-7-(2-methoxyethoxy)quinazolin-4-yloxy]phenyl}-3-[1-p-tolyl-3-(trifluoromethyl)-1H-pyrazol-5-yl]urea Using the procedure described in Example 162B, phenyl 1-p-tolyl-3-(trifluoromethyl)-1H-pyrazol-5-ylcarbamate described in Example 172B (0.145 g, 0.4 mmol) was reacted with 3-(6-methoxy-7-(2-methoxyethoxy)quinazolin-4-yloxy)aniline from Example 117B (0.137 g, 0.4 mmol), and 4-(dimethylamino)pyridine (0.025 g) in THF (6 mL), to afford 1-{3-[6-methoxy-7-(2-methoxyethoxy)quinazolin-4-yloxy]phenyl}-3-[1-p-tolyl-3-(trifluoromethyl)-1H-pyrazol-5-yl]urea as solid (0.190 g, 78%). $^1$H NMR (300 MHz, DMSO-d$_6$) δ 9.32 (s, 1H), 8.75 (s, 1H), 8.54 (s, 1H), 7.55 (m, 2H), 7.36 (m, 6H), 7.19 (d, 1H), 6.95 (d, 1H), 6.84 (s, 1H), 4.34 (m, 2H), 3.98 (s, 3H), 3.77 (m, 2H), 3.35 (s, 3H), 2.41 (s, 3H); LC-MS (ESI) m/z 609 (M+H)$^+$.

Example 228

Preparation of 1-[3-(1,3-difluoro-2-methylpropan-2-yl)-1-phenyl-1H-pyrazol-5-yl]-3-{3-[6-methoxy-7-(2-methoxyethoxy)quinazolin-4-yloxy]phenyl}urea Using the procedure described in Example 159B, phenyl 341,3-difluoro-2-methylpropan-2-yl)-1-phenyl-1H-pyrazol-5-ylcarbamate as described in Example 167B (0.186 g, 0.5 mmol), 3-(6-methoxy-7-(2-methoxyethoxy)quinazolin-4-yloxy)aniline from Example 117B (0.137 g, 0.4 mmol), and N,N-diisopropylethylamine (0.8 mL) in THF (6 mL) at 50° C. for 6 hours, to afford 1-[3-(1,3-difluoro-2-methylpropan-2-yl)-1-phenyl-1H-pyrazol-5-yl]-3-{3-[6-methoxy-7-(2-methoxyethoxy)quinazolin-4-yloxy]phenyl}urea as solid (0.106 g, 43%). $^1$H NMR (300 MHz, DMSO-d$_6$) δ 9.26 (s, 1H), 8.57 (s, 1H), 8.55 (s, 1H), 7.56 (m, 6H), 7.40 (m, 3H), 7.18 (d, 1H), 6.94 (d, 1H), 6.50 (s, 1H), 4.70 (m, 2H), 4.54 (m, 2H), 4.33 (m, 2H), 3.98 (s, 3H), 3.78 (m, 2H), 3.35 (s, 3H), 1.30 (s, 3H); LC-MS (ESI) m/z 619 (M+H)$^+$.

Example 229

Preparation of 1-(3-(6-methoxy-7-(2-methoxyethoxy)quinazolin-4-yloxy)phenyl)-3-(3-(trifluoromethyl)isoxazol-5-yl)urea

Example 229A

Step 1: (Trimethylsilyl)diazomethane (21 mL, 2M in diethyl ether) was added dropwise to a solution of 4,4,4-trifluoro-3-oxobutanenitrile (3.79 g, 26 mmol) in anhydrous diethyl ether (25 mL) previously cooled to 0° C. The resulting mixture was allowed to slowly warm to room temperature and stirred overnight. The solvent was removed under reduced pressure to give 4,4,4-trifluoro-3-methoxybut-2-enenitrile, which was directly used in the next step without further purification. $^1$H NMR (300 MHz, CDCl$_3$) δ 5.00 (s, 1H), 4.16 (s, 3H).

Example 229A

Step 2: Hydroxylamine hydrochloride (2.88 g, 41.5 mmol) was dissolved in methanol (20 mL) and cooled to 0° C. in an ice-bath. Sodium methoxide (2.24 g, 41.5 mmol) was added and the resulting suspension stirred at room temperature for 15 minutes. The suspension was cooled to 0° C., 4,4,4-trifluoro-3-methoxybut-2-enenitrile (26 mmol) was added dropwise and the mixture allowed to slowly warm to room temperature. The mixture was then heated to 60° C. overnight. The white solid was removed by filtration, washed with dichloromethane and the filtrate concentrated under reduced pressure to afford 4,4,4-trifluoro-N'-hydroxy-3-methoxybut-2-enimidamide as a solid, which was used directly in the next step without further purification. The solid was taken in ethanol (25 mL) and the solution acidified (pH=1) with 37% aqueous hydrochloric acid. The resulting mixture was heated to 60° C. for 2h. Ethanol was removed under reduced pressure and the residue diluted with dichloromethane. A saturated solution of sodium bicarbonate was added (pH=14) and the organic phase separated. The aqueous phase was back extracted three times with dichloromethane, the organics combined, dried (MgSO$_4$) and concentrated under reduced pressure. The resulting crude material was purified by silica gel chromatography (dichloromethane/ethyl acetate 95:5) to isolate 3-(trifluoromethyl)isoxazol-5-amine (446 mg, 11%) along with 5-(trifluoromethyl)isoxazol-3-amine as a minor product. $^1$H NMR (300 MHz, CDCl$_3$) δ 5.31 (s, 1H), 5.03 (bs, 2H).

Example 229A 3-(Trifluoromethyl)isoxazol-5-amine (446 mg, 2.93 mmol) in tetrahydrofuran (6 mL) was treated with triethylamine (1.1 mL, 8.2 mmol), phenyl choloroformate (0.88 mL, 7.03 mmol) and 4-(dimethylamino)pyridine (357 mg, 2.93 mmol). The reaction mixture was stirred at room for 3h, then filtered through a celite pad, washed with ethyl acetate and concentrated to dryness. The residue was taken into dichloromethane, washed with brine, and the combined organics dried (MgSO$_4$) and concentrated. The residue was purified by silica gel chromatography (hexane/ethyl acetate 8:2) to give phenyl 3-(trifluoromethyl)isoxazol-5-ylcarbamate (269 mg, 33%) as a white solid. $^1$H NMR (300 MHz, CDCl$_3$) δ 7.99 (bs, 1H), 7.4 (t, 2H), 7.35-7.02 (m, 3H), 6.7 (s, 1H)

Example 229B 3-(6-methoxy-7-(2-methoxyethoxy)quinazolin-4-yloxy)aniline from Example 117B (154 mg, 0.41 mmol) and the carbamate from the previous step (146 mg, 0.54 mmol) were dissolved in tetrahydrofuran (2 mL) and treated with N,N-diisopropylethylamine (72 µl, 0.41 mmol). The mixture was stirred at room temperature for 4h. After addition of diethyl ether the precipitating solid was filtered and dried. The material was further purified by preparative HPLC (Phenomenex phenylhexyl reverse phase column) to give 1-(3-(6-methoxy-7-(2-methoxyethoxy)quinazolin-4-yloxy)phenyl)-3-(3-(trifluoromethyl)isoxazol-5-yl)urea (90 mg, 42%) as a white solid. $^1$H NMR (300 MHz, DMSO-d$_6$) δ 10.93 (s, 1H), 9.25 (s, 1H), 8.56 (s, 1H), 7.57 (s, 2H), 7.47-7.42 (m, 2H), 7.34 (d, 1H), 7.03 (d, 1H), 6.49 (s, 1H), 4.34 (bs, 2H), 3.99 (s, 3H), 3.77 (bs, 2H), 3.34 (s, 3H); LC-MS (ESI) m/z 520 (M+H)$^+$.

Example 230

Preparation of 1-[5-(1,3-difluoro-2-methylpropan-2-yl)isoxazol-3-yl]-3-{3-[6-methoxy-7-(2-methoxyethoxy)quinazolin-4-ylthio]phenyl}urea Example 230A To a suspension of sodium hydride (422 mg, 17.6 mmol) in anhydrous tetrahydrofuran (100 mL) cooled to 0° C., 3-aminothiophenol (125 mg, 16.8 mmol) was added dropwise as a solution in tetrahydrofuran (5 mL). The mixture was stirred at 0° C. for 30 minutes. 4-Chloro-6-methoxy-7-(2-methoxyethoxy)quinazoline, previously synthesized, was added and the resulting mixture heated to 50° C. overnight. After removal of the solvent the residue was taken into ethyl acetate/water, the organic layer separated and the aqueous phase extracted twice. The organics were combined, dried (MgSO$_4$) and concentrated under reduced pressure. The residue was triturated in methanol to give 3-(6-methoxy-7-(2-methoxyethoxy)quinazolin-4-ylthio)aniline (2.8 g, 49%) as a solid. $^1$H NMR (300 MHz, DMSO-d$_6$) δ 8.69 (s, 1H), 7.33 (d, 2H), 7.16-7.10 (m, 1H), 6.81 (s, 1H), 6.75-6.67 (m, 2H), 5.35 (bs, 2H), 4.33 (bs, 2H), 4.02 (s, 6H), 3.77 (bs, 2H); LC-MS (ESI) m/z 358 (M+H)$^+$.

Example 230B

The title compound was prepared as described in Example 162B, using phenyl 5-(1,3-difluoro-2-methylpropan-2-yl)isoxazol-3-ylcarbamate as described in Example 162A (0.089 g, 0.3 mmol), 3-(6-methoxy-7-(2-methoxyethoxy)quinazolin-4-ylthio)aniline from the previous step (0.107 g, 0.3 mmol), and 4-(dimethylamino)pyridine (0.03 g) in THF (6 mL), to afford 1-[5-(1,3-difluoro-2-methylpropan-2-yl)isoxazol-3-yl]-3-{3-[6-methoxy-7-(2-methoxyethoxy)quinazolin-4-ylthio]phenyl}urea as solid (0.038 g, 23%). $^1$H NMR (300 MHz, DMSO-d$_6$) δ 9.71 (s, 1H), 9.02 (s, 1H), 8.69 (s, 1H), 7.84 (m, 1H), 7.28-7.54 (m, 5H), 6.78 (s, 1H), 4.72 (s, 2H), 4.56 (s, 2H), 4.33 (m, 2H), 3.99 (s, 3H), 3.77 (m, 2H), 3.34 (s 3H), 1.29 (s, 3H); LC-MS (ESI) m/z 560 (M+H)$^+$.

Example 231

Preparation of 1-(3-fluoro-4-(trifluoromethyl)phenyl)-3-(3-(6-methoxy-7-(2-methoxyethoxy)quinazolin-4-ylthio)phenyl)urea The procedure for Example 138B was used to react 3-fluoro-4-(trifluoromethyl)phenylcarbamate as described in Example 150 (138 mg, 0.46 mmol) with 3-(6-methoxy-7-(2-methoxyethoxy)quinazolin-4-ylthio)aniline described in Example 231A (110 mg, 0.31 mmol). To this solution was added diisopropylethyl amine (80 µL, 0.46 mmol) and DMAP (4.0 mg, 0.03 mmol). The reaction was concentrated to dryness and triturated with dichloromethane to give 122 mg. $^1$H (DMSO-d6) 9.43 (s, 1H), 9.15 (s, 1H), 8.70 (s, 1H), 7.84 (s, 1H), 7.70 (m, 2H), 7.60 (m, 1H), 7.50 (m, 1H), 7.40 (m, 4H), 4.34 (m, 2H), 4.00 (s, 3H), 3.78 (m, 2H), 3.38 (m, 3H). LCMS (ESI) m/z 563 (M+H)

Example 232

Preparation of 1-(5-isopropylisoxazol-3-yl)-3-(3-(6-methoxy-7-(2-methoxyethoxy)quinazolin-4-ylthio)phenyl)urea Using the procedure described in Example 113C 3-(6-methoxy-7-(2-methoxyethoxy)quinazolin-4-ylthio)aniline described in Example 231A (107 mg, 0.3 mmol) was reacted with phenyl 5-isopropylisoxazol-3-ylcarbamate described in Example 133A (110 mg, 0.45 mmol). The mixture was stirred at 50° C. overnight. Upon cooling to room temperature, the product precipitated out of the solution. The solid was filtered off and washed with diethyl ether to give 1-(5-isopropylisoxazol-3-yl)-3-(3-(6-methoxy-7-(2-methoxyethoxy)quinazolin-4-ylthio)phenyl)urea (72.22 mg, 47%) as a solid. $^1$H NMR (300 MHz, DMSO-d$_6$) δ 9.58 (s, 1H), 9.02 (s, 1H), 8.69 (s, 1H), 7.84 (s, 1H), 7.53-7.28 (m, 5H), 6.51 (s, 1H), 4.34 (bs, 2H), 4.00 (s, 3H), 3.76 (bs, 2H), 3.34 (s, 3H), 3.04-3.00 (m, 1H), 1.23 (s, 6H); LC-MS (ESI) m/z 510 (M+H)⁺.

Example 233

Preparation of 1-(3-methoxy-4-(trifluoromethyl) phenyl)-3-(3-(6-methoxy-7-(2-methoxyethoxy) quinazolin-4-ylthio)phenyl)urea The procedure for Example 138B was used to react phenyl 3-methoxy-4-(trifluoromethyl)phenylcarbamate described in Example 190B (144 mg, 0.46 mmol) with 3-(6-methoxy-7-(2-methoxyethoxy)quinazolin-4-ylthio)aniline described in Example 231A (110 mg, 0.31 mmol). To this solution was added diisopropylethyl amine (80 µL, 0.46 mmol) and DMAP (4.0 mg, 0.03 mmol). The reaction was concentrated to dryness and purified by silica gel chromatography eluting with ethyl acetate/dichloromethane 0-50% over 75 minutes. The main peak collected and concentrated, then triturated with dichloromethane to give a solid weighing 43 mg. $^1$H (DMSO-d6) 9.19 (s, 1H), 9.04 (s, 1H), 8.70 (s, 1H), 7.84 (s, 1H), 7.6-7.40 (m, 4H), 7.35 (m, 2H), 7.25 (m, 1H), 7.00 (m, 1H), 4.34 (m, 2H), 4.00 (s, 3H), 3.84 (s, 3H), 3.78 (m, 2H). LCMS (ESI) m/z 575 (M+H)

Example 234

Preparation of 1-(3-(2-fluoropropan-2-yl)isoxazol-5-yl)-3-(3-(6-methoxy-7-(2-methoxyethoxy)quinazolin-4-ylthio)phenyl)urea The procedure for Example 138B was used to react phenyl 3-(2-fluoropropan-2-yl)isoxazol-5-ylcarbamate from Example 42A (86 mg, 0.33 mmol) with 3-(6-methoxy-7-(2-methoxyethoxy)quinazolin-4-ylthio)aniline described in Example 231A (97 mg, 0.27 mmol). To this solution was added diisopropylethyl amine (71 µL, 0.41 mmol) and DMAP (5.0 mg, 0.04 mmol). The reaction was concentrated to dryness and partitioned between water and dichloromethane, and extracted twice. The combined extracts were washed with brine, dried over magnesium sulfate, filtered and concentrated. The oil was purified by silica gel chromatography eluting with ethyl acetate/dichloromethane 12-70% over 18 column volumes. The appropriate peak was concentrated to a white solid weighing 18 mg. $^1$H (DMSO-d6) 10.42 (s, 1H), 9.11 (s, 1H), 8.69 (s, 1H), 7.84 (s, 1H), 7.55 (m, 1H), 7.45 (m, 1H), 7.34 (m, 3H), 6.16 (s, 1H), 4.33 (m, 2H), 4.00 (s, 3H), 3.76 (s, 2H), 1.70 (s, 3H), 1.63 (s, 3H). LCMS (ESI) m/z 528 (M+H)

Example 235

Preparation of 1-(5-cyclopentylisoxazol-3-yl)-3-(3-(6-methoxy-7-(2-methoxyethoxy)quinazolin-4-ylthio)phenyl)urea Using the procedure described in Example 113C compound 3-(6-methoxy-7-(2-methoxyethoxy)quinazolin-4-ylthio)aniline described in Example 231A (114 mg, 0.32 mmol) was reacted with phenyl 5-isopropylisoxazol-3-ylcarbamate described in Example 135A (130 mg, 0.48 mmol). Upon addition of dietyl ether, the solid was filtered off and washed with diethyl ether to give 1-(5-cyclopentylisoxazol-3-yl)-3-(3-(6-methoxy-7-(2-methoxyethoxy)quinazolin-4-ylthio)phenyl)urea (91.12 mg, 53%) as a white solid. $^1$H NMR (300 MHz, DMSO-d$_6$) δ 9.52 (s, 1H), 9.07 (s, 1H), 8.68 (s, 1H), 7.79 (s, 1H), 7.59-7.41 (m, 2H), 7.41-7.24 (m, 3H), 6.50 (s, 1H), 4.39-4.24 (m, 2H), 4.00 (s, 3H), 3.88-3.66 (m, 2H), 3.34 (s, 3H), 3.25-3.04 (m, 1H), 2.09-1.88 (m, 2H), 1.75-1.48 (m, 6H); LC-MS (ESI) m/z 536 (M+H)⁺.

Example 236

Preparation of 1-(3-tert-butyl-1-phenyl-1H-pyrazol-5-yl)-3-(3-(6-methoxy-7-(2-methoxyethoxy)quinazolin-4-ylthio)phenyl)urea The procedure for Example 138B was used to react carbamate phenyl 3-tert-butyl-1-phenyl-1H-pyrazol-5-ylcarbamate described in Example 154A (151 mg, 0.45 mmol) with 3-(6-methoxy-7-(2-methoxyethoxy)quinazolin-4-ylthio)aniline described in Example 231A (107 mg, 0.30 mmol). To this solution was added diisopropylethyl amine (80 µL, 0.45 mmol) and DMAP (4 mg, 0.03 mmol). After heating for 2 hours the reaction was concentrated to dryness. The resulting solid was triturated with 1:1 dichloromethane/hexane and the solid removed by filtration to give 26 mg. $^1$H (DMSO-d6) 9.23 (s, 1H), 8.68 (s, 1H), 8.47 (s, 1H), 7.79 (s, 1H), 7.55 (m, 4H), 7.40 (m, 5H), 7.25 (s, 1H), 6.35 (s, 1H), 4.33 (m, 2H), 3.99 (s, 3H), 3.75 (m, 2H), 3.34 (s, 3H), 1.25 (s, 9H); LCMS (ESI) m/z 599 (M+H).

Example 237

Preparation of ethyl 2-[3-tert-butyl-5-(3-{3-[6-methoxy-7-(2-methoxyethoxy)quinazolin-4-ylthiol]phenyl}ureido)-1H-pyrazol-1-yl]acetate Using the procedure described in Example 159B, ethyl 2-[3-tert-butyl-5-(phenoxycarbonylamino)-1H-pyrazol-1-yl]acetate described in Example 166A (0.138 g, 0.4 mmol), 3-(6-methoxy-7-(2-methoxyethoxy)quinazolin-4-ylthio) aniline described in Example 231A (0.143 g, 0.4 mmol), and N,N-diisopropylethylamine (0.5 mL) in THF (6 mL) at 50° C. for 7 hours, to afford ethyl 2-[3-tert-butyl-5-(3-{3-[6-methoxy-7-(2-methoxyethoxy)quinazolin-4-ylthio]phenyl}ureido)-1H-pyrazol-1-yl]acetate as solid (0.071 g, 29%). $^1$H NMR (300 MHz, DMSO-d$_6$) δ 8.98 (br, 1H), 8.74 (s, 1H), 8.60 (s, 1H), 7.83 (s, 1H), 7.34-7.52 (m, 4H), 7.26 (d, 1H), 6.12 (s, 1H), 4.85 (s, 2H), 4.33 (m, 2H), 4.15 (q, 2H), 4.00 (s, 3H), 3.77 (m, 2H), 3.34 (s, 3H), 1.20 (s and t, 12H); LC-MS (ESI) m/z 609 (M+H)⁺.

Example 238

Preparation of 1-[3-(1,3-difluoro-2-methylpropan-2-yl)-1-phenyl-1H-pyrazol-5-yl]-3-{3-[6-methoxy-7-(2-methoxyethoxy)quinazolin-4-ylthio]phenyl}urea Using the procedure described in Example 159B, phenyl 341,3-difluoro-2-methylpropan-2-yl)-1-phenyl-1H-pyrazol-5-ylcarbamate described in Example 167B (0.186 g, 0.5 mmol), 3-(6-methoxy-7-(2-methoxyethoxy)quinazolin-4-ylthio)aniline described in Example 231A (0.143 g, 0.4 mmol), and N,N-diisopropylethylamine (0.8 mL) in THF (6 mL) at 50° C. for 6 hours, which was purified by silica gel chromatography with EtOAc/hexane as eluants and preparative HPLC (C$_{18}$ column and 55-70% MeCN/H$_2$O with 0.05% AcOH) to afford 1-[3-(1,3-difluoro-2-methylpropan-2-yl)-1-phenyl-1H-pyrazol-5-yl]-3-{3-[6-methoxy-7-(2-methoxyethoxy)quinazolin-4-ylthio]phenyl}urea as solid (0.072 g, 28%). $^1$H NMR (300 MHz, DMSO-d$_6$) δ 9.27 (s, 1H), 8.68 (s, 1H), 8.56 (s, 1H), 7.80 (s, 1H), 7.56 (m, 4H), 7.33-7.47 (m, 5H), 7.24 (d, 1H), 6.51 (s, 1H), 4.71 (m, 2H), 4.55 (m, 2H), 4.33 (m, 2H), 3.99 (s, 3H), 3.77 (m, 2H), 3.34 (s, 3H), 1.31 (s, 3H); LC-MS (ESI) m/z 635 (M+H)+.

Example 239

Preparation of 1-{3-[6-methoxy-7-(2-methoxyethoxy)quinazolin-4-ylthio]phenyl}-3-[1-methyl-3-(trifluoromethyl)-1H-pyrazol-5-yl]urea Using the procedure described in Example 159B, using phenyl 1-methyl-3-(trifluoromethyl)-1H-pyrazol-5-ylcarbamate described in Example 164B (0.114 g, 0.4 mmol), 3-(6-methoxy-7-(2-methoxyethoxy)quinazolin-4-ylthio) aniline described in Example 231A (0.143 g, 0.4 mmol), and N,N-diisopropylethylamine (0.3 mL) in THF (6 mL) at 50° C. for 3 hours, to afford 1-{3-[6-methoxy-7-(2-methoxyethoxy)quinazolin-4-ylthio]phenyl}-3-[1-methyl-3-(trifluoromethyl)-1H-pyrazol-5-yl]urea as solid (0.033 g, 15%). $^1$H NMR (300 MHz, CDCl$_3$) δ 9.4 (br, 1H), 8.75 (s, 1H), 7.79 (m, 1H), 7.62 (d, 1H), 7.27-7.46 (m, 5H), 6.36 (s, 1H), 4.34 (t, 2H), 4.04 (s, 3H), 3.90 (s and t, 5H), 3.49 (s, 3H); LC-MS (ESI) m/z 549 (M+H)+.

Example 240

Preparation of 1-{3-[6-methoxy-7-(2-methoxyethoxy)quinazolin-4-ylthio]phenyl}-3-[1-methyl-3-(trifluoromethyl)-1H-pyrazol-5-yl]urea Using the procedure described in Example 159B, phenyl 1-methyl-5-(trifluoromethyl)-1H-pyrazol-3-ylcarbamate described in Example 165A (0.114 g, 0.4 mmol), 3-(6-methoxy-7-(2-methoxyethoxy)quinazolin-4-ylthio)aniline described in Example 231A (0.143 g, 0.4 mmol), and N,N-diisopropylethylamine (0.5 mL) in THF (6 mL) at 50° C. for 3 hours, to afford 1-{3-[6-methoxy-7-(2-methoxyethoxy)quinazolin-4-ylthio]phenyl}-3-[1-methyl-3-(trifluoromethyl)-1H-pyrazol-5-yl]urea as solid (0.015 g, 7%). $^1$H NMR (300 MHz, CDCl$_3$) δ 9.45 (br, 1H), 8.76 (s, 1H), 7.78 (m, 1H), 7.63 (d, 1H), 7.43 (t, 1H), 7.26-7.38 (m, 4H), 6.32 (s, 1H), 4.34 (t, 2H), 4.04 (s, 3H), 3.89 (s and t, 5H), 3.49 (s, 3H); LC-MS (ESI) m/z 549 (M+H)+.

Example 241

Preparation of 1-[3-(2-ethoxypropan-2-yl)-1-phenyl-1H-pyrazol-5-yl]-3-{3-[6-methoxy-7-(2-methoxyethoxy)quinazolin-4-ylthio]phenyl}urea Using the procedure described in Example 159B, phenyl 342-ethoxypropan-2-yl)-1-phenyl-1H-pyrazol-5-ylcarbamate described in Example 168B (0.115 g, 0.33 mmol), 3-(6-methoxy-7-(2-methoxyethoxy)quinazolin-4-ylthio)aniline described in Example 231A (0.118 g, 0.33 mmol), and N,N-diisopropylethylamine (0.8 mL) in THF (6 mL) at 50° C. for 5 hours, to afford 1-[3-(2-ethoxypropan-2-yl)-1-phenyl-1H-pyrazol-5-yl]-3-{3-[6-methoxy-7-(2-methoxyethoxy)quinazolin-4-ylthio]phenyl}urea as solid (0.111 g, 54%). $^1$H NMR (300 MHz, DMSO-d$_6$) δ 9.25 (br, 1H), 8.68 (s, 1H), 8.54 (s, 1H), 7.79 (s, 1H), 7.54 (m, 4H), 7.37 (m, 5H), 7.25 (d, 1H), 6.42 (s, 1H), 4.33 (m, 2H), 3.99 (s, 3H), 3.76 (m, 2H), 3.34 (s, 3H), 3.25 (q, 2H), 1.46 (s, 6H), 1.04 (t, 3H); LC-MS (ESI) m/z 583 (M-OEt)+.

Example 242

Preparation of 1-[1-(4-fluorophenyl)-3-(trifluoromethyl)-1H-pyrazol-5-yl]-3-{3-[6-methoxy-7-(2-methoxyethoxy)quinazolin-4-ylthio]phenyl}urea The title compound was prepared as described in Example Example 162B, using phenyl 1-(4-fluorophenyl)-3-(trifluoromethyl)-1H-pyrazol-5-ylcarbamate described in Example 171B (0.146 g, 0.4 mmol), 3-(6-methoxy-7-(2-methoxyethoxy)quinazolin-4-ylthio)aniline described in Example 231A (0.143 g, 0.4 mmol), and 4-(dimethylamino)pyridine (0.025 g) in THF (6 mL), to afford 1-[1-(4-fluorophenyl)-3-(trifluoromethyl)-1H-pyrazol-5-yl]-3-{3-[6-methoxy-7-(2-methoxyethoxy)quinazolin-4-ylthio]phenyl}urea as solid (0.062 g, 25%). $^1$H NMR (300 MHz, DMSO-d$_6$) δ 9.29 (s, 1H), 8.79 (s, 1H), 8.68 (d, 1H), 7.78 (s, 1H), 7.68 (m, 2H), 7.45 (m, 4H), 7.37 (s, 1H), 7.33 (s, 1H), 7.27 (d, 1H), 6.87 (s, 1H), 4.33 (m, 2H), 4.02 (s, 3H), 3.76 (m, 2H), 3.34 (s, 3H); LC-MS (ESI) m/z 629 (M+H)+.

Example 243

Preparation of 1-{3-[6-methoxy-7-(2-methoxyethoxy)quinazolin-4-ylthio]phenyl}-3-[1-p-tolyl-3-(trifluoromethyl)-1H-pyrazol-5-yl]urea The title compound was prepared as described in Example 162B, using phenyl 1-p-tolyl-3-(trifluoromethyl)-1H-pyrazol-5-ylcarbamate described in Example 172B (0.145 g, 0.4 mmol), 3-(6-methoxy-7-(2-methoxyethoxy)quinazolin-4-ylthio)aniline described in Example 231A (0.143 g, 0.4 mmol), and 4-(dimethylamino)pyridine (0.025 g) in THF (6 mL), to afford 1-{3-[6-methoxy-7-(2-methoxyethoxy)quinazolin-4-ylthio]phenyl}-3-[1-p-tolyl-3-(trifluoromethyl)-1H-pyrazol-5-yl]urea as solid (0.177 g, 71%). $^1$H NMR (300 MHz, DMSO-d$_6$) δ 9.32 (s, 1H), 8.74 (s, 1H), 8.68 (d, 1H), 7.78 (s, 1H), 7.45 (m, 6H), 7.37 (s, 1H), 7.33 (s, 1H), 7.27 (d, 1H), 6.85 (s, 1H), 4.34 (m, 2H), 3.99 (s, 3H), 3.76 (m, 2H), 3.35 (s, 3H), 2.41 (s, 3H); LC-MS (ESI) m/z 625 (M+H)+.

Example 244

Preparation of 1-{3-[6-methoxy-7-(2-methoxyethoxy)quinazolin-4-ylthio]phenyl}-3-[1-phenyl-5-(trifluoromethyl)-1H-pyrazol-3-yl]urea The title compound was prepared as described in Example 169C with phenyl 1-phenyl-5-(trifluoromethyl)-1H-pyrazol-3-ylcarbamte described in Example 169B (0.115 g, 0.33 mmol) and the amine described in Example 231A (0.118 g, 0.33 mmol), to afford 1-{3-[6-methoxy-7-(2-methoxyethoxy)quinazolin-4-ylthio]phenyl}-3-[1-phenyl-5-(trifluoromethyl)-1H-pyrazol-3-yl]urea as solid (0.096 g, 48%). $^1$H NMR (300 MHz, DMSO-d$_6$) δ 9.47 (s, 1H), 9.01 (s, 1H), 8.70 (s, 1H), 7.86 (s, 1H), 7.56 (m, 6H), 7.45 (t, 1H), 7.40 (m, 2H), 7.28 (d, 1H), 7.14 (s, 1H), 4.35 (m, 2H), 4.00 (s, 3H), 3.77 (m, 2H), 3.34 (s, 3H); LC-MS (ESI) m/z 611 (M+H)+.

Example 245

Preparation of 1-(3-(2-fluoropropan-2-yl)isoxazol-5-yl)-3-(3-(7-methoxy-6-(4,4-dioxo-3-thiomorpholinopropoxy)quinazolin-4-ylthio)phenyl)urea Example 245A In a round bottomed flask, sodium hydride (121 mg, 3.14 mmol), a 60% dispersion in mineral oil, was suspended in 20 mL of dry THF. To this suspension 3-aminothiophenol (394 mg, 3.14 mmol) was added and the reaction stirred for 30 minutes. To this solution 4-chloro-6-(3-chloropropoxy)-7-methoxyquinazoline (900 mg, 3.14 mmol) and the reaction stirred overnight. The reaction was quenched with water, concentrated, and partitioned between water and ethyl acetate. After extracting twice, the extracts were combined, dried over magnesium sulfate, filtered and concentrated to give 3-(6-(3-chloropropoxy)-7-methoxyquinazolin-4-ylthio) aniline as a yellow solid and used without further purification. $^1$H(DMSO-d6) 8.70 (s, 1H), 7.34 (s, 1H), 7.15 (m, 1H), 6.80 (s, 1H), 6.75 (m, 2H), 4.28 (m, 2H), 3.99 (s, 3H), 3.84 (m, 2H), 2.38 (m, 2H); LCMS (ESI) m/z 376 (M+H).

Example 245B

The procedure in Example 138B was used to react phenyl 3-(2-fluoropropan-2-yl)isoxazol-5-ylcarbamate from Example 42A (60 mg, 0.23 mmol) with the amine from the previous step (60 mg, 0.13 mmol). To this solution was added thiomorpholine dioxide (35 µL, 0.20 mmol) and DMAP (10 mg, 0.08 mmol). After heating for 2 hour the reaction was concentrated to dryness. The resulting solid was triturated with ether and the solid collected by vacuum filtration to give 88.5 mg. $^1$H (DMSO-d6) 10.45 (s, 1H), 9.15 (s, 1H), 8.85 (s, 1H), 7.55 (m, 1H), 7.45 (m, 1H), 7.35 (m, 2H), 6.19 (s, 1H), 5.33 (s, 2H), 4.25 (m, 2H), 3.95 (s, 3H), 3.15 (m, 4H), 2.90 (m, 4H), 2.65 (m, 2H), 2.00 (t, 2H), 1.70 (s, 3H), 1.60 (s, 1H). LCMS (ESI) m/z 645 (M+H).

Example 246

Preparation of 1-(4-methoxy-3-(trifluoromethyl) phenyl)-3-(3-(7-methoxy-6-(3-(4,4-dioxothiomorpholino)propoxy)quinazolin-4-ylthio)phenyl)urea Example 246A Step 1: Following the procedure for Example 138B 3-(6-(3-chloropropoxy)-7-methoxyquinazolin-4-ylthio)aniline described in Example 246A (150 mg, 0.40 mmol) was dissolved in 10 mL of dry THF. To this solution was added phenyl 4-methoxy-3-(trifluoromethyl)phenylcarbamate described in Example 138A (150 mg, 0.48 mmol), diisopropylethylamine (140 µL, 103 mg, 0.80 mmol), and DMAP (10 mg). The solution was stirred overnight at room temperature, and then heated at 70 C for 3 hrs. The solution was concentrated to dryness and dissolved in a minimal volume of dichloromethane and the product precipitated with hexane. The solid was collected by filtration. LCMS (ESI) m/z 594 (M+H)

Example 246A

Step 2: The above chloride was dissolved in 10 mL of dry acetone, to this solution sodium iodide (925 mg, 6.17 mmol) was added and the solution heated at reflux overnight. The solution was then concentrated to dryness and triturated with dichloromethane. The solid sodium chloride was removed by filtration, and the filtrate concentrated to an oil. $^1$H (DMSO-d6) 8.67 (s, 1H), 8.07 (s, 1H), 7.82 (s, 1H), 7.71 (s, 1H), 7.51 (s, 1H), 7.40 (m, 3H), 7.24 (m, 4H), 6.81 (m, 2H), 4.30 (m, 2H), 4.01 (s, 3H), 3.79 (m, 5H), 3.45 (m, 2H), 2.44 (m, 2H); LCMS (ESI) m/z 685 (M+H).

Example 246A
Step 3: The crude oil was dissolved in 5 mL of dry DMF and thiomorpholine dioxide (55 mg, 0.4 mmol) was added and the reaction stirred at room temperature overnight. At the end of this time the reaction was diluted with methanol and purified by reversed phase HPLC using a gradient of acetonitrile/water 40-70% over one hour. The major peak was collected and concentrated to a white solid weighing 26.7 mg. $^1$H (DMSO-d6) 9.0 (s, 1H), 8.90 (s, 1H), 8.70 (s, 1H), 7.85 (s, 2H), 7.55 (m, 2H), 7.5 (m, 1H), 7.35 (s, 2H), 7.20 (m, 2H), 4.25 (m, 2H), 3.95 (m, 2H), 3.85 (s, 2H), 3.15 (m, 2H), 2.85 (m, 2H), 2.60 (m, 2H), 2.0 (m, 2H); LCMS (ESI) m/z 692 (M+H).

Example 247

Preparation of 1-(3-(6,7-bis(2-methoxyethoxy) quinazolin-4-ylthio)phenyl)-3-(3-tert-butylisoxazol-5-yl)urea Example 247A 3-Aminothiophenol (56 mg, 0.45 mmol) was treated with cesium carbonate (193 g, 0.59 mmol) in anhydrous tetrahydrofuran (22 mL) and the mixture stirred at room temperature for 30 minutes. 4-chloro-6,7-bis(2-methoxyethoxy)quinazoline (142 mg, 0.45 mmol) from Example 12A was added and the mixture stirred at 60° C. overnight. After cooling to room temperature the mixture was diluted with chloroform, water and brine were added and the organic phase separated. The water phase was extracted three times with chloroform, dried (MgSO$_4$) and concentrated under reduced pressure. The residue was purified by silica gel chromatography (dichloromethane/methanol 9:1) to afford 3-(6,7-bis(2-methoxyethoxy)quinazolin-4-ylthio)aniline (140 mg, 77%) as a solid. $^1$H NMR (300 MHz, CDCl$_3$) δ 8.75 (s, 1H), 7.41 (s, 1H), 7.26 (t, 2H), 6.99-6.94 (m, 2H), 6.74 (d, 1H), 4.30 (s, 4H), 3.99 (bs, 6H), 3.87 (s, 6H); LC-MS (ESI) m/z 402 (M+H)$^+$.

Example 247B

The title compound was prepared as described in Example 113C by using compound 3-(6,7-bis(2-methoxyethoxy) quinazolin-4-ylthio)aniline (138 mg, 0.34 mmol) and phenyl 3-tert-butylisoxazol-5-ylcarbamate described in Example 132A (116 mg, 0.45 mmol) to give 1-(3-(6,7-bis(2-methoxyethoxy)quinazolin-4-ylthio)phenyl)-3-(3-tert-butylisoxazol-5-yl)urea (100 mg, 52%) as a solid. $^1$H NMR (300 MHz, DMSO-d$_6$) δ 10.20 (s, 1H), 9.05 (s, 1H), 8.69 (s, 1H), 7.85 (s, 1H), 7.46 (d, 1H), 7.45-7.38 (m, 3H), 7.31 (d, 1H), 6.05 (s, 1H), 4.36-4.32 (m, 4H), 3.79-3.76 (m, 4H), 3.37 (s, 6H), 1.24 (s, 9H); LC-MS (ESI) m/z 568 (M+H)$^+$.

Example 248

Preparation of 1-(3-(2-fluoropropan-2-yl)isoxazol-5-yl)-3-(3-(6-methoxy-7-(2-morpholinoethoxy) quinazolin-4-ylthio)phenyl)urea Example 248A In a round bottomed flask 3-aminothiophenol (279 mg, 2.23 mmol) was dissolved in 10 mL of dry THF. To this solution was added sodium hydride, 60% suspension in mineral oil, (86 mg, 2.23 mmol) and the reaction stirred for 30 minutes. 4-chloro-7-(2-chloro-ethoxy)-6-methoxy-quinazoline (610 mg, 2.23 mmol) from Example 35A was added as a 10 mL solution in THF, and the reaction stirred overnight at room temperature. The solution was then concentrated to dryness, and partitioned between ethyl acetate and water, and extracted with an additional portion of ethyl acetate. The extracts were combined, dried with magnesium sulfate, filtered, and concentrated to give 3-(7-(2-chloroethoxy)-6-methoxyquinazolin-4-ylthio)aniline as a yellow solid weighing 600 mg. $^1$H NMR (300 MHz, DMSO-d$_6$) δ 8.70 (s, 1H), 7.47 (d, 2H), 7.17 (m, 1H), 6.83 (s, 1H), 6.72 (m, 2H), 4.51 (m, 2H), 4.05 (m, 3H), 3.89 (s, 3H), 3.51 (bs, 2H); LC-MS (ESI) m/z 362 (M+H)$^+$.

Example 248B

The procedure for Example 138B was used to react phenyl 3-(2-fluoropropan-2-yl)isoxazol-5-ylcarbamate from Example 42A (54 mg, 0.20 mmol) with the aniline from the previous step (75 mg, 0.18 mmol). To this solution was added diisopropylethyl amine (47 μL, 0.27 mmol) and DMAP (2.0 mg, 0.02 mmol). The reaction was concentrated to dryness and partitioned between water and dichloromethane, and extracted twice. The combined extracts were washed with brine, dried over magnesium sulfate, filtered and concentrated. The oil was purified by silica gel chromatography (eluting with methanol/dichloromethane 1-8%) to afford the title compound as a white solid (31 mg, 30% yield). $^1$H NMR (300 MHz, DMSO-d$_6$) δ 10.42 (s, 1H), 9.11 (s, 1H), 8.69 (s, 1H), 7.6-7.2 (m, 6H), 6.16 (s, 1H), 4.33 (m, 2H), 4.00 (s, 3H), 3.60 (m, 7H), 2.80 (m, 2H), 1.70 (s, 3H), 1.63 (s, 3H). LC-MS (ESI) m/z 583 (M+H)$^+$.

Example 249

Preparation of 1-(4-methoxy-3-(trifluoromethyl)phenyl)-3-(3-(6-methoxy-7-(2-morpholinoethoxy)quinazolin-4-ylthio)phenyl)urea The procedure for Example 138B was used to react phenyl 4-methoxy-3-(trifluoromethyl)phenylcarbamate described in Example 138A (62 mg, 0.20 mmol) with 3-(7-(2-chloroethoxy)-6-methoxyquinazolin-4-ylthio)aniline described in Example 249A (75 mg, 0.18 mmol). To this solution was added diisopropylethyl amine (47 μL, 0.27 mmol) and DMAP (2.0 mg, 0.02 mmol). The reaction was concentrated to dryness and partitioned between water and dichloromethane, and extracted twice. The combined extracts were washed with brine, dried over magnesium sulfate, filtered and concentrated. The oil was purified by silica gel chromatography eluting with methanol/dichloromethane 1-8% over 18 column volumes. The appropriate peak was concentrated to a white solid (18.6 mg, 15%). $^1$H (DMSO-d6) 9.3 (m, 2H), 8.7 (s, 1H), 7.85 (s, 2H), 7.6 (m, 3H), 7.5-7.2 (m, 5H) 4.4 (m, 3H), 4.0 (m, 4H), 3.8 (m, 6H), 2.8 (m, 2H). LCMS (ESI) m/z 630 (M+H)

Example 250

Preparation of 1-(4-methoxy-3-(trifluoromethyl)phenyl)-3-(3-(6-methoxy-7-(2-morpholinoethoxy)quinazolin-4-yloxy)phenyl)urea Example 250A Step 1: To morpholine (5 mL) was added 7-(2-chloroethoxy)-6-methoxy-quinazolin-4-ol (600 mg, 2.36 mmol) from Example 35A and the mixture heated at 100° C. for 4 hours. After cooling to room temperature, the mixture was diluted with DCM and filtered. The resulting solid was washed with MeOH and H$_2$O to give 4-hydroxy-6-methoxy-7-(2-morpholinoethoxy)quinazoline (328 mg, 1.07 mmol, 46%). $^1$H NMR (300 MHz, DMSO-d$_6$) δ 12.08 (br s, 1H), 7.98 (s, 1H), 7.44 (s, 1H), 7.17 (s, 1H), 4.23 (t, 2H), 3.87 (s, 3H), 3.58 (t, 4H), 3.41-3.32 (m, 4H), 2.75 (t, 2H); LC-MS (ESI) m/z 306 (M+H)$^+$.

Example 250A

Step 2: The procedure described in Example 4A Step 2 but using 4-hydroxy-6-methoxy-7-(2-morpholinoethoxy)quinazoline (325 mg, 1.07 mmol) afforded 4-(2-(4-chloro-6-methoxyquinazolin-7-yloxy)ethyl)morpholine (196 mg, 0.61 mmol, 57%). LC-MS (ESI) m/z 324 (M+H)$^+$.

Example 250A

Step 3: 3-Aminophenol (338 mg, 3.09 mmol) was treated with cesium carbonate (2 g, 6.2 mmol) in anhydrous isopropanol (10 mL) and the mixture stirred at room temperature for 30 minutes. 4-(2-(4-chloro-6-methoxyquinazolin-7-yloxy)ethyl)morpholine from the previous step (1 g, 3.09 mmol) was added and the mixture stirred at 80° C. for 2h. Cesium carbonate was filtered off, washed with isopropanol and the filtrate concentrated under reduced pressure. The residue was purified by silica gel chromatography (dichloromethane/methanol 9:1) to afford 3-(6-methoxy-7-(2-morpholinoethoxy)quinazolin-4-yloxy)aniline (236 mg, 22%) as a browish solid. $^1$H NMR (300 MHz, DMSO-d$_6$) δ 8.54 (s, 1H), 7.51 (s, 1H), 7.41 (s, 1H), 7.09 (t, 1H), 6.50-6.37 (m, 3H), 5.30 (bs, 2H), 4.34-4.30 (m, 2H), 3.91 (s, 3H), 3.60 (s, 4H), 2.82-2.70 (m, 2H) 2.59-2.42 (m, 4H); LC-MS (ESI) m/z 397 (M+H)$^+$.

Example 250B

Using the procedure described in Example 230B 3-(6-methoxy-7-(2-morpholinoethoxy)quinazolin-4-yloxy)aniline (90 mg, 0.23 mmol) was reacted with phenyl 4-methoxy-3-(trifluoromethyl)phenylcarbamate described in Example 138A (99 mg, 0.32 mmol) and 4-(dimethylamino)pyridine (28 mg, 0.23 mmol) to give 1-(4-methoxy-3-(trifluoromethyl)phenyl)-3-(3-(6-methoxy-7-(2-morpholinoethoxy)quinazolin-4-yloxy)phenyl)urea (38.72 mg, 27%) as a white solid. $^1$H NMR (300 MHz, DMSO-d$_6$) δ 8.92 (bs, 1H), 8.85 (bs, 1H), 8.56 (s, 1H), 7.60-7.51 (m, 3H), 7.43-7.35 (m, 2H), 7.26-7.19 (m, 2H), 6.92 (d, 1H), 4.33 (bs, 2H), 3.99 (s, 3H), 3.84 (s, 2H), 3.61 (s, 4H), 2.90-2.69 (m, 2H), 2.65-2.55 (m, 2H); LC-MS (ESI) m/z 614 (M+H)$^+$.

Example 251

Preparation of 1-(3-(2-fluoropropan-2-yl)isoxazol-5-yl)-3-(3-(6-methoxy-7-(2-morpholinoethoxy)quinazolin-4-yloxy)phenyl)urea Using the procedure described in Example 229B by using 3-(6-methoxy-7-(2-morpholinoethoxy)quinazolin-4-yloxy)aniline described in Example 251A Step 3 (146 mg, 0.37 mmol) was reacted with phenyl 3-(2-fluoropropan-2-yl)isoxazol-5-ylcarbamate from Example 42A (117 mg, 0.44 mmol) and 4-(dimethylamino)pyridine (45 mg, 0.37 mmol) to give 1-(3-(2-fluoropropan-2-yl)isoxazol-5-yl)-3-(3-(6-methoxy-7-(2-morpholinoethoxy)quinazolin-4-yloxy)phenyl)urea (101.6 mg, 49%) as a solid. $^1$H NMR (300 MHz, DMSO-d$_6$) δ 10.41 (s, 1H), 9.11 (s, 1H), 8.56 (s, 1H), 7.57 (s, 2H), 7.44-7.40 (m, 2H), 7.32 (d, 1H), 7.00 (d, 1H), 6.15 (s, 1H), 4.35-4.33 (m, 2H), 3.98 (s, 3H), 3.62-3.60 (m, 4H), 2.85-2.70 (m, 2H), 2.52-2.50 (m, 4H), 1.70 (s, 3H), 1.63 (s, 3H); LC-MS (ESI) m/z 567 (M+H)$^+$.

Example 252

Preparation of 1-(1-tert-butyl-1H-pyrazol-4-yl)-3-(3-(6,7-dimethoxyquinazolin-4-yloxy)phenyl)urea

Example 252A

Step 1: 1-tert-butyl-1H-pyrazol-4-amine was synthesized according to the procedure described in *Bull. Chem. Soc. Jpn.* 1996, 69, 1997-2002.

Example 252A

Step 2: To a solution containing 1-tert-butyl-1H-pyrazol-4-amine (0.995 g, 7.16 mmmol) in THF (20 mL), phenylchloroformate (1.00 mL, 8.02 mmol) and $K_2CO_3$ (1.32 g, 9.52 mmol) were added at room temperature. After stirring overnight, the mixture was filtered and the solid washed with THF. The filtrate was concentrated to dryness and the residue was dissolved in DCM and the organic solution was washed with brine and dried over $MgSO_4$ to yield phenyl 1-tert-butyl-1H-pyrazol-4-ylcarbamate as a solid (1.65 g, 89%). $^1$H NMR (300 MHz, $CDCl_3$) δ 7.85 (1H, s), 7.30 (6H, m), 1.60 (9H, s).

Example 252A

Step 3: To a solution of 1-(1-tert-butyl-1H-pyrazol-4-yl)-3-(3-hydroxyphenyl)urea (0.782 g, 3.02 mmol) in anhydrous THF (10 mL), 3-aminophenol was added at room temperature. The mixture was stirred at 120 C for 2 h in a sealed tube. The reaction mixture was concentrated to dryness and the residue was dissolved in ethyl acetate. The organic solution was washed with water, brine and dried over $MgSO_4$. The solvent was evaporated and the crude residue was purified on silica gel column, using a mixture of DCM/MeOH as mobile phase to yield 1-(1-tert-butyl-1H-pyrazol-4-yl)-3-(3-hydroxyphenyl)urea (0.169 g, 20%). $^1$HNMR (dmso-d6): δ 9.25 (1H, s), 8.48 (1H, s), 8.20 (1H, s), 7.80 (1H, s), 7.39 (1H, s), 7.02 (2H, m), 6.77 (1H, d), 6.35 (1H, d), 1.49 (9H, s).

Example 252B

To a solution of 1-(1-tert-butyl-1H-pyrazol-4-yl)-3-(3-hydroxyphenyl)urea (0.10 g, 0.62 mmol) in anhydrous THF (8 mL), $Cs_2CO_3$ (0.403 g, 1.23 mmol) were added. After stirring the heterogeneous mixture for 1 h, 4-chloro-6,7-dimethoxyquinazoline (0.138 g, 0.62 mmol) was added at room temperature. The reaction mixture was stirred at 55 C overnight. The mixture was filtered and the filtrate was concentrated to dryness. The crude was purified on HPLC. The titled compound was obtained as a white solid. Yield: 0.122 mg (42%). $^1$HNMR (dmso-d6): δ 8.86 (1H, s), 8.55 (1H, s), 8.40 (1H, s), 7.80 (1H, s), 7.59 (1H, s), 7.54 (1H, s), 7.35 (3H, m), 7.23 (1H, d), 6.88 (1H, d), 3.98 (6H, s), 1.50 (9H, s). LC/MS: M+1: 463.

Example 253

Preparation of 1-(5-tert-butylisoxazol-3-yl)-3-(3-(6,7-dimethoxyquinazolin-4-ylsulfinyl)phenyl)urea To a stirring solution of 1-(5-tert-butylisoxazol-3-yl)-3-(3-(6,7-dimethoxyquinazolin-4-ylthio)phenyl)urea (120 mg, 0.25 mmol) from Example 46 in dichloromethane (2.5 mL) was added 3-chloroperoxybenzoic acid (56 mg, 77% max, 0.25 mmol). The reaction was quenched after 5 minutes with sat. $NaHCO_3$(aq), extracted with EtOAc, dried over $MgSO_4$, filtered, and concentrated in vacuo. The crude product was purified by column chromatography (25-100% EtOAc/hexanes) then repurified (12-100% EtOAc/hexanes) to give 1-(5-tert-butylisoxazol-3-yl)-3-(3-(6,7-dimethoxyquinazolin-4-ylsulfinyl)phenyl)urea (21 mg, 0.42 mmol, 17%). $^1$H NMR (300 MHz, DMSO-$d_6$) δ 9.58 (s, 1H), 9.16-9.12 (m, 2H), 8.33-8.28 (m, 2H), 7.49-7.34 (m, 4H), 6.50 (s, 1H), 4.03 (s, 3H), 3.99 (s, 3H), 1.30 (s, 9H); LC-MS (ESI) m/z 496 $(M+H)^+$.

Example 254

Preparation of 1-(3-(6,7-dimethoxyquinazolin-4-yloxy)phenyl)-3-(3-(trifluoromethyl)isoxazol-5-yl)urea According to the procedure described in Example 113C, 3-(6,7-dimethoxyquinazolin-4-yloxy)aniline(104 mg, 0.35 mmol) and phenyl 3-(trifluoromethyl)isoxazol-5-ylcarbamate described in Example 229A (124 mg, 0.45 mmol) were reacted to give 1-(3-(6,7-dimethoxyquinazolin-4-yloxy)phenyl)-3-(3-(trifluoromethyl)isoxazol-5-yl)urea (9.23 mg, 6%) as a white solid. $^1$H NMR (300 MHz, DMSO-$d_6$) δ 10.90 (bs, 1H), 9.30 (bs, 1H), 8.59 (bs, 1H), 7.8-7.20 (m, 5H), 7.06 (bs, 1H), 6.50 (s, 1H), 4.09 (s, 6H); LC-MS (ESI) m/z 476 $(M+H)^+$.

Example 255

Preparation of 1-(3-(6,7-dimethoxyquinazolin-4-yloxy)phenyl)-3-(3-(1-hydroxy-2-methylpropan-2-yl)isoxazol-5-yl)urea

Example 255A

Step 1: 5-Hydroxy-4,4-dimethyl-3-oxopentanenitrile (1 equivalent) and sodium hydroxide (2 equivalents) with a reaction pH of 10-13 was reacted in a similar manner to that described in Example 122A Step 2, to afford 245-aminoisoxazol-3-yl)-2-methylpropan-1-ol as a colorless solid which can be used in the next step without further purification. $^1$H NMR (300 MHz, $CDCl_3$) δ 5.04 (s, 1H), 4.47 (brs, 2H), 3.65 (s, 2H), 2.50 (brs, 1H), 1.28 (s, 6H); LC-MS (ESI) m/z 157 $(M+H)^1$.

Example 255A

Step 2: 2-(5-Aaminoisoxazol-3-yl)-2-methylpropan-1-ol (100 mg, 0.60 mmol) was reacted according to the procedure described in Example 122A Step 3 to afford phenyl 3-(1-hydroxy-2-methylpropan-2-yl)isoxazol-5-ylcarbamate as a colorless solid (77 mg, 46%) that was not purified further.

Example 255B 3-(6,7-Dimethoxyquinazolin-4-yloxy)aniline (40 mg, 0.13 mmol) and the carbamate from the previous step (50 mg, 0.18 mmol) were reacted according to the procedure described in Example 122B. Purification via preparative TLC eluting with 10% methanol in dichloromethane afforded 14346,7-dimethoxyquinazolin-4-yloxy)phenyl)-3-(3-(1-hydroxy-2-methylpropan-2-yl)isoxazol-5-yl)urea as a pinkish solid (38 mg, 59%). $^1$H NMR (300 MHz, DMSO-$d_6$) δ 10.21 (brs, 1H), 9.08 (brs, 1H), 8.56 (s, 1H), 7.57 (s, 2H), 7.38-7.40 (m, 2H), 7.30 (m, 1H), 6.99 (m, 1H), 6.02 (s, 1H), 4.80 (brs, 1H), 3.98-4.00 (2×s, 6H), 3.39 (s, 2H), 1.16 (s, 6H); LC-MS (ESI) m/z 480 $(M+H)^+$.

Example 256

Preparation of 1-(5-tert-butyl-isoxazol-3-yl)-3-(3-{7-[3-(1,1-dioxo-thiomorpholin-4-yl)-propoxy]6-methoxy-quinazolin-4-yloxy}-phenyl)-urea To a solution of 1-(5-tert-butyl-isoxazol-3-yl)-3-{3-[7-(3-chloro-propoxy)-6-methoxy-quinazolin-4-yloxy]-phenyl}-urea (described in Example 27B, 235 mg, 0.446 mmol) in DMF (3 mL) was added thiomorpholine 1,1-dioxide (181 mg, 1.338 mmol) followed by diisopropyl ethylamine (0.233 mL, 1.338 mmol) and tetrabutyl ammonium iodide (164 mg, 0.446 mmol). The reaction mixture was heated at 60° C. for 4 days. Formation of the product was determined by LCMS. The crude reaction mixture was purified by preparative HPLC (phenylhexyl reverse phase column eluted with gradient of solvent A=0.05% HOAc/H$_2$O and solvent B=0.05% HOAc/CH$_3$CN) to afford 1-(5-tert-butyl-isoxazol-3-yl)-3-(3-{7-[3-(1,1-dioxo-thiomorpholin-4-yl)-propoxy]-6-methoxy-quinazolin-4-yloxy}-phenyl)-urea as a white solid (87 mg, 31%). $^1$H NMR (300 MHz, DMSO-d$_6$) δ 9.80-9.35 (brs, 2H), 8.52 (s, 1H), 7.55 (d, 2H), 7.35 (m, 3H), 7.25 (d, 1H), 6.92 (d, 1H), 6.45 (s, 1H), 4.25 (m, 2H), 3.95 (s, 3H), 3.10 (s, 4H), 2.80 (s, 4H), 2.60 (s, 2H), 1.95 (s, 1H), 1.20 (s, 9H); LC-MS (ESI) m/z 625 (M+H)$^+$.

Example 257

Preparation of 1-(3-(2-fluoropropan-2-yl)isoxazol-5-yl)-3-(3-(7-hydroxy-6-methoxyquinazolin-4-yloxy)phenyl)urea

Example 257A 3-(2-fluoropropan-2-yl)isoxazol-5-amine (11.26 g, 78.19 mmol) described in Example 42A in THF (300 mL) was treated with potassium carbonate (21.58 g, 156 mmol) and p-chlorophenyl chloroformate (14.94 g, 78.19 mmol). After stirring at rt for 1 h, additional p-chlorophenyl chloroformate (7.5 g, 39.26 mmol) was introduced, and the reaction mixture was stirred at rt overnight. The mixture was filtered through a celite pad, washed with ethyl acetate and concentrated to dryness. The residue was taken into ethyl acetate, washed with brine, and the organics dried (MgSO$_4$) and concentrated. The residue was purified by silica gel chromatography (eluting with 10 to 50% ethyl acetate in hexanes) to give 4-chlorophenyl 3-(2-fluoropropan-2-yl)isoxazol-5-ylcarbamate (16.51 g, 71%) as a cream solid. $^1$H NMR (300 MHz, CDCl$_3$) δ 7.87 (brs, 1H), 7.36-7.41 (m, 2H), 7.13-7.17 (m, 2H), 6.27 (s, 1H), 1.74 (d, J=21 Hz, 6H); LC-MS (ESI) m/z 299 (M+H)$^+$.

Example 257B

To a stirred solution of 4-(3-aminophenoxy)-6-methoxyquinazolin-7-ol (200 mg, 0.71 mmol) (prepared as described in example 95A, steps 1 through 3) in anhydrous DMF (6 mL), was added 4-chlorophenyl 3-(2-fluoropropan-2-yl)isoxazol-5-ylcarbamate (212 mg, 0.71 mmol) and the mixture was heated to 60° C. for 2.5 h. Concentration in vacuo followed by purification via preparative reverse phase HPLC (eluted with a gradient of solvent B=0.05% HOAc/CH$_3$CN and solvent A=0.05% HOAc/H$_2$O), afforded 1-(3-(2-fluoropropan-2-yl)isoxazol-5-yl)-3-(3-(7-hydroxy-6-methoxyquinazolin-4-yloxy)phenyl)urea (41 mg, 13%) as a colorless solid. $^1$H NMR (300 MHz, DMSO-d$_6$) δ 10.64 (brs, 1H), 9.13 (brs, 1H), 8.48 (s, 1H), 7.55-7.56 (m, 2H), 7.41 (dd, J=8.1, 8.1 Hz, 1H), 7.32 (m, 1H), 7.23 (s, 1H), 6.98 (m, 1H), 6.15 (s, 1H), 3.99 (s, 3H), 1.66 (d, J=22 Hz, 6H); LC-MS (ESI) m/z 454 (M+H)$^+$.

Example 258

Preparation of 1-(3-(2-fluoropropan-2-yl)isoxazol-5-yl)-3-(3-(6-hydroxy-7-methoxyquinazolin-4-yloxy)phenyl)urea To a stirred solution of 4-(3-aminophenoxy)-7-methoxyquinazolin-6-ol (200 mg, 0.710 mmol) (prepared as described in example 107A, steps 1 through 7) in anhydrous DMF (6 mL), was added 4-chlorophenyl 3-(2-fluoropropan-2-yl)isoxazol-5-ylcarbamate described in Example 257A (317 mg, 1.07 mmol) and the mixture was heated to 60° C. for 3 h. Concentration in vacuo followed by trituration of the resulting solid with methanol afforded, after filtration and drying, 1-(3-(2-fluoropropan-2-yl)isoxazol-5-yl)-3-(3-(6-hydroxy-7-methoxyquinazolin-4-yloxy)phenyl)urea (162 mg, 50%) as a colorless solid. $^1$H NMR (300 MHz, DMSO-d$_6$) δ 10.40 (s, 1H), 10.30 (s, 1H), 9.08 (s, 1H), 8.50 (s, 1H), 7.53 (dd, J=2.1, 2.1 Hz, 1H), 7.50 (s, 1H), 7.37-7.44 (m, 2H), 7.32 (dd, J=8.4, 1.8 Hz, 1H), 6.97 (dd, J=8.4, 1.8 Hz, 1H), 6.15 (s, 1H), 4.00 (s, 3H), 1.66 (d, J=22 Hz, 6H); LC-MS (ESI) m/z 454 (M+H)$^+$.

Example 259

Preparation of 1-(3-(6,7-dimethoxyquinazolin-4-yloxy)phenyl)-3-(5-(1,1,1-trifluoro-2-methylpropan-2-yl)isoxazol-3-yl)urea

Example 259A

Step 1: Reaction was carried out in two separate batches, employing 5 g of 3,3,3-trifluoro-2,2-dimethylpropionic acid in each batch. To a stirred solution of 3,3,3-trifluoro-2,2-dimethylpropionic acid (5 g, 32 mmol) in anhydrous dichloromethane (20 mL) at 0° C. (under an argon atmosphere), was added dropwise a solution of (trimethylsilyl)diazomethane (18 mL of a 2M solution in diethyl ether, 35 mmol) (gas evolution observed). The resulting yellow solution was allowed to warm to rt and stirred for a further 48 h. An additional 5 mL of 2M (trimethylsilyl)diazomethane solution (10 mmol) was added, and stirring continued for a further 5 h whereupon a further 6 mL of 2 M (trimethylsilyl)diazomethane solution (12 mmol) was added. After stirring for a further 15 h, the reaction mixture was concentrated in vacuo (keeping bath temperature below 30° C.). The resulting oil was redissolved in diethyl ether (200 mL), washed with saturated sodium hydrogencarbonate solution (100 mL), separated, and dried over MgSO$_4$. Filtration followed by concentration in vacuo (keeping bath temperature below 30° C.) gave crude product. Crude product from both batches were combined to afford crude methyl 3,3,3-trifluoro-2,2-dimethylpropanoate (7.69 g) as a yellow oil which was taken on without further purification. $^1$H NMR (300 MHz, CDCl$_3$) δ 3.86 (s, 3H), 1.40 (s, 6H).

Example 259A

Step 2: Reaction was carried out in two separate batches, employing 3.85 g of methyl 3,3,3-trifluoro-2,2-dimethylpropanoate in each batch. To a stirred refluxing suspension of sodium hydride (1.41 g of a 60% dispersion in mineral oil, 35 mmol) in dry THF (30 mL) (under an argon atmosphere) was added a mixture of crude methyl 3,3,3-trifluoro-2,2-dimethylpropanoate (3.85 g) and dry acetonitrile (1.85 mL, 35 mmol), dropwise over the course of 45 mins. The resulting pale yellow suspension was heated at 70° C. for a further 15 h. After cooling to rt, both reaction batches were combined whereupon the solvent was removed in vacuo. The resulting orange foam was redissolved in water (200 mL) and washed with diethyl ether (2×200 mL), to remove residual mineral oil. The aqueous layer was separated, acidified to pH 2 with aqueous 2N hydrochloric acid and extracted with diethyl ether (3×200 mL). The combined ether layers were dried over MgSO$_4$, filtered, then concentrated under reduced pressure to afford 5,5,5-trifluoro-4,4-dimethyl-3-oxopentanenitrile as a yellow oil (4.27 g, 37% from 3,3,3-trifluoro-2,2-dimethylpropionic acid) which was used in the next step without further purification. $^1$H NMR (300 MHz, CDCl$_3$) δ 3.77 (s, 2H), 1.43 (s, 6H).

Example 259A

Step 3: A mixture of 5,5,5-trifluoro-4,4-dimethyl-3-oxopentanenitrile (3 g, 16.76 mmol), hydroxylamine sulfate (3.30 g, 20.11 mmol) and sodium hydrogencarbonate (3.52 g, 41.90 mmol) in a mixture of 10% methanol in water (60 mL), was heated at 65° C. for 15 h. After cooling to rt, a further 30 mL of 10% methanol in water was added, and the mixture was divided into 9×10 mL batches. Each batch was adjusted to pH 1 with concentrated hydrochloric acid and each placed into a 20 mL volume microwave vial fitted with a stirrer bar. After sealing, each batch was placed in a Biotage Microwave Synthesizer and heated (with stirring) at 140° C. for 5 min (maximum internal pressure attained was 7 bar). Each batch was cooled and neutralized with saturated aqueous sodium hydrogencarbonate solution. All processed batches were combined and concentrated in vacuo and the aqueous solution extracted with 10% isopropanol in chloroform (3×150 mL). The combined organic layers were washed with brine (200 mL), separated, dried over MgSO$_4$ and filtered. Concentration in vacuo afforded 5-(1,1,1-trifluoro-2-methylpropan-2-yl)isoxazol-3-amine (2.34 g, 71%) as a light yellow solid which taken on without further purification. $^1$H NMR (300 MHz, CDCl$_3$) δ 5.80 (s, 1H), 3.98 (brs, 2H), 1.53 (s, 6H); LC-MS (ESI) m/z 195 (M+H)$^+$.

Example 259A

Step 4: 5-(1,1,1-trifluoro-2-methylpropan-2-yl)isoxazol-3-amine (123 mg, 0.63 mmol) in THF (2 mL) was treated with potassium carbonate (113 mg, 0.819 mmol) and p-chlorophenyl chloroformate (180 mg, 0.95 mmol). The reaction mixture was stirred at rt overnight. The mixture was filtered through a celite pad, washed with ethyl acetate and concentrated to dryness. The residue was taken into ethyl acetate, washed with brine, and the organics dried (MgSO$_4$) and concentrated. The residue was purified by silica gel chromatography (hexane/ethyl acetate 8:2) to give 4-chlorophenyl 5-(1,1,1-trifluoro-2-methylpropan-2-yl)isoxazol-3-ylcarbamate (85 mg, 39%) as a white solid. $^1$H NMR (300 MHz, CDCl$_3$) δ 7.83 (brs, 1H), 7.38 (d, J=9 Hz, 2H), 7.15 (d, J=9 Hz, 2H), 6.82 (s, 1H), 1.59 (s, 6H); LC-MS (ESI) m/z 349 (M+H)$^+$.

Example 259B

To a stirred solution of 3-(6,7-dimethoxyquinazolin-4-yloxy)aniline (36 mg, 0.122 mmol) described in Example 113A in anhydrous THF (0.5 mL), was added 4-chlorophenyl 5-(1,1,1-trifluoro-2-methylpropan-2-yl)isoxazol-3-ylcarbamate from the previous step (85 mg, 0.244 mmol) and 4-(dimethylamino)pyridine (7.3 mg, 0.06 mmol). The mixture was stirred at rt for 6 h. Concentration in vacuo followed by purification by silica gel chromatography (dichloromethane/methanol 9:1) and trituration of the resulting solid with diethyl ether afforded, after filtration and drying, 1-(3-(6,7-dimethoxyquinazolin-4-yloxy)phenyl)-3-(5-(1,1,1-trifluoro-2-methylpropan-2-yl)isoxazol-3-yl)urea (22.8 mg, 18%) as a colorless solid. $^1$H NMR (300 MHz, DMSO-d$_6$) δ 9.76 (s, 1H), 9.04 (s, 1H), 8.56 (s, 1H), 7.56-7.59 (m, 2H), 7.38-7.44 (m, 2H), 7.27 (m, 1H), 6.99 (m, 1H), 6.88 (s, 1H), 4.00 (s, 6H), 1.54 (s, 6H); LC-MS (ESI) m/z 518 (M+H)$^+$.

Example 260

Preparation of 1-(3-(6-ethoxy-7-methoxyquinazolin-4-yloxy)phenyl)-3-(5-(1,1,1-trifluoro-2-methylpropan-2-yl)isoxazol-3-yl)urea Example 260A (Preparation of phenyl 5-(1,1,1-trifluoro-2-methylpropan-2-yl)isoxazol-3-ylcarbamate)

To a stirred mixture of 5-(1,1,1-trifluoro-2-methylpropan-2-yl)isoxazol-3-amine prepared as described in Example 259A (2.34 g, 12.06 mmol) and potassium carbonate (5 g, 36 mmol) in dry dichloromethane (50 mL) at 0° C., was added a solution of phenyl chloroformate (2.83 g, 18 mmol) in anhydrous dichloromethane (5 mL). The reaction mixture was warmed to room temperature and stirred for a further 15 h, then additional phenyl chloroformate (1 g, 6.3 mmol) was added and stirring was continued for a further 3 h. The reaction mixture was partitioned between water (200 mL) and dichloromethane (500 mL). The organic layer was separated, washed with brine (100 mL), dried over MgSO$_4$, and then concentrated under reduced pressure to give a yellow oil. Purification via silica gel flash chromatography (eluting with 5% to 50% ethyl acetate in hexanes) afforded phenyl 5-(1,1,1-trifluoro-2-methylpropan-2-yl)isoxazol-3-ylcarbamate (2.63 g, 69%) as a colorless solid. $^1$H NMR (300 MHz, CDCl$_3$) δ 8.16 (brs, 1H), 7.38-7.43 (m, 2H), 7.17-7.29 (m, 3H), 6.85 (s, 1H), 1.57 (s, 6H); LC-MS (ESI) m/z 315 (M+H)$^+$.

Example 260B (Preparation of 3-(6-ethoxy-7-methoxyquinazolin-4-yloxy)aniline)

To a stirred suspension of cesium carbonate (3.60 g, 11.06 mmol) in THF (50 mL) was added 3-aminophenol (0.91 g, 8.38 mmol). After stirring for 30 minutes at rt, 4-chloro-6-ethoxy-7-methoxyquinazoline described in Example 11A (2.00 g, 8.38 mmol) was added and the reaction mixture was heated at 50° C. for 15 h. The reaction mixture was cooled to rt and diluted with ethyl acetate. The solution was washed with aqueous 1 M NaOH solution, then brine, and dried over MgSO$_4$. Filtration and concentrated under reduced pressure, gave a solid that was triturated with ethyl acetate. Filtration and drying afforded 3-(6-ethoxy-7-methoxyquinazolin-4-yloxy)aniline (1.30 g, 50%) as a cream solid, which did not require further purification. $^1$H NMR (400 MHz, DMSO-d$_6$) δ 8.54 (s, 1H), 7.48 (s, 1H), 7.36 (s, 1H), 7.08 (dd, J=8, 8 Hz, 1H), 6.36-6.49 (m, 3H), 5.30 (brs, 2H), 4.21 (q, J=7 Hz, 2H), 3.98 (s, 3H), 1.41 (t, J=7 Hz, 3H); LC-MS (ESI) m/z 312 (M+H)$^+$.

Example 260C

To a stirred solution of 3-(6-ethoxy-7-methoxyquinazolin-4-yloxy)aniline (100 mg, 0.322 mmol) and phenyl 5-(1,1,1-trifluoro-2-methylpropan-2-yl)isoxazol-3-ylcarbamate (151 mg, 0.482 mmol) in anhydrous THF (5 mL), was added 4-(dimethylamino)pyridine (6 mg, 0.0492 mmol) and the mixture was stirred at rt for 15 h. Concentration in vacuo followed by purification via silica gel column chromatography (eluted with a gradient of 20% ethyl acetate in hexanes to 100% ethyl acetate), afforded 1-(3-(6-ethoxy-7-methoxyquinazolin-4-yloxy)phenyl)-3-(5-(1,1,1-trifluoro-2-methylpropan-2-yl)isoxazol-3-yl)urea (48 mg, 28%) as a colorless solid. $^1$H NMR (300 MHz, DMSO-d$_6$) δ 9.74 (brs, 1H), 9.01 (s, 1H), 8.55 (s, 1H), 7.54-7.59 (m, 2H), 7.37-7.43 (m, 2H), 7.26 (m, 1H), 6.98 (m, 1H), 6.87 (s, 1H), 4.24 (q, J=7 Hz, 2H), 4.00 (s, 3H), 1.53 (s, 6H), 1.43 (t, J=7 Hz, 3H); LC-MS (ESI) m/z 532 (M+H)$^+$.

Example 261

Preparation of 1-(3-(6,7-dimethoxyquinazolin-4-ylthio)phenyl)-3-(5-(1,1,1-trifluoro-2-methylpropan-2-yl)isoxazol-3-yl)urea

Example 262

Preparation of 1-(3-(6-ethoxy-7-methoxyquinazolin-4-ylthio)phenyl)-3-(5-(1,1,1-trifluoro-2-methylpropan-2-yl)isoxazol-3-yl)urea

Example 262A

To a stirred suspension of cesium carbonate (3.60 g, 11.06 mmol) in THF (60 mL) was added 3-aminobenzenethiol (1.00 g, 7.99 mmol). After stirring for 30 minutes at rt, 4-chloro-6-ethoxy-7-methoxyquinazoline described in Example 11A (1.91 g, 7.99 mmol) was added and the reaction mixture was heated at rt for 15 h. The reaction mixture was cooled to rt and concentrated under reduced pressure to give a solid. Purification by silica gel column chromatography (eluting with 2% methanol in dichloromethane) afforded 3-(6-ethoxy-7-methoxyquinazolin-4-ylthio)aniline (1.20 g, 46%) as a cream solid, which did not require further purification. $^1$H NMR (400 MHz, DMSO-d$_6$) δ 8.69 (s, 1H), 7.33 (s, 1H), 7.30 (s, 1H), 7.12 (dd, J=8, 8 Hz, 1H), 6.79 (s, 1H), 6.66-6.73 (m, 2H), 5.33 (brs, 2H), 4.21 (q, J=7 Hz, 2H), 3.98 (s, 3H), 1.43 (t, J=7 Hz, 3H); LC-MS (ESI) m/z 328 (M+H)$^+$.

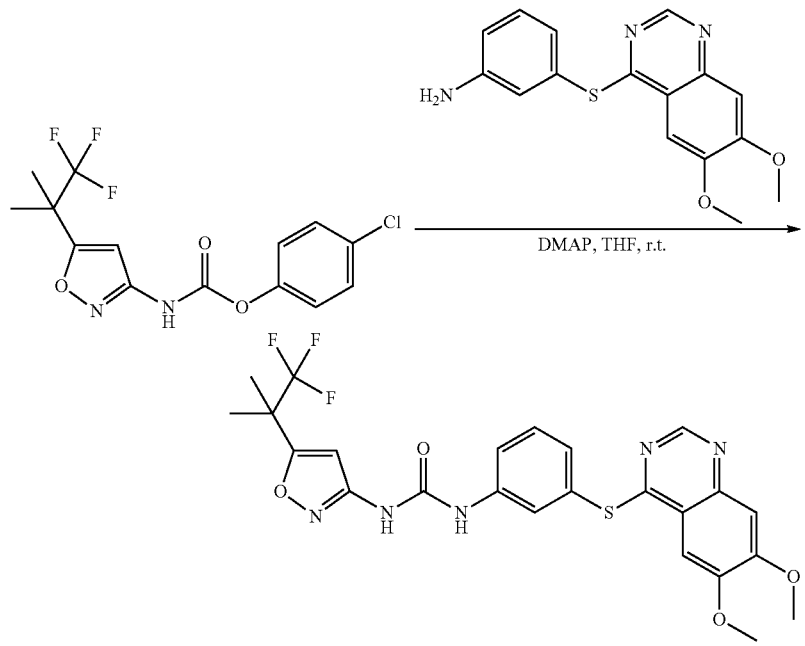

Example 262B

To a stirred solution of 3-(6-ethoxy-7-methoxyquinazolin-4-ylthio)aniline (100 mg, 0.305 mmol) and phenyl 5-(1,1,1-trifluoro-2-methylpropan-2-yl)isoxazol-3-ylcarbamate described in Example 260A (144 mg, 0.458 mmol) in anhydrous THF (5 mL), was added 4-(dimethylamino)pyridine (6 mg, 0.0492 mmol) and the mixture was stirred at rt for 15 h. Concentration in vacuo followed by purification via silica gel column chromatography (eluted with a gradient of 20% ethyl acetate in hexanes to 100% ethyl acetate), afforded 1-(3-(6-ethoxy-7-methoxyquinazolin-4-ylthio)phenyl)-3-(5-(1,1,1-trifluoro-2-methylpropan-2-yl)isoxazol-3-yl)urea (35 mg, 21%) as a colorless solid. $^1$H NMR (300 MHz, DMSO-d$_6$) δ

To a stirred solution of 3-(6,7-dimethoxyquinazolin-4-ylthio)aniline described in Example 115B (144 mg, 0.46 mmol) in anhydrous THF (5.6 mL), was added 4-chlorophenyl 5-(1,1,1-trifluoro-2-methylpropan-2-yl)isoxazol-3-ylcarbamate described in Example 259A (161 mg, 0.46 mmol) and 4-(dimethylamino)pyridine (31 mg, 0.25 mmol). The mixture was stirred at rt for 15 h. To the suspension was added diethyl ether. Sonication and filtration afforded 1-(3-(6,7-dimethoxyquinazolin-4-ylthio)phenyl)-3-(5-(1,1,1-trifluoro-2-methylpropan-2-yl)isoxazol-3-yl)urea (134 mg, 55%) as a colorless solid. $^1$H NMR (300 MHz, DMSO-d$_6$) δ 9.77 (s, 1H), 9.04 (s, 1H), 8.70 (s, 1H), 7.86 (s, 1H), 7.28-7.54 (m, 5H), 6.89 (s, 1H), 3.99 (s, 6H), 1.54 (s, 6H); LC-MS (ESI) m/z 534 (M+H)$^+$.

9.74 (brs, 1H), 9.02 (s, 1H), 8.69 (s, 1H), 7.85 (m, 1H), 7.28-7.51 (m, 5H), 6.88 (s, 1H), 4.23 (q, J=7 Hz, 2H), 3.99 (s, 3H), 1.54 (s, 6H), 1.45 (t, J=7 Hz, 3H); LC-MS (ESI) m/z 548 (M+H)$^+$.

Example 263

Preparation of 143-(7-hydroxy-6-methoxyquinazolin-4-yloxy)phenyl)-3-(5-(1,1,1-trifluoro-2-methylpropan-2-yl)isoxazol-3-yl)urea To a stirred solution of 4-(3-aminophenoxy)-6-methoxyquinazolin-7-ol (100 mg, 0.35 mmol) prepared as described in example 95A in anhydrous DMF (3 mL), was added phenyl 5-(1,1,1-trifluoro-2-methylpropan-2-yl)isoxazol-3-ylcarbamate described in Example 260A (111 mg, 0.35 mmol) and the mixture was heated to 60° C. for 2 h. Additional phenyl 5-(1,1,1-trifluoro-2-methylpropan-2-yl)isoxazol-3-ylcarbamate (50 mg, 0.16 mmol) was added and heating was continued for a further 72 h. Concentration in vacuo followed by purification via preparative reverse phase HPLC (eluted with a gradient of solvent B=0.05% HOAc/CH$_3$CN and solvent A=0.05% HOAc/H$_2$O), afforded 1-(3-(7-hydroxy-6-methoxyquinazolin-4-yloxy)phenyl)-3-(5-(1,1,1-trifluoro-2-methylpropan-2-yl)isoxazol-3-yl)urea (40 mg, 23%) as a colorless solid. $^1$H NMR (300 MHz, DMSO-d$_6$) δ 10.93 (brs, 1H), 9.83 (s, 1H), 9.11 (s, 1H), 8.47 (s, 1H), 7.56 (dd, J=2.1, 2.1 Hz, 1H), 7.53 (s, 1H), 7.40 (dd, J=8.1, 8.1 Hz, 1H), 7.26 (dd, J=8.1, 8.1 Hz, 1H), 7.21 (s, 1H), 6.96 (m, 1H), 6.88 (s, 1H), 3.98 (s, 3H), 1.54 (s, 6H); LC-MS (ESI) m/z 504 (M+H)$^+$.

Example 264

Preparation of 1-(3-(6-hydroxy-7-methoxyquinazolin-4-yloxy)phenyl)-3-(5-(1,1,1-trifluoro-2-methylpropan-2-yl)isoxazol-3-yl)urea To a stirred solution of 4-(3-aminophenoxy)-7-methoxyquinazolin-6-ol (70 mg, 0.247 mmol) described in Example 107A in anhydrous DMF (3 mL), was added phenyl 5-(1,1,1-trifluoro-2-methylpropan-2-yl)isoxazol-3-ylcarbamate described in Example 260A (90 mg, 0.287 mmol) and the mixture was heated to 60° C. for 15 h. Concentration in vacuo followed by trituration of the resulting solid with methanol afforded, after filtration and drying, 1-(3-(6-hydroxy-7-methoxyquinazolin-4-yloxy)phenyl)-3-(5-(1,1,1-trifluoro-2-methylpropan-2-yl)isoxazol-3-yl)urea (73 mg, 59%) as a colorless solid. $^1$H NMR (300 MHz, DMSO-d$_6$) δ 10.30 (s, 1H), 9.75 (s, 1H), 9.01 (s, 1H), 8.49 (s, 1H), 7.55 (dd, J=2.1, 2.1 Hz, 1H), 7.50 (s, 1H), 7.37-7.43 (m, 2H), 7.27 (dd, J=9, 1.2 Hz, 1H), 6.97 (dd, J=8.1, 2.1 Hz, 1H), 6.88 (s, 1H), 4.00 (s, 3H), 1.54 (s, 6H); LC-MS (ESI) m/z 504 (M+H)$^+$.

Example 265

Preparation of 1-(3-(6,7-dimethoxyquinazolin-4-yloxy)-2-fluorophenyl)-3-(5-(1,1,1-trifluoro-2-methylpropan-2-yl)isoxazol-3-yl)urea Example 265A Step 1: A solution of 2-fluoro-3-methoxybenzoic acid (5.00 g, 29.39 mmol) and diisopropylethylamine (4.56 g, 35.27 mmol) in a mixture of anhydrous toluene (25 mL) and anhydrous tert-butanol (25 mL) was stirred over activated 4 A molecular sieves (4 g) for 1 h. Diphenyl phosphoryl azide (9.71 g, 35.27 mmol) was added and the mixture was heated at reflux for 15 h. The reaction mixture was cooled and filtered. To the filtrate was added ethyl acetate (200 mL) and the solution was washed with water (2×100 mL) and brine (100 mL). The organic phase was separated and dried over MgSO$_4$. Filtration followed by concentration under reduced pressure gave crude tert-butyl 2-fluoro-3-methoxyphenylcarbamate. The crude product was dissolved in a solution of 6M HCl in ethyl acetate (20 mL, 0.12 mol) and the mixture stirred at rt for 2 h. The resulting precipitate was filtered and dried. The solid was taken up in a saturated aqueous solution of sodium hydrogen carbonate (50 mL) and the mixture extracted with dichloromethane (2×100 mL). The combined organic layers were dried over Na$_2$SO$_4$, filtered, and concentrated under reduced pressure to afford 2-fluoro-3-methoxyaniline (3.00 g, 72%) as brown oil, which was taken on without further purification. $^1$H NMR (400 MHz, DMSO-d$_6$) δ 6.80-7.02 (m, 3H), 3.82 (s, 3H); LC-MS (ESI) m/z 142 (M+H)$^+$.

Example 265A

Step 2: To a stirred solution of 2-fluoro-3-methoxyaniline (3.0 g, 21.26 mmol) in dichloromethane (80 mL), at 0° C., was added a 4.0 M solution of boron tribromide in dichloromethane (10.63 mL, 42.52 mmol). The reaction mixture was allowed to warm to rt and stirring was continued for a further 15 h. The reaction mixture was quenched via the addition of methanol. After concentration under reduced pressure, the residue was taken up in water, basified with saturated sodium hydrogen carbonate solution, and extracted with ethyl acetate. The combined ethyl acetate layers were washed with brine, dried over MgSO$_4$, and concentrated under reduced pressure to afford 3-amino-2-fluorophenol (2.70 g, 100%) as a brown solid which was taken on without further purification. $^1$H NMR (400 MHz, DMSO-d$_6$) δ 9.36 (brs, 1H), 6.62 (dd, J=8, 8 Hz, 1H), 6.12-6.23 (m, 2H), 5.14 (brs, 2H); LC-MS (ESI) m/z 128 (M+H)$^+$.

Example 265A

Step 3: To a stirred slurry of cesium carbonate (10.25 g, 31.47 mmol) in a 9:1 mixture of THF/DMF (100 mL) at rt, was added 3-amino-2-fluorophenol (2.00 g, 15.74 mmol) in one portion. After stirring for 30 min at rt, 4-chloro-6,7-dimethoxyquinazoline (3.54 g, 15.74 mmol) was added and the reaction mixture was heated at 50° C. for 18 h. The reaction was cooled to rt, then diluted with dichloromethane. The solution was washed with water, then brine, and dried over MgSO$_4$. Filtration followed by concentration under reduced pressure gave a solid that was triturated with a mixture of 10% dichloromethane in ethyl acetate. Filtration afforded 3-(6,7-dimethoxyquinazolin-4-yloxy)-2-fluoroaniline (2.10 g, 42%) as a colorless solid. $^1$H NMR (400 MHz, DMSO-d$_6$) δ 8.56 (s, 1H), 7.54 (s, 1H), 7.40 (s, 1H), 6.93 (dd, J=8.4, 8.4 Hz, 1H), 6.71 (dd, J=8.4, 8.4 Hz, 1H), 6.53 (m, 1H), 5.37 (brs, 2H), 3.99 (s, 3H), 3.98 (s, 3H); LC-MS (ESI) m/z 316 (M+H)$^+$.

Example 265B

To a stirred solution of 3-(6,7-dimethoxyquinazolin-4-yloxy)-2-fluoroaniline from the previous step (150 mg, 0.476 mmol) and phenyl 5-(1,1,1-trifluoro-2-methylpropan-2-yl)isoxazol-3-ylcarbamate described in Example 260A (224 mg, 0.714 mmol) in anhydrous THF (5 mL), was added 4-(dimethylamino)pyridine (6 mg, 0.0492 mmol) and the mixture was stirred at rt for 15 h. An additional amount of 5-(1,1,1-trifluoro-2-methylpropan-2-yl)isoxazol-3-ylcarbamate (50 mg, 0.159 mmol) was added, and stirred for an additional 15 h. Concentration in vacuo followed by purification via silica gel column chromatography (eluted with a gradient of 20% ethyl acetate in hexanes to 100% ethyl acetate), afforded 1-(3-(6,7-dimethoxyquinazolin-4-yloxy)-2-fluorophenyl)-3-(5-(1,1,1-trifluoro-2-methylpropan-2-yl)isoxazol-3-yl)urea (137 mg, 54%) as a colorless solid. $^1$H NMR (300 MHz, DMSO-$d_6$) δ 10.01 (brs, 1H), 8.89 (s, 1H), 8.58 (s, 1H), 8.07 (m, 1H), 7.59 (s, 1H), 7.43 (s, 1H), 7.27 (m, 1H), 7.16 (m, 1H), 6.91 (s, 1H), 4.00 (s, 6H), 1.56 (s, 6H); LC-MS (ESI) m/z 536 (M+H)$^+$.

Example 266

Preparation of 1-(3-(6,7-dimethoxyquinazolin-4-yloxy)-4-fluorophenyl)-3-(5-(1,1,1-trifluoro-2-methylpropan-2-yl)isoxazol-3-yl)urea Example 266A Step 1: To a stirred solution of 4-fluoro-3-methoxyaniline (4.80 g, 34 mmol) in dichloromethane (50 mL), at −10° C., was added a 4.0 M solution of boron tribromide in dichloromethane (20 mL, 80 mmol). The reaction mixture was allowed to warm to rt and stirring was continued for a further 15 h. The reaction mixture was quenched via the addition of methanol. After concentration under reduced pressure, the residue was taken up in water, basified with saturated sodium hydrogen carbonate solution, and extracted with ethyl acetate. The combined ethyl acetate layers were washed with brine, dried over MgSO$_4$, and concentrated under reduced pressure to afford 5-amino-2-fluorophenol (4.00 g, 93%) as a solid which was taken on without further purification. $^1$H NMR (400 MHz, CDCl$_3$) δ 6.87 (dd, J=9.2, 9.2 Hz, 1H), 6.35 (m, 1H), 6.16 (m, 1H), 5.09 (brs, 1H), 3.56 (brs, 2H); LC-MS (ESI) m/z 128 (M+H)$^+$.

Example 266A

Step 2: To a stirred slurry of cesium carbonate (9.53 g, 29 mmol) in a mixture of THF/DMF (9/1, 200 mL) at rt, was added 5-amino-2-fluorophenol (2.10 g, 14.6 mmol) in one portion. After stirring for 30 min at rt, 4-chloro-6,7-dimethoxyquinazoline (3.61 g, 16 mmol) was added and the reaction mixture was heated at 50° C. for 30 h. The reaction was cooled to rt, then diluted with ethyl acetate. The solution was washed with 1 N sodium hydroxide solution, then brine, and dried over MgSO$_4$. Filtration followed by concentration under reduced pressure gave a solid that was triturated with methanol. Filtration afforded 3-(6,7-dimethoxyquinazolin-4-yloxy)-4-fluoroaniline (3.10 g, 67%) as a yellow solid. $^1$H NMR (400 MHz, DMSO-$d_6$) δ 8.57 (s, 1H), 7.54 (s, 1H), 7.41 (s, 1H), 7.05 (dd, J=9.2, 9.2 Hz, 1H), 6.47-6.56 (m, 2H), 5.19 (brs, 2H), 4.00 (s, 3H), 3.99 (s, 3H); LC-MS (ESI) m/z 316 (M+H)$^+$.

Example 266B

To a stirred solution of 3-(6,7-dimethoxyquinazolin-4-yloxy)-4-fluoroaniline from the previous step (150 mg, 0.476 mmol) and phenyl 5-(1,1,1-trifluoro-2-methylpropan-2-yl)isoxazol-3-ylcarbamate described in Example 260A (179 mg, 0.571 mmol) in anhydrous THF (5 mL), was added 4-(dimethylamino)pyridine (6 mg, 0.0492 mmol) and the mixture was stirred at rt for 15 h. Concentration in vacuo followed by purification via silica gel column chromatography (eluted with a gradient of 20% ethyl acetate in hexanes to 100% ethyl acetate), afforded 1-(3-(6,7-dimethoxyquinazolin-4-yloxy)-4-fluorophenyl)-3-(5-(1,1,1-trifluoro-2-methylpropan-2-yl)isoxazol-3-yl)urea (35 mg, 14%) as a colorless solid. $^1$H NMR (300 MHz, DMSO-$d_6$) δ 9.79 (brs, 1H), 9.01 (s, 1H), 8.58 (s, 1H), 7.70 (m, 1H), 7.58 (s, 1H), 7.30-7.42 (m, 3H), 6.86 (s, 1H), 4.00 (s, 6H), 1.54 (s, 6H); LC-MS (ESI) m/z 536 (M+H)$^+$.

Example 267

Preparation of 1-(3-(6,7-dimethoxyquinazolin-4-yloxy)phenyl)-3-(3-(1,1,1-trifluoro-2-methylpropan-2-yl)isoxazol-5-yl)urea Example 267A Step 1: 5,5,5-trifluoro-4,4-dimethyl-3-oxopentanenitrile (524 mg, 2.9 mmol) described in Example 259A Steps 1 and 2 was taken in water (2.9 ml), treated with sodium hydroxide (240 mg, 6 mmol) and the resulting solution stirred at rt for 15 min. After this time hydroxylamine hydrochloride (213 mg, 3.07 mmol) was added and the mixture was heated at 80° C. for 2.5 h. After cooling to rt chloroform was added (20 mL) and the organic phase separated. The water phase was back extracted three times, the organics were combined, dried over MgSO$_4$ and concentrated to afford 3-(1,1,1-trifluoro-2-methylpropan-2-yl)isoxazol-5-amine (150 mg, 27%) as a solid, which was used without further purification. $^1$H NMR (300 MHz, CDCl$_3$) δ 5.19 (s, 1H), 4.50 (brs, 2H), 1.54 (s, 6H); LC-MS (ESI) m/z 195 (M+H)$^+$.

Example 267A

Step 2: 3-(1,1,1-trifluoro-2-methylpropan-2-yl)isoxazol-5-amine (150 mg, 0.77 mmol) dissolved in THF (2.5 mL) was treated with potassium carbonate (139 mg, 1.0 mmol) and p-chlorophenyl choloroformate (412 mg, 2.15 mmol). The reaction mixture was stirred at rt overnight. The mixture was filtered through a celite pad, washed with ethyl acetate and concentrated to dryness. The residue was taken into ethyl acetate, washed with brine, and the organics dried over MgSO$_4$ and concentrated. The residue was purified by silica gel chromatography (hexane/ethyl acetate 8:2) to afford 4-chlorophenyl 3-(1,1,1-trifluoro-2-methylpropan-2-yl)isoxazol-5-ylcarbamate (210 mg, 78%) as a colorless solid. $^1$H NMR (300 MHz, CDCl$_3$) δ 7.72 (brs, 1H), 7.39 (d, J=12 Hz, 2H), 7.16 (d, J=12 Hz, 2H), 6.27 (s, 1H), 1.57 (s, 6H); LC-MS (ESI) m/z 349 (M+H)$^+$.

Example 267B

To a stirred solution of 3-(6,7-dimethoxyquinazolin-4-yloxy)aniline (89 mg, 0.3 mmol) described in Example 113A in anhydrous THF (1.5 mL), was added 4-chlorophenyl 3-(1,1,1-trifluoro-2-methylpropan-2-yl)isoxazol-5-ylcarbamate from the previous step (104 mg, 0.3 mmol) and 4-(dimethylamino)pyridine (18 mg, 0.15 mmol). The mixture was stirred at rt for 6 h. Concentration in vacuo followed by purification by silica gel chromatography (dichloromethane/ethyl acetate 1:1) afforded 1-(3-(6,7-dimethoxyquinazolin-4-yloxy)phenyl)-3-(3-(1,1,1-trifluoro-2-methylpropan-2-yl)isoxazol-5-yl)urea (79.9 mg, 51%) as a colorless solid. $^1$H NMR (300 MHz, DMSO-$d_6$) δ 10.44 (s, 1H), 9.11 (s, 1H), 8.56 (s, 1H), 7.56-7.58 (m, 2H), 7.40-7.45 (m, 2H), 7.29-7.32 (m, 2H), 6.99-7.02 (m, 2H), 6.18 (s, 1H), 4.00 (s, 6H), 1.24 (s, 6H); LC-MS (ESI) m/z 518 (M+H)+.

Example 268

Preparation of 1-(3-(6,7-dimethoxyquinazolin-4-ylthio)phenyl)-3-(3-(1,1,1-trifluoro-2-methylpropan-2-yl)isoxazol-5-yl)urea To a stirred solution of 3-(6,7-dimethoxyquinazolin-4-ylthio)aniline (76 mg, 0.24 mmol) described in Example 115B in anhydrous THF (1.5 mL), was added 4-chlorophenyl 3-(1,1,1-trifluoro-2-methylpropan-2-yl)isoxazol-5-ylcarbamate from Example 267A (84 mg, 0.24 mmol) and 4-(dimethylamino)pyridine (15 mg, 0.12 mmol). The mixture was stirred at rt for 6 h. To the suspension was added diethyl ether. Sonication and filtration afforded 1-(3-(6,7-dimethoxyquinazolin-4-ylthio)phenyl)-3-(3-(1,1,1-trifluoro-2-methylpropan-2-yl)isoxazol-5-yl)urea (88.8 mg, 69%) as a colorless solid. $^1$H NMR (300 MHz, DMSO-$d_6$) δ 10.48 (s, 1H), 9.17 (s, 1H), 8.69 (s, 1H), 7.85 (s, 1H), 7.56 (d, J=9 Hz, 1H), 7.43-7.48 (m, 1H), 7.30-7.36 (m, 3H), 6.19 (s, 1H), 3.99 (s, 6H), 1.49 (s, 6H); LC-MS (ESI) m/z 534 (M+H)+.

Example 269

Preparation of 1-(5-(6,7-dimethoxyquinazolin-4-yloxy)-2,4-difluorophenyl)-3-(3-(2-fluoropropan-2-yl)isoxazol-5-yl)urea

Example 269A

To a stirred suspension of cesium carbonate (3.25 g, 10.0 mmoles) in dry DMF (20 mL) was added 5-amino-2,4-difluorophenol (1.00 g, 6.9 mmoles). This solution was heated to 80° C. for 1 hour, and 4-chloro-6,7-dimethoxyquinazoline (1.59 g, 7.1 mmoles) was added and the reaction heated for an additional hour. At the end of this time the reaction was poured into water (200 mL) and extracted with two portions (200 mL) of ethyl acetate. The extracts were combined and dried over MgSO$_4$. Filtration and concentration afforded 5-(6,7-dimethoxyquinazolin-4-yloxy)-2,4-difluoroaniline as a crude red oil. Purification by silica gel chromatography eluting with an ethyl acetate/hexane gradient, 30%-70% over 70 minutes gave a slightly impure oil containing DMF. This oil was crystallized using ethyl acetate hexane to give a white solid.
$^1$H NMR (300 MHz, DMSO-$d_6$) δ 8.56 (s, 1H), 7.53 (s, 1H), 7.39 (s, 1H), 7.27 (m, 1H), 6.76 (m, 3H), 5.22 (s, 2H), 3.98 (s, 6H); LCMS (ESI) m/z 334 (M+H)+

Example 269B

To a stirred solution of 5-(6,7-dimethoxyquinazolin-4-yloxy)-2,4-difluoroaniline (100 mg, 0.3 mmoles) from the previous step and phenyl 3-(2-fluoropropan-2-yl)isoxazol-5-ylcarbamate described in Example 42A (96 mg, 0.32 mmoles) in anhydrous DMF (10 mL), was added 4-(dimethylamino)pyridine (20 mg, 0.16 mmoles) and diisopropylethylamine (80 µL, 0.45 mmoles) and the reaction heated to 70 C overnight. The reaction was then concentrated to an oil and purified by silica gel chromatography eluting with a gradient of ethyl acetate/dichloromethane, 3-80%, to afford 1-(5-(6,7-dimethoxyquinazolin-4-yloxy)-2,4-difluorophenyl)-3-(3-(2-fluoropropan-2-yl)isoxazol-5-yl)urea (46.33 mg, 31% yield) as a white solid. $^1$H (300 MHz, DMSO-$d_6$) δ 10.58 (s, 1H), 8.92 (s, 1H), 8.57 (s, 1H), 8.13 (m, 1H), 7.67 (m, 1H), 7.57 (s, 1H), 7.41 (s, 1H), 6.12 (s, 1H), 3.98 (s, 6H), 1.65 (d, J=21 Hz, 6H); LCMS (ESI) m/z (M+H)+ 504.

Example 270

Preparation of 1-(5-tert-butylisoxazol-3-yl)-3-(5-(6,7-dimethoxyquinazolin-4-yloxy)-2,4-difluorophenyl)urea

Example 270A

To a solution of 5-tert-butylisoxazol-3-amine (35.00 g, 250 mmol) in THF (300 mL), potassium carbonate (45.61 g, 330 mmol) and phenyl chloroformate (43.84 g, 280 mmol) were added and the solution stirred at rt overnight. The reaction mixture was filtered through Celite and the pad washed thoroughly with THF. The filtrate was concentrated to a solid and portioned between brine and DCM, then extracted with 2 additional portions of DCM. The combined extracts were dried over magnesium sulfate, filtered and concentrated to a solid. The resulting solid was recrystallized from 10% DCM/ether and hexane. The solid collected by filtration to afford phenyl 5-tert-butylisoxazol-3-ylcarbamate (50.72 g, 78% yield). 1H NMR (300 MHz, DMSO d6) δ 1.35 (s, 9H), 6.43 (s, 1H), 7.20 (m, 3H), 7.44 (m, 2H).

Example 270B

To a solution of 5-(6,7-dimethoxyquinazolin-4-yloxy)-2,4-difluoroaniline (100 mg, 0.3 mmol) in THF (10 mL), DIEA (58 mg, 0.45 mmol), DMAP (20 mg, 0.16 mmol), and phenyl 5-tert-butylisoxazol-3-ylcarbamate (117 mg, 0.32 mmol) were added and the mixture heated overnight at 70° C. The mixture was poured into water and extracted with EtOAc three times. The extracts were dried over magnesium sulfate, filtered, and concentrated. The residue was purified using silica gel chromatography eluting with EtOAc/Hexane (3-80%). The appropriate fractions were concentrated to afford 1-(5-tert-butylisoxazol-3-yl)-3-(5-(6,7-dimethoxyquinazolin-4-yloxy)-2,4-difluorophenyl)urea (37.56 mg, 25% yield). $^1$H NMR (300 MHz, CDCl$_3$) δ 1.35 (s, 9H), 4.05 (s, 6H), 6.09 (s, 1H), 6.85 (s, 1H), 7.28 (s, 1H), 7.35 (s, 1H), 8.28 (m, 1H), 8.70 (s, 1H), 9.50 (s, 1H). LC-MS (ESI) m/z 500 (M+H)+

Example 271

Preparation of 1-(5-(6,7-dimethoxyquinazolin-4-yloxy)-2,4-difluorophenyl)-3-(1-phenyl-3-(trifluoromethyl)-1H-pyrazol-5-yl)urea 1-(5-(6,7-Dimethoxyquinazolin-4-yloxy)-2,4-difluorophenyl)-3-(1-phenyl-3-(trifluoromethyl)-1H-pyrazol-5-yl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting phenyl 3-tert-butyl-1-p-tolyl-1H-pyrazol-5-ylcarbamate with phenyl 1-phenyl-3-(trifluoromethyl)-1H-pyrazol-5-ylcarbamate in Example 161, and 3-(6,7-dimethoxyquinazolin-4-yloxy)aniline with 5-(6,7-dimethoxyquinazolin-4-yloxy)-2,4-difluoroaniline in Example 269 (0.153 g, 65%). $^1$H NMR (300 MHz, DMSO-$d_6$) δ 3.99 (s, 3H), 4.00 (s, 3H), 6.85 (s, 1H), 7.43 (s, 1H), 7.58-7.67 (m, 7H), 8.18 (t, 1H), 8.57 (s, 1H), 9.21 (s, 1H), 9.26 (s, 1H); LC-MS (ESI) m/z 587 (M+H)+.

Example 272

Preparation of 1-(3-tert-butyl-1-p-tolyl-1H-pyrazol-5-yl)-3-(5-(6,7-dimethoxyquinazolin-4-yloxy)-2,4-difluorophenyl)urea The title compound was prepared from 5-(6,7-dimethoxyquinazolin-4-yloxy)-2,4-difluoroaniline (100 mg, 0.3 mmol) and phenyl 3-tert-butyl-1-p-tolyl-1H-pyrazol-5-ylcarbamate (140 mg, 0.4 mmol) using the procedure in Example 115C to give 1-(3-tert-butyl-1-p-tolyl-1H-pyrazol-5-yl)-3-(5-(6,7-dimethoxyquinazolin-4-yloxy)-2,4-difluorophenyl)urea (170 mg, 0.29 mmol, 96%). $^1$H NMR (300 MHz, DMSO-$d_6$) δ 9.15 (s, 1H), 8.86 (s, 1H), 8.58 (s, 1H), 8.22 (t, 1H), 7.61 (t, 1H), 7.58 (s, 1H), 7.42-7.34 (m, 5H), 6.35 (s, 1H), 4.01 (s, 3H), 4.00 (s, 3H), 2.39 (s, 3H), 1.28 (s, 9H); LC-MS (ESI) m/z 589 (M+H)$^+$.

Example 273

Preparation of 1-(3-tert-butyl-1-phenyl-1H-pyrazol-5-yl)-3-(5-(6,7-dimethoxyquinazolin-4-yloxy)-2,4-difluorophenyl)urea The title compound was prepared from 3-tert-butyl-1-phenyl-1H-pyrazol-5-ylcarbamate described in Example 153A (100 mg, 0.30 mmol) and 5-(6,7-dimethoxyquinazolin-4-yloxy)-2,4-difluoroaniline (100 mg, 0.30 mmol) using the procedure in Example 115C to give 1-(3-(6,7-dimethoxyquinazolin-4-yloxy)phenyl)-3-(1-p-tolyl-3-(1-(trifluoromethyl)cyclopropyl)-1H-pyrazol-5-yl)urea (90 mg, 0.16 mmol, 52%). $^1$H NMR (300 MHz, DMSO-$d_6$) δ 9.16 (s, 1H), 8.92 (s, 1H), 8.59 (s, 1H), 8.23 (2, 1H), 7.54-7.43 (m, 8H), 6.38 (s, 1H), 4.00 (s, 6H), 1.25 (s, 9H); LC-MS (ESI) m/z 575 (M+H)$^+$.

Example 274

Preparation of 1-(3-tert-butyl-1-p-tolyl-1H-pyrazol-5-yl)-3-(3-(6,7-dimethoxyquinazolin-4-yloxy)phenyl)urea

Example 274A

Step 1: A mixture of 4,4-dimethyl-3-oxopentanenitrile (2.503 g, 20 mmol) and p-tolylhydrazine hydrochloride (3.173 g, 20 mmol) in EtOH was heated at 90° C. for 8 hours. The reaction was quenched by adding water and extracted with DCM. Extracts were dried over MgSO$_4$ and concentrated to give 3-tert-butyl-1-p-tolyl-1H-pyrazol-5-amine as solid (4.537 g, 99%). $^1$H NMR (300 MHz, CDCl$_3$) δ 1.31 (s, 9H), 2.36 (s, 3H), 3.69 (s, 2H), 5.51 (s, 1H), 7.25 (d, 2H), 7.44 (d, 2H); LC-MS (ESI) m/z 230 (M+H)$^+$.

Example 274A

Step 2: To a suspension of 3-tert-butyl-1-p-tolyl-1H-pyrazol-5-amine (4.53 g, 19.8 mmol) and K$_2$CO$_3$ (4.146 g, 30 mmol) in THF (30 mL) was added phenyl chloroformate (4.071 g, 26 mmol). It was stirred at room temperature overnight. The reaction was quenched by adding water and extracted with DCM. Extracts were dried over MgSO$_4$ and concentrated. The crude product was purified on a silica gel column using a mixture of EtOAc-hexane as eluent to give phenyl 3-tert-butyl-1-p-tolyl-1H-pyrazol-5-ylcarbamate as solid (5.12 g, 74%). $^1$H NMR (300 MHz, CDCl$_3$) δ 1.34 (s, 9H), 2.43 (s, 3H), 6.5 (s, 1H), 7.0 (s, 1H), 7.15 (d, 2H), 7.36 (m, 7H); LC-MS (ESI) m/z 350 (M+H)$^+$.

Example 274B

A mixture of phenyl 3-tert-butyl-1-p-tolyl-1H-pyrazol-5-ylcarbamate (0.14 g, 0.4 mmol), 3-(6,7-dimethoxyquinazolin-4-yloxy)aniline from Example 113 (0.119 g, 0.4 mmol) and DMAP (0.025 g) in THF (6 mL) was stirred at room temperature overnight. The reaction was quenched by adding DCM and concentrated. To the residue was added Et2O to give 1-(3-tert-butyl-1-p-tolyl-1H-pyrazol-5-yl)-3-(3-(6,7-dimethoxyquinazolin-4-yloxy)phenyl)urea as solid (0.181 g, 82%). $^1$H NMR (300 MHz, DMSO-$d_6$) δ 1.25 (s, 9H), 2.37 (s, 3H), 3.98 (s, 3H), 3.99 (s, 3H), 6.33 (s, 1H), 6.93 (d, 1H), 7.16 (d, 1H), 7.32-7.40 (m, 6H), 7.55 (d, 2H), 8.41 (s, 1H), 8.55 (s, 1H), 9.23 (s, 1H); LC-MS (ESI) m/z 553 (M+H)$^+$.

Example 275

Preparation of 1-(3-tert-butyl-1-p-tolyl-1H-pyrazol-5-yl)-3-(3-(6,7-dimethoxyquinazolin-4-ylthio)phenyl)urea 1-(3-tert-Butyl-1-p-tolyl-1H-pyrazol-5-yl)-3-(3-(6,7-dimethoxyquinazolin-4-ylthio)phenyl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting 3-(6,7-dimethoxyquinazolin-4-yloxy)aniline with 3-(6,7-dimethoxyquinazolin-4-ylthio)aniline in Example 115 (0.174 g, 77% yield). $^1$H NMR (300 MHz, DMSO-$d_6$) δ 1.26 (s, 9H), 2.37 (s, 3H), 3.99 (s, 6H), 6.34 (s, 1H), 7.24 (dd, 1H), 7.32-7.44 (m, 8H), 7.79 (s, 1H), 8.40 (s, 1H), 8.69 (s, 1H), 9.23 (s, 1H); LC-MS (ESI) m/z 569 (M+H)$^+$.

Example 276

Preparation of 1-(3-tert-butyl-1-p-tolyl-1H-pyrazol-5-yl)-3-(3-(6-methoxy-7-(2-methoxyethoxy)quinazolin-4-yloxy)phenyl)urea 1-(3-tert-butyl-1-p-tolyl-1H-pyrazol-5-yl)-3-(3-(6-methoxy-7-(2-methoxyethoxy)quinazolin-4-yloxy)phenyl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting 3-(6,7-dimethoxyquinazolin-4-yloxy)aniline with 3-(6-methoxy-7-(2-methoxyethoxy)quinazolin-4-yloxy)aniline in Example 117 (0.196 g, 82% yield). $^1$H NMR (300 MHz, DMSO-$d_6$) δ 1.25 (s, 9H), 2.37 (s, 3H), 3.35 (s, 3H), 3.76 (t, 2H), 3.98 (s, 3H), 4.34 (t, 2H), 6.33 (s, 1H), 6.93 (d, 1H), 7.16 (d, 1H), 7.31-7.41 (m, 6H), 7.56 (s, 2H), 8.41 (s, 1H), 8.55 (s, 1H), 9.22 (s, 1H); LC-MS (ESI) m/z 597 (M+H)$^+$.

Example 277

Preparation of 1-(3-tert-butyl-1-p-tolyl-1H-pyrazol-5-yl)-3-(3-(6-methoxy-7-(2-methoxyethoxy)quinazolin-4-ylthio)phenyl)urea 1-(3-tert-Butyl-1-p-tolyl-1H-pyrazol-5-yl)-3-(3-(6-methoxy-7-(2-methoxyethoxy)quinazolin-4-ylthio)phenyl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting 3-(6,7-dimethoxyquinazolin-4-yloxy)aniline with 3-(6-methoxy-7-(2-methoxyethoxy)quinazolin-4-ylthio)aniline in Example 231 (0.153 g, 62% yield). $^1$H NMR (300 MHz, DMSO-$d_6$) δ 1.26 (s, 9H), 2.37 (s, 3H), 3.34 (s, 3H), 3.76 (t, 2H), 3.99 (s, 3H), 4.33 (t, 2H), 6.34 (s, 1H), 7.23 (dd, 1H), 7.25-7.44 (m, 8H), 7.79 (s, 1H), 8.41 (s, 1H), 8.68 (s, 1H), 9.24 (s, 1H); LC-MS (ESI) m/z 613 (M+H)$^+$.

Example 278

Preparation of 1-(3-(2-cyanopropan-2-yl)phenyl)-3-(3-(6,7-dimethoxyquinazolin-4-yloxy)phenyl)urea Example 278A Step 1: To an ice-cold suspension of 95% NaH (1.03 g, 43 mmol) in anhydrous THF (15 ml) was added dropwise a solution of 2-(3-nitrophenyl)acetonitrile (2.2 g, 13.58 mmol) in 5 ml THF. The mixture was stirred at 0° C. for 30 min. After this time methyl iodide (6.8 ml, 107 mmol) was added dropwise at 0° C. After the addition was complete the reaction mixture was allowed to warm to rt and stirred overnight. The solvent was removed under reduced pressure and the residue taken in EtOAc, washed with water and brine and the organics combined, dried (MgSO4) and concentrated. The residue was purified by silica gel chromatography (hexane/ethyl acetate 5%) to afford 2-methyl-2-(3-nitrophenyl)propanenitrile (800 mg, 31%) as a solid. 1H NMR (300 MHz, DMSO-d6) δ 1.85 (s, 6H), 4.50 (brs, 2H), 7.74-7.79 (m, 1H), 8.04 (d, J=12 Hz, 1H), 8.27 (d, J=12 Hz, 1H), 8.33 (s, 1H); LC-MS (ESI) m/z 191 (M+H)$^+$.

Example 278A

Step 2: To a suspension of tin (II) chloride bis hydrate (3.3 g, 13.1 mmol) in EtOH (25 mL) was added 2-methyl-2-(3-nitrophenyl)propanenitrile (800 mg, 4.2 mmol). The reaction mixture was stirred at 90° C. for 1 h. After cooling down to rt, the solvent was removed under reduced pressure and the residue taken in DCM, washed with water and a saturated solution of sodium hydrogen carbonate until pH=8. After combining, the organics were dried (MgSO$_4$) and concentrated. The residue was purified by silica gel chromatography (hexane/ethyl acetate 15%) to afford 2-(3-aminophenyl)-2-methylpropanenitrile (490 mg, 73%) as a colorless solid. $^1$H NMR (300 MHz, CDCl$_3$) δ 1.69 (s, 6H), 3.75 (brs, 2H), 6.64 (d, J=9 Hz, 1H), 6.80-6.83 (m, 2H), 7.15-7.19 (m, 1H); LC-MS (ESI) m/z 161 (M+H)$^+$.

Example 278A

Step 3: To a solution of 2-(3-aminophenyl)-2-methylpropanenitrile (490 mg, 3.06 mmol) and potassium carbonate (552 mg, 4 mmol) in anhydrous THF (4.2 ml) was added dropwise phenyl chloroformate (0.81 ml, 6.4 mmol) as a solution in THF (2 ml). The reaction mixture was stirred at rt overnight. The solvent was removed and the residue taken in DCM, washed with water and brine and the organics combined, dried (MgSO$_4$) and concentrated. The crude was purified by silica gel chromatography (hexane/ethyl acetate 15%) to afford phenyl 3-(2-cyanopropan-2-yl)phenylcarbamate (828 mg, 96%) as a solid. $^1$H NMR (300 MHz, CDCl$_3$) δ 1.72 (s, 6H), 7.20-7.28 (m, 4H), 7.35-7.41 (m, 4H), 7.65 (s, 1H); LC-MS (ESI) m/z 281 (M+H)$^+$.

Example 278B

To a solution of 3-(6,7-dimethoxyquinazolin-4-yloxy) aniline (47 mg, 0.15 mmol), prepared as described in Example 113A, in THF (3 ml) was added DMAP (18 mg, 0.15 mmol) and phenyl 3-(2-cyanopropan-2-yl)phenylcarbamate (89 mg, 0.3 mmol). The reaction mixture was stirred at rt for 24 h. Concentration under reduced pressure gave a residue which was purified by preparative HPLC (Phenomenex phenylhexyl reverse phase column). The obtained solid was triturated with anhydrous diethyl ether to afford 1-(3-(2-cyanopropan-2-yl)phenyl)-3-(3-(6,7-dimethoxyquinazolin-4-yloxy)phenyl)urea (14.9 mg, 20%) as a solid. $^1$H NMR (300 MHz, DMSO-$d_6$) δ 1.66 (s, 6H), 3.99 (s, 6H), 6.92 (d, J=8.7 Hz, 1H), 7.11 (d, J=7.8 Hz, 1H), 7.30-7.40 (m, 4H), 7.57-7.66 (m, 4H), 8.56 (s, 1H), 8.90 (d, J=7.5 Hz, 2H); LC-MS (ESI) m/z 484 (M+H)$^1$ Example 279

Preparation of 1-(3-(2-cyanopropan-2-yl)phenyl)-3-(3-(6,7-dimethoxyquinazolin-4-ylthio)phenyl)urea To a solution of 3-(6,7-dimethoxyquinazolin-4-ylthio) aniline (94 mg, 0.3 mmol), prepared as described in Example 115B, in THF (3 ml) was added DMAP (18 mg, 0.15 mmol) and phenyl 3-(2-cyanopropan-2-yl)phenylcarbamate (92 mg, 0.33 mmol) described in Example 278A. The reaction mixture was stirred at rt for 24 h. Concentration under reduced pressure gave a residue which was triturated with anhydrous diethyl ether to afford 1-(3-(2-cyanopropan-2-yl)phenyl)-3-(3-(6,7-dimethoxyquinazolin-4-ylthio)phenyl)urea (64.1 mg, 43%) as a solid. $^1$H NMR (300 MHz, DMSO-$d_6$) δ 1.67 (s, 6H), 3.99 (s, 6H), 7.11 (d, J=6.6 Hz, 1H), 7.25 (d, J=7.5 Hz, 1H), 7.30-7.45 (m, 5H), 7.53 (d, J=8.1 Hz, 1H), 7.66 (s, 1H), 7.84 (s, 1H), 8.70 (s, 1H), 8.91 (d, J=6.6 Hz, 2H); LC-MS (ESI) m/z 500 (M+H)$^+$.

Example 280

Preparation of 1-(3-(2-cyanopropan-2-yl)phenyl)-3-(3-(6-methoxy-7-(2-methoxyethoxy)quinazolin-4-yloxy)phenyl)urea Using the procedure described in Example 279 a solution of 3-(6-methoxy-7-(2-methoxyethoxy)quinazolin-4-yloxy) aniline (103 mg, 0.3 mmol), prepared as described in Example 117B, in THF (3 ml) was added DMAP (18 mg, 0.15 mmol) and phenyl 3-(2-cyanopropan-2-yl)phenylcarbamate (92 mg, 0.33 mmol) described in Example 278A to afford 1-(3-(2-cyanopropan-2-yl)phenyl)-3-(3-(6-methoxy-7-(2-methoxyethoxy)quinazolin-4-yloxy)phenyl)urea (86.6 mg, 55%) as a solid. $^1$H NMR (300 MHz, DMSO-$d_6$) δ 1.66 (s, 6H), 3.78 (s, 3H), 3.98 (s, 4H), 4.34 (s, 3H), 6.95 (d, J=7.8 Hz, 1H), 7.11 (d, J=7.8 Hz, 1H), 7.26-7.41 (m, 5H), 7.58-7.66 (s, 3H), 8.54 (s, 1H), 8.90 (d, J=8.4 Hz, 2H); LC-MS (ESI) m/z 528 (M+H)$^+$.

Example 281

Preparation of 1-(3-(2-cyanopropan-2-yl)phenyl)-3-(3-(6-methoxy-7-(2-methoxyethoxy)quinazolin-4-ylthio)phenyl)urea Using the procedure described in Example 278B, to a solution of 3-(6-methoxy-7-(2-methoxyethoxy)quinazolin-4-ylthio)aniline (102 mg, 0.3 mmol), prepared as described in Example 230A, in THF (3 ml) was added DMAP (18 mg, 0.15 mmol) and phenyl 3-(2-cyanopropan-2-yl)phenylcarbamate (92 mg, 0.33 mmol) described in Example 278A to afford 1-(3-(2-cyanopropan-2-yl)phenyl)-3-(3-(6-methoxy-7-(2- methoxyethoxy)quinazolin-4-ylthio)phenyl)urea (37.2 mg, 23%) as a solid. $^1$H NMR (300 MHz, DMSO-d$_6$) δ 1.67 (s, 6H), 3.76 (s, 3H), 4.00 (s, 4H), 4.34 (s, 3H), 7.11 (d, J=6 Hz, 1H), 7.24-7.43 (m, 7H), 7.66 (s, 1H), 7.84 (s, 1H), 8.69 (s, 1H), 8.92 (d, J=9 Hz, 2H); LC-MS (ESI) m/z 544 (M+H)$^+$.

Example 282

Preparation of 1-(3-tert-butyl-1-(2,4-dimethylphenyl)-1H-pyrazol-5-yl)-3-(3-(6,7-dimethoxyquinazolin-4-yloxy)phenyl)urea Example 282A Step 1: To a heated solution of 2,4-dimethylphenylhydrazine hydrochloride (1.38 g, 8 mmol) in EtOH/water/1M NaOH (20 mL/12 mL/8 mL) at 50° C., 4,4-dimethyl-3-oxopentanenitrile (1.0 g, 8 mmol) was added and the reaction heated until finished by LC-MS. The solution was partitioned between EtOAc and water, and extracted twice. The extracts were washed with brine, dried with magnesium sulfate, filtered, and concentrated. Purification using silica gel chromatography eluting with an EtOAC/hexane gradient (5-20%) gave 3-tert-butyl-1-(2,4-dimethylphenyl)-1H-pyrazol-5-amine (700 mg, 36% yield). $^1$H NMR (300 MHz, DMSO d$_6$) δ 1.09 (s, 9H), 1.98 (s, 3H), 2.32 (s, 3H), 4.76 (s, 2H), 5.26 (s, 1H), 7.11 (m, 3H). LC-MS (ESI) m/z 244 (M+H)$^+$.

Example 282A

Step 2: To a solution of 3-tert-butyl-1-(2,4-dimethylphenyl)-1H-pyrazol-5-amine (700 mg, 2.9 mmol) in DCM (20 mL) was added K$_2$CO$_3$ (4.32 mmol) and phenyl chloroformate (6.48 mmol) and the reaction stirred overnight. The solvent was decanted and the solids washed with DCM. The combined organics were concentrated and purified using silica gel chromatography eluting with an EtOAC/hexane gradient (5-20%) gave phenyl 3-tert-butyl-1-(2,4-dimethylphenyl)-1H-pyrazol-5-ylcarbamate (472 mg, 45% yield). $^1$H NMR (300 MHz, DMSO d$_6$) δ 1.09 (s, 9H), 1.98 (s, 3H), 2.36 (s, 3H), 6.26 (s, 1H), 7.00 (s, 2H), 7.14 (m, 4H), 7.37 (m, 2H), 9.80 (bs, 1H); LC-MS (ESI) m/z 364 (M+H)$^+$ Example 282B The title compound was prepared from 3-(6,7-dimethoxyquinazolin-4-yloxy)aniline (89 mg, 0.3 mmol) and phenyl 3-tert-butyl-1-(2,4-dimethylphenyl)-1H-pyrazol-5-ylcarbamate from Step A (120 mg, 0.33 mmol) using the procedure in Example 115C to give 1-(3-tert-butyl-1-(2,4-dimethylphenyl)-1H-pyrazol-5-yl)-3-(3-(6,7-dimethoxyquinazolin-4-yloxy)phenyl)urea (141 mg, 0.25 mmol, 83%). $^1$H NMR (300 MHz, DMSO-d$_6$) δ 9.15 (s, 1H), 8.55 (s, 1H), 8.19 (s, 1H), 7.58 (s, 1H), 7.55 (s, 1H), 7.39 (s, 1H), 7.36 (t, 1H), 7.23-7.11 (m, 4H), 6.94 (d, 1H), 6.33 (s, 1H), 4.00 (s, 3H), 3.98 (s, 3H), 2.37 (s, 3H), 1.95 (s, 3H), 1.26 (s, 9H); LC-MS (ESI) m/z 567 (M+H)$^+$.

Example 283

Preparation of 1-(3-tert-butyl-1-(2,4-dimethylphenyl)-1H-pyrazol-5-yl)-3-(3-(6-methoxy-7-(2-methoxyethoxy)quinazolin-4-ylthio)phenyl)urea The title compound was prepared from 3-(6-methoxy-7-(2-methoxyethoxy)quinazolin-4-ylthio)aniline described in Example 230A (94 mg, 0.27 mmol) and phenyl 3-tert-butyl-1-(2,4-dimethylphenyl)-1H-pyrazol-5-ylcarbamate (120 mg, 0.33 mmol) using the procedure in Example 115C to give 1-(3-tert-butyl-1-(2,4-dimethylphenyl)-1H-pyrazol-5-yl)-3-(3-(6-methoxy-7-(2-methoxyethoxy)quinazolin-4-ylthio)phenyl)urea (130 mg, 0.21 mmol, 77%). $^1$H NMR (300 MHz, DMSO-d$_6$) δ 9.15 (s, 1H), 8.68 (s, 1H), 8.18 (s, 1H), 7.79 (s, 1H), 7.43-7.38 (m, 2H), 7.36 (s, 1H), 7.32 (s, 1H), 7.25-7.16 (m, 4H), 6.34 (s, 1H), 4.33 (t, 2H), 3.99 (s, 3H), 3.76 (t, 2H), 3.34 (s, 3H), 2.37 (s, 3H), 1.95 (s, 3H), 1.27 (s, 9H); LC-MS (ESI) m/z 627 (M+H)$^+$.

Example 284

Preparation of 1-(3-tert-butyl-1-(2,4-dimethylphenyl)-1H-pyrazol-5-yl)-3-(3-(6,7-dimethoxyquinazolin-4-ylthio)phenyl)urea The title compound was prepared from 3-(6,7-dimethoxyquinazolin-4-ylthio)aniline (94 mg, 0.3 mmol) and the carbamate described in Example 282A (120 mg, 0.33 mmol) using the procedure in Example 115C to give 1-(3-tert-butyl-1-(2,4-dimethylphenyl)-1H-pyrazol-5-yl)-3-(3-(6,7-dimethoxyquinazolin-4-ylthio)phenyl)urea (152 mg, 0.26 mmol, 87%). $^1$H NMR (300 MHz, DMSO-d$_6$) δ 9.15 (s, 1H), 8.68 (s, 1H), 8.18 (s, 1H), 7.79 (s, 1H), 7.43-7.38 (m, 2H), 7.34 (s, 1H), 7.32 (s, 1H), 7.26-7.16 (m, 4H), 6.33 (s, 1H), 3.99 (s, 6H), 2.37 (s, 3H), 1.95 (s, 3H), 1.27 (s, 9H); LC-MS (ESI) m/z 583 (M+H)$^+$.

Example 285

Preparation of 1-(3-tert-butyl-1-m-tolyl-1H-pyrazol-5-yl)-3-(3-(6,7-dimethoxyquinazolin-4-yloxy)phenyl)urea The title compound was prepared from 3-(6,7-dimethoxyquinazolin-4-yloxy)aniline (89 mg, 0.3 mmol) and phenyl 3-tert-butyl-1-(2,4-dimethylphenyl)-1H-pyrazol-5-ylcarbamate (115 mg, 0.33 mmol) using the procedure in Example 115C to give 1-(3-tert-butyl-1-m-tolyl-1H-pyrazol-5-yl)-3-(3-(6,7-dimethoxyquinazolin-4-yloxy)phenyl)urea (164 mg, 0.30 mmol, 99%). $^1$H NMR (300 MHz, DMSO-d$_6$) δ 9.24 (s, 1H), 8.56 (s, 1H), 8.45 (s, 1H), 7.57 (s, 1H), 7.55 (s, 1H), 7.44-7.28 (m, 5H), 7.23 (d, 1H), 7.18 (d, 1H), 6.93 (d, 1H), 6.35 (s, 1H), 3.99 (s, 3H), 3.98 (s, 3H), 2.38 (s, 3H), 1.26 (s, 9H); LC-MS (ESI) m/z 553 (M+H)$^+$.

Example 286

Preparation of 1-(3-tert-butyl-1-m-tolyl-1H-pyrazol-5-yl)-3-(3-(6,7-dimethoxyquinazolin-4-ylthio)phenyl)urea Example 286A Step 1: The procedure described in Example 282A Step 1 was followed to obtain 1-p-tolyl-3-(1-(trifluoromethyl)cyclopropyl)-1H-pyrazol-5-amine, by substituting m-tolylhydrazine for 2,4-dimethylphenylhydrazine hydrochloride to afford 3-tert-butyl-1-m-tolyl-1H-pyrazol-5-amine (903 mg, 58% yield). LC-MS (ESI) m/z 230 (M+H)$^+$.

Example 286A

Step 2: Phenyl 3-tert-butyl-1-m-tolyl-1H-pyrazol-5-ylcarbamate was obtained using the procedure described in Example 282A Step 2, using 3-tert-butyl-1-m-tolyl-1H-pyrazol-5-amine from the previous step (650 mg, 47% yield). $^1$H NMR (300 MHz, DMSO $d_6$) δ 1.30 (s, 9H), 2.39 (s, 3H), 6.35 (s, 1H), 7.10 (bs, 2H), 7.23 (m, 2H), 7.42 (m, 5H), 10.0 (bs, 1H); LC-MS (ESI) m/z 350 (M+H)$^+$.

Example 286B

The title compound was prepared from 3-(6,7-dimethoxyquinazolin-4-ylthio)aniline (94 mg, 0.3 mmol) and phenyl 3-tert-butyl-1-m-tolyl-1H-pyrazol-5-ylcarbamate from the previous step (115 mg, 0.33 mmol) using the procedure in Example 115C to give 1-(3-tert-butyl-1-m-tolyl-1H-pyrazol-5-yl)-3-(3-(6,7-dimethoxyquinazolin-4-ylthio)phenyl)urea (145 mg, 0.26 mmol, 85%). $^1$H NMR (300 MHz, DMSO-$d_6$) δ 9.25 (s, 1H), 8.69 (s, 1H), 8.45 (s, 1H), 7.80 (s, 1H), 7.48-7.16 (m, 9H), 6.36 (s, 1H), 3.99 (s, 6H), 2.38 (s, 3H), 1.27 (s, 9H); LC-MS (ESI) m/z 569 (M+H)$^+$.

Example 287

Preparation of 1-(3-tert-butyl-1-m-tolyl-1H-pyrazol-5-yl)-3-(3-(6-methoxy-7-(2-methoxyethoxy)quinazolin-4-ylthio)phenyl)urea The title compound was prepared from 3-(6-methoxy-7-(2-methoxyethoxy)quinazolin-4-ylthio)aniline (94 mg, 0.27 mmol) and phenyl 3-tert-butyl-1-m-tolyl-1H-pyrazol-5-ylcarbamate (115 mg, 0.33 mmol) using the procedure in Example 115C to give the title compound (145 mg, 0.24 mmol, 88%). $^1$H NMR (300 MHz, DMSO-$d_6$) δ 9.25 (s, 1H), 8.67 (s, 1H), 8.45 (s, 1H), 7.81 (s, 1H), 7.48-7.21 (m, 9H), 6.37 (s, 1H), 4.32 (t, 2H), 3.99 (s, 3H), 3.76 (t, 2H), 3.36 (s, 3H), 2.38 (s, 3H), 1.27 (s, 9H); LC-MS (ESI) m/z 613 (M+H)$^+$.

Example 288

Preparation of 1-(3-tert-butyl-1-p-tolyl-1H-pyrazol-5-yl)-3-(3-(6,7-dimethoxyquinazolin-4-yloxy)-2-methylphenyl)urea Following the procedure for Example 298A, substituting 3-amino-4-chlorophenol with 3-amino-2-methylphenol, and precipitating the compound out of water, after collecting by filtration and drying, 3-(6,7-dimethoxyquinazolin-4-yloxy)-2-methylaniline was isolated in 88% yield. $^1$H NMR (300 MHz, DMSO $d_6$) δ 1.79 (s, 3H), 3.96 (s, 6H), 6.36 (d, 1H), 6.56 (d, 1H), 6.95 (t, 1H), 7.37 (s, 1H), 7.56 (s, 1H), 8.49 (s, 1H); LC-MS (ESI) m/z 312 (M+H)$^1$ The title compound was prepared from 3-(6,7-dimethoxyquinazolin-4-yloxy)-2-methylaniline (93 mg, 0.3 mmol) and phenyl 3-tert-butyl-1-p-tolyl-1H-pyrazol-5-ylcarbamate (105 mg, 0.3 mmol) using the procedure in Example 115C to give 1-(3-tert-butyl-1-p-tolyl-1H-pyrazol-5-yl)-3-(3-(6,7-dimethoxyquinazolin-4-yloxy)-2-methylphenyl)urea (134 mg, 0.24 mmol, 79%). $^1$H NMR (300 MHz, DMSO-$d_6$) δ 8.75 (s, 1H), 8.52 (s, 1H), 8.41 (s, 1H), 7.72 (d, 1H), 7.60 (s, 1H), 7.47-7.32 (m, 5H), 7.25 (t, 1H), 6.96 (d, 1H), 6.37 (s, 1H), 3.99 (s, 6H), 2.36 (s, 3H), 1.95 (s, 3H), 1.28 (s, 9H); LC-MS (ESI) m/z 567 (M+H)$^+$.

Example 289

Preparation of 1-(3-tert-butyl-1-phenyl-1H-pyrazol-5-yl)-3-(3-(6,7-dimethoxyquinazolin-4-yloxy)-2-methylphenyl)urea The title compound was prepared from phenyl 3-tert-butyl-1-phenyl-1H-pyrazol-5-ylcarbamate (100 mg, 0.30 mmol) and 3-(6,7-dimethoxyquinazolin-4-yloxy)-2-methylaniline (94 mg, 0.30 mmol) using Example 115C to give 1-(3-tert-butyl-1-phenyl-1H-pyrazol-5-yl)-3-(3-(6,7-dimethoxyquinazolin-4-yloxy)-2-methylphenyl)urea (106 mg, 0.19 mmol, 64%). $^1$H NMR (300 MHz, DMSO-$d_6$) δ 8.80 (s, 1H), 8.55 (s, 1H), 8.41 (s, 1H), 7.72 (d, 1H), 7.59-7.51 (m, 5H), 7.39 (br s, 2H), 7.24 (t, 1H), 6.96 (d, 1H), 6.39 (s, 1H), 4.02 (s, 6H), 1.96 (s, 3H), 1.28 (s, 9H); LC-MS (ESI) m/z 553 (M+H)$^+$.

Example 290

Preparation of 1-(5-tert-butylisoxazol-3-yl)-3-(3-(6,7-dimethoxyquinazolin-4-yloxy)-2-methylphenyl)urea Following the procedure for Example 270B, substituting the aniline with 3-(6,7-dimethoxyquinazolin-4-yloxy)-2-methylaniline, and after silica gel chromatography, 1-(5-tert-butylisoxazol-3-yl)-3-(3-(6,7-dimethoxyquinazolin-4-yloxy)-2-methylphenyl)urea was isolated in 22% yield. $^1$H NMR (300 MHz, CDCl$_3$) δ 1.35 (s, 9H), 2.22 (S, 3H), 4.05 (s, 6H), 6.08 (s, 1H), 7.05 (m, 1H), 7.25 (m, 2H), 7.62 (s, 1H), 7.95 (m, 1H), 8.75 (s, 1H), 9.15 (s, 1H). LC-MS (ESI) m/z 478 (M+H)$^+$ Example 291

Preparation of 1-(3-(6,7-Dimethoxyquinazolin-4-yloxy)-2-methylphenyl)-3-(1-phenyl-3-(trifluoromethyl)-1H-pyrazol-5-yl)urea 1-(3-(6,7-Dimethoxyquinazolin-4-yloxy)-2-methylphenyl)-3-(1-phenyl-3-(trifluoromethyl)-1H-pyrazol-5-yl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting phenyl 3-tert-butyl-1-p-tolyl-1H-pyrazol-5-ylcarbamate with phenyl 1-phenyl-3-(trifluoromethyl)-1H-pyrazol-5-ylcarbamate in Example 161, and 3-(6,7-dimethoxyquinazolin-4-yloxy)aniline with 3-(6,7-dimethoxyquinazolin-4-yloxy)-2-methylaniline (0.040 g, 18%). $^1$H NMR (300 MHz, DMSO-$d_6$) δ 1.93 (s, 3H), 3.98 (s, 3H), 3.99 (s, 3H), 6.89 (s, 1H), 6.99 (d, 1H), 7.26 (t, 1H), 7.40 (s, 1H), 7.56-7.68 (m, 7H), 8.51 (s, 1H), 8.54 (s, 1H), 9.11 (s, 1H); LC-MS (ESI) m/z 565 (M+H)$^+$.

Example 292

Preparation of 1-(3-(6,7-dimethoxyquinazolin-4-yloxy)-2-methylphenyl)-3-(5-(2-fluoropropan-2-yl) isoxazol-3-yl)urea The title compound was made following the procedure for Example 290B but substituting the carbamate with phenyl 5-(2-fluoropropan-2-yl)isoxazol-3-ylcarbamate. After purification using silica gel chromatography, 14346,7-dimethoxyquinazolin-4-yloxy)-2-methylphenyl)-3-(5-(2-fluoropropan-2-yl)isoxazol-3-yl)urea was isolated in 21% yield. $^1$H NMR (300 MHz, DMSO $d_6$) δ 1.71 (d, 6H), 2.00 (s, 3H), 4.00 (s, 6H), 6.16 (s, 1H), 7.04 (m, 1H), 7.29 (m, 1H), 7.40 (s, 1H), 7.60 (s, 1H), 7.75 (m, 1H), 8.34 (s, 1H), 8.52 (s, 1H), 10.61 (s, 1H). LC-MS (ESI) m/z 482 (M+H)$^+$.

Example 293

Preparation of 1-(3-(6,7-dimethoxyquinazolin-4-yloxy)-4-fluorophenyl)-3-(3-(2-fluoropropan-2-yl)isoxazol-5-yl)urea A mixture of 4-chlorophenyl 3-(2-fluoropropan-2-yl)isoxazol-5-ylcarbamate (prepared as described in Example 257A) (170 mg, 0.571 mmol), 3-(6,7-dimethoxyquinazolin-4-yloxy)-4-fluoroaniline (prepared as described in Example 266A steps 1 and 2) (150 mg, 0.475 mmol) and N,N-4-(dimethylamino)pyridine (10 mg, 0.082 mmol) in THF (5 mL) was stirred at rt for 15 h. The reaction mixture was concentrated under reduced pressure to give the crude product. Purification via silica gel flash chromatography (eluting with a gradient of 20% ethyl acetate in hexanes to 100% ethyl acetate) afforded 1-(3-(6,7-dimethoxyquinazolin-4-yloxy)-4-fluorophenyl)-3-(3-(2-fluoropropan-2-yl)isoxazol-5-yl)urea (147 mg, 64%) as a colorless solid. $^1$H NMR (300 MHz, DMSO-$d_6$) 810.44 (brs, 1H), 9.08 (brs, 1H), 8.58 (s, 1H), 7.69 (m, 1H), 7.59 (s, 1H), 7.35-7.42 (m, 3H), 6.14 (s, 1H), 4.00 (s, 6H), 1.67 (d, J=21 Hz, 6H); LC-MS (ESI) m/z 486 (M+H)$^+$.

Example 294

Preparation of 1-(5-(1,3-difluoro-2-methylpropan-2-yl)isoxazol-3-yl)-3-(3-(6,7-dimethoxyquinazolin-4-yloxy)-4-fluorophenyl)urea A mixture of phenyl 5-(1,3-difluoro-2-methylpropan-2-yl)isoxazol-3-ylcarbamate (prepared as described in Example 162A steps 1 and 2) (169 mg, 0.571 mmol), 3-(6,7-dimethoxyquinazolin-4-yloxy)-2-fluoroaniline (prepared as described in Example 265A steps 1 through 3) (150 mg, 0.475 mmol) and N,N-4-(dimethylamino)pyridine (10 mg, 0.082 mmol) in THF (5 mL) was stirred at rt for 15 h. Additional phenyl 5-(1,3-difluoro-2-methylpropan-2-yl)isoxazol-3-ylcarbamate (75 mg, 0.238 mmol) was added and the mixture stirred for a further 19 h. The reaction mixture was concentrated under reduced pressure to give the crude product. Purification via silica gel flash chromatography (eluting with a gradient of 20% ethyl acetate in hexanes to 100% ethyl acetate) afforded 1-(5-(1,3-difluoro-2-methylpropan-2-yl)isoxazol-3-yl)-3-(3-(6,7-dimethoxyquinazolin-4-yloxy)-4-fluorophenyl)urea (147 mg, 60%) as a colorless solid. $^1$H NMR (300 MHz, DMSO-$d_6$) 89.73 (brs, 1H), 8.99 (brs, 1H), 7.71 (s, 1H), 7.70 (m, 1H), 7.58 (s, 1H), 7.31-7.42 (m, 3H), 6.76 (s, 1H), 4.63 (d, J=48 Hz, 4H), 4.01 (s, 6H), 1.32 (s, 3H); LC-MS (ESI) m/z 518 (M+H)$^+$.

Example 295

Preparation of 1-(3-tert-butyl-1-phenyl-1H-pyrazol-5-yl)-3-(3-(6,7-dimethoxyquinazolin-4-yloxy)-2-fluorophenyl)urea A mixture of phenyl 3-tert-butyl-1-phenyl-1H-pyrazol-5-ylcarbamate (prepared as described in Example 153A) (239 mg, 0.71 mmol), 3-(6,7-dimethoxyquinazolin-4-yloxy)-2-fluoroaniline (prepared as described in Example 265A steps 1 through 3) (150 mg, 0.475 mmol) and N,N-4-(dimethylamino)pyridine (10 mg, 0.082 mmol) in THF (5 mL) was stirred at rt for 15 h. The reaction mixture was concentrated under reduced pressure to give the crude product. Purification via silica gel flash chromatography (eluting with a gradient of 20% ethyl acetate in hexanes to 100% ethyl acetate) afforded 1-(3-tert-butyl-1-phenyl-1H-pyrazol-5-yl)-3-(3-(6,7-dimethoxyquinazolin-4-yloxy)-2-fluorophenyl)urea (167 mg, 63%) as a colorless solid. $^1$H NMR (300 MHz, DMSO-$d_6$) 89.07 (brs, 1H), 8.85 (brs, 1H), 8.57 (s, 1H), 8.07 (m, 1H), 7.39-7.58 (m, 7H), 7.23 (m, 1H), 7.20 (m, 1H), 6.42 (s, 1H), 4.00 (s, 3H), 3.99 (s, 3H), 1.29 (s, 9H); LC-MS (ESI) m/z 557 (M+H)$^+$.

Example 296

Preparation of 1-(3-(6,7-dimethoxyquinazolin-4-yloxy)-2-fluorophenyl)-3-(3-(2-fluoropropan-2-yl)isoxazol-5-yl)urea A mixture of 4-chlorophenyl 3-(2-fluoropropan-2-yl)isoxazol-5-ylcarbamate (prepared as described in Example 257A) (213 mg, 0.714 mmol), 3-(6,7-dimethoxyquinazolin-4-yloxy)-2-fluoroaniline (prepared as described in Example 265A steps 1 through 3) (150 mg, 0.475 mmol) and N,N-4-(dimethylamino)pyridine (10 mg, 0.082 mmol) in THF (5 mL) was stirred at rt for 15 h. The reaction mixture was concentrated under reduced pressure to give the crude product. Purification via silica gel flash chromatography (eluting with a gradient of 20% ethyl acetate in hexanes to 100% ethyl acetate) afforded 1-(3-(6,7-dimethoxyquinazolin-4-yloxy)-2-fluorophenyl)-3-(3-(2-fluoropropan-2-yl)isoxazol-5-yl)urea (147 mg, 64%) as a colorless solid. $^1$H NMR (300 MHz, DMSO-$d_6$) 810.55 (brs, 1H), 8.89 (brs, 1H), 8.58 (s, 1H), 8.03 (m, 1H), 7.59 (s, 1H), 7.43 (s, 1H), 7.28 (m, 1H), 7.18 (m, 1H), 6.20 (s, 1H), 4.00 (s, 6H), 1.69 (d, J=21 Hz, 6H); LC-MS (ESI) m/z 486 (M+H)$^+$.

Example 297

Preparation of 1-(5-(1,3-difluoro-2-methylpropan-2-yl)isoxazol-3-yl)-3-(3-(6,7-dimethoxyquinazolin-4-yloxy)-2-fluorophenyl)urea A mixture of phenyl 5-(1,3-difluoro-2-methylpropan-2-yl)isoxazol-3-ylcarbamate (prepared as described in Example 162A steps 1 and 2) (211 mg, 0.714 mmol), 3-(6,7-dimethoxyquinazolin-4-yloxy)-2-fluoroaniline (prepared as described in Example 265A steps 1 through 3) (150 mg, 0.475 mmol) and N,N-4-(dimethylamino)pyridine (10 mg, 0.082 mmol) in THF (5 mL) was stirred at rt for 36 h. The reaction mixture was concentrated under reduced pressure to give the crude product. Purification via silica gel flash chromatography (eluting with a gradient of 20% ethyl acetate in hexanes to 100% ethyl acetate) afforded 1-(5-(1,3-difluoro-2-methylpropan-2-yl)isoxazol-3-yl)-3-(3-(6,7-dimethoxyquinazolin-4-yloxy)-2-fluorophenyl)urea (104 mg, 42%) as a colorless solid. $^1$H NMR (300 MHz, DMSO-$d_6$) 89.96 (brs, 1H), 8.87 (brs, 1H), 8.58 (s, 1H), 8.08 (m, 1H), 7.59 (s, 1H), 7.43 (s, 1H), 7.27 (m, 1H), 7.15 (m, 1H), 6.81 (s, 1H), 4.66 (d, J=47 Hz, 4H), 4.01 (s, 6H), 1.34 (s, 3H); LC-MS (ESI) m/z 518 (M+H)$^+$.

Example 298

Preparation of 1-(3-tert-butyl-1-p-tolyl-1H-pyrazol-5-yl)-3-(2-chloro-5-(6,7-dimethoxyquinazolin-4-yloxy)phenyl)urea

Example 298A

A solution of 3-amino-4-chlorophenol (1.00 g, 7.0 mmol) and cesium carbonate (3.38 g, 10.4 mmol) in DMF (20 mL) were heated at 80 C for 1 hr. The chloroquinazoline (1.61 g, 7.2 mmol) was added and the mixture heated for an additional hour. The mixture was poured into water (300 mL) and extracted with EtOAc twice. The combined extracts were washed with brine, dried with magnesium sulfate, filtered and concentrated. The residue was purified using silica gel chromatography eluting with EtOAc/hexane (30-70%), the main peak collected and triturated with DCM to afford 2-chloro-5-(6,7-dimethoxyquinazolin-4-yloxy)aniline. $^1$H NMR (300 MHz, DMSO d$_6$) δ 3.96 (s, 6H), 5.55 (s, 2H), 6.45 (t, 1H), 6.76 (d, 1H), 7.25 (d, 1H), 7.36 (s, 1H), 7.50 (s, 1H), 8.55 (s, 1H); LC-MS (ESI) m/z 332 (M+H)$^+$ Example 298B The title compound was prepared from 2-chloro-5-(6,7-dimethoxyquinazolin-4-yloxy)aniline (100 mg, 0.3 mmol) and phenyl 3-tert-butyl-1-p-tolyl-1H-pyrazol-5-ylcarbamate (140 mg, 0.4 mmol) using the procedure in Example 115C to give 1-(3-tert-butyl-1-p-tolyl-1H-pyrazol-5-yl)-3-(2-chloro-5-(6,7-dimethoxyquinazolin-4-yloxy)phenyl)urea (80 mg, 0.14 mmol, 46%). $^1$H NMR (300 MHz, DMSO-d$_6$) δ 9.27 (s, 1H), 8.82 (s, 1H), 8.56 (s, 1H), 8.12 (d, 1H), 7.57-7.54 (m, 2H), 7.40-7.33 (m, 5H), 7.03 (dd, 1H), 6.34 (s, 1H), 4.00 (s, 3H), 3.98 (s, 3H), 2.37 (s, 3H), 1.27 (s, 9H); LC-MS (ESI) m/z 587 (M+H)$^+$.

Example 299

Preparation of 1-(5-tert-butylisoxazol-3-yl)-3-(2-chloro-5-(6,7-dimethoxyquinazolin-4-yloxy)phenyl) urea Following the procedure for Example 270B, but substituting the aniline with 2-chloro-5-(6,7-dimethoxyquinazolin-4-yloxy)aniline, 1-(5-tert-butylisoxazol-3-yl)-3-(2-chloro-5-(6,7-dimethoxyquinazolin-4-yloxy)phenyl)urea (19% yield) was obtained. $^1$H NMR (300 MHz, CDCl$_3$) δ 1.35 (s, 9H), 4.05 (s, 6H), 6.08 (s, 1H), 7.00 (m, 1H), 7.35 (m, 2H), 7.55 (s, 1H), 8.35 (s, 1H), 8.82 (s, 1H), 9.22 (s, 1H). LC-MS (ESI) m/z 498 (M+H)$^+$ Example 300

Preparation of 1-(2-chloro-5-(6,7-dimethoxyquinazolin-4-yloxy)phenyl)-3-(1-phenyl-3-(trifluoromethyl)-1H-pyrazol-5-yl)urea The title compound was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, but substituting phenyl 3-tert-butyl-1-p-tolyl-1H-pyrazol-5-ylcarbamate with phenyl 1-phenyl-3-(trifluoromethyl)-1H-pyrazol-5-ylcarbamate in Example 161, and 3-(6,7-dimethoxyquinazolin-4-yloxy)aniline with 2-chloro-5-(6,7-dimethoxyquinazolin-4-yloxy)aniline (0.075 g, 32%). $^1$H NMR (300 MHz, DMSO-d$_6$) δ 3.99 (s, 3H), 4.00 (s, 3H), 6.86 (s, 1H), 7.08 (d, 1H), 7.41 (s, 1H), 7.56-7.63 (m, 7H), 8.09 (d, 1H), 8.56 (s, 1H), 8.95 (s, 1H), 9.63 (s, 1H); LC-MS (ESI) m/z 585 (M+H)$^+$.

Example 301

Preparation of 1-(3-tert-butyl-1-phenyl-1H-pyrazol-5-yl)-3-(2-chloro-5-(6,7-dimethoxyquinazolin-4-yloxy)phenyl)urea The title compound was prepared from 3-tert-butyl-1-phenyl-1H-pyrazol-5-ylcarbamate (100 mg, 0.30 mmol) and 2-chloro-5-(6,7-dimethoxyquinazolin-4-yloxy)aniline (100 mg, 0.30 mmol) using the procedure in Example 115C to give 1-(3-tert-butyl-1-phenyl-1H-pyrazol-5-yl)-3-(2-chloro-5-(6,7-dimethoxyquinazolin-4-yloxy)phenyl)urea (34 mg, 0.06 mmol, 20%). $^1$H NMR (300 MHz, DMSO-d$_6$) δ 9.33 (s, 1H), 8.81 (s, 1H), 8.56 (s, 1H), 8.11 (s, 1H), 7.57-7.52 (m, 6H), 7.44-7.40 (m, 2H), 7.01 (d, 1H), 6.36 (s, 1H), 3.98 (s, 6H), 1.24 (s, 9H); LC-MS (ESI) m/z 573 (M)'.

Example 302

Preparation of 1-(3-(6,7-dimethoxyquinazolin-4-yloxy)phenyl)-3-(5-(2-methyl-1-morpholinopropan-2-yl)isoxazol-3-yl)urea Example 302A Step 1: To a stirred solution of phenyl 5-(1-hydroxy-2-methylpropan-2-yl)isoxazol-3-ylcarbamate (prepared as described in Example 131A steps 1 through 4) (250 mg, 0.91 mmol) and pyridine (0.15 mL, 1.81 mmol) in dichloromethane (5 mL) at 0° C., was added dropwise, 4-nitrophenylsulfonyl chloride (245 mg, 1.08 mmol) in dichloromethane (3 mL). The reaction mixture was warmed to 35° C. and stirred for a further 15 h. Concentration under reduced pressure gave the crude product which was purified via silica gel column chromatography (eluting with 20% ethyl acetate in petroleum ether) to afford 2-methyl-2-(3-(phenoxycarbonylamino)isoxazol-5-yl)propyl 4-nitrobenzenesulfonate (250 mg, 60%) as a yellow solid. $^1$H NMR (400 MHz, CDCl$_3$) δ 8.36-8.39 (m, 2H), 8.01-8.03 (m, 2H), 7.88 (m, 1H), 7.43-7.45 (m, 2H), 7.21-7.31 (m, 3H), 6.54 (s, 1H), 4.19 (s, 2H), 1.38 (s, 6H).

Example 302A

Step 2: A stirred mixture of 2-methyl-2-(3-(phenoxycarbonylamino)isoxazol-5-yl)propyl 4-nitrobenzenesulfonate (130 mg, 0.22 mmol), magnesium oxide (45 mg, 0.87 mmol), 1,4-dioxane (8 mL) and water (2 mL) was stirred at 60° C. for 5 h. The reaction mixture was cooled to rt and filtrated. The filtrate was concentrated under reduced pressure to give the crude product. Purification via recrystallization from a 1:1 mixture of diethyl ether and hexane, afforded 2-(3-aminoisoxazol-5-yl)-2-methylpropyl 4-nitrobenzenesulfonate (66 mg, 69%) as a pale yellow solid. $^1$H NMR (400 MHz, CDCl$_3$) δ 8.38-8.40 (m, 2H), 7.99-8.00 (m, 2H), 5.55 (s, 1H), 4.13 (s, 2H), 1.32 (s, 6H).

Example 302A

Step 3: Six equivalent batches of a stirred mixture of 2-(3-aminoisoxazol-5-yl)-2-methylpropyl 4-nitrobenzenesulfonate (50 mg, 0.15 mmol), morpholine (0.016 mL, 0.179 mmol), DBU (0.027 mL, 0.179 mmol) and acetonitrile (0.75 mL) were heated in a microwave reactor at 140° C. for 2.5 h. After cooling to rt, the reactions were combined and concentrated under reduced pressure. The residue was partitioned between chloroform and saturated aqueous sodium carbonate solution. The organic layer was separated and washed with brine. The organic layer was separated and dried over sodium sulfate, filtrated and concentrated under reduced pressure to give the crude product. Purification via silica gel column chromatography (eluting with a gradient of 100% chloroform to 5% methanol in chloroform) afforded 5-(2-methyl-1-morpholinopropan-2-yl)isoxazol-3-amine (20 mg, 10%) as a solid.

Example 302A

Step 4: To a stirred mixture of 5-(2-methyl-1-morpholinopropan-2-yl)isoxazol-3-amine (20 mg, 0.010 mmol) and potassium carbonate (25 mg, 0.181 mmol) in THF (6 mL) at 0° C., was added dropwise phenyl chloroformate (0.010 mL, 0.08 mmol). The reaction mixture was warmed to rt and stirred for a further 15 h. The reaction mixture was filtrated and the filtrate washed with saturated aqueous sodium carbonate, then brine, and concentrated under reduced pressure. The residue was dissolved in dichoromethane and dried over sodium sulfate then filtrated. The filtrate was concentrated under reduced pressure to give the crude product. Purification via recrystallization from a mixture of diethyl ether and hexanes, afforded phenyl 5-(2-methyl-1-morpholinopropan-2-yl)isoxazol-3-ylcarbamate (22 mg) which was used in the next step without further purification.

Example 302B

A stirred solution of phenyl 5-(2-methyl-1-morpholinopropan-2-yl)isoxazol-3-ylcarbamate (22 mg), N,N-diisopropylethylamine (12 mg, 0.093 mmol) and 3-(6,7-dimethoxyquinazolin-4-yloxy)aniline (prepared as described in Example 113A) (15 mg, 0.051 mmol) in THF (0.5 mL) was heated at 60° C. for 15 h. The reaction mixture was cooled to rt and partitioned between saturated aqueous sodium carbonate and dichloromethane. The organic layer was separated and concentrated under reduced pressure to give the crude product. Purification via preparative TLC afforded 1434 6,7-dimethoxyquinazolin-4-yloxy)phenyl)-3-(5-(2-methyl-1-morpholinopropan-2-yl)isoxazol-3-yl)urea (5 mg, 1% over three steps) as a solid. $^1$H NMR (400 MHz, CDCl$_3$) δ 9.35 (brs, 1H), 8.65 (brs, 2H), 7.66 (s, 1H), 7.57 (s, 1H), 7.29-7.41 (m, 3H), 7.01 (m, 1H), 6.10 (s, 1H), 4.09 (s, 6H), 3.63-3.66 (m, 4H), 2.40-2.70 (m, 6H), 1.32 (s, 6H); LC-MS (ESI) m/z 549 (M+H)$^+$.

Example 303

Preparation of 1-(3-tert-butyl-1-(4-methylpyridin-3-yl)-1H-pyrazol-5-yl)-3-(3-(6,7-dimethoxyquinazolin-4-yloxy)phenyl)urea

Example 303A

Step 1: 3-Bromo-4-methyl-pyridine (1.0 g, 5.81 mmol) in 5 mL dry toluene was treated with benzophenone hydrazone (1.25 g, 6.39 mmol), 4,5-bis(diphenylphosphino)-9,9-dimethylxanthene (335 mg, 0.58 mmol), and sodium tert-butoxide (840 mg, 8.72 mmol). The mixture was degassed with argon for 15 minutes. Added Pd(II)(OAc)$_2$ (130 mg, 0.58 mmol) and stirred at 90° C. for 14 hours. Extracted using EtOAc/H$_2$O (3×200 mL EtOAc, 1x 100 mL H$_2$O, 1×100 mL brine). Dried using Na$_2$SO$_4$ and then purified by flash chromatography (silica, 10-50% EtOAc/Hexane) to afford 3-(2-(diphenylmethylene)hydrazinyl)-4-methylpyridine (1.00 g, 3.48 mmol, 60%). $^1$H NMR (300 MHz, DMSO-d$_6$) δ 8.79 (s, 1H), 7.97 (d, 1H), 7.67-7.52 (m, 6H), 7.45-7.36 (m, 5H), 7.06 (d, 1H), 1.91 (s, 3H); LC-MS (ESI) m/z 488 (M+H)$^+$.

Example 303A

Step 2: 3-(2-(Diphenylmethylene)hydrazinyl)-4-methylpyridine (1.3 g, 4.52 mmol) in 3 mL THF was treated with 4,4-dimethyl-3-oxopentanenitrile (850 mg, 6.79 mmol) and 6N HCl (3.8 mL, 22.6 mmol). Stirred the mixture at 50° C. for 24 hours. Extracted using EtOAc/(sat.)NaHCO$_3$ (3×100 mL (sat.)NaHCO$_3$, 1×100 mL brine). Dried using MgSO$_4$ and then purified by flash chromatography (silica, 5-100% EtOAc/Hexane) to afford 3-tert-butyl-1-(4-methylpyridin-3-yl)-1H-pyrazol-5-amine (844 mg, 3.67 mmol, 81%). $^1$H NMR (300 MHz, DMSO-d$_6$) δ 8.46 (d, 1H), 8.40 (s, 1H), 7.38 (d, 1H), 5.32 (s, 1H), 5.03 (br s, 2H), 2.08 (s, 3H), 1.20 (s, 9H); LC-MS (ESI) m/z 231 (M+H)$^+$. Example 303A Step 3: 3-tert-Butyl-1-(4-methylpyridin-3-yl)-1H-pyrazol-5-amine (844 mg, 3.66 mmol) was treated with phenyl chloroformate (1.90 mL, 15.0 mmol) according to the procedure in Example 118A to afford phenyl 3-tert-butyl-1-(4-methylpyridin-3-yl)-1H-pyrazol-5-ylcarbamate (1.09 g, 3.11 mmol, 85%). $^1$H NMR (300 MHz, DMSO-d$_6$) δ 10.09 (br s, 1H), 8.53 (d, 1H), 8.43 (s, 1H), 7.44 (d, 1H), 7.39-7.34 (m, 2H), 7.22 (t, 1H), 6.98 (br s, 2H), 6.35 (s, 1H), 2.09 (s, 1H), 1.27 (s, 9H); LC-MS (ESI) m/z 351 (M+H)$^+$.

Example 303B 3-tert-Butyl-1-(4-methylpyridin-3-yl)-1H-pyrazol-5-ylcarbamate (105 mg, 0.30 mmol) was treated with 3-(6,7-dimethoxyquinazolin-4-yloxy)aniline (89 mg, 0.30 mmol) (prepared as described in Example 113A) using the procedure in Example 115C to give 1-(3-tert-butyl-1-(4-methylpyridin-3-yl)-1H-pyrazol-5-yl)-3-(3-(6,7-dimethoxyquinazolin-4-yloxy)phenyl)urea (145 mg, 0.26 mmol, 87%). $^1$H NMR (300 MHz, DMSO-d$_6$) δ 9.02 (s, 1H), 8.58-8.51 (m, 3H), 8.38 (s, 1H), 7.54-7.47 (m, 3H), 7.38-7.32 (m, 2H), 7.12 (d, 1H), 6.91 (d, 1H), 6.36 (s, 1H), 3.98 (s, 6H), 2.06 (s, 3H), 1.24 (s, 9H); LC-MS (ESI) m/z 554 (M+H)$^+$.

Example 304

Preparation of 1-(3-(6,7-dimethoxyquinazolin-4-yloxy)phenyl)-3-(3-(perfluoroethyl)-1-phenyl-1H-pyrazol-5-yl)urea

Example 304A

Step 1: A stirred suspension of sodium hydride (15.6 g of a 60% dispersion in mineral oil, 0.39 mol) in THF (100 mL) was heated to 50° C. To this was added a mixture of ethyl 2,2,3,3,3-pentafluoropropanoate (25 g, 0.13 mol) and dry acetonitrile (5.3 g, 0.13 mol), dropwise, and the resulting colorless suspension was heated at 50° C. for 4 h. After cooling to rt the reaction mixture was concentrated under reduced pressure and the residue poured into water (100 mL) and extracted with diethyl ether (100 mL). The aqueous layer was separated, acidified to pH 2 with aqueous 2 M HCl and extracted with diethyl ether (2×200 mL). The combined diethyl ether layers were dried over magnesium sulfate then concentrated under reduced pressure to afford 4,4,5,5,5-pentafluoro-3-oxopentanenitrile an orange oil (17 g) which was used in the next step without further purification.

Example 304A

Step 2: A stirred mixture of 4,4,5,5,5-pentafluoro-3-oxopentanenitrile (500 mg, 2.66 mmol) and phenylhydrazine hydrochloride (386 mg, 2.66 mmol) in ethanol (5 mL) was heated at 90° C. for 4 h. The reaction mixture was concentrated under reduced pressure, and the obtained oil purified by silica gel flash column chromatography (eluting with a gradient of 100% petroleum ether to 10% ethyl acetate in petroleum ether) to afford 3-(perfluoroethyl)-1-phenyl-1H-pyrazol-5-amine (320 mg, 43%) as a solid. $^1$H NMR (400 MHz, CDCl₃) 87.51-7.60 (m, 4H), 7.45 (m, 1H), 5.91 (s, 1H), 3.96 (brs, 2H); LC-MS (ESI) m/z 278 (M+H)$^+$.

Example 304A

Step 3: To a stirred mixture of 3-(perfluoroethyl)-1-phenyl-1H-pyrazol-5-amine (300 mg, 1.08 mmol) and potassium carbonate (223 mg, 1.62 mmol) in THF (3 mL) at rt, was added a solution of phenyl chloroformate (169 mg, 1.08 mmol) in THF (2 mL) dropwise. After stirring for a further 15 h at rt, the reaction mixture was filtered and the filtrate concentrated under reduced pressure to give an oil. Purification via silica gel flash column chromatography (eluting with a gradient of 100% petroleum ether to 5% ethyl acetate in petroleum ether) afforded phenyl 3-(perfluoroethyl)-1-phenyl-1H-pyrazol-5-ylcarbamate (360 mg, 84%) as a solid. $^1$H NMR (400 MHz, CDCl₃) δ 7.55-7.62 (m, 5H), 7.39-7.43 (m, 2H), 7.29 (m, 1H), 7.14 (m, 2H), 6.91 (m, 1H); LC-MS (ESI) m/z 398 (M+H)$^+$.

Example 304B

A stirred mixture of phenyl 3-(perfluoroethyl)-1-phenyl-1H-pyrazol-5-ylcarbamate (199 mg, 0.50 mmol), 3-(6,7-dimethoxyquinazolin-4-yloxy)aniline (prepared as described in Example 113A) (100 mg, 0.34 mmol), N,N-diethylisopropylamine (88 mg, 0.68 mmol) in THF (1 mL) was heated at 60° C. for 15 h. After cooling to rt, the reaction mixture was partitioned between saturated aqueous sodium hydrogen carbonate solution and dichloromethane. The organic layer was separated, dried over magnesium sulfate and concentrated under reduced pressure to afford the crude product. Purification via preparative HPLC afforded 1-(3-(6,7-dimethoxyquinazolin-4-yloxy)phenyl)-3-(3-(perfluoroethyl)-1-phenyl-1H-pyrazol-5-yl)urea (80 mg, 39%) as a colorless solid. $^1$H NMR (400 MHz, DMSO-d₆) 89.35 (s, 1H), 8.82 (s, 1H), 8.54 (s, 1H), 7.55-7.61 (m, 7H), 7.36-7.40 (m, 2H), 7.18 (m, 1H), 6.95 (m, 1H), 6.88 (s, 1H), 3.99 (s, 3H), 3.98 (s, 3H); LC-MS (ESI) m/z 601 (M+H)$^+$.

Example 305

Preparation of 1-(3-tert-butyl-1-(2-methylpyridin-3-yl)-1H-pyrazol-5-yl)-3-(3-(6,7-dimethoxyquinazolin-4-yloxy)phenyl)urea

Example 305A

Step 1: 3-Bromo-2-methyl-pyridine (1.0 g, 5.80 mmol) in 15 mL dry toluene was treated with benzophenone hydrazone (1.25 g, 6.39 mmol), 4,5-Bis(diphenylphosphino)-9,9-dimethylxanthene (170 mg, 0.29 mmol), sodium tert-butoxide (835 mg, 8.70 mmol), and Pd(II)(OAc)₂ (67 mg, 0.30 mmol). Heated to 120° C. in the microwave for five minutes. Extracted using EtOAc/H₂O (3×100 mL EtOAc, 1×100 mL H₂O, 1x 100 mL brine). Dried using Na₂SO₄ and then purified by flash chromatography (silica, 10-50% EtOAc/Hexane) to afford 3-(2-(diphenylmethylene)hydrazinyl)-2-methylpyridine (1.25 g, 4.35 mmol, 75%). $^1$H NMR (300 MHz, DMSO-d₆) δ 7.95 (d, 1H), 7.85 (d, 1H), 7.70-7.53 (m, 6H), 7.45-7.34 (m, 5H), 7.20 (d, 1H), 2.07 (s, 3H); LC-MS (ESI) m/z 288 (M+H)$^+$.

Example 305A

Step 2: 3-(2-(Diphenylmethylene)hydrazinyl)-2-methylpyridine (1.25 g, 4.35 mmol) was treated with 4,4-dimethyl-3-oxopentanenitrile (810 mg, 6.50 mmol) and 6N HCl (3.6 mL, 22.0 mmol) according to the procedure described for Example 303A Step 2. Purification by flash chromatography (silica, 0-10% MeOH/DCM) afforded 3-tert-butyl-1-(2-methylpyridin-3-yl)-1H-pyrazol-5-amine (679 mg, 2.95 mmol, 68%). $^1$H NMR (300 MHz, DMSO-d₆) δ 8.48 (d, 1H), 7.67 (d, 1H), 7.33 (d, 1H), 5.31 (s, 1H), 5.00 (br s, 2H), 2.23 (s, 3H), 1.21 (s, 9H); LC-MS (ESI) m/z 231 (M+H)$^+$.

Example 305A

Step 3: Following the procedure in Example 118A, 3-tert-butyl-1-(2-methylpyridin-3-yl)-1H-pyrazol-5-amine (679 mg, 2.94 mmol) was treated with phenyl chloroformate (1.50 mL, 12.0 mmol) to afford phenyl 3-tert-butyl-1-(2-methylpyridin-3-yl)-1H-pyrazol-5-ylcarbamate (722 mg, 2.06 mmol, 70%). $^1$H NMR (300 MHz, DMSO-d₆) δ 10.24 (br s, 1H), 8.71 (s, 1H), 8.07 (d, 1H), 7.68 (br s, 1H), 7.41-7.36 (m, 2H), 7.23 (t, 1H), 7.04 (br s, 2H), 6.37 (s, 1H), 2.36 (s, 3H), 1.28 (s, 9H); LC-MS (ESI) m/z 351 (M+H)$^+$.

Example 305B

Phenyl 3-tert-butyl-1-(2-methylpyridin-3-yl)-1H-pyrazol-5-ylcarbamate (105 mg, 0.3 mmol) was treated with 3-(6,7-dimethoxyquinazolin-4-yloxy)aniline (89 mg, 0.30 mmol) (prepared as described in Example 113A) using the procedure in Example 115C to afford 1-(3-tert-butyl-1-(2-methylpyridin-3-yl)-1H-pyrazol-5-yl)-3-(3-(6,7-dimethoxyquinazolin-4-yloxy)phenyl)urea (33 mg, 0.06 mmol, 20%). $^1$H NMR (300 MHz, DMSO-d₆) δ 8.99 (s, 1H), 8.60 (d, 1H), 8.54 (s, 1H), 8.35 (s, 1H), 7.80 (d, 1H), 7.54 (s, 2H), 7.45-7.32 (m, 3H), 7.12 (d, 1H), 6.91 (d, 1H), 6.35 (s, 1H), 3.99 (s, 3H), 3.97 (s, 3H), 2.20 (s, 3H) 1.25 (s, 9H); LC-MS (ESI) m/z 554 (M+H)$^+$.

Example 306

Preparation of 1-(3-(6,7-dimethoxyquinazolin-4-yloxy)phenyl)-3-(1-phenyl-3-(1,1,1-trifluoro-2-methylpropan-2-yl)-1H-pyrazol-5-yl)urea

Example 306A

To a solution of 1-phenyl-3-(1,1,1-trifluoro-2-methylpropan-2-yl)-1H-pyrazol-5-amine (590 mg, 2.2 mmol) and potassium carbonate (304 mg, 2.85 mmol) in anhydrous DCM (5.2 ml) was added dropwise phenyl chloroformate (0.30 ml, 2.4 mmol) as a solution in DCM (2.5 ml). The reaction mixture was stirred at rt overnight, then filtered and concentrated under reduced pressure. The crude was purified by silica gel chromatography (hexane/ethyl acetate 35%) to afford phenyl 1-phenyl-3-(1,1,1-trifluoro-2-methylpropan-2-yl)-1H-pyrazol-5-ylcarbamate (748 mg, 87%) as a solid. $^1$H NMR (300 MHz, CDCl₃) δ 1.60 (s, 6H), 6.65 (brs, 1H), 7.02-7.55 (m, 11H); LC-MS (ESI) m/z 390 (M+H)$^+$.

Example 306B

To a solution of 3-(6,7-dimethoxyquinazolin-4-yloxy) aniline (89 mg, 0.3 mmol), prepared as described in Example 113A, in THF (3.3 ml) was added DMAP (20 mg, 0.16 mmol) and phenyl 1-phenyl-3-(1,1,1-trifluoro-2-methylpropan-2-yl)-1H-pyrazol-5-ylcarbamate (104 mg, 0.3 mmol) described in the previous step. The reaction mixture was stirred at rt overnight, then concentrated under reduced pressure. The crude was purified by silica gel chromatography (hexane/ ethyl acetate 25-100%) and triturated in diethyl ether to afford 1-(3-(6,7-dimethoxyquinazolin-4-yloxy)phenyl)-3-(1-phenyl-3-(1,1,1-trifluoro-2-methylpropan-2-yl)-1H-pyrazol-5-yl)urea (103 mg, 62%) as a solid. $^1$H NMR (300 MHz, DMSO-d$_6$) δ 1.56 (s, 6H), 4.02 (s, 6H), 6.55 (s, 1H), 6.94 (d, J=9 Hz, 1H), 7.17 (d, J=9 Hz, 1H), 7.34-7.57 (m, 9H), 8.55-8.59 (m, 2H), 9.28 (s, 1H); LC-MS (ESI) m/z 593 (M+H)$^+$.

Example 307

Preparation of 1-(3-(6,7-dimethoxyquinazolin-4-ylthio)phenyl)-3-(1-phenyl-3-(1,1,1-trifluoro-2-methylpropan-2-yl)-1H-pyrazol-5-yl)urea Using the procedure described in Example 306B, to a solution of 3-(6,7-dimethoxyquinazolin-4-ylthio)aniline (94 mg, 0.3 mmol), prepared as described in Example 115B, in THF (3 ml) was added DMAP (23 mg, 0.18 mmol) and phenyl 1-phenyl-3-(1,1,1-trifluoro-2-methylpropan-2-yl)-1H-pyrazol-5-ylcarbamate (117 mg, 0.3 mmol) described in Example 306A to afford 1-(3-(6,7-dimethoxyquinazolin-4-ylthio)phenyl)-3-(1-phenyl-3-(1,1,1-trifluoro-2-methylpropan-2-yl)-1H-pyrazol-5-yl)urea (109 mg, 60%) as a solid. $^1$H NMR (300 MHz, DMSO-d$_6$) δ 1.57 (s, 6H), 4.04 (s, 6H), 6.55 (s, 1H), 7.25 (d, J=6 Hz, 1H), 7.33-7.49 (m, 5H), 7.55-7.60 (m, 4H), 7.80 (s, 1H), 8.59 (s, 1H), 8.69 (s, 1H), 9.29 (s, 1H); LC-MS (ESI) m/z 609 (M+H)$^+$.

Example 308

Preparation of 1-(3-(2-cyanopropan-2-yl)-1-phenyl-1H-pyrazol-5-yl)-3-(3-(6,7-dimethoxyquinazolin-4-yloxy)phenyl)urea Example 308A Step 1: To a solution of 2,2-dimethyl-3-oxopentanedinitrile (500 mg, 3.7 mmol) prepared as described in Example 125A Step 1, in anhydrous EtOH (33 ml) was added phenylhydrazine hydrochloride (763 mg, 3.7 mmol) and the reaction mixture was heated at 60° C. for 2 h. The solvent was removed under reduced pressure and the residue taken in EtOAc, washed with water and brine and the organics combined, dried (MgSO$_4$) and concentrated. The residue was purified by silica gel chromatography (hexane/ethyl acetate 1:1) to afford 2-(5-amino-1-phenyl-1H-pyrazol-3-yl)-2-methylpropanenitrile (451 mg, 54%) as a solid. $^1$H NMR (300 MHz, CDCl$_3$) δ 1.76 (s, 6H), 3.84 (brs, 2H), 5.69 (s, 1H), 7.26-7.57 (m, 5H); LC-MS (ESI) m/z 227 (M+H)$^+$.

Example 308A

Step 2: Using the procedure described in Example 306A, to a solution of 2-(5-amino-1-phenyl-1H-pyrazol-3-yl)-2-methylpropanenitrile (451 mg, 2 mmol) and potassium carbonate (359 mg, 2.6 mmol) in anhydrous DCM (4 ml) was added dropwise phenyl chloroformate (0.28 ml, 2.2 mmol) as a solution in DCM (2 ml) to afford phenyl 3-(2-cyanopropan-2-yl)-1-phenyl-1H-pyrazol-5-ylcarbamate (527 mg, 76%). $^1$H NMR (300 MHz, CDCl$_3$) δ 1.74 (s, 6H), 6.66 (s, 1H), 7.05-7.60 (m, 11H); LC-MS (ESI) m/z 347 (M+H)$^+$.

Example 308B

Using the procedure described in Example 306B, to a solution of 3-(6,7-dimethoxyquinazolin-4-yloxy)aniline (89 mg, 0.3 mmol), prepared as described in Example 113A, in THF (3.3 ml) was added DMAP (20 mg, 0.16 mmol) and phenyl 3-(2-cyanopropan-2-yl)-1-phenyl-1H-pyrazol-5-ylcarbamate (104 mg, 0.3 mmol) described in the previous step to afford 1-(3-(2-cyanopropan-2-yl)-1-phenyl-1H-pyrazol-5-yl)-3-(3-(6,7-dimethoxyquinazolin-4-yloxy)phenyl)urea (77.6 mg, 42%) as a solid. $^1$H NMR (300 MHz, DMSO-d$_6$) δ 1.72 (s, 6H), 3.99 (s, 6H), 6.57 (s, 1H), 6.94 (d, J=6 Hz, 1H), 7.18 (d, J=6.6 Hz, 1H), 7.17-7.20 (m, 2H), 7.35-7.56 (m, 7H), 8.56 (s, 1H), 8.64 (s, 1H), 9.28 (s, 1H); LC-MS (ESI) m/z 550 (M+H)$^+$.

Example 309

Preparation of 1-(3-(2-cyanopropan-2-yl)-1-phenyl-1H-pyrazol-5-yl)-3-(3-(6,7-dimethoxyquinazolin-4-ylthio)phenyl)urea Using the procedure described in Example 306B, to a solution of 3-(6,7-dimethoxyquinazolin-4-ylthio)aniline (94 mg, 0.3 mmol), prepared as described in Example 115B, in THF (3.3 ml) was added DMAP (20 mg, 0.16 mmol) and phenyl 3-(2-cyanopropan-2-yl)-1-phenyl-1H-pyrazol-5-ylcarbamate (104 mg, 0.3 mmol) described in in Example 308A to afford 1-(3-(2-cyanopropan-2-yl)-1-phenyl-1H-pyrazol-5-yl)-3-(3-(6,7-dimethoxyquinazolin-4-ylthio)phenyl)urea (68.87 mg, 40%) as a solid. $^1$H NMR (300 MHz, DMSO-d$_6$) δ 1.74 (s, 6H), 4.04 (s, 6H), 6.58 (s, 1H), 7.26-7.86 (m, 10H), 8.63-8.69 (m, 2H), 9.28 (s, 1H); LC-MS (ESI) m/z 609 (M+H)$^+$.

Example 310

Preparation of 1-(5-tert-butylisoxazol-3-yl)-3-(3-(2-chloro-6,7-dimethoxyquinazolin-4-yloxy)phenyl)urea To a stirred solution of 1-(5-tert-butylisoxazol-3-yl)-3-(3-hydroxyphenyl)urea (prepared as described in Example 1A) (80 mg, 0.291 mmol) in anhydrous degassed DMF (2 mL) at rt and under an argon atmosphere, was added potassium tert-butoxide (65 mg, 0.581 mmol). The reaction mixture was stirred at rt for a further 2 h. A solution of 2,4-dichloro-6,7-dimethoxyquinazoline (75 mg, 0.291 mmol) in anhydrous DMF (1 mL) was added and the reaction mixture was stirred at rt for a further 15 h. The reaction mixture was partitioned between a mixture of ethyl acetate (20 mL) and brine solution (20 mL), and the organic layer separated. The aqueous layer was extracted further with ethyl acetate (1×20 mL) and the combined organic layers dried over magnesium sulfate. Concentration under reduced pressure gave the crude product which was purified via silica gel flash chromatography (eluting with a gradient of 25% ethyl acetate in hexanes to 100% ethyl acetate) to afford 1-(5-tert-butylisoxazol-3-yl)-3-(3-(2-chloro-6,7-dimethoxyquinazolin-4-yloxy)phenyl)urea (46 mg, 32%) as a solid. $^1$H NMR (300 MHz, CDCl$_3$) 89.60 (brs, 1H), 9.03 (brs, 1H), 7.61 (m, 1H), 7.57 (m, 1H), 7.39-7.46 (m, 2H), 7.31 (m,1H), 7.01 (m, 1H), 6.48 (s, 1H), 4.00 (s, 3H), 3.98 (s, 3H), 1.28 (s, 9H); LC-MS (ESI) m/z 498 (M+H)+.

Example 311

Preparation of 1-(3-(1,1-difluoroethyl)-1-(pyridin-3-yl)-1H-pyrazol-5-yl)-3-(3-(6,7-dimethoxyquinazolin-4-yloxy)phenyl)urea Example 311A Step 1: 3-Hydrazinopyridine hydrochloride (435 mg, 3.0 mmol) was treated with 4,4-difluoro-3-oxopentanenitrile (400 mg, 3.0 mmol) (prepared as described in Example 152A Step 1) according to the procedure in Example 161A Step 3 to afford 3-(1,1-difluoroethyl)-1-(pyridin-3-yl)-1H-pyrazol-5-amine (62 mg, 0.27 mmol, 9%). $^1$H NMR (300 MHz, MeOD) δ 8.86 (s, 1H), 8.60 (d, 1H), 8.12 (d, 1H), 7.62 (t, 1H), 5.82 (s, 1H), 1.92 (t, 3H); LC-MS (ESI) m/z 225 (M+H)$^+$.

Example 311A

Step 2: Following the procedure in Example 118A, 3-(1,1-difluoroethyl)-1-(pyridin-3-yl)-1H-pyrazol-5-amine (60 mg, 0.27 mmol) was treated with phenyl chloroformate (0.13 mL, 1.07 mmol) to afford phenyl 3-(1,1-difluoroethyl)-1-(pyridin-3-yl)-1H-pyrazol-5-ylcarbamate (27 mg, 0.078 mmol, 30%). $^1$H NMR (300 MHz, MeOD) δ 8.90 (s, 1H), 8.70 (s, 1H), 8.15 (d, 1H), 7.69 (d, 1H), 7.44-7.12 (m, 5H), 4.87 (s, 3H); LC-MS (ESI) m/z 345 (M+H)$^+$.

Example 311B

Following the procedure in Example 115C, phenyl 3-(1,1-difluoroethyl)-1-(pyridin-3-yl)-1H-pyrazol-5-ylcarbamate (27 mg, 0.078 mmol) was treated with 3-(6,7-dimethoxyquinazolin-4-yloxy)aniline (26 mg, 0.086 mmol) (prepared as described in Example 113A) to afford 1-(3-(1,1-difluoroethyl)-1-(pyridin-3-yl)-1H-pyrazol-5-yl)-3-(3-(6,7-dimethoxyquinazolin-4-yloxy)phenyl)urea (27 mg, 0.049 mmol, 63%). $^1$H NMR (300 MHz, DMSO-d$_6$) δ 9.23 (s, 1H), 8.82-8.78 (m, 2H), 8.70 (d, 1H), 8.54 (s, 1H), 8.04 (d, 1H), 7.65-7.61 (m, 2H), 7.54-7.51 (m, 2H), 7.19 (d, 1H), 6.93 (d, 1H), 6.69 (s, 1H), 3.99 (s, 6H), 2.00 (t, 3H); LC-MS (ESI) m/z 548 (M+H)$^+$.

Example 312

Preparation of 1-(3-tert-butyl-1-(6-methylpyridin-3-yl)-1H-pyrazol-5-yl)-3-(3-(6,7-dimethoxyquinazolin-4-yloxy)phenyl)urea Example 312A Step 1: Using the procedure described in Example 308A Step 1, to a solution of 4,4-dimethyl-3-oxopentanenitrile (782 mg, 6.25 mmol) in anhydrous EtOH (30 ml) was added 5-hydrazinyl-2-methylpyridine (1 g, 8.12 mmol) and the reaction mixture was heated at 80° C. overnight. The residue was purified by silica gel chromatography (DCM/EtOAc 10-50%) to afford 3-tert-butyl-1-(6-methylpyridin-3-yl)-1H-pyrazol-5-amine (95 mg, 7%). $^1$H NMR (300 MHz, CDCl$_3$) δ 1.34 (s, 9H), 2.59 (s, 3H), 3.67 (brs, 2H), 5.56 (s, 1H), 7.25 (d, J=9 Hz, 1H), 7.81 (d, J=9 Hz, 1H), 8.74 (s, 1H); LC-MS (ESI) m/z 231 (M+H)$^+$.

Example 312A

Step 2: Using the procedure described in Example 306A, to a solution of 3-tert-butyl-1-(6-methylpyridin-3-yl)-1H-pyrazol-5-amine (95 mg, 0.41 mmol) and potassium carbonate (75 mg, 0.54 mmol) in anhydrous DCM (1.5 ml) was added dropwise phenyl chloroformate (0.16 ml, 1.24 mmol) as a solution in DCM (1 ml). The crude was purified by silica gel chromatography (DCM/EtOAc 7-60%) to afford phenyl 3-tert-butyl-1-(6-methylpyridin-3-yl)-1H-pyrazol-5-ylcarbamate (61 mg, 42%). $^1$H NMR (300 MHz, CDCl$_3$) δ 1.34 (s, 9H), 2.63 (s, 3H), 6.47 (s, 1H), 6.83 (d, J=8 Hz, 1H), 6.91-6.93 (m, 3H), 7.12 (s, 1H), 7.21-7.40 (m, 2H), 7.78 (d, J=8 Hz, 1H), 8.68 (d, J=2 Hz, 1H); LC-MS (ESI) m/z 351 (M+H)$^+$.

Example 312B

Using the procedure described in Example 306B, to a solution of 3-(6,7-dimethoxyquinazolin-4-yloxy)aniline (54 mg, 0.18 mmol), prepared as described in Example 113A, in THF (2 ml) was added DMAP (20 mg, 0.16 mmol) and phenyl 3-tert-butyl-1-(6-methylpyridin-3-yl)-1H-pyrazol-5-ylcarbamate (62 mg, 0.18 mmol), described in the previous step, to afford 1-(3-tert-butyl-1-(6-methylpyridin-3-yl)-1H-pyrazol-5-yl)-3-(3-(6,7-dimethoxyquinazolin-4-yloxy)phenyl)urea (59 mg, 60%) as a solid. $^1$H NMR (300 MHz, DMSO-d$_6$) δ 1.26 (s, 9H), 2.53 (s, 3H), 3.98 (s, 6H), 6.37 (s, 1H), 6.92 (d, J=7.8 Hz, 1H), 7.18 (d, J=8.4 Hz, 1H), 7.36-7.43 (m, 3H), 7.54-7.55 (m, 2H), 7.83 (d, J=8.4 Hz, 1H), 8.51 (s, 1H), 8.55 (s, 1H), 8.61 (d, J=3 Hz, 1H), 9.18 (s, 1H); LC-MS (ESI) m/z 554 (M+H)$^+$.

Example 313

Preparation of 1-(3-tert-butyl-1-(2-oxo-1,2-dihydropyridin-4-yl)-1H-pyrazol-5-yl)-3-(3-(6,7-dimethoxyquinazolin-4-yloxy)phenyl)urea Example 313A Step 1: To a solution of hydrazine (8 mL) in DME (40 mL) was added dihydroxypyridine (2.00 g, 18 mmol) and the reaction heated at reflux overnight. The solution was cooled to rt, and the solids removed by filtration. The filtrate was concentrated and the resulting solid crystallized from hot EtOH to afford 4-hydrazinylpyridin-2(1H)-one (1.75 g, 78% yield). LC-MS (ESI) m/z 126 (M+H)$^+$.

Example 313A

Step 2: Following the procedure for Example 282A Step 1, 4-hydrazinylpyridin-2(1H)-one was heated at 80° C. overnight with 4,4-dimethyl-3-oxopentanenitrile. The reaction mixture was concentrated, triturated with DCM, and purified using silica gel chromatography eluting with a MeOH/DCM gradient (2-10%) to afford 4-(5-amino-3-tert-butyl-1H-pyrazol-1-yl)pyridin-2(1H)-one (307 mg, 33% yield). $^1$H NMR (300 MHz, DMSO d$_6$) δ 1.18 (s, 9H), 5.43 (s, 1H), 5.47 (s, 2H), 6.55 (s, 1H), 6.66 (m, 1H), 7.37 (d, 1H), 11.40 (s, 1H); LC-MS (ESI) m/z 233 (M+H)$^+$ Example 313A Step 3: Following the procedure for Example 282A Step 2, substituting 4-(5-amino-3-tert-butyl-1H-pyrazol-1-yl)pyridin-2(1H)-one for 3-tert-butyl-1-(2,4-dimethylphenyl)-1H-pyrazol-5-amine and reacting with phenyl chloroformate. Purification using silica gel chromatography eluting with EtOAC/hexane (12-100%) to afford phenyl 3-tert-butyl-1-(2-oxo-1,2-dihydropyridin-4-yl)-1H-pyrazol-5-ylcarbamate (100 mg, 21% yield). $^1$H NMR (300 MHz, DMSO d$_6$) δ 1.30 (s, 9H), 5.50 (s, 1H), 5.72 (s, 2H), 7.41 (m, 4H), 7.52 (m, 3H), 7.74 (s, 1H), 8.45 (d, 1H); LC-MS (ESI) m/z 353 (M+H)$^+$ Example 313B The title compound was prepared from 3-(6,7-dimethoxyquinazolin-4-yloxy)aniline (75 mg, 0.25 mmol) and the carbamate from the previous step (100 mg, 0.28 mmol) using the procedure in Example 115C to give 1-(3-tert-butyl-1-(2-oxo-1,2-dihydropyridin-4-yl)-1H-pyrazol-5-yl)-3-(3-(6,7-dimethoxyquinazolin-4-yloxy)phenyl)urea (107 mg, 0.20 mmol, 79%). $^1$H NMR (300 MHz, DMSO-d$_6$) δ 11.64 (br s, 1H), 9.35 (s, 1H), 8.65 (br s, 1H), 8.56 (s, 1H), 7.57 (s, 1H), 7.56 (s, 1H), 7.48 (d, 1H), 7.42-7.35 (m, 2H), 7.25 (d, 1H), 6.94 (d, 1H), 6.57 (d, 1H), 6.50 (s, 1H), 6.39 (s, 1H), 3.99 (s, 3H), 3.98 (s, 3H), 1.26 (s, 9H); LC-MS (ESI) m/z 556 (M+H)$^+$.

Example 314

Preparation of 1-(3-(6,7-dimethoxyquinazolin-4-yloxy)phenyl)-3-(1-(5-fluoropyridin-3-yl)-3-isopropyl-1H-pyrazol-5-yl)urea Example 314A Step 1: In degassed, dry toluene (35 mL) 5-bromo-5-fluoropyridine (2.29 g, 13 mmol), benzophenone hydrazide (2.80 g, 14.3 mmol), sodium tert-butoxide (1.90 g, 19.8 mmol), palladium acetate (292 mg, 1.3 mmol), and 4,5-bis(diphenylphosphino)-9,9-dimethylxanthene (752 mg, 1.3 mmol) were added and the reaction mixture heated at 85° C. overnight. The mixture was cooled to rt and partitioned between EtOAc/water and extracted twice. The combined extracts were washed with brine and dried over magnesium sulfate, filtered and concentrated. The resulting residue was purified using silica gel chromatography eluting with 12-100% EtOAc/hexanes to afford 3-(2-(diphenylmethylene)hydrazinyl)-5-fluoropyridine (3.28 g, 86% yield). $^1$H NMR (300 MHz, DMSO d$_6$) δ 7.34 (m, 5H), 7.54 (m, 3H), 7.63 (m, 3H), 7.94 (m, 1H), 8.40 (m, 1H), 9.38 (s, 1H); LC-MS (ESI) m/z 292 (M+H)$^+$ Example 314A Step 2: To a solution 4-methyl-3-oxopentanenitrile (333 mg, 3 mmol) and 3-(2-(diphenylmethylene)hydrazinyl)-5-fluoropyridine (580 mg, 2 mmol) in THF (10 mL) was added 6 M HCl (1.8 mL) and the solution heated to 50° C. overnight. The solution was then cooled to rt, concentrated and partitioned between DCM and water, the aqueous layer decanted, and the organics concentrated. The residue was purified using silica gel chromatography eluting with EtOAc/hexane (12-100%) followed by a MeOH/DCM flush (10%) to elute 1-(5-fluoropyridin-3-yl)-3-isopropyl-1H-pyrazol-5-amine. LC-MS (ESI) m/z 221 (M+H)$^+$ Example 314A Step 3: Following the procedure for Example 282A Step 2, 1-(5-fluoropyridin-3-yl)-3-isopropyl-1H-pyrazol-5-amine was treated with phenyl chloroformate. Purification using silica gel chromatography eluting with MeOH/DCM (0-10%) afforded phenyl 1-(5-fluoropyridin-3-yl)-3-isopropyl-1H-pyrazol-5-ylcarbamate (235 mg, 35% yield) for steps B and C. $^1$H NMR (300 MHz, DMSO d$_6$) δ 1.25 (s, 6H), 2.93 (m, 1H), 6.40 (s, 1H), 7.15 (bs, 2H), 7.29 (m, 2H), 7.42 (m, 3H), 8.00 (m, 1H), 8.65 (s, 1H), 8.72 (s, 1H), 10.32 (s, 1H); LC-MS (ESI) m/z 341 (M+H)$^+$

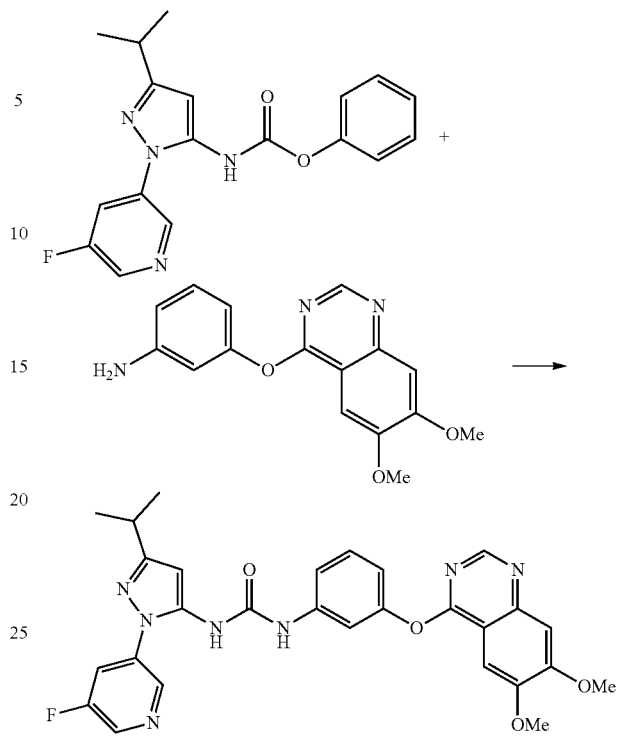

Example 314B

The title compound was prepared from 3-(6,7-dimethoxyquinazolin-4-yloxy)aniline (75 mg, 0.25 mmol) and the carbamate from the previous step (102 mg, 0.3 mmol) using the procedure in Example 115C to give 1-(3-(6,7-dimethoxyquinazolin-4-yloxy)phenyl)-3-(1-(5-fluoropyridin-3-yl)-3-isopropyl-1H-pyrazol-5-yl)urea (121 mg, 0.22 mmol, 89%). $^1$H NMR (300 MHz, DMSO-d$_6$) δ 9.22 (s, 1H), 8.71 (s, 1H), 8.68 (s, 1H), 8.62 (d, 1H), 8.55 (s, 1H), 8.00 (t, 1H), 7.97 (t, 1H), 7.55 (s, 1H), 7.52 (t, 1H), 7.39 (s, 1H), 7.37 (t, 1H), 7.21 (d, 1H), 6.93 (d, 1H), 6.38 (s, 1H), 3.99 (s, 3H), 3.98 (s, 3H), 2.90 (septet, 1H), 1.22 (d, 6H); LC-MS (ESI) m/z 544 (M+H)$^+$.

Example 315

Preparation of 1-(3-(1,1-difluoroethyl)-1-(4-methoxyphenyl)-1H-pyrazol-5-yl)-3-(3-(6,7-dimethoxyquinazolin-4-yloxy)phenyl)urea Example 315A Step 1: Following the procedure for Example 282A Step 1, substituting p-methoxyphenylhydrazine for 2,4-dimethylphenylhydrazine hydrochloride and 4,4-difluoro-3-oxopentanenitrile was substituted for 4,4-Dimethyl-3-oxopentanenitrile. Concentration and purification using silica gel chromatography eluting with EtOAc/hexanes (5-40%) afforded 3-(1,1-difluoroethyl)-1-(4-methoxyphenyl)-1H-pyrazol-5-amine in 11% yield. LC-MS (ESI) m/z 254 (M+H)$^+$.

Example 315A

Step 2: 3-(1,1-difluoroethyl)-1-(4-methoxyphenyl)-1H-pyrazol-5-amine was converted to the phenyl carbamate using the procedure for Example 282A Step 2. Purification using silica gel chromatography eluting with EtOAc/hexane (5-40%) afforded phenyl 3-(1,1-difluoroethyl)-1-(4-methoxyphenyl)-1H-pyrazol-5-ylcarbamate in 64% yield. LC-MS (ESI) m/z 374 (M–H)⁻

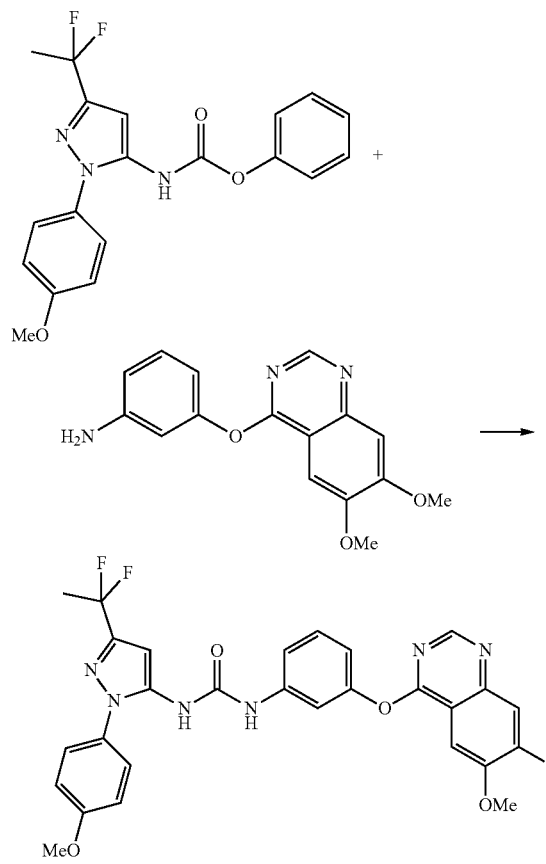

Example 315B

The title compound was prepared from 3-(6,7-dimethoxyquinazolin-4-yloxy)aniline (45 mg, 0.15 mmol) and the carbamate from the previous step (75 mg, 0.2 mmol) using the procedure in Example 115C to give 1-(3-(1,1-difluoroethyl)-1-(4-methoxyphenyl)-1H-pyrazol-5-yl)-3-(3-(6,7-dimethoxyquinazolin-4-yloxy)phenyl)urea (40 mg, 0.07 mmol, 46%). ¹H NMR (300 MHz, DMSO-d₆) δ 9.25 (s, 1H), 8.56 (s, 1H), 8.55 (s, 1H), 7.55 (s, 1H), 7.54 (s, 1H), 7.46 (d, 2H), 7.39 (s, 1H), 7.38 (t, 1H), 7.18 (d, 1H), 7.13 (d, 2H), 6.94 (d, 1H), 6.62 (s, 1H), 3.99 (s, 3H), 3.98 (s, 3H), 3.84 (s, 3H), 1.98 (s, 3H); LC-MS (ESI) m/z 577 (M+H)⁺.

Example 316

Preparation of 1-(3-(1,1-difluoroethyl)-1-(5-fluoropyridin-3-yl)-1H-pyrazol-5-yl)-3-(3-(6,7-dimethoxyquinazolin-4-yloxy)phenyl)urea Example 316A Step 1: Following the procedure for Example 314A Step 2, substituting 4,4-difluoro-3-oxopentanenitrile for 4-methyl-3-oxopentanenitrile and increasing the temperature to 75° C., 3-(1,1-difluoroethyl)-1-(5-fluoropyridin-3-yl)-1H-pyrazol-5-amine was isolated by silica gel chromatography eluting with an EtOAC/hexane gradient (5-75%) to give 52% yield. LC-MS (ESI) m/z 243 (M+H)⁺

Example 316A

Step 2: The phenyl carbamate of 3-(1,1-difluoroethyl)-1-(5-fluoropyridin-3-yl)-1H-pyrazol-5-amine was prepared using the procedure found in Example 315A Step 2. After trituration with DCM, phenyl 3-(1,1-difluoroethyl)-1-(5-fluoropyridin-3-yl)-1H-pyrazol-5-ylcarbamate was isolated in 73% yield. LC-MS (ESI) m/z 363 (M–H)⁻

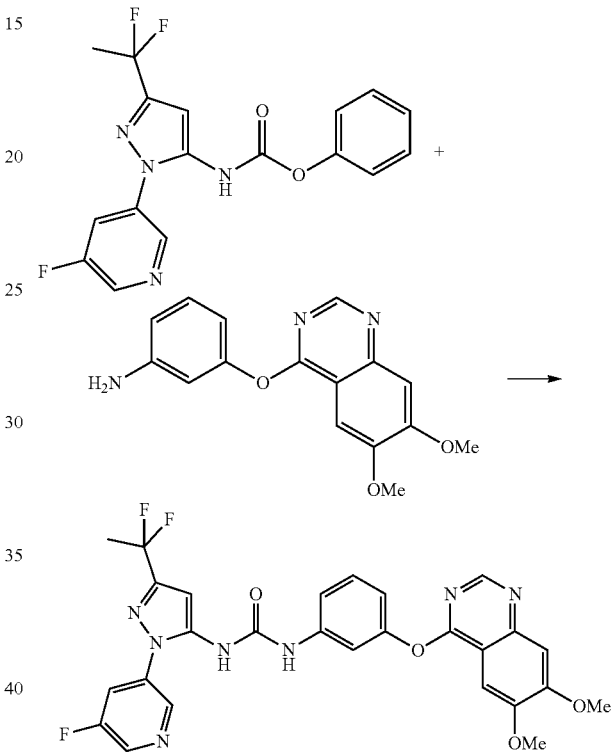

Example 316B

The title compound was prepared from 3-(6,7-dimethoxyquinazolin-4-yloxy)aniline (75 mg, 0.25 mmol) and the carbamate from the previous step (108 mg, 0.3 mmol) using the procedure in Example 115C to give 1-(3-(1,1-difluoroethyl)-1-(5-fluoropyridin-3-yl)-1H-pyrazol-5-yl)-3-(3-(6,7-dimethoxyquinazolin-4-yloxy)phenyl)urea (40 mg, 0.07 mmol, 28%). ¹H NMR (300 MHz, DMSO-d₆) δ 9.30 (s, 1H), 8.92 (s, 1H), 8.76 (s, 1H), 8.75 (s, 1H), 8.56 (s, 1H), 8.15 (t, 1H), 8.12 (t, 1H), 7.55 (s, 1H), 7.52 (t, 1H), 7.42-7.35 (m, 2H), 7.22 (d, 1H), 6.95 (d, 1H), 6.71 (s, 1H), 3.99 (s, 3H), 3.98 (s, 3H), 2.01 (t, 3H); LC-MS (ESI) m/z 566 (M+H)⁺.

Example 317

Preparation of 1-(3-tert-butyl-1-(6-oxo-1,6-dihydropyridin-3-yl)-1H-pyrazol-5-yl)-3-(3-(6,7-dimethoxyquinazolin-4-yloxy)phenyl)urea Example 317A Step 1: 5-Bromo-2(1H)-pyridone (2.0 g, 11.5 mmol) in 25 mL dry toluene was treated with benzophenone hydrazone (2.50 g, 12.7 mmol), 4,5-bis(diphenylphosphino)-9,9-dimethylxanthene (200 mg, 0.345 mmol), and sodium tert-butoxide (2.2 g, 23 mmol). The mixture was degassed with argon for 15 minutes. Added Pd(II)(OAc)$_2$ (80 mg, 0.345 mmol) and stirred at 90° C. for 16 hours. Extracted using EtOAc/H$_2$O (3×150 mL EtOAc, 1x 150 mL brine). Dried using Na$_2$SO$_4$ and then purified by flash chromatography (silica, 0-12% MeOH/DCM) to afford 5-(2-(diphenylmethylene)hydrazinyl)pyridin-2(1H)-one (950 mg, 3.28 mmol, 29%). $^1$H NMR (300 MHz, DMSO-d$_6$) δ 11.12 (s, 1H), 8.49 (s, 1H), 7.61-7.25 (m, 12H), 6.31 (d, 1H); LC-MS (ESI) m/z 290 (M+H)$^+$.

Example 317A

Step 2: 5-(2-(Diphenylmethylene)hydrazinyl)pyridin-2(1H)-one (950 mg, 3.29 mmol) was treated with 4,4-dimethyl-3-oxopentanenitrile (620 mg, 4.93 mmol) and 6N HCl (2.70 mL, 16.4 mmol) according to the procedure in Example 303A Step 2. Purification by flash chromatography (silica, 1-8% MeOH/DCM) afforded 5-(5-amino-3-tert-butyl-1H-pyrazol-1-yl)pyridin-2(1H)-one (46 mg, 0.20 mmol, 6%). $^1$H NMR (300 MHz, DMSO-d$_6$) δ 11.65 (br s, 1H), 7.55-7.51 (m, 2H), 6.39 (d, 1H), 5.29 (s, 1H), 5.11 (s, 2H), 1.21 (s, 9H); LC-MS (ESI) m/z 233 (M+H)$^+$.

Example 317A

Step 3: Following the procedure in Example 118A, 5-(5-amino-3-tert-butyl-1H-pyrazol-1-yl)pyridin-2(1H)-one (46 mg, 0.19 mmol) was treated with phenyl chloroformate (0.10 mL, 0.79 mmol) to afford phenyl 3-tert-butyl-1-(6-oxo-1,6-dihydropyridin-3-yl)-1H-pyrazol-5-ylcarbamate (8 mg, 0.023 mmol, 12%). $^1$H NMR (300 MHz, MeOD) δ 7.68 (d, 2H), 7.38 (t, 2H), 7.23 (t, 1H), 7.09 (br s, 2H), 6.63 (d, 1H), 6.34 (s, 1H), 1.30 (s, 9H); LC-MS (ESI) m/z 353 (M+H)$^+$.

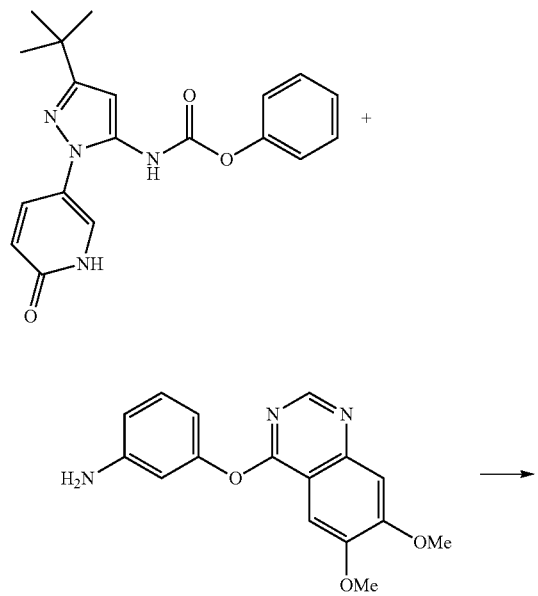

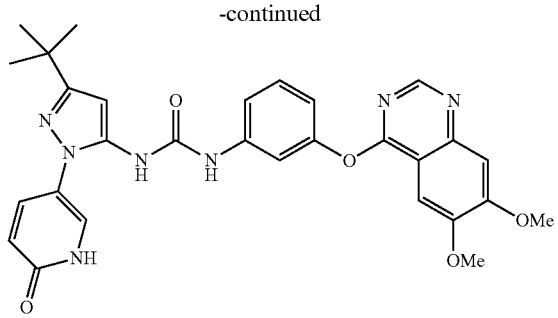

Example 317B

Following the procedure in Example 115C, phenyl 3-tert-butyl-1-(6-oxo-1,6-dihydropyridin-3-yl)-1H-pyrazol-5-ylcarbamate (8 mg, 0.0227 mmol) was treated with 3-(6,7-dimethoxyquinazolin-4-yloxy)aniline (8 mg, 0.025 mmol) (prepared as described in Example 113A) to afford 1-(3-tert-butyl-1-(6-oxo-1,6-dihydropyridin-3-yl)-1H-pyrazol-5-yl)-3-(3-(6,7-dimethoxyquinazolin-4-yloxy)phenyl)urea (7.8 mg, 0.014 mmol, 62%). $^1$H NMR (300 MHz, DMSO-d$_6$) δ 12.1 (br s, 1H), 9.03 (br s, 1H), 8.56 (br s, 2H), 7.53-7.26 (m, 7H), 6.91 (d, 1H), 6.43-6.35 (m, 2H), 4.05 (s, 6H), 1.22 (s, 9H); LC-MS (ESI) m/z 556 (M+H)$^+$.

Example 318

Preparation of 1-(3-(1,1-difluoroethyl)-1-phenyl-1H-pyrazol-5-yl)-3-(3-(6,7-dimethoxyquinazolin-4-yloxy)phenyl)urea Example 318A Step 1: A stirred mixture of 4,4-difluoro-3-oxopentanenitrile (prepared as described in Example 152A Step 1) (1 g, 7.52 mmol) and phenyl hydrazine hydrochloride (1.08 g, 7.52 mmol) in ethanol (30 mL) was heated at 70° C. for 8 h. After cooling to rt, the mixture was concentrated under reduced pressure. The residue was partitioned between dichloromethane (200 mL) and saturated aqueous sodium hydrogen carbonate solution (200 mL). The organic layer was separated and dried over magnesium sulfate and filtered. Concentration under reduced pressure gave an oil, which was purified via silica gel column chromatography (eluting with a gradient of 5% to 65% ethyl acetate in hexanes) to afford 3-(1,1-difluoroethyl)-1-phenyl-1H-pyrazol-5-amine (528 mg, 31%) as a yellow oil. $^1$H NMR (300 MHz, CDCl$_3$) δ 7.36-7.57 (m, 5H), 5.81 (s, 1H), 3.84 (brs, 2H), 2.01 (t, J=18 Hz, 3H); LC-MS (ESI) m/z 224 (M+H)$^+$.

Example 318A

Step 2: A mixture of 3-(1,1-difluoroethyl)-1-phenyl-1H-pyrazol-5-amine (528 mg, 2.37 mmol), potassium carbonate (979 mg, 7.10 mmol) and phenyl chloroformate (556 mg, 3.55 mmol) in anhydrous dichloromethane (20 mL) was stirred at rt for 15 h. Additional phenyl chloroformate (556 mg, 3.55 mmol) and potassium carbonate (979 mg, 7.10 mmol) was added and the mixture stirred for a further 4 h. The mixture was concentrated under reduced pressure and the residue partitioned between ethyl acetate and saturated aqueous sodium hydrogen carbonate solution. The organic layer was separated, washed with water, saturated aqueous sodium hydrogen carbonate solution, then dried over magnesium sulfate and filtered. Concentration under reduced pressure gave an oil which was purified via silica gel column chromatography (eluting with a gradient of 12% ethyl acetate in hexanes to 100% ethyl acetate) to afford phenyl 3-(1,1-difluoroethyl)-1-phenyl-1H-pyrazol-5-ylcarbamate (400 mg, 49%) as an oil. $^1$H NMR (300 MHz, CDCl$_3$) δ 7.51-7.58 (m, 5H), 7.35-7.41 (m, 2H), 7.26 (m, 1H), 7.15 (m, 2H), 7.00 (brs, 1H), 6.80 (s, 1H), 2.04 (t, J=18 Hz, 3H); LC-MS (ESI) m/z 344 (M+H)$^+$.

Example 318B

Using the procedure described in Example 306B, to a solution of 3-(6,7-dimethoxyquinazolin-4-yloxy)aniline (89 mg, 0.3 mmol), prepared as described in Example 113A, in THF (3.3 ml) was added DMAP (20 mg, 0.16 mmol) and phenyl 3-(1,1-difluoroethyl)-1-phenyl-1H-pyrazol-5-ylcarbamate (103 mg, 0.3 mmol), described in in the previous step. The crude was purified by silica gel chromatography (DCM/MeOH 0-15%) and triturated in diethyl ether to afford 1-(3-(1,1-difluoroethyl)-1-phenyl-1H-pyrazol-5-yl)-3-(3-(6,7-dimethoxyquinazolin-4-yloxy)phenyl)urea (102 mg, 62%) as a solid. $^1$H NMR (300 MHz, DMSO-d$_6$) δ 1.99 (t, J=18 Hz, 3H), 3.99 (s, 6H), 6.66 (s, 1H), 6.94 (d, J=9.6 Hz, 1H), 7.18 (d, J=9.6 Hz, 1H), 7.35-7.40 (m, 2H), 7.51-7.60 (m, 7H), 8.55 (s, 1H), 8.66 (s, 1H), 9.26 (s, 1H); LC-MS (ESI) m/z 547 (M+H)$^+$.

Example 319

Preparation of 1-(3-(1,1-difluoroethyl)-1-phenyl-1H-pyrazol-5-yl)-3-(3-(6,7-dimethoxyquinazolin-4-ylthio)phenyl)urea Using the procedure described in Example 306B, to a solution of 3-(6,7-dimethoxyquinazolin-4-ylthio)aniline (94 mg, 0.3 mmol), prepared as described in Example 115B, in THF (3.3 ml) was added DMAP (20 mg, 0.16 mmol) and phenyl 3-(1,1-difluoroethyl)-1-phenyl-1H-pyrazol-5-ylcarbamate (103 mg, 0.3 mmol), described in Example 318A. The crude was purified by silica gel chromatography (DCM/MeOH 0-15%) and triturated in diethyl ether to afford 14-(3-(1,1-difluoroethyl)-1-phenyl-1H-pyrazol-5-yl)-3-(3-(6,7-dimethoxyquinazolin-4-ylthio)phenyl)urea (127 mg, 75%) as a solid. $^1$HNMR (300 MHz, DMSO-d$_6$) δ 1.99 (t, J=18 Hz, 3H), 3.99 (s, 6H), 6.67 (s, 1H), 7.25 (d, J=7.2 Hz, 1H), 7.34 (d, J=5 Hz, 2H), 7.38-7.59 (m, 7H), 7.77 (s, 1H), 8.66 (s, 1H), 8.68 (s, 1H), 9.27 (s, 1H); LC-MS (ESI) m/z 563 (M+H)$^+$.

Example 320

Preparation of 1-(3-tert-butyl-1-(2-methylpyridin-4-yl)-1H-pyrazol-5-yl)-3-(3-(6,7-dimethoxyquinazolin-4-yloxy)phenyl)urea Example 320A Step 1: To a solution of 4-bromo-2-methylpyridine (0.7 ml, 5.81 mmol) in anhydrous toluene, previously degassed with Ar, were added benzophenone hydrazone (1.25 g, 6.4 mmol), 4,5-bis(diphenylphosphino)-9,9-dimethylxanthene (336 mg, 0.58 mmol), palladium (II) acetate (130 mg, 0.581 mmol), and sodium tert-butoxide (838 mg, 8.72 mmol). The reaction mixture was sealed and stirred at 85° C. overnight, then filtered through celite, washed with DCM and concentrated under reduced pressure. The residue was taken in EtOAc, washed with water, extracted, and the organics were combined and dried (MgSO$_4$). The crude was purified by silica gel chromatography (hexane/ethyl acetate 10-100%) to afford 5-(2-(diphenylmethylene)hydrazinyl)-2-methylpyridine (1.6 g, 95%). $^1$H NMR (300 MHz, CDCl$_3$) δ 2.47 (s, 3H), 6.76 (d, J=2 Hz, 1H), 6.83 (s, 1H), 7.31-7.36 (m, 5H), 7.53-7.63 (m, 6H), 8.20 (d, J=6 Hz, 1H); LC-MS (ESI) m/z 288 (M+H)$^+$.

Example 320A

Step 2: To a solution of 5-(2-(diphenylmethylene)hydrazinyl)-2-methylpyridine (500 mg, 1.74 mmol), from the previous step, in anhydrous THF (4 ml) were added 4,4-dimethyl-3-oxopentanenitrile (327 mg, 2.61 mmol) and a 6N solution of hydrogen chloride (0.26 ml) dropwise. The reaction mixture was stirred at 50° C. overnight. The solvent was removed under reduced pressure and the residue purified by silica gel chromatography (DCM/MeOH 0-10%) to afford 3-tert-butyl-1-(2-methylpyridin-4-yl)-1H-pyrazol-5-amine (350 mg, 87%). $^1$H NMR (300 MHz, CDCl$_3$) δ 1.30 (s, 9H), 2.48 (s, 3H), 3.82 (brs, 2H), 5.57 (s, 1H), 7.45 (d, J=6 Hz, 1H), 7.46 (s, 1H), 8.51 (d, J=6 Hz, 1H); LC-MS (ESI) m/z 231 (M+H)$^+$.

Example 320A

Step 3: Using the procedure described in Example 306A, to a solution of 3-tert-butyl-1-(2-methylpyridin-4-yl)-1H-pyrazol-5-amine (496 mg, 2.2 mmol), from the previous step, and potassium carbonate (395 mg, 2.9 mmol) in anhydrous DCM (8 ml) was added dropwise phenyl chloroformate (0.83 ml, 6.6 mmol) as a solution in DCM (5 ml). The crude was purified by silica gel chromatography (DCM/MeOH 0-10%) to afford phenyl 3-tert-butyl-1-(2-methylpyridin-4-yl)-1H-pyrazol-5-ylcarbamate (130 mg, 17%). $^1$H NMR (300 MHz, CDCl$_3$) δ 1.27 (s, 9H), 2.54 (s, 3H), 6.45 (s, 1H), 6.81 (d, J=8 Hz, 1H), 7.12-7.28 (m, 5H), 7.29-7.43 (m, 2H) 8.49 (d, J=6 Hz, 1H); LC-MS (ESI) m/z 351 (M+H)$^+$.

Example 320B

Using the procedure described in Example 306B, to a solution of 3-(6,7-dimethoxyquinazolin-4-yloxy)aniline (88 mg, 0.29 mmol), prepared as described in Example 113A, in THF (2 ml) was added DMAP (20 mg, 0.16 mmol) and 3-tert-butyl-1-(2-methylpyridin-4-yl)-1H-pyrazol-5-ylcarbamate (130 mg, 0.37 mmol) described in the previous step. The crude was purified by silica gel chromatography (DCM/MeOH 0-10%) to afford 1-(3-tert-butyl-1-(2-methylpyridin-4-yl)-1H-pyrazol-5-yl)-3-(3-(6,7-dimethoxyquinazolin-4-yloxy)phenyl)urea (63 mg, 39%) as a solid. $^1$H NMR (300 MHz, DMSO-d$_6$) δ 1.27 (s, 9H), 2.49 (s, 3H), 3.98 (s, 6H), 6.40 (s, 1H), 6.95 (d, J=7.8 Hz, 1H), 7.22 (d, J=7.8 Hz, 1H), 7.39-7.44 (m, 3H), 7.45-7.55 (m, 3H), 8.49 (d, J=6 Hz, 1H), 8.52 (s, 1H), 8.66 (s, 1H), 9.27 (s, 1H); LC-MS (ESI) m/z 554 (M+H)$^+$.

Example 321

Preparation of 1-(3-tert-butyl-1-ethyl-1H-pyrazol-5-yl)-3-(3-(6,7-dimethoxyquinazolin-4-ylthio)phenyl)urea Example 321A Step 1: A stirred solution of ethylhydrazine oxalate (1.0 g, 6.66 mmol) and 4,4-dimethyl-3-oxopentanenitrile (1.0 g, 7.98 mmol) in ethanol (5 mL) was refluxed for 15 h. After cooling to rt, the reaction mixture was concentrated under reduced pressure and the obtained crude product was recrystallized from a mixture of diethyl ether and petroleum ether to afford 3-tert-butyl-1-ethyl-1H-pyrazol-5-amine oxalate (0.8 g, 47%) as colorless solid. $^1$H NMR (400 MHz, DMSO-d$_6$) δ5.15 (s, 1H), 3.82 (q, J=7.2 Hz, 2H), 1.02-1.19 (m, 12H); LC-MS (ESI) m/z 168 (M+H)$^+$.

Example 321A

Step 2: To a stirred mixture of 3-tert-butyl-1-ethyl-1H-pyrazol-5-amine oxalate (350 mg, 1.36 mmol), potassium carbonate (280 mg, 2 mmol) and N,N-diisopropylethylamine (170 mg, 1.3 mmol) in dichloromethane (3 mL) at rt, was added dropwise, phenyl chloroformate (220 mg, 1.4 mmol) and the reaction mixture was stirred for a further 3 h. The reaction mixture was filtrated, the filtrate concentrated under reduced pressure and the residue partitioned between dichloromethane and water. The organic layer was separated and washed with brine, then concentrated under reduced pressure to give a solid which was recrystallized from diethyl ether to afford phenyl 3-tert-butyl-1-ethyl-1H-pyrazol-5-ylcarbamate (300 mg, 77%) as a colorless solid. LC-MS (ESI) m/z 288 (M+H)$^+$.

Example 321B

A stirred solution of phenyl 3-tert-butyl-1-ethyl-1H-pyrazol-5-ylcarbamate (150 mg, 0.523 mmol), N,N-diisopropylethylamine (80 mg, 0.62 mmol) and 3-(6,7-dimethoxyquinazolin-4-ylthio)aniline (prepared as described in Example 115B) (100 mg, 0.31 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-ethyl-1H-pyrazol-5-yl)-3-(3-(6,7-dimethoxyquinazolin-4-ylthio)phenyl)urea (30 mg, 19%) as a pale yellow solid. $^1$H NMR (400 MHz, DMSO-d$_6$) δ9.12 (s, 1H), 8.70 (s, 1H), 8.53 (s, 1H), 7.85 (s, 1H), 7.52 (m, 1H), 7.43 (m, 1H), 7.35-7.36 (m, 2H), 7.25 (m, 1H), 6.04 (s, 1H), 4.00 (s, 6H), 3.93 (m, 2H), 1.21-1.29 (m, 12H); LC-MS (ESI) m/z 507 (M+H)$^+$.

Example 322

Preparation of 1-(3-tert-butyl-1-(pyridin-3-yl)-1H-pyrazol-5-yl)-3-(3-(6,7-dimethoxyquinazolin-4-yloxy)phenyl)urea Example 322A Step 1: Following the procedure in Example 161A Step 3, 3-hydrazinylpyridine (501 mg, 4.0 mmol) and 4,4-dimethyl-3-oxopentanenitrile (437 mg, 4.0 mmol) were reacted to give 3-tert-butyl-1-(pyridin-3-yl)-1H-pyrazol-5-amine (667 mg, 3.09 mmol, 77%), LC-MS (ESI) m/z 217 (M+H)$^+$.

Example 322A

Step 2: Following the procedure in Example 118A, 3-tert-butyl-1-(pyridin-3-yl)-1H-pyrazol-5-amine (665 mg, 3.08 mmol) and phenyl chloroformate (705 mg, 4.5 mmol) were reacted to give phenyl 3-tert-butyl-1-(pyridin-3-yl)-1H-pyrazol-5-ylcarbamate (984 mg, 2.93 mmol, 95%). $^1$H NMR (300 MHz, DMSO-d$_6$) δ 7.42-7.39 (m, 3H), 7.30-7.26 (m, 5H), 6.85 (t, 1H), 6.82 (d, 2H), 1.21 (s, 9H); LC-MS (ESI) m/z 337 (M+H)$^+$.

Example 322B

The title compound was prepared from the carbamate in the previous step (49 mg, 0.15 mmol) and 3-(6,7-dimethoxyquinazolin-4-yloxy)aniline (44 mg, 0.15 mmol) using the procedure in Example 115C to give 1-(3-tert-butyl-1-(pyridin-3-yl)-1H-pyrazol-5-yl)-3-(3-(6,7-dimethoxyquinazolin-4-yloxy)phenyl)urea (15 mg, 0.028 mmol, 19%). $^1$H NMR (300 MHz, MeOD) δ 8.76 (s, 1H), 8.55 (s, 1H), 8.43 (s, 1H), 8.01 (s, 1H), 7.56-7.46 (m, 3H), 7.33-7.21 (m, 3H), 6.92 (s, 1H), 6.40 (s, 1H), 3.99 (s, 6H), 1.32 (s, 9H); LC-MS (ESI) m/z 540 (M+H)$^+$.

Example 323

Preparation of 1-(3-tert-butyl-1-(pyridin-3-yl)-1H-pyrazol-5-yl)-3-(3-(6,7-dimethoxyquinazolin-4-ylthio)phenyl)urea 1-(3-tert-Butyl-1-(pyridin-3-yl)-1H-pyrazol-5-yl)-3-(3-(6,7-dimethoxyquinazolin-4-ylthio)phenyl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting phenyl 3-tert-butyl-1-p-tolyl-1H-pyrazol-5-ylcarbamate with phenyl 3-tert-butyl-1-(pyridin-3-yl)-1H-pyrazol-5-ylcarbamate in Example 322A, and 3-(6,7-dimethoxyquinazolin-4-yloxy)aniline with 3-(6,7-dimethoxyquinazolin-4-ylthio)aniline in Example 115 (0.018 g, 8%). $^1$H NMR (300 MHz, DMSO-d$_6$) δ 1.28 (s, 9H), 3.99 (s, 6H), 6.40 (s, 1H), 7.24 (d, 1H), 7.33 (s, 1H), 7.35 (s, 1H), 7.40 (t, 1H), 7.45 (d, 1H), 7.57 (dd, 1H), 7.78 (s, 1H), 7.97 (dd, 1H), 8.59 (d, 2H), 8.69 (s, 1H), 8.78 (s, 1H), 9.24 (s, 1H); LC-MS (ESI) m/z 556 (M+H)$^+$.

Example 324

Preparation of 1-(3-(6,7-dimethoxyquinazolin-4-yloxy)phenyl)-3-(3-isopropyl-1-phenyl-1H-pyrazol-5-yl)urea Example 324A Step 1: Using the procedure described in Example 308A Step 1, to a solution of 4-methyl-3-oxopentanenitrile (303 mg, 2.7 mmol) prepared as described in Example 122A Step 1, in anhydrous EtOH (6 ml) was added phenylhydrazine hydrochloride (473 mg, 3.3 mmol) and the reaction mixture was heated at 65° C. overnight. The residue was purified by silica gel chromatography (hexane/ethyl acetate 2-50%) to afford 3-isopropyl-1-phenyl-1H-pyrazol-5-amine (423 mg, 77%) as a solid. $^1$H NMR (300 MHz, CDCl$_3$) δ 1.22 (d, J=6 Hz, 6H), 3.86 (brs, 2H), 5.35 (s, 1H), 7.21-7.49 (m, 5H); LC-MS (ESI) m/z 202 (M+H)$^+$.

Example 324A

Step 2: Using the procedure described in Example 306A, to a solution of 3-isopropyl-1-phenyl-1H-pyrazol-5-amine (423 mg, 2.1 mmol) and potassium carbonate (378 mg, 2.7 mmol) in anhydrous DCM (8 ml) was added dropwise phenyl chloroformate (0.39 ml, 3.1 mmol) as a solution in DCM (2 ml) to afford phenyl 3-isopropyl-1-phenyl-1H-pyrazol-5-ylcarbamate (229 mg, 54%). $^1$H NMR (300 MHz, CDCl$_3$) δ 1.27 (d, J=6 Hz, 6H), 3.01 (m, 1H), 6.46 (s, 1H), 7.14-7.36 (m, 2H), 7.38-7.57 (m, 8H); LC-MS (ESI) m/z 322 (M+H)$^+$.

Example 324B

Using the procedure described in Example 306B, to a solution of 3-(6,7-dimethoxyquinazolin-4-yloxy)aniline (92 mg, 0.31 mmol), prepared as described in Example 113A, in THF (2 ml) was added DMAP (20 mg, 0.16 mmol) and phenyl 3-isopropyl-1-phenyl-1H-pyrazol-5-ylcarbamate (100 mg, 0.31 mmol) described in the previous step. The suspension was triturated with anhydrous diethyl ether to afford 1-(3-(6,7-dimethoxyquinazolin-4-yloxy)phenyl)-3-(3-isopropyl-1-phenyl-1H-pyrazol-5-yl)urea (98 mg, 60%) as a solid. $^1$H NMR (300 MHz, DMSO-d$_6$) δ 1.21 (d, J=6.9 Hz, 6H), 2.87 (m, 1H), 3.99 (s, 6H), 6.31 (s, 1H), 6.92 (d, J=7.8 Hz, 1H), 7.18 (d, J=7.8 Hz, 1H), 7.34-7.40 (m, 3H), 7.52-7.55 (m, 6H), 8.47 (s, 1H), 8.55 (s, 1H), 9.21 (s, 1H); LC-MS (ESI) m/z 525 (M+H)$^+$.

Example 325

Preparation of 1-(3-(6,7-dimethoxyquinazolin-4-ylthio)phenyl)-3-(3-isopropyl-1-phenyl-1H-pyrazol-5-yl)urea Using the procedure described in Example 306A, to a solution of 3-(6,7-dimethoxyquinazolin-4-ylthio)aniline (125 mg, 0.4 mmol), prepared as described in Example 115B, in THF (2 ml) was added DMAP (20 mg, 0.16 mmol) and phenyl 3-isopropyl-1-phenyl-1H-pyrazol-5-ylcarbamate (129 mg, 0.4 mmol) described in Example 324A. The suspension was filtered and triturated with anhydrous diethyl ether to afford 1-(3-(6,7-dimethoxyquinazolin-4-ylthio)phenyl)-3-(3-isopropyl-1-phenyl-1H-pyrazol-5-yl)urea (154 mg, 71%) as a solid. $^1$H NMR (300 MHz, DMSO-d$_6$) δ 1.22 (d, J=7.2 Hz, 6H), 2.88 (m, 1H), 3.99 (s, 6H), 6.32 (s, 1H), 7.24 (d, J=7.5 Hz, 1H), 7.25-7.53 (m, 10H), 7.79 (m, 1H), 8.47 (s, 1H), 8.69 (s, 1H), 9.21 (s, 1H); LC-MS (ESI) m/z 541 (M+H)$^+$.

Example 326

Preparation of 1-(3-tert-butyl-1-(5-fluoropyridin-3-yl)-1H-pyrazol-5-yl)-3-(3-(6,7-dimethoxyquinazolin-4-yloxy)phenyl)urea Example 326A Step 1: To a stirred and degassed solution of 3-bromo-5-fluoropyridine (1 g, 5.68 mmol), benzophenone hydrazone (1.23 g, 6.25 mmol) and 4,5-bis(diphenylphosphino)-9,9-dimethylxanthene (329 mg, 0.57 mmol) in anhydrous toluene (15 mL) at rt under an argon atmosphere, was added palladium acetate (128 mg, 0.57 mmol). The vessel was sealed and heated at 85° C. for 15 h. The reaction mixture was cooled to rt and partitioned between ethyl acetate and water. The organic layer was separated and washed with water, then brine, then dried over magnesium sulfate and filtered. Concentration under reduced pressure gave a brown solid which was purified via silica gel column chromatography (eluting with a gradient of 12% ethyl acetate in hexanes to 100% ethyl acetate) to afford 3-(2-(diphenylmethylene)hydrazinyl)-5-fluoropyridine (1.35 g, 82%) as a yellow solid. $^1$H NMR (300 MHz, DMSO-d$_6$) δ 9.41 (s, 1H), 8.41 (s, 1H), 7.95 (s, 1H), 7.30-7.65 (m, 11H); LC-MS (ESI) m/z 292 (M+H)$^+$.

Example 326A

Step 2: A stirred mixture of 3-(2-(diphenylmethylene)hydrazinyl)-5-fluoropyridine (1.35 g, 4.64 mmol), 4,4-dimethyl-3-oxopentanenitrile (871 mg, 6.96 mmol) and p-toluenebenzenesulfonic acid monohydrate (4.41 g, 23 mmol) in ethanol (18 mL) was heated at 90° C. for 15 h. After cooling to rt, the mixture was concentrated under reduced pressure and the residue partitioned between ethyl acetate and saturated aqueous sodium hydrogen carbonate solution. The organic layer was separated, washed with water, saturated aqueous sodium hydrogen carbonate solution, then dried over magnesium sulfate and filtered. Concentration under reduced pressure gave an oil which was purified via silica gel column chromatography (eluting with a gradient of 12% ethyl acetate in hexanes to 100% ethyl acetate) to afford 3-tert-butyl-1-(5-fluoropyridin-3-yl)-1H-pyrazol-5-amine (384 mg, 35%) as a solid. $^1$H NMR (300 MHz, DMSO-d$_6$) δ 8.77 (s, 1H), 8.47 (s, 1H), 7.92 (s, 1H), 5.51 (s, 1H), 5.46 (brs, 2H), 1.20 (s, 9H); LC-MS (ESI) m/z 235 (M+H)$^+$.

Example 326A

Step 3: Using the procedure described in Example 306A, to a solution of 3-tert-butyl-1-(5-fluoropyridin-3-yl)-1H-pyrazol-5-amine (423 mg, 2.1 mmol), described in the previous step, and potassium carbonate (290 mg, 2.1 mmol) in anhydrous DCM (3.4 ml) was added dropwise phenyl chloroformate (0.61 ml, 4.8 mmol) as a solution in DCM (2 ml) to afford phenyl 3-tert-butyl-1-(5-fluoropyridin-3-yl)-1H-pyrazol-5-ylcarbamate (411 mg, 72%). $^1$H NMR (300 MHz, CDCl$_3$) δ 1.28 (s, 9H), 6.47 (s, 1H), 6.95-7.41 (m, 7H), 7.72-7.82 (m, 1H), 8.40 (d, J=8 Hz, 1H); LC-MS (ESI) m/z 355 (M+H)$^+$.

Example 326B

Using the procedure described in Example 306A, to a solution of 3-(6,7-dimethoxyquinazolin-4-yloxy)aniline (89 mg, 0.3 mmol), prepared as described in Example 113A, in THF (3.3 ml) was added DMAP (20 mg, 0.16 mmol) and phenyl 3-tert-butyl-1-(5-fluoropyridin-3-yl)-1H-pyrazol-5-ylcarbamate (159 mg, 0.45 mmol), described in the previous step, to afford 1-(3-tert-butyl-1-(5-fluoropyridin-3-yl)-1H-pyrazol-5-yl)-3-(3-(6,7-dimethoxyquinazolin-4-yloxy)phenyl)urea (84 mg, 50%) as a solid. $^1$H NMR (300 MHz, DMSO-d$_6$) δ 1.27 (s, 9H), 3.97-3.99 (m, 6H), 6.42 (s, 1H), 6.93 (d, J=7.8 Hz, 1H), 7.20 (d, J=8.1 Hz, 1H), 7.34-7.40 (m, 2H), 7.54 (d, J=5.1 Hz, 2H), 7.98 (d, J=10 Hz, 1H), 8.55 (s, 1H), 8.61-8.71 (m, 3H), 9.24 (s, 1H); LC-MS (ESI) m/z 558 (M+H)$^+$.

Example 327

Preparation of 1-(3-tert-butyl-1-(5-fluoropyridin-3-yl)-1H-pyrazol-5-yl)-3-(3-(6,7-dimethoxyquinazolin-4-ylthio)phenyl)urea Using the procedure described in Example 306A, to a solution of 3-(6,7-dimethoxyquinazolin-4-ylthio)aniline (94 mg, 0.3 mmol), prepared as described in Example 115B, in THF (3.3 ml) was added DMAP (20 mg, 0.16 mmol) and phenyl 3-tert-butyl-1-(5-fluoropyridin-3-yl)-1H-pyrazol-5-ylcarbamate (159 mg, 0.45 mmol) described in Example 326A to afford 1-(3-tert-butyl-1-(5-fluoropyridin-3-yl)-1H-pyrazol-5-yl)-3-(3-(6,7-dimethoxyquinazolin-4-ylthio)phenyl)urea (107 mg, 62%) as a solid. $^1$H NMR (300 MHz, DMSO-d$_6$) δ 1.28 (s, 9H), 3.99 (m, 6H), 6.43 (s, 1H), 7.25 (d, J=7.5 Hz, 1H), 7.34 (d, J=4.5 Hz, 2H), 7.38-7.47 (m, 2H), 7.54 (s, 1H), 7.98 (d, J=9.9 Hz, 1H), 8.61-8.72 (m, 4H), 9.25 (s, 1H); LC-MS (ESI) m/z 574 (M+H)$^+$.

Example 328

Preparation of 1-(3-tert-butyl-1-(4-cyanophenyl)-1H-pyrazol-5-yl)-3-(3-(6,7-dimethoxyquinazolin-4-yloxy)phenyl)urea Example 328A Step 1: Using the procedure described in Example 308A Step 1, to a solution of 4,4-dimethyl-3-oxopentanenitrile (1 g, 7.99 mmol) in anhydrous EtOH (55 ml) was added 4-cyanophenyl hydrazine hydrochloride (473 mg, 3.3 mmol) and the reaction mixture was heated at 80° C. overnight. The residue was purified by silica gel chromatography (DCM/EtOAc 40%) to afford 4-(5-amino-3-tert-butyl-1H-pyrazol-1-yl)benzonitrile (350 mg, 18%) as a solid. $^1$H NMR (300 MHz, CDCl$_3$) δ 1.3 (s, 9H), 3.75 (brs, 2H), 7.72 (d, J=8.7 Hz, 2H), 7.83 (d, J=8.7 Hz, 2H); LC-MS (ESI) m/z 241 (M+H)$^+$.

Example 328A

Step 2: Using the procedure described in Example 306A, to a solution of 4-(5-amino-3-tert-butyl-1H-pyrazol-1-yl)benzonitrile (350 mg, 1.45 mmol) and potassium carbonate (263 mg, 1.9 mmol) in anhydrous DCM (3 ml) was added dropwise phenyl chloroformate (0.91 ml, 7.3 mmol) as a solution in DCM (1.5 ml). The crude was purified by silica gel chromatography (DCM/EtOAc 6-50%) to afford phenyl 3-tert-butyl-1-(4-cyanophenyl)-1H-pyrazol-5-ylcarbamate (320 mg, 61%). $^1$H NMR (300 MHz, CDCl$_3$) δ 1.34 (s, 9H), 6.45 (s, 1H), 7.26-7.28 (m, 3H), 7.31-7.38 (m, 2H), 7.75-7.82 (m, 4H); LC-MS (ESI) m/z 362 (M+H)$^+$.

Example 328B

Using the procedure described in Example 306A, to a solution of 3-(6,7-dimethoxyquinazolin-4-yloxy)aniline (89 mg, 0.3 mmol), prepared as described in Example 113A, in THF (3.3 ml) was added DMAP (20 mg, 0.16 mmol) and phenyl 3-tert-butyl-1-(4-cyanophenyl)-1H-pyrazol-5-ylcarbamate (108 mg, 0.3 mmol), described in the previous step, to afford 1-(3-tert-butyl-1-(4-cyanophenyl)-1H-pyrazol-5-yl)-3-(3-(6,7-dimethoxyquinazolin-4-yloxy)phenyl)urea (60 mg, 60%) as a solid. $^1$H NMR (300 MHz, DMSO-d$_6$) δ 1.21 (s, 9H), 3.99 (s, 6H), 6.40 (s, 1H), 6.93 (d, J=7.8 Hz, 1H), 7.21 (d, J=8.1 Hz, 1H), 7.34-7.40 (m, 2H), 7.52-7.55 (m, 2H), 7.79 (d, J=7.8 Hz, 2H), 7.99 (d, J=7.8 Hz, 2H), 8.55 (s, 1H), 8.62 (s, 1H), 9.24 (s, 1H); LC-MS (ESI) m/z 564 (M+H)$^+$.

Example 329

Preparation of 1-(3-tert-butyl-1-(4-cyanophenyl)-1H-pyrazol-5-yl)-3-(3-(6,7-dimethoxyquinazolin-4-ylthio)phenyl)urea Using the procedure described in Example 306A, to a solution of 3-(6,7-dimethoxyquinazolin-4-ylthio)aniline (94 mg, 0.3 mmol), prepared as described in Example 115B, in THF (3.3 ml) was added DMAP (20 mg, 0.16 mmol) and phenyl 3-tert-butyl-1-(4-cyanophenyl)-1H-pyrazol-5-ylcarbamate (108 mg, 0.3 mmol) described in Example 328A, to afford 1-(3-tert-butyl-1-(4-cyanophenyl)-1H-pyrazol-5-yl)-3-(3-(6,7-dimethoxyquinazolin-4-ylthio)phenyl)urea (8 mg, 4%) as a solid. $^1$H NMR (300 MHz, DMSO-d$_6$) δ 1.28 (s, 9H), 3.99 (m, 6H), 6.41 (s, 1H), 7.24-7.41 (m, 6H), 7.79 (d, J=8.7 Hz, 2H), 7.98 (d, J=8.7 Hz, 2H), 8.62 (s, 1H), 8.69 (s, 1H), 9.25 (s, 1H); LC-MS (ESI) m/z 580 (M+H)$^+$.

Example 330

Preparation of 1-(3-tert-butyl-1-cyclohexyl-1H-pyrazol-5-yl)-3-(3-(6,7-dimethoxyquinazolin-4-yloxy)phenyl)urea Example 330A Step 1: A stirred solution of cyclohexylhydrazine hydrochloride (1.5 g, 9.96 mmol) and 4,4-dimethyl-3-oxopentanenitrile (1.5 g, 11.98 mmol) in ethanol (5 mL) was refluxed for 15 h. After cooling to rt, the reaction mixture was concentrated under reduced pressure and the obtained crude product was recrystallized from a mixture of diethyl ether and petroleum ether to afford 3-tert-butyl-1-cyclohexyl-1H-pyrazol-5-amine hydrochloride (1.0 g, 39%) as colorless solid. $^1$H NMR (400 MHz, DMSO-d$_6$) δ 13.24 (brs, 1H), 7.02 (brs, 2H), 5.52 (s, 1H), 4.30 (m, 1H), 1.63-1.98 (m, 7H), 1.10-1.40 (m, 12H); LC-MS (ESI) m/z 222 (M+H)$^+$.

Example 330A

Step 2: To a stirred mixture of 3-tert-butyl-1-cyclohexyl-1H-pyrazol-5-amine hydrochloride (260 mg, 1 mmol) and potassium carbonate (210 mg, 1.5 mmol) in THF (3 mL) at rt, was added dropwise a solution of phenyl chloroformate (170 mg, 1.1 mmol) in THF (2 mL) and the reaction mixture was stirred for a further 15 h. N,N-Diisopropylethylamine (129 mg, 1 mmol) was added to the reaction mixture and stirring continued for an additional 4 h. The reaction mixture was filtrated, the filtrate concentrated under reduced pressure and the residue partitioned between dichloromethane and water. The organic layer was separated and washed with brine, then concentrated under reduced pressure to give a solid which was recrystallized from diethyl ether to afford crude phenyl 3-tert-butyl-1-cyclohexyl-1H-pyrazol-5-ylcarbamate (200 mg) which was used without further purification. LC-MS (ESI) m/z 342 (M+H)$^+$.

Example 330B

A stirred solution of phenyl 3-tert-butyl-1-cyclohexyl-1H-pyrazol-5-ylcarbamate (200 mg), N,N-Diisopropylethylamine (67 mg, 0.52 mmol) and 3-(6,7-dimethoxyquinazolin-4-yloxy)aniline (prepared as described in Example 113A) (80 mg, 0.26 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-cyclohexyl-1H-pyrazol-5-yl)-3-(3-(6,7-dimethoxyquinazolin-4-yloxy)phenyl) urea (55 mg, 10% over two steps) as a pale yellow solid. $^1$H NMR (400 MHz, DMSO-d$_6$) δ9.10 (s, 1H), 8.57 (s, 1H), 8.47 (s, 1H), 7.57-7.60 (m, 2H), 7.37-7.41 (m, 2H), 7.24 (m, 1H), 6.93 (m, 1H), 6.01 (s, 1H), 4.00 (s, 3H), 3.99 (s, 3H), 3.94 (m, 1H), 1.62-1.82 (m, 8H), 1.24-1.35 (m, 2H), 1.24 (s, 9H); LC-MS (ESI) m/z 545 (M+H)⁺.

Example 331

Preparation of 1-(3-tert-butyl-1-cyclohexyl-1H-pyrazol-5-yl)-3-(3-(6,7-dimethoxyquinazolin-4-ylthio)phenyl)urea A stirred solution of phenyl 3-tert-butyl-1-cyclohexyl-1H-pyrazol-5-ylcarbamate prepared as described in Example 330A (200 mg, 0.59 mmol), N,N-diisopropylethylamine (67 mg, 0.52 mmol) and 3-(6,7-dimethoxyquinazolin-4-ylthio)aniline (prepared as described in Example 115B) (85 mg, 0.27 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-cyclohexyl-1H-pyrazol-5-yl)-3-(3-(6,7-dimethoxyquinazolin-4-ylthio)phenyl)urea (52 mg, 18%) as a pale yellow solid. ¹H NMR (400 MHz, DMSO-d₆) δ9.17 (s, 1H), 8.71 (s, 1H), 8.53 (s, 1H), 7.84 (s, 1H), 7.26-7.55 (m, 5H), 6.06 (s, 1H), 4.00 (s, 6H), 3.94 (m, 1H), 1.62-1.81 (m, 7H), 1.24-1.36 (m, 12H); LC-MS (ESI) m/z 561 (M+H)⁺.

Example 332

Preparation of 1-(3-tert-butyl-1-isobutyl-1H-pyrazol-5-yl)-3-(3-(6,7-dimethoxyquinazolin-4-yloxy)phenyl)urea

Example 332A

Step 1: A stirred solution of isobutylhydrazine hydrochloride (1 g, 8 mmol) and 4,4-dimethyl-3-oxopentanenitrile (1.2 g, 9.6 mmol) in ethanol (5 mL) was refluxed for 15 h. After cooling to rt, the reaction mixture was concentrated under reduced pressure and the obtained crude product was recrystallized from a mixture of diethyl ether and petroleum ether to afford 3-tert-butyl-1-isobutyl-1H-pyrazol-5-amine hydrochloride (0.8 g, 43%) as colorless solid. ¹H NMR (400 MHz, DMSO-d₆) δ14.06 (brs, 1H), 6.93 (brs, 2H), 5.52 (s, 1H), 3.92 (m, 2H), 2.16 (m, 1H), 1.26 (s, 9H), 0.83 (m, 6H); LC-MS (ESI) m/z 196 (M+H)⁺.

Example 332A

Step 2: Following the procedure described for Example 330A Step 2, reaction of 3-tert-butyl-1-isobutyl-1H-pyrazol-5-amine hydrochloride with phenyl chloroformate, afforded phenyl 3-tert-butyl-1-isobutyl-1H-pyrazol-5-ylcarbamate which was used in the subsequent step.

Example 332B

A stirred solution of phenyl 3-tert-butyl-1-isobutyl-1H-pyrazol-5-ylcarbamate (150 mg, 0.47 mmol), N,N-Diisopropylethylamine (80 mg, 0.62 mmol) and 3-(6,7-dimethoxyquinazolin-4-yloxy)aniline (prepared as described in Example 113A) (92 mg, 0.31 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-isobutyl-1H-pyrazol-5-yl)-3-(3-(6,7-dimethoxyquinazolin-4-yloxy)phenyl)urea (60 mg, 38%) as a pale yellow solid. ¹H NMR (400 MHz, DMSO-d₆) δ9.09 (s, 1H), 8.57 (s, 1H), 8.49 (s, 1H), 7.61 (m, 1H), 7.57 (m, 1H), 7.37-7.41 (m, 2H), 7.24 (m, 1H), 6.94 (m, 1H), 6.01 (s, 1H), 4.00 (s, 3H), 3.99 (s, 3H), 3.71 (d, J=7.6 Hz, 2H), 2.07 (m, 1H), 1.20 (s, 9H), 0.83 (d, J=6.4 Hz, 6H); LC-MS (ESI) m/z 519 (M+H)⁺.

Example 333

Preparation of 1-(3-tert-butyl-1-isobutyl-1H-pyrazol-5-yl)-3-(3-(6,7-dimethoxyquinazolin-4-ylthio)phenyl)urea A stirred solution of phenyl 3-tert-butyl-1-isobutyl-1H-pyrazol-5-ylcarbamate described in Example 332A(150 mg, 0.47 mmol), N,N-diisopropylethylamine (80 mg, 0.62 mmol) and 3-(6,7-dimethoxyquinazolin-4-ylthio)aniline (prepared as described in Example 115B) (100 mg, 0.31 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-isobutyl-1H-pyrazol-5-yl)-3-(3-(6,7-dimethoxyquinazolin-4-ylthio)phenyl)urea (52 mg, 32%) as a pale yellow solid. ¹H NMR (400 MHz, DMSO-d₆) δ9.07 (s, 1H), 8.70 (s, 1H), 8.48 (s, 1H), 7.85 (s, 1H), 7.24-7.53 (m, 5H), 6.07 (s, 1H), 4.00 (s, 6H), 3.72 (d, J=7.2 Hz, 2H), 2.07 (m, 1H), 1.20 (s, 9H), 0.83 (d, J=6.8 Hz, 6H); LC-MS (ESI) m/z 535 (M+H)⁺.

Example 334

Preparation of 1-(3-tert-butyl-1-isopropyl-1H-pyrazol-5-yl)-3-(3-(6,7-dimethoxyquinazolin-4-yloxy)phenyl)urea

Example 334A

Step 1: A stirred solution of isopropylhydrazine hydrochloride (500 mg, 4.54 mmol) and 4,4-dimethyl-3-oxopentanenitrile (679 mg, 5.44 mmol) in ethanol (5 mL) was refluxed for 15 h. After cooling to rt, the reaction mixture was concentrated under reduced pressure and the obtained crude product was recrystallized from a mixture of diethyl ether and petroleum ether to afford 3-tert-butyl-1-isopropyl-1H-pyrazol-5-amine hydrochloride (500 mg, 51%) as colorless solid. ¹H NMR (400 MHz, CDCl₃) δ5.55 (s, 1H), 5.05 (brs, 2H), 3.62 (m, 1H), 1.68 (d, J=6.4 Hz, 6H), 1.43 (s, 9H); LC-MS (ESI) m/z 182 (M+H)⁺.

Example 334A

Step 2: To a mixture of phenyl chloroformate (170 mg, 1.1 mmol) and potassium carbonate (210 mg, 1.5 mmol) in DCM (3 mL) at 0° C., was added dropwise a solution of 3-tert-butyl-1-isopropyl-1H-pyrazol-5-amine hydrochloride (220 mg, 1 mmol) in N,N-diisopropylethylamine (130 mg, 1 mmol) and the reaction mixture was stirred at 0° C. for 3 h. The mixture was filtrated, concentrated under reduced pressure, and the residue dissolved in dichloromethane. The organic phase was washed water, brine and concentrated under reduced pressure to give the crude product which was purified via recrystallization from diethyl ether to afford phenyl 3-tert-butyl-1-isopropyl-1H-pyrazol-5-ylcarbamate (300 mg, 100%) as a colorless solid. LC-MS (ESI) m/z 302 (M+H)⁺.

Example 334B

A stirred solution of phenyl 3-tert-butyl-1-isopropyl-1H-pyrazol-5-ylcarbamate (150 mg, 0.50 mmol), N,N-Diisopropylethylamine (80 mg, 0.62 mmol) and 3-(6,7-dimethoxyquinazolin-4-yloxy)aniline (prepared as described in Example 113A) (92 mg, 0.31 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-isopropyl-1H-pyrazol-5-yl)-3-(3-(6,7-dimethoxyquinazolin-4-yloxy)phenyl)urea (62 mg, 40%) as a colorless solid. ¹H NMR (400 MHz, DMSO-d₆) δ 9.08 (s, 1H), 8.57 (s, 1H), 8.43 (s, 1H), 7.55-7.59 (m, 2H), 7.37-7.40 (m, 2H), 7.24 (m, 1H), 6.93 (m, 1H), 6.00 (s, 1H), 4.35 (m, 1H), 4.00 (s, 3H), 3.99 (s, 3H), 1.34 (d, J=6.4 Hz, 6H), 1.24 (s, 9H); LC-MS (ESI) m/z 505 (M+H)⁺.

Example 335

Preparation of 1-(3-tert-butyl-1-isopropyl-1H-pyrazol-5-yl)-3-(3-(6,7-dimethoxyquinazolin-4-ylthio)phenyl)urea A stirred solution of phenyl 3-tert-butyl-1-isopropyl-1H-pyrazol-5-ylcarbamate described in Example 334A(150 mg, 0.50 mmol), N,N-Diisopropylethylamine (80 mg, 0.62 mmol) and 3-(6,7-dimethoxyquinazolin-4-yloxy)aniline (prepared as described in Example 113A) (100 mg, 0.31 mmol) in THF (1.0 mL) was heated at 60° C. for 15 h. After cooling to rt, the reaction solution was partitioned between dichloromethane and a saturated aqueous solution of sodium carbonate. The organic phase was separated and concentrated under reduced pressure. The crude product was purified via silica gel column chromatography (eluting with a gradient of 40:1 to 20:1 dichloromethane: methanol) then reverse-phase preparative HPLC to afford 1-(3-tert-butyl-1-isopropyl-1H-pyrazol-5-yl)-3-(3-(6,7-dimethoxyquinazolin-4-ylthio)phenyl)urea (60 mg, 37%) as a colorless solid. ¹H NMR (400 MHz, DMSO-d₆) δ 9.26 (s, 1H), 8.71 (s, 1H), 8.60 (s, 1H), 7.83 (m, 1H), 7.53 (m, 1H), 7.43 (m, 1H), 7.35-7.36 (m, 2H), 7.25 (m, 1H), 6.02 (s, 1H), 4.32 (m, 1H), 4.00 (s, 6H), 1.34 (d, J=6.4 Hz, 6H), 1.21 (s, 9H); LC-MS (ESI) m/z 521 (M+H)⁺.

Example 336

Preparation of 1-(3-tert-butyl-1-(pyridin-4-yl)-1H-pyrazol-5-yl)-3-(3-(6,7-dimethoxyquinazolin-4-yloxy)phenyl)urea Example 336A Step 1: Following the procedure in Example 161A Step 3, 4-hydrazinopyridine hydrochloride (1.0 g, 6.87 mmol) and 4,4-dimethyl-3-oxopentanenitrile (860 mg, 6.87 mmol) were reacted to give 3-tert-butyl-1-(pyridin-4-yl)-1H-pyrazol-5-amine (250 mg, 1.16 mmol, 17%). ¹H NMR (300 MHz, DMSO-d₆) δ 8.55 (br s, 2H), 7.69 (br s, 2H), 5.55 (br s, 2H), 5.46 (s, 1H), 1.22 (s, 9H); LC-MS (ESI) m/z 217 (M+H)⁺.

Example 336A

Step 2: Following the procedure in Example 118A, 3-tert-butyl-1-(pyridin-4-yl)-1H-pyrazol-5-amine (250 mg, 1.16 mmol) and phenyl chloroformate (0.60 mL, 4.65 mmol) were reacted to give phenyl 3-tert-butyl-1-(pyridin-4-yl)-1H-pyrazol-5-ylcarbamate (90 mg, 0.27 mmol, 23%). ¹H NMR (300 MHz, DMSO-d₆) δ 10.15 (br s, 1H), 8.72 (d, 2H), 7.76 (d, 2H), 7.40-7.05 (m, 5H), 6.45 (s, 1H), 1.29 (s, 9H); LC-MS (ESI) m/z 337 (M+H)⁺.

Example 336B

The title compound was prepared from the carbamate from the previous step (45 mg, 0.13 mmol) and 3-(6,7-dimethoxyquinazolin-4-yloxy)aniline (40 mg, 0.13 mmol) using the procedure in Example 115C to give 1-(3-tert-butyl-1-(pyridin-4-yl)-1H-pyrazol-5-yl)-3-(3-(6,7-dimethoxyquinazolin-4-yloxy)phenyl)urea (22 mg, 0.041 mmol, 31%). ¹H NMR (300 MHz, DMSO-d₆) δ 9.30 (s, 1H), 8.72-8.64 (m, 3H), 8.56 (s, 1H), 7.68-7.62 (m, 2H), 7.51 (br s, 2H), 7.41-7.33 (m, 2H), 7.24 (d, 1H), 6.95 (d, 1H), 6.41 (s, 1H), 3.99 (s, 6H), 1.29 (s, 9H); LC-MS (ESI) m/z 540 (M+H)⁺.

Example 337

Preparation of 1-(3-tert-butyl-1-(pyridin-4-yl)-1H-pyrazol-5-yl)-3-(3-(6,7-dimethoxyquinazolin-4-ylthio)phenyl)urea The title compound was prepared from the carbarbamate from Example 336A (45 mg, 0.13 mmol) and 3-(6,7-dimethoxyquinazolin-4-ylthio)aniline (42 mg, 0.13 mmol) using the procedure in Example 115C to give 1-(3-tert-butyl-1-(pyridin-4-yl)-1H-pyrazol-5-yl)-3-(3-(6,7-dimethoxyquinazolin-4-yloxy)phenyl)urea (13 mg, 0.023 mmol, 18%). ¹H NMR (300 MHz, DMSO-d₆) δ 9.32 (s, 1H), 8.70-8.61 (m, 4H), 7.81 (s, 1H), 7.68-7.65 (m, 2H), 7.51 (d, 1H), 7.42 (t, 1H), 7.35-7.33 (m, 2H), 7.25 (d, 1H), 6.42 (s, 1H), 3.99 (s, 6H), 1.30 (s, 9H); LC-MS (ESI) m/z 556 (M+H)⁺.

Example 338

Preparation of 1-(3-(6,7-dimethoxyquinazolin-4-yloxy)phenyl)-3-(1-m-tolyl-3-(trifluoromethyl)-1H-pyrazol-5-yl)urea Example 338A Step 1: Following the procedure in Example 161A Step 3, m-tolylhydrazine hydrochloride (1.15 g, 7.30 mmol) and 4,4,4-trifluoro-3-oxobutanenitrile (1.0 g, 7.30 mmol) were reacted to give 1-m-tolyl-3-(trifluoromethyl)-1H-pyrazol-5-amine (380 mg, 1.57 mmol, 22%). ¹H NMR (300 MHz, DMSO-d₆) δ 7.60-7.20 (m, 4H), 5.82-5.61 (m, 3H), 2.59 (s, 3H); LC-MS (ESI) m/z 242 (M+H)⁺.

Example 338A

Step 2: Following the procedure in Example 118A, 1-m-tolyl-3-(trifluoromethyl)-1H-pyrazol-5-amine (380 mg, 1.58 mmol) and phenyl chloroformate (0.60 mL, 4.74 mmol) were reacted to give phenyl 1-m-tolyl-3-(trifluoromethyl)-1H-pyrazol-5-ylcarbamate (330 mg, 0.91 mmol, 58%). $^1$H NMR (300 MHz, DMSO-d$_6$) δ 10.4 (br s, 1H), 7.62-6.85 (m, 10H), 2.46 (s, 3H); LC-MS (ESI) m/z 362 (M+H)$^+$.

Example 338B

The title compound was prepared from the carbamate from the previous step (108 mg, 0.30 mmol) and 3-(6,7-dimethoxyquinazolin-4-yloxy)aniline (90 mg, 0.30 mmol) using the procedure in Example 115C to give 1-(3-(6,7-dimethoxyquinazolin-4-yloxy)phenyl)-3-(1-m-tolyl-3-(trifluoromethyl)-1H-pyrazol-5-yl)urea (140 mg, 0.25 mmol, 83%). $^1$H NMR (300 MHz, DMSO-d$_6$) δ 9.32 (s, 1H), 8.77 (s, 1H), 8.55 (s, 1H), 7.55-7.36 (m, 8H), 7.21 (d, 1H), 6.95 (d, 1H), 6.85 (s, 1H), 3.97 (s, 6H), 2.41 (s, 3H); LC-MS (ESI) m/z 565 (M+H)$^+$.

Example 339

Preparation of 1-(3-(6,7-dimethoxyquinazolin-4-ylthio)phenyl)-3-(1-m-tolyl-3-(trifluoromethyl)-1H-pyrazol-5-yl)urea The title compound was prepared from the carbamate from Example 338A (108 mg, 0.30 mmol) and 3-(6,7-dimethoxyquinazolin-4-ylthio)aniline (94 mg, 0.30 mmol) using the procedure in Example 115C to give 14346,7-dimethoxyquinazolin-4-ylthio)phenyl)-3-(1-m-tolyl-3-(trifluoromethyl)-1H-pyrazol-5-yl)urea (137 mg, 0.24 mmol, 79%). $^1$H NMR (300 MHz, DMSO-d$_6$) δ 9.31 (s, 1H), 8.76 (s, 1H), 8.68 (s, 1H), 7.78 (s, 1H), 7.52-7.25 (m, 9H), 6.86 (s, 1H), 3.98 (s, 6H), 2.41 (s, 3H); LC-MS (ESI) m/z 581 (M+H)$^+$.

Example 340

Preparation of 1-(3-tert-butyl-1-(2-chlorophenyl)-1H-pyrazol-5-yl)-3-(3-(6,7-dimethoxyquinazolin-4-yloxy)phenyl)urea Example 340A Step 1: Following the procedure in Example 161A Step 3, 2-chlorophenylhydrazine hydrochloride (1.43 g, 8.0 mmol) and 4,4-dimethyl-3-oxopentanenitrile (1.0 g, 8.0 mmol) were reacted to give 3-tert-butyl-1-(2-chlorophenyl)-1H-pyrazol-5-amine (1.30 g, 5.22 mmol, 65%). $^1$H NMR (300 MHz, DMSO-d$_6$) δ 7.60 (d, 1H), 7.48-7.42 (m, 3H), 5.28 (s, 1H), 4.94 (s, 2H), 1.19 (s, 9H); LC-MS (ESI) m/z 250 (M+H)$^+$.

Example 340A

Step 2: Following the procedure in Example 118A, 3-tert-butyl-1-(2-chlorophenyl)-1H-pyrazol-5-amine (1.30 g, 5.21 mmol) and phenyl chloroformate (2.0 mL, 15.63 mmol) were reacted to give phenyl 3-tert-butyl-1-(2-chlorophenyl)-1H-pyrazol-5-ylcarbamate. $^1$H NMR (300 MHz, DMSO-d$_6$) δ 10.18 (br s, 1H), 7.67 (d, 1H), 7.55-7.48 (m, 3H), 7.41-7.36 (m, 2H), 7.24 (t, 1H), 7.02 (br s, 2H), 6.31 (s, 1H), 1.23 (s, 9H); LC-MS (ESI) m/z 370 (M+H)$^+$.

Example 340B

The title compound was prepared from the carbamate from the previous step (111 mg, 0.30 mmol) and 3-(6,7-dimethoxyquinazolin-4-yloxy)aniline (90 mg, 0.30 mmol) using the procedure in Example 115C to give 1-(3-(tert-butyl-1-(2-chlorophenyl)-1H-pyrazol-5-yl)-3-(3-(6,7-dimethoxyquinazolin-4-yloxy)phenyl)urea (92 mg, 0.16 mmol, 53%). $^1$H NMR (300 MHz, DMSO-d$_6$) δ 9.06 (s, 1H), 8.55 (s, 1H), 8.35 (s, 1H), 7.73 (d, 1H), 7.57-7.54 (m, 5H), 7.38-7.34 (m, 2H), 7.13 (d, 1H), 6.93 (d, 1H), 6.35 (s, 1H), 3.99 (s, 6H), 1.25 (s, 9H); LC-MS (ESI) m/z 573 (M)'.

Example 341

Preparation of 1-(3-tert-butyl-1-(2-chlorophenyl)-1H-pyrazol-5-yl)-3-(3-(6,7-dimethoxyquinazolin-4-ylthio)phenyl)urea The title compound was prepared from the carbamate in Example 340A (111 mg, 0.30 mmol) and 3-(6,7-dimethoxyquinazolin-4-ylthio)aniline (94 mg, 0.30 mmol) using the procedure in Example 115C to give 1-(3-tert-butyl-1-(2-chlorophenyl)-1H-pyrazol-5-yl)-3-(3-(6,7-dimethoxyquinazolin-4-ylthio)phenyl)urea (120 mg, 0.20 mmol, 68%). $^1$H NMR (300 MHz, DMSO-d$_6$) δ 9.06 (s, 1H), 8.68 (s, 1H), 8.34 (s, 1H), 7.80 (s, 1H), 7.72 (d, 1H), 7.60-7.54 (m, 3H), 7.41-7.32 (m, 4H), 7.25 (d, 1H), 6.35 (s, 1H), 3.98 (s, 6H), 1.25 (s, 9H); LC-MS (ESI) m/z 589 (M+H)$^+$.

Example 342

Preparation of 1-(3-tert-butyl-1-o-tolyl-1H-pyrazol-5-yl)-3-(3-(6,7-dimethoxyquinazolin-4-yloxy)phenyl)urea Example 342A Step 1: Following the procedure for Example 282A Step 1, substituting 2,4-dimethylphenylhydrazine hydrochloride for o-tolylhydrazine afforded 3-tert-butyl-1-o-tolyl-1H-pyrazol-5-amine (973 mg, 53% yield). LC-MS (ESI) m/z 230 (M+H)$^+$ Example 342A Step 2: Following the procedure for Example 282A Step 2, using 3-tert-butyl-1-o-tolyl-1H-pyrazol-5-amine from step A afforded phenyl 3-tert-butyl-1-o-tolyl-1H-pyrazol-5-ylcarbamate (730 mg, 49% yield). LC-MS (ESI) m/z 350 (M+H)$^+$ Example 342B The title compound was prepared from 3-(6,7-dimethoxyquinazolin-4-yloxy)aniline (89 mg, 0.3 mmol) and the carbamate from the previous step (115 mg, 0.33 mmol) using procedure in Example 115C to give 1-(3-tert-butyl-1-o-tolyl-1H-pyrazol-5-yl)-3-(3-(6,7-dimethoxyquinazolin-4-yloxy)phenyl)urea (111 mg, 0.20 mmol, 67%). $^1$H NMR (300 MHz, DMSO-d$_6$) δ 9.13 (s, 1H), 8.55 (s, 1H), 8.23 (s, 1H), 7.57 (s, 1H), 7.55 (s, 1H), 7.46-7.33 (m, 6H), 7.12 (d, 1H), 6.93 (d, 1H), 6.34 (s, 1H), 4.00 (s, 3H), 3.98 (s, 3H), 2.00 (s, 3H), 1.26 (s, 9H); LC-MS (ESI) m/z 553 (M+H)$^+$.

Example 343

Preparation of 1-(3-tert-butyl-1-o-tolyl-1H-pyrazol-5-yl)-3-(3-(6,7-dimethoxyquinazolin-4-ylthio)phenyl)urea The title compound was prepared from 3-(6,7-dimethoxyquinazolin-4-ylthio)aniline (94 mg, 0.3 mmol) and the carbamate from Example 343A (115 mg, 0.33 mmol) using the procedure in Example 115C to give 1-(3-tert-butyl-1-o-tolyl- 1H-pyrazol-5-yl)-3-(3-(6,7-dimethoxyquinazolin-4-ylthio) phenyl)urea (118 mg, 0.21 mmol, 77%). $^1$H NMR (300 MHz, DMSO-d$_6$) δ 9.13 (s, 1H), 8.68 (s, 1H), 8.23 (s, 1H), 7.79 (s, 1H), 7.43-7.32 (m, 8H), 7.23 (d, 1H), 6.35 (s, 1H), 3.99 (s, 6H), 2.01 (s, 3H), 1.27 (s, 9H); LC-MS (ESI) m/z 569 (M+H)$^+$.

Example 344

Preparation of 1-(3-tert-Butyl-1-(pyridin-2-yl)-1H-pyrazol-5-yl)-3-(3-(6,7-dimethoxyquinazolin-4-yloxy)phenyl)urea Example 344A Step 1: 3-tert-Butyl-1-(pyridin-2-yl)-1H-pyrazol-5-amine was obtained following the procedure described in Example 274A Step 1 for synthesis of 3-tert-butyl-1-p-tolyl-1H-pyrazol-5-amine, substituting p-tolylhydrazine hydrochloride with 2-hydrazinylpyridine dihydrochloride (1.874 g, 85% yield). LC-MS (ESI) m/z 217 (M+H)$^+$.

Example 344A

Step 2: Phenyl 3-tert-butyl-1-(pyridin-2-yl)-1H-pyrazol-5-ylcarbamate was obtained following the procedure described in Example 274A Step 2 for synthesis of phenyl 3-tert-butyl-1-p-tolyl-1H-pyrazol-5-ylcarbamate, substituting 3-tert-butyl-1-p-tolyl-1H-pyrazol-5-amine with 3-tert-butyl-1-(pyridin-2-yl)-1H-pyrazol-5-amine (2.845 g, 99%). $^1$H NMR (300 MHz, CDCl$_3$) δ 1.34 (s, 9H), 6.62 (s, 1H), 7.24 (m, 4H), 7.42 (t, 2H), 7.83 (t, 1H), 8.09 (d, 1H), 8.36 (d, 1H), 11.84 (s, 1H); LC-MS (ESI) m/z 337 (M+H)$^+$.

Example 344B 1-(3-tert-Butyl-1-(pyridin-2-yl)-1H-pyrazol-5-yl)-3-(3-(6,7-dimethoxyquinazolin-4-yloxy)phenyl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting phenyl 3-tert-butyl-1-p-tolyl-1H-pyrazol-5-ylcarbamate with phenyl 3-tert-butyl-1-(pyridin-2-yl)-1H-pyrazol-5-ylcarbamate (0.127 g, 59%). $^1$H NMR (300 MHz, DMSO-d$_6$) δ 1.28 (s, 9H), 3.99 (s, 3H), 4.00 (s, 3H), 6.59 (s, 1H), 6.98 (d, 1H), 7.32 (m, 2H), 7.40 (m, 2H), 7.57 (s, 1H), 7.66 (s, 1H), 7.91 (d, 1H), 8.01 (t, 1H), 8.48 (d, 1H), 8.57 (s, 1H), 10.13 (s, 1H), 11.27 (s, 1H); LC-MS (ESI) m/z 540 (M+H)$^+$.

Example 345

Preparation of 1-(3-tert-butyl-1-(pyridin-2-yl)-1H-pyrazol-5-yl)-3-(3-(6,7-dimethoxyquinazolin-4-ylthio)phenyl)urea 1-(3-tert-Butyl-1-(pyridin-2-yl)-1H-pyrazol-5-yl)-3-(3-(6,7-dimethoxyquinazolin-4-ylthio)phenyl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting phenyl 3-tert-butyl-1-p-tolyl-1H-pyrazol-5-ylcarbamate with phenyl 3-tert-butyl-1-(pyridin-2-yl)-1H-pyrazol-5-ylcarbamate in Example 344A, and 3-(6,7-dimethoxyquinazolin-4-yloxy)aniline with 3-(6,7-dimethoxyquinazolin-4-ylthio)aniline in Example 115 (0.017 g, 7.7%). $^1$H NMR (300 MHz, DMSO-d$_6$) δ 1.29 (s, 9H), 4.00 (s, 6H), 6.60 (s, 1H), 7.27-7.36 (m, 4H), 7.46 (t, 1H), 7.63 (d, 1H), 7.91 (d, 2H), 8.02 (dt, 1H), 8.47 (d, 1H), 8.71 (s, 1H), 10.12 (s, 1H), 11.28 (s, 1H); LC-MS (ESI) m/z 556 (M+H)$^+$.

Example 346

Preparation of 1-(3-(6,7-dimethoxyquinazolin-4-yloxy)phenyl)-3-(1-p-tolyl-3-(1-(trifluoromethyl) cyclopropyl)-1H-pyrazol-5-yl)urea Example 346A Step 1: To a solution of 3-oxo-3-(1-(trifluoromethyl)cyclopropyl)propanenitrile (500 mg, 2.8 mmol) (from Example 137A Step 2) in EtOH (10 mL) was added water (7.2 mL) and 1 M NaOH (2.8 mL) followed by p-tolylhydrazine hydrochloride (444 mg, 2.8 mmol) and the solution heated at 80° C. overnight. The solution was cooled to rt, diluted with water and extracted with 2 portions of EtOAc. The combined extracts were washed with brine, dried over magnesium sulfate, filtered, and concentrated. The crude solid was purified using silica gel chromatography using a gradient of 5-25% EtOAc/hexane to give 1-p-tolyl-3-(1-(trifluoromethyl)cyclopropyl)-1H-pyrazol-5-amine (452 mg, 57% yield). LC-MS (ESI) m/z 282 (M+H)$^+$ Example 346A Step 2: To a solution of 1-p-tolyl-3-(1-(trifluoromethyl) cyclopropyl)-1H-pyrazol-5-amine (574 mg, 2.0 mmol) in DCM (20 mL) was added K$_2$CO$_3$ (423 mg, 3.06 mmol) and phenyl chloroformate (386 μL, 3.06 mmol). The solution was stirred at rt overnight. The reaction mixture was filtered and the solids washed with DCM, the filtrate concentrated and purified using silica gel chromatography eluting with an EtOAC/Hexane gradient (5-20%) to give phenyl 1-p-tolyl-3-(1-(trifluoromethyl)cyclopropyl)-1H-pyrazol-5-ylcarbamate (1.04 g, quantitative yield). $^1$H NMR (300 MHz, DMSO d$_6$) δ 1.33 (m, 4H), 2.34 (s, 3H), 6.51 (s, 1H), 7.12 (m, 2H), 7.23 (m, 1H), 7.37 (m, 6H), 10.13 (s, 1H); LC-MS (ESI) m/z 402 (M+H)$^+$ Example 346B The title compound was prepared from 3-(6,7-dimethoxyquinazolin-4-yloxy)aniline (89 mg, 0.3 mmol) and the carbamate from the previous step (120 mg, 0.3 mmol) using the procedure in Example 115C to give 1-(3-(6,7-dimethoxyquinazolin-4-yloxy)phenyl)-3-(1-p-tolyl-3-(1-(trifluoromethyl)cyclopropyl)-1H-pyrazol-5-yl)urea (170 mg, 0.28 mmol, 94%). $^1$H NMR (300 MHz, DMSO-d$_6$) δ 9.27 (s, 1H), 8.55 (br s, 2H), 7.56 (br s, 2H), 7.54-7.32 (m, 6H), 7.17 (d, 1H), 6.94 (d, 1H), 6.54 (s, 1H), 3.99 (s, 6H), 2.38 (s, 3H), 1.40-1.25 (m, 4H); LC-MS (ESI) m/z 605 (M+H)$^+$.

Example 347

Preparation of 1-(3-(6,7-dimethoxyquinazolin-4-ylthio)phenyl)-3-(1-p-tolyl-3-(1-(trifluoromethyl) cyclopropyl)-1H-pyrazol-5-yl)urea The title compound was prepared from 3-(6,7-dimethoxyquinazolin-4-ylthio)aniline (94 mg, 0.3 mmol) and the carbamate from Example 346A (120 mg, 0.3 mmol) using the procedure in Example 115C to give 1-(3-(6,7-dimethoxyquinazolin-4-ylthio)phenyl)-3-(1-p-tolyl-3-(1-(trifluoromethyl)cyclopropyl)-1H-pyrazol-5-yl)urea (152 mg, 0.25 mmol, 82%). ¹H NMR (300 MHz, DMSO-d₆) δ 9.28 (s, 1H), 8.69 (s, 1H), 8.55 (s, 1H), 7.79 (s, 1H), 7.51-7.32 (m, 8H), 7.25 (d, 1H), 6.54 (s, 1H), 3.99 (s, 6H), 2.38 (s, 3H), 1.38-1.27 (m, 4H); LC-MS (ESI) m/z 621 (M+H)⁺.

Example 348

Preparation of 1-(3-(6,7-dimethoxyquinazolin-4-yloxy)phenyl)-3-(3-isopropyl-1-(4-methoxyphenyl)-1H-pyrazol-5-yl)urea

Example 348A

Step 1: Using the procedure described in Example 308A Step 1, to a solution of 4-methyl-3-oxopentanenitrile (514 mg, 4.5 mmol) prepared as described in Example 122A Step 1, in anhydrous EtOH (15 ml) was added (4-methoxyphenyl) hydrazine hydrochloride (524 mg, 3.0 mmol) and the reaction mixture was heated at 80° C. overnight. The residue was purified by silica gel chromatography (DCM/EtOAc 1:1) to afford 3-isopropyl-1-(4-methoxyphenyl)-1H-pyrazol-5-amine (333 mg, 48%) as a solid. ¹H NMR (300 MHz, CDCl₃) δ 1.26 (d, J=7 Hz, 6H), 2.92 (m, 1H), 3.66 (s, 2H), 3.83 (s, 3H), 5.46 (s, 1H), 6.96 (d, J=9 Hz, 2H), 7.44 (d, J=9 Hz, 2H); LC-MS (ESI) m/z 232 (M+H)⁺.

Example 348A

Step 2: Using the procedure described in Example 306A, to a solution of 3-isopropyl-1-(4-methoxyphenyl)-1H-pyrazol-5-amine (333 mg, 1.45 mmol) and potassium carbonate (261 mg, 1.89 mmol) in anhydrous DCM (5.3 ml) was added dropwise phenyl chloroformate (0.55 ml, 4.34 mmol) as a solution in DCM (3.5 ml). The crude was purified by silica gel chromatography (DCM/MeOH 0-10%) to afford phenyl 3-isopropyl-1-(4-methoxyphenyl)-1H-pyrazol-5-ylcarbamate (500 mg, 98%). ¹H NMR (300 MHz, CDCl₃) δ 1.30 (d, J=7 Hz, 6H), 2.99 (m, 1H), 3.87 (s, 3H), 6.41 (s, 1H), 7.03 (d, J=9 Hz, 2H), 7.11-7.14 (m, 2H), 7.23-7.26 (m, 2H), 7.35-7.42 (m, 4H); LC-MS (ESI) m/z 352 (M+H)⁺.

Example 348B

Using the procedure described in Example 306A, to a solution of 3-(6,7-dimethoxyquinazolin-4-yloxy)aniline (89 mg, 0.3 mmol), prepared as described in Example 113A, in THF (3.3 ml) was added DMAP (20 mg, 0.16 mmol) and phenyl 3-isopropyl-1-(4-methoxyphenyl)-1H-pyrazol-5-ylcarbamate (105 mg, 0.3 mmol), described in the previous step, to afford 1-(3-(6,7-dimethoxyquinazolin-4-yloxy)phenyl)-3-(3-isopropyl-1-(4-methoxyphenyl)-1H-pyrazol-5-yl)urea (65 mg, 39%) as a solid. ¹H NMR (300 MHz, DMSO-d₆) δ 1.20 (d, J=7 Hz, 6H), 2.85 (m, 1H), 3.81 (s, 3H), 3.97 (s, 6H), 6.27 (s, 1H), 6.91 (d, J=7.5 Hz, 1H), 7.07 (d, J=9 Hz, 2H), 7.16 (d, J=9 Hz, 1H), 7.33-7.41 (m, 4H), 7.55 (s, 2H), 8.35 (s, 1H), 8.55 (s, 1H), 9.18 (s, 1H); LC-MS (ESI) m/z 555 (M+H)⁺.

Example 349

Preparation of 1-(3-(6,7-dimethoxyquinazolin-4-ylthio)phenyl)-3-(3-isopropyl-1-(4-methoxyphenyl)-1H-pyrazol-5-yl)urea Using the procedure described in Example 306A, to a solution of 3-(6,7-dimethoxyquinazolin-4-ylthio)aniline (94 mg, 0.3 mmol), prepared as described in Example 115B, in THF (3.3 ml) was added DMAP (23 mg, 0.18 mmol) and phenyl 3-isopropyl-1-(4-methoxyphenyl)-1H-pyrazol-5-ylcarbamate (105 mg, 0.3 mmol), described in Example 348A, to afford 1-(3-(6,7-dimethoxyquinazolin-4-ylthio)phenyl)-3-(3-isopropyl-1-(4-methoxyphenyl)-1H-pyrazol-5-yl)urea (101 mg, 59%) as a solid. ¹H NMR (300 MHz, DMSO-d₆) δ 1.21 (d, J=7 Hz, 6H), 2.86 (s, 1H), 3.81 (s, 3H), 3.99 (s, 6H), 6.28 (s, 1H), 7.07 (d, J=8.7 Hz, 2H), 7.23 (d, J=7.5 Hz, 1H), 7.34 (d, J=5 Hz, 2H), 7.39-7.44 (m, 4H), 7.79 (s, 1H), 8.35 (s, 1H), 8.68 (s, 1H), 9.18 (s, 1H); LC-MS (ESI) m/z 571 (M+H)⁺.

Example 350

Preparation of 1-(3-(6,7-dimethoxyquinazolin-4-yloxy)phenyl)-3-(3-isopropyl-1-(pyridin-3-yl)-1H-pyrazol-5-yl)urea

Example 350A

Step 1: Using the procedure described in Example 308A Step 1, to a solution of 4-methyl-3-oxopentanenitrile (303 mg, 2.7 mmol) prepared as described in Example 122A Step 1, in anhydrous EtOH (13 ml) was added 3-hydrazinylpyridine hydrochloride (450 mg, 3.1 mmol) and the reaction mixture was heated at 80° C. overnight to afford 3-isopropyl-1-(pyridin-3-yl)-1H-pyrazol-5-amine (179 mg, 28%) as a solid. ¹H NMR (300 MHz, CDCl₃) δ 1.25 (d, J=7 Hz, 6H), 2.90-2.99 (m, 1H), 3.93 (brs, 2H), 5.50 (s, 1H), 7.36-7.38 (m, 1H), 7.96 (d, J=8 Hz, 1H), 8.49 (d, J=7 Hz, 1H), 8.67 (s, 1H); LC-MS (ESI) m/z 203 (M+H)⁺.

Example 350A

Step 2: Using the procedure described in Example 306A, to a solution of 3-isopropyl-1-(pyridin-3-yl)-1H-pyrazol-5-amine (179 mg, 0.89 mmol) and potassium carbonate (159 mg, 1.2 mmol) in anhydrous DCM (3 ml) was added dropwise phenyl chloroformate (0.33 ml, 2.6 mmol) as a solution in DCM (0.2 ml). The crude was purified by silica gel chromatography (DCM/MeOH 0-10%) to afford phenyl 3-isopropyl-1-(pyridin-3-yl)-1H-pyrazol-5-ylcarbamate (217 mg, 76%). ¹H NMR (300 MHz, CDCl₃) δ 1.29 (s, 6H), 2.99 (m, 1H), 6.39 (s, 1H), 6.67 (s, 1H), 7.08-7.32 (m, 6H), 7.99 (d, J=7 Hz, 1H), 8.34 (s, 1H), 8.45 (d, J=7 Hz, 1H); LC-MS (ESI) m/z 323 (M+H)⁺.

Example 350B

Using the procedure described in Example 306B, to a solution of 3-(6,7-dimethoxyquinazolin-4-yloxy)aniline (91 mg, 0.3 mmol), prepared as described in Example 113A, in THF (2 ml) was added DMAP (20 mg, 0.16 mmol) and phenyl 3-isopropyl-1-(pyridin-3-yl)-1H-pyrazol-5-ylcarbamate (110 mg, 0.34 mmol), described in the previous step. The crude was purified by silica gel chromatography (DCM/MeOH 2-10%) to afford 1-(3-(6,7-dimethoxyquinazolin-4-yloxy)phenyl)-3-(3-isopropyl-1-(pyridin-3-yl)-1H-pyrazol-5-yl)urea (91 mg, 58%) as a solid. ¹H NMR (300 MHz, DMSO-d₆) δ 1.22 (d, J=7 Hz, 6H), 2.89 (m, 1H), 3.99 (s, 6H), 6.35 (s, 1H), 6.92 (d, J=7.8 Hz, 1H), 7.19 (d, J=7.8 Hz, 1H), 7.34-7.39 (m, 2H), 7.52-7.55 (m, 3H), 7.97 (d, J=7.2 Hz, 1H), 8.55 (s, 1H), 8.58-8.60 (m, 2H), 8.77 (d, J=2.4 Hz, 1H), 9.19 (s, 1H); LC-MS (ESI) m/z 526 (M+H)⁺.

Example 351

Preparation of 1-(3-(6,7-dimethoxyquinazolin-4-ylthio)phenyl)-3-(3-isopropyl-1-(pyridin-3-yl)-1H-pyrazol-5-yl)urea Using the procedure described in Example 306A, to a solution of 3-(6,7-dimethoxyquinazolin-4-ylthio)aniline (92 mg, 0.3 mmol), prepared as described in Example 115B, in THF (2 ml) was added DMAP (20 mg, 0.16 mmol) and phenyl 3-isopropyl-1-(pyridin-3-yl)-1H-pyrazol-5-ylcarbamate (106 mg, 0.33 mmol), described in Example 350A. The crude was purified by silica gel chromatography (DCM/MeOH 2-10%) to afford 1-(3-(6,7-dimethoxyquinazolin-4-ylthio)phenyl)-3-(3-isopropyl-1-(pyridin-3-yl)-1H-pyrazol-5-yl)urea (47 mg, 28%) as a solid. $^1$H NMR (300 MHz, DMSO-$d_6$) δ 1.23 (d, J=7 Hz, 6H), 2.90 (m, 1H), 3.99 (s, 6H), 6.36 (s, 1H), 7.24 (d, J=7.5 Hz, 1H), 7.35 (d, J=4.8 Hz, 1H), 7.40-7.47 (m, 3H), 7.56 (dd, J=4.8, 1H), 7.77 (s, 1H), 7.97 (d, J=8.1 Hz, 1H), 8.58 (d, J=4.8 Hz, 2H), 8.69 (s, 1H), 8.78 (d, J=2.4 Hz, 1H), 9.19 (s, 1H); LC-MS (ESI) m/z 542 (M+H)$^+$.

Example 352

Preparation of 1-(3-(6,7-dimethoxyquinazolin-4-yloxy)phenyl)-3-(3-ethyl-1-phenyl-1H-pyrazol-5-yl)urea

Example 352A

Step 1: A stirred suspension of sodium hydride (12 g of a 60% dispersion in mineral oil, 0.30 mol, which was washed with petroleum ether twice in dry THF) in THF (100 mL) was heated to 75° C. To this was added a mixture of ethyl propionate (20.42 g, 0.20 mol) and dry acetonitrile (12.32 g, 0.30 mol), dropwise, and the resulting colorless suspension was heated at 70° C. for 24 h. After cooling to rt the reaction mixture was concentrated under reduced pressure and the residue poured into water (100 mL) and extracted with ethyl acetate (100 mL). The aqueous layer was separated, acidified to pH 2 with aqueous 2 M HCl and extracted with diethyl ether (2×200 mL). The combined diethyl ether layers were dried over magnesium sulfate then concentrated under reduced pressure to afford 3-oxopentanenitrile as yellow oil (20 g) which was used in the next step without further purification.

Example 352A

Step 2: A stirred mixture of 3-oxopentanenitrile (19.42 g, 0.20 mol) and phenylhydrazine (23.62 g, 0.20 mol) in ethanol (200 mL) was heated at 90° C. for 15 h. The reaction mixture was quenched with water and extracted with dichloromethane. The combined dichloromethane layers were dried over magnesium sulfate, concentrated under reduced pressure, and dried under vacuum to afford the light yellow oil which was purified by silica gel flash column chromatography (eluting with a mixture of 20% ethyl acetate in petroleum ether). The obtained solid was recrystallized from a mixture of 10% petroleum ether in ethyl acetate, to afford 3-ethyl-1-phenyl-1H-pyrazol-5-amine (14 g, 37% over two steps) as a yellow solid. $^1$H NMR (400 MHz, DMSO-$d_6$) δ7.57-7.59 (m, 2H), 7.43-7.46 (m, 2H), 7.27 (m, 1H), 5.36 (s, 1H), 5.26 (s, 2H), 2.45 (q, J=7.6 Hz, 2H), 1.15 (t, J=7.6 Hz, 3H); LC-MS (ESI) m/z 188 (M+H)$^+$.

Example 352A

Step 3: To a stirred mixture of 3-ethyl-1-phenyl-1H-pyrazol-5-amine (1.00 g, 5.34 mmol) and potassium carbonate (1.48 g, 10.68 mmol) in THF (50 mL) at −5° C., was added phenyl chloroformate (1.00 g, 6.41 mmol) dropwise. After stirring for a further 30 min at −5° C., the reaction mixture it was warmed to rt and stirred for a further 15 h. The mixture was quenched with water and extracted with dichloromethane. The combined dichloromethane layers were dried over magnesium sulfate, concentrated under reduced pressure, and dried under vacuum to afford an oil. Recrystallization from petroleum ether gave phenyl 3-ethyl-1-phenyl-1H-pyrazol-5-ylcarbamate (1.00 g, 61%) as a colorless solid. $^1$H NMR (400 MHz, DMSO-$d_6$) δ 10.07 (brs, 1H), 6.74-7.59 (m, 10H), 6.30 (s, 1H), 2.60 (q, J=7.6 Hz, 2H), 1.21 (t, J=7.6 Hz, 3H); LC-MS (ESI) m/z 308 (M+H)$^+$.

Example 352B

A stirred mixture of phenyl 3-ethyl-1-phenyl-1H-pyrazol-5-ylcarbamate (0.15 g, 0.50 mmol) and 3-(6,7-dimethoxyquinazolin-4-yloxy)aniline (prepared as described in Example 113A) (0.15 g, 0.50 mmol) in DMSO (2 mL) was heated at 70° C. for 15 h. After cooling to rt, the reaction mixture was diluted with ethyl acetate (50 mL) and washed with water (2×20 mL). The organic layer was separated, dried over magnesium sulfate, and concentrated under reduced pressure to afford an oil. Purification via preparative silica gel thin-layer chromatography (eluting with a mixture of 8% methanol in dichloromethane containing 0.5% ammonia) followed by recrystallization from diethyl ether afforded 1-(3-(6,7-dimethoxyquinazolin-4-yloxy)phenyl)-3-(3-ethyl-1-phenyl-1H-pyrazol-5-yl)urea (80 mg, 32%) as a colorless solid. $^1$H NMR (400 MHz, DMSO-$d_6$) 89.21 (s, 1H), 8.55 (s, 1H), 8.50 (s, 1H), 7.52-7.55 (m, 6H), 7.34-7.42 (m, 3H), 7.18 (m, 1H), 6.92 (m, 1H), 6.30 (s, 1H), 3.99 (s, 3H), 3.98 (s, 3H), 2.56 (m, 2H), 1.19 (m, 3H); LC-MS (ESI) m/z 511 (M+H)$^+$.

Example 353

Preparation of 1-(3-cyclopropyl-1-phenyl-1H-pyrazol-5-yl)-3-(3-(6,7-dimethoxyquinazolin-4-yloxy)phenyl)urea

Example 353A

Step 1: A stirred suspension of sodium hydride (5.47 g of a 60% dispersion in mineral oil, 137 mmol) in THF (200 mL) was heated to 75° C. To this was added a mixture of ethyl cyclopropanecarboxylate (10 g, 88 mmol) and acetonitrile (5.62 g, 137 mmol), dropwise over the course of 30 min. The resulting suspension was heated at 70° C. for a further 15 h. After cooling to rt, the reaction mixture was poured into water and the resulting solution was extracted with ethyl ether. The aqueous layer was separated, acidified to pH 2 with aqueous 2M HCl, and extracted with ethyl ether. The combined ether layers were dried over magnesium sulfate and then concentrated under reduced pressure to give a yellow oil (10 g). The yellow oil was dissolved in a mixture of ethanol (200 mL) and phenylhydrazine (10.46 g, 97 mmol), and the resulting solution was heated to reflux for 28 h. After cooling to rt, the reaction mixture was concentrated under reduced pressure and the residue was washed with ethyl ether to afford 3-cyclopropyl-1-phenyl-1H-pyrazol-5-amine (8.32 g, 47%) as a pale yellow solid. $^1$H NMR (400 MHz, DMSO-$d_6$) δ7.56-7.57 (m, 2H), 7.43-7.47 (m, 2H), 7.27 (m, 1H), 5.25 (s, 2H), 5.19 (s, 1H), 1.76 (m, 1H), 0.80-0.85 (m, 2H), 0.60-0.63 (m, 2H).

Example 353A

Step 2: To a stirred solution of 3-cyclopropyl-1-phenyl-1H-pyrazol-5-amine (1.00 g, 5.03 mmol) and triethylamine (0.66 g, 6.53 mmol) at rt, was added phenyl chloroformate (0.94 g, 6.01 mmol). The reaction mixture was stirred at rt for 15 h. The reaction mixture was partitioned between a mixture of dichloromethane (20 mL) and water (20 mL) and the organic layer was washed thrice with water, dried over sodium sulfate, filtered and concentrated under reduced pressure to give yellow oil. Trituration with cyclohexane afforded phenyl 3-cyclopropyl-1-phenyl-1H-pyrazol-5-ylcarbamate (1.01 g, 63%) as a colorless solid. $^1$H NMR (400 MHz, DMSO-$d_6$) δ 10.05 (s, 1H), 6.71-7.55 (m, 10H), 6.18 (s, 1H), 1.92 (m, 1H), 0.91 (m, 2H), 0.73 (m, 2H).

Example 353B

A stirred mixture of phenyl 3-cyclopropyl-1-phenyl-1H-pyrazol-5-ylcarbamate (125 mg, 0.39 mmol) and 3-(6,7-dimethoxyquinazolin-4-yloxy)aniline (prepared as described in Example 113A) (100 mg, 0.34 mmol) in DMSO (1 mL) was heated to 70° C. for 18 h. After cooling to rt, water (20 mL) was added. The resulting suspension was filtered and the collected solid purified via preparative silica gel thin-layer chromatography (eluting with a mixture of 10:10:1 ethyl acetate: dichloromethane: methanol) to give a solid which was triturated with diethyl ether (50 mL) to afford 1-(3-cyclopropyl-1-phenyl-1H-pyrazol-5-yl)-3-(3-(6,7-dimethoxyquinazolin-4-yloxy)phenyl)urea (58 mg, 33%) as a colorless solid. $^1$H NMR (400 MHz, DMSO-$d_6$) δ 9.21 (s, 1H), 8.55 (s, 1H), 8.49 (s, 1H), 7.51-7.55 (m, 6H), 7.34-7.39 (m, 3H), 7.17 (m, 1H), 6.91 (m, 1H), 6.14 (s, 1H), 3.99 (s, 3H), 3.98 (s, 3H), 1.86 (m, 1H), 0.86-0.88 (m, 2H), 0.65-0.67 (m, 2H); LC-MS (ESI) m/z 523 (M+H)$^+$.

Example 354

Preparation of 1-(3-cyclopropyl-1-phenyl-1H-pyrazol-5-yl)-3-(3-(6,7-dimethoxyquinazolin-4-ylthio)phenyl)urea A stirred mixture of phenyl 3-cyclopropyl-1-phenyl-1H-pyrazol-5-ylcarbamate as described in Example 353A (250 mg, 0.78 mmol) and 3-(6,7-dimethoxyquinazolin-4-ylthio)aniline (prepared as described in Example 115B) (200 mg, 0.64 mmol) in DMSO (1 mL) was heated to 40° C. for 48 h. After cooling to rt, water (20 mL) was added. The resulting suspension was filtered and the collected solid purified via preparative silica gel thin-layer chromatography (eluting with a mixture of 10:10:1 ethyl acetate: dichloromethane: methanol) to give a solid which was triturated with diethyl ether (50 mL) to afford 1-(3-cyclopropyl-1-phenyl-1H-pyrazol-5-yl)-3-(3-(6,7-dimethoxyquinazolin-4-ylthio)phenyl) urea (162 mg, 47%) as a colorless solid. $^1$H NMR (400 MHz, DMSO-$d_6$) δ 9.21 (s, 1H), 8.68 (s, 1H), 8.49 (s, 1H), 7.77 (s, 1H), 7.22-7.51 (m, 10H), 6.15 (s, 1H), 3.99 (s, 6H), 1.86 (m, 1H), 0.85-0.91 (m, 2H), 0.65-0.68 (m, 2H); LC-MS (ESI) m/z 539 (M+H)$^+$.

Example 355

Preparation of 1-(3-cyclobutyl-1-phenyl-1H-pyrazol-5-yl)-3-(3-(6,7-dimethoxyquinazolin-4-yloxy)phenyl)urea Example 355A Step 1: A stirred suspension of sodium hydride (12 g of a 60% dispersion in mineral oil, 0.30 mol, which was washed with petroleum ether twice in dry THF) was heated to 75° C. To this was added a mixture of ethyl cyclobutanecarboxylate (25.64 g, 0.20 mol) and dry acetonitrile (12.32 g, 0.30 mol), dropwise, and the resulting colorless suspension was heated at 70° C. for 24 h. After cooling to rt the reaction mixture was concentrated under reduced pressure and the residue poured into water (100 mL) and extracted with ethyl acetate (100 mL). The aqueous layer was separated, acidified to pH 2 with aqueous 2 M HCl and extracted with diethyl ether (2×200 mL). The combined diethyl ether layers were dried over magnesium sulfate then concentrated under reduced pressure to afford 3-cyclobutyl-3-oxopropanenitrile as yellow oil which was used in the next step without further purification.

Example 355A

Step 2: A stirred mixture of 3-cyclobutyl-3-oxopropanenitrile (24.6 g, 0.20 mol) and phenylhydrazine (23.62 g, 0.20 mol) in ethanol (200 mL) was heated at 90° C. for 15 h. The reaction mixture was quenched with water and extracted with dichloromethane. The combined dichloromethane layers were dried over magnesium sulfate, concentrated under reduced pressure to give a solid which was triturated with a mixture of 10% petroleum ether in ethyl acetate, followed by trituration with diethyl ether to afford 3-cyclobutyl-1-phenyl-1H-pyrazol-5-amine (18.20 g, 43% over two steps) as a colorless solid. $^1$H NMR (400 MHz, DMSO-$d_6$) δ 7.55-7.57 (m, 2H), 7.42-7.46 (m, 2H), 7.26 (m, 1H), 5.40 (s, 1H), 5.25 (s, 2H), 3.33 (m, 1H), 2.05-2.50 (m, 4H), 1.82-1.96 (m, 2H).

Example 355A

Step 3: To a stirred mixture of 3-cyclobutyl-1-phenyl-1H-pyrazol-5-amine (1.00 g, 4.69 mmol) and potassium carbonate (1.48 g, 10.68 mmol) in THF (50 mL) at −5° C., was added phenyl chloroformate (0.88 g, 5.62 mmol) dropwise. After stirring for a further 30 min at −5° C., the reaction mixture was warmed to rt and stirred for a further 15 h. The mixture was quenched with water and extracted with dichloromethane. The combined dichloromethane layers were dried over magnesium sulfate, concentrated under reduced pressure, and dried under vacuum to afford an oil. Recrystallization from petroleum ether gave phenyl 3-cyclobutyl-1-phenyl-1H-pyrazol-5-ylcarbamate (1.30 g, 83%) as a colorless solid. $^1$H NMR (400 MHz, CDCl$_3$) δ 6.53-7.53 (m, 12H), 3.57 (m, 1H), 2.26-2.38 (m, 4H), 1.64-2.07 (m, 2H); LC-MS (ESI) m/z 334 (M+H)$^+$.

Example 355B 1-(3-cyclobutyl-1-phenyl-1H-pyrazol-5-yl)-3-(3-(6,7-dimethoxyquinazolin-4-yloxy)phenyl)urea was prepared from phenyl 3-cyclobutyl-1-phenyl-1H-pyrazol-5-ylcarbamate and 3-(6,7-dimethoxyquinazolin-4-yloxy)aniline (prepared as described in Example 113A) according to the procedure given in Example 352B. $^1$H NMR (400 MHz, DMSO-$d_6$) δ 9.21 (s, 1H), 8.55 (s, 1H), 8.49 (s, 1H), 7.51-7.55 (m, 6H), 7.34-7.42 (m, 3H), 7.18 (m, 1H), 6.92 (m, 1H), 6.36 (s, 1H), 3.99 (s, 3H), 3.98 (s, 3H), 3.35 (m, 1H), 2.08-2.26 (m, 4H), 1.84-1.99 (m, 2H); LC-MS (ESI) m/z 537 (M+H)$^+$.

Example 356

Preparation of 1-(3-cyclobutyl-1-phenyl-1H-pyrazol-5-yl)-3-(3-(6,7-dimethoxyquinazolin-4-ylthio)phenyl)urea 1-(3-cyclobutyl-1-phenyl-1H-pyrazol-5-yl)-3-(3-(6,7-dimethoxyquinazolin-4-ylthio)phenyl)urea was prepared from phenyl 3-cyclobutyl-1-phenyl-1H-pyrazol-5-ylcarbamate and 3-(6,7-dimethoxyquinazolin-4-ylthio)aniline (prepared as described in Example 115B) according to the procedure given in Example 352B. $^1$H NMR (400 MHz, DMSO-d$_6$) δ 9.24 (s, 1H), 8.69 (s, 1H), 8.50 (s, 1H), 7.78 (s, 1H), 7.22-7.53 (m, 10H), 6.38 (m, 1H), 3.99 (s, 6H), 3.44 (m, 1H), 2.14-2.50 (m, 4H), 1.23-1.99 (m, 2H); LC-MS (ESI) m/z 553 (M+H)$^+$.

Example 357

Preparation of 1-(1-benzyl-3-tert-butyl-1H-pyrazol-5-yl)-3-(3-(6,7-dimethoxyquinazolin-4-yloxy)phenyl)urea Example 357A Step 1: Following the procedure in Example 161A Step 3, benzylhydrazine (977 mg, 8.0 mmol) and 4,4-dimethyl-3-oxopentanenitrile (1.0 g, 8.0 mmol) to give 1-benzyl-3-tert-butyl-1H-pyrazol-5-amine (666 mg, 2.90 mmol, 36%). $^1$H NMR (300 MHz, DMSO-d$_6$) δ 7.32-7.21 (m, 3H), 7.09 (d, 2H), 5.17 (s, 1H), 5.05 (d, 4H), 1.15 (s, 9H); LC-MS (ESI) m/z 230 (M+H)$^+$.

Example 357A

Step 2: Following the procedure in Example 118A, 1-benzyl-3-tert-butyl-1H-pyrazol-5-amine (666 mg, 2.64 mmol) and phenyl chloroformate (1.0 mL, 8.0 mmol) to give phenyl 1-benzyl-3-tert-butyl-1H-pyrazol-5-ylcarbamate (565 mg, 1.62 mmol, 61%). $^1$H NMR (300 MHz, DMSO-d$_6$) δ 10.20 (br s, 1H), 7.43-7.10 (m, 10H), 6.14 (s, 1H), 5.29 (s, 1H), 1.22 (s, 9H); LC-MS (ESI) m/z 350 (M+H)$^+$.

Example 357B

The title compound was prepared from the carbamate from the previous step (105 mg, 0.30 mmol) and 3-(6,7-dimethoxyquinazolin-4-yloxy)aniline (90 mg, 0.30 mmol) using the procedure in Example 115C to give 1-(1-benzyl-3-tert-butyl-1H-pyrazol-5-yl)-3-(3-(6,7-dimethoxyquinazolin-4-yloxy)phenyl)urea (50 mg, 0.090 mmol, 30%). $^1$H NMR (300 MHz, DMSO-d$_6$) δ 9.00 (s, 1H), 8.59 (br s, 2H), 7.58-6.93 (m, 11H), 6.16 (s, 1H), 5.20 (br s, 2H), 3.98 (s, 6H), 1.21 (s, 9H); LC-MS (ESI) m/z 553 (M+H)$^+$.

Example 358

Preparation of 1-(1-benzyl-3-tert-butyl-1H-pyrazol-5-yl)-3-(3-(6,7-dimethoxyquinazolin-4-ylthio)phenyl)urea The title compound was prepared from the carbamate in Example 357A (105 mg, 0.30 mmol) and 3-(6,7-dimethoxyquinazolin-4-ylthio)aniline (95 mg, 0.30 mmol) using the procedure in Example 115C to give 1-(1-benzyl-3-tert-butyl-1H-pyrazol-5-yl)-3-(3-(6,7-dimethoxyquinazolin-4-ylthio)phenyl)urea (26 mg, 0.046 mmol, 15%). $^1$H NMR (300 MHz, DMSO-d$_6$) δ 9.00 (s, 1H), 8.68 (s, 1H), 8.59 (s, 1H), 7.81 (s, 1H), 7.41-7.24 (m, 8H), 7.06 (br s, 2H), 6.15 (s, 1H), 5.19 (br s, 2H), 3.98 (s, 6H), 1.21 (s, 9H); LC-MS (ESI) m/z 569 (M+H)$^+$.

Example 359

Preparation of 1-(3-tert-butyl-1-(3-fluorophenyl)-1H-pyrazol-5-yl)-3-(3-(6,7-dimethoxyquinazolin-4-yloxy)phenyl)urea Example 359A Step 1: The title compound was prepared from 3-Fluorophenylhydrazine hydrochloride (1.30 g, 8.0 mmol) and 4,4-Dimethyl-3-oxopentanenitrile (1.0 g, 8.0 mmol) using the procedure in Example 161A Step 3 to give 3-tert-butyl-1-(3-fluorophenyl)-1H-pyrazol-5-amine (1.24 g, 5.32 mmol, 67%). $^1$H NMR (300 MHz, DMSO-d$_6$) δ 7.49-7.41 (m, 3H), 7.10 (br s, 1H), 5.41 (s, 1H), 5.35 (br s, 2H), 1.21 (s, 9H); LC-MS (ESI) m/z 234 (M+H)$^+$.

Example 359A

Step 2: The title compound was prepared from 3-tert-butyl-1-(3-fluorophenyl)-1H-pyrazol-5-amine (1.24 mg, 5.32 mmol) and phenyl chloroformate (2.0 mL, 16.0 mmol) using the procedure in Example 118A to give phenyl 3-tert-butyl-1-(3-fluorophenyl)-1H-pyrazol-5-ylcarbamate (926 mg, 2.62 mmol, 49%). $^1$H NMR (300 MHz, DMSO-d$_6$) δ 9.23 (s, 1H), 8.68 (s, 1H), 8.53 (s, 1H), 7.79-7.23 (m, 8H), 6.38 (s, 1H), 1.27 (s, 9H); LC-MS (ESI) m/z 354 (M+H)$^+$.

Example 359B

The title compound was prepared from the carbamate from the previous step (105 mg, 0.30 mmol) and 3-(6,7-dimethoxyquinazolin-4-yloxy)aniline (90 mg, 0.30 mmol) using the procedure in Example 115C to give 1-(3-tert-butyl-1-(3-fluorophenyl)-1H-pyrazol-5-yl)-3-(3-(6,7-dimethoxyquinazolin-4-yloxy)phenyl)urea (39 mg, 0.070 mmol, 23%). $^1$H NMR (300 MHz, DMSO-d$_6$) δ 9.26 (s, 1H), 8.56 (br s, 2H), 7.58-7.54 (m, 3H), 7.45-7.35 (m, 4H), 7.25-7.20 (m, 2H), 6.92 (d, 1H), 6.39 (s, 1H), 3.99 (s, 6H), 1.27 (s, 9H); LC-MS (ESI) m/z 557 (M+H)$^+$.

Example 360

Preparation of 1-(3-tert-butyl-1-(3-fluorophenyl)-1H-pyrazol-5-yl)-3-(3-(6,7-dimethoxyquinazolin-4-ylthio)phenyl)urea The title compound was prepared from the carbamate in Example 359A (105 mg, 0.30 mmol) and 3-(6,7-dimethoxyquinazolin-4-ylthio)aniline (95 mg, 0.30 mmol) using the procedure in Example 115C to give 1-(3-tert-butyl-1-(3-fluorophenyl)-1H-pyrazol-5-yl)-3-(3-(6,7-dimethoxyquinazolin-4-ylthio)phenyl)urea (45 mg, 0.079 mmol, 26%). $^1$H NMR (300 MHz, DMSO-d$_6$) δ 9.26 (s, 1H), 8.69 (s, 1H), 8.55 (s, 1H), 7.80 (s, 1H), 7.57-7.23 (m, 9H), 6.38 (s, 1H), 4.01 (s, 6H), 1.27 (s, 9H); LC-MS (ESI) m/z 573 (M+H)$^+$.

Example 361

Preparation of 1-(3-tert-butyl-1-(4-methoxyphenyl)-1H-pyrazol-5-yl)-3-(3-(6,7-dimethoxyquinazolin-4-yloxy)phenyl)urea Example 361A Step 1: The title compound was prepared from 4-methoxyphenylhydrazine hydrochloride (1.39 g, 8.0 mmol) and 4,4- dimethyl-3-oxopentanenitrile (1.0 g, 8.0 mmol) using the procedure in Example 161A Step 3 to give 3-tert-butyl-1-(4-methoxyphenyl)-1H-pyrazol-5-amine (1.24 g, 4.08 mmol, 63%). $^1$H NMR (300 MHz, DMSO-d$_6$) δ 7.42 (d, 2H), 7.00 (d, 2H), 5.33 (s, 1H), 5.05 (s, 2H), 1.20 (s, 9H); LC-MS (ESI) m/z 246 (M+H)$^+$.

Example 361A

Step 2: The title compound was prepared from 3-tert-butyl-1-(4-methoxyphenyl)-1H-pyrazol-5-amine (1.24 g, 5.06 mmol) and phenyl chloroformate (1.90 mL, 15.0 mmol) using the procedure in Example 118A to give phenyl 3-tert-butyl-1-(4-methoxyphenyl)-1H-pyrazol-5-ylcarbamate (1.24 g, 3.40 mmol, 67%). $^1$H NMR (300 MHz, DMSO-d$_6$) δ 9.96 (br s, 1H), 7.44-7.06 (m, 9H), 6.31 (s, 1H), 3.81 (s, 3H), 1.27 (s, 9H); LC-MS (ESI) m/z 366 (M+H)$^+$.

Example 361B

The title compound was prepared from the carbamate from the previous step (109 mg, 0.30 mmol) and 3-(6,7-dimethoxyquinazolin-4-yloxy)aniline (89 mg, 0.30 mmol) using the procedure in Example 115C to give 1-(3-tert-butyl-1-(4-methoxyphenyl)-1H-pyrazol-5-yl)-3-(3-(6,7-dimethoxyquinazolin-4-yloxy)phenyl)urea (51 mg, 0.090 mmol, 30%). $^1$H NMR (300 MHz, DMSO-d$_6$) δ 9.21 (s, 1H), 8.55 (s, 1H), 8.36 (s, 1H), 7.58-7.40 (m, 6H), 7.18-6.91 (m, 4H), 6.32 (s, 1H), 3.99 (s, 6H), 3.81 (s, 3H), 1.25 (s, 9H); LC-MS (ESI) m/z 569 (M+H)$^+$.

Example 362

Preparation of 1-(3-tert-butyl-1-(4-methoxyphenyl)-1H-pyrazol-5-yl)-3-(3-(6,7-dimethoxyquinazolin-4-ylthio)phenyl)urea The title compound was prepared from the carbamate in Example 361A (110 mg, 0.30 mmol) and 3-(6,7-dimethoxyquinazolin-4-ylthio)aniline (94 mg, 0.30 mmol) using the procedure in Example 115C to give 1-(3-tert-butyl-1-(4-methoxyphenyl)-1H-pyrazol-5-yl)-3-(3-(6,7-dimethoxyquinazolin-4-ylthio)phenyl)urea (41 mg, 0.070 mmol, 23%). $^1$H NMR (300 MHz, DMSO-d$_6$) δ 9.21 (s, 1H), 8.68 (s, 1H), 8.35 (s, 1H), 7.80 (s, 1H), 7.42-7.32 (m, 6H), 7.24 (d, 1H), 7.08-7.06 (m, 2H), 6.32 (s, 1H), 3.98 (s, 6H), 3.81 (s, 3H), 1.24 (s, 9H); LC-MS (ESI) m/z 585 (M+H)$^+$.

Example 363

Preparation of 1-(3-tert-butyl-1-(3-chlorophenyl)-1H-pyrazol-5-yl)-3-(3-(6,7-dimethoxyquinazolin-4-yloxy)phenyl)urea Example 363A Step 1: The title compound was prepared from 3-chlorophenylhydrazine hydrochloride (1.43 g, 8.0 mmol) and 4,4-dimethyl-3-oxopentanenitrile (1.0 g, 8.0 mmol) using the procedure in Example 161A Step 3 to give 3-tert-butyl-1-(3-chlorophenyl)-1H-pyrazol-5-amine (1.42 g, 5.70 mmol, 71%). $^1$H NMR (300 MHz, DMSO-d$_6$) δ 7.67 (s, 1H), 7.61 (d, 1H), 7.46 (t, 1H), 7.30 (d, 1H), 5.42 (s, 1H), 5.34 (s, 2H), 1.09 (s, 9H); LC-MS (ESI) m/z 250 (M+H)$^+$.

Example 363A

Step 2: The title compound was prepared from 3-tert-butyl-1-(3-chlorophenyl)-1H-pyrazol-5-amine (1.42 g, 5.69 mmol) and phenyl chloroformate (2.2 mL, 17.1 mmol) using the procedure in Example 118A to give phenyl 3-tert-butyl-1-(3-chlorophenyl)-1H-pyrazol-5-ylcarbamate (394 mg, 1.07 mmol, 19%). $^1$H NMR (300 MHz, DMSO-d$_6$) δ 10.17 (br s, 1H), 7.62-7.58 (m, 3H), 7.48-7.39 (m, 3H), 7.25 (t, 1H), 7.09 (br s, 2H), 6.40 (s, 1H), 1.28 (s, 9H); LC-MS (ESI) m/z 370 (M+H)$^+$.

Example 363B

The title compound was prepared from the carbamate from the previous step (111 mg, 0.30 mmol) and 3-(6,7-dimethoxyquinazolin-4-yloxy)aniline (89 mg, 0.30 mmol) using the procedure in Example 115C to give 1-(3-tert-butyl-1-(3-chlorophenyl)-1H-pyrazol-5-yl)-3-(3-(6,7-dimethoxyquinazolin-4-yloxy)phenyl)urea (65 mg, 0.11 mmol, 38%). $^1$H NMR (300 MHz, DMSO-d$_6$) δ 9.25 (s, 1H), 8.56 (br s, 2H), 7.63-7.35 (m, 8H), 7.22 (d, 1H), 6.94 (d, 1H), 6.38 (s, 1H), 3.99 (s, 6H), 1.27 (s, 9H); LC-MS (ESI) m/z 573 (M)'.

Example 364

Preparation of 1-(3-tert-butyl-1-(3-chlorophenyl)-1H-pyrazol-5-yl)-3-(3-(6,7-dimethoxyquinazolin-4-ylthio)phenyl)urea The title compound was prepared from the carbamate from Example 363A (111 mg, 0.30 mmol) and 3-(6,7-dimethoxyquinazolin-4-ylthio)aniline (94 mg, 0.30 mmol) using the procedure in Example 115C to give 1-(3-tert-butyl-1-(3-chlorophenyl)-1H-pyrazol-5-yl)-3-(3-(6,7-dimethoxyquinazolin-4-ylthio)phenyl)urea (101 mg, 0.17 mmol, 57%). $^1$H NMR (300 MHz, DMSO-d$_6$) δ 9.26 (s, 1H), 8.69 (s, 1H), 8.56 (s, 1H), 7.80 (s, 1H), 7.63-7.26 (m, 6H), 6.39 (s, 1H), 3.98 (s, 6H), 1.27 (s, 9H); LC-MS (ESI) m/z 589 (M)'.

Example 365

Preparation of 1-(3-tert-butyl-1-(4-chlorophenyl)-1H-pyrazol-5-yl)-3-(3-(6,7-dimethoxyquinazolin-4-yloxy)phenyl)urea Example 365A Step 1: Following the procedure in Example 161A Step 3, 4-chlorophenylhydrazine hydrochloride (1.43 g, 8.0 mol) and 4,4-dimethyl-3-oxopentanenitrile (1.0 g, 8.0 mmol) were reacted to give 3-tert-butyl-1-(4-chlorophenyl)-1H-pyrazol-5-amine (653 mg, 2.62 mmol, 33%). $^1$H NMR (300 MHz, DMSO-d$_6$) δ 7.61 (d, 1H), 7.49 (d, 2H), 5.39 (s, 1H), 5.28 (s, 1H), 1.09 (s, 9H); LC-MS (ESI) m/z 250 (M+H)$^+$.

Example 365A

Step 2: Following the procedure in Example 118A, 3-tert-butyl-1-(4-chlorophenyl)-1H-pyrazol-5-amine (653 mg, 2.62 mmol) and phenyl chloroformate (1.0 mL, 7.85 mmol) were reacted to give phenyl 3-tert-butyl-1-(4-chlorophenyl)-1H-pyrazol-5-ylcarbamate (575 mg, 1.56 mmol, 59%). $^1$H NMR (300 MHz, DMSO-d$_6$) δ 10.19 (br s, 1H), 7.63-7.60 (m, 4H), 7.39-7.36 (m, 2H), 7.23 (t, 1H), 7.06 (br s, 2H), 6.38 (s, 1H), 1.28 (s, 9H); LC-MS (ESI) m/z 370 (M+H)$^+$.

Example 365B

The title compound was prepared from the carbarmate from the previous step (111 mg, 0.30 mmol) and 3-(6,7- dimethoxyquinazolin-4-yloxy)aniline (89 mg, 0.30 mmol) using the procedure in Example 115C to give 1-(3-tert-butyl-1-(4-chlorophenyl)-1H-pyrazol-5-yl)-3-(3-(6,7-dimethoxyquinazolin-4-yloxy)phenyl)urea (82 mg, 0.14 mmol, 48%). $^1$H NMR (300 MHz, DMSO-d$_6$) δ 9.20 (s, 1H), 8.55-8.49 (m, 2H), 7.60-7.54 (m, 6H), 7.39-7.34 (m, 2H), 7.18 (d, 1H), 6.92 (d, 1H), 6.35 (s, 1H), 3.99 (s, 6H), 1.25 (s, 9H); LC-MS (ESI) m/z 573 (M)'.

Example 366

Preparation of 1-(3-tert-butyl-1-(4-chlorophenyl)-1H-pyrazol-5-yl)-3-(3-(6,7-dimethoxyquinazolin-4-ylthio)phenyl)urea The title compound was prepared from the carbamate in Example 365A (111 mg, 0.30 mmol) and 3-(6,7-dimethoxyquinazolin-4-ylthio)aniline (94 mg, 0.30 mmol) using the procedure in Example 115C to give 1-(3-tert-butyl-1-(4-chlorophenyl)-1H-pyrazol-5-yl)-3-(3-(6,7-dimethoxyquinazolin-4-ylthio)phenyl)urea (65 mg, 0.11 mmol, 37%). $^1$H NMR (300 MHz, DMSO-d$_6$) δ 9.21 (s, 1H), 8.68 (s, 1H), 8.49 (s, 1H), 7.79 (s, 1H), 7.57 (br s, 4H), 7.48-7.22 (m, 5H), 6.36 (s, 1H), 3.98 (s, 6H), 1.26 (s, 9H); LC-MS (ESI) m/z 589 (M+H)$^+$.

Example 367

Preparation of 1-(5-tert-butylisoxazol-3-yl)-3-(5-(6,7-dimethoxyquinazolin-4-yloxy)-2-fluorophenyl)urea

Example 367A

To a stirred suspension of phenyl 5-tert-butylisoxazol-3-ylcarbamate (prepared as described in Example 270A) (260 mg, 1 mmol) and 3-amino-4-fluorophenol (127 mg, 1 mmol) in acetonitrile (15 mL) at rt, was added DBU (0.3 mL, 2 mmol). The mixture was heated at 50° C. for 1 h. The reaction mixture was cooled to rt, concentrated under reduced pressure, and the residue purified via silica gel column chromatography to afford 1-(5-tert-butylisoxazol-3-yl)-3-(2-fluoro-5-hydroxyphenyl)urea (200 mg, 68%) as a solid. $^1$H NMR (400 MHz, DMSO-d$_6$) δ 9.68 (m, 2H), 8.41 (m, 1H), 7.68 (m, 1H), 6.56-6.65 (m, 2H), 6.45 (s, 1H), 1.29 (s, 9H); LC-MS (ESI) m/z 294 (M+H)$^+$.

Example 367B

To a stirred solution of 1-(5-tert-butylisoxazol-3-yl)-3-(2-fluoro-5-hydroxyphenyl)urea (200 mg, 0.68 mmol) and 4-chloro-6,7-dimethoxyquinazoline (153 mg, 0.68 mmol) in DMF (4 mL) at rt, was added potassium carbonate (188 mg, 1.36 mmol). The reaction mixture was stirred at 35° C. for 15 h. The mixture was poured into water, and the resulting brown solid was filtrated, washed with water, and dried to afford the crude product. Purification via reverse-phase preparative HPLC afforded 1-(5-tert-butylisoxazol-3-yl)-3-(5-(6,7-dimethoxyquinazolin-4-yloxy)-2-fluorophenyl)urea (25 mg, 8%) as a solid. $^1$H NMR (400 MHz, DMSO-d$_6$) δ9.86 (brs, 1H), 8.85 (brs, 1H), 8.57 (s, 1H), 8.16 (m, 1H), 7.55 (s, 1H), 7.40-7.44 (m, 2H), 7.16 (m, 1H), 6.50 (s, 1H), 3.99 (s, 3H), 3.97 (s, 3H), 1.30 (s, 9H); LC-MS (ESI) m/z 482 (M+H)$^+$.

Example 368

Preparation of 1-(3-tert-butyl-1-phenyl-1H-pyrazol-5-yl)-3-(5-(6,7-dimethoxyquinazolin-4-yloxy)-2-fluorophenyl)urea

Example 368A

To a stirred suspension of phenyl 3-tert-butyl-1-phenyl-1H-pyrazol-5-ylcarbamate (prepared as described in example 153A) (335 mg, 1 mmol) and 3-amino-4-fluorophenol (127 mg, 1 mmol) in acetonitrile (15 mL) at rt, was added DBU (0.3 mL, 2 mmol). The mixture was heated at 50° C. for 1 h. The reaction mixture was cooled to rt, concentrated under reduced pressure, and the residue purified via silica gel column chromatography to afford 1-(3-tert-butyl-1-phenyl-1H-pyrazol-5-yl)-3-(2-fluoro-5-hydroxyphenyl)urea (217 mg, 59%) as a solid. LC-MS (ESI) m/z 369 (M+H)$^+$.

Example 368B

To a stirred solution of 1-(3-tert-butyl-1-phenyl-1H-pyrazol-5-yl)-3-(2-fluoro-5-hydroxyphenyl)urea (217 mg, 0.59 mmol) and 4-chloro-6,7-dimethoxyquinazoline (132 mg, 0.59 mmol) in DMF (4 mL) at rt, was added potassium carbonate (163 mg, 1.18 mmol). The reaction mixture was stirred at 35° C. for 15 h. The mixture was poured into water, and the resulting brown solid was filtrated, washed with water, and dried to afford the crude product. Purification via reverse-phase preparative HPLC afforded 1-(3-tert-butyl-1-phenyl-1H-pyrazol-5-yl)-3-(5-(6,7-dimethoxyquinazolin-4-yloxy)-2-fluorophenyl)urea (19 mg, 6%) as a solid. $^1$H NMR (400 MHz, DMSO-d$_6$) δ9.02 (brs, 1H), 8.89 (brs, 1H), 8.57 (s, 1H), 8.16 (m, 1H), 7.53-7.59 (m, 5H), 7.37-7.46 (m, 3H), 7.15 (m, 1H), 6.43 (s, 1H), 4.00 (s, 3H), 3.98 (s, 3H), 1.29 (s, 9H); LC-MS (ESI) m/z 557 (M+H)$^+$.

Example 369

Preparation of 1-(3-tert-butyl-1-(4-tert-butylphenyl)-1H-pyrazol-5-yl)-3-(3-(6,7-dimethoxyquinazolin-4-yloxy)phenyl)urea

Example 369A

Step 1: Using the procedure in Example 161A Step 3, 4-tert-butylphenyl-hydrazine monohydrochloride (1.00 g, 4.98 mmol) and 4,4-dimethyl-3-oxopentanenitrile (625 mg, 4.98 mmol) were reacted to give 3-tert-butyl-1-(4-tert-butylphenyl)-1H-pyrazol-5-amine (996 mg, 3.67 mmol, 51%). $^1$H NMR (300 MHz, DMSO-d$_6$) δ 7.46 (br s, 4H), 5.35 (s, 1H), 5.15 (br s, 2H), 1.30 (s, 9H), 1.20 (s, 9H); LC-MS (ESI) m/z 272 (M+H)$^+$.

Example 369A

Step 2: Using the procedure in Example 118A, 3-tert-butyl-1-(4-tert-butylphenyl)-1H-pyrazol-5-amine (996 mg, 3.67 mmol) and phenyl chloroformate (1.40 mL, 11.0 mmol) were reacted to give phenyl 3-tert-butyl-1-(4-tert-butylphenyl)-1H-pyrazol-5-ylcarbamate (957 mg, 2.45 mmol, 66%). $^1$H NMR (300 MHz, DMSO-d$_6$) δ 10.05 (br s, 1H), 7.56-7.08 (m, 8H), 6.77 (s, 1H), 6.33 (s, 1H), 1.33 (s, 9H), 1.28 (s, 9H); LC-MS (ESI) m/z 392 (M+H)$^+$.

Example 369B

The title compound was prepared from the carbamate from the previous step (117 mg, 0.30 mmol) and 3-(6,7-dimethoxyquinazolin-4-yloxy)aniline (89 mg, 0.30 mmol) using the procedure in Example 115C to give 1-(3-tert-butyl-1-(4-tert-butylphenyl)-1H-pyrazol-5-yl)-3-(3-(6,7-dimethoxyquinazolin-4-yloxy)phenyl)urea (86 mg, 0.14 mmol, 48%). $^1$H NMR (300 MHz, DMSO-d$_6$) δ 9.23 (s, 1H), 8.55 (s, 1H), 8.49 (s, 1H), 7.58-7.34 (m, 8H), 7.18 (d, 1H), 6.93 (d, 1H), 6.35 (s, 1H), 3.99 (s, 6H), 1.32 (s, 9H); LC-MS (ESI) m/z 595 (M+H)$^+$.

Example 370

Preparation of 1-(3-tert-butyl-1-(4-tert-butylphenyl)-1H-pyrazol-5-yl)-3-(3-(6,7-dimethoxyquinazolin-4-ylthio)phenyl)urea The title compound was prepared from the carbamate described in Example 369A (117 mg, 0.30 mmol) and 3-(6,7-dimethoxyquinazolin-4-ylthio)aniline (94 mg, 0.30 mmol) using the procedure in Example 115C to give 1-(3-tert-butyl-1-(4-tert-butylphenyl)-1H-pyrazol-5-yl)-3-(3-(6,7-dimethoxyquinazolin-4-ylthio)phenyl)urea (104 mg, 0.17 mmol, 57%). $^1$H NMR (300 MHz, DMSO-d$_6$) δ 9.23 (s, 1H), 8.68 (s, 1H), 8.48 (s, 1H), 7.81 (s, 1H), 7.55-7.33 (m, 8H), 7.24 (d, 1H), 6.35 (s, 1H), 3.98 (s, 6H), 1.32 (s, 9H); LC-MS (ESI) m/z 611 (M+H)$^+$.

Example 371

Preparation of 1-(3-tert-butyl-1-(2-fluorophenyl)-1H-pyrazol-5-yl)-3-(3-(6,7-dimethoxyquinazolin-4-ylthio)phenyl)urea Example 371A Step 1: using the procedure in Example 161A Step 3, 2-fluorophenylhydrazine hydrochloride (1.30 g, 8.0 mmol) and 4,4-dimethyl-3-oxopentanenitrile (1.0 g, 8.0 mmol) were reacted to give 3-tert-butyl-1-(2-fluorophenyl)-1H-pyrazol-5-amine (1.23 g, 5.28 mmol, 66%). $^1$H NMR (300 MHz, DMSO-d$_6$) δ 7.46-7.29 (m, 4H), 5.31 (s, 1H), 5.05 (br s, 2H), 1.20 (s, 9H); LC-MS (ESI) m/z 234 (M+H)$^+$.

Example 371A

Step 2: Using the procedure in Example 118A, 3-tert-butyl-1-(2-fluorophenyl)-1H-pyrazol-5-amine (1.23 g, 5.27 mmol) and phenyl chloroformate (2.0 mL, 16.0 mmol) were reacted to give phenyl 3-tert-butyl-1-(2-fluorophenyl)-1H-pyrazol-5-ylcarbamate (1.21 g, 3.42 mmol, 59%). $^1$H NMR (300 MHz, DMSO-d$_6$) δ 10.13 (s, 1H), 7.55-7.35 (m, 6H), 7.23 (t, 1H), 7.08 (br s, 2H), 6.34 (s, 1H), 1.29 (s, 9H); LC-MS (ESI) m/z 354 (M+H)$^+$.

Example 371B

The title compound was prepared from the carbamate in previous step (105 mg, 0.30 mmol) and 3-(6,7-dimethoxyquinazolin-4-ylthio)aniline (95 mg, 0.30 mmol) using the procedure in Example 115C to give 1-(3-tert-butyl-1-(2-fluorophenyl)-1H-pyrazol-5-yl)-3-(3-(6,7-dimethoxyquinazolin-4-ylthio)phenyl)urea (54 mg, 0.094 mmol, 31%). $^1$H NMR (300 MHz, DMSO-d$_6$) δ 9.10 (s, 1H), 8.68 (s, 1H), 8.44 (s, 1H), 7.79 (s, 1H), 7.58-7.32 (m, 8H), 7.24 (d, 1H), 6.37 (s, 1H), 3.98 (s, 6H), 1.25 (s, 9H); LC-MS (ESI) m/z 573 (M+H)$^+$.

Example 372

Preparation of 1-(3-tert-butyl-1-(2-fluorophenyl)-1H-pyrazol-5-yl)-3-(3-(6,7-dimethoxyquinazolin-4-yloxy)phenyl)urea The title compound was prepared from the carbamate described in Example 371A (105 mg, 0.30 mmol) and 3-(6,7-dimethoxyquinazolin-4-yloxy)aniline (90 mg, 0.30 mmol) using the procedure in Example 115C to give 1-(3-tert-butyl-1-(2-fluorophenyl)-1H-pyrazol-5-yl)-3-(3-(6,7-dimethoxyquinazolin-4-yloxy)phenyl)urea (58 mg, 0.10 mmol, 35%). $^1$H NMR (300 MHz, DMSO-d$_6$) δ 9.10 (s, 1H), 8.55 (s, 1H), 8.45 (s, 1H), 7.57-7.39 (m, 8H), 7.16 (s, 1H), 6.94 (s, 1H), 6.37 (s, 1H), 3.99 (s, 6H), 1.25 (s, 9H); LC-MS (ESI) m/z 557 (M+H)$^+$.

Example 373

Preparation of 1-(3-tert-butyl-1-(4-(trifluoromethyl)phenyl)-1H-pyrazol-5-yl)-3-(3-(6,7-dimethoxyquinazolin-4-yloxy)phenyl)urea Example 373A Step 1: The title compound was prepared from 4-(trifluoromethyl)-phenylhydrazine (1.41 g, 8.0 mmol) and 4,4-dimethyl-3-oxopentanenitrile (1.0 g, 8.0 mmol) using the procedure in Example 161A Step 3 to give to give 3-tert-butyl-1-(4-(trifluoromethyl)phenyl)-1H-pyrazol-5-amine (1.36 g, 4.81 mmol, 60%). $^1$H NMR (300 MHz, DMSO-d$_6$) δ 7.81 (d, 2H), 7.80 (d, 2H), 5.44 (s, 3H), 1.22 (s, 9H); LC-MS (ESI) m/z 284 (M+H)$^+$.

Example 373A

Step 2: The title compound was prepared from 3-tert-butyl-1-(4-(trifluoromethyl)phenyl)-1H-pyrazol-5-amine (1.36 g, 4.80 mmol) and phenyl chloroformate (1.82 mL, 14.4 mmol) using the procedure in Example 118A to give phenyl 3-tert-butyl-1-(4-(trifluoromethyl)phenyl)-1H-pyrazol-5-ylcarbamate (113 mg, 2.80 mmol, 58%). $^1$H NMR (300 MHz, DMSO-d$_6$) δ 10.20 (br s, 1H), 7.93 (d, 2H), 7.81 (d, 2H), 7.40-7.10 (m, 5H), 6.44 (s, 1H), 1.29 (s, 9H); LC-MS (ESI) m/z 404 (M+H)$^+$.

Example 373B

The title compound was prepared from the carbamate from the previous step (114 mg, 0.28 mmol) and 3-(6,7-dimethoxyquinazolin-4-yloxy)aniline (84 mg, 0.28 mmol) using the procedure in Example 115C to give 1-(3-tert-butyl-1-(4-(trifluoromethyl)phenyl)-1H-pyrazol-5-yl)-3-(3-(6,7-dimethoxyquinazolin-4-yloxy)phenyl)urea (117 mg, 0.19 mmol, 69%). $^1$H NMR (300 MHz, DMSO-d$_6$) δ 9.23 (s, 1H), 8.63 (s, 1H), 8.55 (s, 1H), 7.91-7.79 (m, 4H), 7.55 (br s, 2H), 7.40-7.35 (m, 2H), 7.21 (d, 1H), 6.94 (d, 1H), 6.41 (s, 1H), 3.98 (s, 6H), 1.24 (s, 9H); LC-MS (ESI) m/z 607 (M+H)$^+$.

Example 374

Preparation of 1-(3-tert-butyl-1-(4-(trifluoromethyl)phenyl)-1H-pyrazol-5-yl)-3-(3-(6,7-dimethoxyquinazolin-4-ylthio)phenyl)urea The title compound was prepared from the carbamate described in Example 373A (121 mg, 0.30 mmol) and 3-(6, 7-dimethoxyquinazolin-4-ylthio)aniline (94 mg, 0.30 mmol) using the procedure in Example 115C to give 1-(3-tert-butyl-1-(4-(trifluoromethyl)phenyl)-1H-pyrazol-5-yl)-3-(3-(6,7-dimethoxyquinazolin-4-ylthio)phenyl)urea (41 mg, 0.066 mmol, 22%). $^1$H NMR (300 MHz, DMSO-d$_6$) δ 9.24 (s, 1H), 8.68 (s, 1H), 8.62 (s, 1H), 7.90-7.79 (m, 5H), 7.49-7.23 (m, 5H), 6.41 (s, 1H), 3.98 (s, 6H), 1.28 (s, 9H); LC-MS (ESI) m/z 623 (M+H)$^+$.

Example 375

Preparation of 1-(3-tert-butyl-1-(2-(trifluoromethyl)phenyl)-1H-pyrazol-5-yl)-3-(3-(6,7-dimethoxyquinazolin-4-ylthio)phenyl)urea Example 375A Step 1: The title compound was prepared from 2-(trifluoromethyl)-phenylhydrazine (1.41 g, 8.0 mmol) and 4,4-dimethyl-3-oxopentanenitrile (1.0 g, 8.0 mmol) using the procedure in Example 161A Step 3 to give 3-tert-butyl-1-(2-(trifluoromethyl)phenyl)-1H-pyrazol-5-amine (1.45 g, 5.12 mmol, 64%). $^1$H NMR (300 MHz, DMSO-d$_6$) δ 7.86 (d, 1H), 7.75 (t, 1H), 7.65 (t, 1H), 7.49 (d, 1H), 5.27 (s, 1H), 4.97 (s, 1H), 1.18 (s, 9H); LC-MS (ESI) m/z 284 (M+H)$^+$.

Example 375A

Step 2: The title compound was prepared from 3-tert-butyl-1-(2-(trifluoromethyl)phenyl)-1H-pyrazol-5-amine (1.45 g, 5.12 mmol) and phenyl chloroformate (1.95 mL, 15.4 mmol) using the procedure in Example 118A to give phenyl 3-tert-butyl-1-(2-(trifluoromethyl)phenyl)-1H-pyrazol-5-ylcarbamate (1.46 g, 3.62 mmol, 71%). $^1$H NMR (300 MHz, DMSO-d$_6$) δ 10.20 (br s, 1H), 7.92 (d, 1H), 7.85 (t, 1H), 7.74 (t, 1H), 7.54 (d, 1H), 7.38-7.36 (m, 2H), 7.23 (t, 1H), 7.09 (br s, 2H), 6.32 (s, 1H), 1.25 (s, 9H); LC-MS (ESI) m/z 404 (M+H)$^+$.

Example 375B

The title compound was prepared from the carbamate from the previous step (121 mg, 0.30 mmol) and 3-(6,7-dimethoxyquinazolin-4-ylthio)aniline (94 mg, 0.30 mmol) using the procedure in Example 115C to give 1-(3-tert-butyl-1-(2-(trifluoromethyl)phenyl)-1H-pyrazol-5-yl)-3-(3-(6,7-dimethoxyquinazolin-4-ylthio)phenyl)urea (120 mg, 0.19 mmol, 64%). $^1$H NMR (300 MHz, DMSO-d$_6$) δ 8.97 (s, 1H), 8.69 (s, 1H), 8.33 (s, 1H), 7.99-7.79 (m, 4H), 7.63 (d, 1H), 7.41-7.24 (m, 5H), 6.34 (s, 1H), 3.98 (s, 6H), 1.23 (s, 9H); LC-MS (ESI) m/z 623 (M+H)$^+$.

Example 376

Preparation of 1-(3-tert-butyl-1-(2-(trifluoromethyl)phenyl)-1H-pyrazol-5-yl)-3-(3-(6,7-dimethoxyquinazolin-4-yloxy)phenyl)urea The title compound was prepared from the carbamate in Example 375A (114 mg, 0.28 mmol) and 3-(6,7-dimethoxyquinazolin-4-yloxy)aniline (84 mg, 0.28 mmol) using the procedure in Example 115C to give 1-(3-tert-butyl-1-(2-(trifluoromethyl)phenyl)-1H-pyrazol-5-yl)-3-(3-(6,7-dimethoxyquinazolin-4-yloxy)phenyl)urea (101 mg, 0.17 mmol, 59%). $^1$H NMR (300 MHz, DMSO-d$_6$) δ 8.97 (s, 1H), 8.55 (s, 1H), 8.33 (s, 1H), 7.98 (d, 1H), 7.89-7.80 (m, 2H), 7.64-7.54 (m, 3H), 7.39-7.33 (m, 2H), 7.12 (d, 1H), 6.93 (d, 1H), 6.33 (s, 1H), 3.99 (s, 6H), 1.23 (s, 9H); LC-MS (ESI) m/z 607 (M+H)$^+$.

Example 377

Preparation of 1-(3-(6,7-dimethoxyquinazolin-4-yloxy)phenyl)-3-(5-(1-(trifluoromethyl)cyclopropyl)isoxazol-3-yl)urea Example 377A Step 1: A mixture of 3-oxo-3-(1-(trifluoromethyl)cyclopropyl)propanenitrile (1 g, 5.65 mmol) (prepared as described in example 137A step 1), hydroxylamine sulfate (1.11 g, 6.78 mmol) and sodium hydrogencarbonate (1.2 g, 14.13 mmol) in a mixture of 10% methanol in water (20 mL), was heated at 65° C. for 15 h. After cooling to rt, the mixture was adjusted to pH 1 with concentrated hydrochloric acid and separated into two equal 10 mL batches and placed into two separate 20 mL microwave vials fitted with a stirrer bar. After sealing, each batch was placed in a Biotage Microwave Synthesizer and heated (with stirring) at 140° C. for 5 min. Each batch was cooled and neutralized with saturated aqueous sodium hydrogencarbonate solution. Both processed batches were combined and concentrated in vacuo and the aqueous solution extracted, twice, with dichloromethane. The combined organic layers were washed with brine, separated, dried over MgSO$_4$ and filtered. Concentration in vacuo afforded 5-(1-(trifluoromethyl)cyclopropyl)isoxazol-3-amine (687 mg, 64%) as a light yellow solid which taken on without further purification. LC-MS (ESI) m/z 193 (M+H)$^+$.

Example 377A

Step 2: To a stirred mixture of 5-(1-(trifluoromethyl)cyclopropyl)isoxazol-3-amine (687 mg, 3.58 mmol) and potassium carbonate (987 mg, 7.0 mmol) in dry dichloromethane (30 mL) at 0° C., was added a solution of phenyl chloroformate (848 mg, 5.42 mmol) in anhydrous dichloromethane (5 mL). The reaction mixture was warmed to room temperature and stirred for a further 15 h. The reaction mixture was filtered and the filtrate concentrated under reduced pressure to give an oil. Purification via silica gel flash chromatography afforded phenyl 5-(1-(trifluoromethyl)cyclopropyl)isoxazol-3-ylcarbamate (727 mg, 65%) as a colorless solid. $^1$H NMR (300 MHz, DMSO-d$_6$) δ 11.34 (brs, 1H), 7.40-7.47 (m, 2H), 7.20-7.31 (m, 3H), 6.80 (s, 1H), 1.45-1.56 (m, 4H); LC-MS (ESI) m/z 313 (M+H)$^+$.

Example 377B

The title compound was prepared from 3-(6,7-dimethoxyquinazolin-4-yloxy)aniline (90 mg, 0.3 mmol) and the carbamate from the previous step (112 mg, 0.36 mmol) using the procedure in Example 115C to give 1-(3-(6,7-dimethoxyquinazolin-4-yloxy)phenyl)-3-(5-(1-(trifluoromethyl)cyclopropyl)isoxazol-3-yl)urea (107 mg, 0.21 mmol, 69%). $^1$H NMR (300 MHz, DMSO-d$_6$) δ 9.73 (s, 1H), 9.10 (s, 1H), 8.56 (s, 1H), 7.58 (s, 1H), 7.57 (s, 1H), 7.41 (t, 1H), 7.39 (s, 1H), 7.26 (d, 1H), 6.98 (d, 1H), 6.85 (s, 1H), 3.99 (s, 3H), 3.98 (s, 3H), 1.56-1.41 (m, 4H); LC-MS (ESI) m/z 516 (M+H)$^+$.

Example 378

Preparation of 1-(3-(6,7-dimethoxyquinazolin-4-ylthio)phenyl)-3-(5-(1-(trifluoromethyl)cyclopropyl)isoxazol-3-yl)urea The title compound was prepared from 3-(6,7-dimethoxyquinazolin-4-ylthio)aniline (95 mg, 0.3 mmol) and the carbamate in Example 377A (112 mg, 0.36 mmol) using the procedure in Example 115C to give 1-(3-(6,7-dimethoxyquinazolin-4-ylthio)phenyl)-3-(5-(1-(trifluoromethyl)cyclopropyl)isoxazol-3-yl)urea (108 mg, 0.20 mmol, 68%). $^1$H NMR (300 MHz, DMSO-$d_6$) δ 9.73 (s, 1H), 9.01 (s, 1H), 8.69 (s, 1H), 7.84 (s, 1H), 7.52 (d, 1H), 7.45 (t, 1H), 7.35 (s, 1H), 7.34 (s, 1H), 7.29 (d, 1H), 6.86 (s, 1H), 3.99 (s, 6H), 1.56-1.45 (m, 4H); LC-MS (ESI) m/z 532 (M+H)$^+$.

Example 379

Preparation of 1-(3-tert-butyl-1-(3-(trifluoromethyl)phenyl)-1H-pyrazol-5-yl)-3-(3-(6,7-dimethoxyquinazolin-4-yloxy)phenyl)urea Example 379A Step 1: Following the procedure in Example 161A Step 3, 3-trifluoromethylphenylhydrazine hydrochloride (781 mg, 4.44 mmol) and 4,4-Dimethyl-3-oxopentanenitrile (500 mg, 4.0 mmol) were reacted to give 3-tert-butyl-1-(3-(trifluoromethyl)phenyl)-1H-pyrazol-5-amine (344 mg, 1.21 mmol, 30%). No NMR taken. LC-MS (ESI) m/z 284 (M+H)$^+$.

Example 379A Step 2

Following the procedure in Example 118A, 3-tert-butyl-1-(3-(trifluoromethyl)phenyl)-1H-pyrazol-5-amine (344 mg, 1.21 mmol) and phenyl chloroformate (0.25 mL, 1.82 mmol) were reacted to give phenyl 3-tert-butyl-1-(3-(trifluoromethyl)phenyl)-1H-pyrazol-5-ylcarbamate (119 mg, 0.42 mmol, 35%). $^1$H NMR (300 MHz, DMSO-$d_6$) δ 10.05 (s, 1H), 7.62-7.50 (m, 3H), 7.58-7.43 (m, 3H), 7.23 (t, 1H), 7.12 (br s, 2H), 6.39 (s, 1H), 1.29 (s, 9H); LC-MS (ESI) m/z 404 (M+H)$^+$.

Example 379B

The title compound was prepared from the carbamate from the previous step (114 mg, 0.28 mmol) and 3-(6,7-dimethoxyquinazolin-4-yloxy)aniline (84 mg, 0.28 mmol) using the procedure in Example 115C to give 1-(3-tert-butyl-1-(3-(trifluoromethyl)phenyl)-1H-pyrazol-5-yl)-3-(3-(6,7-dimethoxyquinazolin-4-yloxy)phenyl)urea (107 mg, 0.18 mmol, 63%). $^1$H NMR (300 MHz, DMSO-$d_6$) δ 9.23 (s, 1H), 8.55 (br s, 2H), 7.87 (br s, 2H), 7.75 (br s, 2H), 7.51 (d, 2H), 7.36 (t, 2H), 7.18 (d, 1H), 6.91 (d, 1H), 6.38 (s, 1H), 3.97 (s, 6H), 1.27 (s, 9H); LC-MS (ESI) m/z 607 (M+H)$^+$.

Example 380

Preparation of 1-(3-tert-butyl-1-(3-(trifluoromethyl)phenyl)-1H-pyrazol-5-yl)-3-(3-(6,7-dimethoxyquinazolin-4-ylthio)phenyl)urea The title compound was prepared from the carbamate in Example 379A (121 mg, 0.30 mmol) and 3-(6,7-dimethoxyquinazolin-4-ylthio) aniline (94 mg, 0.30 mmol) using the procedure in Example 115C to give 1-(3-tert-butyl-1-(3-(trifluoromethyl)phenyl)-1H-pyrazol-5-yl)-3-(3-(6,7-dimethoxyquinazolin-4-ylthio)phenyl)urea (105 mg, 0.17 mmol, 56%). $^1$H NMR (300 MHz, DMSO-$d_6$) δ 9.24 (s, 1H), 8.68 (s, 1H), 8.57 (s, 1H), 7.88 (s, 2H), 7.75 (br s, 3H), 7.45-7.23 (m, 5H), 6.39 (s, 1H), 3.98 (s, 6H), 1.28 (s, 9H); LC-MS (ESI) m/z 623 (M+H)$^+$.

Example 381

Preparation of 1-(3-(2-cyanopropan-2-yl)isoxazol-5-yl)-3-(3-(6,7-dimethoxyquinazolin-4-ylthio)phenyl)urea A mixture of phenyl 3-(2-cyanopropan-2-yl)isoxazol-5-ylcarbamate (prepared as described in Example 125A steps 1 through 3) (95 mg, 0.35 mmol), 3-(6,7-dimethoxyquinazolin-4-ylthio)aniline (prepared as described in Example 115B) (100 mg, 0.319 mmol) and N,N-4-(dimethylamino)pyridine (10 mg, 0.082 mmol) in THF (5 mL) was stirred at rt for 15 h. The reaction mixture was concentrated under reduced pressure to give the crude product which was partitioned between dichloromethane (10 mL) and water (10 mL). The organic layer was separated and dried over magnesium sulfate. Concentration under reduced pressure gave a solid which was triturated with methanol to afford 1-(3-(2-cyanopropan-2-yl)isoxazol-5-yl)-3-(3-(6,7-dimethoxyquinazolin-4-ylthio)phenyl)urea (50 mg, 32%) as a colorless solid. $^1$H NMR (300 MHz, DMSO-$d_6$) δ 10.52 (brs, 1H), 9.14 (brs, 1H), 8.70 (s, 1H), 7.86 (s, 1H), 7.57 (m, 1H), 7.46 (m, 1H), 7.30-7.36 (m, 3H), 6.28 (s, 1H), 3.99 (s, 6H), 1.68 (s, 6H); LC-MS (ESI) m/z 491 (M+H)$^+$.

Example 382

Preparation of 1-(3-(6,7-dimethoxyquinazolin-4-ylthio)phenyl)-3-(3-(trifluoromethyl)isoxazol-5-yl)urea Example 382A To a solution of 3-(trifluoromethyl)isoxazol-5-amine (165 mg, 1.08 mmol) described in Example 229A and potassium carbonate (359 mg, 2.6 mmol) in anhydrous THF (3 ml) was added dropwise 4-chlorophenyl chloroformate (763 mg, 4 mmol) as a solution in THF (2 ml). The reaction mixture was stirred at rt overnight. The solvent was removed and the residue taken in DCM, washed with water and brine and the organics combined, dried (MgSO$_4$) and concentrated. The crude was purified by silica gel chromatography (hexane/ethyl acetate 9:1) to afford phenyl 4-chlorophenyl 3-(trifluoromethyl)isoxazol-5-ylcarbamate (239 mg, 78%) as a solid. $^1$H NMR (300 MHz, CDCl$_3$) δ 5.95 (s, 1H), 6.93 (d, J=9 Hz, 2H), 7.15 (d, J=9 Hz, 2H), 8.91 (brs, 1H).

Example 382B

To a solution of 3-(6,7-dimethoxyquinazolin-4-ylthio)aniline (92 mg, 0.3 mmol), prepared as described in Example 115B, in THF (3 ml) was added DMAP (18 mg, 0.15 mmol) and phenyl 4-chlorophenyl 3-(trifluoromethyl)isoxazol-5-ylcarbamate (92 mg, 0.33 mmol) described in the previous step. Concentration under reduced pressure gave a residue which was triturated with anhydrous diethyl ether and MeOH to afford 1-(3-(6,7-dimethoxyquinazolin-4-ylthio)phenyl)-3-(3-trifluoromethyl)isoxazol-5-yl) urea (112 mg, 76%) as a solid. $^1$H NMR (300 MHz, DMSO-$d_6$) δ 3.76 (s, 6H), 6.49 (s, 1H), 7.31-7.36 (m, 3H), 7.44-7.49 (m, 2H), 7.59 (d, J=6 Hz, 1H), 7.86 (s, 1H), 8.70 (s, 1H), 9.31 (s, 1H); LC-MS (ESI) m/z 492 (M+H)$^+$.

Example 383

Preparation of 1-(3-(6,7-dimethoxyquinazolin-4-ylthio)phenyl)-3-(1-phenyl-3-(1-(trifluoromethyl)cyclopropyl)-1H-pyrazol-5-yl)urea The title compound was prepared from 3-(6,7-dimethoxyquinazolin-4-ylthio)aniline (94 mg, 0.3 mmol) and the carbamate from Example 137A (116 mg, 0.3 mmol) using the procedure in Example 115C to give 14346,7-dimethoxyquinazolin-4-ylthio)phenyl)-3-(1-phenyl-3-(1-(trifluoromethyl)cyclopropyl)-1H-pyrazol-5-yl)urea (160 mg, 0.26 mmol, 88%). $^1$H NMR (300 MHz, DMSO-d$_6$) δ 9.28 (s, 1H), 8.69 (s, 1H), 8.61 (s, 1H), 7.79 (s, 1H), 7.58-7.50 (m, 4H), 7.49-7.38 (m, 3H), 7.34 (d, 2H), 7.25 (d, 1H), 6.56 (s, 1H), 3.99 (s, 6H), 1.35-1.29 (m, 4H); LC-MS (ESI) m/z 607 (M+H)$^+$.

Example 384

Preparation of 1-(3-(7-ethoxy-6-methoxyquinazolin-4-yloxy)phenyl) -3-(1-phenyl-3-(trifluoromethyl)-1H-pyrazol-5-yl)urea Example 384A To a stirred slurry of cesium carbonate (2.99 g, 9.20 mmol) in anhydrous THF (50 mL) at rt, was added 3-aminophenol (1.00 g, 9.17 mmol). After stirring for 30 mins, 4-chloro-7-ethoxy-6-methoxyquinazoline (prepared as described in Example 6A Steps 1 through 5) (2.19 g, 9.20 mmol) was added and the reaction mixture was heated at 50° C. for 18 h. The mixture was cooled to rt and concentrated under reduced pressure and the resulting solid was washed with water (three times) then ethyl acetate (three times) to afford 3-(7-ethoxy-6-methoxyquinazolin-4-yloxy)aniline (1.75 g, 61%) as yellow solid. $^1$H NMR (400 MHz, DMSO-d$_6$) δ 8.54 (s, 1H), 7.51 (s, 1H), 7.35 (s, 1H), 7.09 (m, 1H), 6.37-6.50 (m, 3H), 5.31 (brs, 2H), 4.25 (q, J=7 Hz, 2H), 3.97 (s, 3H), 1.44 (t, J=7 Hz, 3H); LC-MS (ESI) m/z 312 (M+H)$^+$.

Example 384B

The title compound was prepared from the carbamate described in Example 161A or B (70 mg, 0.20 mmol) and the aniline from the previous step (62 mg, 0.20 mmol) using the procedure in Example 115C to give 1-(3-(7-ethoxy-6-methoxyquinazolin-4-yloxy)phenyl)-3-(1-phenyl-3-(trifluoromethyl)-1H-pyrazol-5-yl)urea (30 mg, 0.053 mmol, 26%). $^1$H NMR (300 MHz, DMSO-d$_6$) δ 9.31 (s, 1H), 8.80 (s, 1H), 8.54 (s, 1H), 7.62-7.54 (m, 7H), 7.41-7.35 (m, 2H), 7.20 (d, 1H), 6.94 (d, 1H), 6.87 (s, 1H), 4.26 (q, 2H), 3.98 (s, 6H), 1.44 (t, 3H); LC-MS (ESI) m/z 565 (M+H)$^+$.

Example 385

Preparation of 1-(3-(7-ethoxy-6-methoxyquinazolin-4-yloxy)phenyl)-3-(3-(2-fluoropropan-2-yl)isoxazol-5-yl)urea The title compound was prepared from the aniline described in Example 384A (62 mg, 0.2 mmol) and Example 42A (78 mg, 0.26 mmol) using the procedure in Example 115C to give 1-(3-(7-ethoxy-6-methoxyquinazolin-4-yloxy)phenyl)-3-(3-(2-fluoropropan-2-yl)isoxazol-5-yl)urea (73 mg, 0.15 mmol, 76%). $^1$H NMR (300 MHz, DMSO-d$_6$) δ 10.38 (s, 1H), 9.09 (s, 1H), 8.55 (s, 1H), 7.55 (m, 2H), 7.42 (t, 1H), 7.37 (s, 1H), 7.31 (d, 1H), 7.00 (d, 1H), 6.15 (s, 1H), 4.26 (q, 2H), 3.99 (s, 3H), 1.66 (d, 6H), 1.44 (t, 3H); LC-MS (ESI) m/z 482 (M+H)$^+$.

Example 386

Preparation of 1-(5-(1,3-difluoro-2-methylpropan-2-yl)isoxazol-3-yl)-3-(3-(7-ethoxy-6-methoxyquinazolin-4-yloxy)phenyl)urea The title compound was prepared from the carbamate described in Example 162A (60 mg, 0.20 mmol) and the aniline described in Example 384A (62 mg, 0.20 mmol) using the procedure in Example 115C to give 1-(5-(1,3-difluoro-2-methylpropan-2-yl)isoxazol-3-yl)-3-(3-(7-ethoxy-6-methoxyquinazolin-4-yloxy)phenyl)urea (28 mg, 0.055 mmol, 27%). $^1$H NMR (300 MHz, MeOD) δ 8.49 (s, 1H), 7.62-7.59 (m, 2H), 7.41 (t, 1H), 7.32-7.28 (m, 2H), 7.00 (d, 1H), 6.66 (s, 1H), 4.69 (s, 2H), 4.54 (s, 2H), 4.26 (q, 2H), 4.03 (s, 3H), 1.53 (t, 3H); LC-MS (ESI) m/z 514 (M+H)$^+$.

Example 387

Preparation of 1-(3-tert-butyl-1-phenyl-1H-pyrazol-5-yl)-3-(3-(7-ethoxy-6-methoxyquinazolin-4-yloxy) phenyl)urea The title compound was prepared using the carbamate described in Example 153A (67 mg, 0.20 mmol) and the aniline described in Example 384A (62 mg, 0.2 mmol) using the procedure in Example 115C to give 1-(3-tert-butyl-1-phenyl-1H-pyrazol-5-yl)-3-(3-(7-ethoxy-6-methoxyquinazolin-4-yloxy)phenyl)urea (42 mg, 0.076 mmol, 38%). $^1$H NMR (300 MHz, DMSO-d$_6$) δ 9.21 (s, 1H), 8.54 (s, 1H), 8.45 (s, 1H), 7.56-7.52 (m, 6H), 7.39-7.35 (m, 3H), 7.17 (d, 1H), 6.91 (d, 1H), 6.35 (s, 1H), 4.26 (q, 2H), 3.97 (s, 3H), 1.45 (t, 3H), 1.26 (s, 9H); LC-MS (ESI) m/z 553 (M+H)$^+$.

Example 388

Preparation of 1-(5-(1,3-difluoro-2-methylpropan-2-yl)isoxazol-3-yl)-3-(3-(7-ethoxy-6-methoxyquinazolin-4-ylthio)phenyl)urea Example 388A To a stirred slurry of sodium hydride (350 mg of a 60% dispersion in mineral oil, 8.80 mmol) in anhydrous THF (50 mL) at rt, was added 3-aminobenzenethiol (1.00 g, 9.17 mmol). After stirring for 30 mins, 4-chloro-7-ethoxy-6-methoxyquinazoline (prepared as described in Example 6A Steps 1 through 5) (1.91 g, 8.03 mmol) was added and the reaction mixture was stirred at rt for a further 4 h. The mixture was concentrated under reduced pressure and the resulting solid was washed with water (three times) then ethyl acetate (three times) to afford 3-(7-ethoxy-6-methoxyquinazolin-4-ylthio) aniline (2.36 g, 90%) as yellow solid. $^1$H NMR (400 MHz, DMSO-d$_6$) δ 8.69 (s, 1H), 7.30-7.31 (m, 2H), 7.13 (m, 1H), 6.80 (s, 1H), 6.72-6.74 (m, 2H), 5.31 (brs, 2H), 4.25 (q, J=7 Hz, 2H), 3.97 (s, 3H), 1.43 (t, J=7 Hz, 3H); LC-MS (ESI) m/z 328 (M+H)$^+$.

Example 388B

The title compound was prepared using the carbamate in Example 162A (60 mg, 0.20 mmol) and the aniline from the previous step (66 mg, 0.20 mmol) using the procedure in Example 115C to give 1-(5-(1,3-difluoro-2-methylpropan-2-yl)isoxazol-3-yl)-3-(3-(7-ethoxy-6-methoxyquinazolin-4-ylthio)phenyl)urea (61 mg, 0.12 mmol, 57%). $^1$H NMR (300 MHz, DMSO-d$_6$) δ 9.70 (s, 1H), 9.02 (s, 1H), 8.68 (s, 1H), 7.84 (s, 1H), 7.51-7.27 (m, 5H), 6.78 (s, 1H), 4.71 (s, 2H), 4.56 (s, 2H), 4.25 (q, 2H), 3.99 (s, 3H), 1.43 (t, 3H), 1.32 (s, 3H); LC-MS (ESI) m/z 530 (M+H)+.

Example 389

Preparation of 1-(3-(7-ethoxy-6-methoxyquinazolin-4-ylthio)phenyl)-3-(3-(2-fluoropropan-2-yl)isoxazol-5-yl)urea The title compound was prepared from the aniline described in Example 388A (65 mg, 0.2 mmol) and the carbamate from Example 42A (78 mg, 0.26 mmol) using the procedure in Example 115C to give 1-(3-(7-ethoxy-6-methoxyquinazolin-4-ylthio)phenyl)-3-(3-(2-fluoropropan-2-yl) isoxazol-5-yl)urea (81 mg, 0.16 mmol, 81%). $^1$H NMR (300 MHz, DMSO-$d_6$) δ 10.40 (s, 1H), 9.10 (s, 1H), 8.68 (s, 1H), 7.84 (s, 1H), 7.56 (d, 1H), 7.46 (t, 1H), 7.34-7.29 (m, 3H), 6.16 (s, 1H), 4.26 (q, 2H), 3.99 (s, 3H), 1.66 (d, 6H), 1.43 (t, 3H); LC-MS (ESI) m/z 498 (M+H)+.

Example 390

Preparation of 1-(3-tert-butyl-1-phenyl-1H-pyrazol-5-yl)-3-(3-(6-ethoxy-7-methoxyquinazolin-4-yloxy)phenyl)urea The title compound was prepared from the carbamate described in Example 153A (67 mg, 0.20 mmol) and the aniline described in Example 260B (62 mg, 0.20 mmol) using the procedure in Example 115C to give 1-(3-tert-butyl-1-phenyl-1H-pyrazol-5-yl)-3-(3-(6-ethoxy-7-methoxyquinazolin-4-yloxy)phenyl)urea (47 mg, 0.085 mmol, 43%). $^1$H NMR (300 MHz, DMSO-$d_6$) δ 9.30 (s, 1H), 8.58 (s, 1H), 8.46 (s, 1H), 7.60-7.50 (m, 6H), 7.45-7.36 (m, 3H), 7.20 (d, 1H), 6.89 (d, 1H), 6.42 (s, 1H), 4.25 (q, 2H), 3.98 (s, 3H), 1.43 (t, 3H), 1.24 (s, 9H); LC-MS (ESI) m/z 553 (M+H)+.

Example 391

Preparation of 1-(3-(6-ethoxy-7-methoxyquinazolin-4-yloxy)phenyl)-3-(1-phenyl-3-(trifluoromethyl)-1H-pyrazol-5-yl)urea The title compound was prepared from the carbamate described in Example 161 A or B (70 mg, 0.20 mmol) and the aniline described in Example 260B (62 mg, 0.20 mmol) using the procedure in Example 115C to give 1-(3-(6-ethoxy-7-methoxyquinazolin-4-yloxy)phenyl)-3-(1-phenyl-3-(trifluoromethyl)-1H-pyrazol-5-yl)urea (39 mg, 0.069 mmol, 35%). $^1$H NMR (300 MHz, DMSO-$d_6$) δ 9.30 (s, 1H), 8.78 (s, 1H), 8.54 (s, 1H), 7.60-7.50 (m, 6H), 7.45-7.36 (m, 2H), 7.20 (d, 1H), 6.94 (d, 1H), 6.86 (s, 1H), 4.24 (q, 2H), 3.99 (s, 3H), 1.42 (t, 3H); LC-MS (ESI) m/z 565 (M+H)+.

Example 392

Preparation of 1-(3-(6-ethoxy-7-methoxyquinazolin-4-yloxy)phenyl)-3-(3-(2-fluoropropan-2-yl)isoxazol-5-yl)urea The title compound was prepared from the aniline described in Example 260B (62 mg, 0.2 mmol) and the carabamate described in Example 42A (78 mg, 0.26 mmol) using the procedure in Example 115C to give 1-(3-(6-ethoxy-7-methoxyquinazolin-4-yloxy)phenyl)-3-(3-(2-fluoropropan-2-yl)isoxazol-5-yl)urea (72 mg, 0.15 mmol, 75%). $^1$H NMR (300 MHz, DMSO-$d_6$) δ 10.38 (s, 1H), 9.09 (s, 1H), 8.56 (s, 1H), 7.56 (s, 1H), 7.54 (s, 1H), 7.42 (t, 1H), 7.39 (s, 1H), 7.31 (d, 1H), 6.99 (d, 1H), 6.15 (s, 1H), 4.24 (q, 2H), 4.00 (s, 3H), 1.66 (d, 6H), 1.43 (t, 3H); LC-MS (ESI) m/z 482 (M+H)+.

Example 393

Preparation of 1-(5-(1,3-difluoro-2-methylpropan-2-yl)isoxazol-3-yl)-3-(3-(6-ethoxy-7-methoxyquinazolin-4-yloxy)phenyl)urea The title compound was prepared from the carbamate described in Example 162A (60 mg, 0.20 mmol) and the aniline described in Example 260B (62 mg, 0.20 mmol) using the procedure in Example 115C to give 1-(5-(1,3-difluoro-2-methylpropan-2-yl)isoxazol-3-yl)-3-(3-(6-ethoxy-7-methoxyquinazolin-4-yloxy)phenyl)urea (32 mg, 0.062 mmol, 31%). $^1$H NMR (300 MHz, MeOD) δ 8.45 (s, 1H), 7.57-7.55 (m, 2H), 7.38-7.35 (m, 2H), 7.29-7.24 (m, 2H), 6.97-6.93 (m, 2H), 6.64 (s, 1H), 4.67 (s, 2H), 4.52 (s, 2H), 4.20 (q, 2H), 4.01 (s, 3H), 1.49 (t, 3H), 1.38 (s, 3H); LC-MS (ESI) m/z 514 (M+H)+.

Example 394

Preparation of 1-(3-(6-ethoxy-7-methoxyquinazolin-4-ylthio)phenyl)-3-(3-(2-fluoropropan-2-yl)isoxazol-5-yl)urea The title compound was prepared from the aniline described in Example 262A (65 mg, 0.2 mmol) and the carbamate in Example 42A (78 mg, 0.26 mmol) using the procedure in Example 115C to give 1-(3-(6-ethoxy-7-methoxyquinazolin-4-ylthio)phenyl)-3-(3-(2-fluoropropan-2-yl)isoxazol-5-yl)urea (71 mg, 0.14 mmol, 71%). $^1$H NMR (300 MHz, DMSO-$d_6$) δ 10.40 (s, 1H), 9.09 (s, 1H), 8.69 (s, 1H), 7.84 (s, 1H), 7.58-7.23 (m, 5H), 6.16 (s, 1H), 4.26 (q, 2H), 3.99 (s, 3H), 1.66 (d, 6H), 1.44 (t, 3H); LC-MS (ESI) m/z 498 (M+H)+.

Example 395

Preparation of 1-(5-(1,3-difluoro-2-methylpropan-2-yl)isoxazol-3-yl)-3-(3-(6-ethoxy-7-methoxyquinazolin-4-ylthio)phenyl)urea The title compound was prepared from the carbamate described in Example 162A (60 mg, 0.20 mmol) and the aniline described in Example 262A (66 mg, 0.20 mmol) using the procedure in Example 115C to give 1-(5-(1,3-difluoro-2-methylpropan-2-yl)isoxazol-3-yl)-3-(3-(6-ethoxy-7-methoxyquinazolin-4-ylthio)phenyl)urea (50 mg, 0.095 mmol, 47%). $^1$H NMR (300 MHz, DMSO-$d_6$) δ 9.69 (s, 1H), 9.01 (s, 1H), 8.68 (s, 1H), 7.84 (s, 1H), 7.52-7.27 (m, 5H), 6.77 (s, 1H), 4.71 (s, 2H), 4.54 (s, 2H), 4.23 (q, 2H), 3.99 (s, 3H), 1.43 (t, 3H), 1.34 (s, 3H); LC-MS (ESI) m/z 530 (M+H)+.

Example 396

Preparation of (1-(3-(6-methoxy-7-(2-morpholinoethoxy)quinazolin-4-yloxy)phenyl)-3-(1-phenyl-3-(trifluoromethyl)-1H-pyrazol-5-yl)urea 1-(3-(6-Methoxy-7-(2-morpholinoethoxy)quinazolin-4-yloxy)phenyl)-3-(1-phenyl-3-(trifluoromethyl)-1H-pyrazol-5-yl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting phenyl 3-tert-butyl-1-p-tolyl-1H-pyrazol-5-ylcarbamate with phenyl 1-phenyl-3-(trifluoromethyl)-1H-pyrazol-5-ylcarbamate in Example 161, and 3-(6,7-dimethoxyquinazolin-4-yloxy)aniline with 3-(6-methoxy-7-(2-morpholinoethoxy)quinazolin-4-yloxy) aniline in Example 250 (0.075 g, 32%). $^1$H NMR (300 MHz, DMSO-d$_6$) δ 2.80 (t, 2H), 3.34 (m, 4H), 3.60 (m, 4H), 3.98 (s, 3H), 4.33 (t, 2H), 6.87 (s, 1H), 6.96 (d, 1H), 7.19 (d, 1H), 7.38 (t, 1H), 7.43 (s, 1H), 7.55-7.61 (m, 7H), 8.54 (s, 1H), 8.80 (s, 1H), 9.33 (s, 1H); LC-MS (ESI) m/z 650 (M+H)$^+$.

Example 397

Preparation of 1-(3-(6,7-Dimethoxyquinazolin-4-yloxy)-4-fluorophenyl)-3-(1-phenyl-3-(trifluoromethyl)-1H-pyrazol-5-yl)urea Example 397A Step 1: 1-(4-fluoro-3-methoxyphenyl)-3-(1-phenyl-3-(trifluoromethyl)-1H-pyrazol-5-yl)urea was obtained following the procedure described in Example 274B for synthesis of 1-(3-tert-butyl-1-p-tolyl-1H-pyrazol-5-yl)-3-(3-(6,7-dimethoxyquinazolin-4-yloxy)phenyl)urea, substituting 3-(6,7-dimethoxyquinazolin-4-yloxy)aniline with 4-fluoro-3-methoxyaniline, and phenyl 3-tert-butyl-1-p-tolyl-1H-pyrazol-5-ylcarbamate with 1-phenyl-3-(trifluoromethyl)-1H-pyrazol-5-ylcarbamate in Example 161 (0.153 g, 62% yield). $^1$H NMR (300 MHz, CDCl$_3$) δ 3.84 (s, 3H), 6.17 (m, 1H), 6.31 (dd, 1H), 6.57 (m, 2H), 6.86 (t, 2H), 6.99 (dd, 1H), 7.10 (dd, 1H), 7.42-7.51 (m, 3H); LC-MS (ESI) m/z 395 (M+H)$^+$.

Example 397A

Step 2: To a solution of 1-(4-fluoro-3-methoxyphenyl)-3-(1-phenyl-3-(trifluoromethyl)-1H-pyrazol-5-yl)urea (0.985 g, 2.5 mmol) in DCM (30 mL) at ice-water bath was dropped a 1.0 M solution of BBr$_3$ in DCM (25 mL) and it was stirred for 2 hours. The reaction mixture was quenched with saturated NaHCO$_3$ solution and extracted with DCM. Extracts were dried over MgSO$_4$ and concentrated. The crude product was purified on a silica gel column using a mixture of EtOAc-hexane as eluent to give phenyl 1-(4-fluoro-3-hydroxyphenyl)-3-(1-phenyl-3-(trifluoromethyl)-1H-pyrazol-5-yl)urea as solid (0.327 g, 34%). $^1$H NMR (300 MHz, DMSO-d$_6$) δ 6.59 (s, 1H), 6.65 (d, 1H), 6.78 (dd, 1H), 7.34 (m, 2H), 7.49 (m, 2H), 7.57 (d, 1H), 7.65 (d, 1H), 8.54 (s, 1H), 8.94 (s, 1H), 10.00 (s, 1H); LC-MS (ESI) m/z 381 (M+H)$^+$.

Example 397B

After a mixture of 1-(4-fluoro-3-hydroxyphenyl)-3-(1-phenyl-3-(trifluoromethyl)-1H-pyrazol-5-yl)urea (0.22 g, 0.58 mmol) and Cs$_2$CO$_3$ (0.325 g, 1 mmol) in THF (10 mL) was stirred at room temperature for 1 hour, to it was added 4-chloro-6,7-dimethoxyquinazoline (0.13 g, 0.58 mmol). It was stirred at 40° C. for 14 hours. The mixture was quenched by water and extracted with DCM. Extracts were dried over MgSO$_4$ and concentrated. It was purified on a silica gel column using a mixture of EtOAc-hexane as eluent to give 14346,7-dimethoxyquinazolin-4-yloxy)-4-fluorophenyl)-3-(1-phenyl-3-(trifluoromethyl)-1H-pyrazol-5-yl)urea (0.064 g, 19% yield). $^1$H NMR (300 MHz, DMSO-d$_6$) δ 3.99 (s, 3H), 4.00 (s, 3H), 6.87 (s, 1H), 7.24 (m, 1H), 7.36 (t, 1H), 7.42 (s, 1H), 7.59 (m, 6H), 7.67 (dd, 1H), 8.56 (s, 1H), 8.83 (s, 1H), 9.32 (s, 1H); LC-MS (ESI) m/z 569 (M+H)$^+$.

Example 398

Preparation of 1-(3-tert-butyl-1-(4-methoxyphenyl)-1H-pyrazol-5-yl)-3-(3-(6,7-dimethoxyquinazolin-4-yloxy)phenyl)urea Example 398A Step 1: 5-Bromo-2-methoxy-pyridine (1.1 g, 5.85 mmol) in 15 mL dry toluene was treated with benzophenone hydrazone (1.25 g, 6.45 mmol), (2-Biphenyl)ditert-butylphosphine (55 mg, 0.18 mmol), sodium tert-butoxide (845 mg, 8.80 mmol), and Pd$_2$(dba)$_3$ (55 mg, 0.06 mmol). Heated to 120° C. in the microwave for five minutes. Extracted using EtOAc/H$_2$O (3×100 mL EtOAc, 1×100 mL H$_2$O, 1×100 mL brine). Dried using Na$_2$SO$_4$ and then purified by flash chromatography (silica, 2-10% MeOH/DCM) to afford 5-(2-(diphenylmethylene)hydrazinyl)-2-methoxypyridine (1.20 g, 3.96 mmol, 68%). $^1$H NMR (300 MHz, DMSO-d$_6$) δ 8.83 (s, 1H), 8.09 (s, 1H), 7.67-7.29 (m, 11H), 6.70 (d, 1H), 3.77 (s, 3H); LC-MS (ESI) m/z 304 (M+H)$^+$.

Example 398A

Step 2: 5-(2-(Diphenylmethylene)hydrazinyl)-2-methoxypyridine (1.20 g, 3.96 mmol) was treated with 4,4-dimethyl-3-oxopentanenitrile (740 mg, 5.90 mmol) and 6N HCl (3.3 mL, 20.0 mmol) according to the procedure described for Example 303A Step 2. Purification by flash chromatography (silica, 20-100% EtOAc/Hexane) afforded 3-tert-butyl-1-(6-methoxypyridin-3-yl)-1H-pyrazol-5-amine (736 mg, 2.99 mmol, 76%). $^1$H NMR (300 MHz, DMSO-d$_6$) δ 8.31 (d, 1H), 7.83 (d, 1H), 6.89 (d, 1H), 5.37 (s, 1H), 5.17 (br s, 2H), 3.89 (s, 3H), 1.20 (s, 9H); LC-MS (ESI) m/z 247 (M+H)$^+$.

Example 398A

Step 3: 3-tert-Butyl-1-(6-methoxypyridin-3-yl)-1H-pyrazol-5-amine (736 mg, 2.98 mmol) was treated with phenyl chloroformate (1.50 mL, 12.0 mmol) according to the procedure in Example 118A to afford phenyl 3-tert-butyl-1-(6-methoxypyridin-3-yl)-1H-pyrazol-5-ylcarbamate (665 mg, 1.82 mmol, 61%). $^1$H NMR (300 MHz, DMSO-d$_6$) δ 10.07 (br s, 1H), 8.31 (s, 1H), 7.83 (d, 1H), 7.39 (t, 2H), 7.23 (t, 1H), 7.08 (br s, 2H), 6.98 (d, 1H), 6.36 (s, 1H), 3.92 (s, 1H), 1.27 (s, 9H); LC-MS (ESI) m/z 367 (M+H)$^+$.

Example 398B

Phenyl 3-tert-butyl-1-(6-methoxypyridin-3-yl)-1H-pyrazol-5-ylcarbamate (110 mg, 0.3 mmol) was treated with 3-(6,7-dimethoxyquinazolin-4-yloxy)aniline (89 mg, 0.30 mmol) (prepared as described in Example 113A) according to the procedure in Example 115C to afford 1-(3-tert-butyl-1-(4-methoxyphenyl)-1H-pyrazol-5-yl)-3-(3-(6,7-dimethoxyquinazolin-4-yloxy)phenyl)urea (74 mg, 0.13 mmol, 44%). $^1$H NMR (300 MHz, DMSO-d$_6$) δ 9.14 (s, 1H), 8.55 (s, 1H), 8.46 (s, 1H), 8.31 (s, 1H), 7.82 (d, 1H), 7.55 (s, 2H), 7.38-7.33 (m, 2H), 7.18 (d, 1H), 6.99-6.90 (m, 2H), 6.35 (s, 1H), 3.99 (s, 3H), 3.97 (s, 3H), 3.91 (s, 3H), 1.25 (s, 9H); LC-MS (ESI) m/z 570 (M+H)$^+$.

Example 399

Preparation of 1-(3-(6,7-dimethoxyquinazolin-4-ylthio)phenyl)-3-(3-ethyl-1-phenyl-1H-pyrazol-5-yl)urea A stirred mixture of phenyl 3-ethyl-1-phenyl-1H-pyrazol-5-ylcarbamate (prepared as described in Example 352A Step 3) (0.15 g, 0.50 mmol) and 3-(6,7-dimethoxyquinazolin-4-ylthio)aniline (prepared as described in Example 115B) (0.16 g, 0.50 mmol) in DMSO (2 mL) was heated at 70° C. for 15 h. After cooling to rt, the reaction mixture was diluted with ethyl acetate (50 mL) and washed with water (2×20 mL). The organic layer was separated, dried over magnesium sulfate, and concentrated under reduced pressure to afford an oil which was recrystallized from diethyl ether. Further purification via preparative silica gel thin-layer chromatography (eluting with a mixture of 8% methanol in dichloromethane containing 0.5% ammonia) afforded 1-(3-(6,7-dimethoxyquinazolin-4-ylthio)phenyl)-3-(3-ethyl-1-phenyl-1H-pyrazol-5-yl)urea (90 mg, 35%) as a colorless solid. $^1$H NMR (400 MHz, DMSO-$d_6$) δ9.38 (s, 1H), 8.67 (s, 1H), 8.61 (s, 1H), 7.77 (s, 1H), 7.17-7.53 (m, 10H), 6.30 (s, 1H), 3.98 (s, 6H), 2.56 (m, 2H), 1.19 (m, 3H); LC-MS (ESI) m/z 527 (M+H)$^+$.

Example 400

Competition Binding Assay to Determine Binding Constants ($K_d$) for Interactions Between Compounds and RAF Kinases Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005310). For the binding assays, streptavidin-coated magnetic beads were treated with biotinylated affinity ligands for 30 min at room temperature to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17× PBS, 0.05% Tween 20, 6 mM DTT). Test compounds were prepared as 100× stocks in DMSO and rapidly diluted into the aqueous environment. DMSO was added to control assays lacking a test compound. Primary screen interactions were performed in polypropylene 384-well plates in a final volume of 34 μL, while $K_d$ determinations were performed in polystyrene 96-well plates in a final volume of 135 pt. The assay plates were incubated at room temperature with shaking for 1 hour, long enough for binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 2 μM non-biotinylated affinity ligand) and incubated at room temperature with shaking for 30 min. The kinase concentration in the eluates was measured by quantitative PCR. Each kinase was tested individually against each compound. $K_{ds}$ were determined using eleven serial threefold dilutions. A selectivity score, which is a quantitative measure of selectivity of a compound against a panel of enzymes, may be calculated for a compound by dividing the number of enzymes for which a compound meets a set criteria, (for example, a binding constant of 100 nM or less), by the total number of enzymes tested. Table 1 provides a kinase selectivity score, S35, which was calculated for each compound by dividing the number of kinases for which a compound displayed inhibition of 65% or greater compared to negative control lacking inhibitors (DMSO only), divided by the 290 distinct kinases tested excluding mutant variants. (Note, for those compounds tested in a larger kinase panel, as indicated by an asterisk (*) next to the S35 score, the divisor is 321 (i.e. the larger panel contains 321 distinct kinases, excluding mutant variants.)).

Example 401

MEK Phosphorylation ELISA

A MEK1 phosphorylation ELISA (Biosource, MEK1 [pSpS218/222] kit, Catalog # KHO0321) was used to measure the inhibition of MEK1 phosphorylation in the A375 human melanoma cell line in the presence of the compounds provided herein. The A375 cell line contains wild-type N-Ras but has a constitutively active BRAF carrying the V600E mutation. A total MEK ELISA was also run in parallel in order to measure the amount of both phosphorylated and unphosphorylated MEK 1(Biosource, tMEK kit, Catalog # KH00291).

A375 cells (from American Type Culture Collection) were plated at 50,000 cells per well in DMEM (Mediatech) with 10% fetal bovine serum (Omega Scientific) into a 96 well plate and incubated overnight in a 37° C. incubator with 10% CO2. The cells were then washed with PBS and the medium replaced with 0.5% FBS for incubation overnight. A solution of the test compound in DMSO was added to each well at varying concentrations, or alternatively, a solution of positive control (an internal compound previously determined to have an IC50 of less than 20 nM in this phospho-MEK assay), or negative control (DMSO) was added to the wells at varying concentrations. The cells were incubated with compound or control for two hours at 37° C. The compound solution was aspirated off and the cells washed with cold PBS. The cells were then lysed for 30 minutes in the cold with Cell Extraction Buffer containing Phosphatase Inhibitors (catalog # FNN0011, Invitrogen) and protease inhibitors (catalog #11873580001, Roche Applied Science). The plate was centrifuged for 30 minutes to pellet out the cell debris. The cleared lysates were transferred to a 96-well Nunc plate and the ELISA protocol described by the manufacturer in Catalog # KH00321 or KH00291 was followed. The reaction was read at 450 nM using an ELISA plate reader. The percent inhibition of MEK1 phosphorylation was determined for each compound at each concentration, and the concentration of the test compound necessary for inhibiting 50% of MEK1 phosphorylation ($IC_{50}$) was calculated. The results are summarized in Table 1.

Example 402

A375 Proliferation Assay

A375 cells (derived from a human melanoma cell line containing wild-type N-Ras but which also has a constitutively active BRAF carrying the V600E mutation obtained from ATCC), were plated at 10,000 cells per well into a 96 well TC-treated plate in M3 medium (Mediatech Cell grow) containing 10% fetal bovine serum (Omega-Scientific) and incubated overnight in a 37° C. incubator under 10% CO2. The following day, the medium was replaced with 0.5% FBS in M3 for overnight incubation. At day three, a solution of the test compound in DMSO was added to each well at varying concentrations, or alternatively, a solution of positive control (an internal compound previously determined to have an $IC_{50}$ of less than 20 nM in the phospho-MEK assay) in DMSO, or negative control (DMSO) was added to the wells at varying concentrations. The cells were incubated with compound or control for 72 hours at 37° C. under 10% CO2. Following incubation, Cell Titer Blue reagent (Promega) was added to each well containing compounds or controls, and then incubated for 3 hours at 37° C. under 10% CO2. Proliferation was measured by fluorescence with excitation at 560 nm and emission at 590 nm using SoftMax Pro. The percent inhibition of proliferation was determined for each compound at each concentration, and the concentration of the test compound necessary for inhibiting cell proliferation by 50% ($IC_{50}$) was calculated. The results are summarized in Table 1.

Since modifications will be apparent to those of skill in the art, it is intended that the claimed subject matter be limited only by the scope of the appended claims.

What is claimed is:

1. A pharmaceutical composition, comprising from about 1 mg to about 2000 mg of a compound that is

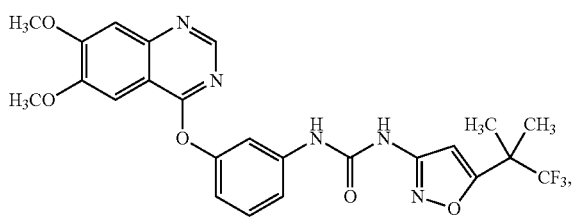 [SMILES: COc1cc2ncnc(Oc3cccc(NC(=O)Nc4cc(C(C)(C)C(F)(F)F)on4)c3)c2cc1OC]

or a pharmaceutically acceptable salt thereof, and at least one pharmaceutically acceptable carrier, excipient or diluent.

2. A pharmaceutical composition according to claim 1, comprising from about 10 mg to about 1000 mg of a compound that is

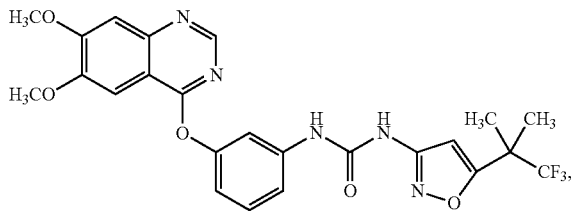 [SMILES: COc1cc2ncnc(Oc3cccc(NC(=O)Nc4cc(C(C)(C)C(F)(F)F)on4)c3)c2cc1OC]

or a pharmaceutically acceptable salt thereof.

3. A pharmaceutical composition according to claim 1, comprising from about 20 mg to about 500 mg of a compound that is

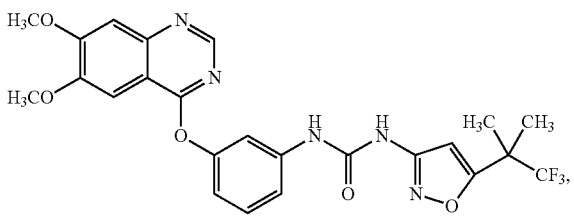 [SMILES: COc1cc2ncnc(Oc3cccc(NC(=O)Nc4cc(C(C)(C)C(F)(F)F)on4)c3)c2cc1OC]

or a pharmaceutically acceptable salt thereof.

4. A pharmaceutical composition according to claim 1, comprising from about 25 mg to about 250 mg of a compound that is

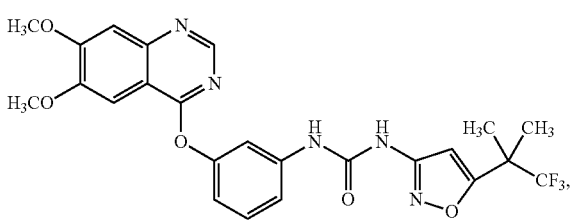 [SMILES: COc1cc2ncnc(Oc3cccc(NC(=O)Nc4cc(C(C)(C)C(F)(F)F)on4)c3)c2cc1OC]

or a pharmaceutically acceptable salt thereof.

5. A pharmaceutical composition according to claim 1, wherein said pharmaceutical composition is in a dosage form suitable for oral administration to a patient.

6. A pharmaceutical composition according to claim 5, wherein said dosage form is a tablet, capsule, troche, lozenge, pastille, cachet, pellet, gum, bulk powder, effervescent powder, non-effervescent powder, solution, emulsion, suspension, wafer, sprinkle, elixir, or syrup.

7. A pharmaceutical composition according to claim 6 wherein said dosage form is a tablet, capsule, cachet, effervescent powder, non-effervescent powder, solution, emulsion, suspension, or syrup.

8. A pharmaceutical composition according to claim 6, wherein said dosage form is a tablet, capsule, solution, emulsion, suspension, or syrup.

9. A pharmaceutical composition according to claim 6, wherein said dosage form is a tablet or capsule.

10. A pharmaceutical composition according to claim 6, wherein said dosage form is a tablet.

11. A pharmaceutical composition according to claim 6, wherein said dosage form is a capsule.

* * * * *